US012617832B2

(12) United States Patent　　(10) Patent No.:　US 12,617,832 B2
Barzel et al.　　(45) Date of Patent:　May 5, 2026

(54) GENETIC ENGINEERING OF B CELL RECEPTORS AND USES THEREOF IN ANTIGEN-INDUCED ANTIBODY SECRETION

(71) Applicant: Ramot at Tel-Aviv University Ltd., Tel Aviv (IL)

(72) Inventors: Adi Barzel, Tel Aviv (IL); Alessio D. Nahmad, Tel Aviv (IL); Tal Akriv, Tel Aviv (IL); Miriam Fried, Tel Aviv (IL); Iris Dotan, Tel Aviv (IL); Daniel Nataf, Tel Aviv (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 1260 days.

(21) Appl. No.: 17/200,357

(22) Filed: Mar. 12, 2021

(65) Prior Publication Data

US 2021/0269771 A1　　Sep. 2, 2021

Related U.S. Application Data

(63) Continuation-in-part of application No. PCT/IL2019/051026, filed on Sep. 12, 2019.

(60) Provisional application No. 62/840,429, filed on Apr. 30, 2019, provisional application No. 62/730,561, filed on Sep. 13, 2018.

(51) Int. Cl.
| | |
|---|---|
| *C07K 14/705* | (2006.01) |
| *A61K 35/17* | (2025.01) |
| *A61K 40/10* | (2025.01) |
| *A61K 40/13* | (2025.01) |
| *A61K 40/24* | (2025.01) |
| *A61K 40/46* | (2025.01) |
| *C07K 16/00* | (2006.01) |
| *C07K 16/10* | (2006.01) |
| *C12N 5/0781* | (2010.01) |
| *C12N 15/85* | (2006.01) |
| *C12N 15/90* | (2006.01) |

(52) U.S. Cl.
CPC ........ *C07K 14/70503* (2013.01); *A61K 35/17* (2013.01); *A61K 40/10* (2025.01); *A61K 40/13* (2025.01); *A61K 40/24* (2025.01); *A61K 40/46* (2025.01); *C07K 16/00* (2013.01); *C07K 16/1027* (2013.01); *C07K 16/1045* (2013.01); *C12N 5/0635* (2013.01); *C12N 15/85* (2013.01); *C12N 15/907* (2013.01); *C07K 2317/51* (2013.01); *C07K 2317/52* (2013.01); *C07K 2317/56* (2013.01); *C07K 2317/76* (2013.01); *C12N 2501/50* (2013.01); *C12N 2501/52* (2013.01); *C12N 2510/02* (2013.01); *C12N 2830/20* (2013.01)

(58) Field of Classification Search
None
See application file for complete search history.

(56) References Cited

U.S. PATENT DOCUMENTS

| | | |
|---|---|---|
| 5,714,352 A | 2/1998 | Jakobovits |
| 2016/0289637 A1 | 10/2016 | Goldberg et al. |
| 2021/0024632 A1 | 1/2021 | Danger et al. |

FOREIGN PATENT DOCUMENTS

| | | |
|---|---|---|
| WO | 2013/134880 A1 | 9/2013 |
| WO | WO-2016161446 A1 | 10/2016 |
| WO | 2017/005923 A1 | 1/2017 |
| WO | 2017/214376 A1 | 12/2017 |
| WO | 2019/028417 A1 | 2/2019 |
| WO | 2019/079772 A1 | 4/2019 |

OTHER PUBLICATIONS

Jacobsen et al. 2017 One-step generation of monoclonal B cell receptor mice capable of class switch recombination and somatic hypermutation. Journal of Experimental Medicine doi: 10.1084/jem.20172064 (Year: 2017).*
Li et al. Comparison of Identical and Functional Igh Alleles Reveals a Nonessential Role for Eu in Somatic Hypermutation and Class-Switch Recombination. J Immunol (2010) 185 (10): 6049-6057 (Year: 2010).*
Zhang et al. Effect of CpG Dinucleotides within IgH Switch Region Repeats on Immunoglobulin Class Switch Recombination. Mol Immunol. Apr. 18, 2015;66(2):284-2 (Year: 2015).*
Baughn, L. B. et al. (2011). Recombinase-mediated cassette exchange as a novel method to study somatic hypermutation in Ramos cells. *MBio*, 2(5), e00186-11.
Fang, J. et al. (2005). Stable antibody expression at therapeutic levels using the 2A peptide. *Nature Biotechnology*, 23(5), 584-590.
Grimm, D. et al. (2008). In vitro and in vivo gene therapy vector evolution via multispecies interbreeding and retargeting of adeno-associated viruses. *Journal of Virology*, 82(12), 5887-5911.
Jacobsen, J. T. et al. (2018). One-step generation of monoclonal B cell receptor mice capable of isotype switching and somatic hypermutation. *Journal of Experimental Medicine*, 215(10), 2686-2695.
Lenden Hasse, H. et al. (2017) Generation and CRISPR/Cas9 editing of transformed progenitor B cells as a pseudo-physiological system to study DNA repair gene function in V(D)J recombination. *Journal of Immunological Methods*, 451, 71-77.
Ran, F. A. C. L. et al. (2015). In vivo genome editing using *Staphylococcus aureus* Cas9. *Nature*, 520(7546), 186-191.
Adeno-associated virus 6, complete genome, Nucleotide—NCBI, www.ncbi.nlm.nih.gov/nuccore/AF028704.1, GenBank: AF028704.1, Jan. 12, 1998, accessed on Jun. 7, 2021, pp. 1-2.

(Continued)

*Primary Examiner* — Jennifer Dunston
*Assistant Examiner* — Tiffany Nicole Grooms
(74) *Attorney, Agent, or Firm* — Mark S. Cohen; PEARL COHEN ZEDEK LATZER BARATZ LLP

(57) ABSTRACT

The present invention relates to methods and compositions for engineering B cells to express transgenic B cell receptor (BCR) for antigen-induced antibody secretion, compositions, methods and uses thereof in immunotherapy.

8 Claims, 89 Drawing Sheets

Specification includes a Sequence Listing.

(56) References Cited

OTHER PUBLICATIONS

Adeno-associated virus—8, complete genome, Nucleotide—NCBI, www.ncbi.nlm.nih.gov/nuccore/NC_006261.1, NCBI Reference Sequence: NC_006261.1, Aug. 13, 1998, accessed on Jun. 7, 2021, pp. 1-3.

Baughn, et al., Recombinase-Mediated Cassette Exchange as a Novel Method to Study Somatic Hypermutation in Ramos Cells, mbio.asm.org, Sep./Oct. 2011, pp. 1-9, vol. 2, issue 5.

Fusil, et al., A Lentiviral Vector Allowing Physiologically Regulated Membrane-anchored and Secreted Antibody Expression Depending on B-cell Maturation Status, Molecular Therapy, Nov. 2015, pp. 1734-1747, vol. 23, No. 11.

Greiner, et al., CRISPR-Mediated Editing of the B Cell Receptor in Primary Human B Cells, iScience, Feb. 22, 2019, pp. 369-378, vol. 1.

Hartweger, HIV-specific humoral immune responses by CRISPR/Cas9-edited B cells, J. Exp. Med., 2019, pp. 1301-1310, vol. 216, No. 6.

HIV-1 isolated THRO clone 18 from USA envelope glycoprotein (evn) gene, complete cds, Nucleotide—NCBI, www.ncbi.nlm.nih.gov/nuccore/AY835448, GenBank: AY835448.1, Aug. 1, 2005, accessed on Jun. 7, 2021, pp. 1-2.

Hwang, et al., Sequence intrinsic somatic mutation mechanisms contribute to affinity maturation of VRC01-class HIV-1 broadly neutralizing antibodies, PNAS, Aug. 8, 2017, pp. 8614-8619, vol. 114, No. 32.

Laskov, et al., Preferential targeting of somatic hypermutation to hotspot motifs and hypermutable sites and generation of mutational clusters in the IgVH alleles of a rheumatoid factor producing lymphoblastoid cell line, Molecular Immunology, 2011, pp. 733-745, vol. 48.

Lin, et al., One-step CRISPR/Cas9 method for the rapid generation of human antibody heavy chain knock-in mice, The EMBO Journal, 2018, pp. 1-16,.

Luo, et al., Engineering human hematopoietic stem/progenitor cells to produce a broadly neutralizing anti-HIV antibody after in vitro maturation to human B lymphocytes, Blood, Feb. 12, 2009, pp. 1422-1431, vol. 113, No. 7.

Moffett, et al., B cells engineered to express pathogen-specific antibodies protect against infection, Sci. Immunol, May 17, 2019, pp. 1-27, vol. 4(35).

Nahmad, et al., Engineered B cells expressing an anti-HIV antibody enable memory retention, isotype switching and clonal expansion, Nature Communicatins, 2020, pp. 1-10, vol. 11:5851.

Pigson, et al., Immunogenomic engineering of a plug-and-(dis)play hybridoma platform, Nature Communications, 2016, pp. 1-10, vol. 7:12535.

Rogozin, et al., Cutting Edge: DGYW/WRCH Is a Better Predictor of Mutability at G:C Bases in Ig Hypermutation Than the Widely Accepted RGYW/WRCY Motif and Probably Reflects a Two-Step Activation-Induced Cytidine Deaminase-Triggered Process, J. Immunol., 2004, pp. 3382-3384, vol. 172.

Voss, et al., Reprogramming the antigen specificity of B cells using genome-editing technologies, eLife, 2019, pp. 1-22, vol. 8:e42995.

Yeap, Sequence-Intrinsic Mechanisms that Target AID Mutational Outcomes on Antibody Genes, Cell, Nov. 19, 2015, pp. 1124-1137, vol. 163(5).

* cited by examiner

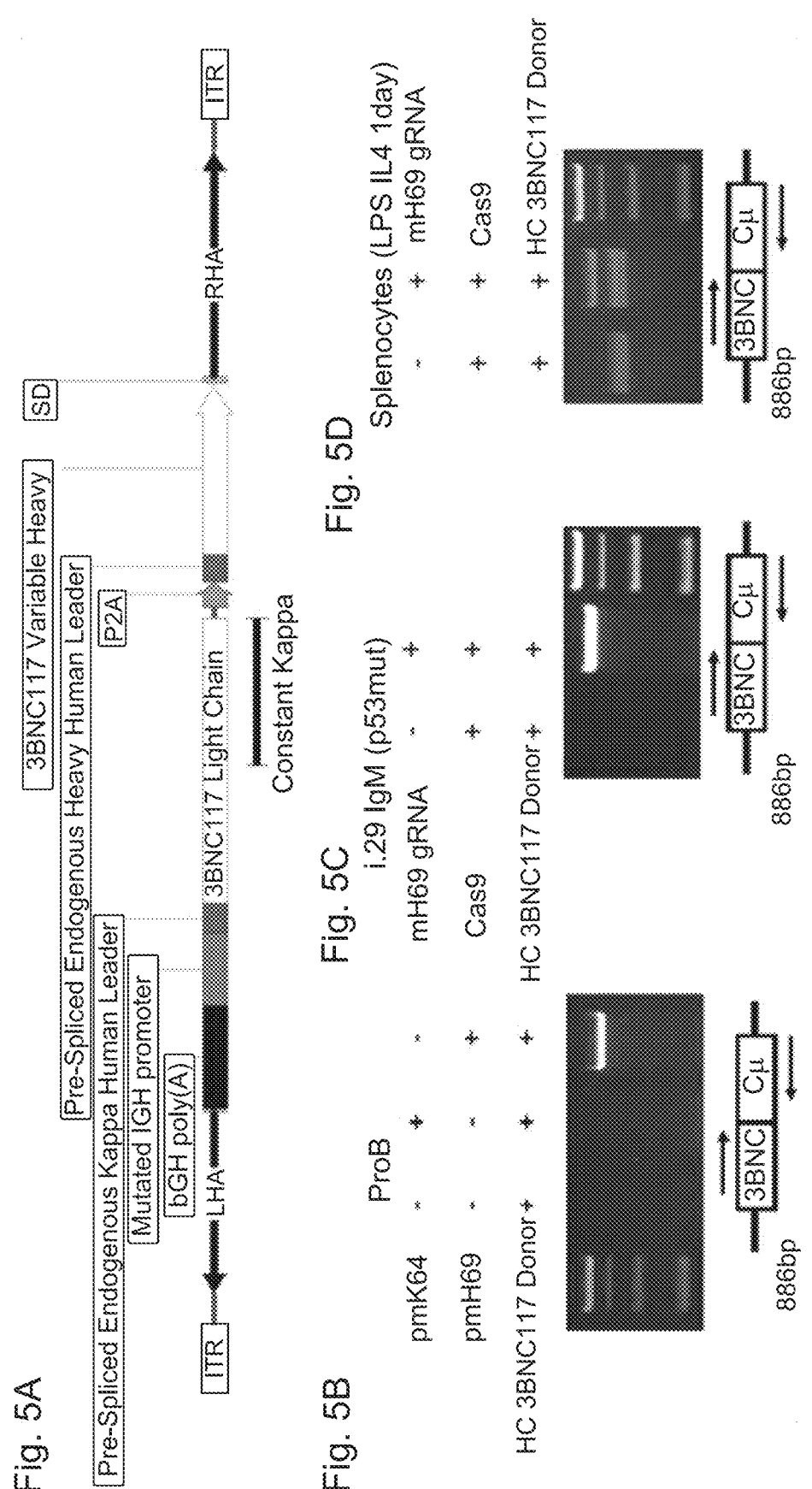

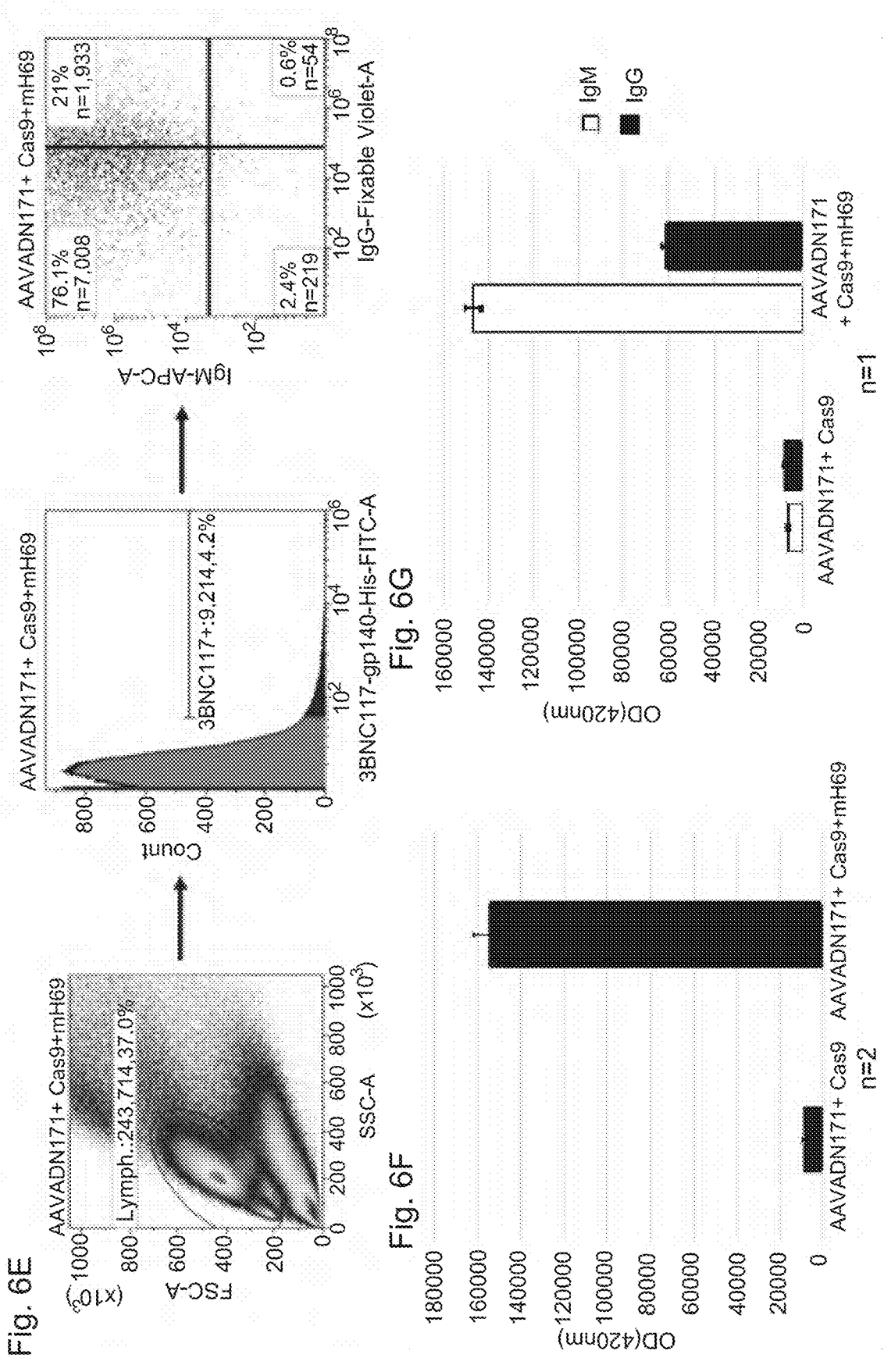

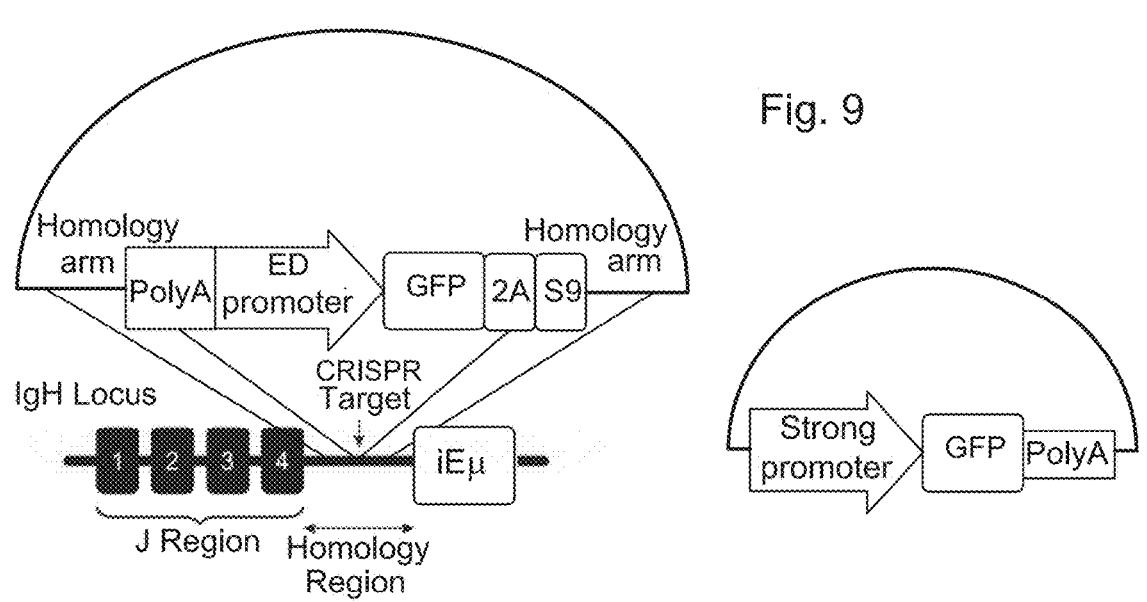
Fig. 9
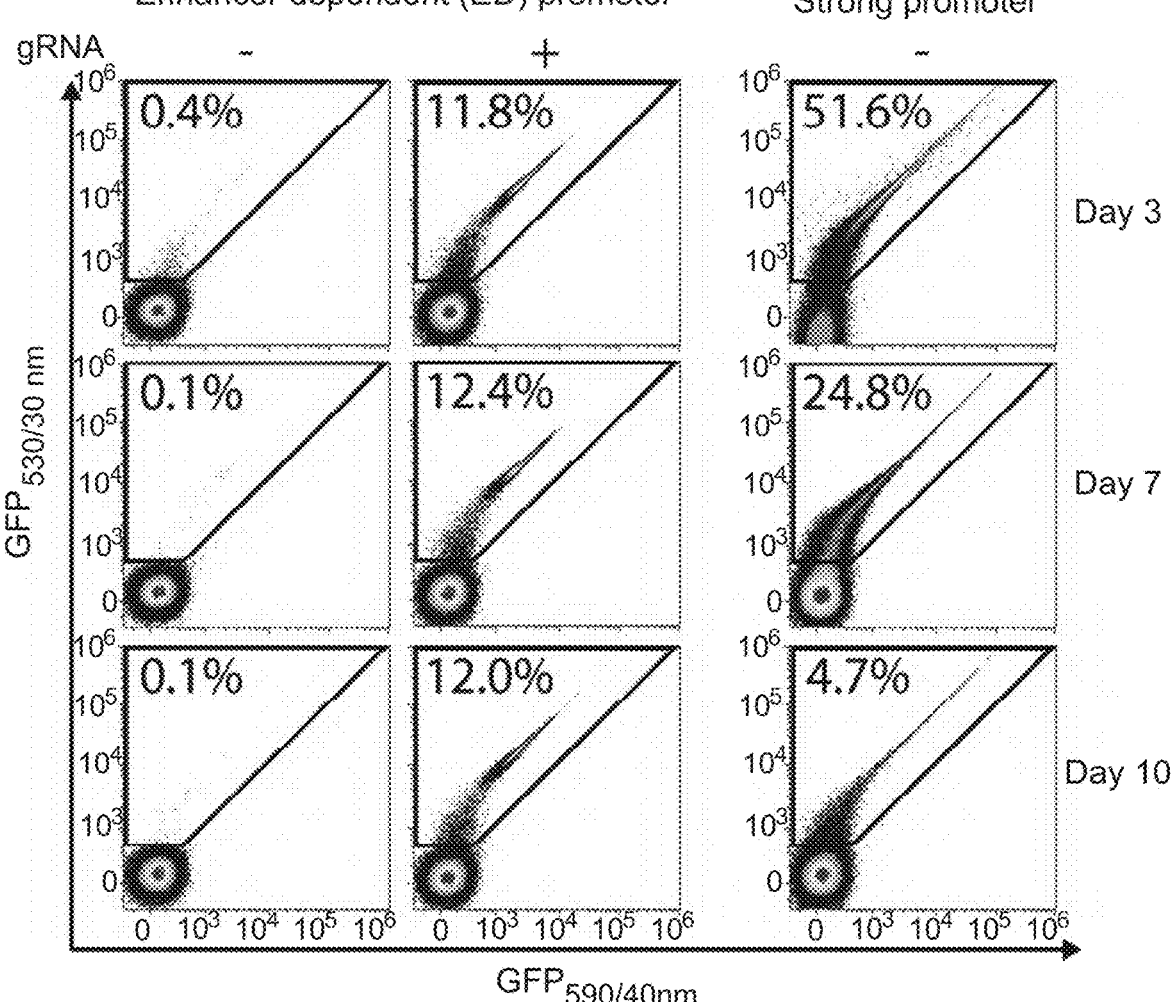

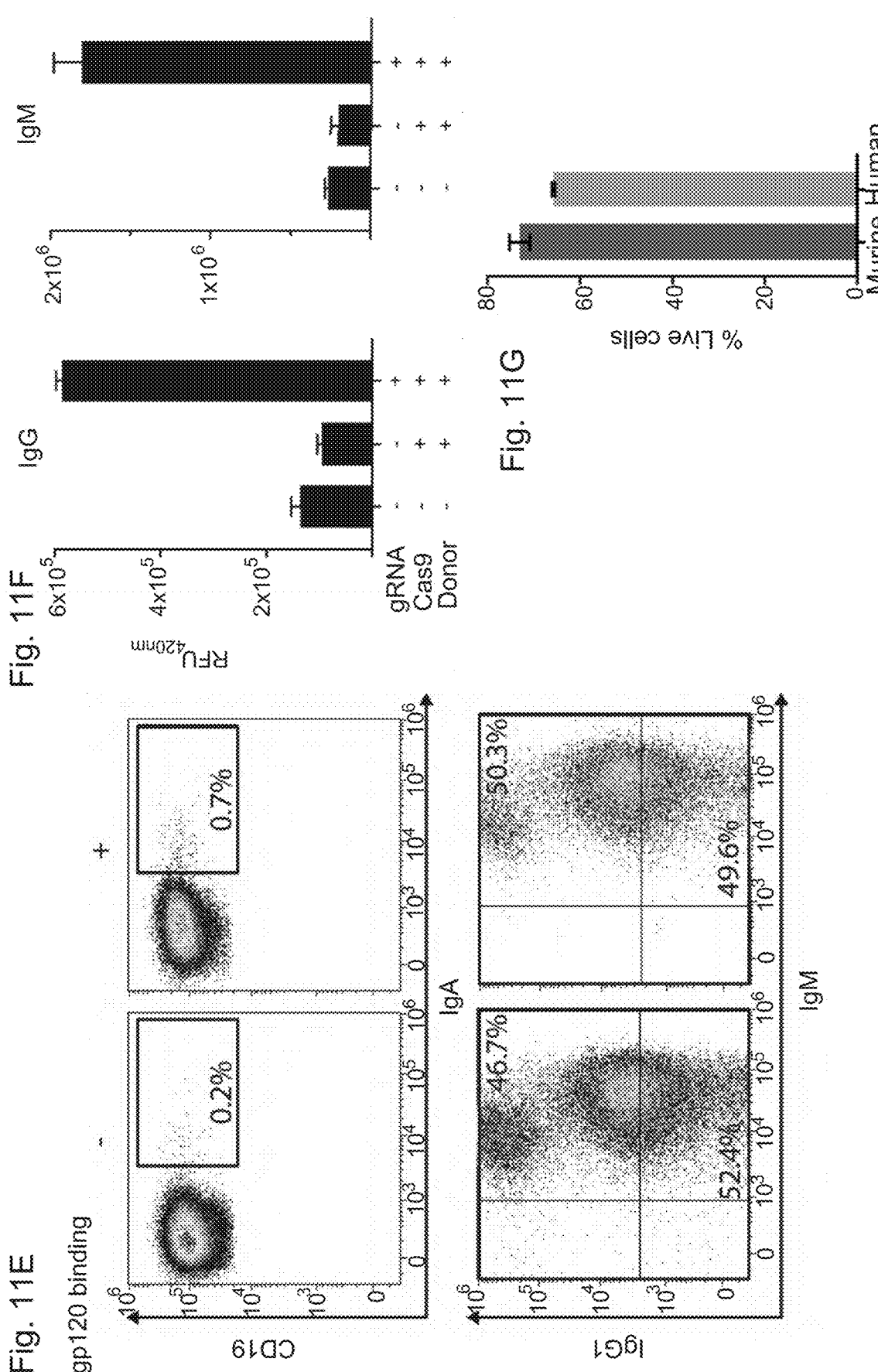

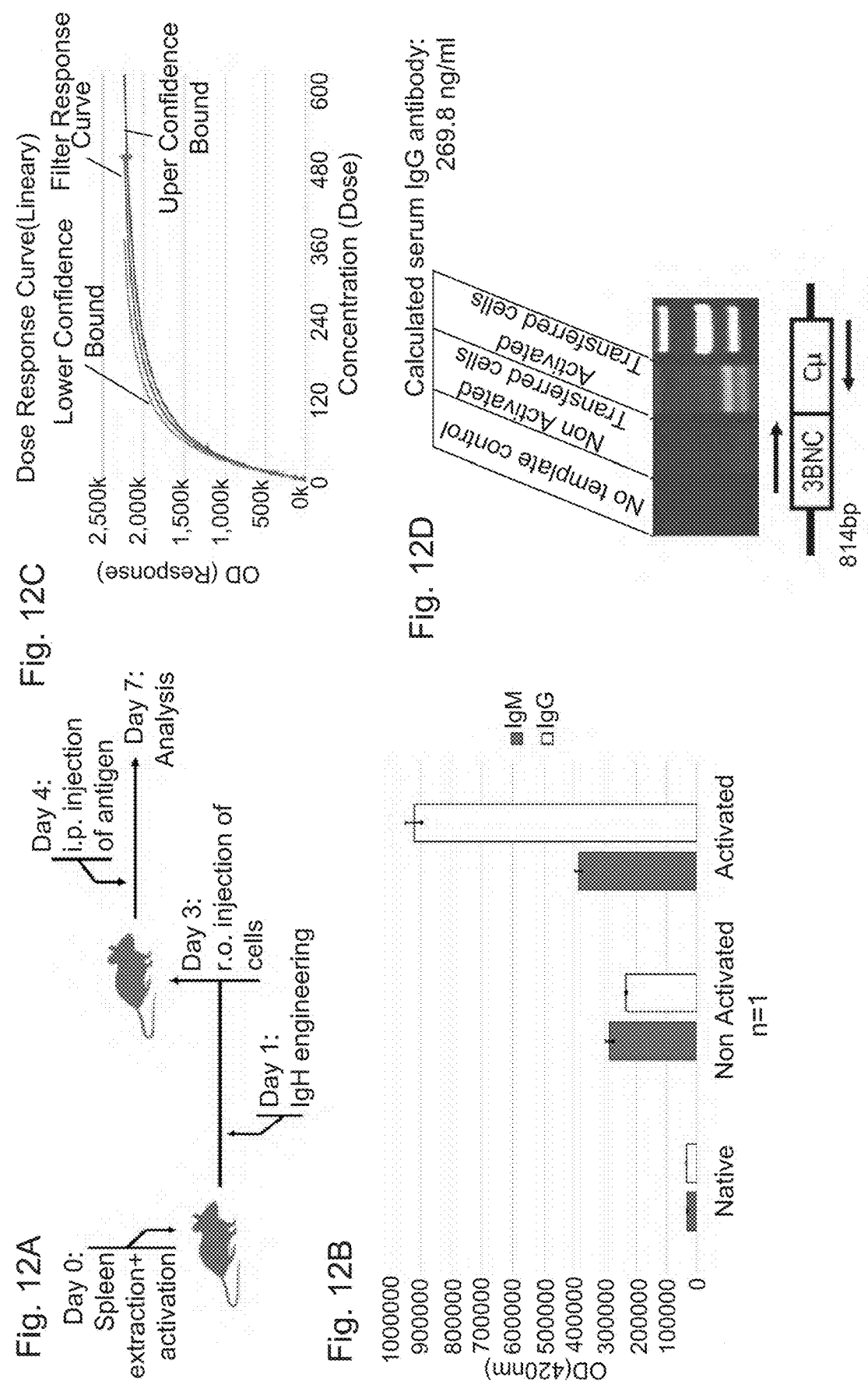

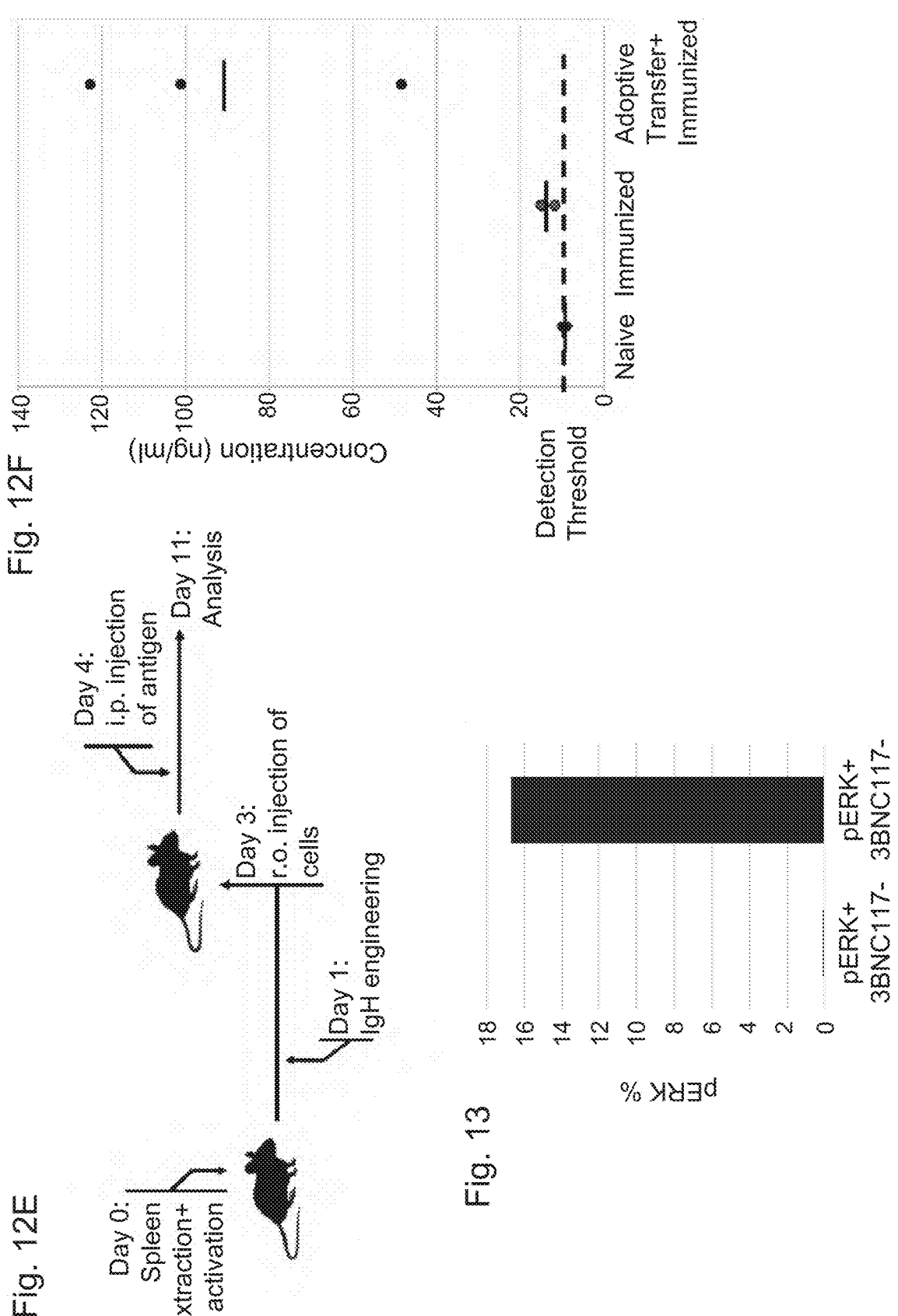

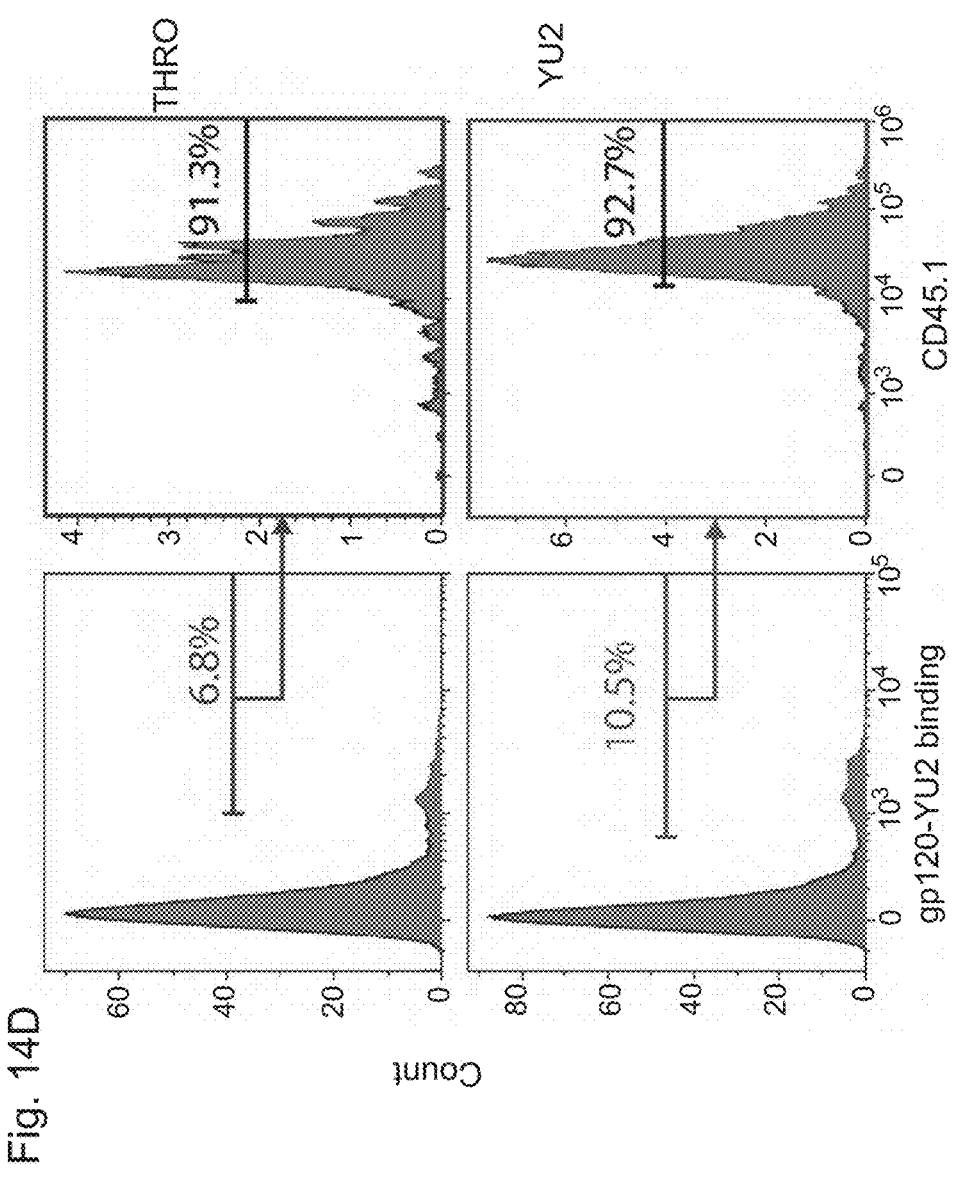
Fig. 14D
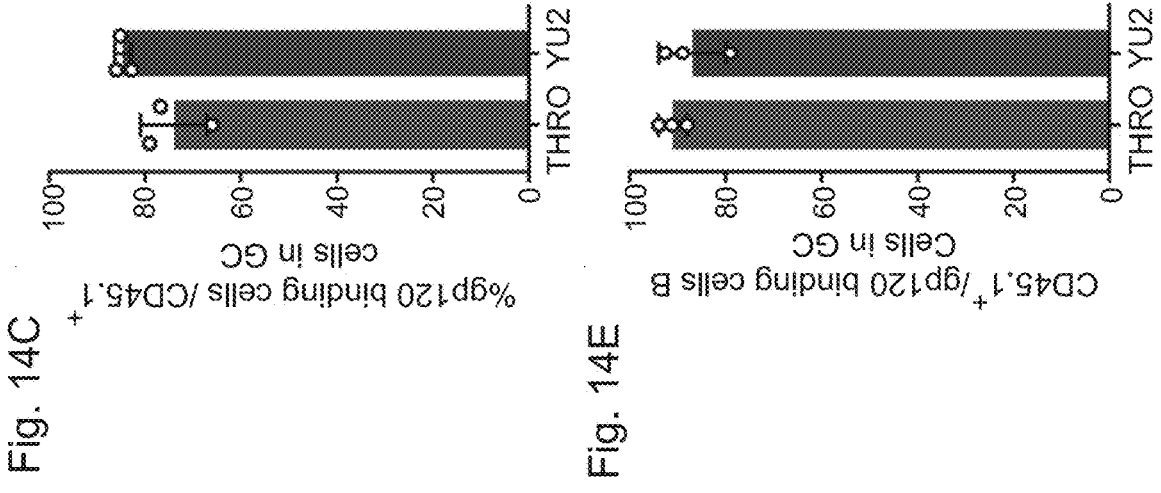
Fig. 14C
Fig. 14E

Fig. 17A
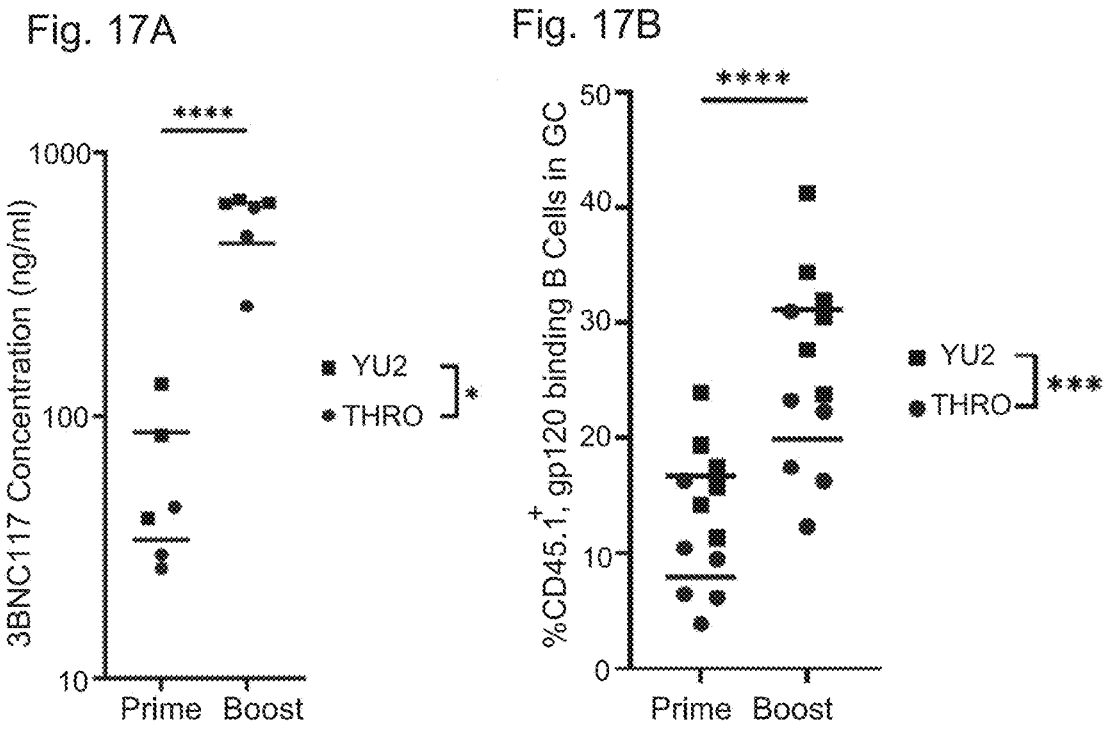
Fig. 17B
Fig. 17C
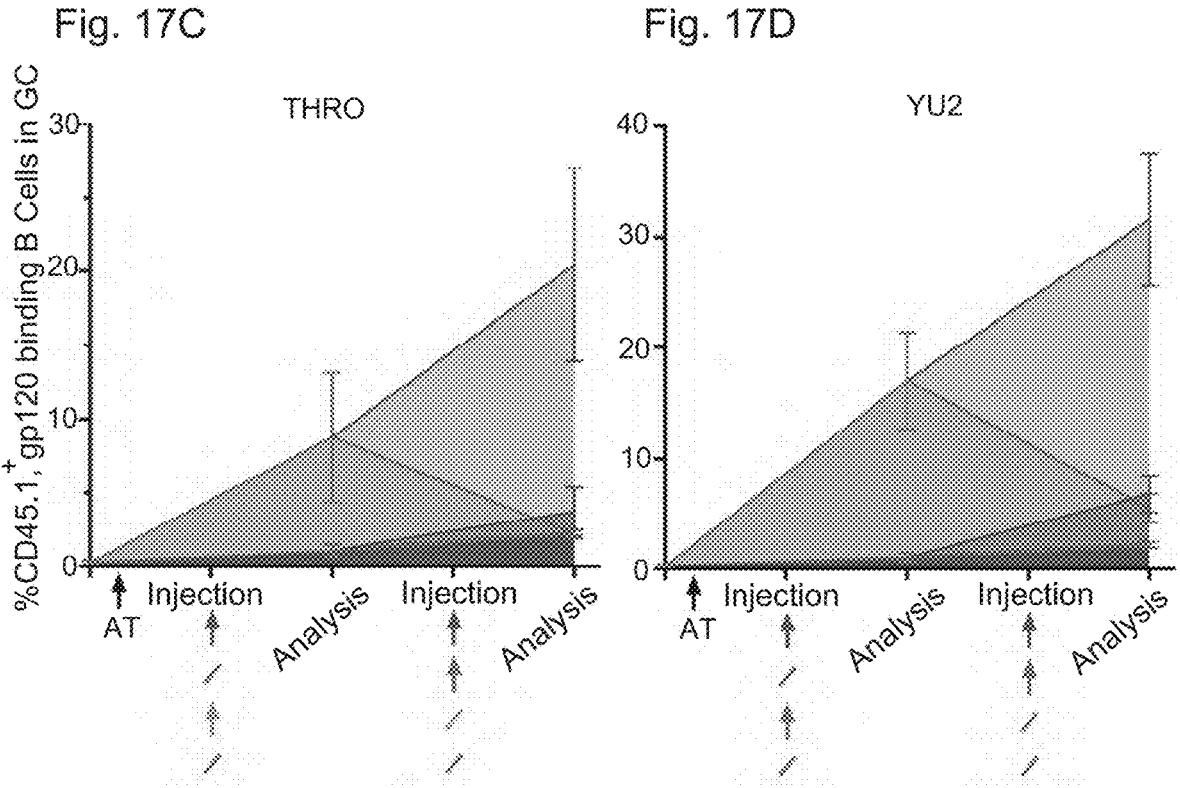
Fig. 17D

Fig. 20A
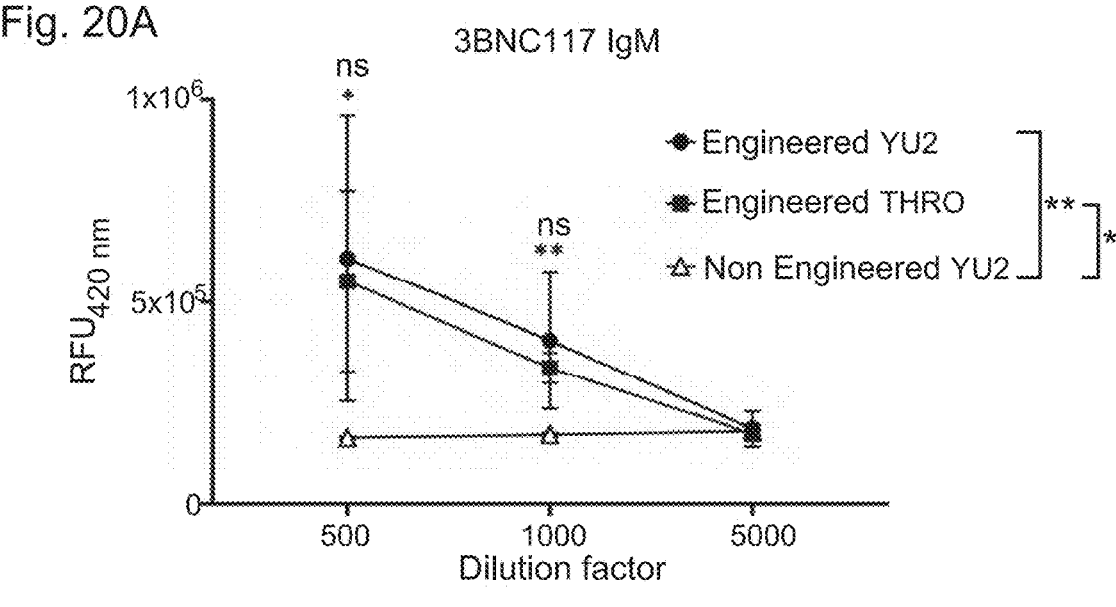
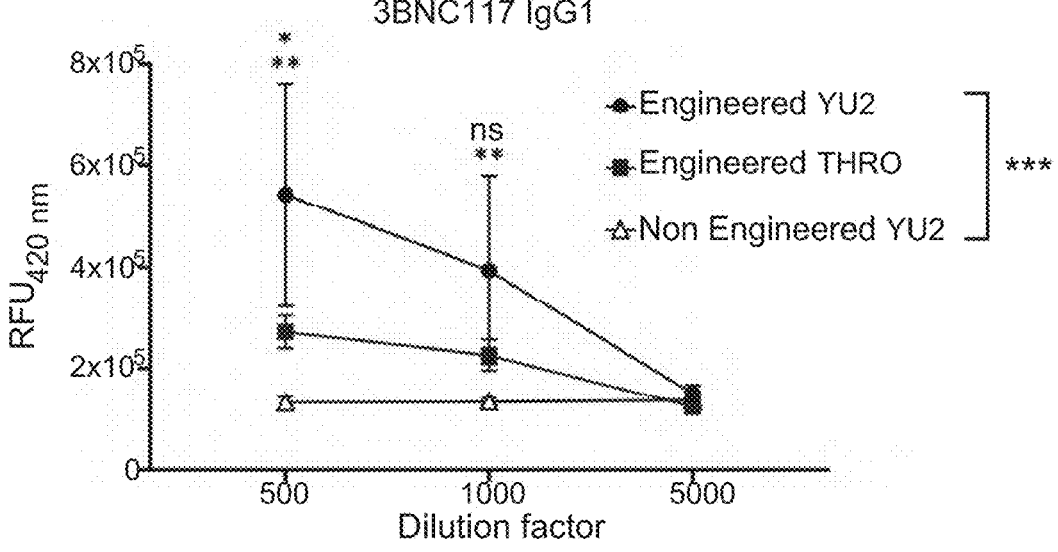
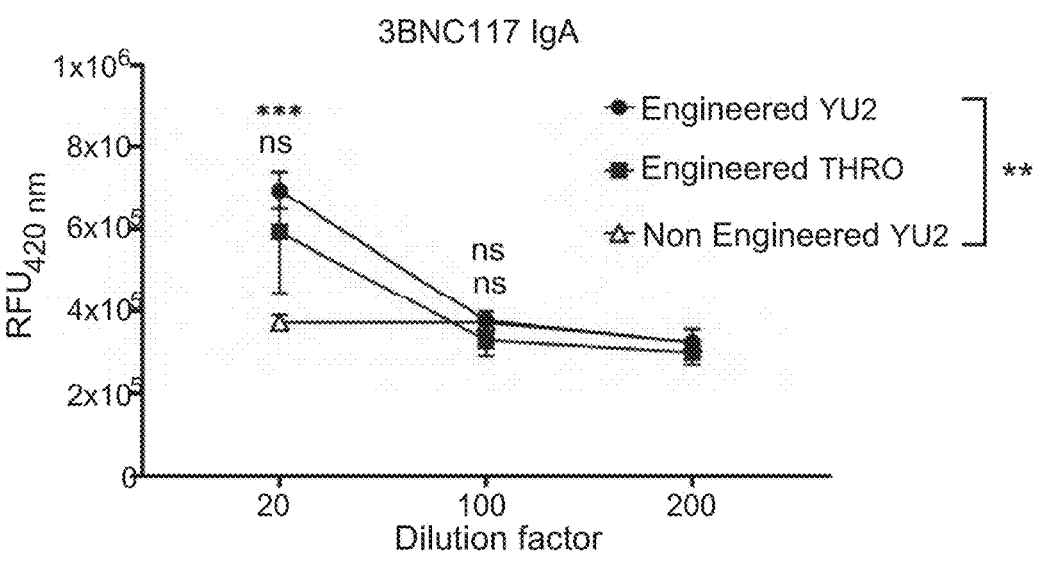

Fig. 20B
Fig. 20E
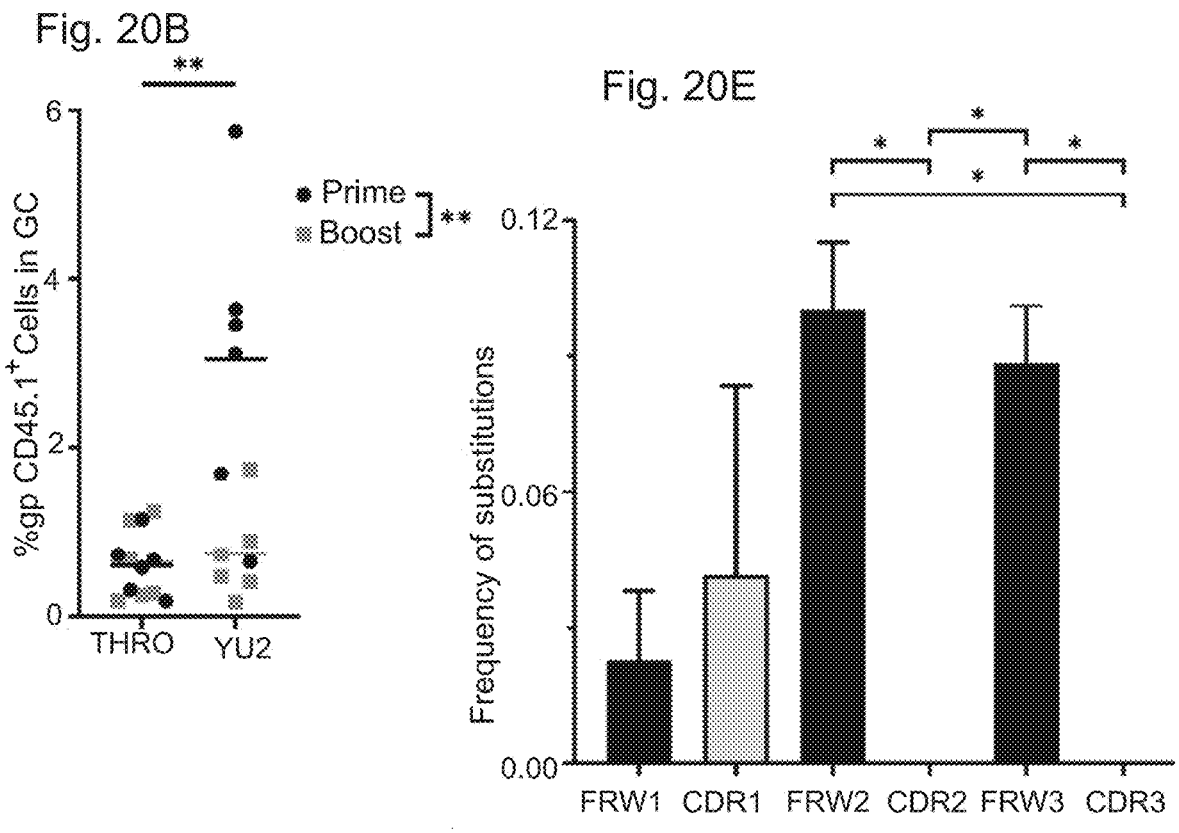
Fig. 20C
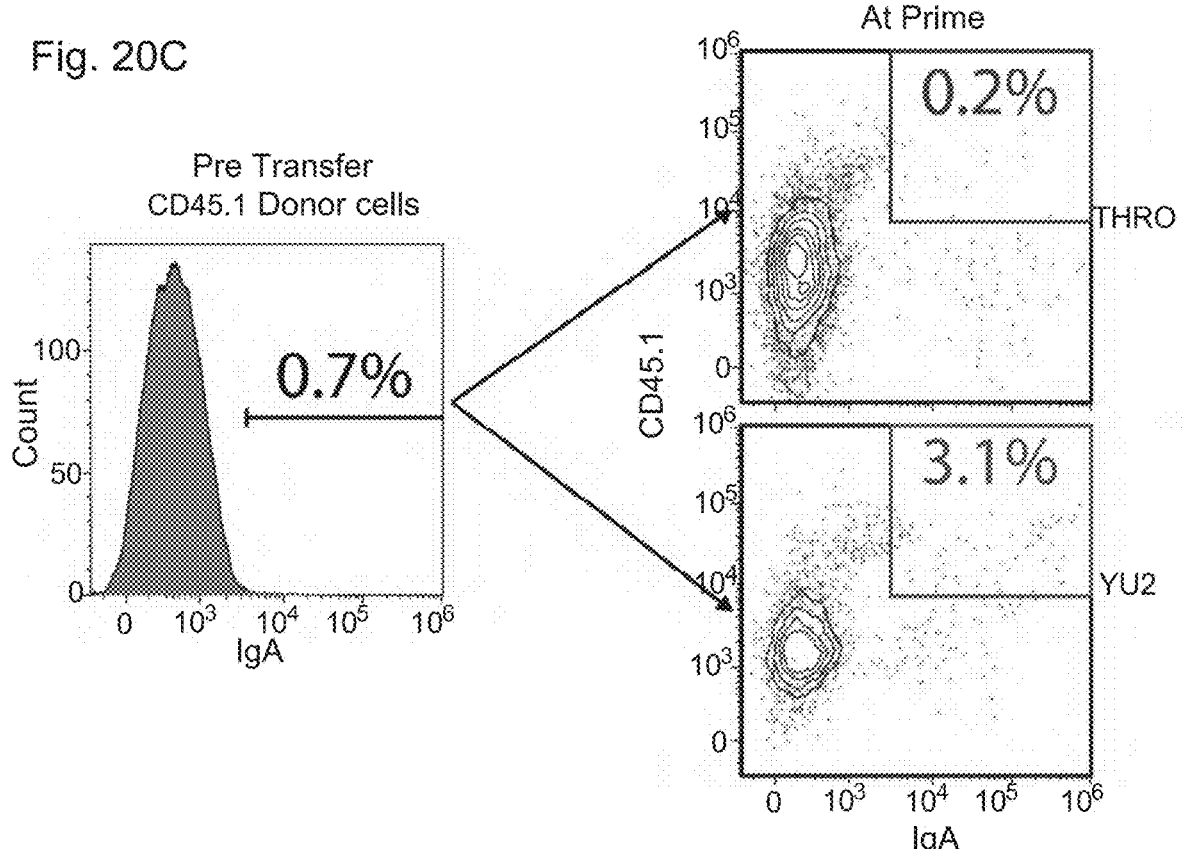

Fig. 25A
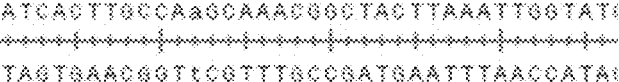
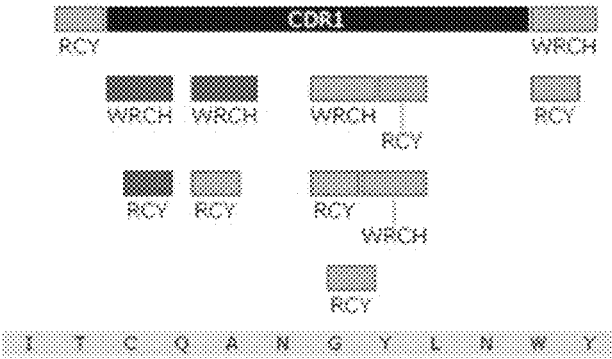
Fig. 25B
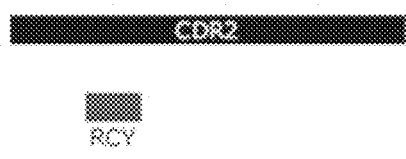
Fig. 25C
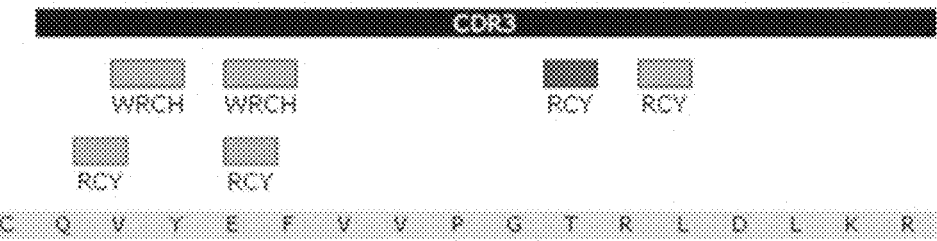

Fig. 26A
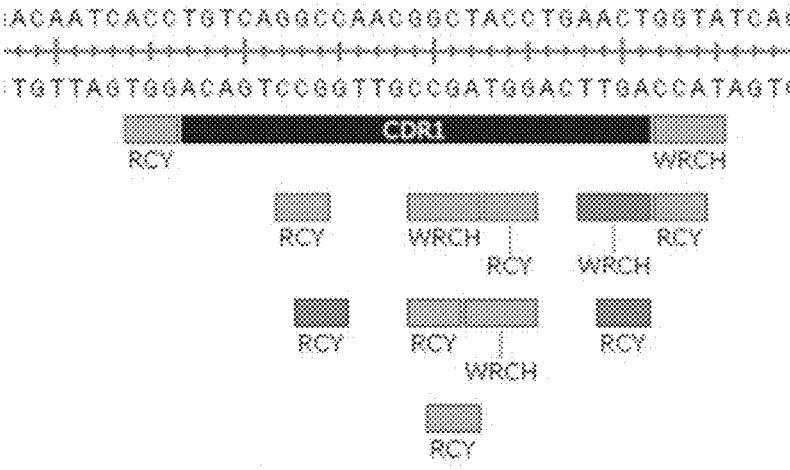
Fig. 26B
Fig. 26C
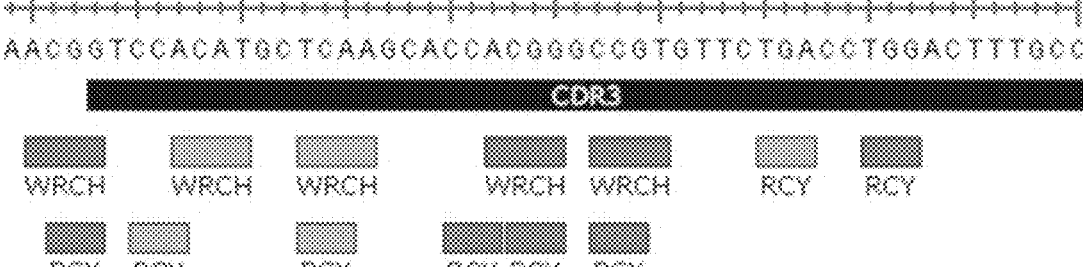

Light Chain

CDRL1 WT

CDRL1 SHM OPT

CDRL2 WT

CDRL2 SHM OPT

CDRL3 WT

CDRL3 SHM OPT

Heavy Chain

CDRH1 WT

CDRH1 SHM OPT

CDRH2 WT

CDRH2 SHM OPT

CDRH3 WT

CDRH3 SHM OPT

THRO

YU2

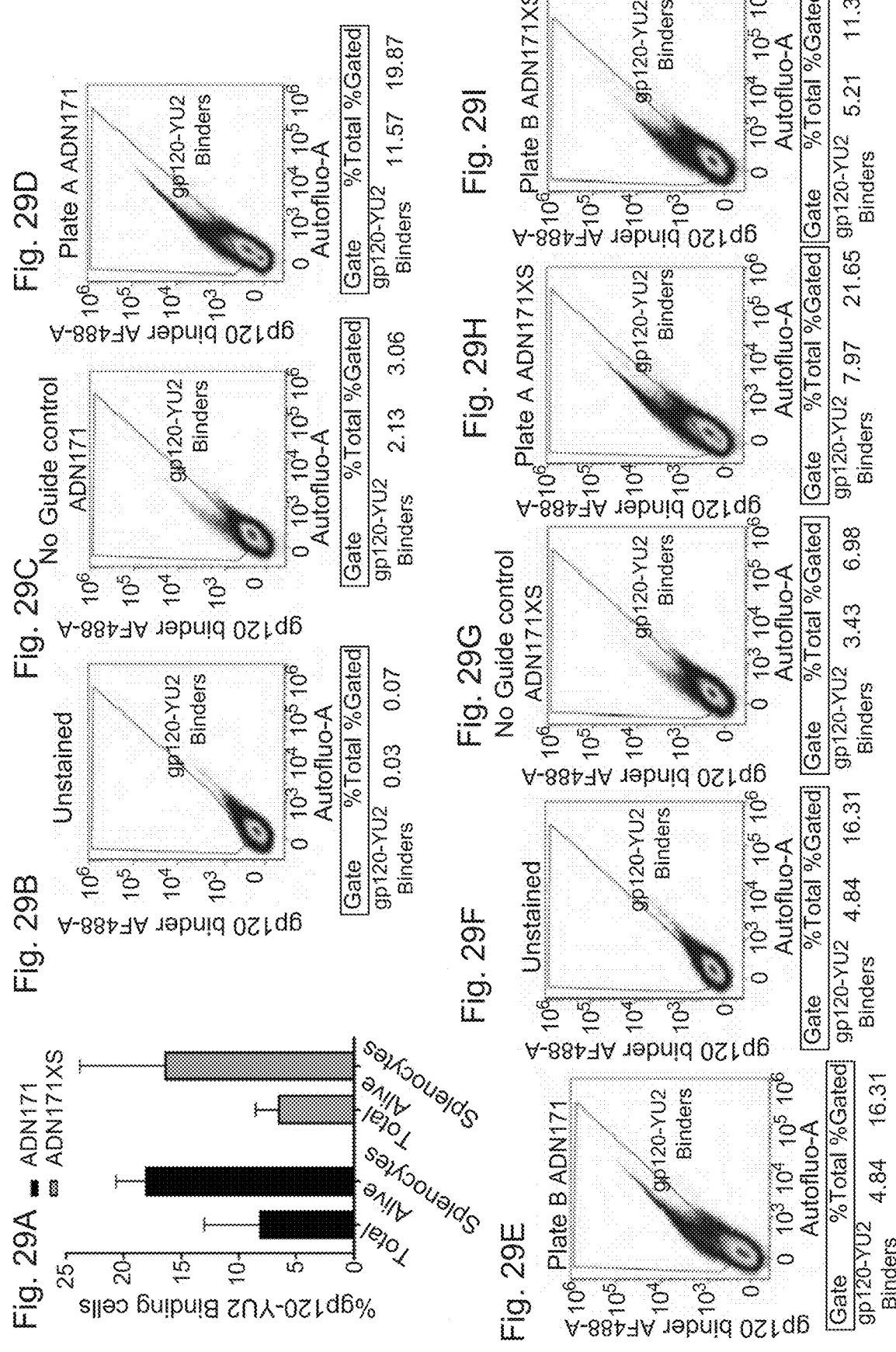

Fig. 32A
Fig. 32B
Fig. 33
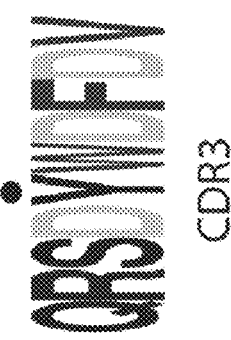
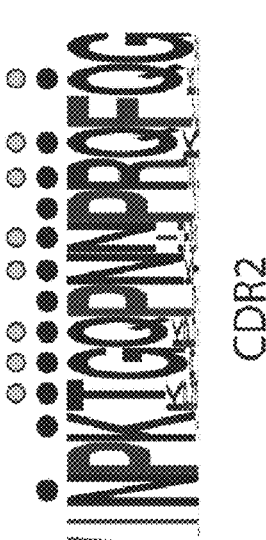
CDR1
CDR2
CDR3
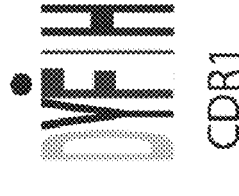

Fig. 35A
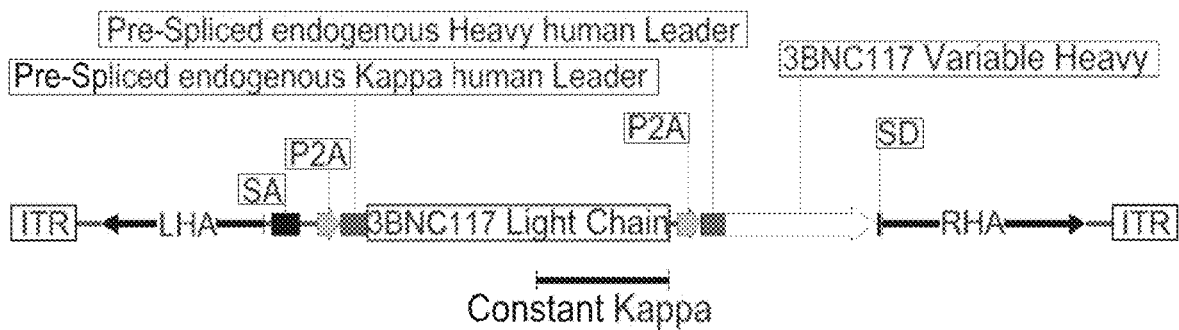
Fig. 35B
SA Junction
Fig. 35C
SD Junction
Fig. 35D
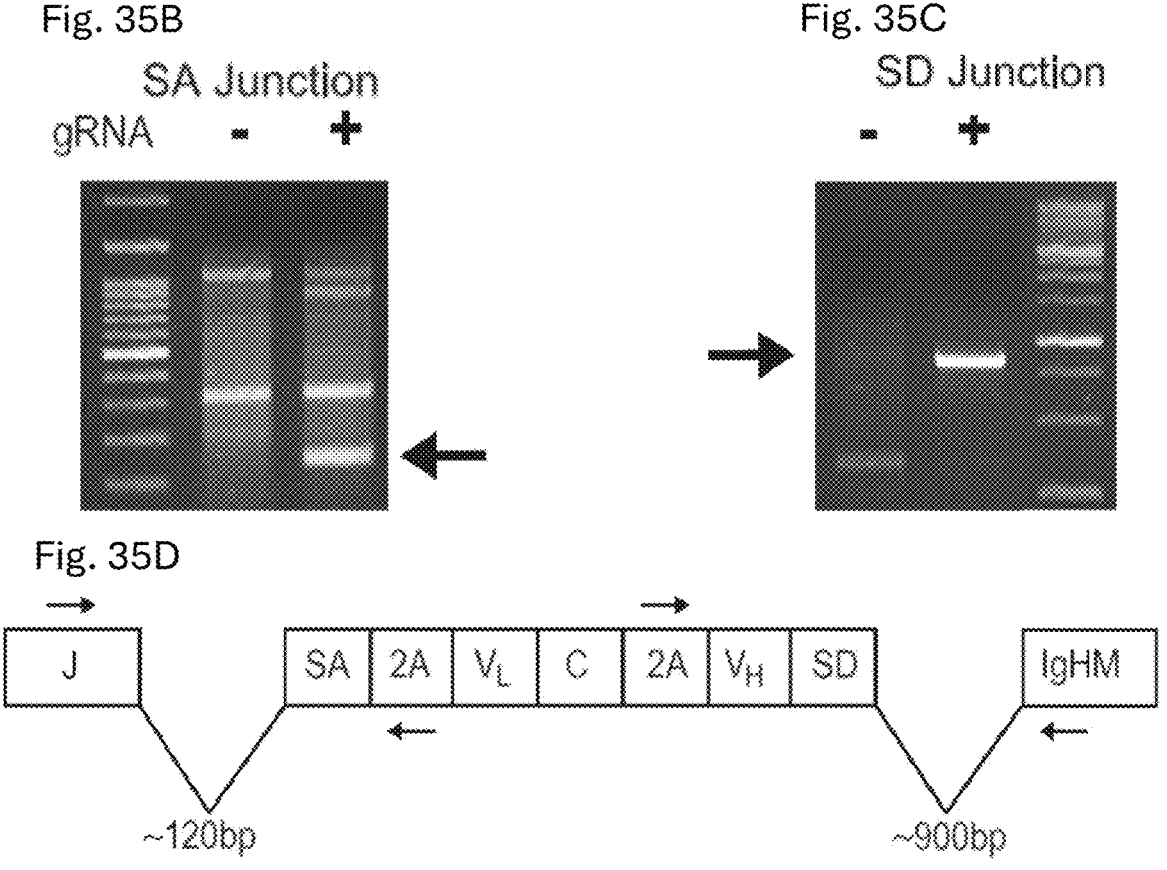

Fig. 36B

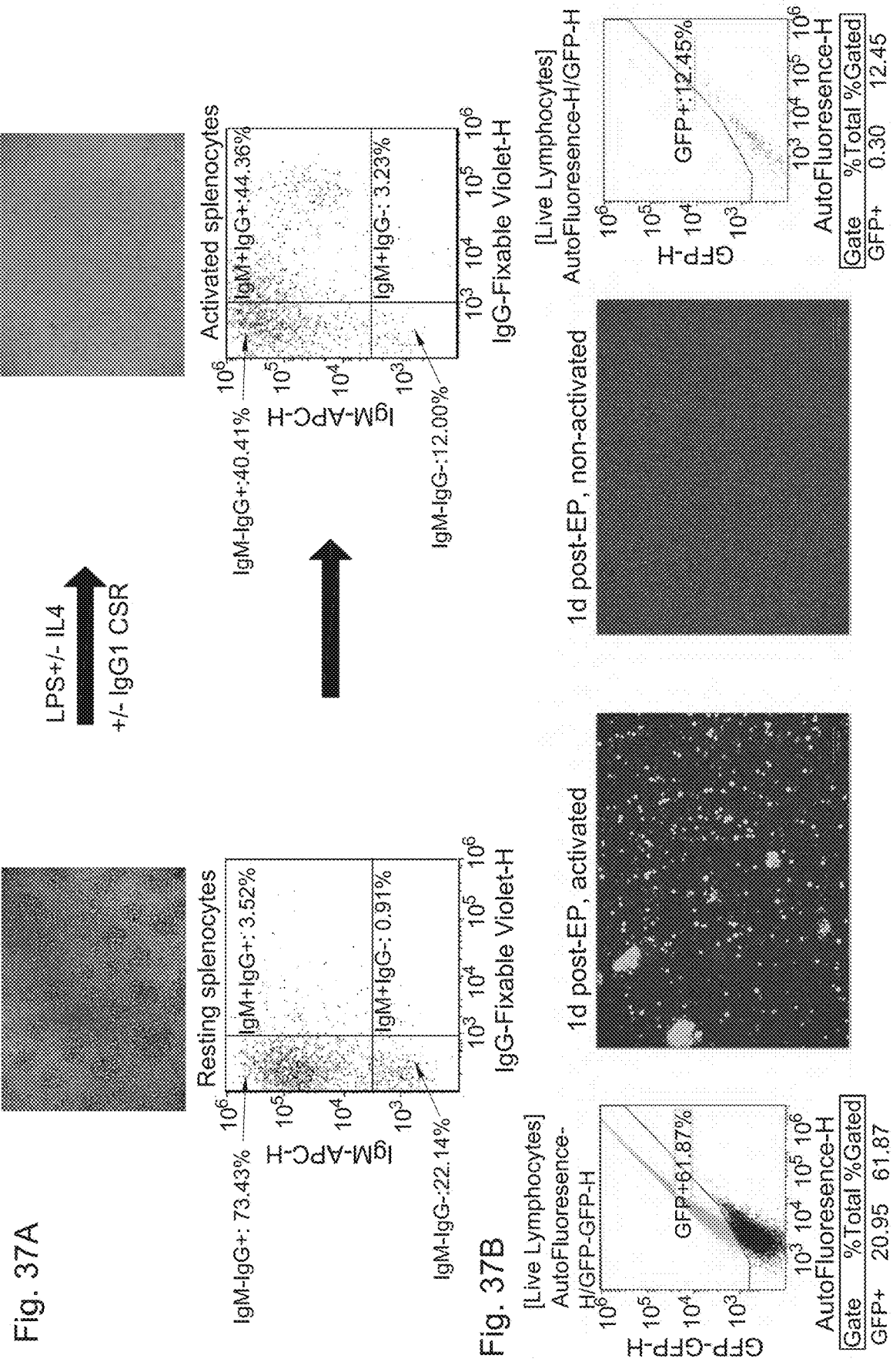

Fig. 39B
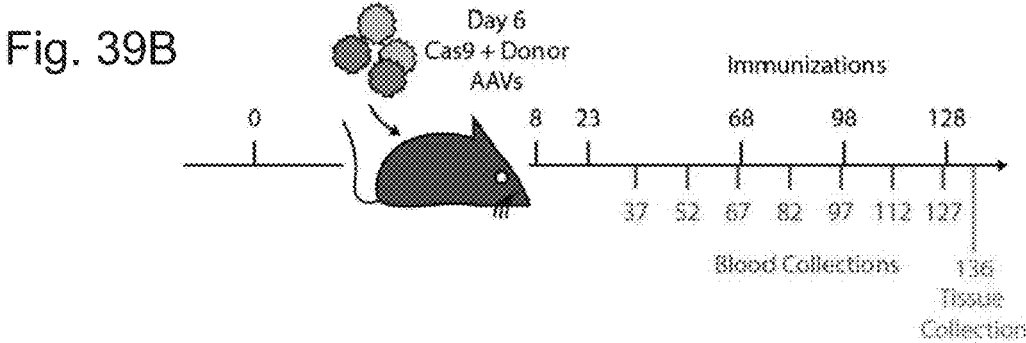
Fig. 39C
Fig. 39D
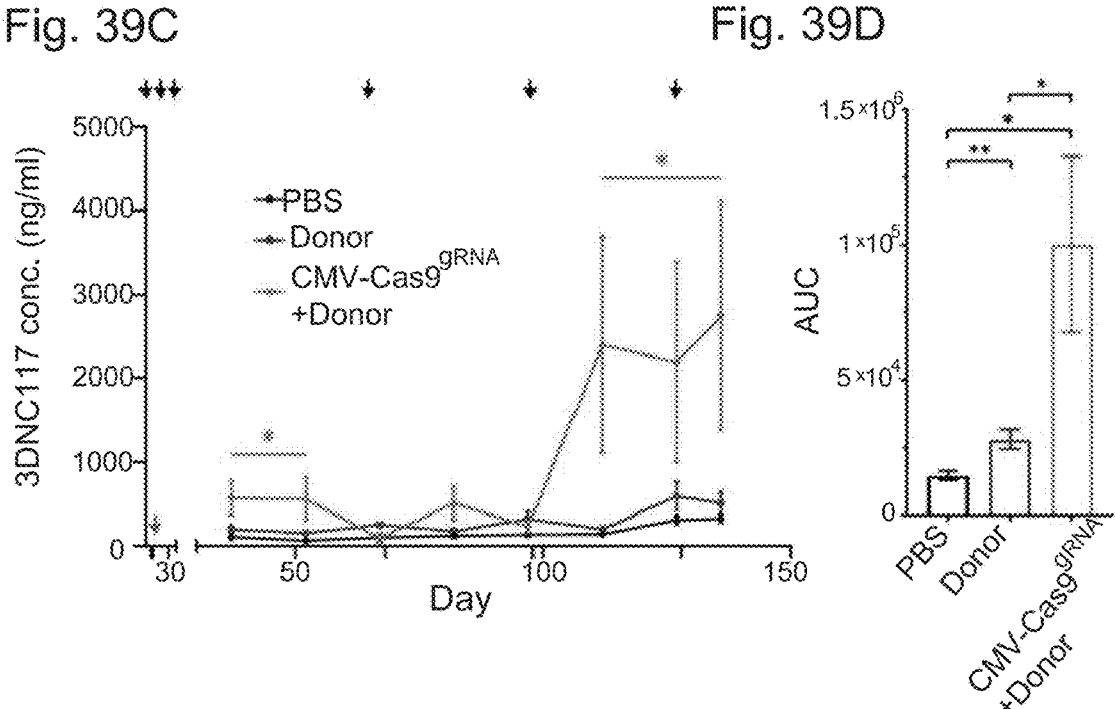
Fig. 39E
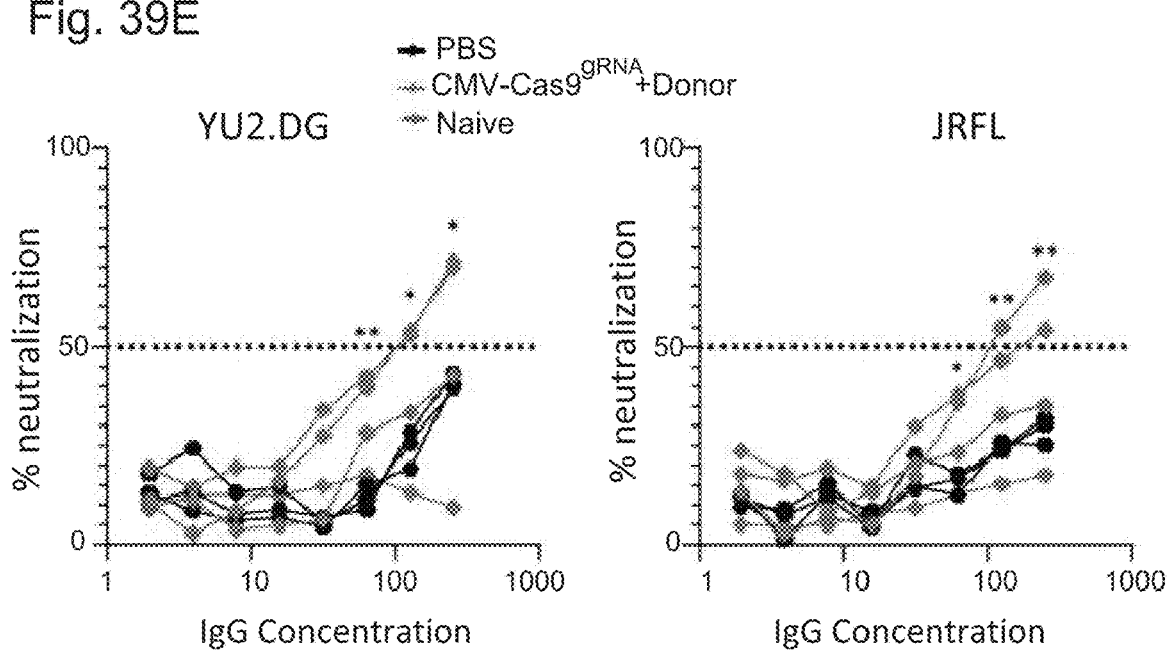

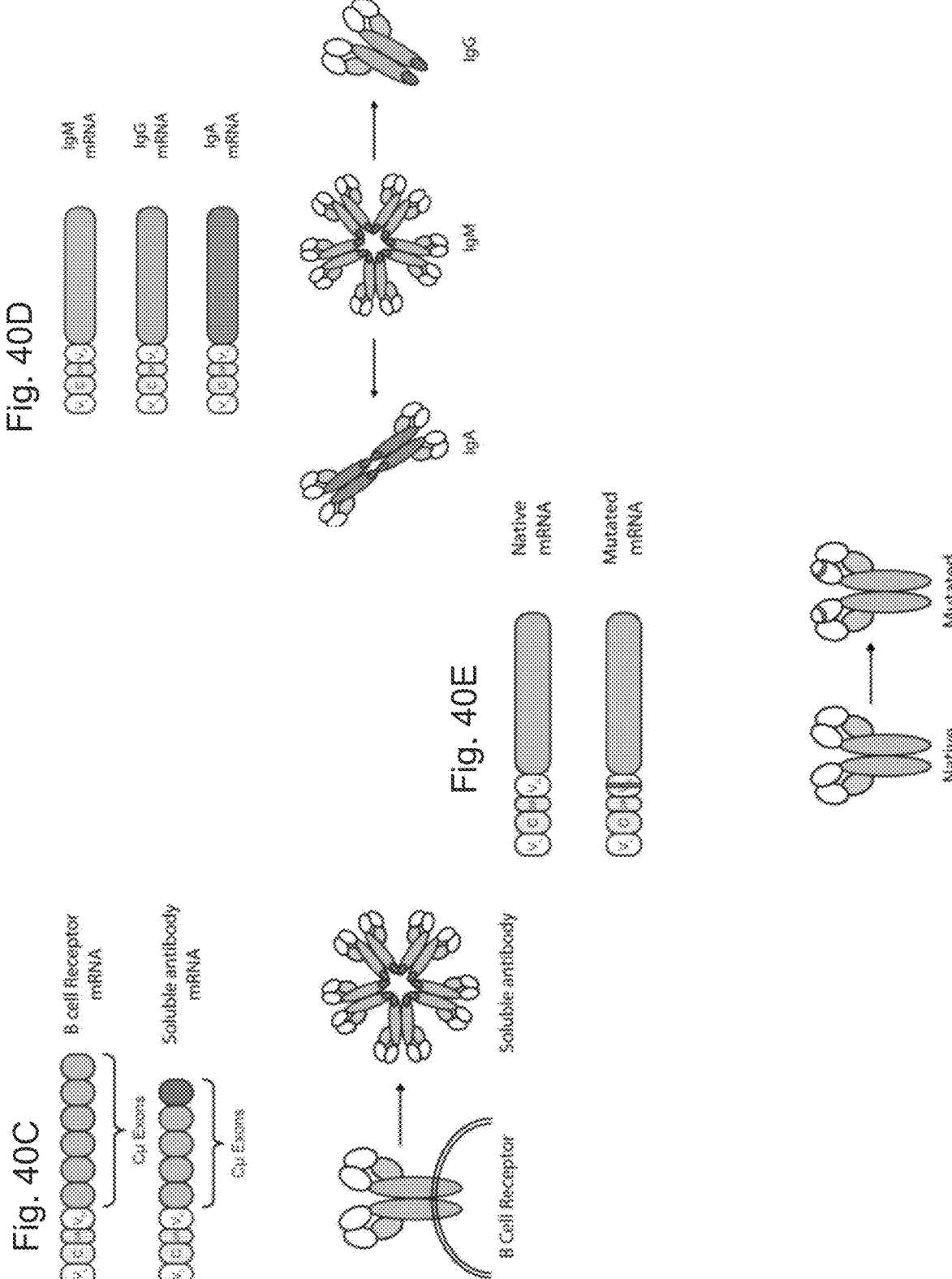

Fig. 42C

IgHCμ

3BNC117 VH

Reference
Donor + Cas9gRNA 1 IgM

TGGGGCAGTGGAACCCAAGTTACTGTTTCGTTCAGAGAGTTCAGTCCTTTCCCAATGTCTTTCCCCCTCGT
TGGGGCAGTGGAACCCAAGTTACTGTTTCGTTCAGAGAGTTCAGTCCTTTCCCAATGTCTTTCCCCCTCGT

IgHCγ

3BNC117 VH

Reference IgHCγ1
Reference IgHCγ2b
Reference IgHCγ3
Reference IgHCγ2c/a
Donor 3

CCAAAACGACACCCCATCTGTCTATCCACTGGC
CCAAAACAACACCCCATCAGTCTATCCACTGGC
CTACAACAACAGCCCATCTGTCTATCCCTTGGT
CCAAAACAACAAGCCCATCTGTCTATCCACTGGC
CCAAAACGACACCCCATCTGTCTATCCACTGGC

TGGGGCAGTGGAACCCAAGTTACTGTTTCGTTCAGCCAAAACGACACCCCATCTGTCTATCCACTGGC
TGGGGCAGTGGAACCCAAGTTACTGTTTCGTTCAGCCAAAACGACACCCCATCTGTCTATCCATTGGC

Donor + Cas9gRNA 1 IgG

TGGGGCAGTGGAACCCAAGTTACTGTTTCGTTCAGCCAAAACGACACCCCATCGGTCTATCCACTGGC

Fig. 43A          IgM
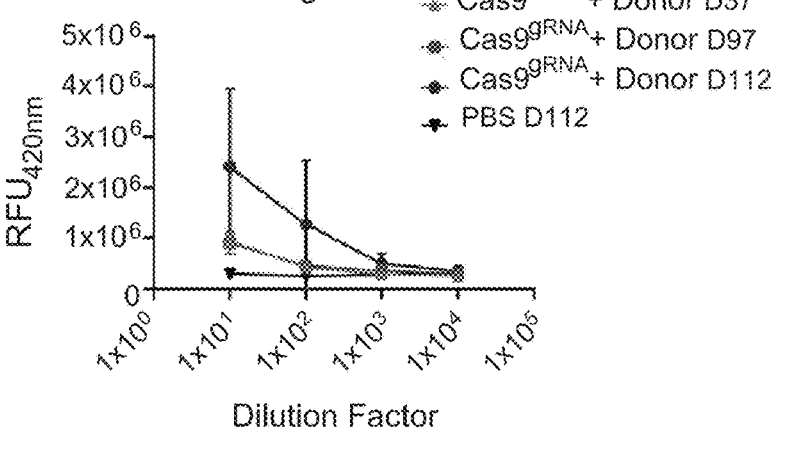
Fig. 43B          IgG1
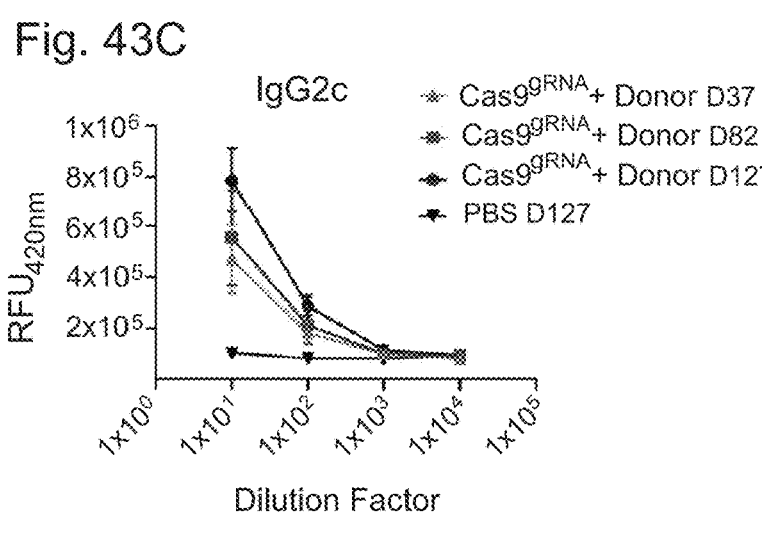
Fig. 43C          IgG2c
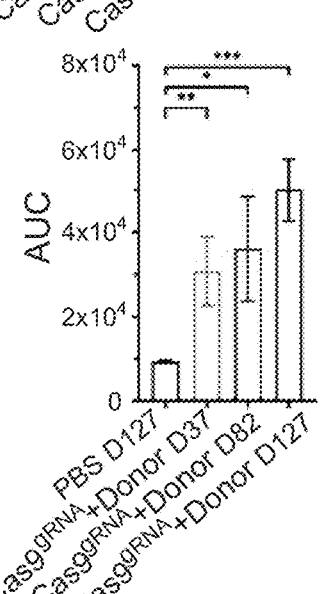

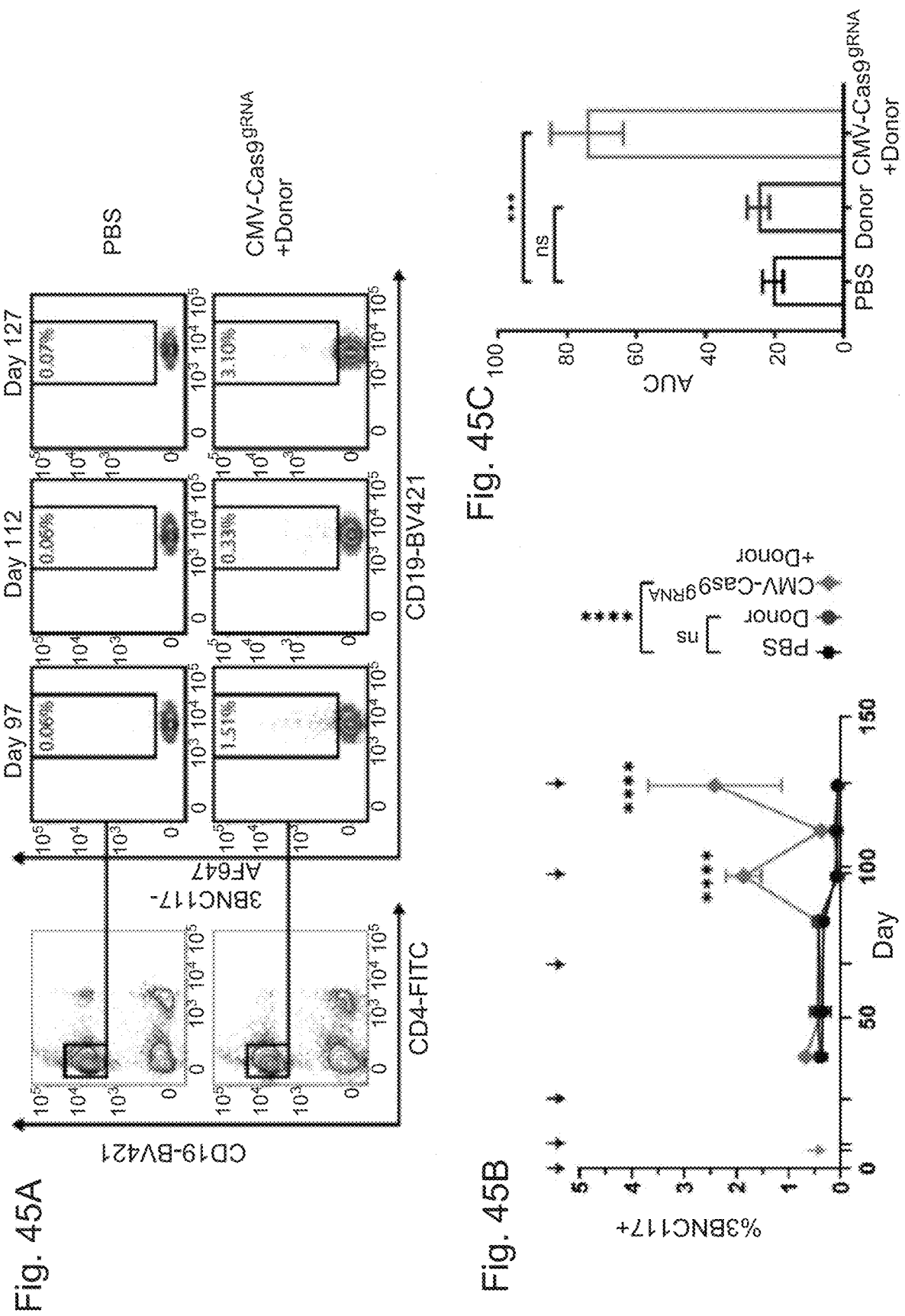

Fig. 45D
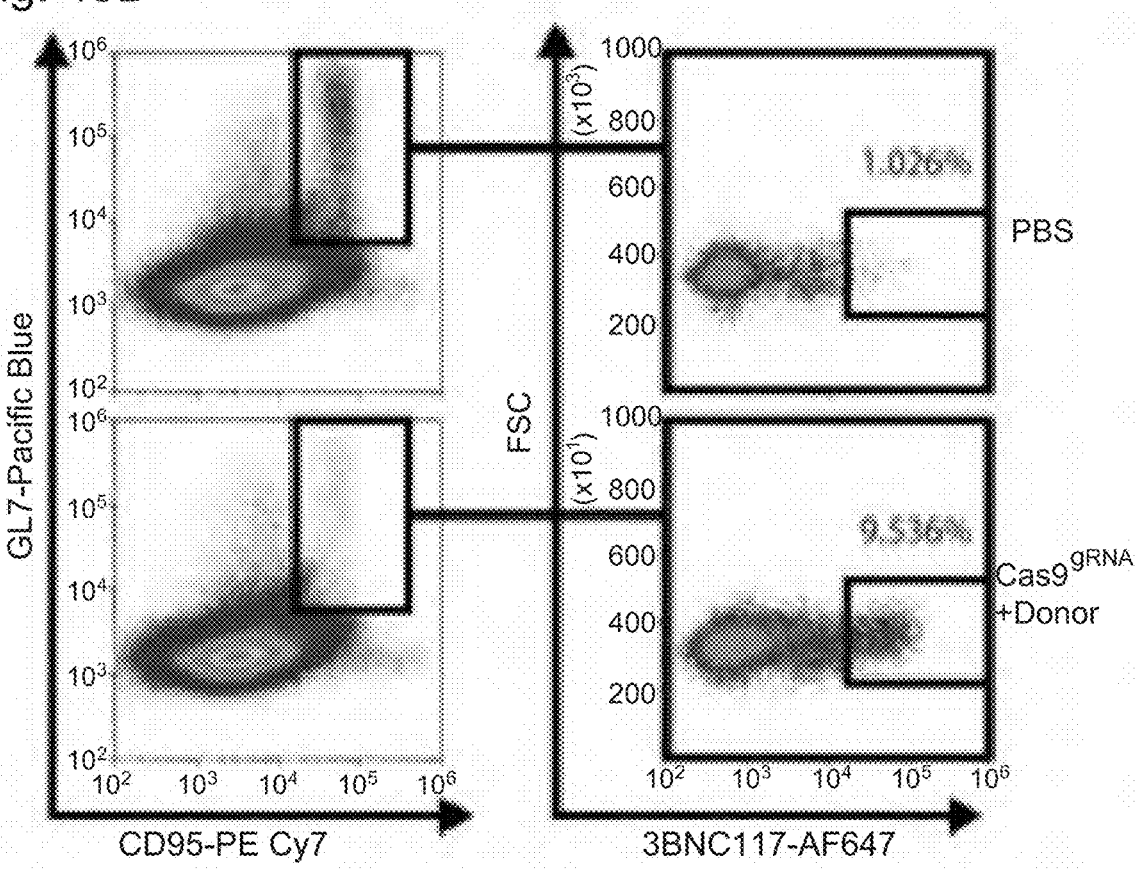
Fig. 45E
Fig. 45F
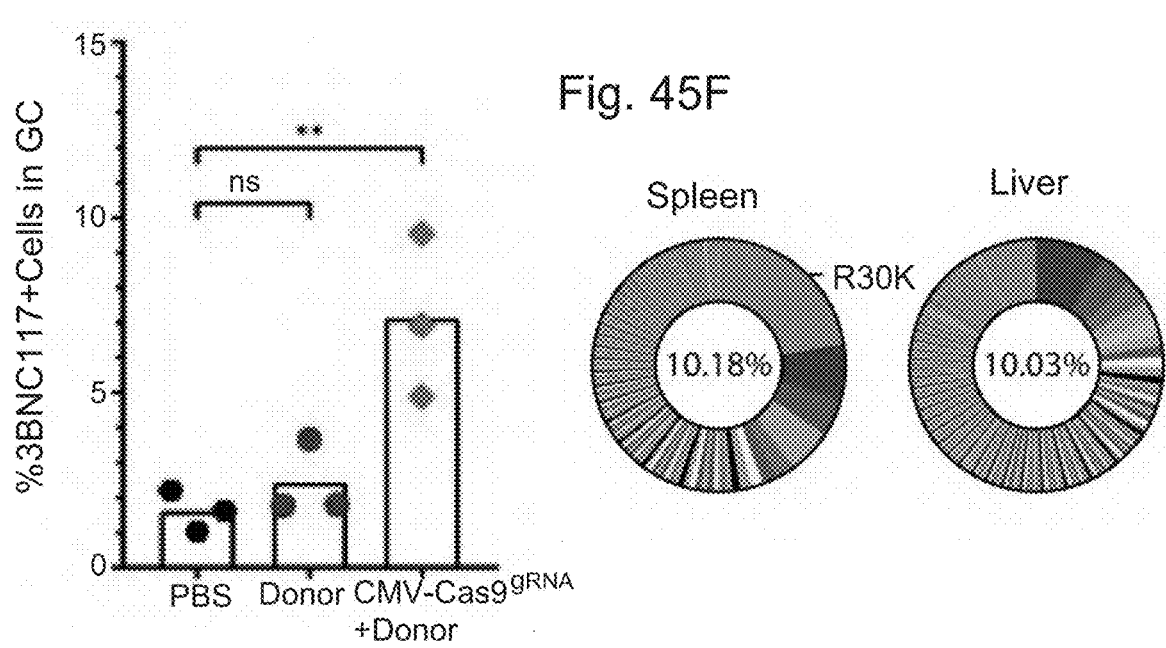

SEQUENCE LISTING

```
<160> NUMBER OF SEQ ID NOS: 292

<210> SEQ ID NO 1
<211> LENGTH: 17
<212> TYPE: DNA
<213> ORGANISM: Artificial Sequence
<220> FEATURE:
<223> OTHER INFORMATION: Furine Cleavage F1
<220> FEATURE:
<221> NAME/KEY: misc_feature
<223> OTHER INFORMATION: Synthetic

<400> SEQUENCE: 1
cgcgcgaaac gcggaag                                              17

<210> SEQ ID NO 2
<211> LENGTH: 21
<212> TYPE: DNA
<213> ORGANISM: Artificial Sequence
<220> FEATURE:
<223> OTHER INFORMATION: P2A F1
<220> FEATURE:
<221> NAME/KEY: misc_feature
<223> OTHER INFORMATION: Synthetic

<400> SEQUENCE: 2
gagacgtgga ggagaaccct g                                         21

<210> SEQ ID NO 3
<211> LENGTH: 39
<212> TYPE: DNA
<213> ORGANISM: Artificial Sequence
<220> FEATURE:
<223> OTHER INFORMATION: mini P for 170 F
<220> FEATURE:
<221> NAME/KEY: misc_feature
<223> OTHER INFORMATION: Synthetic

<400> SEQUENCE: 3
atgtccattc tagatcttaa gtttgtgagg tgtgtcgac                      39

<210> SEQ ID NO 4
<211> LENGTH: 32
<212> TYPE: DNA
<213> ORGANISM: Artificial Sequence
<220> FEATURE:
<223> OTHER INFORMATION: GFP for 151 F
<220> FEATURE:
<221> NAME/KEY: misc_feature
<223> OTHER INFORMATION: Synthetic

<400> SEQUENCE: 4
atctagacct aggatgcccg ccatgaagat cg                             32
```

```
<210> SEQ ID NO 5
<211> LENGTH: 25
<212> TYPE: DNA
<213> ORGANISM: Artificial Sequence
<220> FEATURE:
<223> OTHER INFORMATION: mIgHJ degenerate F
<220> FEATURE:
<221> NAME/KEY: misc_feature
<223> OTHER INFORMATION: Synthetic

<400> SEQUENCE: 5
ggraccwcts tcacmgtctc ctcag                                        25

<210> SEQ ID NO 6
<211> LENGTH: 23
<212> TYPE: DNA
<213> ORGANISM: Artificial Sequence
<220> FEATURE:
<223> OTHER INFORMATION: m3'IgHJ4-F1
<220> FEATURE:
<221> NAME/KEY: misc_feature
<223> OTHER INFORMATION: Synthetic

<400> SEQUENCE: 6
ggatatttgt ccctgaggga gcc                                          23

<210> SEQ ID NO 7
<211> LENGTH: 24
<212> TYPE: DNA
<213> ORGANISM: Artificial Sequence
<220> FEATURE:
<223> OTHER INFORMATION: m3'IgHJ4-R1
<220> FEATURE:
<221> NAME/KEY: misc_feature
<223> OTHER INFORMATION: Synthetic

<400> SEQUENCE: 7
gctccaccag acctctctag acag                                         24

<210> SEQ ID NO 8
<211> LENGTH: 23
<212> TYPE: DNA
<213> ORGANISM: Artificial Sequence
<220> FEATURE:
<223> OTHER INFORMATION: mIgHM CH2 R1
<220> FEATURE:
<221> NAME/KEY: misc_feature
<223> OTHER INFORMATION: Synthetic

<400> SEQUENCE: 8
cgtggtggga cgaacacatt tac                                          23

<210> SEQ ID NO 9
<211> LENGTH: 23
<212> TYPE: DNA
<213> ORGANISM: Artificial Sequence
<220> FEATURE:
<223> OTHER INFORMATION: mIgHG M R1
<220> FEATURE:
<221> NAME/KEY: misc_feature
<223> OTHER INFORMATION: Synthetic

<400> SEQUENCE: 9
ccaccacaga ggagaagatc cac                                          23

<210> SEQ ID NO 10
<211> LENGTH: 22
<212> TYPE: DNA
```

-continued

```
<213> ORGANISM: Artificial Sequence
<220> FEATURE:
<223> OTHER INFORMATION: mIgHA CH2 R1
<220> FEATURE:
<221> NAME/KEY: misc_feature
<223> OTHER INFORMATION: Synthetic

<400> SEQUENCE: 10
catgtgaggc tggcatctga ac                                          22

<210> SEQ ID NO 11
<211> LENGTH: 21
<212> TYPE: DNA
<213> ORGANISM: Artificial Sequence
<220> FEATURE:
<223> OTHER INFORMATION: mIgHG1 CH1 R
<220> FEATURE:
<221> NAME/KEY: misc_feature
<223> OTHER INFORMATION: Synthetic

<400> SEQUENCE: 11
ccaggtcact gtcactggct c                                           21

<210> SEQ ID NO 12
<211> LENGTH: 22
<212> TYPE: DNA
<213> ORGANISM: Artificial Sequence
<220> FEATURE:
<223> OTHER INFORMATION: mIgHJ4 F1
<220> FEATURE:
<221> NAME/KEY: misc_feature
<223> OTHER INFORMATION: Synthetic

<400> SEQUENCE: 12
ggtcaaggaa cctcagtcac cg                                          22

<210> SEQ ID NO 13
<211> LENGTH: 24
<212> TYPE: DNA
<213> ORGANISM: Artificial Sequence
<220> FEATURE:
<223> OTHER INFORMATION: mIgHM M1 R1
<220> FEATURE:
<221> NAME/KEY: misc_feature
<223> OTHER INFORMATION: Synthetic

<400> SEQUENCE: 13
gcagtggtcc acaggttctc aaag                                        24

<210> SEQ ID NO 14
<211> LENGTH: 21
<212> TYPE: DNA
<213> ORGANISM: Artificial Sequence
<220> FEATURE:
<223> OTHER INFORMATION: copGFPm R1
<220> FEATURE:
<221> NAME/KEY: misc_feature
<223> OTHER INFORMATION: Synthetic

<400> SEQUENCE: 14
gtgttggtgt agccgccgtt g                                           21

<210> SEQ ID NO 15
<211> LENGTH: 28
<212> TYPE: DNA
<213> ORGANISM: Mus musculus
<220> FEATURE:
<221> NAME/KEY: misc_feature
<223> OTHER INFORMATION: mH69 with PAM as in genome
```

<400> SEQUENCE: 15
tccgatgcat agggacaaag agtggagt                                          28

<210> SEQ ID NO 16
<211> LENGTH: 22
<212> TYPE: DNA
<213> ORGANISM: Artificial Sequence
<220> FEATURE:
<223> OTHER INFORMATION: mH69 as in the plasmid
<220> FEATURE:
<221> NAME/KEY: misc_feature
<223> OTHER INFORMATION: Synthetic

<400> SEQUENCE: 16
tccgatgcat agggacaaag ag                                                22

<210> SEQ ID NO 17
<211> LENGTH: 20
<212> TYPE: DNA
<213> ORGANISM: Artificial Sequence
<220> FEATURE:
<223> OTHER INFORMATION: mH69 as sgRNA
<220> FEATURE:
<221> NAME/KEY: misc_feature
<223> OTHER INFORMATION: Synthetic

<400> SEQUENCE: 17
cgatgcatag ggacaaagag                                                   20

<210> SEQ ID NO 18
<211> LENGTH: 57
<212> TYPE: DNA
<213> ORGANISM: Artificial Sequence
<220> FEATURE:
<223> OTHER INFORMATION: 2A peptide sequence
<220> FEATURE:
<221> NAME/KEY: misc_feature
<223> OTHER INFORMATION: Synthetic

<400> SEQUENCE: 18
gctactaact tcagcctgct gaagcaggct ggagacgtgg aggagaaccc tggacct        57

<210> SEQ ID NO 19
<211> LENGTH: 21
<212> TYPE: DNA
<213> ORGANISM: Artificial Sequence
<220> FEATURE:
<223> OTHER INFORMATION: Furin-GSG sequence
<220> FEATURE:
<221> NAME/KEY: misc_feature
<223> OTHER INFORMATION: Synthetic

<400> SEQUENCE: 19
cgcgcgaaac gcggaagcgg a                                                 21

<210> SEQ ID NO 20
<211> LENGTH: 155
<212> TYPE: DNA
<213> ORGANISM: Artificial Sequence
<220> FEATURE:
<223> OTHER INFORMATION: mutminiP
<220> FEATURE:
<221> NAME/KEY: misc_feature
<223> OTHER INFORMATION: Synthetic

<400> SEQUENCE: 20
ggtacctttt cattccttcc tctccagttc ttctctagat ggactaggtc cttaactagc      60

-continued

```
gaattcggat ccctgtctca tgaatatgca aatcaggtga gtccatggtg gtaaatatag    120
ggatgtcgac acacctcaca aacttaagat ctaga    155

<210> SEQ ID NO 21
<211> LENGTH: 13
<212> TYPE: DNA
<213> ORGANISM: Artificial Sequence
<220> FEATURE:
<223> OTHER INFORMATION: SPLICE DONOR in ADN157CF2 and ADN191
<220> FEATURE:
<221> NAME/KEY: misc_feature
<223> OTHER INFORMATION: Synthetic

<400> SEQUENCE: 21
ctcctcaggt aag    13

<210> SEQ ID NO 22
<211> LENGTH: 50
<212> TYPE: DNA
<213> ORGANISM: Artificial Sequence
<220> FEATURE:
<223> OTHER INFORMATION: SPLICE DONOR in ADN171
<220> FEATURE:
<221> NAME/KEY: misc_feature
<223> OTHER INFORMATION: Synthetic

<400> SEQUENCE: 22
ccaggtcact gtctcgtcag gtgagtcctc gaggagtgga gtggggcact    50

<210> SEQ ID NO 23
<211> LENGTH: 50
<212> TYPE: DNA
<213> ORGANISM: Artificial Sequence
<220> FEATURE:
<223> OTHER INFORMATION: 50bp SD in ADN157CF2
<220> FEATURE:
<221> NAME/KEY: misc_feature
<223> OTHER INFORMATION: Synthetic

<400> SEQUENCE: 23
aggagaaccc tggacctctc tcctcaggta agggagtgga gtggggcact    50

<210> SEQ ID NO 24
<211> LENGTH: 50
<212> TYPE: DNA
<213> ORGANISM: Artificial Sequence
<220> FEATURE:
<223> OTHER INFORMATION: 50bp SD in ADN171
<220> FEATURE:
<221> NAME/KEY: misc_feature
<223> OTHER INFORMATION: Synthetic

<400> SEQUENCE: 24
cagtgacagt ttcttctacc tcctcaggta agggagtgga gtggggcact    50

<210> SEQ ID NO 25
<211> LENGTH: 50
<212> TYPE: DNA
<213> ORGANISM: Artificial Sequence
<220> FEATURE:
<223> OTHER INFORMATION: 50bp SD ADN171
<220> FEATURE:
<221> NAME/KEY: misc_feature
<223> OTHER INFORMATION: Synthetic

<400> SEQUENCE: 25
ccaggtcact gtctcgtcag gtgagtcctc gaggagtgga gtggggcact    50
```

```
<210> SEQ ID NO 26
<211> LENGTH: 74
<212> TYPE: DNA
<213> ORGANISM: Artificial Sequence
<220> FEATURE:
<223> OTHER INFORMATION: SD 152/153/155
<220> FEATURE:
<221> NAME/KEY: misc_feature
<223> OTHER INFORMATION: Synthetic

<400> SEQUENCE: 26
ctgacaggag gcaagaagac agattcttac ccctccattt ctcttttatc cctctctggt      60
cctcagagag tcag                                                        74

<210> SEQ ID NO 27
<211> LENGTH: 195
<212> TYPE: DNA
<213> ORGANISM: Artificial Sequence
<220> FEATURE:
<223> OTHER INFORMATION: SD156
<220> FEATURE:
<221> NAME/KEY: misc_feature
<223> OTHER INFORMATION: Synthetic

<400> SEQUENCE: 27
ctcgaggcag tttcgtcctg tataccaggt tcacctacta ccatatctag ccctgcctgc      60
cttaagagta gcaacaagga aatagcaggg tgtagaggga tctcctgtct gacaggaggc     120
aagaagacag attcttaccc ctccatttct cttttatccc tctctggtcc tcagagagtc     180
agtccttccc aaatg                                                      195

<210> SEQ ID NO 28
<211> LENGTH: 46
<212> TYPE: DNA
<213> ORGANISM: Artificial Sequence
<220> FEATURE:
<223> OTHER INFORMATION: 159 (ADNSA)
<220> FEATURE:
<221> NAME/KEY: misc_feature
<223> OTHER INFORMATION: Synthetic

<400> SEQUENCE: 28
ctgacttctt ctttctcttt cttcagagag agagagagag agagag                    46

<210> SEQ ID NO 29
<211> LENGTH: 639
<212> TYPE: DNA
<213> ORGANISM: Artificial Sequence
<220> FEATURE:
<223> OTHER INFORMATION: Palivizumab light chain in ADN191
<220> FEATURE:
<221> NAME/KEY: misc_feature
<223> OTHER INFORMATION: Synthetic

<400> SEQUENCE: 29
gacatccaga tgacacagag cccctctaca ctgagcgcca gcgtgggaga cagagtgacc      60
atcacatgca gtgccagct gagcgtgggc tacatgcact ggtatcagca gaagcctggc     120 aaggcccta agctgctgat ctacgacaca agcaagctgg cctctggcgt gccctctaga     180
ttttctggca gcggctctgg caccgagttc accctgacaa tctctagcct gcagcctgac     240
gacttcgcca cctactactg cttccaaggc tctggctacc ccttcacatt cggcggaggc     300
accaagctgg aaatcaaggg ggctgatgct gcaccaactg tatccatctt cccaccatcc     360
```

-continued

```
agtgagcagt taacatctgg aggtgcctca gtcgtgtgct tcttgaacaa cttctacccc     420
aaagacatca atgtcaagtg gaagattgat ggcagtgaac gacaaaatgg cgtcctgaac     480
agttggactg atcaggacag caaagacagc acctacagca tgagcagcac cctcacgttg     540
accaaggacg agtatgaacg acataacagc tatacctgtg aggccactca caagacatca     600
acttcaccca ttgtcaagag cttcaacagg aatgagtgt                            639

<210> SEQ ID NO 30
<211> LENGTH: 370
<212> TYPE: DNA
<213> ORGANISM: Artificial Sequence
<220> FEATURE:
<223> OTHER INFORMATION: Palivizumab heavy chain in ADN191
<220> FEATURE:
<221> NAME/KEY: misc_feature
<223> OTHER INFORMATION: Synthetic

<400> SEQUENCE: 30
caagtgaccc tgagagagtc tggccccgct ctggttaagc ccacacagac cctgacactg      60
acctgcacct tcagcggctt cagcctgagc acaagcggca tgtctgtcgg ctggatcaga     120
cagcctcctg gcaaggctct ggaatggctg gccgacattt ggtgggacga caagaaggac     180
tacaacccca gcctgaagtc cagactgacc atcagcaagg acaccagcaa gaaccaggtg     240
gtgctgaaag tgaccaacat ggaccctgcc gacaccgcca cctactactg cgccagatcc     300
atgatcacca ctggtactt cgacgtctgg ggcgccggca ccacagtgac agtttcttct     360
acctcctcag                                                             370

<210> SEQ ID NO 31
<211> LENGTH: 684
<212> TYPE: DNA
<213> ORGANISM: Artificial Sequence
<220> FEATURE:
<223> OTHER INFORMATION: 3BNC117 Light chain in ADN171
<220> FEATURE:
<221> NAME/KEY: misc_feature
<223> OTHER INFORMATION: Synthetic

<400> SEQUENCE: 31
atggacatga gggtccctgc tcagctcctg gggctcctgc tgctctggct ctctggagcc      60
agatgtgaca tccagatgac ccagtctcca tcctccctgt ctgcctctgt gggagatacc     120
gtcactatca cttgccaagc aaacggctac ttaaattggt atcaacagag gcgagggaaa     180
gccccaaaac tcctgatcta cgatgggtcc aaattggaaa gaggggtccc atcaaggttt     240
agtggaagaa gatgggggca agaatataat ctgaccatca caatctgca gcccgaagac     300 attgcaacat attttgtca agtgtatgag tttgtcgtcc ctgggaccag actggatttg     360
aaacgggctg atgctgcacc aactgtatcc atcttccac catccagtga gcagttaaca     420
tctggaggtg cctcagtcgt gtgcttcttg aacaacttct accccaaaga catcaatgtc     480
aagtggaaga ttgatggcag tgaacgacaa aatggcgtcc tgaacagttg gactgatcag     540
gacagcaaag acagcaccta cagcatgagc agcaccctca cgttgaccaa ggacgagtat     600
gaacgacata acagctatac ctgtgaggcc actcacaaga tcaacttc acccattgtc     660 aagagcttca acaggaatga gtgt                                             684

<210> SEQ ID NO 32
<211> LENGTH: 427
<212> TYPE: DNA
<213> ORGANISM: Artificial Sequence
```

-continued

```
<220> FEATURE:
<223> OTHER INFORMATION: 3BNC117 heavy chain in ADN191
<220> FEATURE:
<221> NAME/KEY: misc_feature
<223> OTHER INFORMATION: Synthetic

<400> SEQUENCE: 32
atggactgga cctggaggat cctcttcttg gtggcagcag ccacaggagc ccactcccag      60
gtccaattgt tacagtctgg ggcagcggtg acgaagcccg gggcctcagt gagagtctcc     120
tgcgaggctt ctggatacaa cattcgtgac tactttattc attggtggcg acaagcccca     180
ggacagggcc ttcagtgggt gggatggatc aatcctaaga caggacagcc aaacaatcct     240
cgtcaatttc aaggtagagt cagtctgact cgacacgcgt cgtgggactt tgacacattt     300
tccttttaca tggacctgaa ggcactaaga tcggacgaca cggccgttta tttctgtgcg     360
cgacagcgca gcgactattg ggatttcgac gtctggggca gtggaaccca ggtcactgtc     420
tcgtcag                                                              427

<210> SEQ ID NO 33
<211> LENGTH: 119
<212> TYPE: DNA
<213> ORGANISM: Mus musculus
<220> FEATURE:
<221> NAME/KEY: misc_feature
<223> OTHER INFORMATION: 119bp nucleotide sequence containing the mH69
      site

<400> SEQUENCE: 33
agttgtggaa tatacttcag gaccacctct gtgacagcat ttatacagta tccgatgcat      60
agggacaaag agtggagtgg ggcactttct ttagatttgt gaggaatgtt ccgcactag     119

<210> SEQ ID NO 34
<211> LENGTH: 395
<212> TYPE: DNA
<213> ORGANISM: Artificial Sequence
<220> FEATURE:
<223> OTHER INFORMATION: Left Homology Arm used in all the donors
<220> FEATURE:
<221> NAME/KEY: misc_feature
<223> OTHER INFORMATION: Synthetic

<400> SEQUENCE: 34
gtaagaatgg cctctccagg tctttatttt taacctttgt tatggagttt tctgagcatt      60
gcagactaat cttggatatt tgtccctgag ggagccggct gagagaagtt gggaaataaa     120
ctgtctaggt atctcagagc ctttaggaca gattatctcc acatctttga aaaactaaga     180
atctgtgtga tggtgttggt ggagtccctg gatgatggga tagggacttt ggaggctcat     240
ttgaagaaga tgctaaaaca atcctatggc tggaggata gttggggctg tagttggaga     300
ttttcagttt ttagaataaa agtattagtt gtggaatata cttcaggacc acctctgtga     360
cagcatttat acagtatccg atgcataggg acaaa                               395

<210> SEQ ID NO 35
<211> LENGTH: 492
<212> TYPE: DNA
<213> ORGANISM: Artificial Sequence
<220> FEATURE:
<223> OTHER INFORMATION: Right Homology Arm as used in all the donors
<220> FEATURE:
<221> NAME/KEY: misc_feature
<223> OTHER INFORMATION: Synthetic

<400> SEQUENCE: 35
```

-continued

```
gagtggagtg gggcactttc tttagatttg tgaggaatgt tccgcactag attgtttaaa      60
acttcatttg ttggaaggag agctgtctta gtgattgagt caagggagaa aggcatctag     120
cctcggtctc aaaagggtag ttgctgtcta gagaggtctg gtggagcctg caaaagtcca     180
gctttcaaag gaacacagaa gtatgtgtat ggaatattag aagatgttgc ttttactctt     240
aagttggttc ctaggaaaaa tagttaaata ctgtgacttt aaaatgtgag agggtttca      300 agtactcatt tttttaaatg tccaaaattc ttgtcaatca gtttgaggtc ttgtttgtgt     360
agaactgata ttacttaaag tttaaccgag gaatgggagt gaggctctct cataacctat     420
tcagaactga cttttaacaa taataaatta agtttcaaat atttttaaat gaattgagca     480
atgttgagtt gg                                                          492
```

```
<210> SEQ ID NO 36
<211> LENGTH: 1098
<212> TYPE: DNA
<213> ORGANISM: Artificial Sequence
<220> FEATURE:
<223> OTHER INFORMATION: sequence of Fig. 3C
<220> FEATURE:
<221> NAME/KEY: misc_feature
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (886)..(886)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (902)..(904)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (931)..(931)
<223> OTHER INFORMATION: n is a, c, g, or t
<220> FEATURE:
<221> NAME/KEY: misc_feature
<222> LOCATION: (937)..(938)
<223> OTHER INFORMATION: n is a, c, g, or t
<220> FEATURE:
<221> NAME/KEY: misc_feature
<222> LOCATION: (941)..(941)
<223> OTHER INFORMATION: n is a, c, g, or t
<220> FEATURE:
<221> NAME/KEY: misc_feature
```

```
<222> LOCATION: (949)..(949)
<223> OTHER INFORMATION: n is a, c, g, or t
<220> FEATURE:
<221> NAME/KEY: misc_feature
<222> LOCATION: (952)..(952)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(970)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
<220> FEATURE:
<221> NAME/KEY: misc_feature
<222> LOCATION: (986)..(987)
<223> OTHER INFORMATION: n is a, c, g, or t
<220> FEATURE:
<221> NAME/KEY: misc_feature
<222> LOCATION: (989)..(991)
<223> OTHER INFORMATION: n is a, c, g, or t
<220> FEATURE:
<221> NAME/KEY: misc_feature
<222> LOCATION: (993)..(994)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t
<220> FEATURE:
<221> NAME/KEY: misc_feature
<222> LOCATION: (999)..(1003)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1008)..(1009)
<223> OTHER INFORMATION: n is a, c, g, or t
<220> FEATURE:
<221> NAME/KEY: misc_feature
<222> LOCATION: (1011)..(1013)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1022)..(1024)
<223> OTHER INFORMATION: n is a, c, g, or t
<220> FEATURE:
<221> NAME/KEY: misc_feature
<222> LOCATION: (1026)..(1028)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1035)..(1037)
<223> OTHER INFORMATION: n is a, c, g, or t
<220> FEATURE:
<221> NAME/KEY: misc_feature
<222> LOCATION: (1040)..(1042)
<223> OTHER INFORMATION: n is a, c, g, or t
<220> FEATURE:
```

-continued

<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1047)..(1053)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1059)..(1064)
<223> OTHER INFORMATION: n is a, c, g, or t
<220> FEATURE:
<221> NAME/KEY: misc_feature
<222> LOCATION: (1067)..(1068)
<223> OTHER INFORMATION: n is a, c, g, or t
<220> FEATURE:
<221> NAME/KEY: misc_feature
<222> LOCATION: (1073)..(1073)
<223> OTHER INFORMATION: n is a, c, g, or t
<220> FEATURE:
<221> NAME/KEY: misc_feature
<222> LOCATION: (1075)..(1075)
<223> OTHER INFORMATION: n is a, c, g, or t
<220> FEATURE:
<221> NAME/KEY: misc_feature
<222> LOCATION: (1078)..(1078)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1089)..(1092)
<223> OTHER INFORMATION: n is a, c, g, or t
<220> FEATURE:
<221> NAME/KEY: misc_feature
<222> LOCATION: (1094)..(1094)
<223> OTHER INFORMATION: n is a, c, g, or t
<220> FEATURE:
<221> NAME/KEY: misc_feature
<222> LOCATION: (1096)..(1098)
<223> OTHER INFORMATION: n is a, c, g, or t

<400> SEQUENCE: 36
nnnnccnccn catcctgcag acgggggccc catgttcgcc ttccgccgcg tggaggagct        60
gcacagcaac accgagctgg gcatcgtgga gtaccagcac gccttcaaga cccccatcgc       120
cttcgccaga tctcgagtcc gcgcgaaacg cggaagcgga gctactaact tcagcctgct       180
gaagcaggct ggagacgtgg aggagaaccc tggacctctc tcctcagaga gtcagtcctt       240
cccaaatgtc ttccccctcg tctcctgcga gagccccctg tctgataaga atctggtggc       300
catgggctgc ctggcccggg acttcctgcc cagcaccatt tccttcacct ggaactacca       360
gaacaacact gaagtcatcc agggtatcag aaccttccca acactgagga caggggggcaa      420 gtacctagcc acctcgcagg tgttgctgtc tcccaagagc atccttgaag gttcagatga       480
atacctggta tgcaaaatcc actacggagg caaaaacaaa gatctgcatg tgcccattcc       540
agctgtcgca gagatgaacc ccaatgtaaa tgtgttcgtc ccaccacggg atggcttctc       600
tggccctgca ccacgcaagt ctaaactcat ctgcgaggcc acgaacttcg ctccaaaacc       660
gatcacagta tcctggctaa aggatgggaa gctcgtggaa tctggcttca ccacagatcc       720
ggtgaccatc gagaacaaag gatccacacc ccaaacctac aaggtcataa gcacacttac       780
catctctgaa atcgactggc tgaacctgaa tgtgtacacc tgccgtgtgg atcacagggg       840
tctcaccttc ttgaagaacg tgtcctccac atgtgctgcc agtcantccn cagacatcct       900
annnttcana atcccccctn ctttgnggac ntcctcnnca nctagtccnc tnanctgacg      960
tgtgangann aaaaannntg gccacnngnn ngnnacngnn nnnanctnnt nnngcttctn     1020
annntnnncg anccnnnggn nncncannnn nnncntggnn nnnntcnncg cgnanggnag     1080 aanctttttnn nncnannn                                                  1098

<210> SEQ ID NO 37
<211> LENGTH: 78
<212> TYPE: DNA
<213> ORGANISM: Artificial Sequence
<220> FEATURE:
<223> OTHER INFORMATION: HGH leader
<220> FEATURE:
<221> NAME/KEY: misc_feature
<223> OTHER INFORMATION: Synthetic

<400> SEQUENCE: 37
atggcgacgg gttcaagaac ttccctactt cttgcatttg gcctgctttg tttgccgtgg       60
ttacaggagg gctcggca                                                    78

<210> SEQ ID NO 38
<211> LENGTH: 370
<212> TYPE: DNA
<213> ORGANISM: Artificial Sequence
<220> FEATURE:
<223> OTHER INFORMATION: 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 38
caggtccaat tgttacagtc tggggcagcg gtgacgaagc ccgggggcctc agtgagagtc      60 tcctgcgagg cttctggata caacattcgt gactacttta ttcattggtg gcgacaagcc     120
ccaggacagg gccttcagtg ggtgggatgg atcaatccta agacaggaca gccaaacaat     180
cctcgtcaat ttcaaggtag agtcagtctg actcgacacg cgtcgtggga ctttgacaca     240
ttttcctttt acatggacct gaaggcacta agatcggacg acacggccgt ttatttctgt     300
gcgcgacagc gcagcgacta ttgggatttc gacgtctggg gcagtggaac ccaggtcact     360
gtctcgtcag                                                            370

<210> SEQ ID NO 39
<211> LENGTH: 34
<212> TYPE: DNA
<213> ORGANISM: Artificial Sequence
<220> FEATURE:
<223> OTHER INFORMATION: Top DNA sequence in Figure 12A (coding strand)
<220> FEATURE:
<221> NAME/KEY: misc_feature
<223> OTHER INFORMATION: Synthetic

<400> SEQUENCE: 39
tggatacaac attcgtgact actttattca ttgg                                  34

<210> SEQ ID NO 40
<211> LENGTH: 34
<212> TYPE: DNA
<213> ORGANISM: Artificial Sequence
<220> FEATURE:
<223> OTHER INFORMATION: Bottom DNA sequence in Figure 12A
      (complementary strand)
<220> FEATURE:
<221> NAME/KEY: misc_feature
<223> OTHER INFORMATION: Synthetic

<400> SEQUENCE: 40
acctatgttg taagcactga tgaaataagt aacc                                    34

<210> SEQ ID NO 41
<211> LENGTH: 30
<212> TYPE: DNA
<213> ORGANISM: Artificial Sequence
<220> FEATURE:
<223> OTHER INFORMATION: CDR1 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 41
ggatacaaca ttcgtgacta ctttattcat                                        30

<210> SEQ ID NO 42
<211> LENGTH: 10
<212> TYPE: PRT
<213> ORGANISM: Artificial Sequence
<220> FEATURE:
<223> OTHER INFORMATION: CDR1 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 42

Gly Tyr Asn Ile Arg Asp Tyr Phe Ile His
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Amino acid sequence on Figure 12A
<220> FEATURE:
<221> NAME/KEY: misc_feature
<223> OTHER INFORMATION: Synthetic

<400> SEQUENCE: 43

Gly Tyr Asn Ile Arg Asp Tyr Phe Ile His Trp
1               5                   10

<210> SEQ ID NO 44
<211> LENGTH: 55
<212> TYPE: DNA
<213> ORGANISM: Artificial Sequence
<220> FEATURE:
<223> OTHER INFORMATION: Top DNA sequence in Figure 12B (coding strand)
<220> FEATURE:
<221> NAME/KEY: misc_feature
<223> OTHER INFORMATION: Synthetic

<400> SEQUENCE: 44
atggatcaat cctaagacag gacagccaaa caatcctcgt caatttcaag gtaga           55

<210> SEQ ID NO 45
<211> LENGTH: 55
<212> TYPE: DNA
<213> ORGANISM: Artificial Sequence
<220> FEATURE:
<223> OTHER INFORMATION: Bottom DNA sequence in Figure 12B
      (complementary strand)
<220> FEATURE:

<221> NAME/KEY: misc_feature
<223> OTHER INFORMATION: Synthetic

<400> SEQUENCE: 45
tacctagtta ggattctgtc ctgtcggttt gttaggagca gttaaagttc catct        55

<210> SEQ ID NO 46
<211> LENGTH: 51
<212> TYPE: DNA
<213> ORGANISM: Artificial Sequence
<220> FEATURE:
<223> OTHER INFORMATION: CDR2 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 46
tggatcaatc ctaagacagg acagccaaac aatcctcgtc aatttcaagg t        51

<210> SEQ ID NO 47
<211> LENGTH: 17
<212> TYPE: PRT
<213> ORGANISM: Artificial Sequence
<220> FEATURE:
<223> OTHER INFORMATION: CDR2 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 47

Trp Ile Asn Pro Lys Thr Gly Gln Pro Asn Asn Pro Arg Gln Phe Gln
1               5                   10                  15

Gly

<210> SEQ ID NO 48
<211> LENGTH: 18
<212> TYPE: PRT
<213> ORGANISM: Artificial Sequence
<220> FEATURE:
<223> OTHER INFORMATION: Amino acid sequence of Figure 12B
<220> FEATURE:
<221> NAME/KEY: misc_feature
<223> OTHER INFORMATION: Synthetic

<400> SEQUENCE: 48

Trp Ile Asn Pro Lys Thr Gly Gln Pro Asn Asn Pro Arg Gln Phe Gln
1               5                   10                  15

Gly Arg

<210> SEQ ID NO 49
<211> LENGTH: 56
<212> TYPE: DNA
<213> ORGANISM: Artificial Sequence
<220> FEATURE:
<223> OTHER INFORMATION: Top DNA sequence in Figure 12C (coding strand)
<220> FEATURE:
<221> NAME/KEY: misc_feature
<223> OTHER INFORMATION: Synthetic

<400> SEQUENCE: 49
acacggccgt ttatttctgt gcgcgacagc gcagcgacta ttgggatttc gacgtc        56

<210> SEQ ID NO 50
<211> LENGTH: 56
<212> TYPE: DNA

<210> ORGANISM: Artificial Sequence
<220> FEATURE:
<223> OTHER INFORMATION: Bottom DNA sequence in Figure 12C
      (complementary strand)
<220> FEATURE:
<221> NAME/KEY: misc_feature
<223> OTHER INFORMATION: Synthetic

<400> SEQUENCE: 50
tgtgccggca aataaagaca cgcgctgtcg cgtcgctgat aaccctaaag ctgcag          56

<210> SEQ ID NO 51
<211> LENGTH: 54
<212> TYPE: DNA
<213> ORGANISM: Artificial Sequence
<220> FEATURE:
<223> OTHER INFORMATION: CDR3 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 51
acggccgttt atttctgtgc gcgacagcgc agcgactatt gggatttcga cgtc          54

<210> SEQ ID NO 52
<211> LENGTH: 18
<212> TYPE: PRT
<213> ORGANISM: Artificial Sequence
<220> FEATURE:
<223> OTHER INFORMATION: CDR3 of 3BNC117 Variable Heavy following first
      modifications used in ADN170 derivatives
<220> FEATURE:
<221> NAME/KEY: misc_feature
<223> OTHER INFORMATION: Synthetic

<400> SEQUENCE: 52

Thr Ala Val Tyr Phe Cys Ala Arg Gln Arg Ser Asp Tyr Trp Asp Phe
1               5                   10                  15

Asp Val

<210> SEQ ID NO 53
<211> LENGTH: 19
<212> TYPE: PRT
<213> ORGANISM: Artificial Sequence
<220> FEATURE:
<223> OTHER INFORMATION: Amino acid sequence on Figure 12C
<220> FEATURE:
<221> NAME/KEY: misc_feature
<223> OTHER INFORMATION: Synthetic

<400> SEQUENCE: 53

Asp Thr Ala Val Tyr Phe Cys Ala Arg Gln Arg Ser Asp Tyr Trp Asp
1               5                   10                  15

Phe Asp Val

<210> SEQ ID NO 54
<211> LENGTH: 378
<212> TYPE: DNA
<213> ORGANISM: Artificial Sequence
<220> FEATURE:
<223> OTHER INFORMATION: 3BNC117 Variable Heavy following GeneART
      optimization
<220> FEATURE:
<221> NAME/KEY: misc_feature
<223> OTHER INFORMATION: Synthetic

<400> SEQUENCE: 54

-continued

```
caggttcagc tgctgcaatc tggcgccgct gtgacaaaac ctggcgcctc tgttagagtg          60
tcctgcgagg ctagcggcta caacatcaga gactacttca tccactggtg gcggcaggct         120
ccaggacagg gacttcaatg ggtcggatgg atcaacccca agaccggcca gcctaacaac         180
cccagacagt tccagggcag agtgtccctg acaagcacg ccagctggga cttcgacacc          240
ttcagcttct acatggacct gaaggccctg agaagcgacg ataccgccgt gtacttctgc         300
gccagacaga gatccgacta ctgggatttc gacgtgtggg gcagtggaac ccaggtcact         360
gtctcgtcag gtgagtcc                                                       378
```

```
<210> SEQ ID NO 55
<211> LENGTH: 37
<212> TYPE: DNA
<213> ORGANISM: Artificial Sequence
<220> FEATURE:
<223> OTHER INFORMATION: Top DNA sequence in Figure 13A (coding strand)
<220> FEATURE:
<221> NAME/KEY: misc_feature
<223> OTHER INFORMATION: Synthetic

<400> SEQUENCE: 55
tagcggctac aacatcagag actacttcat ccactgg                                   37
```

```
<210> SEQ ID NO 56
<211> LENGTH: 37
<212> TYPE: DNA
<213> ORGANISM: Artificial Sequence
<220> FEATURE:
<223> OTHER INFORMATION: Bottom DNA sequence in Figure 13A
      (complementary strand)
<220> FEATURE:
<221> NAME/KEY: misc_feature
<223> OTHER INFORMATION: Synthetic

<400> SEQUENCE: 56
atcgccgatg ttgtagtctc tgatgaagta ggtgacc                                   37
```

```
<210> SEQ ID NO 57
<211> LENGTH: 30
<212> TYPE: DNA
<213> ORGANISM: Artificial Sequence
<220> FEATURE:
<223> OTHER INFORMATION: CDR1 of 3BNC117 Variable Heavy following
      GeneART optimization
<220> FEATURE:
<221> NAME/KEY: misc_feature
<223> OTHER INFORMATION: Synthetic

<400> SEQUENCE: 57
ggctacaaca tcagagacta cttcatccac                                           30
```

```
<210> SEQ ID NO 58
<211> LENGTH: 12
<212> TYPE: PRT
<213> ORGANISM: Artificial Sequence
<220> FEATURE:
<223> OTHER INFORMATION: Amino acid sequence on Figure 13A
<220> FEATURE:
<221> NAME/KEY: misc_feature
<223> OTHER INFORMATION: Synthetic

<400> SEQUENCE: 58

Ser Gly Tyr Asn Ile Arg Asp Tyr Phe Ile His Trp
1               5                   10
```

```
<210> SEQ ID NO 59
```

<211> LENGTH: 54
<212> TYPE: DNA
<213> ORGANISM: Artificial Sequence
<220> FEATURE:
<223> OTHER INFORMATION: Top DNA sequence in Figure 13B (coding strand)
<220> FEATURE:
<221> NAME/KEY: misc_feature
<223> OTHER INFORMATION: Synthetic

<400> SEQUENCE: 59
atggatcaac cccaagaccg gccagcctaa caaccccaga cagttccagg gcag          54

<210> SEQ ID NO 60
<211> LENGTH: 54
<212> TYPE: DNA
<213> ORGANISM: Artificial Sequence
<220> FEATURE:
<223> OTHER INFORMATION: Bottom DNA sequence in Figure 13B
      (complementary strand)
<220> FEATURE:
<221> NAME/KEY: misc_feature
<223> OTHER INFORMATION: Synthetic

<400> SEQUENCE: 60
tacctagttg gggttctggc cggtcggatt gttggggtct gtcaaggtcc cgtc          54

<210> SEQ ID NO 61
<211> LENGTH: 50
<212> TYPE: DNA
<213> ORGANISM: Artificial Sequence
<220> FEATURE:
<223> OTHER INFORMATION: CDR2 of 3BNC117 Variable Heavy following
      GeneART optimization
<220> FEATURE:
<221> NAME/KEY: misc_feature
<223> OTHER INFORMATION: Synthetic

<400> SEQUENCE: 61
tggatcaacc ccaagaccgg ccagcctaac aaccccagac agttccaggg          50

<210> SEQ ID NO 62
<211> LENGTH: 56
<212> TYPE: DNA
<213> ORGANISM: Artificial Sequence
<220> FEATURE:
<223> OTHER INFORMATION: Top DNA sequence in Figure 13C (coding strand)
<220> FEATURE:
<221> NAME/KEY: misc_feature
<223> OTHER INFORMATION: Synthetic

<400> SEQUENCE: 62
ataccgccgt gtacttctgc gccagacaga gatccgacta ctgggatttc gacgtg          56

<210> SEQ ID NO 63
<211> LENGTH: 56
<212> TYPE: DNA
<213> ORGANISM: Artificial Sequence
<220> FEATURE:
<223> OTHER INFORMATION: Bottom DNA sequence in Figure 13C
      (complementary strand)
<220> FEATURE:
<221> NAME/KEY: misc_feature
<223> OTHER INFORMATION: Synthetic

<400> SEQUENCE: 63
tatggcggca catgaagacg cggtctgtct ctaggctgat gaccctaaag ctgcac          56

<210> SEQ ID NO 64
<211> LENGTH: 54

-continued

```
<212> TYPE: DNA
<213> ORGANISM: Artificial Sequence
<220> FEATURE:
<223> OTHER INFORMATION: CDR3 of 3BNC117 Variable Heavy following
      GeneART optimization
<220> FEATURE:
<221> NAME/KEY: misc_feature
<223> OTHER INFORMATION: Synthetic

<400> SEQUENCE: 64
accgccgtgt acttctgcgc cagacagaga tccgactact gggatttcga cgtg          54

<210> SEQ ID NO 65
<211> LENGTH: 378
<212> TYPE: DNA
<213> ORGANISM: Artificial Sequence
<220> FEATURE:
<223> OTHER INFORMATION: 3BNC117 Variable Heavy following ADN's SHM
      optimization
<220> FEATURE:
<221> NAME/KEY: misc_feature
<223> OTHER INFORMATION: Synthetic

<400> SEQUENCE: 65
caggttcagc tgctgcaatc tggcgccgct gtgacaaaac ctggcgcctc tgttagagtg     60
tcctgcgagg ctagcggcta caacatcaga gactacttca tccactggtg gcggcaggct    120
ccaggacagg gacttcaatg ggtcggctgg atcaacccca aaaccgggca gcctaacaac    180
cccagacagt tccagggcag agtgtccctg acaagacacg ccagctggga cttcgacacc    240
ttcagcttct acatggacct gaaggccctg agaagcgacg atacagccgt gtacttctgt    300
gctcggcagc ggtccgacta ctgggacttc gacgtgtggg gcagtggaac ccaagttact    360
gtttcgtcag gtgagtcc                                                  378

<210> SEQ ID NO 66
<211> LENGTH: 37
<212> TYPE: DNA
<213> ORGANISM: Artificial Sequence
<220> FEATURE:
<223> OTHER INFORMATION: Top DNA sequence in Figure 14A (coding strand)
<220> FEATURE:
<221> NAME/KEY: misc_feature
<223> OTHER INFORMATION: Synthetic

<400> SEQUENCE: 66
tagcggctac aacatcagag actacttcat ccactgg                              37

<210> SEQ ID NO 67
<211> LENGTH: 37
<212> TYPE: DNA
<213> ORGANISM: Artificial Sequence
<220> FEATURE:
<223> OTHER INFORMATION: Bottom DNA sequence in Figure 14A
      (complementary strand)
<220> FEATURE:
<221> NAME/KEY: misc_feature
<223> OTHER INFORMATION: Synthetic

<400> SEQUENCE: 67
atcgccgatg ttgtagtctc tgatgaagta ggtgacc                              37

<210> SEQ ID NO 68
<211> LENGTH: 30
<212> TYPE: DNA
<213> ORGANISM: Artificial Sequence
<220> FEATURE:
<223> OTHER INFORMATION: CDR1 of 3BNC117 Variable Heavy following ADN's
```

SHM optimization
<220> FEATURE:
<221> NAME/KEY: misc_feature
<223> OTHER INFORMATION: Synthetic

<400> SEQUENCE: 68
ggctacaaca tcagagacta cttcatccac                                                       30

<210> SEQ ID NO 69
<211> LENGTH: 57
<212> TYPE: DNA
<213> ORGANISM: Artificial Sequence
<220> FEATURE:
<223> OTHER INFORMATION: Top DNA sequence in Figure 14B (coding strand)
<220> FEATURE:
<221> NAME/KEY: misc_feature
<223> OTHER INFORMATION: Synthetic

<400> SEQUENCE: 69
cggctggatc aaccccaaaa ccgggcagcc taacaacccc agacagttcc agggcag        57

<210> SEQ ID NO 70
<211> LENGTH: 57
<212> TYPE: DNA
<213> ORGANISM: Artificial Sequence
<220> FEATURE:
<223> OTHER INFORMATION: Bottom DNA sequence in Figure 14B
      (complementary strand)
<220> FEATURE:
<221> NAME/KEY: misc_feature
<223> OTHER INFORMATION: Synthetic

<400> SEQUENCE: 70
gccgacctag ttggggtttt ggcccgtcgg attgttgggg tctgtcaagg tcccgtc        57

<210> SEQ ID NO 71
<211> LENGTH: 50
<212> TYPE: DNA
<213> ORGANISM: Artificial Sequence
<220> FEATURE:
<223> OTHER INFORMATION: CDR2 of 3BNC117 Variable Heavy following ADN's
      SHM optimization
<220> FEATURE:
<221> NAME/KEY: misc_feature
<223> OTHER INFORMATION: Synthetic

<400> SEQUENCE: 71
tggatcaacc ccaaaaccgg gcagcctaac aaccccagac agttccaggg              50

<210> SEQ ID NO 72
<211> LENGTH: 19
<212> TYPE: PRT
<213> ORGANISM: Artificial Sequence
<220> FEATURE:
<223> OTHER INFORMATION: Amino acid seq of Figure 14B
<220> FEATURE:
<221> NAME/KEY: misc_feature
<223> OTHER INFORMATION: Synthetic

<400> SEQUENCE: 72

Gly Trp Ile Asn Pro Lys Thr Gly Gln Pro Asn Asn Pro Arg Gln Phe
1               5                   10                  15

Gln Gly Arg

<210> SEQ ID NO 73
<211> LENGTH: 56
<212> TYPE: DNA
<213> ORGANISM: Artificial Sequence

```
<220> FEATURE:
<223> OTHER INFORMATION: Top DNA sequence on Figure 14C (coding strand)
<220> FEATURE:
<221> NAME/KEY: misc_feature
<223> OTHER INFORMATION: Synthetic

<400> SEQUENCE: 73
atacagccgt gtacttctgt gctcggcagc ggtccgacta ctgggacttc gacgtg           56

<210> SEQ ID NO 74
<211> LENGTH: 56
<212> TYPE: DNA
<213> ORGANISM: Artificial Sequence
<220> FEATURE:
<223> OTHER INFORMATION: Bottom DNA sequence on Figure 14C
      (complementary strand)
<220> FEATURE:
<221> NAME/KEY: misc_feature
<223> OTHER INFORMATION: Synthetic

<400> SEQUENCE: 74
tatgtcggca catgaagaca cgagccgtcg ccaggctgat gaccctgaag ctgcac           56

<210> SEQ ID NO 75
<211> LENGTH: 54
<212> TYPE: DNA
<213> ORGANISM: Artificial Sequence
<220> FEATURE:
<223> OTHER INFORMATION: CDR3 of 3BNC117 Variable Heavy following ADN's
      SHM optimization
<220> FEATURE:
<221> NAME/KEY: misc_feature
<223> OTHER INFORMATION: Synthetic

<400> SEQUENCE: 75
acagccgtgt acttctgtgc tcggcagcgg tccgactact gggacttcga cgtg             54

<210> SEQ ID NO 76
<211> LENGTH: 300
<212> TYPE: DNA
<213> ORGANISM: Artificial Sequence
<220> FEATURE:
<223> OTHER INFORMATION: 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 76
gacatccaga tgacccagtc tccatcctcc ctgtctgcct ctgtgggaga taccgtcact       60
atcacttgcc aagcaaacgg ctacttaaat tggtatcaac agaggcgagg gaaagcccca      120
aaactcctga tctacgatgg gtccaaattg gaaagagggg tcccatcaag gtttagtgga      180
agaagatggg ggcaagaata taatctgacc atcaacaatc tgcagcccga agacattgca      240
acatattttt gtcaagtgta tgagtttgtc gtccctggga ccagactgga tttgaaacgg      300

<210> SEQ ID NO 77
<211> LENGTH: 36
<212> TYPE: DNA
<213> ORGANISM: Artificial Sequence
<220> FEATURE:
<223> OTHER INFORMATION: Top DNA sequence in Figure 15A (coding strand)
<220> FEATURE:
<221> NAME/KEY: misc_feature
<223> OTHER INFORMATION: Synthetic

<400> SEQUENCE: 77
```
atcacttgcc aagcaaacgg ctacttaaat tggtat                                          36

<210> SEQ ID NO 78
<211> LENGTH: 36
<212> TYPE: DNA
<213> ORGANISM: Artificial Sequence
<220> FEATURE:
<223> OTHER INFORMATION: Bottom DNA sequence in Figure 15A
      (complementary strand)
<220> FEATURE:
<221> NAME/KEY: misc_feature
<223> OTHER INFORMATION: Synthetic

<400> SEQUENCE: 78
tagtgaacgg ttcgtttgcc gatgaattta accata                                          36

<210> SEQ ID NO 79
<211> LENGTH: 27
<212> TYPE: DNA
<213> ORGANISM: Artificial Sequence
<220> FEATURE:
<223> OTHER INFORMATION: CDR1 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 79
tgccaagcaa acggctactt aaattgg                                                     27

<210> SEQ ID NO 80
<211> LENGTH: 9
<212> TYPE: PRT
<213> ORGANISM: Artificial Sequence
<220> FEATURE:
<223> OTHER INFORMATION: CDR1 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 80

Cys Gln Ala Asn Gly Tyr Leu Asn Trp
1               5

<210> SEQ ID NO 81
<211> LENGTH: 12
<212> TYPE: PRT
<213> ORGANISM: Artificial Sequence
<220> FEATURE:
<223> OTHER INFORMATION: Amino acid sequence in Figure 15A
<220> FEATURE:
<221> NAME/KEY: misc_feature
<223> OTHER INFORMATION: Synthetic

<400> SEQUENCE: 81

Ile Thr Cys Gln Ala Asn Gly Tyr Leu Asn Trp Tyr
1               5                   10

<210> SEQ ID NO 82
<211> LENGTH: 24
<212> TYPE: DNA
<213> ORGANISM: Artificial Sequence
<220> FEATURE:
<223> OTHER INFORMATION: Top DNA sequence in Figure 15B (coding strand)
<220> FEATURE:
<221> NAME/KEY: misc_feature
<223> OTHER INFORMATION: Synthetic

<400> SEQUENCE: 82

```
acgatgggtc caaattggaa agag                                              24

<210> SEQ ID NO 83
<211> LENGTH: 24
<212> TYPE: DNA
<213> ORGANISM: Artificial Sequence
<220> FEATURE:
<223> OTHER INFORMATION: Bottom DNA sequence in Figure 15B
      (complementary strand)
<220> FEATURE:
<221> NAME/KEY: misc_feature
<223> OTHER INFORMATION: Synthetic

<400> SEQUENCE: 83
tgctacccag gtttaacctt tctc                                              24

<210> SEQ ID NO 84
<211> LENGTH: 21
<212> TYPE: DNA
<213> ORGANISM: Artificial Sequence
<220> FEATURE:
<223> OTHER INFORMATION: CDR2 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 84
gatgggtcca aattggaaag a                                                 21

<210> SEQ ID NO 85
<211> LENGTH: 7
<212> TYPE: PRT
<213> ORGANISM: Artificial Sequence
<220> FEATURE:
<223> OTHER INFORMATION: CDR2 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 85

Asp Gly Ser Lys Leu Glu Arg
1               5

<210> SEQ ID NO 86
<211> LENGTH: 8
<212> TYPE: PRT
<213> ORGANISM: Artificial Sequence
<220> FEATURE:
<223> OTHER INFORMATION: Amino acid sequence in Figure 15B
<220> FEATURE:
<221> NAME/KEY: misc_feature
<223> OTHER INFORMATION: Synthetic

<400> SEQUENCE: 86

Tyr Asp Gly Ser Lys Leu Glu Arg
1               5

<210> SEQ ID NO 87
<211> LENGTH: 50
<212> TYPE: DNA
<213> ORGANISM: Artificial Sequence
<220> FEATURE:
<223> OTHER INFORMATION: Top DNA sequence in Figure 15C (coding strand)
<220> FEATURE:
<221> NAME/KEY: misc_feature
<223> OTHER INFORMATION: Synthetic
```

-continued

```
<400> SEQUENCE: 87
gtcaagtgta tgagtttgtc gtccctggga ccagactgga tttgaaacgg                50

<210> SEQ ID NO 88
<211> LENGTH: 50
<212> TYPE: DNA
<213> ORGANISM: Artificial Sequence
<220> FEATURE:
<223> OTHER INFORMATION: Bottom DNA sequence in Figure 15C
      (complementary strand)
<220> FEATURE:
<221> NAME/KEY: misc_feature
<223> OTHER INFORMATION: Synthetic

<400> SEQUENCE: 88
cagttcacat actcaaacag cagggaccct ggtctgacct aaactttgcc                50

<210> SEQ ID NO 89
<211> LENGTH: 48
<212> TYPE: DNA
<213> ORGANISM: Artificial Sequence
<220> FEATURE:
<223> OTHER INFORMATION: CDR3 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 89
caagtgtatg agtttgtcgt ccctgggacc agactggatt tgaaacgg                  48

<210> SEQ ID NO 90
<211> LENGTH: 16
<212> TYPE: PRT
<213> ORGANISM: Artificial Sequence
<220> FEATURE:
<223> OTHER INFORMATION: CDR3 of 3BNC117 Variable Light following first
      modifications used in ADN170 derivatives
<220> FEATURE:
<221> NAME/KEY: misc_feature
<223> OTHER INFORMATION: Synthetic

<400> SEQUENCE: 90

Gln Val Tyr Glu Phe Val Val Pro Gly Thr Arg Leu Asp Leu Lys Arg
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: Amino acid sequence in Figure 15C
<220> FEATURE:
<221> NAME/KEY: misc_feature
<223> OTHER INFORMATION: Synthetic

<400> SEQUENCE: 91

Cys Gln Val Tyr Glu Phe Val Val Pro Gly Thr Arg Leu Asp Leu Lys
1               5                   10                  15

Arg

<210> SEQ ID NO 92
<211> LENGTH: 300
<212> TYPE: DNA
<213> ORGANISM: Artificial Sequence
<220> FEATURE:
<223> OTHER INFORMATION: 3BNC117 Variable Light following GeneART
      optimization
```

<220> FEATURE:
<221> NAME/KEY: misc_feature
<223> OTHER INFORMATION: Synthetic

<400> SEQUENCE: 92
gacatccaga tgacacagag ccctagcagc ctgtctgcca gcgtgggaga caccgtgaca      60
atcacctgtc aggccaacgg ctacctgaac tggtatcagc agagaagagg caaggcccct     120
aagctgctga tctacgacgg cagcaagctg gaaagaggcg tgccctctag attcagcggc     180
agaagatggg gccaagagta caacctgacc atcaacaacc tgcagcctga ggatatcgcc     240 acatacttt gccaggtgta cgagttcgtg gtgcccggca aagactgga cctgaaacgg      300

<210> SEQ ID NO 93
<211> LENGTH: 41
<212> TYPE: DNA
<213> ORGANISM: Artificial Sequence
<220> FEATURE:
<223> OTHER INFORMATION: Top DNA sequence in Figure 16A (coding strand)
<220> FEATURE:
<221> NAME/KEY: misc_feature
<223> OTHER INFORMATION: Synthetic

<400> SEQUENCE: 93
acaatcacct gtcaggccaa cggctacctg aactggtatc a                          41

<210> SEQ ID NO 94
<211> LENGTH: 41
<212> TYPE: DNA
<213> ORGANISM: Artificial Sequence
<220> FEATURE:
<223> OTHER INFORMATION: Bottom DNA sequence in Figure 16A
     (complementary strand)
<220> FEATURE:
<221> NAME/KEY: misc_feature
<223> OTHER INFORMATION: Synthetic

<400> SEQUENCE: 94
tgttagtgga cagtccggtt gccgatggac ttgaccatag t                          41

<210> SEQ ID NO 95
<211> LENGTH: 27
<212> TYPE: DNA
<213> ORGANISM: Artificial Sequence
<220> FEATURE:
<223> OTHER INFORMATION: CDR1 of 3BNC117 Variable Light following
     GeneART optimization
<220> FEATURE:
<221> NAME/KEY: misc_feature
<223> OTHER INFORMATION: Synthetic

<400> SEQUENCE: 95
tgtcaggcca acggctacct gaactgg                                          27

<210> SEQ ID NO 96
<211> LENGTH: 14
<212> TYPE: PRT
<213> ORGANISM: Artificial Sequence
<220> FEATURE:
<223> OTHER INFORMATION: Amino acid sequence in Figure 16A
<220> FEATURE:
<221> NAME/KEY: misc_feature
<223> OTHER INFORMATION: Synthetic

<400> SEQUENCE: 96

Thr Ile Thr Cys Gln Ala Asn Gly Tyr Leu Asn Trp Tyr Gln
1               5                  10

-continued

```
<210> SEQ ID NO 97
<211> LENGTH: 26
<212> TYPE: DNA
<213> ORGANISM: Artificial Sequence
<220> FEATURE:
<223> OTHER INFORMATION: Top DNA sequence in Figure 16B (coding strand)
<220> FEATURE:
<221> NAME/KEY: misc_feature
<223> OTHER INFORMATION: Synthetic

<400> SEQUENCE: 97
cgacggcagc aagctggaaa gaggcg                                          26

<210> SEQ ID NO 98
<211> LENGTH: 26
<212> TYPE: DNA
<213> ORGANISM: Artificial Sequence
<220> FEATURE:
<223> OTHER INFORMATION: Bottom DNA sequence in Figure 16B
      (complementary strand)
<220> FEATURE:
<221> NAME/KEY: misc_feature
<223> OTHER INFORMATION: Synthetic

<400> SEQUENCE: 98
gctgccgtcg ttcgacctttt ctccgc                                        26

<210> SEQ ID NO 99
<211> LENGTH: 23
<212> TYPE: DNA
<213> ORGANISM: Artificial Sequence
<220> FEATURE:
<223> OTHER INFORMATION: CDR2 of 3BNC117 Variable Light following
      GeneART optimization
<220> FEATURE:
<221> NAME/KEY: misc_feature
<223> OTHER INFORMATION: Synthetic

<400> SEQUENCE: 99
gacggcagca agctggaaag agg                                            23

<210> SEQ ID NO 100
<211> LENGTH: 8
<212> TYPE: PRT
<213> ORGANISM: Artificial Sequence
<220> FEATURE:
<223> OTHER INFORMATION: Amino acid sequence in Figure 16B
<220> FEATURE:
<221> NAME/KEY: misc_feature
<223> OTHER INFORMATION: Synthetic

<400> SEQUENCE: 100

Asp Gly Ser Lys Leu Glu Arg Gly
1               5

<210> SEQ ID NO 101
<211> LENGTH: 52
<212> TYPE: DNA
<213> ORGANISM: Artificial Sequence
<220> FEATURE:
<223> OTHER INFORMATION: Top DNA sequence in Figure 16C (coding strand)
<220> FEATURE:
<221> NAME/KEY: misc_feature
<223> OTHER INFORMATION: Synthetic

<400> SEQUENCE: 101
ttgccaggtg tacgagttcg tggtgcccgg cacaagactg gacctgaaac gg           52
```

<210> SEQ ID NO 102
<211> LENGTH: 52
<212> TYPE: DNA
<213> ORGANISM: Artificial Sequence
<220> FEATURE:
<223> OTHER INFORMATION: Bottom DNA sequence in Figure 16C
      (complementary strand)
<220> FEATURE:
<221> NAME/KEY: misc_feature
<223> OTHER INFORMATION: Synthetic

<400> SEQUENCE: 102
aacggtccac atgctcaagc accacgggcc gtgttctgac ctggactttg cc          52

<210> SEQ ID NO 103
<211> LENGTH: 48
<212> TYPE: DNA
<213> ORGANISM: Artificial Sequence
<220> FEATURE:
<223> OTHER INFORMATION: CDR3 of 3BNC117 Variable Light following
      GeneART optimization
<220> FEATURE:
<221> NAME/KEY: misc_feature
<223> OTHER INFORMATION: Synthetic

<400> SEQUENCE: 103
caggtgtacg agttcgtggt gcccggcaca agactggacc tgaaacgg               48

<210> SEQ ID NO 104
<211> LENGTH: 34
<212> TYPE: DNA
<213> ORGANISM: Artificial Sequence
<220> FEATURE:
<223> OTHER INFORMATION: Top DNA sequence on Figure 17A (coding strand)
<220> FEATURE:
<221> NAME/KEY: misc_feature
<223> OTHER INFORMATION: Synthetic

<400> SEQUENCE: 104
tacctgccaa gctaacggct acctgaactg gtat                             34

<210> SEQ ID NO 105
<211> LENGTH: 34
<212> TYPE: DNA
<213> ORGANISM: Artificial Sequence
<220> FEATURE:
<223> OTHER INFORMATION: Bottom DNA sequence on Figure 17A
      (complementary strand)
<220> FEATURE:
<221> NAME/KEY: misc_feature
<223> OTHER INFORMATION: Synthetic

<400> SEQUENCE: 105
atggacggtt cgattgccga tggacttgac cata                             34

<210> SEQ ID NO 106
<211> LENGTH: 27
<212> TYPE: DNA
<213> ORGANISM: Artificial Sequence
<220> FEATURE:
<223> OTHER INFORMATION: CDR1 of 3BNC117 Variable Light following ADN's
      SHM optimization
<220> FEATURE:
<221> NAME/KEY: misc_feature
<223> OTHER INFORMATION: Synthetic

<400> SEQUENCE: 106
tgccaagcta acggctacct gaactgg                                     27

<210> SEQ ID NO 107
<211> LENGTH: 11
<212> TYPE: PRT
<213> ORGANISM: Artificial Sequence
<220> FEATURE:
<223> OTHER INFORMATION: Amino acid sequence in Figure 17A
<220> FEATURE:
<221> NAME/KEY: misc_feature
<223> OTHER INFORMATION: Synthetic

<400> SEQUENCE: 107

Thr Cys Gln Ala Asn Gly Tyr Leu Asn Trp Tyr
1               5                   10

<210> SEQ ID NO 108
<211> LENGTH: 25
<212> TYPE: DNA
<213> ORGANISM: Artificial Sequence
<220> FEATURE:
<223> OTHER INFORMATION: Top DNA sequence on Figure 17B (coding strand)
<220> FEATURE:
<221> NAME/KEY: misc_feature
<223> OTHER INFORMATION: Synthetic

<400> SEQUENCE: 108
cgacggcagc aagctggaaa gaggc                                        25

<210> SEQ ID NO 109
<211> LENGTH: 25
<212> TYPE: DNA
<213> ORGANISM: Artificial Sequence
<220> FEATURE:
<223> OTHER INFORMATION: Bottom DNA sequence on Figure 17B
     (complementary strand)
<220> FEATURE:
<221> NAME/KEY: misc_feature
<223> OTHER INFORMATION: Synthetic

<400> SEQUENCE: 109
gctgccgtcg ttcgaccttt ctccg                                        25

<210> SEQ ID NO 110
<211> LENGTH: 21
<212> TYPE: DNA
<213> ORGANISM: Artificial Sequence
<220> FEATURE:
<223> OTHER INFORMATION: CDR2 of 3BNC117 Variable Light following ADN's
     SHM optimization
<220> FEATURE:
<221> NAME/KEY: misc_feature
<223> OTHER INFORMATION: Synthetic

<400> SEQUENCE: 110
gacggcagca agctggaaag a                                            21

<210> SEQ ID NO 111
<211> LENGTH: 52
<212> TYPE: DNA
<213> ORGANISM: Artificial Sequence
<220> FEATURE:
<223> OTHER INFORMATION: Top DNA sequence on Figure 17C (coding strand)
<220> FEATURE:
<221> NAME/KEY: misc_feature
<223> OTHER INFORMATION: Synthetic

<400> SEQUENCE: 111
ctgccaagtg tacgagttcg tggtgcccgg caccagactg gacctgaagc gg          52

<210> SEQ ID NO 112

<211> LENGTH: 52
<212> TYPE: DNA
<213> ORGANISM: Artificial Sequence
<220> FEATURE:
<223> OTHER INFORMATION: Bottom DNA sequence on Figure 17C
      (complementary strand)
<220> FEATURE:
<221> NAME/KEY: misc_feature
<223> OTHER INFORMATION: Synthetic

<400> SEQUENCE: 112
gacggttcac atgctcaagc accacgggcc gtggtctgac ctggacttcg cc          52

<210> SEQ ID NO 113
<211> LENGTH: 48
<212> TYPE: DNA
<213> ORGANISM: Artificial Sequence
<220> FEATURE:
<223> OTHER INFORMATION: CDR3 of 3BNC117 Variable Light following ADN's
      SHM optimization
<220> FEATURE:
<221> NAME/KEY: misc_feature
<223> OTHER INFORMATION: Synthetic

<400> SEQUENCE: 113
caagtgtacg agttcgtggt gcccggcacc agactggacc tgaagcgg              48

<210> SEQ ID NO 114
<211> LENGTH: 300
<212> TYPE: DNA
<213> ORGANISM: Artificial Sequence
<220> FEATURE:
<223> OTHER INFORMATION: 3BNC117 Variable Light following ADN's SHM
      optimization
<220> FEATURE:
<221> NAME/KEY: misc_feature
<223> OTHER INFORMATION: Synthetic

<400> SEQUENCE: 114
gacatccaga tgacacagag ccctagcagc ctgtctgcca gcgtgggaga caccgtgaca    60
attacctgcc aagctaacgg ctacctgaac tggtatcagc agagaagagg caaggcccct   120
aagctgctga tctacgacgg cagcaagctg gaaagaggcg tgccctctag attcagcggc   180
agaagatggg gccaagagta caacctgacc atcaacaacc tgcagcctga ggatatcgcc   240
acatacttct gccaagtgta cgagttcgtg gtgcccggca ccagactgga cctgaagcgg   300

<210> SEQ ID NO 115
<211> LENGTH: 18
<212> TYPE: PRT
<213> ORGANISM: Artificial Sequence
<220> FEATURE:
<223> OTHER INFORMATION: Sequencing of 3BNC117 Variable heavy CDR2
      following SHM optimization in mice
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: may be substituted by Phe or Gly
<220> FEATURE:
<221> NAME/KEY: MISC_FEATURE
<222> LOCATION: (2)..(2)
<223> OTHER INFORMATION: may be substituted by Leu
<220> FEATURE:
<221> NAME/KEY: MISC_FEATURE
<222> LOCATION: (3)..(3)
<223> OTHER INFORMATION: may be substituted by Phe or Val
<220> FEATURE:
<221> NAME/KEY: MISC_FEATURE
<222> LOCATION: (4)..(4)
<223> OTHER INFORMATION: may be substituted by Lys
<220> FEATURE:
<221> NAME/KEY: MISC_FEATURE
<222> LOCATION: (5)..(5)
<223> OTHER INFORMATION: may be substituted by Leu
<220> FEATURE:
<221> NAME/KEY: MISC_FEATURE
<222> LOCATION: (6)..(6)
<223> OTHER INFORMATION: may be substituted by Thr, Arg, Met or Asn
<220> FEATURE:
<221> NAME/KEY: MISC_FEATURE
<222> LOCATION: (7)..(7)
<223> OTHER INFORMATION: may be substituted by Lys, Pro, Asn, Gln or Ala
<220> FEATURE:
<221> NAME/KEY: MISC_FEATURE
<222> LOCATION: (7)..(7)
<223> OTHER INFORMATION: may be substituted by Lys, Pro, Asn, Gln or Ala
<220> FEATURE:
<221> NAME/KEY: MISC_FEATURE
<222> LOCATION: (8)..(8)
<223> OTHER INFORMATION: may be substituted by Lys, Pro, Asn, Gln or Ala
<220> FEATURE:
<221> NAME/KEY: MISC_FEATURE
<222> LOCATION: (9)..(9)
<223> OTHER INFORMATION: may be substituted by Lys, Pro, His, Arg, Thr,
      Leu or Trp
<220> FEATURE:
<221> NAME/KEY: MISC_FEATURE
<222> LOCATION: (10)..(10)
<223> OTHER INFORMATION: may be substituted by Gln, His, Thr or Ala
<220> FEATURE:
<221> NAME/KEY: MISC_FEATURE
<222> LOCATION: (11)..(11)
<223> OTHER INFORMATION: may be substituted by  Lys or Thr
<220> FEATURE:
<221> NAME/KEY: MISC_FEATURE
<222> LOCATION: (12)..(12)
<223> OTHER INFORMATION: may be substituted by His, Thr, Met, Lys, Ser,
      Pro or Val
<220> FEATURE:
<221> NAME/KEY: MISC_FEATURE
<222> LOCATION: (13)..(13)
<223> OTHER INFORMATION: may be substituted by His, Ser, Leu or Arg
<220> FEATURE:
<221> NAME/KEY: MISC_FEATURE
<222> LOCATION: (14)..(14)
<223> OTHER INFORMATION: may be substituted by Ser, Gly, Cys, Leu, His
      or Val
<220> FEATURE:
<221> NAME/KEY: MISC_FEATURE
<222> LOCATION: (15)..(15)
<223> OTHER INFORMATION: may be substituted by Lys or His
<220> FEATURE:
<221> NAME/KEY: MISC_FEATURE
<222> LOCATION: (16)..(16)
<223> OTHER INFORMATION: may be substituted by Val, Leu or Cys
<220> FEATURE:
<221> NAME/KEY: MISC_FEATURE
<222> LOCATION: (17)..(17)
<223> OTHER INFORMATION: may be substituted by Lys, Pro, His or Leu
<220> FEATURE:
<221> NAME/KEY: MISC_FEATURE
<222> LOCATION: (18)..(18)
<223> OTHER INFORMATION: may be substituted by Val or Cys

<400> SEQUENCE: 115

Gly Trp Ile Asn Pro Lys Thr Gly Gln Pro Asn Asn Pro Arg Gln Phe
1               5                   10                  15

Gln Gly

<210> SEQ ID NO 116
<211> LENGTH: 126
<212> TYPE: PRT
<213> ORGANISM: Artificial Sequence
<220> FEATURE:

```
<223> OTHER INFORMATION: Sequencing of 3BNC117 Variable heavy following
      SHM optimization in mice
<220> FEATURE:
<221> NAME/KEY: misc_feature
<223> OTHER INFORMATION: Synthetic
<220> FEATURE:
<221> NAME/KEY: MISC_FEATURE
<222> LOCATION: (49)..(49)
<223> OTHER INFORMATION: may be substituted by Phe or Gly
<220> FEATURE:
<221> NAME/KEY: MISC_FEATURE
<222> LOCATION: (50)..(50)
<223> OTHER INFORMATION: may be substituted by Leu
<220> FEATURE:
<221> NAME/KEY: MISC_FEATURE
<222> LOCATION: (51)..(51)
<223> OTHER INFORMATION: may be substituted by Phe or Val
<220> FEATURE:
<221> NAME/KEY: MISC_FEATURE
<222> LOCATION: (52)..(52)
<223> OTHER INFORMATION: may be substituted by Lys
<220> FEATURE:
<221> NAME/KEY: MISC_FEATURE
<222> LOCATION: (53)..(53)
<223> OTHER INFORMATION: may be substituted by Leu
<220> FEATURE:
<221> NAME/KEY: MISC_FEATURE
<222> LOCATION: (54)..(54)
<223> OTHER INFORMATION: may be substituted by Thr, Arg, Met or Asn
<220> FEATURE:
<221> NAME/KEY: MISC_FEATURE
<222> LOCATION: (55)..(55)
<223> OTHER INFORMATION: may be substituted by Lys, Pro, Asn, Gln or Ala
<220> FEATURE:
<221> NAME/KEY: MISC_FEATURE
<222> LOCATION: (56)..(56)
<223> OTHER INFORMATION: may be substituted by Arg, Glu, Asp or Val
<220> FEATURE:
<221> NAME/KEY: MISC_FEATURE
<222> LOCATION: (57)..(57)
<223> OTHER INFORMATION: may be substituted by Lys, Pro, His, Arg, Thr,
      Leu or Trp
<220> FEATURE:
<221> NAME/KEY: MISC_FEATURE
<222> LOCATION: (58)..(58)
<223> OTHER INFORMATION: may be substituted by Gln, His, Thr or Ala
<220> FEATURE:
<221> NAME/KEY: MISC_FEATURE
<222> LOCATION: (59)..(59)
<223> OTHER INFORMATION: may be substituted by Lys or Thr
<220> FEATURE:
<221> NAME/KEY: MISC_FEATURE
<222> LOCATION: (60)..(60)
<223> OTHER INFORMATION: may be substituted by His, Thr, Met, Lys, Ser,
      Pro or Val
<220> FEATURE:
<221> NAME/KEY: MISC_FEATURE
<222> LOCATION: (61)..(61)
<223> OTHER INFORMATION: may be substituted by His, Ser, Leu or Arg
<220> FEATURE:
<221> NAME/KEY: MISC_FEATURE
<222> LOCATION: (62)..(62)
<223> OTHER INFORMATION: may be substituted by Ser, Gly, Cys, Leu, His
      or Val
<220> FEATURE:
<221> NAME/KEY: MISC_FEATURE
<222> LOCATION: (63)..(63)
<223> OTHER INFORMATION: may be substituted by Lys or His
<220> FEATURE:
<221> NAME/KEY: MISC_FEATURE
<222> LOCATION: (64)..(64)
<223> OTHER INFORMATION: may be substituted by Val, Leu or Cys
<220> FEATURE:
<221> NAME/KEY: MISC_FEATURE
<222> LOCATION: (65)..(65)
<223> OTHER INFORMATION: may be substituted by Lys, Pro, His or Leu
<220> FEATURE:
<221> NAME/KEY: MISC_FEATURE
<222> LOCATION: (66)..(66)
```

<223> OTHER INFORMATION: may be substituted by Val or Cys
<220> FEATURE:
<221> NAME/KEY: MISC_FEATURE
<222> LOCATION: (67)..(68)
<223> OTHER INFORMATION: may be substituted by Gly
<220> FEATURE:
<221> NAME/KEY: MISC_FEATURE
<222> LOCATION: (69)..(69)
<223> OTHER INFORMATION: may be substituted by Arg or Gly
<220> FEATURE:
<221> NAME/KEY: MISC_FEATURE
<222> LOCATION: (70)..(70)
<223> OTHER INFORMATION: may be substituted by Arg or Val
<220> FEATURE:
<221> NAME/KEY: MISC_FEATURE
<222> LOCATION: (71)..(71)
<223> OTHER INFORMATION: may be substituted by Pro, Ile or His
<220> FEATURE:
<221> NAME/KEY: MISC_FEATURE
<222> LOCATION: (72)..(72)
<223> OTHER INFORMATION: may be substituted by Gly or Trp
<220> FEATURE:
<221> NAME/KEY: MISC_FEATURE
<222> LOCATION: (73)..(73)
<223> OTHER INFORMATION: may be substituted by Asn, Asp or Thr
<220> FEATURE:
<221> NAME/KEY: MISC_FEATURE
<222> LOCATION: (74)..(74)
<223> OTHER INFORMATION: may be substituted by Phe or Gly
<220> FEATURE:
<221> NAME/KEY: MISC_FEATURE
<222> LOCATION: (75)..(75)
<223> OTHER INFORMATION: may be substituted by Ala, Asp or Val
<220> FEATURE:
<221> NAME/KEY: MISC_FEATURE
<222> LOCATION: (76)..(76)
<223> OTHER INFORMATION: may be substituted by Leu
<220> FEATURE:
<221> NAME/KEY: MISC_FEATURE
<222> LOCATION: (77)..(79)
<223> OTHER INFORMATION: may be null
<220> FEATURE:
<221> NAME/KEY: MISC_FEATURE
<222> LOCATION: (80)..(80)
<223> OTHER INFORMATION: may be substituted by Asp, Phe, Lys, Leu or Ile
<220> FEATURE:
<221> NAME/KEY: MISC_FEATURE
<222> LOCATION: (81)..(81)
<223> OTHER INFORMATION: may be substituted by  Leu, Asp or Trp
<220> FEATURE:
<221> NAME/KEY: MISC_FEATURE
<222> LOCATION: (82)..(82)
<223> OTHER INFORMATION: may be substituted by Asp, Ala or Thr
<220> FEATURE:
<221> NAME/KEY: MISC_FEATURE
<222> LOCATION: (83)..(83)
<223> OTHER INFORMATION: may be substituted by Val, Leu, Asp or Cys
<220> FEATURE:
<221> NAME/KEY: MISC_FEATURE
<222> LOCATION: (84)..(84)
<223> OTHER INFORMATION: may be substituted by Ser

<400> SEQUENCE: 116

Gln Val Gln Leu Leu Gln Ser Gly Ala Ala Val Thr Lys Pro Gly Ala
1               5                   10                  15

Ser Val Arg Val Ser Cys Glu Ala Ser Gly Tyr Asn Ile Arg Asp Tyr
            20                  25                  30

Phe Ile His Trp Trp Arg Gln Ala Pro Gly Gln Gly Leu Gln Trp Val
        35                  40                  45

Gly Trp Ile Asn Pro Lys Thr Gly Gln Pro Asn Asn Pro Arg Gln Phe
    50                  55                  60

Gln Gly Arg Val Ser Leu Thr Arg His Ala Ser Trp Asp Phe Asp Thr
65                  70                  75                  80

-continued

```
Phe Ser Phe Tyr Met Asp Leu Lys Ala Leu Arg Ser Asp Asp Thr Ala
                85              90              95
```

```
Val Tyr Phe Cys Ala Arg Gln Arg Ser Asp Tyr Trp Asp Phe Asp Val
            100             105             110
```

```
Trp Gly Ser Gly Thr Gln Val Thr Val Ser Ser Gly Glu Ser
        115             120             125
```

<210> SEQ ID NO 117
<211> LENGTH: 23
<212> TYPE: DNA
<213> ORGANISM: Artificial Sequence
<220> FEATURE:
<223> OTHER INFORMATION: gRNA mouse IgH
<220> FEATURE:
<221> NAME/KEY: misc_feature
<223> OTHER INFORMATION: Synthetic

<400> SEQUENCE: 117
cgatgcatag ggacaaagag tgg                                                          23

<210> SEQ ID NO 118
<211> LENGTH: 23
<212> TYPE: DNA
<213> ORGANISM: Artificial Sequence
<220> FEATURE:
<223> OTHER INFORMATION: gRNA mouse IgK
<220> FEATURE:
<221> NAME/KEY: misc_feature
<223> OTHER INFORMATION: Synthetic

<400> SEQUENCE: 118
tggtgcagca tcagcccctg agg                                                          23

<210> SEQ ID NO 119
<211> LENGTH: 23
<212> TYPE: DNA
<213> ORGANISM: Artificial Sequence
<220> FEATURE:
<223> OTHER INFORMATION: gRNA human IgH
<220> FEATURE:
<221> NAME/KEY: misc_feature
<223> OTHER INFORMATION: Synthetic

<400> SEQUENCE: 119
ggaaagagaa ctgtcggagt ggg                                                          23

<210> SEQ ID NO 120
<211> LENGTH: 23
<212> TYPE: DNA
<213> ORGANISM: Artificial Sequence
<220> FEATURE:
<223> OTHER INFORMATION: gRNA human IgK
<220> FEATURE:
<221> NAME/KEY: misc_feature
<223> OTHER INFORMATION: Synthetic

<400> SEQUENCE: 120
tggtgcagcc acagttcctg agg                                                          23

<210> SEQ ID NO 121
<211> LENGTH: 41
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<223> OTHER INFORMATION: Synthetic -continued

<400> SEQUENCE: 121
attaattaag cggccgcgta agaatggcct ctccaggtct t                            41

<210> SEQ ID NO 122
<211> LENGTH: 31
<212> TYPE: DNA
<213> ORGANISM: Artificial Sequence
<220> FEATURE:
<223> OTHER INFORMATION: Reverse primer
<220> FEATURE:
<221> NAME/KEY: misc_feature
<223> OTHER INFORMATION: Synthetic

<400> SEQUENCE: 122
ctccactcct cgagtttgtc cctatgcatc g                                       31

<210> SEQ ID NO 123
<211> LENGTH: 27
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<223> OTHER INFORMATION: Synthetic

<400> SEQUENCE: 123
ggacaaactc gaggagtgga gtggggc                                            27

<210> SEQ ID NO 124
<211> LENGTH: 58
<212> TYPE: DNA
<213> ORGANISM: Artificial Sequence
<220> FEATURE:
<223> OTHER INFORMATION: Reverse
<220> FEATURE:
<221> NAME/KEY: misc_feature
<223> OTHER INFORMATION: Synthetic

<400> SEQUENCE: 124
acgcgtgtac actagtccaa ctcaacattg ctcaattcat ttaaaaatat ttgaaact         58

<210> SEQ ID NO 125
<211> LENGTH: 1587
<212> TYPE: DNA
<213> ORGANISM: Artificial Sequence
<220> FEATURE:
<223> OTHER INFORMATION: fragment for the 3BNC117-wt donor
<220> FEATURE:
<221> NAME/KEY: misc_feature
<223> OTHER INFORMATION: Synthetic

<400> SEQUENCE: 125
ctcgactgtg ccttctagtt gccagccatc tgttgtttgc ccctcccccg tgccttcctt        60
gaccctggaa ggtgccactc ccactgtcct ttcctaataa aatgaggaaa ttgcatcgca      120
ttgtctgagt aggtgtcatt ctattctggg gggtggggtg gggcaggaca gcaaggggga      180
ggattgggaa gacaatagca ggcatgctgg ggatgcggtg ggctctatgg ggtacctttt      240
cattccttcc tctccagttc ttctctagat ggactaggct cttaactagc gaattcggat      300
ccctgtctca tgaatatgca aatcaggtga gtccatggtg gtaaatatag ggatgtcgac      360
acacctcaca aacttaagat ctagaatgga catgagggtc cctgctcagc tcctgggggct     420 cctgctgctc tggctctctg gagccagatg tgacatccag atgacccagt ctccatcctc      480

```
cctgtctgcc tctgtgggag ataccgtcac tatcacttgc caagcaaacg gctacttaaa      540
ttggtatcaa cagaggcgag ggaaagcccc aaaactcctg atctacgatg ggtccaaatt      600
ggaaagaggg gtcccatcaa ggtttagtgg aagaagatgg gggcaagaat ataatctgac      660
catcaacaat ctgcagcccg aagacattgc aacatatttt tgtcaagtgt atgagtttgt      720
cgtccctggg accagactgg atttgaaacg ggctgatgct gcaccaactg tatccatctt      780
cccaccatcc agtgagcagt taacatctgg aggtgcctca gtcgtgtgct tcttgaacaa      840
cttctacccc aaagacatca atgtcaagtg gaagattgat ggcagtgaac gacaaaatgg      900
cgtcctgaac agttggactg atcaggacag caaagacagc acctacagca tgagcagcac      960
cctcacgttg accaaggacg agtatgaacg acataacagc tatacctgtg aggccactca     1020
caagacatca acttcaccca ttgtcaagag cttcaacagg aatgagtgtc gcgcgaaacg     1080
cggaagcgga gctactaact tcagcctgct gaagcaggct ggagacgtgg aggagaaccc     1140
tggacctatg gactggacct ggaggatcct cttcttggtg gcagcagcca caggagccca     1200
ctcccaggtc caattgttac agtctggggc agcggtgacg aagcccgggg cctcagtgag     1260
agtctcctgc gaggcttctg gatacaacat tcgtgactac tttattcatt ggtggcgaca     1320
agccccagga cagggccttc agtgggtggg atggatcaat cctaagacag gacagccaaa     1380
caatcctcgt caatttcaag gtagagtcag tctgactcga cacgcgtcgt gggactttga     1440
cacattttcc ttttacatgg acctgaaggc actaagatcg gacgacacgg ccgtttattt     1500
ctgtgcgcga cagcgcagcg actattggga tttcgacgtc tggggcagtg gaacccaggt     1560
cactgtctcg tcaggtgagt cctcgag                                          1587
```

```
<210> SEQ ID NO 126
<211> LENGTH: 48
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<223> OTHER INFORMATION: Synthetic

<400> SEQUENCE: 126
cgcgatgcat taattaagcg gccgcgtaag aatggccact ctagggcc                    48

<210> SEQ ID NO 127
<211> LENGTH: 29
<212> TYPE: DNA
<213> ORGANISM: Artificial Sequence
<220> FEATURE:
<223> OTHER INFORMATION: Reverse primer
<220> FEATURE:
<221> NAME/KEY: misc_feature
<223> OTHER INFORMATION: Synthetic

<400> SEQUENCE: 127
cccactccct cgaggacagt tctctttcc                                         29

<210> SEQ ID NO 128
<211> LENGTH: 28
<212> TYPE: DNA
<213> ORGANISM: Artificial Sequence
<220> FEATURE:
<223> OTHER INFORMATION: Forward primer
<220> FEATURE:
<221> NAME/KEY: misc_feature
<223> OTHER INFORMATION: Synthetic
```

<400> SEQUENCE: 128
aactgtcctc gagggagtgg gtgaatcc                                                        28

<210> SEQ ID NO 129
<211> LENGTH: 49
<212> TYPE: DNA
<213> ORGANISM: Artificial Sequence
<220> FEATURE:
<223> OTHER INFORMATION: Reverse primer
<220> FEATURE:
<221> NAME/KEY: misc_feature
<223> OTHER INFORMATION: Synthetic

<400> SEQUENCE: 129
gatatcacgc gtgtacacta gtacagcact gtgctagtat ttcttagct                                 49

<210> SEQ ID NO 130
<211> LENGTH: 1589
<212> TYPE: DNA
<213> ORGANISM: Artificial Sequence
<220> FEATURE:
<223> OTHER INFORMATION: Fragment for the human donor plasmid
<220> FEATURE:
<221> NAME/KEY: misc_feature
<223> OTHER INFORMATION: Synthetic

<400> SEQUENCE: 130
cctcgactgt gccttctagt tgccagccat ctgttgtttg cccctccccc gtgccttcct         60
tgaccctgga aggtgccact cccactgtcc tttcctaata aaatgaggaa attgcatcgc         120
attgtctgag taggtgtcat tctattctgg ggggtggggt ggggcaggac agcaaggggg         180
aggattggga agacaatagc aggcatgctg gggatgcggt gggctctatg gggtaccttt         240
tcattccttc ctctccagtt cttctctaga tggactaggt ccttaactag cgaattcgga         300
tccctgtctc atgaatatgc aaatcaggtg agtccatggt ggtaaatata gggatgtcga         360
cacacctcac aaacttaaga tctagaatgg acatgagggt ccctgctcag ctcctggggc         420
tcctgctgct ctggctctct ggagccagat gtgacatcca gatgacccag tctccatcct         480
ccctgtctgc ctctgtggga gataccgtca ctatcacttg ccaagcaaac ggctacttaa         540
attggtatca acagaggcga gggaaagccc caaaactcct gatctacgat gggtccaaat         600
tggaaagagg ggtcccatca aggtttagtg gaagaagatg ggggcaagaa tataatctga         660
ccatcaacaa tctgcagccc gaagacattg caacatattt ttgtcaagtg tatgagtttg         720
tcgtccctgg gaccagactg gatttgaaac gaacggtggc tgcaccatct gtcttcatct         780
tcccgccatc tgatgagcag ttgaaatctg gaactgcctc tgttgtgtgc ctgctgaata         840
acttctatcc cagagaggcc aaagtacagt ggaaggtgga taacgccctc caatcgggca         900
actcccagga gagtgtcaca gagcaggaca gcaaggacag cacctacagc ctcagcagca         960
ccctgacgct gagcaaagca gactacgaga acacaaagt ctacgcctgc gaagtcaccc         1020
atcagggcct gagctcgccc gtcacaaaga gcttcaacag gggagagtgt cgcgcgaaac         1080
gcggaagcgg agctactaac ttcagcctgc tgaagcaggc tggagacgtg gaggagaacc         1140
ctggacctat ggactggacc tggaggatcc tcttcttggt ggcagcagcc acaggagccc         1200
actcccaggt ccaattgtta cagtctgggg cagcggtgac gaagcccggg gcctcagtga         1260
gagtctcctg cgaggcttct ggatacaaca ttcgtgacta ctttattcat tggtggcgac         1320 aagcccagg acagggcctt cagtgggtgg gatggatcaa tcctaagaca ggacagccaa         1380
acaatcctcg tcaatttcaa ggtagagtca gtctgactcg acacgcgtcg tgggactttg         1440

-continued acacattttc cttttacatg gacctgaagg cactaagatc ggacgacacg gccgtttatt      1500
tctgtgcgcg acagcgcagc gactattggg atttcgacgt ctggggcagt ggaacccagg      1560
tcactgtctc gtcaggtgag tcctcgagg                                        1589

<210> SEQ ID NO 131
<211> LENGTH: 17
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: Synthetic

<400> SEQUENCE: 131
cgcgcgaaac gcggaag                                                        17

<210> SEQ ID NO 132
<211> LENGTH: 23
<212> TYPE: DNA
<213> ORGANISM: Artificial Sequence
<220> FEATURE:
<223> OTHER INFORMATION: primer for mouse IgG2a (reverse)
<220> FEATURE:
<221> NAME/KEY: misc_feature
<223> OTHER INFORMATION: Synthetic

<400> SEQUENCE: 132
ccaccacaga ggagaagatc cac                                                 23

<210> SEQ ID NO 133
<211> LENGTH: 23
<212> TYPE: DNA
<213> ORGANISM: Artificial Sequence
<220> FEATURE:
<223> OTHER INFORMATION: primer for mouse IgM (reverse)
<220> FEATURE:
<221> NAME/KEY: misc_feature
<223> OTHER INFORMATION: Synthetic

<400> SEQUENCE: 133
cgtggtggga cgaacacatt tac                                                 23

<210> SEQ ID NO 134
<211> LENGTH: 22
<212> TYPE: DNA
<213> ORGANISM: Artificial Sequence
<220> FEATURE:
<223> OTHER INFORMATION: for mouse IgA (reverse)
<220> FEATURE:
<221> NAME/KEY: misc_feature
<223> OTHER INFORMATION: Synthetic

<400> SEQUENCE: 134
catgtgaggc tggcatctga ac                                                  22

<210> SEQ ID NO 135
<211> LENGTH: 23
<212> TYPE: DNA
<213> ORGANISM: Artificial Sequence
<220> FEATURE:
<223> OTHER INFORMATION: PRIMER mouse IgH (forward)
<220> FEATURE:
<221> NAME/KEY: misc_feature
<223> OTHER INFORMATION: Synthetic

<400> SEQUENCE: 135

-continued

```
ggatatttgt ccctgaggga gcc                                        23

<210> SEQ ID NO 136
<211> LENGTH: 26
<212> TYPE: DNA
<213> ORGANISM: Artificial Sequence
<220> FEATURE:
<223> OTHER INFORMATION: PRIMER mouse IgH (reverse)
<220> FEATURE:
<221> NAME/KEY: misc_feature
<223> OTHER INFORMATION: Synthetic

<400> SEQUENCE: 136
gccatcttga ctccaactca acattg                                     26

<210> SEQ ID NO 137
<211> LENGTH: 21
<212> TYPE: DNA
<213> ORGANISM: Artificial Sequence
<220> FEATURE:
<223> OTHER INFORMATION: Primer mouse IgK(forward)
<220> FEATURE:
<221> NAME/KEY: misc_feature
<223> OTHER INFORMATION: Synthetic

<400> SEQUENCE: 137
agtccaactg ttcaggacgc c                                          21

<210> SEQ ID NO 138
<211> LENGTH: 26
<212> TYPE: DNA
<213> ORGANISM: Artificial Sequence
<220> FEATURE:
<223> OTHER INFORMATION: Primer mouse IgK(reverse)
<220> FEATURE:
<221> NAME/KEY: misc_feature
<223> OTHER INFORMATION: Synthetic

<400> SEQUENCE: 138
gtgtggctaa aaattgtccc atgtgg                                     26

<210> SEQ ID NO 139
<211> LENGTH: 23
<212> TYPE: DNA
<213> ORGANISM: Artificial Sequence
<220> FEATURE:
<223> OTHER INFORMATION: PRIMER human IgH(forward)
<220> FEATURE:
<221> NAME/KEY: misc_feature
<223> OTHER INFORMATION: Synthetic

<400> SEQUENCE: 139
gctgaggaat gtgtctcagg agc                                        23

<210> SEQ ID NO 140
<211> LENGTH: 29
<212> TYPE: DNA
<213> ORGANISM: Artificial Sequence
<220> FEATURE:
<223> OTHER INFORMATION: PRIMER human IgH (reverse)
<220> FEATURE:
<221> NAME/KEY: misc_feature
<223> OTHER INFORMATION: Synthetic

<400> SEQUENCE: 140
cctcaattcc agacacatat cactcatgg                                  29
```

```
<210> SEQ ID NO 141
<211> LENGTH: 23
<212> TYPE: DNA
<213> ORGANISM: Artificial Sequence
<220> FEATURE:
<223> OTHER INFORMATION: human IgK (forward)
<220> FEATURE:
<221> NAME/KEY: misc_feature
<223> OTHER INFORMATION: Synthetic

<400> SEQUENCE: 141
gctggaacag tcagaaggtg gag                                                    23

<210> SEQ ID NO 142
<211> LENGTH: 20
<212> TYPE: DNA
<213> ORGANISM: Artificial Sequence
<220> FEATURE:
<223> OTHER INFORMATION: PRIMER human IgK (reverse)
<220> FEATURE:
<221> NAME/KEY: misc_feature
<223> OTHER INFORMATION: Synthetic

<400> SEQUENCE: 142
gctgtccttg ctgtcctgct                                                        20

<210> SEQ ID NO 143
<211> LENGTH: 4683
<212> TYPE: DNA
<213> ORGANISM: Adeno-associated virus 6
<220> FEATURE:
<221> NAME/KEY: misc_feature
<223> OTHER INFORMATION: complete genome, GenBank: AF028704.1

<400> SEQUENCE: 143
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagcgcca tgccgggggtt ttacgagatt gtgattaagg tccccagcga     360
ccttgacgag catctgcccg gcatttctga cagctttgtg aactgggtgg ccgagaagga     420
atgggagttg ccgccagatt ctgacatgga tctgaatctg attgagcagg cacccctgac     480
cgtggccgag aagctgcagc gcgacttcct ggtccagtgg cgccgcgtga gtaaggcccc     540
ggaggccctc ttctttgttc agttcgagaa gggcgagtcc tacttccacc tccatattct     600
ggtggagacc acgggggtca aatccatggt gctgggccgc ttcctgagtc agattaggga     660
caagctggtg cagaccatct accgcgggat cgagccgacc ctgcccaact ggttcgcggt     720
gaccaagacg cgtaatggcg ccggaggggg gaacaaggtg gtggacgagt gctacatccc     780
caactacctc ctgcccaaga ctcagcccga gctgcagtgg gcgtggacta acatggagga     840
gtatataagc gcgtgtttaa acctggccga gcgcaaacgg ctcgtggcgc acgacctgac     900
ccacgtcagc cagacccagg agcagaacaa ggagaatctg aaccccaatt ctgacgcgcc     960
tgtcatccgg tcaaaaacct ccgcacgcta catggagctg gtcgggtggc tggtggaccg    1020
gggcatcacc tccgagaagc agtggatcca ggaggaccag gcctcgtaca tctccttcaa    1080
cgccgcctcc aactcgcggt cccagatcaa ggccgctctg gacaatgccg gcaagatcat    1140
ggcgctgacc aaatccgcgc ccgactacct ggtaggcccc gctccgcccg ccgacattaa    1200
```

```
aaccaaccgc atttaccgca tcctggagct gaacggctac gaccctgcct acgccggctc      1260
cgtctttctc ggctgggccc agaaaaggtt cggaaaacgc aacaccatct ggctgtttgg      1320
gccggccacc acgggcaaga ccaacatcgc ggaagccatc gcccacgccg tgcccttcta      1380
cggctgcgtc aactggacca atgagaactt tcccttcaac gattgcgtcg acaagatggt      1440
gatctggtgg gaggagggca agatgacggc caaggtcgtg gagtccgcca aggccattct      1500
cggcggcagc aaggtgcgcg tggaccaaaa gtgcaagtcg tccgcccaga tcgatcccac      1560
ccccgtgatc gtcacctcca acaccaacat gtgcgccgtg attgacggga acagcaccac      1620
cttcgagcac cagcagccgt tgcaggaccg gatgttcaaa tttgaactca cccgccgtct      1680
ggagcatgac tttggcaagg tgacaaagca ggaagtcaaa gagttcttcc gctgggcgca      1740
ggatcacgtg accgaggtgg cgcatgagtt ctacgtcaga aagggtggag ccaacaagag      1800
acccgccccc gatgacgcgg ataaaagcga gcccaagcgg gcctgcccct cagtcgcgga      1860
tccatcgacg tcagacgcgg aaggagctcc ggtggacttt gccgacaggt accaaaacaa      1920
atgttctcgt cacgcgggca tgcttcagat gctgtttccc tgcaaaacat gcgagagaat      1980
gaatcagaat ttcaacattt gcttcacgca cgggaccaga gactgttcag aatgtttccc      2040
cggcgtgtca gaatctcaac cggtcgtcag aaagaggacg tatcggaaac tctgtgccat      2100
tcatcatctg ctggggcggg ctcccgagat tgcttgctcg gcctgcgatc tggtcaacgt      2160
ggatctggat gactgtgttt ctgagcaata aatgacttaa accaggtatg gctgccgatg      2220
gttatcttcc agattggctc gaggacaacc tctctgaggg cattcgcgag tggtgggact      2280
tgaaacctgg agccccgaaa cccaaagcca accagcaaaa gcaggacgac ggccggggtc      2340
tggtgcttcc tggctacaag tacctcggac ccttcaacgg actcgacaag ggggagcccg      2400
tcaacgcggc ggatgcagcg gccctcgagc acgacaaggc ctacgaccag cagctcaaag      2460
cgggtgacaa tccgtacctg cggtataacc acgccgacgc cgagtttcag gagcgtctgc      2520
aagaagatac gtcttttggg ggcaacctcg ggcgagcagt cttccaggcc aagaagaggg      2580
ttctcgaacc tttttggtctg gttgaggaag gtgctaagac ggctcctgga agaaacgtc      2640 cggtagagca gtcgccacaa gagccagact cctcctcggg cattggcaag acaggccagc      2700
agcccgctaa aaagagactc aattttggtc agactggcga ctcagagtca gtccccgacc      2760
cacaacctct cggagaacct ccagcaaccc ccgctgctgt gggacctact acaatggctt      2820
caggcggtgg cgcaccaatg gcagacaata cgaaggcgc cgacggagtg ggtaatgcct      2880
caggaaattg gcattgcgat tccacatggc tgggcgacag agtcatcacc accagcaccc      2940
gaacatgggc cttgcccacc tataacaacc acctctacaa gcaaatctcc agtgcttcaa      3000 cggggggccag caacgacaac cactacttcg gctacagcac cccctggggg tattttgatt      3060
tcaacagatt ccactgccat ttctcaccac gtgactggca gcgactcatc aacaacaatt      3120
ggggattccg gccaagagaa ctcaacttca agctcttcaa catccaagtc aaggaggtca      3180
cgacgaatga tggcgtcacg accatcgcta ataaccttac cagcacggtt caagtcttct      3240
cggactcgga gtaccagttg ccgtacgtcc tcggctctgc gcaccagggc tgcctccctc      3300
cgttcccggc ggacgtgttc atgattccgc agtacggcta cctaacgctc aacaatggca      3360
gccaggcagt gggacggtca tccttttact gcctggaata tttcccatcg cagatgctga      3420
gaacgggcaa taactttacc ttcagctaca ccttcgagga cgtgcctttc cacagcagct      3480
acgcgcacag ccagagcctg gaccggctga tgaatcctct catcgaccag tacctgtatt      3540
```

-continued

```
acctgaacag aactcagaat cagtccggaa gtgcccaaaa caaggacttg ctgtttagcc      3600
gggggtctcc agctggcatg tctgttcagc ccaaaaactg gctacctgga ccctgttacc      3660
ggcagcagcg cgtttctaaa acaaaaacag acaacaacaa cagcaacttt acctggactg      3720
gtgcttcaaa atataacctt aatgggcgtg aatctataat caaccctggc actgctatgg      3780
cctcacacaa agacgacaaa gacaagttct ttcccatgag cggtgtcatg attttttggaa    3840 aggagagcgc cggagcttca aacactgcat tggacaatgt catgatcaca gacgaagagg      3900
aaatcaaagc cactaacccc gtggccaccg aaagatttgg gactgtggca gtcaatctcc      3960
agagcagcag cacagaccct gcgaccggag atgtgcatgt tatgggagcc ttacctggaa      4020
tggtgtggca agacagagac gtatacctgc agggtcctat ttgggccaaa attcctcaca      4080
cggatggaca ctttcacccg tctcctctca tgggcggctt tggacttaag caccgcctc     4140 ctcagatcct catcaaaaac acgcctgttc ctgcgaatcc tccggcagag ttttcggcta      4200
caaagtttgc ttcattcatc acccagtatt ccacaggaca agtgagcgtg gagattgaat      4260
gggagctgca gaaagaaaac agcaaacgct ggaatcccga agtgcagtat acatctaact      4320
atgcaaaatc tgccaacgtt gatttcactg tggacaacaa tggactttat actgagcctc      4380
gccccattgg cacccgttac ctcacccgtc ccctgtaatt gtgtgttaat caataaaccg      4440
gttaattcgt gtcagttgaa ctttggtctc atgtcgttat tatcttatct ggtcaccata      4500
gcaaccggtt acacattaac tgcttagttg cgcttcgcga ataccctag tgatggagtt     4560 gcccactccc tctatgcgcg ctcgctcgct cggtggggcc ggcagagcag agctctgccg      4620
tctgcggacc tttggtccgc aggccccacc gagcgagcga gcgcgcatag agggagtggg      4680
caa                                                                    4683

<210> SEQ ID NO 144
<211> LENGTH: 4393
<212> TYPE: DNA
<213> ORGANISM: Adeno-associated virus 8
<220> FEATURE:
<221> NAME/KEY: misc_feature
<223> OTHER INFORMATION: complete genome, NC_006261.1

<400> SEQUENCE: 144
cagagaggga gtggccaact ccatcactag gggtagcgcg aagcgcctcc cacgctgccg        60
cgtcagcgct gacgtaaatt acgtcatagg ggagtggtcc tgtattagct gtcacgtgag       120
tgcttttgcg gcattttgcg acaccacgtg gccatttgag gtatatatgg ccgagtgagc       180
gagcaggatc tccattttga ccgcgaaatt tgaacgagca gcagccatgc cgggcttcta       240
cgagatcgtg atcaaggtgc cgagcgacct ggacgagcac ctgccgggca tttctgactc       300
gtttgtgaac tgggtggccg agaaggaatg ggagctgccc ccggattctg acatggatcg       360
gaatctgatc gagcaggcac ccctgaccgt ggccgagaag ctgcagcgcg acttcctggt       420
ccaatggcgc cgcgtgagta aggccccgga ggccctcttc tttgttcagt tcgagaaggg       480
cgagagctac tttcacctgc acgttctggt cgagaccacg ggggtcaagt ccatggtgct       540
aggccgcttc ctgagtcaga ttcgggaaaa gcttggtcca gaccatctac ccgcggggtc       600
gagccccacc ttgcccaact ggttcgcggt gaccaaagac gcggtaatgg cgccggcggg       660
ggggaacaag gtggtggacg agtgctacat ccccaactac ctcctgccca agactcagcc       720
cgagctgcag tgggcgtgga ctaacatgga ggagtatata agcgcgtgct tgaacctggc       780
cgagcgcaaa cggctcgtgg cgcagcacct gacccacgtc agccagacgc aggagcagaa       840
```

-continued

```
caaggagaat ctgaacccca attctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc ccgcggacat tacccagaac cgcatctacc gcatcctcgc    1140
tctcaacggc tacgaccctg cctacgccgg ctccgtcttt ctcggctggg ctcagaaaaa    1200
gttcgggaaa cgcaacacca tctggctgtt tggacccgcc accaccggca agaccaacat    1260
tgcggaagcc atcgcccacg ccgtgcccct ctacggctgc gtcaactgga ccaatgagaa    1320
ctttcccttc aatgattgcg tcgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc caccccgtg atcgtcacct ccaacaccaa    1500
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa aagacccgcc cccgatgacg cggataaaag    1740
cgagcccaag cgggcctgcc cctcagtcgc ggatccatcg acgtcagacg cggaaggagc    1800
tccggtggac tttgccgaca ggtaccaaaa caaatgttct cgtcacgcgg gcatgcttca    1860
gatgctgttt ccctgcaaaa cgtgcgagag aatgaatcag aatttcaaca tttgcttcac    1920
acacggggtc agagactgct cagagtgttt ccccggcgtg tcagaatctc aaccggtcgt    1980
cagaaagagg acgtatcgga aactctgtgc gattcatcat ctgctggggc gggctcccga    2040
gattgcttgc tcggcctgcg atctggtcaa cgtggacctg gatgactgtg tttctgagca    2100
ataaatgact taaaccaggt atggctgccg atggttatct tccagattgg ctcgaggaca    2160
acctctctga gggcattcgc gagtggtggg cgctgaaacc tggagccccg aagcccaaag    2220
ccaaccagca aaagcaggac gacggccggg gtctggtgct tcctggctac aagtacctcg    2280
gacccttcaa cggactcgac aagggggagc ccgtcaacgc ggcggacgca gcggccctcg    2340
agcacgacaa ggcctacgac cagcagctgc aggcgggtga caatccgtac ctgcggtata    2400
accacgccga cgccgagttt caggagcgtc tgcaagaaga tacgtctttt gggggcaacc    2460
tcgggcgagc agtcttccag gccaagaagc gggttctcga acctctcggt ctggttgagg    2520
aaggcgctaa gacggctcct ggaaagaaga gaccggtaga gccatcaccc cagcgttctc    2580
cagactcctc tacgggcatc ggcaagaaag gccaacagcc cgccagaaaa agactcaatt    2640
ttggtcagac tggcgactca gagtcagttc cagaccctca acctctcgga gaacctccag    2700
cagcgccctc tggtgtggga cctaatacaa tggctgcagg cggtggcgca ccaatggcag    2760
acaataacga aggcgccgac ggagtgggta gttcctcggg aaattggcat tgcgattcca    2820
catggctggg cgacagagtc atcaccacca gcacccgaac ctgggccctg cccacctaca    2880
acaaccacct ctacaagcaa atctccaacg ggacatcggg aggagccacc aacgacaaca    2940
cctacttcgg ctacagcacc ccctgggggt attttgactt taacagattc cactgccact    3000
tttcaccacg tgactggcag cgactcatca acaacaactg gggattccgg cccaagagac    3060
tcagcttcaa gctcttcaac atccaggtca aggaggtcac gcagaatgaa ggcaccaaga    3120
ccatcgccaa taacctcacc agcaccatcc aggtgtttac ggactcggag taccagctgc    3180
cgtacgttct cggctctgcc caccagggct gcctgcctcc gttcccggcg gacgtgttca    3240
```

-continued

```
tgattcccca gtacggctac ctaacactca acaacggtag tcaggccgtg ggacgctcct      3300
ccttctactg cctggaatac tttccttcgc agatgctgag aaccggcaac aacttccagt      3360
ttacttacac cttcgaggac gtgcctttcc acagcagcta cgcccacagc cagagcttgg      3420
accggctgat gaatcctctg attgaccagt acctgtacta cttgtctcgg actcaaacaa      3480
caggaggcac ggcaaatacg cagactctgg gcttcagcca aggtgggcct aatacaatgg      3540
ccaatcaggc aaagaactgg ctgccaggac cctgttaccg ccaacaacgc gtctcaacga      3600
caaccgggca aaacaacaat agcaactttg cctggactgc tgggaccaaa taccatctga      3660
atggaagaaa ttcattggct aatcctggca tcgctatggc aacacacaaa gacgacgagg      3720
agcgtttttt tcccagtaac gggatcctga tttttggcaa acaaaatgct gccagagaca      3780
atgcggatta cagcgatgtc atgctcacca gcgaggaaga aatcaaaacc actaaccctg      3840
tggctacaga ggaatacggt atcgtggcag ataacttgca gcagcaaaac acggctcctc      3900
aaattggaac tgtcaacagc caggggggcct tacccggtat ggtctggcag aaccgggacg      3960
tgtacctgca gggtcccatc tgggccaaga ttcctcacac ggacggcaac ttccacccgt      4020
ctccgctgat gggcggcttt ggcctgaaac atcctccgcc tcagatcctg atcaagaaca      4080
cgcctgtacc tgcggatcct ccgaccacct tcaaccagtc aaagctgaac tctttcatca      4140
cgcaatacag caccggacag gtcagcgtgg aaattgaatg ggagctgcag aaggaaaaca      4200
gcaagcgctg gaaccccgag atccagtaca cctccaacta ctacaaatct acaagtgtgg      4260
actttgctgt taatacagaa ggcgtgtact ctgaaccccg ccccattggc acccgttacc      4320
tcacccgtaa tctgtaattg cctgttaatc aataaaccgg ttgattcgtt tcagttgaac      4380
tttggtctct gcg                                                        4393
```

```
<210> SEQ ID NO 145
<211> LENGTH: 50
<212> TYPE: DNA
<213> ORGANISM: Artificial Sequence
<220> FEATURE:
<223> OTHER INFORMATION: SD as provided in the ADN171XS
<220> FEATURE:
<221> NAME/KEY: misc_feature
<223> OTHER INFORMATION: Synthetic

<400> SEQUENCE: 145
ccaagttact gtttcgtcag gtgagtcctc gaggagtgga gtggggcact                50
```

```
<210> SEQ ID NO 146
<211> LENGTH: 2474
<212> TYPE: DNA
<213> ORGANISM: Artificial Sequence
<220> FEATURE:
<223> OTHER INFORMATION: ADN171 cassette
<220> FEATURE:
<221> NAME/KEY: misc_feature
<223> OTHER INFORMATION: Synthetic

<400> SEQUENCE: 146
gtaagaatgg cctctccagg tctttatttt taacctttgt tatggagttt tctgagcatt      60
gcagactaat cttggatatt tgtccctgag ggagccggct gagagaagtt gggaaataaa      120
ctgtctaggg atctcagagc ctttaggaca gattatctcc acatctttga aaaactaaga      180
atctgtgtga tggtgttggt ggagtccctg gatgatggga tagggacttt ggaggctcat      240
ttgaagaaga tgctaaaaca atcctatggc tggagggata gttggggctg tagttggaga      300
```

-continued

```
ttttcagttt ttagaataaa agtattagtt gtggaatata cttcaggacc acctctgtga      360
cagcatttat acagtatccg atgcataggg acaaactcga ctgtgccttc tagttgccag      420
ccatctgttg tttgcccctc ccccgtgcct tccttgaccc tggaaggtgc cactcccact      480
gtcctttcct aataaaatga ggaaattgca tcgcattgtc tgagtaggtg tcattctatt      540
ctggggggtg gggtggggca ggacagcaag ggggaggatt gggaagacaa tagcaggcat      600
gctggggatg cggtgggctc tatggggtac cttttcattc cttcctctcc agttcttctc      660
tagatggact aggtccttaa ctagcgaatt cggatccctg tctcatgaat atgcaaatca      720
ggtgagtcca tggtggtaaa tatagggatg tcgacacacc tcacaaactt aagatctaga      780
atggacatga gggtccctgc tcagctcctg gggctcctgc tgctctggct ctctggagcc      840
agatgtgaca tccagatgac ccagtctcca tcctccctgt ctgcctctgt gggagatacc      900
gtcactatca cttgccaagc aaacggctac ttaaattggt atcaacagag gcgagggaaa      960
gccccaaaac tcctgatcta cgatgggtcc aaattggaaa gaggggtccc atcaaggttt     1020
agtggaagaa gatgggggca agaatataat ctgaccatca caatctgca gcccgaagac      1080 attgcaacat attttgtca agtgtatgag tttgtcgtcc ctgggaccag actggatttg      1140
aaacgggctg atgctgcacc aactgtatcc atcttcccac catccagtga gcagttaaca      1200
tctggaggtg cctcagtcgt gtgcttcttg aacaacttct accccaaaga catcaatgtc      1260
aagtggaaga ttgatggcag tgaacgacaa aatggcgtcc tgaacagttg gactgatcag      1320
gacagcaaag acagcaccta cagcatgagc agcaccctca cgttgaccaa ggacgagtat      1380
gaacgacata acagctatac ctgtgaggcc actcacaaga tcaacttc acccattgtc        1440 aagagcttca acaggaatga gtgtcgcgcg aaacgcggaa gcggagctac taacttcagc      1500
ctgctgaagc aggctggaga cgtggaggag aaccctggac ctatggactg gacctggagg      1560
atcctcttct tggtggcagc agccacagga gcccactccc aggtccaatt gttacagtct      1620
ggggcagcgt gacgaagcc cggggcctca gtgagagtct cctgcgaggc ttctggatac      1680
aacattcgtg actactttat tcattggtgg cgacaagccc caggacaggg ccttcagtgg      1740
gtgggatgga tcaatcctaa gacaggacag ccaaacaatc ctcgtcaatt caaggtaga      1800 gtcagtctga ctcgacacgc gtcgtgggac tttgacacat tttccttta catggacctg      1860 aaggcactaa gatcggacga cacggccgtt tatttctgtg cgcgacagcg cagcgactat      1920
tgggatttcg acgtctgggg cagtggaacc caggtcactg tctcgtcagg tgagtcctcg      1980
aggagtggag tggggcactt tctttagatt tgtgaggaat gttccgcact agattgttta      2040
aaacttcatt tgttggaagg agagctgtct tagtgattga gtcaagggag aaaggcatct      2100
agcctcggtc tcaaaagggt agttgctgtc tagagaggtc tggtggagcc tgcaaaagtc      2160
cagctttcaa aggaacacag aagtatgtgt atggaatatt agaagatgtt gcttttactc      2220
ttaagttggt tcctaggaaa aatagttaaa tactgtgact ttaaaatgtg agagggtttt      2280
caagtactca ttttttaaa tgtccaaaat tcttgtcaat cagtttgagg tcttgtttgt      2340
gtagaactga tattacttaa agtttaaccg aggaatggga gtgaggctct ctcataacct      2400
attcagaact gactttaac aataataaat taagtttcaa atatttaa atgaattgag        2460 caatgttgag ttgg                                                       2474
```

<210> SEQ ID NO 147
<211> LENGTH: 2474
<212> TYPE: DNA
<213> ORGANISM: Artificial Sequence
<220> FEATURE:
<223> OTHER INFORMATION: ADN171XS cassette
<220> FEATURE:
<221> NAME/KEY: misc_feature
<223> OTHER INFORMATION: Synthetic

<400> SEQUENCE: 147

```
gtaagaatgg cctctccagg tctttatttt taacctttgt tatggagttt tctgagcatt      60
gcagactaat cttggatatt tgtccctgag ggagccggct gagagaagtt gggaaataaa     120
ctgtctaggg atctcagagc ctttaggaca gattatctcc acatctttga aaaactaaga     180
atctgtgtga tggtgttggt ggagtccctg gatgatggga tagggacttt ggaggctcat     240
ttgaagaaga tgctaaaaca atcctatggc tggagggata gttggggctg tagttggaga     300 tttttcagttt ttagaataaa agtattagtt gtggaatata cttcaggacc acctctgtga     360
cagcatttat acagtatccg atgcataggg acaaactcga ctgtgccttc tagttgccag     420
ccatctgttg tttgcccctc ccccgtgcct tccttgaccc tggaaggtgc cactcccact     480
gtcctttcct aataaaatga ggaaattgca tcgcattgtc tgagtaggtg tcattctatt     540
ctggggggtg gggtggggca ggacagcaag ggggaggatt gggaagacaa tagcaggcat     600 gctgggatg cggtgggctc tatggggtac ctttttcattc cttcctctcc agttcttctc     660
tagatggact aggtccttaa ctagcgaatt cggatccctg tctcatgaat atgcaaatca     720
ggtgagtcca tggtggtaaa tatagggatg tcgacacacc tcacaaactt aagatctaga     780
atggacatga gggtccctgc tcagctcctg gggctcctgc tgctctggct ctctggagcc     840
agatgtgaca tccagatgac acagagccct agcagcctgt ctgccagcgt gggagacacc     900
gtgacaatta cctgccaagc taacggctac ctgaactggt atcagcagag aagaggcaag     960
gcccctaagc tgctgatcta cgacggcagc aagctggaaa gaggcgtgcc ctctagattc    1020
agcggcagaa gatggggcca agagtacaac ctgaccatca caacctgca gcctgaggat    1080 atcgccacat acttctgcca agtgtacgag ttcgtggtgc ccggcaccag actggacctg    1140
aagcgggctg atgctgcacc aactgtatcc atcttccac catccagtga gcagttaaca    1200
tctggaggtg cctcagtcgt gtgcttcttg aacaacttct accccaaaga catcaatgtc    1260
aagtggaaga ttgatggcag tgaacgacaa aatggcgtcc tgaacagttg gactgatcag    1320
gacagcaaag acagcaccta cagcatgagc agcaccctca cgttgaccaa ggacgagtat    1380
gaacgacata acagctatac ctgtgaggcc actcacaaga catcaacttc acccattgtc    1440
aagagcttca acaggaatga gtgtcgcgcg aaacgcggaa gcggagctac taacttcagc    1500
ctgctgaagc aggctggaga cgtggaggag aaccctggac ctatggactg gacctggagg    1560
atcctcttct tggtggcagc agccacagga gcccactccc aggttcagct gctgcaatct    1620
ggcgccgctg tgacaaaacc tggcgcctct gttagagtgt cctgcgaggc tagcggctac    1680
aacatcagag actacttcat ccactggtgg cggcaggctc caggacaggg acttcaatgg    1740
gtcggctgga tcaaccccaa aaccgggcag cctaacaacc ccagacagtt ccagggcaga    1800
gtgtccctga caagacacgc cagctgggac ttcgacacct tcagcttcta catggacctg    1860
aaggccctga aagcgacga tacagccgtg tacttctgtg tccggcagcg gtccgactac    1920
tgggacttcg acgtgtgggg cagtggaacc caagttactg tttcgtcagg tgagtcctcg    1980
aggagtggag tggggcactt tctttagatt tgtgaggaat gttccgcact agattgttta    2040
aaacttcatt tgttggaagg agagctgtct tagtgattga gtcaagggag aaaggcatct    2100
agcctcggtc tcaaaagggt agttgctgtc tagagaggtc tggtggagcc tgcaaaagtc    2160
```

```
cagctttcaa aggaacacag aagtatgtgt atggaatatt agaagatgtt gcttttactc      2220
ttaagttggt tcctaggaaa aatagttaaa tactgtgact ttaaaatgtg agagggtttt      2280
caagtactca ttttttttaa tgtccaaaat tcttgtcaat cagtttgagg tcttgtttgt      2340
gtagaactga tattacttaa agtttaaccg aggaatggga gtgaggctct ctcataacct      2400
attcagaact gacttttaac aataataaat taagtttcaa atatttttaa atgaattgag      2460
caatgttgag ttgg                                                        2474
```

<210> SEQ ID NO 148
<211> LENGTH: 2416
<212> TYPE: DNA
<213> ORGANISM: Artificial Sequence
<220> FEATURE:
<223> OTHER INFORMATION: ADN221 cassette (a human donor cassette)
<220> FEATURE:
<221> NAME/KEY: misc_feature
<223> OTHER INFORMATION: Synthetic

<400> SEQUENCE: 148

```
gtaagaatgg ccactctagg gcctttgttt tctgctactg cctgtggggt ttcctgagca        60
ttgcaggttg gtcctcgggg catgttccga ggggacctgg gcggactggc caggagggga       120
cgggcactgg ggtgccttga ggatctggga gcctctgtgg attttccgat gcctttggaa       180
aatgggactc aggttgggtg cgtctgatgg agtaactgag cctgggggct ggggagccca       240
catttggacg agatgcctga acaaaccagg ggtcttagtg atggctgagg aatgtgtctc       300
aggagcggtg tctgtaggac tgcaagatcg ctgcacagca gcgaatcgtg aaatattttc       360
tttagaatta tgaggtgcgc tgtgtgtcaa cctgcatctt aaattcttta ttggctggaa       420
agagaactgt ccctcgactg tgccttctag ttgccagcca tctgttgttt gcccctcccc       480
cgtgccttcc ttgaccctgg aaggtgccac tcccactgtc ctttcctaat aaaatgagga       540
aattgcatcg cattgtctga gtaggtgtca ttctattctg gggggtgggg tggggcagga       600
cagcaagggg gaggattggg aagacaatag caggcatgct ggggatgcgg tgggctctat       660
ggggtacctt ttcattcctt cctctccagt tcttctctag atggactagg tccttaacta       720
gcgaattcgg atccctgtct catgaatatg caaatcaggt gagtccatgg tggtaaatat       780
agggatgtcg acacacctca caaacttaag atctagaatg gacatgaggg tccctgctca       840
gctcctgggg ctcctgctgc tctggctctc tggagccaga tgtgacatcc agatgaccca       900
gtctccatcc tccctgtctg cctctgtggg agataccgtc actatcactt gccaagcaaa       960
cggctactta aattggtatc aacagaggcg agggaaagcc ccaaaactcc tgatctacga      1020
tgggtccaaa ttggaaagag gggtcccatc aaggtttagt ggaagaagat ggggcaaga      1080 atataatctg accatcaaca atctgcagcc cgaagacatt gcaacatatt tttgtcaagt      1140
gtatgagttt gtcgtccctg gaccagact ggatttgaaa cgaacggtgg ctgcaccatc      1200
tgtcttcatc ttcccgccat ctgatgagca gttgaaatct ggaactgcct ctgttgtgtg      1260
cctgctgaat aacttctatc ccagagaggc caaagtacag tggaaggtgg ataacgccct      1320
ccaatcgggc aactcccagg agagtgtcac agagcaggac agcaaggaca gcacctacag      1380
cctcagcagc accctgacgc tgagcaaagc agactacgag aaacacaaag tctacgcctg      1440
cgaagtcacc catcagggcc tgagctcgcc cgtcacaaag agcttcaaca ggggagagtg      1500
tcgcgcgaaa cgcggaagcg gagctactaa cttcagcctg ctgaagcagg ctggagacgt      1560
ggaggagaac cctggaccta tggactggac ctggaggatc ctcttcttgg tggcagcagc      1620
```

```
cacaggagcc cactcccagg tccaattgtt acagtctggg gcagcggtga cgaagcccgg    1680
ggcctcagtg agagtctcct gcgaggcttc tggatacaac attcgtgact actttattca    1740
ttggtggcga caagccccag gacagggcct tcagtgggtg ggatggatca atcctaagac    1800
aggacagcca aacaatcctc gtcaatttca aggtagagtc agtctgactc gacacgcgtc    1860
gtgggacttt gacacatttt ccttttacat ggacctgaag gcactaagat cggacgacac    1920
ggccgtttat ttctgtgcgc gacagcgcag cgactattgg gatttcgacg tctggggcag    1980
tggaacccag gtcactgtct cgtcaggtga gtcctcgagg ggagtgggtg aatccagcca    2040
ggagggacgc gtagccccgg tcttgatgag agcaggggttg ggggcagggg tagcccagaa    2100
acggtggctg ccgtcctgac aggggcttag ggaggctcca ggacctcagt gccttgaagc    2160
tggtttccaa gagaaaagga ttgtttatct taggaggcat gcttactgtt aaaagacagg    2220
atatgtttga agtggcttct gagaaaaatg gttaagaaaa ttatgactta aaaatgtgag    2280
agattttcaa gtatattaat tttttttaact gtccaagtat ttgaaattct tatcatttga    2340
ttaacaccca tgagtgatat gtgtctggaa ttgaggccaa agcaagctca gctaagaaat    2400
actagcacag tgctgt                                                     2416
```

<210> SEQ ID NO 149
<211> LENGTH: 2527
<212> TYPE: DNA
<213> ORGANISM: Artificial Sequence
<220> FEATURE:
<223> OTHER INFORMATION: ADN191 cassette
<220> FEATURE:
<221> NAME/KEY: misc_feature
<223> OTHER INFORMATION: Synthetic

<400> SEQUENCE: 149

```
gtaagaatgg cctctccagg tctttatttt taacctttgt tatggagttt tctgagcatt      60
gcagactaat cttggatatt tgtccctgag ggagccggct gagagaagtt gggaaataaa     120
ctgtctaggg atctcagagc ctttaggaca gattatctcc acatctttga aaaactaaga     180
atctgtgtga tggtgttggt ggagtccctg gatgatggga tagggacttt ggaggctcat     240
ttgaagaaga tgctaaaaca atcctatggc tggagggata gttggggctg tagttggaga     300
ttttcagttt ttagaataaa agtattagtt gtggaatata cttcaggacc acctctgtga     360
cagcatttat acagtatccg atgcataggg acaaactcga ctgtgccttc tagttgccag     420
ccatctgttg tttgccccctc ccccgtgcct tccttgaccc tggaaggtgc cactcccact     480
gtcctttcct aataaaatga ggaaattgca tcgcattgtc tgagtaggtg tcattctatt     540
ctggggggtg gggtggggca ggacagcaag ggggaggatt gggaagacaa tagcaggcat     600
gctggggatg cggtgggctc tatggggtac cttttcattc cttcctctcc agttcttctc     660
tagatggact aggtccttaa ctagcgaatt cggatccctg tctcatgaat atgcaaatca     720
ggtgagtcca tggtggtaaa tatagggatg tcgacacacc tcacaaactt aagatctaga     780
cctaggatgg cgacgggttc aagaacttcc ctacttcttg catttggcct gctttgtttg     840
ccgtggttac aggagggctc ggcagacatc cagatgacac agagcccctc tacactgagc     900
gccagcgtgg gagacagagt gaccatcaca tgcaagtgcc agctgagcgt gggctacatg     960
cactggtatc agcagaagcc tggcaaggcc cctaagctgc tgatctacga cacaagcaag    1020
ctggcctctg gcgtgccctc tagattttct ggcagcggct ctggcaccga gttcaccctg    1080
acaatctcta gcctgcagcc tgacgacttc gccacctact actgcttcca aggctctggc    1140
```

-continued

```
taccccttca cattcggcgg aggcaccaag ctggaaatca agggggctga tgctgcacca   1200
actgtatcca tcttcccacc atccagtgag cagttaacat ctggaggtgc ctcagtcgtg   1260
tgcttcttga acaacttcta ccccaaagac atcaatgtca agtggaagat tgatggcagt   1320
gaacgacaaa atggcgtcct gaacagttgg actgatcagg acagcaaaga cagcacctac   1380
agcatgagca gcaccctcac gttgaccaag gacgagtatg aacgacataa cagctatacc   1440
tgtgaggcca ctcacaagac atcaacttca cccattgtca agagcttcaa caggaatgag   1500
tgtcgcgcga aacgcggaag cggagctact aacttcagcc tgctgaagca ggctggagac   1560
gtggaggaga accctggacc tatggcgacg ggttcaagaa cttccctact tcttgcattt   1620
ggcctgcttt gtttgccgtg gttacaggag ggctcggcac aagtgaccct gagagagtct   1680
ggccccgctc tggttaagcc cacacagacc ctgacactga cctgcacctt cagcggcttc   1740
agcctgagca caagcggcat gtctgtcggc tggatcagac agcctcctgg caaggctctg   1800
gaatggctgg ccgacatttg gtgggacgac aagaaggact acaaccccag cctgaagtcc   1860
agactgacca tcagcaagga caccagcaag aaccaggtgg tgctgaaagt gaccaacatg   1920
gaccctgccg acaccgccac ctactactgc gccagatcca tgatcaccaa ctggtacttc   1980
gacgtctggg gcgccggcac cacagtgaca gtttcttcta cctcctcagg taagggagtg   2040
gagtggggca ctttctttag atttgtgagg aatgttccgc actagattgt ttaaaacttc   2100
atttgttgga aggagagctg tcttagtgat tgagtcaagg gagaaaggca tctagcctcg   2160
gtctcaaaag ggtagttgct gtctagagag gtctggtgga gcctgcaaaa gtccagcttt   2220
caaaggaaca cagaagtatg tgtatggaat attagaagat gttgctttta ctcttaagtt   2280
ggttcctagg aaaaatagtt aaatactgtg actttaaaat gtgagagggt tttcaagtac   2340
tcattttttt aaatgtccaa aattcttgtc aatcagtttg aggtcttgtt tgtgtagaac   2400
tgatattact taaagtttaa ccgaggaatg ggagtgaggc tctctcataa cctattcaga   2460
actgactttt aacaataata aattaagttt caaatatttt taaatgaatt gagcaatgtt   2520
gagttgg                                                              2527
```

```
<210> SEQ ID NO 150
<211> LENGTH: 318
<212> TYPE: DNA
<213> ORGANISM: Artificial Sequence
<220> FEATURE:
<223> OTHER INFORMATION: Seq 29 includes both the VL and CL. Seq 30
      includes only the VH. VL sequence is
<220> FEATURE:
<221> NAME/KEY: misc_feature
<223> OTHER INFORMATION: Synthetic

<400> SEQUENCE: 150
gacatccaga tgacacagag cccctctaca ctgagcgcca gcgtgggaga cagagtgacc    60
atcacatgca gtgccagct gagcgtgggc tacatgcact ggtatcagca gaagcctggc   120
aaggccccta agctgctgat ctacgacaca agcaagctgg cctctggcgt gccctctaga   180
ttttctggca gcggctctgg caccgagttc accctgacaa tctctagcct gcagcctgac   240
gacttcgcca cctactactg cttccaaggc tctggctacc ccttcacatt cggcggaggc   300
accaagctgg aaatcaag                                                 318
```

```
<210> SEQ ID NO 151
<211> LENGTH: 299
<212> TYPE: DNA
```

<213> ORGANISM: Artificial Sequence
<220> FEATURE:
<223> OTHER INFORMATION: Seq 31 includes both the VL and CL. Seq 30
      includes only the VH. VL sequence is
<220> FEATURE:
<221> NAME/KEY: misc_feature
<223> OTHER INFORMATION: Synthetic

<400> SEQUENCE: 151

```
gacatccaga tgacccagtc tccatcctcc ctgtctgcct ctgtgggaga taccgtcact     60
atcacttgcc aagcaaacgg ctacttaaat tggtatcaac agaggcgagg gaaagcccca    120
aaactcctga tctacgatgg gtccaaattg gaaagagggg tcccatcaag gtttagtgga    180
agaagatggg ggcaagaata taatctgacc atcaacaatc tgcagcccga agacattgca    240
acatattttt gtcaagtgta tgagtttgtc gtccctggga ccagactgga tttgaaacg     299
```

<210> SEQ ID NO 152
<211> LENGTH: 155
<212> TYPE: DNA
<213> ORGANISM: Artificial Sequence
<220> FEATURE:
<223> OTHER INFORMATION: mutated IgH promoter
<220> FEATURE:
<221> NAME/KEY: misc_feature
<223> OTHER INFORMATION: Synthetic

<400> SEQUENCE: 152

```
ggtacctttt cattccttcc tctccagttc ttctctagat ggactaggtc cttaactagc     60
gaattcggat ccctgtctca tgaatatgca aatcaggtga gtccatggtg gtaaatatag    120
ggatgtcgac acacctcaca aacttaagat ctaga                               155
```

<210> SEQ ID NO 153
<211> LENGTH: 1587
<212> TYPE: DNA
<213> ORGANISM: Artificial Sequence
<220> FEATURE:
<223> OTHER INFORMATION: Fragment for the 3BNC117-opt donor
<220> FEATURE:
<221> NAME/KEY: misc_feature
<223> OTHER INFORMATION: Synthetic

<400> SEQUENCE: 153

```
ctcgactgtg ccttctagtt gccagccatc tgttgtttgc ccctcccccg tgccttcctt     60
gaccctggaa ggtgccactc ccactgtcct ttcctaataa aatgaggaaa ttgcatcgca    120
ttgtctgagt aggtgtcatt ctattctggg gggtgggggtg gggcaggaca gcaaggggga    180
ggattgggaa gacaatagca ggcatgctgg ggatgcggtg ggctctatgg ggtacctttt    240
cattccttcc tctccagttc ttctctagat ggactaggtc cttaactagc gaattcggat    300
ccctgtctca tgaatatgca aatcaggtga gtccatggtg gtaaatatag ggatgtcgac    360
acacctcaca aacttaagat ctagaatgga catgagggtc cctgctcagc tcctgggct     420 cctgctgctc tggctctctg agccagatg tgacatccag atgacacaga gccctagcag    480
cctgtctgcc agcgtgggag acaccgtgac aattacctgc caagctaacg gctacctgaa    540
ctggtatcag cagagaagag gcaaggcccc taagctgctg atctacgacg gcagcaagct    600
ggaaagaggc gtgccctcta gattcagcgg cagaagatgg ggccaagagt acaacctgac    660
catcaacaac ctgcagcctg aggatatcgc cacatacttc tgccaagtgt acgagttcgt    720
ggtgcccggc accagactgg acctgaagcg ggctgatgct gcaccaactg tatccatctt    780
cccaccatcc agtgagcagt taacatctgg aggtgcctca gtcgtgtgct tcttgaacaa    840
```

-continued

```
cttctacccc aaagacatca atgtcaagtg gaagattgat ggcagtgaac gacaaaatgg      900
cgtcctgaac agttggactg atcaggacag caaagacagc acctacagca tgagcagcac      960
cctcacgttg accaaggacg agtatgaacg acataacagc tatacctgtg aggccactca     1020
caagacatca acttcaccca ttgtcaagag cttcaacagg aatgagtgtc gcgcgaaacg     1080
cggaagcgga gctactaact tcagcctgct gaagcaggct ggagacgtgg aggagaaccc     1140
tggacctatg gactggacct ggaggatcct cttcttggtg gcagcagcca caggagccca     1200
ctcccaggtt cagctgctgc aatctggcgc cgctgtgaca aaacctggcg cctctgttag     1260
agtgtcctgc gaggctagcg gctacaacat cagagactac ttcatccact ggtggcggca     1320
ggctccagga cagggacttc aatgggtcgg ctggatcaac cccaaaaccg gcagcctaa     1380 caaccccaga cagttccagg gcagagtgtc cctgacaaga cacgccagct gggacttcga     1440
caccttcagc ttctacatgg acctgaaggc cctgagaagc gacgatacag ccgtgtactt     1500
ctgtgctcgg cagcggtccg actactggga cttcgacgtg tggggcagtg gaacccaagt     1560
tactgtttcg tcaggtgagt cctcgag                                        1587
```

<210> SEQ ID NO 154
<211> LENGTH: 102
<212> TYPE: PRT
<213> ORGANISM: Artificial Sequence
<220> FEATURE:
<223> OTHER INFORMATION: NATIVE ANTIBODY
<220> FEATURE:
<221> NAME/KEY: misc_feature
<223> OTHER INFORMATION: Synthetic

<400> SEQUENCE: 154

```
Ala Val Thr Lys Pro Gly Ala Ser Val Arg Val Ser Cys Glu Ala Ser
1               5                   10                  15

Gly Tyr Asn Ile Arg Asp Tyr Phe Ile His Trp Trp Arg Gln Ala Pro
            20                  25                  30

Gly Gln Gly Leu Gln Trp Val Gly Trp Ile Asn Pro Lys Thr Gly Gln
        35                  40                  45

Pro Asn Asn Pro Arg Gln Phe Gln Gly Arg Val Ser Leu Thr Trp Asp
    50                  55                  60

Phe Asp Thr Phe Ser Phe Tyr Met Asp Leu Lys Ala Leu Arg Ser Asp
65                  70                  75                  80

Asp Thr Ala Val Tyr Phe Cys Ala Arg Gln Arg Ser Asp Tyr Trp Asp
                85                  90                  95

Phe Asp Val Trp Gly Ser
            100
```

<210> SEQ ID NO 155
<211> LENGTH: 102
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 155

```
Ala Val Thr Lys Pro Gly Ala Ser Val Arg Val Ser Cys Glu Ala Ser
1               5                   10                  15

Gly Tyr Asn Ile Arg Asp Tyr Phe Ile His Trp Trp Arg Gln Ala Pro
            20                  25                  30
```

```
Gly Gln Gly Leu Gln Trp Val Gly Trp Ile Asn Pro Lys Thr Gly Gln
        35                  40                  45

Pro Asn Asn Pro Arg Gln Phe Gln Gly Arg Val Ser Leu Thr Trp Asp
    50                  55                  60

Phe Asp Thr Phe Ser Phe Tyr Met Asp Leu Lys Ala Leu Arg Ser Asp
65                  70                  75                  80

Asp Thr Ala Val Tyr Phe Cys Thr Arg Gln Arg Ser Asp Tyr Trp Asp
                85                  90                  95

Phe Asp Val Trp Gly Ser
            100
```

```
<210> SEQ ID NO 156
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 156
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 157
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 157
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
```

-continued

```
                        85              90              95

Asp Phe Asp Val Trp Gly Ser
            100

<210> SEQ ID NO 158
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 158

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Gly Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 159
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 159

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100

<210> SEQ ID NO 160
<211> LENGTH: 103
<212> TYPE: PRT
<213> ORGANISM: Artificial Sequence
<220> FEATURE:
```

```
<223> OTHER INFORMATION: variant
<220> FEATURE:
<221> NAME/KEY: misc_feature
<223> OTHER INFORMATION: Synthetic

<400> SEQUENCE: 160

Ala Ala Val Thr Lys Pro Gly Ala Ser Val Arg Leu Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 161
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 161

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 162
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 162

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
```

-continued

```
                20               25               30

Pro Gly Gln Gly Leu Gln Trp Val Gly Trp Ile Asn Pro Lys Thr Gly
            35               40               45

Gln Pro Asn Asn Pro Arg Gln Phe Gln Gly Arg Val Ser Leu Thr Trp
        50               55               60

Asp Phe Asp Thr Phe Ser Phe Tyr Met Asp Leu Lys Ala Leu Arg Ser
65               70               75               80

Asp Asp Thr Ala Val Cys Phe Cys Ala Arg Gln Arg Ser Asp Tyr Trp
                85               90               95

Asp Phe Asp Val Trp Gly Ser
            100

<210> SEQ ID NO 163
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 163

Ala Ala Val Thr Lys Pro Gly Ala Ser Val Arg Val Ser Cys Glu Ala
1               5               10               15

Ser Gly Tyr Asn Ile Arg Asp Tyr Phe Ile His Trp Gly Arg Gln Ala
                20               25               30

Pro Gly Gln Gly Leu Gln Trp Val Gly Trp Ile Asn Pro Lys Thr Gly
            35               40               45

Gln Pro Asn Asn Pro Arg Gln Phe Gln Gly Arg Val Ser Leu Thr Trp
        50               55               60

Asp Phe Asp Thr Phe Ser Phe Tyr Met Asp Leu Lys Ala Leu Arg Ser
65               70               75               80

Asp Asp Thr Ala Val Tyr Phe Cys Ala Arg Gln Arg Ser Asp Tyr Trp
                85               90               95

Asp Phe Asp Val Trp Gly Ser
            100

<210> SEQ ID NO 164
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 164

Ala Ala Val Thr Lys Pro Gly Ala Ser Val Arg Val Ser Cys Glu Ala
1               5               10               15

Ser Gly Tyr Asn Ile Arg Asp Tyr Phe Ile His Trp Trp Arg Gln Ala
                20               25               30

Pro Gly Gln Gly Leu Gln Trp Val Gly Trp Ile Asn Pro Lys Thr Gly
            35               40               45

Gln Pro Asn Asn Pro Arg Gln Phe Gln Gly Arg Val Ser Leu Thr Trp
        50               55               60

Asp Phe Asp Thr Phe Ser Phe Tyr Met Ala Leu Lys Ala Leu Arg Ser
65               70               75               80
```

Asp Asp Thr Ala Val Tyr Phe Cys Ala Arg Gln Arg Ser Asp Tyr Trp
                85                      90                      95

Asp Phe Asp Val Trp Gly Ser
            100

<210> SEQ ID NO 165
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 165

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                      90                      95

Asp Phe Asp Val Trp Gly Ser
            100

<210> SEQ ID NO 166
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 166

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                      90                      95

Asp Phe Asp Val Trp Gly Ser
            100

<210> SEQ ID NO 167
<211> LENGTH: 103
<212> TYPE: PRT
<213> ORGANISM: Artificial Sequence -continued

```
<220> FEATURE:
<223> OTHER INFORMATION: variant

<400> SEQUENCE: 167

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                  90                  95

Asp Phe Asp Val Trp Gly Ser
            100

<210> SEQ ID NO 168
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 168

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Ala Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 169
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 169

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Gly Arg Gln Ala
            20                  25                  30
```

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 170
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 170

Ala Ala Val Thr Lys Pro Gly Ala Ser Val Arg Val Ser Cys Glu Ala
1                   5                   10                  15

Ser Gly Tyr Asn Ile Arg Asp Tyr Phe Ile His Trp Gly Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 171
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 171

Ala Ala Val Thr Lys Pro Gly Ala Ser Val Arg Val Ser Cys Ala Ala
1                   5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 172
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 172

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 173
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 173

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 174
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 174

```
Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 175
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 175

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 176
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 176

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30
```

```
Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100
```

<210> SEQ ID NO 177
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 177

```
Ala Ala Val Thr Lys Pro Gly Ala Ser Val Arg Val Ser Cys Glu Ala
1                   5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Ala Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 178
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 178

```
Ala Ala Val Thr Lys Pro Gly Ala Ser Val Arg Val Ser Cys Glu Ala
1                   5                   10                  15

Ser Gly Tyr Asn Ile Arg Asp Tyr Phe Ile His Trp Gly Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
```

-continued

```
                    85              90              95

Asp Phe Asp Val Trp Gly Ser
            100

<210> SEQ ID NO 179
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 179

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 180
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 180

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 181
<211> LENGTH: 103
<212> TYPE: PRT
<213> ORGANISM: Artificial Sequence
<220> FEATURE:
```

<223> OTHER INFORMATION: variant
<220> FEATURE:
<221> NAME/KEY: misc_feature
<223> OTHER INFORMATION: Synthetic

<400> SEQUENCE: 181

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100

<210> SEQ ID NO 182
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 182

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Gly Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 183
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 183

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala

-continued

```
                20              25              30

Pro Gly Gln Gly Leu Gln Trp Val Gly Trp Ile Asn Pro Lys Thr Gly
            35              40              45

Gln Pro Asn Asn Pro Arg Gln Phe Gln Gly Arg Val Ser Leu Thr Trp
        50              55              60

Asp Phe Asp Ala Phe Ser Phe Tyr Met Asp Leu Lys Ala Leu Arg Ser
65              70              75              80

Asp Asp Thr Ala Val Tyr Phe Cys Ala Arg Gln Arg Ser Asp Tyr Trp
                85              90              95

Asp Phe Asp Val Trp Gly Ser
            100
```

```
<210> SEQ ID NO 184
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 184
```

```
Ala Ala Val Thr Lys Pro Gly Ala Ser Val Arg Val Ser Cys Glu Ala
1               5               10              15

Ser Gly Tyr Asn Ile Arg His Tyr Phe Ile His Trp Trp Arg Gln Ala
                20              25              30

Pro Gly Gln Gly Leu Gln Trp Val Gly Trp Ile Asn Pro Lys Thr Gly
            35              40              45

Gln Pro Asn Asn Pro Arg Gln Phe Gln Gly Arg Val Ser Leu Thr Trp
        50              55              60

Asp Phe Asp Thr Phe Ser Phe Tyr Met Asp Leu Lys Ala Leu Arg Ser
65              70              75              80

Asp Asp Thr Ala Val Tyr Phe Cys Ala Arg Gln Arg Ser Asp Tyr Trp
                85              90              95

Asp Phe Asp Val Trp Gly Ser
            100
```

```
<210> SEQ ID NO 185
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 185
```

```
Ala Ala Val Thr Lys Pro Gly Ala Ser Val Arg Val Ser Cys Glu Ala
1               5               10              15

Ser Gly Tyr Asn Ile Thr Asp Tyr Phe Ile His Trp Trp Arg Gln Ala
                20              25              30

Pro Gly Gln Gly Leu Gln Trp Val Gly Trp Ile Asn Pro Lys Thr Gly
            35              40              45

Gln Pro Asn Asn Pro Arg Gln Phe Gln Gly Arg Val Ser Leu Thr Trp
        50              55              60

Asp Phe Asp Thr Phe Ser Phe Tyr Met Asp Leu Lys Ala Leu Arg Ser
65              70              75              80
```

Asp Asp Thr Ala Val Tyr Phe Cys Ala Arg Gln Arg Ser Asp Tyr Trp
                85                          90                          95

Asp Phe Asp Val Trp Gly Ser
            100

<210> SEQ ID NO 186
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 186

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                          90                          95

Asp Phe Asp Val Trp Gly Ser
            100

<210> SEQ ID NO 187
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 187

Ala Ala Val Thr Lys Pro Gly Ala Ser Val Arg Val Ser Cys Glu Ala
1               5                   10                  15

Ser Gly Tyr Asn Ile Arg His Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                          90                          95

Asp Phe Asp Val Trp Gly Ser
            100

<210> SEQ ID NO 188
<211> LENGTH: 103
<212> TYPE: PRT
<213> ORGANISM: Artificial Sequence -continued

```
<220> FEATURE:
<223> OTHER INFORMATION: variant
<220> FEATURE:
<221> NAME/KEY: misc_feature
<223> OTHER INFORMATION: Synthetic

<400> SEQUENCE: 188

Ala Ala Val Thr Lys Pro Gly Ala Ser Val Arg Val Ser Cys Glu Ala
1               5                   10                  15

Ser Gly Tyr Asn Ile Arg Pro Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 189
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 189

Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 190
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 190

Ala Ala Val Thr Lys Pro Gly Ala Ser Val Arg Val Ser Cys Glu Ala
1               5                   10                  15
```

-continued

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                  90                  95

Asp Phe Asp Val Trp Gly Ser
            100

<210> SEQ ID NO 191
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 191

Ala Ala Val Thr Lys Pro Gly Ala Ser Val Arg Val Ser Cys Glu Ala
1               5                   10                  15

Ser Gly Tyr Asn Ile Arg His Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 192
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 192

Ala Ala Val Thr Lys Pro Gly Ala Ser Val Arg Val Ser Cys Glu Ala
1               5                   10                  15

Ser Gly Tyr Asn Ile Thr Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 193
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 193

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Phe Phe Cys Ala Arg Gln Arg Ser Asp Tyr Trp
                85                  90                  95

Asp Phe Asp Val Trp Gly Ser
            100

<210> SEQ ID NO 194
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 194

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Ala Tyr Trp
                85                  90                  95

Asp Phe Asp Val Trp Gly Ser
            100

<210> SEQ ID NO 195
<211> LENGTH: 103
<212> TYPE: PRT

<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 195

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Cys Trp
                85                  90                  95

Asp Phe Asp Val Trp Gly Ser
            100

<210> SEQ ID NO 196
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 196

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Arg Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 197
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 197

Ala Ala Val Thr Lys Pro Gly Ala Ser Val Arg Val Ser Cys Glu Ala
1               5                   10                  15

-continued

Ser Gly Tyr Asn Ile Arg Asp Tyr Phe Ile His Trp Trp Arg Arg Ala
              20                  25                  30

Pro Gly Gln Gly Leu Gln Trp Val Gly Trp Ile Asn Pro Lys Thr Gly
              35                  40                  45

Gln Pro Asn Asn Pro Arg Gln Phe Gln Gly Arg Val Ser Leu Thr Trp
              50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                  85                  90                  95

Asp Phe Asp Val Trp Gly Ser
              100

<210> SEQ ID NO 198
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 198

Ala Ala Val Thr Lys Pro Gly Ala Ser Val Arg Val Ser Cys Glu Ala
1                   5                   10                  15

Ser Gly Tyr Asn Ile Arg Asp Tyr Phe Ile His Trp Trp Arg Gln Ala
              20                  25                  30

Pro Gly Gln Gly Leu Gln Trp Val Gly Trp Ile Asn Pro Lys Thr Gly
              35                  40                  45

Gln Pro Asn Asn Pro Arg Gln Phe Gln Gly Arg Val Ser Leu Thr Trp
              50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Gly Tyr Trp
                  85                  90                  95

Asp Phe Asp Val Trp Gly Ser
              100

<210> SEQ ID NO 199
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 199

Ala Ala Val Thr Lys Pro Gly Ala Ser Val Arg Val Ser Cys Glu Ala
1                   5                   10                  15

Ser Gly Tyr Asn Ile Ser Asp Tyr Phe Ile His Trp Trp Arg Gln Ala
              20                  25                  30

Pro Gly Gln Gly Leu Gln Trp Val Gly Trp Ile Asn Pro Lys Thr Gly
              35                  40                  45

Gln Pro Asn Asn Pro Arg Gln Phe Gln Gly Arg Val Ser Leu Thr Trp
              50                  55                  60

Asp Phe Asp Thr Phe Ser Phe Tyr Met Asp Leu Lys Ala Leu Arg Ser

```
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
                100

<210> SEQ ID NO 200
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 200

Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
                100

<210> SEQ ID NO 201
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 201

Ala Ala Val Thr Lys Pro Gly Ala Ser Val Arg Val Ser Cys Glu Ala
1               5                   10                  15

Ser Gly Tyr Asn Ile Arg Ala Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
                100

<210> SEQ ID NO 202
<211> LENGTH: 103
```

<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 202

Ala Ala Val Thr Lys Pro Gly Ala Ser Val Arg Val Ser Cys Glu Ala
1               5                   10                  15

Ser Gly Tyr Asn Ile Thr Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 203
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 203

Ala Ala Val Thr Lys Pro Gly Ala Ser Val Arg Val Ser Cys Glu Ala
1               5                   10                  15

Ser Gly Tyr Asn Ile Arg His Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 204
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 204

Ala Ala Val Thr Lys Pro Gly Ala Ser Val Arg Val Ser Cys Glu Ala

```
1               5               10              15

Ser Gly Tyr Asn Ile Arg Asp Tyr Phe Ile His Trp Trp Arg Gln Ala
            20              25              30

Pro Gly Gln Gly Leu Gln Trp Val Gly Trp Ile Asn Pro Lys Thr Gly
        35              40              45

Gln Pro Asn Asn Pro Arg Gln Phe Gln Gly Arg Val Ser Leu Thr Trp
    50              55              60

Asp Phe Asp Thr Phe Ser Phe Tyr Met Asp Leu Lys Ala Leu Arg Ser
65              70              75              80

Asp Asp Thr Ala Val Tyr Phe Cys Ala Arg Gln Arg Ser Asn Tyr Trp
            85              90              95

Asp Phe Asp Val Trp Gly Ser
            100
```

<210> SEQ ID NO 205
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 205

```
Ala Ala Val Thr Lys Pro Gly Ala Ser Val Arg Val Ser Cys Glu Ala
1               5               10              15

Ser Gly Tyr Asn Ile Arg Asp Tyr Phe Ile His Trp Trp Arg Arg Ala
            20              25              30

Pro Gly Gln Gly Leu Gln Trp Val Gly Trp Ile Asn Pro Lys Thr Gly
        35              40              45

Gln Pro Asn Asn Pro Arg Gln Phe Gln Gly Arg Val Ser Leu Thr Trp
    50              55              60

Asp Phe Asp Thr Phe Ser Phe Tyr Met Asp Leu Lys Ala Leu Arg Ser
65              70              75              80

Asp Asp Thr Ala Val Tyr Phe Cys Ala Arg Gln Arg Ser Asp Tyr Trp
            85              90              95

Asp Phe Asp Val Trp Gly Ser
            100
```

<210> SEQ ID NO 206
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 206

```
Ala Ala Val Thr Lys Pro Gly Ala Ser Val Arg Val Ser Cys Glu Ala
1               5               10              15

Ser Gly Tyr Asn Ile Arg His Tyr Phe Ile His Trp Trp Arg Gln Ala
            20              25              30

Pro Gly Gln Gly Leu Gln Trp Val Gly Trp Ile Asn Pro Lys Thr Gly
        35              40              45

Gln Pro Asn Asn Pro Arg Gln Phe Gln Gly Arg Val Ser Leu Thr Trp
    50              55              60
```

-continued

```
Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 207
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic
```

```
<400> SEQUENCE: 207
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Ala Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 208
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic
```

```
<400> SEQUENCE: 208
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Phe Phe Cys Ala Arg Gln Arg Ser Asp Tyr Trp
                85                  90                  95

Asp Phe Asp Val Trp Gly Ser
            100
```

```
<210> SEQ ID NO 209
```

```
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 209

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Gly Val Trp Gly Ser
            100

<210> SEQ ID NO 210
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 210

Ala Ala Val Thr Lys Pro Gly Ala Ser Val Arg Val Ser Cys Glu Ala
1               5                   10                  15

Ser Gly Tyr Asn Ile Thr Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 211
<211> LENGTH: 103
<212> TYPE: PRT
<213> ORGANISM: Artificial Sequence
<220> FEATURE:
<223> OTHER INFORMATION: variant

<400> SEQUENCE: 211

Ala Thr Val Thr Lys Pro Gly Ala Ser Val Arg Val Ser Cys Glu Ala
1               5                   10                  15
```

```
Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 212
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 212
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 213
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 213
```

```
Ala Ala Val Ile Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80
```

-continued

```
Asp Asp Thr Ala Val Tyr Phe Cys Ala Arg Gln Arg Ser Asp Tyr Trp
            85                  90                  95

Asp Phe Asp Val Trp Gly Ser
            100

<210> SEQ ID NO 214
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 214

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Arg
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
            85                  90                  95

Asp Phe Asp Val Trp Gly Ser
            100

<210> SEQ ID NO 215
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 215

Ala Ala Val Thr Lys Pro Gly Ala Ser Val Arg Val Ser Cys Lys Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
            85                  90                  95

Asp Phe Asp Val Trp Gly Ser
            100

<210> SEQ ID NO 216
<211> LENGTH: 103
<212> TYPE: PRT
```

-continued

```
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 216

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Met Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Leu Cys Ala Arg Gln Arg Ser Asp Tyr Trp
                85                  90                  95

Asp Phe Asp Val Trp Gly Ser
            100

<210> SEQ ID NO 217
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 217

Ala Ala Val Thr Lys Pro Gly Ala Pro Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 218
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 218

Asp Ala Val Thr Lys Pro Gly Ala Ser Val Arg Val Ser Cys Glu Ala
1               5                   10                  15
```

-continued

```
Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 219
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 219

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Gly Tyr Trp
                85                  90                  95

Asp Phe Asp Val Trp Gly Ser
            100

<210> SEQ ID NO 220
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 220

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Arg Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
```

-continued

```
65                    70                    75                    80

Asp Asp Thr Thr Val Tyr Phe Cys Ala Arg Gln Arg Ser Asp Tyr Trp
                    85                    90                    95

Asp Phe Asp Val Trp Gly Ser
            100

<210> SEQ ID NO 221
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 221

Ala Ala Val Thr Lys Pro Gly Ala Ser Val Arg Val Ser Cys Glu Ala
1               5                   10                  15

Ser Gly Tyr Asn Ile Arg Asp Tyr Phe Thr His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                    85                    90                    95

Asp Phe Asp Val Trp Gly Ser
            100

<210> SEQ ID NO 222
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 222

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                  90                  95

Asp Phe Asp Val Trp Gly Ser
            100

<210> SEQ ID NO 223
<211> LENGTH: 103
```

```
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 223

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Arg Pro Asn Asn Pro Arg Gln Phe Gln Gly Arg Ala Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 224
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 224

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Arg Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asn Thr Ala Val Tyr Phe Cys Ala Arg Gln Arg Ser Asp Tyr Trp
                85                  90                  95

Asp Phe Asp Val Trp Gly Ser
            100

<210> SEQ ID NO 225
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 225

Ala Ala Val Thr Lys Pro Gly Ala Ser Val Arg Val Ser Cys Glu Ala
```

-continued

```
1               5                    10                   15
```

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
            85                  90                  95

Asp Phe Asp Val Trp Gly Ser
            100

<210> SEQ ID NO 226
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 226

Ala Ala Val Thr Lys Pro Gly Ala Ser Val Arg Val Ser Cys Glu Ala
1               5                    10                   15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Ala Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
            85                  90                  95

Asp Phe Asp Val Trp Gly Ser
            100

<210> SEQ ID NO 227
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 227

Ala Ala Val Thr Lys Pro Gly Ala Ser Val Arg Val Ser Cys Glu Ala
1               5                    10                   15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60
```

-continued

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 228
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 228

Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 229
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 229

Ala Ala Val Thr Lys Pro Gly Ala Ser Val Arg Val Ser Cys Glu Ala
1               5                   10                  15

Ser Gly Tyr Asn Ile Arg Ala Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 230

<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 230

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Arg Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
        100

<210> SEQ ID NO 231
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 231

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Arg Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
        100

<210> SEQ ID NO 232
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 232

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 233
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 233

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Asn Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Leu Tyr Met Ala Leu Lys Ala Leu Arg Gly
65                  70                  75                  80

Asp Asp Thr Ala Val Cys Phe Trp Ala Arg Arg Arg Ser Asp Tyr Trp
                85                  90                  95

Asp Phe Asp Val Trp Gly Ser
            100
```

<210> SEQ ID NO 234
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 234

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Leu Lys Thr Gly
        35                  40                  45

Gln Pro Asn Asn Pro Arg Gln Phe Gln Gly Arg Val Ser Leu Thr Trp
    50                  55                  60
```

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 235
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 235

Ala Ala Val Thr Lys Pro Gly Ala Ser Val Arg Val Ser Cys Glu Ala
1               5                   10                  15

Ser Gly Tyr Asn Ile Arg His Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 236
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 236

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Arg
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

-continued

```
<210> SEQ ID NO 237
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 237

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Ala Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 238
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 238

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Ala Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 239
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 239
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100
```

```
<210> SEQ ID NO 240
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 240
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Ser Ser
            100
```

```
<210> SEQ ID NO 241
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 241
```

```
Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
```

-continued

```
        50              55              60

Asp Phe Asp Thr Phe Ser Phe Tyr Met Asp Leu Lys Ala Leu Arg Ser
65              70              75              80

Asp Asp Thr Ala Val Tyr Phe Cys Ala Arg Gln Arg Ser Asp Tyr Trp
                85              90              95

Asp Phe Asp Val Trp Gly Ser
        100

<210> SEQ ID NO 242
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 242

Ala Ala Gly Thr Lys Pro Gly Ala Ser Val Arg Val Ser Cys Glu Ala
1               5               10              15

Ser Gly Tyr Asn Ile Arg Asp Tyr Phe Ile His Trp Trp Arg Gln Ala
                20              25              30

Pro Gly Gln Gly Leu Gln Trp Val Gly Trp Ile Asn Pro Lys Thr Gly
        35              40              45

Gln Pro Asn Asn Pro Arg Gln Phe Gln Gly Arg Val Ser Leu Thr Trp
        50              55              60

Asp Phe Asp Thr Phe Ser Phe Tyr Met Asp Leu Lys Ala Leu Arg Ser
65              70              75              80

Asp Asp Pro Ala Val Cys Phe Cys Ala Arg Gln Arg Ser Asp Tyr Trp
                85              90              95

Asp Phe Asp Val Trp Gly Arg
        100

<210> SEQ ID NO 243
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 243

Ala Ala Val Thr Lys Pro Gly Ala Ser Val Arg Val Pro Cys Glu Ala
1               5               10              15

Ser Gly Tyr Asn Ile Arg Asp Tyr Phe Ile His Trp Trp Arg Gln Ala
                20              25              30

Pro Gly Gln Gly Leu Gln Trp Val Gly Trp Ile Asn Pro Lys Thr Gly
        35              40              45

Gln Pro Asn Asn Pro Arg Gln Phe Gln Gly Arg Val Ser Leu Thr Trp
        50              55              60

Asp Phe Asp Thr Phe Ser Phe Tyr Met Asp Leu Lys Ala Leu Arg Ser
65              70              75              80

Asp Asp Thr Ala Val Tyr Phe Cys Ala Arg Gln Arg Ser Asp Tyr Trp
                85              90              95

Asp Phe Asp Val Trp Gly Ser
        100
```

-continued

```
<210> SEQ ID NO 244
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 244

Ala Ala Val Thr Lys Pro Gly Ala Ser Val Arg Val Ser Cys Glu Ala
1               5                   10                  15

Ser Gly His Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 245
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 245

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100

<210> SEQ ID NO 246
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic
```

<400> SEQUENCE: 246

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 247
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 247

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Gly Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 248
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 248

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

```
Gln Pro Asn Asn Pro Arg Gln Phe Gln Gly Arg Val Ser Leu Thr Trp
    50                  55                  60

Asp Phe Asp Ala Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 249
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 249

```
Ala Ala Val Thr Lys Pro Gly Ala Ser Val Arg Val Ser Cys Glu Ala
1               5                   10                  15

Ser Gly Tyr Asn Ile Arg Asp Cys Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 250
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 250

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

-continued

<210> SEQ ID NO 251
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 251

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Ala Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 252
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 252

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                  90                  95

Asp Phe Asp Val Trp Gly Ser
            100

<210> SEQ ID NO 253
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 253

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Ala Tyr Trp
                85                  90                  95

Asp Phe Asp Val Trp Gly Ser
            100

<210> SEQ ID NO 254
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 254

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Phe Trp
                85                  90                  95

Asp Phe Asp Val Trp Gly Ser
            100

<210> SEQ ID NO 255
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 255

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly His Gly Leu Gln Trp Val Gly Trp Ile Asn Pro Lys Thr Gly
        35                  40                  45

```
Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 256
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 256
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

```
<210> SEQ ID NO 257
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 257
```

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Ala Ala Val Tyr Phe Cys Ala Arg Gln Arg Ser Asp Tyr Trp
                85                  90                  95

Asp Phe Asp Val Trp Gly Ser
```

-continued

```
             100

<210> SEQ ID NO 258
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 258

Ala Ala Gly Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 259
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 259

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Arg Arg Ser Asp Tyr Trp
                85                  90                  95

Asp Phe Asp Val Trp Gly Ser
            100

<210> SEQ ID NO 260
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
```

<223> OTHER INFORMATION: Synthetic

<400> SEQUENCE: 260

```
Ala Ala Val Thr Lys Pro Gly Ala Ser Val Arg Val Ser Cys Glu Ala
1               5                   10                  15

Ser Gly Tyr Asn Ile Ser Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 261
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 261

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
            35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Ala Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100
```

<210> SEQ ID NO 262
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 262

```
Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
```

-continued

```
            35                    40                    45

Gln Pro Asn Asn Pro Arg Gln Phe Gln Gly Arg Val Ser Leu Thr Trp
        50                    55                    60

Asp Phe Asp Thr Phe Ser Phe Tyr Met Asp Leu Lys Ala Leu Arg Ser
65                    70                    75                    80

Asp Asp Thr Ala Val Cys Phe Cys Ala Arg Gln Arg Ser Asp Tyr Trp
                85                    90                    95

Asp Phe Asp Val Trp Gly Ser
            100

<210> SEQ ID NO 263
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 263

Ala Ala Val Thr Lys Pro Gly Ala Ser Val Arg Val Ser Cys Glu Ala
1                   5                    10                    15

Ser Gly Tyr Asn Ile Arg Pro Tyr Phe Ile His Trp Trp Arg Gln Ala
                20                    25                    30

Pro Gly Gln Gly Leu Gln Trp Val Gly Trp Ile Asn Pro Lys Thr Gly
            35                    40                    45

Gln Pro Asn Asn Pro Arg Gln Phe Gln Gly Arg Val Ser Leu Thr Trp
        50                    55                    60

Asp Phe Asp Thr Phe Ser Phe Tyr Met Asp Leu Lys Ala Leu Arg Ser
65                    70                    75                    80

Asp Asp Thr Ala Val Tyr Phe Cys Ala Arg Gln Arg Ser Asp Tyr Trp
                85                    90                    95

Asp Phe Asp Val Trp Gly Ser
            100

<210> SEQ ID NO 264
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 264

Ala Ala Ala Thr Lys Pro Gly Ala Ser Val Arg Val Ser Cys Glu Ala
1                   5                    10                    15

Ser Gly Tyr Asn Ile Arg Asp Tyr Phe Ile His Trp Trp Arg Gln Ala
                20                    25                    30

Pro Gly Gln Gly Leu Gln Trp Val Gly Trp Ile Asn Pro Lys Thr Gly
            35                    40                    45

Gln Pro Asn Asn Pro Arg Gln Phe Gln Gly Arg Val Ser Leu Thr Trp
        50                    55                    60

Asp Phe Asp Thr Phe Ser Phe Tyr Met Asp Leu Lys Ala Leu Arg Ser
65                    70                    75                    80

Asp Asp Thr Ala Val Tyr Phe Cys Ala Arg Gln Arg Ser Asp Tyr Trp
                85                    90                    95
```

-continued

```
Asp Phe Asp Val Trp Gly Ser
            100

<210> SEQ ID NO 265
<211> LENGTH: 103
<212> TYPE: PRT
<213> ORGANISM: Artificial Sequence
<220> FEATURE:
<223> OTHER INFORMATION: VARIANT
<220> FEATURE:
<221> NAME/KEY: misc_feature
<223> OTHER INFORMATION: Synthetic

<400> SEQUENCE: 265

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Thr Arg Gln Arg Ser Asp Tyr Trp
                85                  90                  95

Asp Phe Asp Val Trp Gly Ser
            100

<210> SEQ ID NO 266
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 266

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Ser Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 267
<211> LENGTH: 103
<212> TYPE: PRT
<213> ORGANISM: Artificial Sequence
<220> FEATURE:
<223> OTHER INFORMATION: variant
<220> FEATURE:
```

-continued

```
<221> NAME/KEY: misc_feature
<223> OTHER INFORMATION: Synthetic

<400> SEQUENCE: 267

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Gly Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 268
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 268

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Gly Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 269
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 269

Ala Ala Val Thr Lys Pro Gly Ala Ser Val Arg Val Ser Cys Ala Ala
1               5                   10                  15

Ser Gly Tyr Asn Ile Arg Asp Tyr Phe Ile His Trp Trp Arg Gln Ala
            20                  25                  30
```

-continued

```
Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 270
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 270

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Arg
                85                  90                  95

Asp Phe Asp Val Trp Gly Ser
            100

<210> SEQ ID NO 271
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 271

Ala Ala Val Thr Lys Pro Gly Ala Ser Val Arg Val Ser Cys Glu Ala
1               5                   10                  15

Ser Gly Tyr Asn Ile Thr Asp Tyr Phe Ile His Trp Trp Arg Gln Ala
                20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95
```

-continued

```
Asp Phe Asp Val Trp Gly Ser
            100

<210> SEQ ID NO 272
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 272

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Arg Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 273
<211> LENGTH: 103
<212> TYPE: PRT
<213> ORGANISM: Artificial Sequence
<220> FEATURE:
<223> OTHER INFORMATION: variant
<220> FEATURE:
<221> NAME/KEY: misc_feature
<223> OTHER INFORMATION: Synthetic

<400> SEQUENCE: 273

Ala Ala Val Thr Lys Pro Gly Ala Ser Val Arg Val Ser Cys Glu Ala
1               5                   10                  15

Ser Gly Tyr Asn Ile Arg Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
    50                  55                  60

Asp Phe Asp Thr Phe Ser Phe Tyr Met Asp Leu Lys Ala Leu Arg Ser
65                  70                  75                  80

Asp Asp Thr Ala Val Cys Phe Cys Ala Arg Gln Arg Ser Asp Tyr Trp
                85                  90                  95

Asp Phe Asp Val Trp Gly Ser
            100

<210> SEQ ID NO 274
<211> LENGTH: 103
<212> TYPE: PRT
<213> ORGANISM: Artificial Sequence
<220> FEATURE:
<223> OTHER INFORMATION: variant
```

```
<220> FEATURE:
<221> NAME/KEY: misc_feature
<223> OTHER INFORMATION: Synthetic

<400> SEQUENCE: 274

Ala Ala Val Thr Lys Pro Gly Ala Ser Val Arg Val Ser Cys Glu Ala
1               5                   10                  15

Ser Gly Tyr Asn Ile Pro Asp Tyr Phe Ile His Trp Trp Arg Gln Ala
            20                  25                  30

Pro Gly Gln Gly Leu Gln Trp Val Gly Trp Ile Asn Pro Lys Thr Gly
        35                  40                  45

Gln Pro Asn Asn Pro Arg Gln Phe Gln Gly Arg Val Ser Leu Thr Trp
        50                  55                  60

Asp Phe Asp Thr Phe Ser Phe Tyr Met Asp Leu Lys Ala Leu Arg Ser
65                  70                  75                  80

Asp Asp Thr Ala Val Tyr Phe Cys Ala Arg Gln Arg Ser Asp Tyr Trp
                85                  90                  95

Asp Phe Asp Val Trp Gly Ser
            100

<210> SEQ ID NO 275
<211> LENGTH: 2274
<212> TYPE: DNA
<213> ORGANISM: Artificial Sequence
<220> FEATURE:
<223> OTHER INFORMATION: ADN174 cassette
<220> FEATURE:
<221> NAME/KEY: misc_feature
<223> OTHER INFORMATION: Synthetic

<400> SEQUENCE: 275
gtaagaatgg cctctccagg tctttatttt taacctttgt tatggagttt tctgagcatt      60
gcagactaat cttggatatt tgtccctgag ggagccggct gagagaagtt gggaaataaa     120
ctgtctaggg atctcagagc ctttaggaca gattatctcc acatctttga aaaactaaga     180
atctgtgtga tggtgttggt ggagtccctg gatgatggga tagggacttt ggaggctcat     240
ttgaagaaga tgctaaaaca atcctatggc tggaggata gttggggctg tagttggaga     300
ttttcagttt ttagaataaa agtattagtt gtggaatata cttcaggacc acctctgtga     360
cagcatttat acagtatccg atgcataggg acaaacgtgt agagggatct cctgtctgac     420
aggaggcaag aagacagatt cttacccctc catttctctt ttatccctct ctggtcctca     480
gagagtcagt ccttcccaaa tgcgcgcgaa acgcggaagc ggagctacta acttcagcct     540
gctgaagcag gctggagacg tggaggagaa ccctggacct atggacatga gggtccctgc     600
tcagctcctg gggctcctgc tgctctggct ctctggagcc agatgtgaca tccagatgac     660
ccagtctcca tcctccctgt ctgcctctgt gggagatacc gtcactatca cttgccaagc     720
aaacggctac ttaaattggt atcaacagag cgagggaaa gccccaaaac tcctgatcta     780
cgatgggtcc aaattggaaa gaggggtccc atcaaggttt agtggaagaa gatggggca     840 agaatataat ctgaccatca acaatctgca gcccgaagac attgcaacat attttttgtca     900 agtgtatgag tttgtcgtcc ctgggaccag actggatttg aaacgggctg atgctgcacc     960
aactgtatcc atcttccac catccagtga gcagttaaca tctggaggtg cctcagtcgt    1020
gtgcttcttg aacaacttct accccaaaga catcaatgtc aagtggaaga ttgatggcag    1080
tgaacgacaa aatggcgtcc tgaacagttg gactgatcag gacagcaaag acagcaccta    1140
cagcatgagc agcaccctca cgttgaccaa ggacgagtat gaacgacata acagctatac    1200
```

-continued

```
ctgtgaggcc actcacaaga catcaacttc acccattgtc aagagcttca acaggaatga    1260
gtgtcgcgcg aaacgcggaa gcggagctac taacttcagc ctgctgaagc aggctggaga    1320
cgtggaggag aaccctggac ctatggactg gacctggagg atcctcttct tggtggcagc    1380
agccacagga gcccactccc aggtccaatt gttacagtct ggggcagcgg tgacgaagcc    1440
cggggcctca gtgagagtct cctgcgaggc ttctggatac aacattcgtg actactttat    1500
tcattggtgg cgacaagccc caggacaggg ccttcagtgg gtgggatgga tcaatcctaa    1560
gacaggacag ccaaacaatc ctcgtcaatt tcaaggtaga gtcagtctga ctcgacacgc    1620
gtcgtgggac tttgacacat tttccttta catggacctg aaggcactaa gatcggacga    1680
cacggccgtt tatttctgtg cgcgacagcg cagcgactat tgggatttcg acgtctgggg    1740
cagtggaacc caggtcactg tctcgtcagg tgagtcctcg aggagtggag tggggcactt    1800
tctttagatt tgtgaggaat gttccgcact agattgttta aaacttcatt tgttggaagg    1860
agagctgtct tagtgattga gtcaagggag aaaggcatct agcctcggtc tcaaaagggt    1920
agttgctgtc tagagaggtc tggtggagcc tgcaaaagtc cagctttcaa aggaacacag    1980
aagtatgtgt atggaatatt agaagatgtt gcttttactc ttaagttggt tcctaggaaa    2040
aatagttaaa tactgtgact ttaaaatgtg agagggtttt caagtactca ttttttttaaa    2100 tgtccaaaat tcttgtcaat cagtttgagg tcttgtttgt gtagaactga tattacttaa    2160
agtttaaccg aggaatggga gtgaggctct ctcataacct attcagaact gacttttaac    2220
aataataaat taagtttcaa atattttaa atgaattgag caatgttgag ttgg           2274
```

<210> SEQ ID NO 276
<211> LENGTH: 27
<212> TYPE: DNA
<213> ORGANISM: Artificial Sequence
<220> FEATURE:
<223> OTHER INFORMATION: primers P2A 174 R
<220> FEATURE:
<221> NAME/KEY: misc_feature
<223> OTHER INFORMATION: Synthetic

<400> SEQUENCE: 276

```
catgtccata ggtccagggt tctcctc                                          27
```

<210> SEQ ID NO 277
<211> LENGTH: 19
<212> TYPE: DNA
<213> ORGANISM: Artificial Sequence
<220> FEATURE:
<223> OTHER INFORMATION: the mIgHJ1 F1 primer
<220> FEATURE:
<221> NAME/KEY: misc_feature
<223> OTHER INFORMATION: Synthetic

<400> SEQUENCE: 277

```
gcacagggac cacggtcac                                                   19
```

<210> SEQ ID NO 278
<211> LENGTH: 21
<212> TYPE: DNA
<213> ORGANISM: Artificial Sequence
<220> FEATURE:
<223> OTHER INFORMATION: mIgHJ2 F1
<220> FEATURE:
<221> NAME/KEY: misc_feature
<223> OTHER INFORMATION: Synthetic

<400> SEQUENCE: 278

-continued gccaaggcac cactctcaca g                                                          21

<210> SEQ ID NO 279
<211> LENGTH: 23
<212> TYPE: DNA
<213> ORGANISM: Artificial Sequence
<220> FEATURE:
<223> OTHER INFORMATION: mIgHJ3 F1
<220> FEATURE:
<221> NAME/KEY: misc_feature
<223> OTHER INFORMATION: Synthetic

<400> SEQUENCE: 279
gactctggtc actgtctctg cag                                                        23

<210> SEQ ID NO 280
<211> LENGTH: 22
<212> TYPE: DNA
<213> ORGANISM: Artificial Sequence
<220> FEATURE:
<223> OTHER INFORMATION: mIgHJ4 F1
<220> FEATURE:
<221> NAME/KEY: misc_feature
<223> OTHER INFORMATION: Synthetic

<400> SEQUENCE: 280
ggtcaaggaa cctcagtcac cg                                                         22

<210> SEQ ID NO 281
<211> LENGTH: 21
<212> TYPE: DNA
<213> ORGANISM: Artificial Sequence
<220> FEATURE:
<223> OTHER INFORMATION: P2A F1
<220> FEATURE:
<221> NAME/KEY: misc_feature
<223> OTHER INFORMATION: Synthetic

<400> SEQUENCE: 281
gagacgtgga ggagaaccct g                                                          21

<210> SEQ ID NO 282
<211> LENGTH: 23
<212> TYPE: DNA
<213> ORGANISM: Artificial Sequence
<220> FEATURE:
<223> OTHER INFORMATION: mIgHM CH2 R1
<220> FEATURE:
<221> NAME/KEY: misc_feature
<223> OTHER INFORMATION: Synthetic

<400> SEQUENCE: 282
cgtggtggga cgaacacatt tac                                                        23

<210> SEQ ID NO 283
<211> LENGTH: 5
<212> TYPE: PRT
<213> ORGANISM: Artificial Sequence
<220> FEATURE:
<223> OTHER INFORMATION: Sequencing of 3BNC117 Variable heavy CDR1
      following SHM optimization in mice
<220> FEATURE:
<221> NAME/KEY: misc_feature
<223> OTHER INFORMATION: Synthetic

<400> SEQUENCE: 283

Asp Tyr Phe Ile His
1               5

```
<210> SEQ ID NO 284
<211> LENGTH: 17
<212> TYPE: PRT
<213> ORGANISM: Artificial Sequence
<220> FEATURE:
<223> OTHER INFORMATION: Sequencing of 3BNC117 Variable heavy CDR2
      following SHM optimization in mice
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: may be substituted by Leu
<220> FEATURE:
<221> NAME/KEY: MISC_FEATURE
<222> LOCATION: (2)..(2)
<223> OTHER INFORMATION: may be substituted by Phe or Val
<220> FEATURE:
<221> NAME/KEY: MISC_FEATURE
<222> LOCATION: (3)..(3)
<223> OTHER INFORMATION: may be substituted by Lys
<220> FEATURE:
<221> NAME/KEY: MISC_FEATURE
<222> LOCATION: (4)..(4)
<223> OTHER INFORMATION: may be substituted by Leu
<220> FEATURE:
<221> NAME/KEY: MISC_FEATURE
<222> LOCATION: (5)..(5)
<223> OTHER INFORMATION: may be substituted by Thr , Arg, Met or Asn
<220> FEATURE:
<221> NAME/KEY: MISC_FEATURE
<222> LOCATION: (6)..(7)
<223> OTHER INFORMATION: may be substituted by Lys, Pro, Asn, Gln or Ala
<220> FEATURE:
<221> NAME/KEY: MISC_FEATURE
<222> LOCATION: (8)..(8)
<223> OTHER INFORMATION: may be substituted by Lys, Pro, His, Arg, Thr,
      Leu or Trp
<220> FEATURE:
<221> NAME/KEY: MISC_FEATURE
<222> LOCATION: (9)..(9)
<223> OTHER INFORMATION: may be substituted by Gln, His, Thr or Ala
<220> FEATURE:
<221> NAME/KEY: MISC_FEATURE
<222> LOCATION: (10)..(10)
<223> OTHER INFORMATION: may be substituted by Lys or Thr
<220> FEATURE:
<221> NAME/KEY: MISC_FEATURE
<222> LOCATION: (11)..(11)
<223> OTHER INFORMATION: may be substituted by His, Thr, Met, Lys, Ser,
      Pro or Val
<220> FEATURE:
<221> NAME/KEY: MISC_FEATURE
<222> LOCATION: (12)..(12)
<223> OTHER INFORMATION: may be substituted by His, Ser, Leu or Arg
<220> FEATURE:
<221> NAME/KEY: MISC_FEATURE
<222> LOCATION: (13)..(13)
<223> OTHER INFORMATION: may be substituted by Ser, Gly, Cys, Leu, His
      or Val
<220> FEATURE:
<221> NAME/KEY: MISC_FEATURE
<222> LOCATION: (14)..(14)
<223> OTHER INFORMATION: may be substituted by Lys or His
<220> FEATURE:
<221> NAME/KEY: MISC_FEATURE
<222> LOCATION: (15)..(15)
<223> OTHER INFORMATION: may be substituted by Val, Leu or Cys
<220> FEATURE:
<221> NAME/KEY: MISC_FEATURE
<222> LOCATION: (16)..(16)
<223> OTHER INFORMATION: may be substituted by Lys, Pro, His or Leu
<220> FEATURE:
<221> NAME/KEY: MISC_FEATURE
<222> LOCATION: (17)..(17)
<223> OTHER INFORMATION: may be substituted by Val or Cys
```

<400> SEQUENCE: 284

Trp Ile Asn Pro Lys Thr Gly Gln Pro Asn Asn Pro Arg Gln Phe Gln
1               5                   10                  15

Gly

<210> SEQ ID NO 285
<211> LENGTH: 10
<212> TYPE: PRT
<213> ORGANISM: Artificial Sequence
<220> FEATURE:
<223> OTHER INFORMATION: Sequencing of 3BNC117 Variable heavy CDR3
      following SHM optimization in mice
<220> FEATURE:
<221> NAME/KEY: misc_feature
<223> OTHER INFORMATION: Synthetic

<400> SEQUENCE: 285

Gln Arg Ser Asp Tyr Trp Asp Phe Asp Val
1               5                   10

<210> SEQ ID NO 286
<211> LENGTH: 68
<212> TYPE: DNA
<213> ORGANISM: Artificial Sequence
<220> FEATURE:
<223> OTHER INFORMATION: Reference and Donor+Cas9gRNA1 IgM
<220> FEATURE:
<221> NAME/KEY: misc_feature
<223> OTHER INFORMATION: Synthetic

<400> SEQUENCE: 286
tggggcagtg gaacccaagt tactgtttcg tcagagagtc agtccttccc aaatgtcttc      60
cccctcgt                                                             68

<210> SEQ ID NO 287
<211> LENGTH: 34
<212> TYPE: DNA
<213> ORGANISM: Artificial Sequence
<220> FEATURE:
<223> OTHER INFORMATION: Reference IgHC gama 1
<220> FEATURE:
<221> NAME/KEY: misc_feature
<223> OTHER INFORMATION: Synthetic

<400> SEQUENCE: 287
ccaaaacgac acccccatct gtctatccac tggc                                34

<210> SEQ ID NO 288
<211> LENGTH: 34
<212> TYPE: DNA
<213> ORGANISM: Artificial Sequence
<220> FEATURE:
<223> OTHER INFORMATION: Reference IgHC gama 2b
<220> FEATURE:
<221> NAME/KEY: misc_feature
<223> OTHER INFORMATION: Synthetic

<400> SEQUENCE: 288
ccaaaacaac acccccatca gtctatccac tggc                                34

<210> SEQ ID NO 289
<211> LENGTH: 34
<212> TYPE: DNA
<213> ORGANISM: Artificial Sequence
<220> FEATURE:
<223> OTHER INFORMATION: Reference IgHC gama 3

-continued

```
<220> FEATURE:
<221> NAME/KEY: misc_feature
<223> OTHER INFORMATION: Synthetic

<400> SEQUENCE: 289
ctacaacaac agccccatct gtctatccct tggt                                    34

<210> SEQ ID NO 290
<211> LENGTH: 68
<212> TYPE: DNA
<213> ORGANISM: Artificial Sequence
<220> FEATURE:
<223> OTHER INFORMATION: Reference IgHC gama 2c/a
<220> FEATURE:
<221> NAME/KEY: misc_feature
<223> OTHER INFORMATION: Synthetic

<400> SEQUENCE: 290
tggggcagtg gaacccaagt tactgtttcg tcagccaaaa caacagcccc atcggtctat        60
ccactggc                                                                 68

<210> SEQ ID NO 291
<211> LENGTH: 68
<212> TYPE: DNA
<213> ORGANISM: Artificial Sequence
<220> FEATURE:
<223> OTHER INFORMATION: Donor 3
<220> FEATURE:
<221> NAME/KEY: misc_feature
<223> OTHER INFORMATION: Synthetic

<400> SEQUENCE: 291
tggggcagtg gaacccaagt tactgtttcg tcagccaaaa cgacacccccc atctgtctat       60 ccattggc                                                                 68

<210> SEQ ID NO 292
<211> LENGTH: 68
<212> TYPE: DNA
<213> ORGANISM: Artificial Sequence
<220> FEATURE:
<223> OTHER INFORMATION: Donor+Cas9gRNA1 IgG
<220> FEATURE:
<221> NAME/KEY: misc_feature
<223> OTHER INFORMATION: Synthetic

<400> SEQUENCE: 292
tggggcagtg gaacccaagt tactgtttcg tcagccaaaa cgacacccccc atcggtctat       60 ccactggc                                                                 68
```

GENETIC ENGINEERING OF B CELL RECEPTORS AND USES THEREOF IN ANTIGEN-INDUCED ANTIBODY SECRETION

CROSS-REFERENCE TO RELATED APPLICATIONS

The present application is a continuation-in-part of international application no. PCT/IL2019/051026, filed Sep. 12, 2019, insofar as it designates the United States, which in turn claims benefit of U.S. provisional applications 62/730,561, filed Sep. 13, 2018, and 62/840,429, filed Apr. 30, 2019. The entire contents of each of these applications are hereby incorporated herein by reference.

FIELD OF THE INVENTION

The invention relates to gene therapy, specifically, immunotherapy. More specifically, the invention relates to methods and compositions for engineering B cells to express transgenic B cell receptor (BCR) for antigen-induced antibody secretion, compositions, methods and uses thereof in immunotherapy.

SEQUENCE LISTING INCORPORATION BY REFERENCE

The instant application contains a Sequence Listing, which has been submitted electronically in ASCII format and is hereby incorporated by reference in its entirety. Said ASCII copy, created on Mar. 12, 2021, is named P2021-03-12SequenceListing_BARZEL2A_ST25.txt and is 220 kilobytes in size.

BACKGROUND ART

References considered to be relevant as background to the presently disclosed subject matter are listed below:
[1] Luo X M, et al. Blood. 2009; 113(7):1422-1431.
[2] Fusil F, et al. Mol Ther. 2015; 23(11):1734-1747.
[3] US20160289637
[4] Lin Y C, et al., EMBO J. 2018 Aug. 7. pii: e99243. doi: 10.15252/embj.201899243.
[5] Greiner, V. et al. iScience 12, 369-378 (2019).
[6] Voss, J. E. et al. Elife (2019). doi:10.7554/eLife.42995.
[7] Hartweger, H. et al. Journal of Experimental Medicine 216, 1301-1310 (2019).
[8] Moffett, H. F. et al. Sci. Immunol. 4, (2019).
[9] WO 2019/028417.
[10] Laskov, R., et al. Mol. Immunol. 48, 733-745 (2011)
[11] Yeap, L. S. et al. Cell 163, 1124-1137 (2015).
[12] Hwang, J. K. et al. Proc. Natl. Acad. Sci. 201709203 (2017). doi:10.1073/pnas.1709203114
Acknowledgement of the above references herein is not to be inferred as meaning that these are in any way relevant to the patentability of the presently disclosed subject matter.

BACKGROUND OF THE INVENTION

Monoclonal Antibodies are used widely to treat diverse medical conditions, including cancer autoimmune diseases. However, monoclonal Antibody therapy is rarely curative. An Antibody has a limited half-life and has to be repeatedly administered at a very high financial cost and with aggravated risk for the development of anti-drug antibodies. The genetic engineering of B cells for antibody secretion may overcome these limitations, but previous attempts used mostly lentiviral vectors and transposons, which integrate promiscuously and do not allow natural activation of the transgenic B cell receptor (BCR) for antigen-induced antibody secretion.

More specifically, B cells naturally express BCRs on their cell membranes. Upon specific binding of an appropriate antigen to the BCR, the B cell may be activated, and it may differentiate into an antibody secreting plasma cell. Antigen-induced activation is a tightly regulated process, which takes place mainly in germinal centers, and which requires the participation of dedicated T cells and dendritic cells. Importantly, antigen-induced B cell activation in the germinal centers allows for affinity maturation, class switch recombination and memory retention.

Several methods have been published regarding cell engineering for antibody secretion.

Luo et al. have engineered human hematopoietic stem/progenitor cells to produce an anti-HIV Ab upon in vitro maturation to B cells [1]. However, expression levels were constitutively low as the lentivector-coded Ab did not allow B cell activation. Fusil et al. [2] used a different lentivector design that allowed B cell activation and differentiation into Ab producing plasma cells. However, the promiscuous and ectopic lentiviral integration as well as the synthetic poly adenyaltion sites that were used prevented native regulation on the transition from BCR expression to antibody secretion and did not allow for affinity maturation upon activation. Goldberg et al., [3] used genome editing to engineer B cells at the IgH locus. However, this publication only discusses introducing an antibody rather than engineering the BCR and therefore antigen induced activation, affinity maturation, class switch recombination and memory retention were not demonstrated. Bastisda et al. [4] describe in vivo CRISPR/Cas9 nuclease mediated strategy to generate knock-in mice of a DNA fragment bearing a pre-arranged human B-cell receptor heavy chain into the native murine immunoglobulin locus. This manipulation is performed in fertilized oocytes thereby manipulating germline B cells that result in deletion of the $D_4$ to $J_{1-4}$ endogenous segments in all B cells produced in the transgenic mice. This publication however, does not concerns engineering of B cells, nor any use thereof in gene therapy, specifically, the use of the engineered B cells as a therapeutic tool in a mammalian subject.

More recently, efficient CRISPR/Cas9-mediated integration of antibody genes was demonstrated into the Ig loci of primary human B cells [5]. Integration of an antibody's variable heavy chain into the immunoglobulin heavy (IgH) locus further allows somatic hyper-mutation (SHM) and class switch recombination in vitro when the endogenous constant segments are utilized using appropriate splicing signals [6]. In immunocompetent mice, adoptive transfer of B cells engineered to express HIV-bNAbs facilitated the production of HIV-neutralizing antibody titers [7]. Integration of single chain anti-RSV antibodies into the IgH locus further allowed protection from infection [8]. However, in these previous studies, antigen induced activation and immunological memory were not detected. Burton et al. [9], discloses methods for engineering B cells by CRISPR/Cas9-mediated integration of antibody genes that modify the Immunoglobulin loci, replacing the heavy chain variable region with a donor cassette comprising the immunoglobulin variable region of an antibody of interest. The insertion of immunoglobulin sequences into the specific J-gene break site disclosed therein, allowed class switch recombination and affinity maturation. Integration into this specific site requires the use of 3' homology arm that correspond to the J intron sequences, however, the 5' homology arm corresponds to genomic segments that are variable and are often deleted in different cells during VDJ recombination. Integration of exogenous DNA to such is therefore not effective, and moreover, requires the provision of specific homology arms for each and every target cell, as universal arms cannot be used.

Engineering BCRs requires a deep understanding of their structure and regulation. A BCR is a tetramer composed of two heavy chains and two light chains. The heavy chain is coded by the IgH locus, which has a very intricate internal structure allowing complex regulation. A first part of the IgH locus entails a large genomic sequence containing "V", "D" and "J" segments that may be assembled in multiple alternative ways during B cell development to code for the variable part of the chain. Upon B cell activation and differentiation into a plasma cell, the same genomic sequences code the variable heavy part of the secreted antibody. A second part of the IgH locus entails a genomic sequence containing "C" segments corresponding to the exons coding for the constant part of the BCR. Developmentally regulated alternative poly-adenylation and alternative splicing at end of the C coding sequence allow the coding of a secreted antibody, which is similar to the BCR but is devoid of the membrane anchoring domains.

The parts of the IgH loci coding for the variable and constant segments are separated by a stretch of DNA coding for an intron. Part of the same stretch of DNA also codes for an enhancer that is essential for B cell specific expression of the locus. Another part of the same stretch is the switch region, which may be a substrate for class switch recombination catalyzed by the enzyme AID.

In activated B lymphocytes, AID initiates antibody variable (V) exon somatic hypermutation (SHM) for affinity maturation in germinal centers. Somatic Hypermutation hotspots are defined as WRCH, DGYW, RCY and RGY motifs of the variable immunoglobulin genes, as described by Laskov et al. [10]. Any transgene inserted at the loci of immunoglobulin genes in AID expressing cells will undergo SHM preferentially in these hotspots.

Yeap et al. have developed a mouse V(D)J exon passenger allele system to assay patterns and levels of intrinsic SHMs of desired test sequences in germinal center B cells i.e. an in vivo assay to study AID-targeting of passenger sequences [11].

Later, Hwang et al. used this approach to assay intrinsic SHM across passenger substrates that represent various stages in the maturation of a human VRC01-class broadly neutralizing Antibody (bnAb) against HIV-1 strains. They identified potentially rate-limiting SHMs and revealed how SHM-targeting frequencies change during this VRC01-class bnAb maturation process [12].

Thus, there is need for novel technologies for the genetic engineering of B cell receptors (BCRs) in B cells enabling natural-like antigen-induced B cell activation. Such functional engineered BCRs allow antigen induced activation, affinity maturation, class switch recombination and memory retention.

SUMMARY OF THE INVENTION

In a first aspect, the present invention relates to a method of genetic engineering of a B cell receptor (BCR) in a mammalian cell of the B cell lineage. More specifically, the method of the invention may comprise the step of contacting the cell with at least one nucleic acid cassette comprising at least one nucleic acid sequence of interest or with any vector or vehicle comprising the cassette. In some specific embodiments, the nucleic acid sequence of interest comprised within the cassette used by the methods of the invention may comprise a nucleic acid sequence coding for at least one variable domain of an immunoglobulin heavy chain (VH) and at least one splice donor site (SD). In some embodiments, the nucleic acid sequence of interest comprised within the cassette used by the methods of the invention may comprise at least one splice acceptor site (SA). In some embodiments, the VH is followed by the SD, specifically, the SD is located downstream to the VH. In yet some further embodiments, the SA may be located upstream to the VH. It should be noted that in some embodiments, the nucleic acid cassette used by the methods of the invention targets the insertion of the nucleic acid sequence of interest into a target genomic sequence within the Immunoglobulin heavy chain (IgH) locus. In more specific embodiments, the target sequence may be located upstream of at least one splice acceptor site of the constant domain of the heavy chain of the BCR.

The invention further provides a method of genetic engineering of a BCR of a cell of the B cell lineage in a mammalian subject in need thereof, by administering to the subject the cassette of the invention or any vehicle or composition thereof.

In yet some further aspect thereof, the invention provides a method of engineering a mammalian cell of the B lineage for antigen-induced secretion of an antibody of interest, or of any fragment thereof, specifically, an antigen-binding fragment thereof. More specifically, the method of the invention may comprise the step of contacting the cell with at least one nucleic acid cassette comprising at least one nucleic acid sequence of interest and at least one SD, or with any vector or vehicle comprising said cassette.

In another aspect, the invention relates to an engineered mammalian cell of the B lineage expressing a genetically engineered BCR. It should be noted that in some embodiments, the cell provided by the invention is transduced or transfected with at least one nucleic acid cassette comprising at least one nucleic acid sequence of interest or of any vector or vehicle comprising the cassette.

In yet a further aspect, the invention provides a genetically engineered BCR comprising an amino acid sequence of interest. It should be noted that the amino acid sequence of interest of the BCR of the invention may comprise at least one variable domain of an immunoglobulin heavy chain.

Another aspect of the invention relates to a nucleic acid cassette comprising at least one nucleic acid sequence of interest. It should be noted that the sequence of interest may comprise a nucleic acid sequence coding for at least one variable domain of an immunoglobulin heavy chain and at least one splice donor site. In some specific embodiments the sequence coding for the VH is followed by the SD site. In some embodiments, the nucleic acid sequence of interest comprised within the cassette used by the methods of the invention may comprise at least one SA. In yet some further embodiments, the SA may be located upstream to the VH.

Another aspect of the invention relates to a host cell transduced or transfected with at least one nucleic acid cassette of the invention.

The invention further provides a pharmaceutical composition comprising at least one nucleic acid cassette, or any vector or cell comprising the cassette of the invention. In some embodiments, the nucleic acid cassette of the composition of the invention may comprise at least one nucleic acid sequence of interest and at least one SD.

In yet another aspect, the invention provides a method for treating, preventing, ameliorating, inhibiting or delaying the onset of a pathologic disorder in a mammalian subject. More specifically, the therapeutic method of the invention may comprise the step of administering to the treated subject an effective amount of at least one of (a) nucleic acid cassette; (b) a vector comprising said nucleic acid cassette; (c) a cell transduced or transfected with the nucleic acid cassette or with any vector comprising said cassette; and (d) a composition comprising at least one of (a), (b) and (c).

Still further aspect of the invention relates to an effective amount of at least one nucleic acid cassette or any vehicle or cell comprising such cassette or any composition thereof for use in a method for treating, preventing, ameliorating, inhibiting or delaying the onset of a pathologic disorder in a mammalian subject.

Another aspect of the invention relates to a method of genetic engineering of a BCR in a primary mammalian cell of the B cell lineage. More specifically, the method comprises the step of contacting the cell with at least one nucleic acid cassette comprising at least one nucleic acid sequence of interest or with any vector or vehicle comprising the cassette. It should be noted that in some embodiments, the nucleic acid sequence of interest comprises a nucleic acid sequence coding for at least one variable domain of an immunoglobulin gene. In more specific embodiments, the nucleic acid sequence further comprises at least one exogenous hotspot motif/s for somatic hypermutation/s.

It should be understood that the somatic hyper mutation/s retain or minimally change the protein translated from said nucleic acid sequence.

In yet another aspect, the invention provides a method of genetic engineering of a BCR of a cell of the B cell lineage in a mammalian subject in need thereof. In more specific embodiments, the method comprising the step of administering to the subject an effective amount of at least one nucleic acid cassette comprising at least one nucleic acid sequence of interest or of any vector or vehicle comprising said cassette. More specifically, the nucleic acid sequence of interest comprises a nucleic acid sequence coding for at least one variable domain of an immunoglobulin gene. In yet some further embodiments, the nucleic acid sequence further comprises at least one exogenous hotspot motif/s for somatic hypermutation/s, said somatic hyper mutation/s retain or minimally change the protein translated from said nucleic acid sequence.

A further aspect of the invention relates to a method of engineering a mammalian cell of the B lineage for antigen-induced secretion of an antibody of interest, or of any antigen-binding fragment thereof. More specifically, the method of the invention may comprise the step of contacting the cell with at least one nucleic acid cassette comprising at least one nucleic acid sequence of interest or with a vector comprising said cassette. More specifically, the nucleic acid sequence of interest comprises a nucleic acid sequence coding for at least one variable domain of an immunoglobulin gene. In yet some further embodiments, the nucleic acid sequence further comprises at least one exogenous hotspot motif/s for somatic hypermutation/s. It should be noted that the somatic hyper mutation/s retain or minimally change the protein translated from said nucleic acid sequence.

Still further, the invention relates in another aspect thereof to an engineered mammalian cell of the B lineage expressing a genetically engineered BCR. The cell of the invention is transduced or transfected with at least one nucleic acid cassette comprising at least one nucleic acid sequence of interest or of any vector or vehicle comprising the cassette.

In some embodiments, the nucleic acid sequence of interest comprises a nucleic acid sequence coding for at least one variable domain of an immunoglobulin gene. In more specific embodiments, the nucleic acid sequence further comprises at least one exogenous hotspot motif/s for somatic hypermutation/s. It should be noted that the somatic hyper mutation/s retain or minimally change the protein translated from said nucleic acid sequence.

In yet some further aspect, the invention provides a genetically engineered BCR comprising an amino acid sequence of interest. More specifically, the nucleic acid sequence of interest encoding the amino acid sequence of the genetically engineered BCR of the invention, may comprises a nucleic acid sequence coding for at least one variable domain of an immunoglobulin gene. In some embodiments, the nucleic acid sequence further comprises at least one exogenous hotspot motif/s for somatic hypermutation/s. More specifically, the somatic hyper mutation/s retain or minimally change the protein translated from said nucleic acid sequence. In yet some further embodiments, the BCR of the invention is engineered by targeted insertion of said nucleic acid sequence of interest into a target genomic sequence within at least one immunoglobulin locus, in a mammalian cell of the B lineage.

Another aspect of the invention relates to a nucleic acid cassette comprising at least one nucleic acid sequence of interest. More specifically, the nucleic acid sequence of interest comprises a nucleic acid sequence coding for at least one variable domain of an immunoglobulin gene. In some embodiments, such nucleic acid sequence further comprises at least one exogenous hotspot motif/s for somatic hypermutation/s. It should be understood that the somatic hyper mutation/s retain or minimally change the protein translated from said nucleic acid sequence. In yet some further embodiments, the nucleic acid cassette targets the insertion of the nucleic acid sequence of interest into a target genomic sequence within at least one immunoglobulin locus, in a mammalian cell of the B lineage.

Still further, in another aspect, the invention provides a host cell transduced or transfected with at least one nucleic acid cassette or any vector or vehicle thereof. It should be noted that the host cell of the invention may be transduced or transfected with any of the nucleic acid cassettes described by the invention.

In yet some further aspect, the invention provides a pharmaceutical composition comprising at least one nucleic acid cassette, or any vector or cell comprising the cassette. More specifically, the cassette of the composition of the invention may comprise at least one nucleic acid sequence of interest comprising a nucleic acid sequence coding for at least one variable domain of an immunoglobulin gene. More specifically, the nucleic acid sequence further comprises at least one exogenous hotspot motif/s for somatic hypermutation/s. In yet some optional embodiments of the compositions of the invention, the composition further comprise at least one of pharmaceutically acceptable carrier/s, diluent/s, excipient/s and additive/s.

Another aspect of the invention relates to a method for treating, preventing, ameliorating, inhibiting or delaying the onset of a pathologic disorder in a mammalian subject. In some embodiments, the method comprising the step of administering to the subject an effective amount of at least one of: (a) nucleic acid cassette; (b) a vector comprising said nucleic acid cassette; and (c) a cell transduced or transfected with the nucleic acid cassette. In some embodiments, the cassette comprises at least one nucleic acid sequence of interest comprising a nucleic acid sequence coding for at least one variable domain of an immunoglobulin gene. In more specific embodiments, the nucleic acid sequence further comprises at least one exogenous hotspot motif/s for somatic hypermutation/s. In some embodiments, the somatic hyper mutation/s retain or minimally change the protein translated from the nucleic acid sequence. In some further embodiments, the nucleic acid cassette targets the insertion of said nucleic acid sequence of interest into a target genomic sequence within at least one immunoglobulin locus in a mammalian cell of the B cell lineage.

Still further, the invention provides an effective amount of at least one nucleic acid cassette or any vehicle or cell comprising said cassette or any composition thereof for use in a method for treating, preventing, ameliorating, inhibiting or delaying the onset of a pathologic disorder in a mammalian subject. In more specific embodiments, the cassette comprises at least one nucleic acid sequence of interest comprising a nucleic acid sequence coding for at least one variable domain of an immunoglobulin gene. Still further, the nucleic acid sequence further comprises at least one exogenous hotspot motif/s for somatic hypermutation/s. In some embodiments, the somatic hyper mutation/s retain or minimally change the protein translated from said nucleic acid sequence.

These and other aspects of the invention will become apparent by the hand of the following drawings.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A-1D: Cleavage by CRISPR/Cas9 of the murine IgH locus using the mH69 guide RNA.

FIG. 1A: Schematic representation of the IgH locus that comprise the "V", "D" and "J" segments that form the variable part of the chain and the "C" segments corresponding to the exons coding for the constant part of the BCR. The mH69 CRISPR/Cas9 cleavage site situated downstream to the J region of the murine immunoglobulin heavy chain is shown in the top frame. The homology arms chosen for the Homology Directed Repair do not include the last J segment (J4) nor the intronic Enhancer (iEµ).

FIG. 1B: TIDE (top frame) and T7E1 (bottom 3 frames) analysis of the CRISPR/Cas9 cleavage efficiency in a pro-B cell line using the mH69 guide RNA delivered by ribonucleoprotein (RNP) transfection.

FIG. 1C: TIDE (top frame) and T7E1 (bottom 3 frames) analysis of the CRISPR/Cas9 cleavage efficiency in a pro-B cell line using transfection of a plasmid expressing both Cas9 and mH69.

FIG. 1D: Locus representation of the human IgH locus.

FIG. 2A: Schematic representation of the ADN151 construct: Left and Right Homology Arms (LHA, RHA respectively) flank the genetic insert composed of a mutated IgH promoter that drives GFP expression upon genomic insertion into the mH69 site at the IgH.

FIG. 2B: Demonstration by PCR of the integration of ADN151 into the mH69 site in a pro B cell line. Arrows designate a primer in the construct and a primer inside the genome outside of the homology arms.

FIG. 2C: GFP expression in in-vitro cultured primary lymphocytes following ADN151 integration into the mH69 site in a pro B cell line. Flow Cytometry analysis at 3, 6, 10 and 14 days after transfection of the donor plasmid with a plasmid expressing Cas9 and the specific gRNA mH69 or a nonspecific gRNA mK64.

Figures 2A, 2B, 2C:
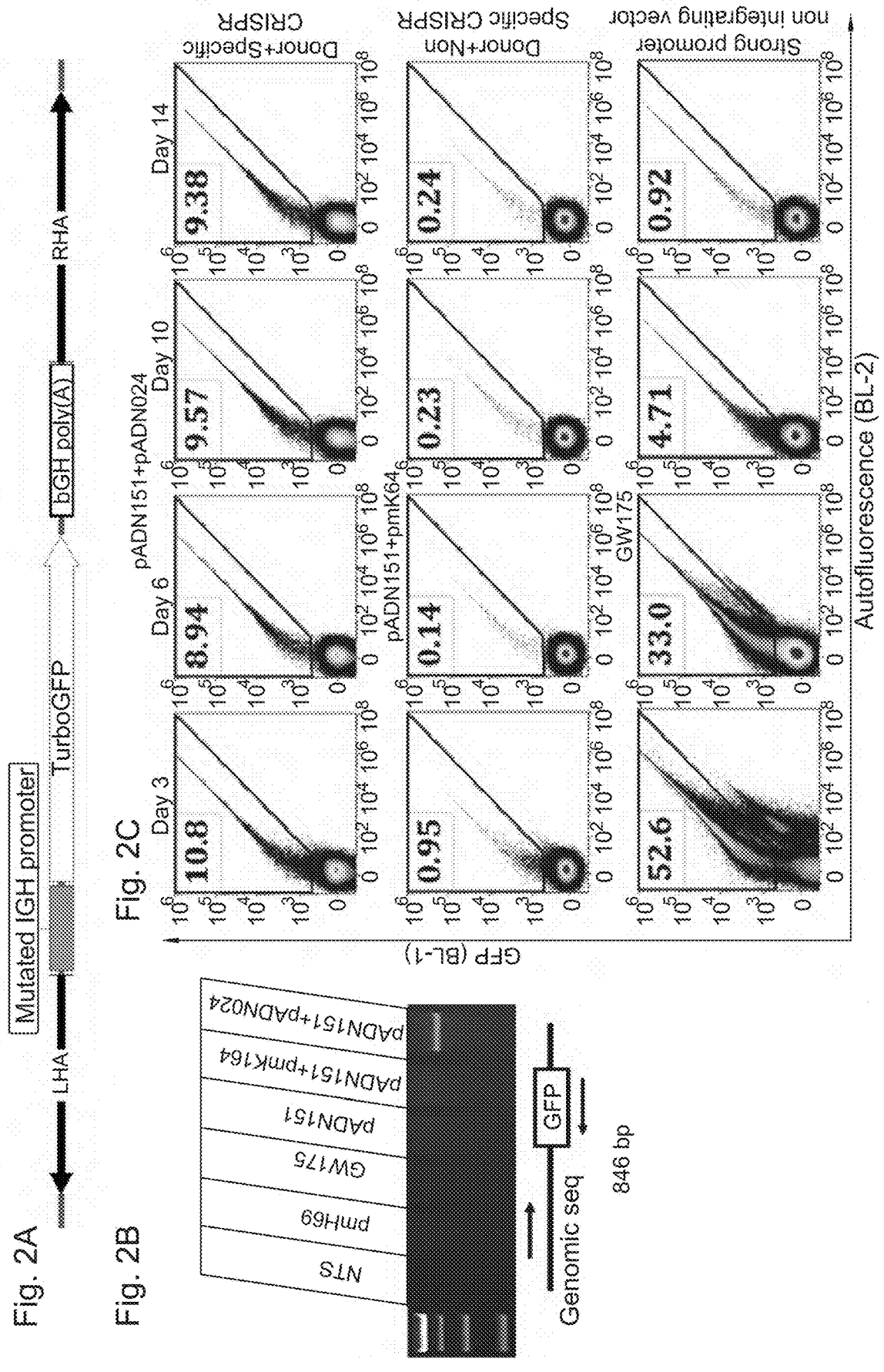
FIG. 2A-2D: Integration of the GFP construct ADN151 into the mH69 cleavage site.
Figure 2D:
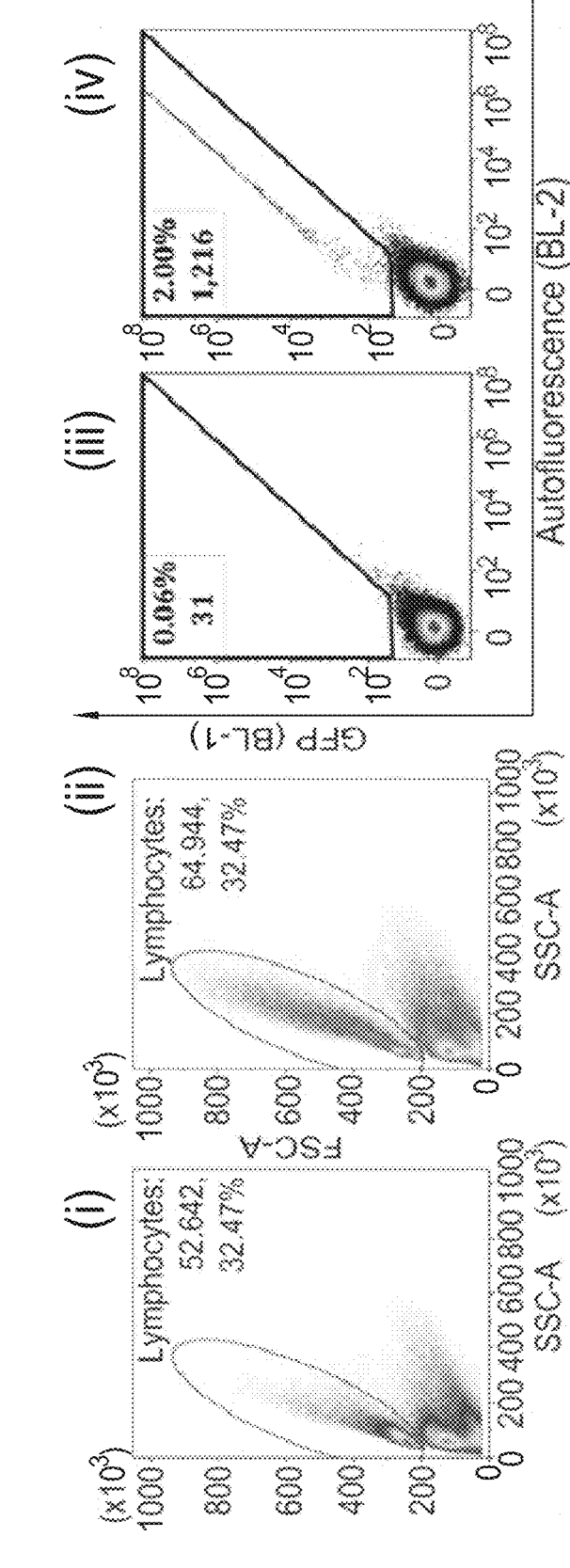

FIG. 2D: GFP expression in in-vitro of activated primary splenic lymphocytes following ADN151 integration into the mH69 site. The two left panels (2D i and 2D ii) show the lymphocyte gating following Cas9 transfection with or without the mH69 guide RNA. The right panels (2D iii and 2D iv) show GFP marking only upon co-transfection of the mH69 guide RNA.

FIG. 3A-3D: Integration of the GFP construct ADN157CF2 into the mH69 cleavage site.

Figures 3A, 3B:
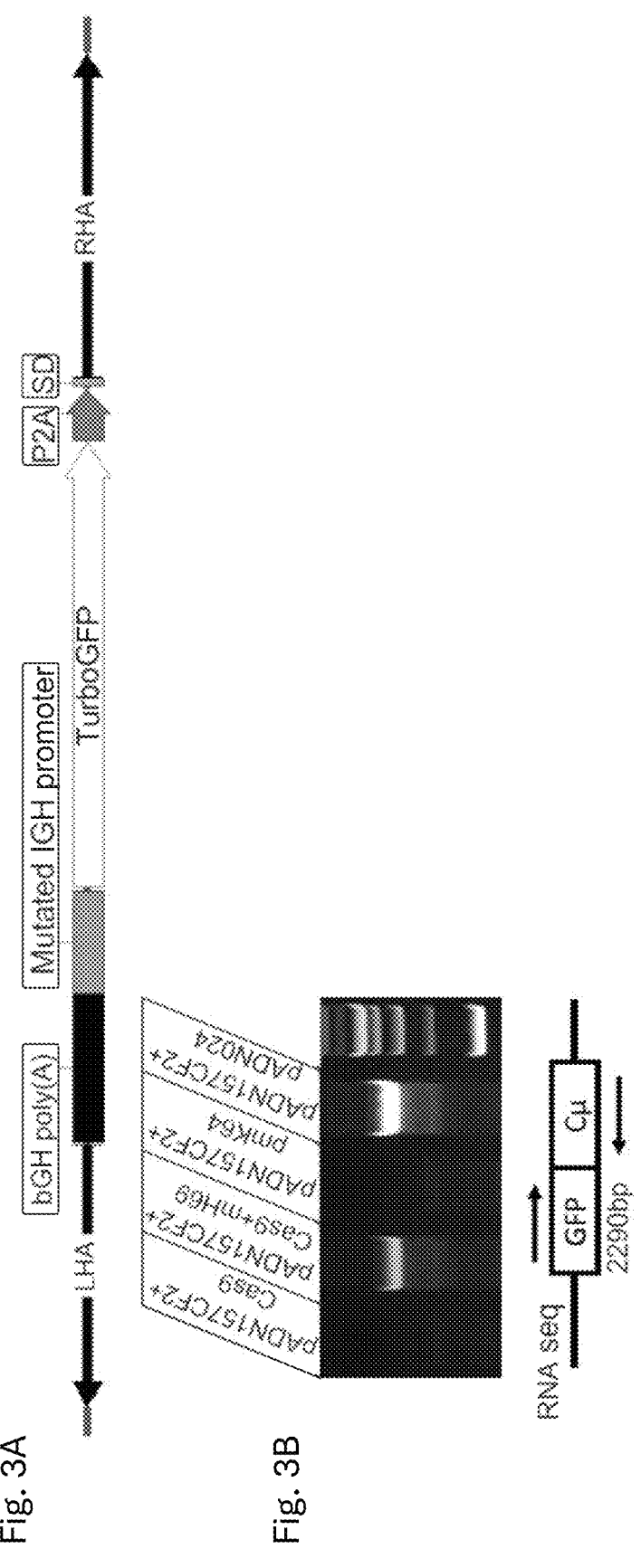

FIG. 3A: Schematic representation of the ADN157CF2 construct. The promoter is preceded by a polyA. The GFP gene is followed by a sequence coding for a 2A peptide and a splice donor.

FIG. 3B: Demonstration by RT-PCR of both transcription and correct splicing following integration of ADN157CF2 into the mH69 site in a pro B cell line. The mH69 inserted as a guide with the Cas9 protein (second lane from left) or as a plasmid (fourth lane from left) were used. pmK64 is a plasmid expressing Cas9 together with a guide cleaving in the kappa locus and is used here as a negative control. Arrows designate a primer inside the first membranal exon of the Cµ and another primer inside the GFP gene.

Figures 3C, 3D:
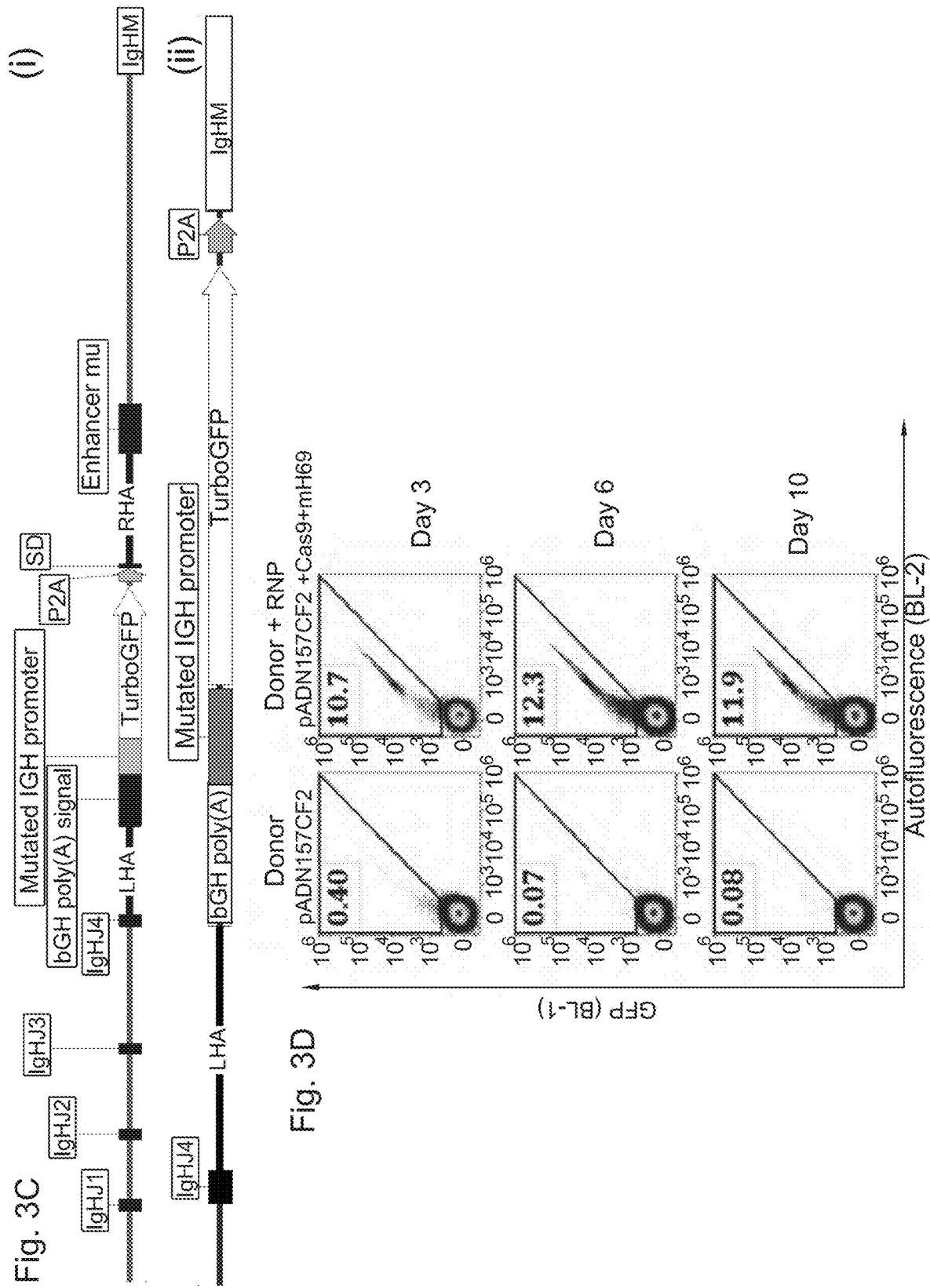

FIG. 3C: Alignments of one of the above positive bands showing splicing that occurs between the inserted sequence and the different exons of the endogenous Cµ. The resulting sequences are denoted by SEQ ID NO. 36.

FIG. 3D: ADN157CF2 integration into the mH69 site allows GFP expression in a pro B cell line. GFP expression was assayed by Flow Cytometry 3,6 and 10 days after transfection of the donor plasmid with or without RNP.

FIG. 4A-4E: Integration of the Palivizumab construct ADN191 into the mH69 cleavage site.

Figures 4A, 4B, 4C, 4D:
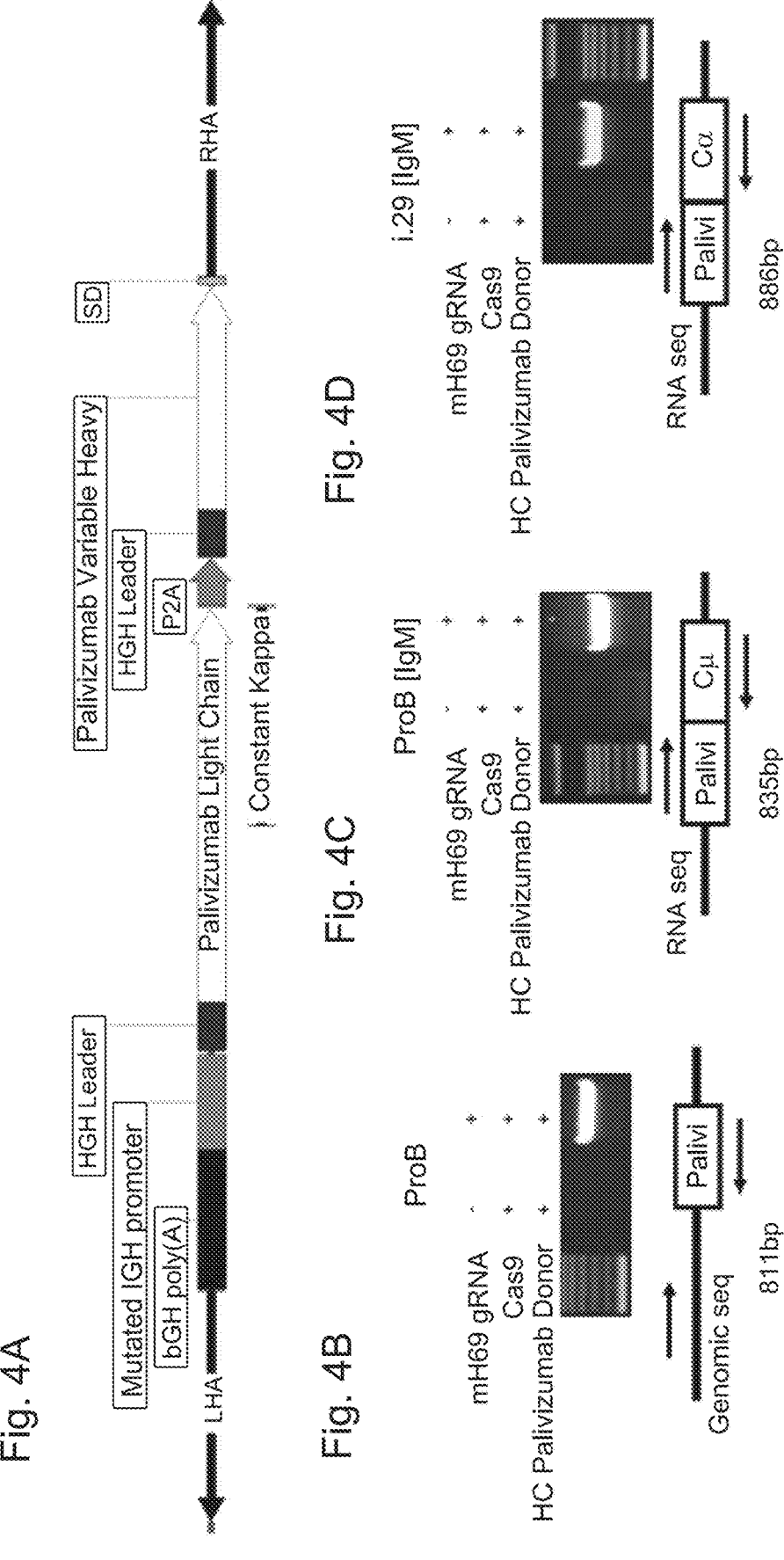

FIG. 4A: Schematic representation of the ADN191 construct. A bicistronic cassette encoding the full light chain of the anti-RSV antibody palivizumab, is followed by a sequence coding for a 2A peptide and the coding sequence for the variable domain of the palivizumab heavy chain, terminating with an SD. An HGH leader sequence precedes each chain to allow ER localization for secretion.

FIG. 4B: Demonstration by PCR of the integration of ADN191 into the mH69 site in a pro B cell line. Arrows designate a primer in the construct and a primer inside the genome outside of the homology arms.

FIG. 4C and FIG. 4D: demonstration by RT-PCR of transcription and splicing with the endogenous Cµ (FIG. 4C) in a pro B cell line and with the endogenous Cα in the B cell line i29 (FIG. 4D) following integration of ADN191 into the mH69 site. Arrows designate a primer in the construct and a primer in the sequence coding the respective constant domain.

Figure 4E:
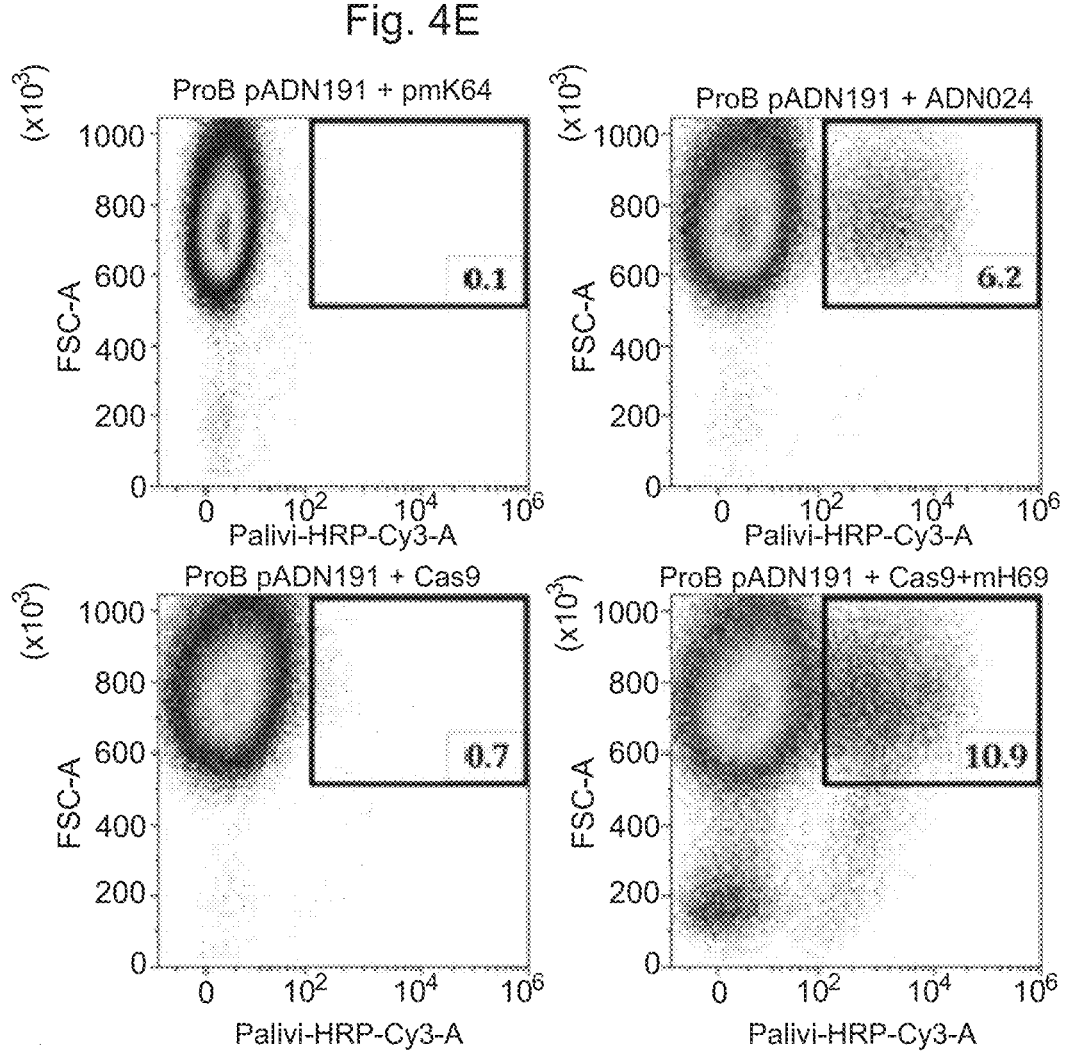

FIG. 4E: Demonstration by flow cytometry of palivizumab expression as a BCR on the membrane of a pro B cell line following CRISPR/Cas9 induced integration into the mH69 site. Flow cytometry scatter plot of the Palivizumab expression, detected by indirect Flow Cytometry using an anti-Palivizumab HRP conjugated together with an anti-HRP Cy3 conjugated. pMK64 is an irrelevant guide and pADN024 encodes the Cas9 protein and the mH69 guide RNA.

FIG. 5A-5G: Integration of the 3BNC117 construct ADN171 into the mH69 cleavage site and RNA expression.

FIG. 5A: Schematic representation of the ADN171 construct. A bicistronic 3BNC117 cassette encoding the full light chain of the anti-HIV antibody 3BNC117 is followed by a sequence coding for a 2A peptide and the coding sequence for the variable domain of the 3BNC117 heavy chain terminating with an SD. Human IgH variable leader sequences are also present.

FIG. 5B-5D: Demonstration by RT-PCR of transcription and splicing with the endogenous Cp in a Pro B cell line (FIG. 5B), i.29 B cell line (p53–/–, IgM+ variant) (FIG. 5C) and activated primary mouse Splenocytes (FIG. 5D). Arrows designate a primer inside the construct and inside the endogenous constant.

Figures 5E, 5F, 5G:
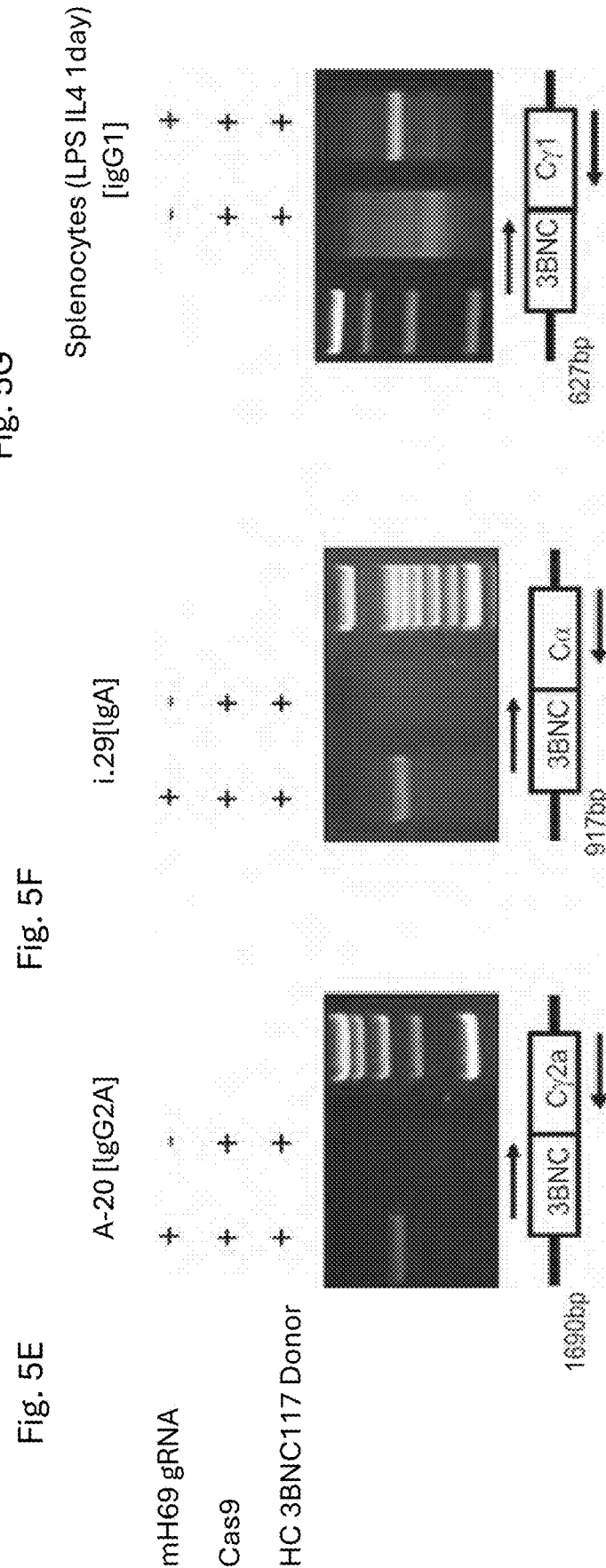

FIG. 5E-5G: Demonstration by RT-PCR of transcription and splicing with the endogenous Cγ2A in the A-20 B cell line (FIG. 5E), the Cα in i.29 B cell line (IgA+ variant) (FIG. 5F) and with the Cγ1 in activated primary mouse Spleno- cytes (FIG. 5G). Arrows designate a primer inside the construct and inside the endogenous constant.

FIG. 6A-6G: 3BNC117 expression as a membranal BCR following ADN171 integration at the mH69 site.

Figure 6A:
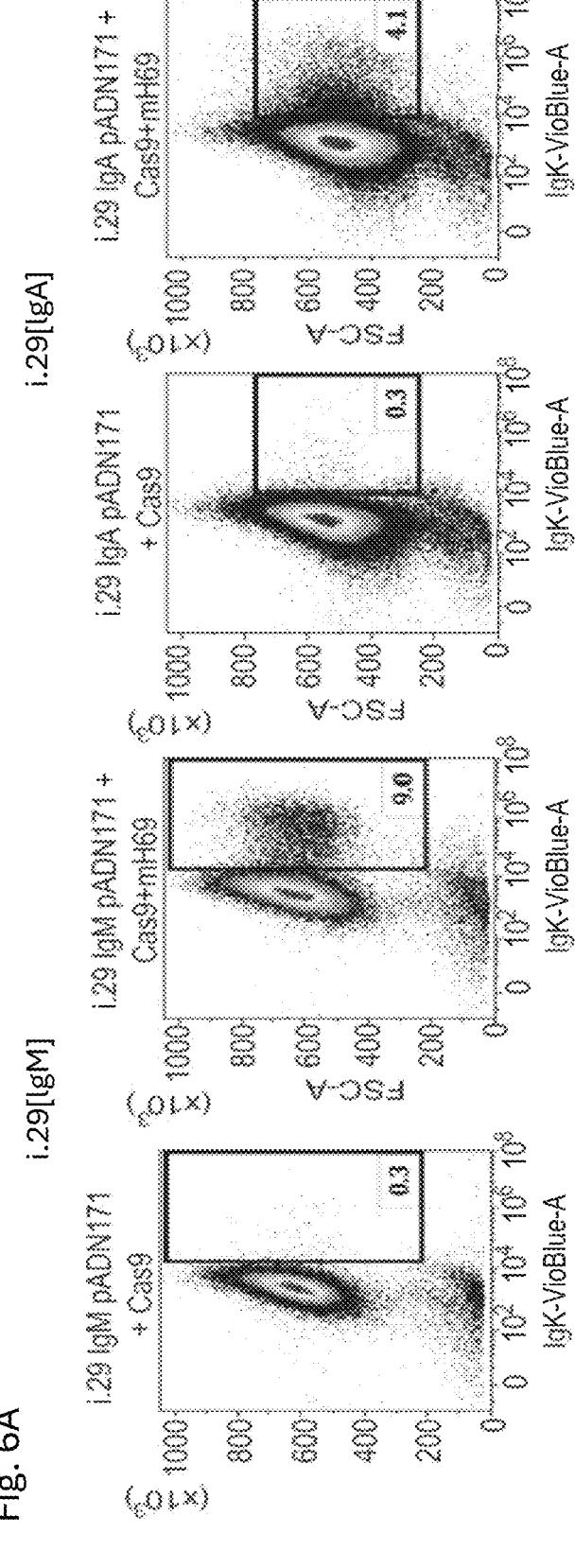
Figure 6B:
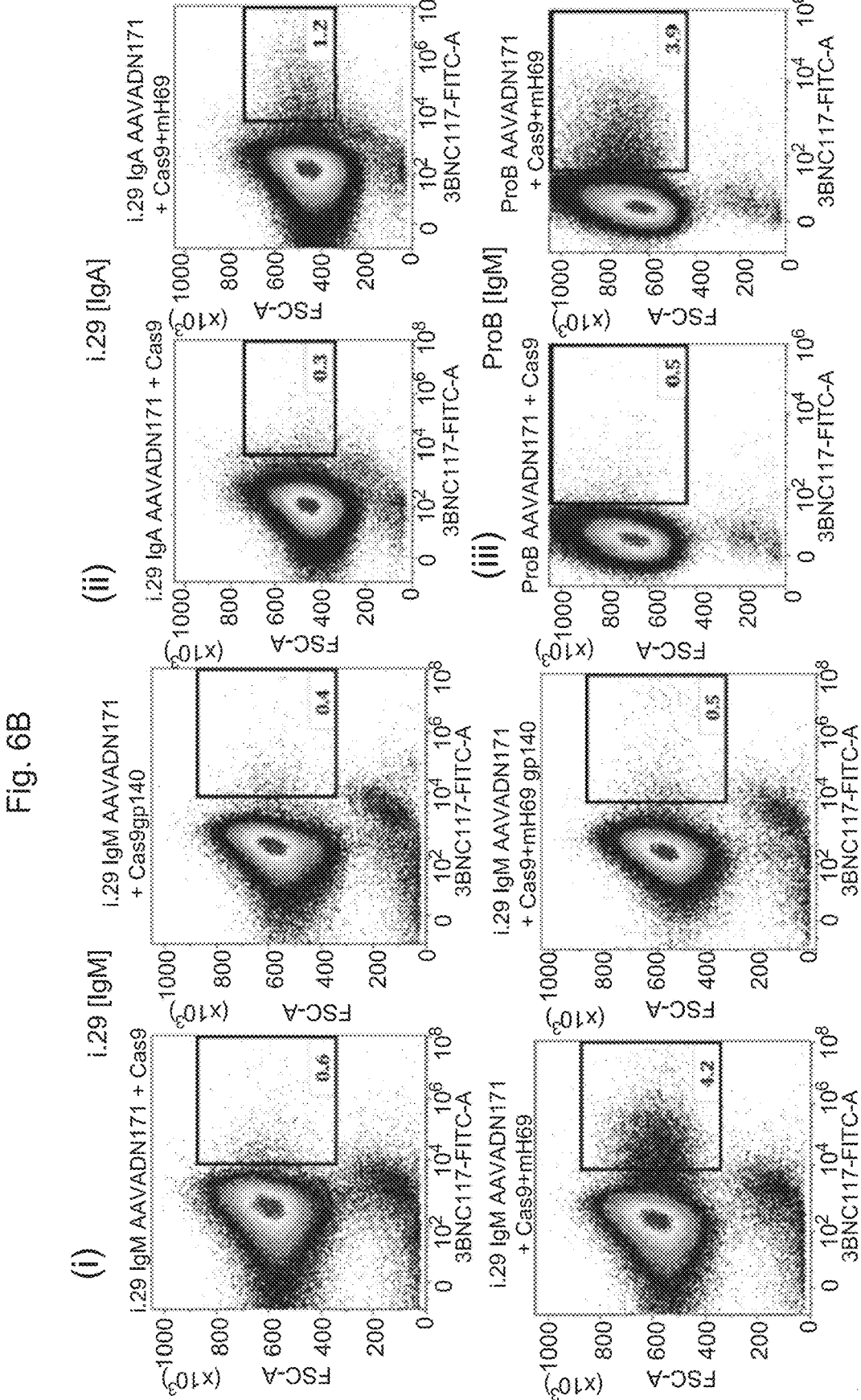

FIG. 6A: Detection of 3BNC117 expression by flow cytometry with an anti-Kappa antibody in otherwise lambda expressing i.29 cells FIG. 6B: Detection of 3BNC117 expression and binding to the HIV antigen gp140 by flow cytometry with His-tagged gp140 captured with a Rabbit anti-His tag and Camel anti-Rabbit FITC conjugated, in the i.29 B cell line, IgM variant (6Bi), i.29 IgA variant (6Bii) and a pro B cell line (6Biii).

Figures 6C, 6D:
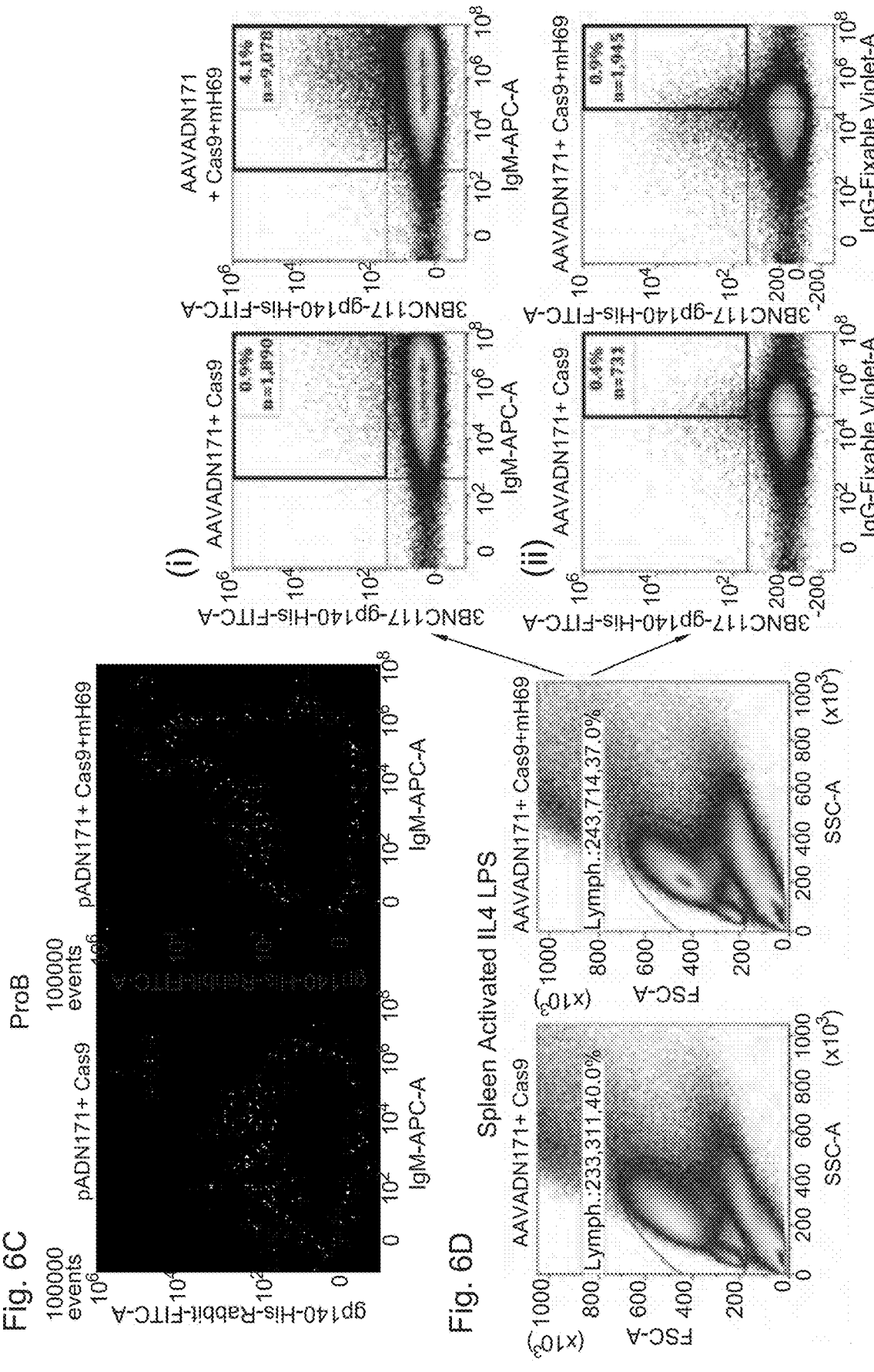

FIG. 6C: Detection of 3BNC117 expression as an IgM BCR and binding to the HIV antigen gp140 by flow cytom- etry with His-tagged gp140 captured with a Rabbit anti-His tag and Camel anti-Rabbit FITC conjugated, and anti-IgM (APC) in a pro B cell line.

FIG. 6D: Detection of 3BNC117 expression as an IgM BCR (top right, 6Di) or IgG BCR (bottom right, D(ii)) and binding to the HIV antigen gp140 by flow cytometry with His-tagged gp140 captured with a Rabbit anti-His tag and Camel anti-Rabbit FITC conjugated, and anti-IgM (APC, top right) or anti IgG (Fix.Vio.) in activated primary sple- nocytes.

FIG. 6E: Analysis by flow cytometry of 3BNC117 expressing activated primary splenocytes using antibodies as above, showing that most of these cells express the 3BNC117 as an IgM BCR.

FIG. 6F: Sandwich ELISA of supernatants collected 3 days after Electroporation and Transduction of activated splenocytes showing specific binding to gp140 with the isotype IgG. Signal was detected above background only when the guide RNA mH69 was included in the electropo- ration together with Cas9.

FIG. 6G: Sandwich ELISA of supernatants collected 3 days after Electroporation and Transduction of activated splenocytes showing specific binding to gp120 with the isotypes IgG and IgM. Signal was detected above back- ground only when the guide RNA mH69 was included in the electroporation together with Cas9.

FIG. 7A-7E: Engineering B cells to express an anti-HIV bNAb.

Figure 7A:
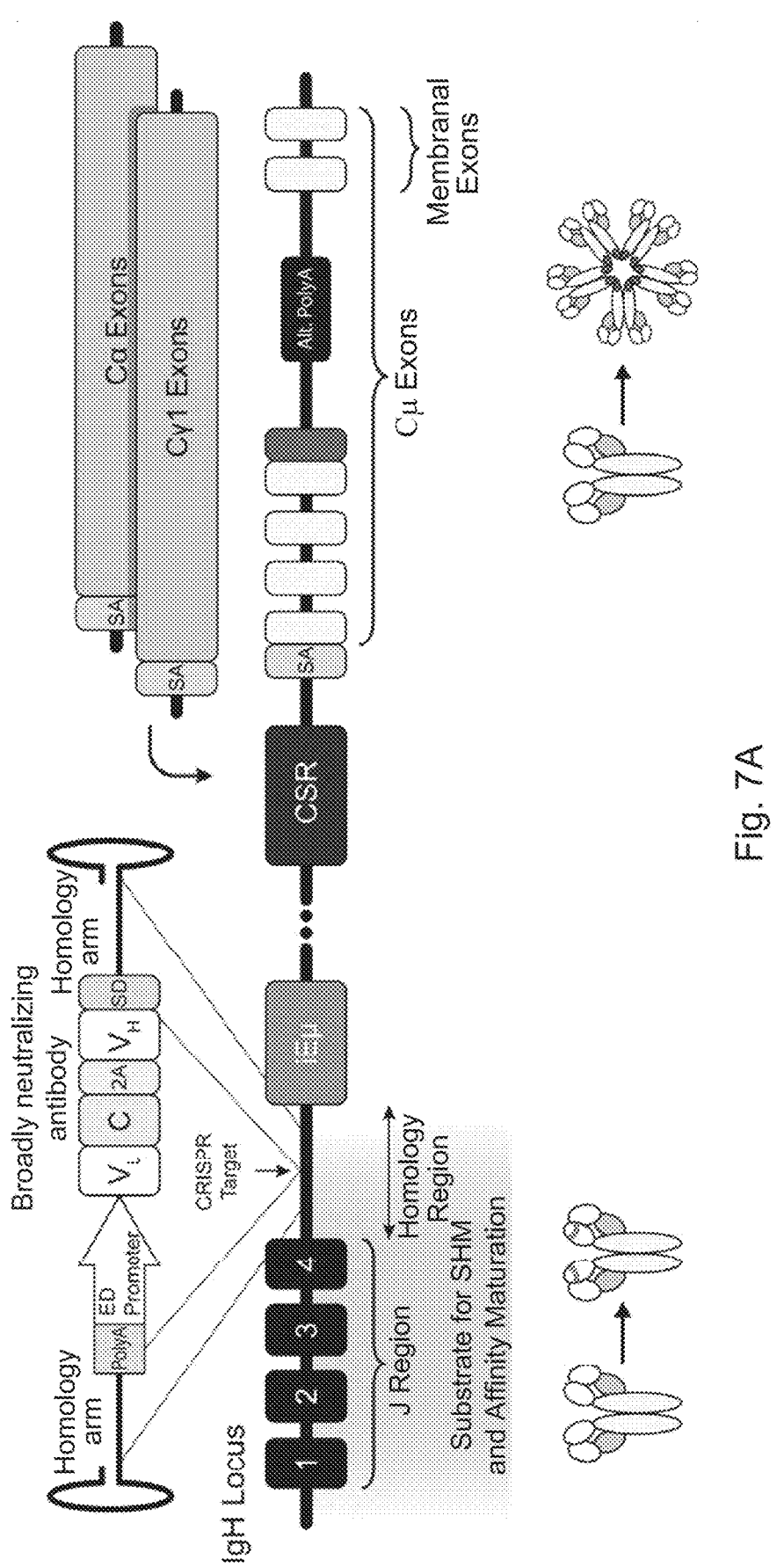

FIG. 7A: Targeting scheme. An AAV-delivered bicistronic cassette encoding the light and heavy chains of the 3BNC117 anti-HIV bNAb cassette (also designated herein as ADN221), under the control of an enhancer dependent (ED) promoter, is targeted to the J-C intron of the IgH locus using CRISPR/Cas9. Splicing with endogenous constant segments allows expression as a BCR and differentiation into memory B cells and Ig secreting plasma cells upon subsequent antigen-induced activation and alternative polyadenylation (Alt. PolyA). Targeting the J-C intron upstream of the intronic enhancer (iEμ) and switch region further facilitates CSR and SHM.

Figures 7B, 7C, 7D:
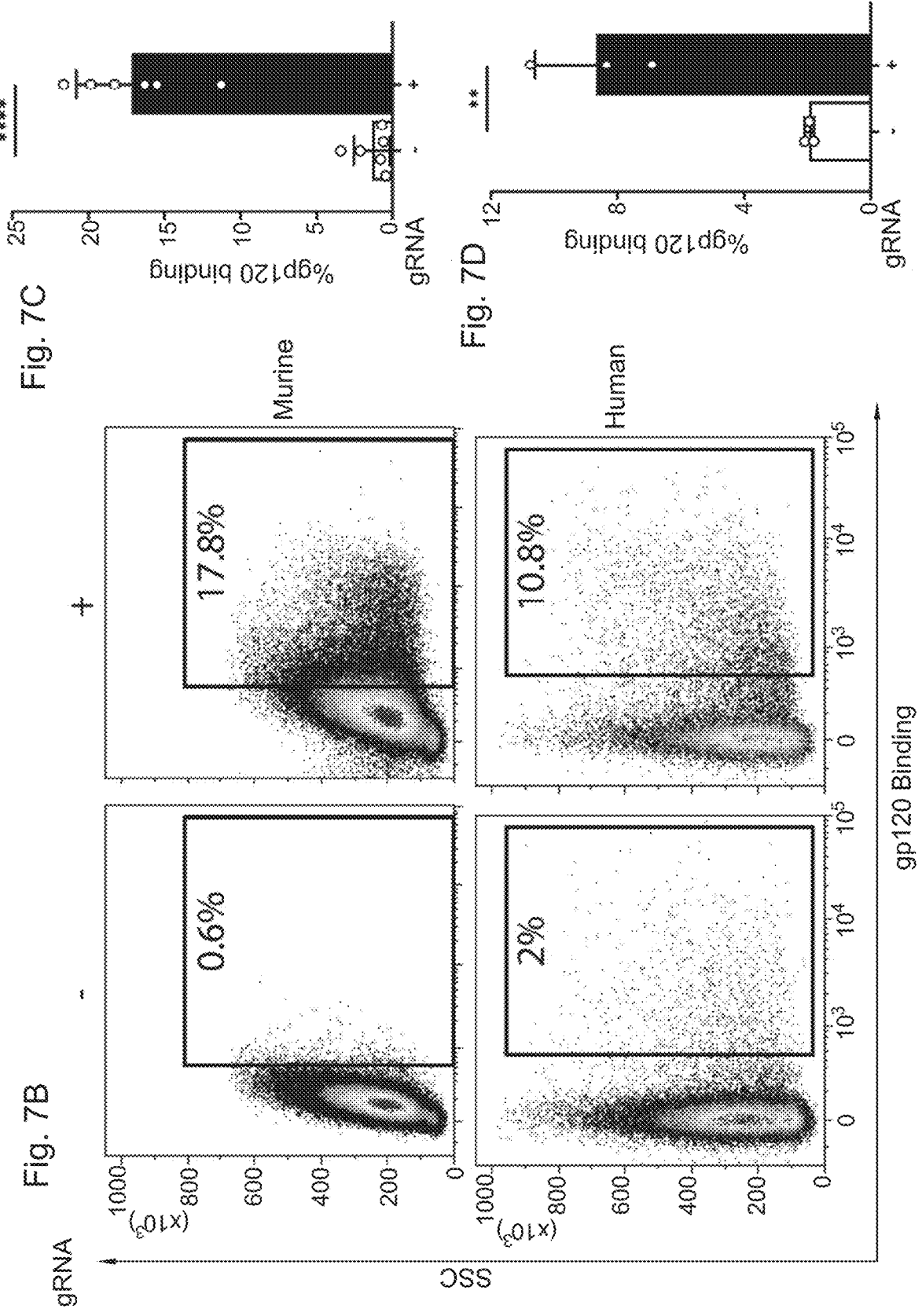

FIG. 7B: Flow cytometry plots measuring binding of the HIV gp120 antigen by the 3BNC117 BCR following TLR activation and engineering of primary cells. Human B cells are collected from blood samples, activated using an anti-RP105 (TLR4 homologue) antibody, electroporated by CRISPR/Cas9 RNP and transduced using rAAV-6. Splenic murine B cells are activated using the TLR4 agonist LPS, electroporated by CRISPR/Cas9 RNP and transduced using rAAV-DJ. Cells transduced with the donor rAAV and with- out gRNA serve as a negative control, gating on live, singlets.

FIG. 7C: Quantification of B for murine primary cells. Each dot represents an independent assay, **=pv<0.0001, =pv<0.001; unpaired t-test.

FIG. 7D: Quantification of B for human primary cells. Each dot represents an independent assay, **=pv<0.0001, =pv<0.001; unpaired t-test.

Figure 7E:
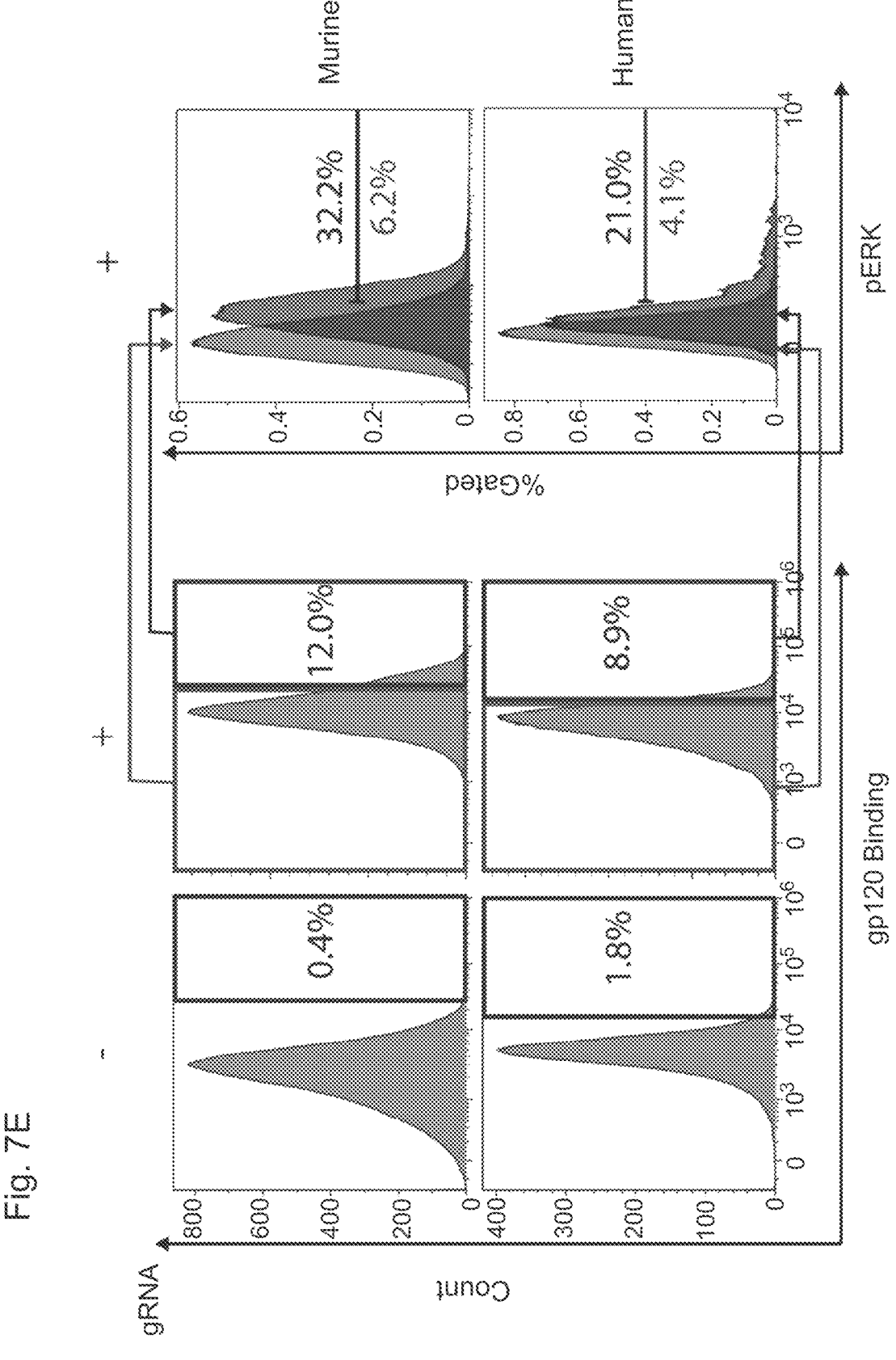

FIG. 7E: Flow cytometric analysis of ERK phosphory- lation in primary murine or human B cells engineered with 3BNC117 and in-vitro activated with the gp120 antigen of the YU2.DG HIV strain, gating on singlets.

Figure 8B:
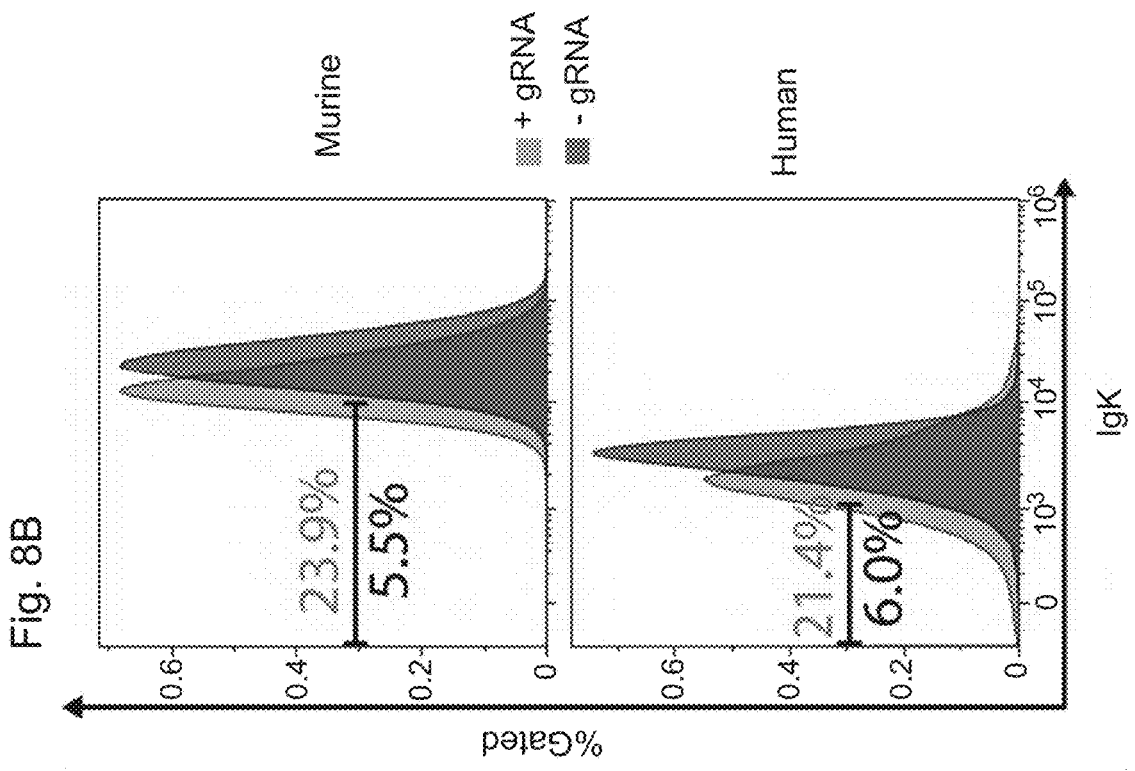
Figure 8A:
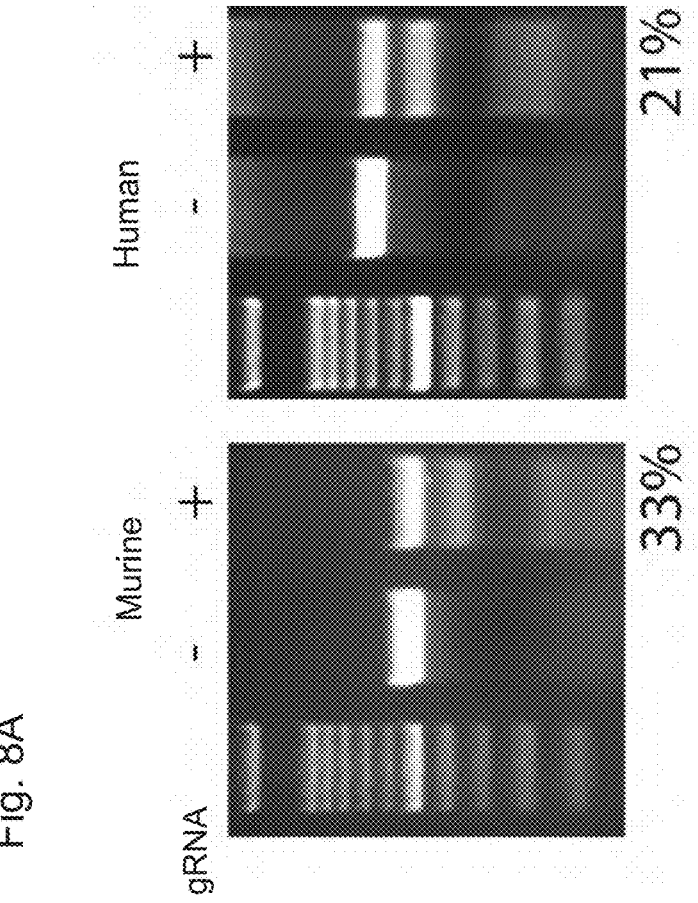

FIG. 8A-8B: Efficiency of gRNA-dependent Cas9 cleav- age

FIG. 8A: T7 Endonuclease 1 assay demonstrating gRNA- dependent Cas9 cleavage at the IgH J-C intron of the ImProB murine B cell line and the Ramos human B cell line.

FIG. 8B: Flow cytometry plots demonstrating gRNA dependent IgK ablation in the human and murine cell lines, as above, pre-gated on live, singlets FIG. 9: CRISPR/Cas9 dependent integration of a GFP gene.

Flow cytometric analysis (bottom) demonstrating CRISPR/Cas9 dependent integration of a GFP gene under an enhancer dependent promoter (ED Promoter, top left scheme) into the IgH locus of ImProB murine cell. GFP expression was monitored at three time points after trans- fection. As a control, transfecting a non-integrating donor vector expressing GFP under a strong promoter (top right scheme) lead to signal dilution over time. Each row corre- sponds to a different time point. Gating on live, singlets.

Figure 10A:
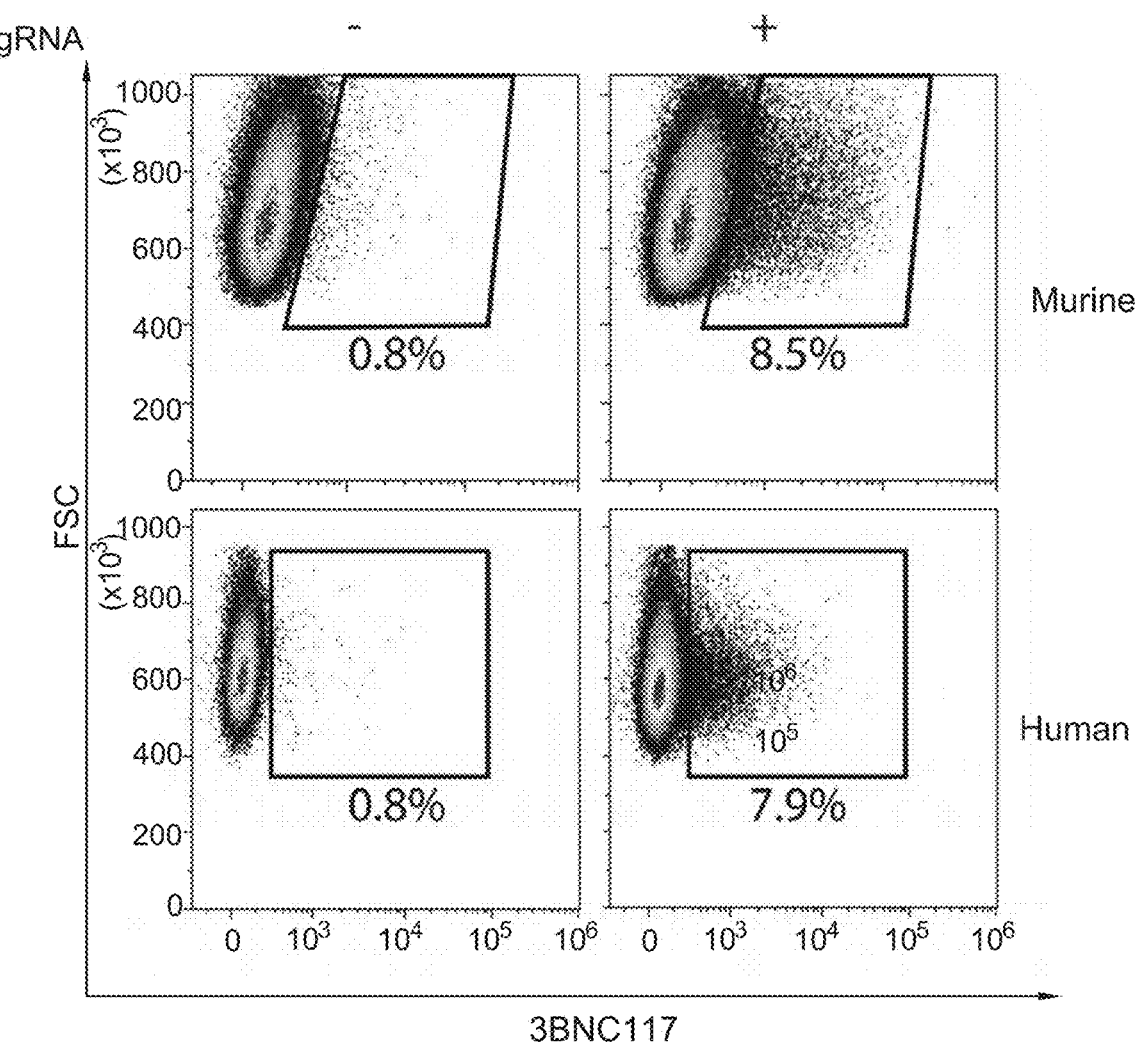
Figure 10B:
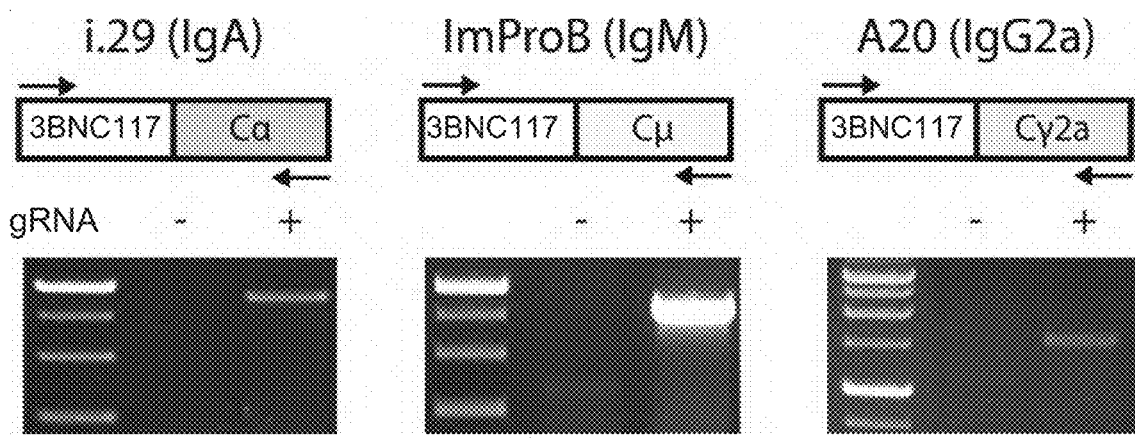

FIG. 10A-10B: 3BNC117 integration at the IgH J-C intron.

FIG. 10A: Flow cytometry plots demonstrating gRNA- dependent 3BNC117 integration at the IgH J-C intron of the ImProB murine B cell line (top) and the Ramos human B cell line (bottom).

FIG. 10B: EtBr gels showing RT-PCR amplification prod- ucts from different cell lines each expressing a different constant domain. Amplification indicates the specific splic- ing between the transgene, 3BNC117, and the endogenous constant. The arrows indicate primer locations.

FIG. 11A-11G: Engineering of primary B cells can be facilitated by TLR-pathway activation.

Figure 11A:
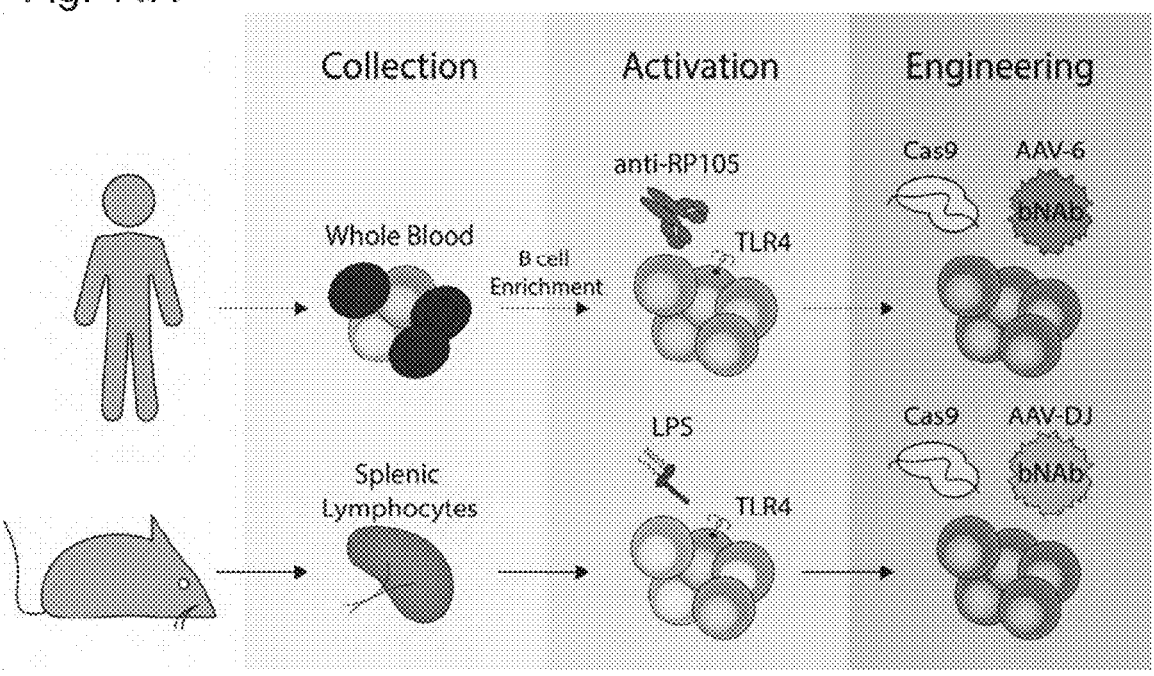

FIG. 11A: Activation and engineering scheme. Human B cells are collected from blood samples, activated using an anti-RP105 (TLR4) antibody, electroporated by CRISPR/ Cas9 RNP and transduced using AAV-6. Splenic B cells are activated using the TLR4 agonist LPS, electroporated by CRISPR/Cas9 RNP and transduced using AAV-DJ.

Figure 11B:
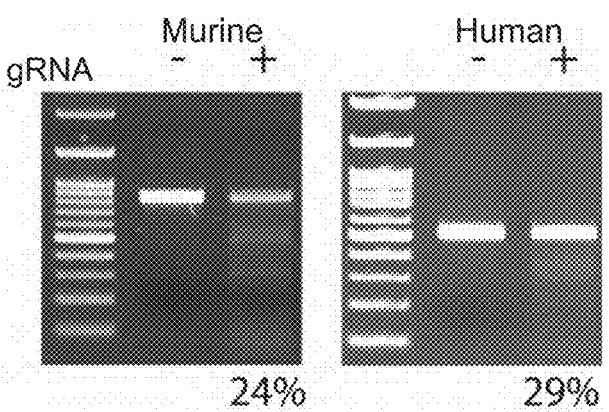
Figure 11C:
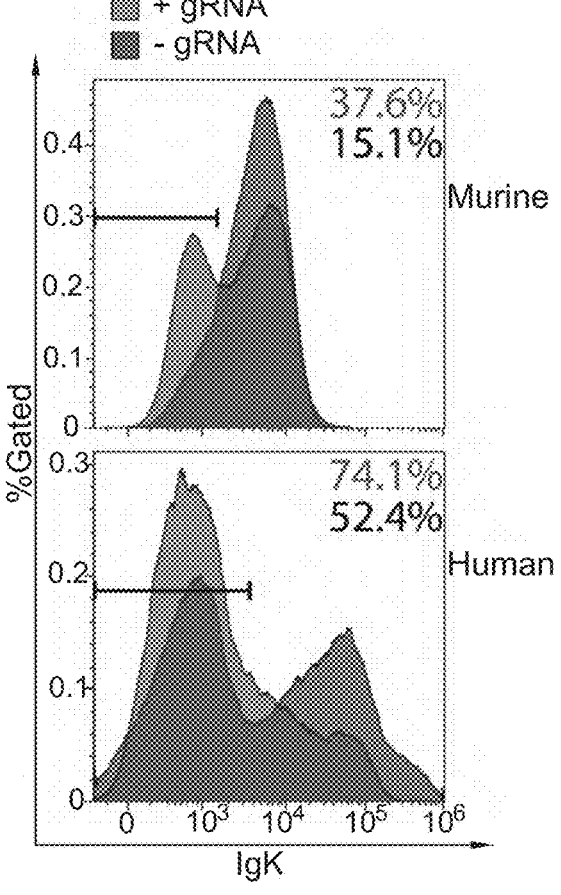

FIG. 11B-11C: gRNA-dependent IgK ablation monitored by the T7 endonuclease 1 assay (FIG. 11B) and by flow cytometry, gating on live, singlets for human cells and live, singlets, CD19+ for murine cells (FIG. 11C).

Figure 11D:
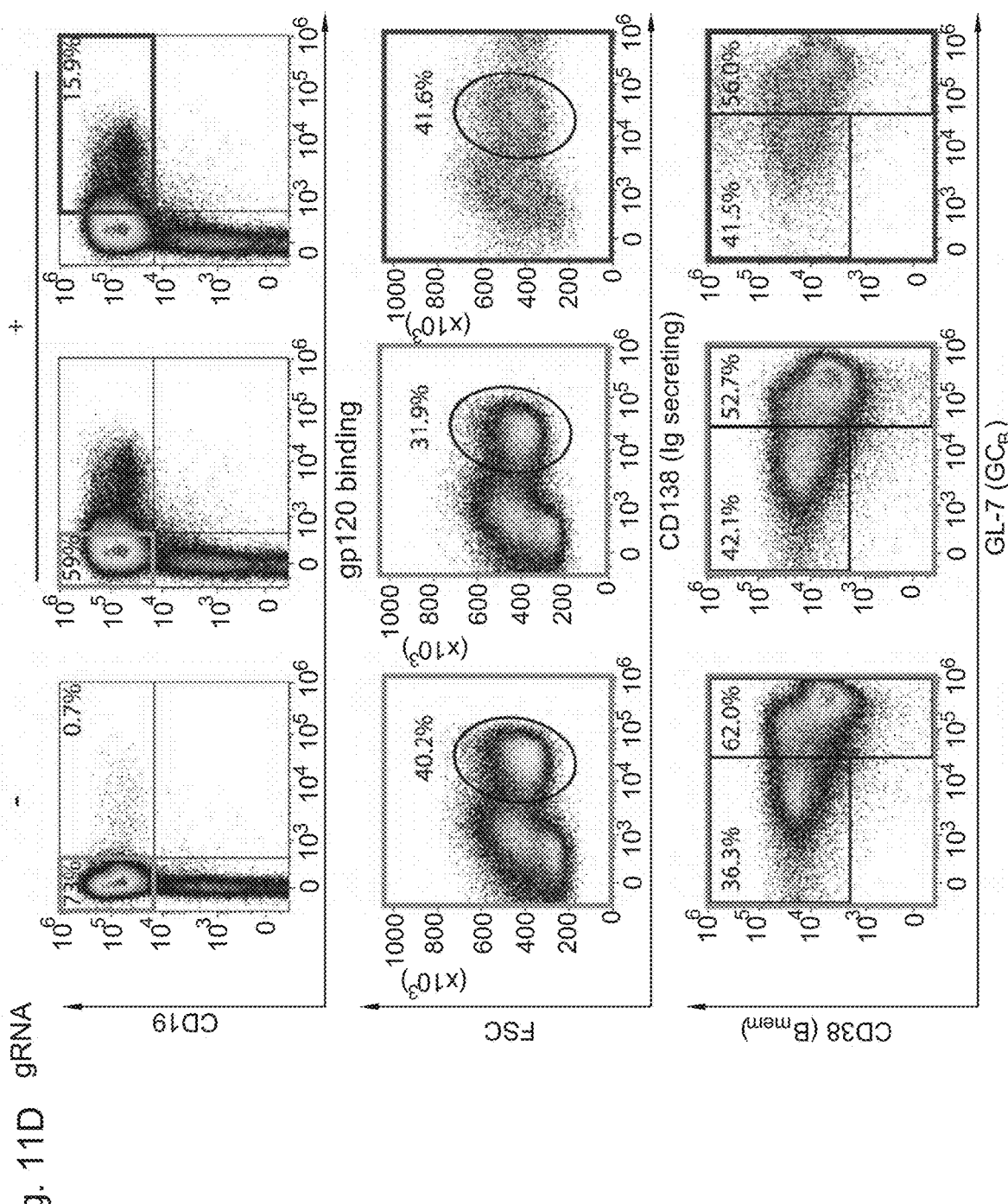

FIG. 11D: Frequency of phenotypes among engineered (dark gray frame of the three right panels) and non-engineered (light gray frame of the six left panels) splenic lymphocytes, from non gRNA transfected cells (−) or gRNA transfected cells (+). For CD138 and CD38/GL-7 plots, cells were gated relative to the color in the first row of their respective column. Pre-gating on live, singlets.

FIG. 11E: Frequency of isotypes among engineered (right) and non-engineered (left) splenic lymphocytes. Gating on live, singlets, CD19+ and gp120 non-binding (−) or gp120 binding (+).

FIG. 11F: ELISA on supernatants collected from murine splenic lymphocytes cultured for 3 days after engineering, as detected by gp140-YU2.DG binding antibodies.

FIG. 11G: Viability quantification of murine (n=6) and human (n=2) primary cells following RNP transfection and AAV transduction, monitored by Propidium Iodide, two days following treatment.

FIG. 12A-12F: Adoptively transferred activated primary splenocytes that were engineered with ADN171 to express the 3BNC117 as a BCR home to the spleen upon immunization with gp140 or with gp120 and secrete anti-gp140 or anti-gp120 antibodies in mice.

FIG. 12A: Illustration of the experimental scheme.

FIG. 12B: ELISA detection of anti-gp140 antibodies secreted with isotypes IgM or IgG, captured with gp140, from Serum of immunized mice at day7.

FIG. 12C: Standard curve for the ELISA in FIG. 7B allows calculating 3BNC117+IgG+ antibodies present in the blood (day7) at 270 ng/ml. Standards are marked with triangles.

FIG. 12D: RT-PCR analysis: extracted splenocytes from adoptively transferred and immunized mice show presence of ADN171 only in pre-activated cells. Arrows designate a primer inside the construct and a primer inside the endogenous Cp.

FIG. 12E: Illustration of the second experimental scheme.

FIG. 12F: ELISA detection of anti-gp120 antibodies at day 11 from sera of mice immunized with gp120 and from sera of adoptively transferred mice with 3BNC117 engineered B cells.

FIG. 13: In-vitro B cell activation as per phosphorylated ERK.

Flow cytometry showing phosphorylation of ERK only in B cells engineered with 3BNC117

FIG. 14A-14E: Adoptively transferred engineered B cells can be activated by immunization.

Figures 14A, 14B:
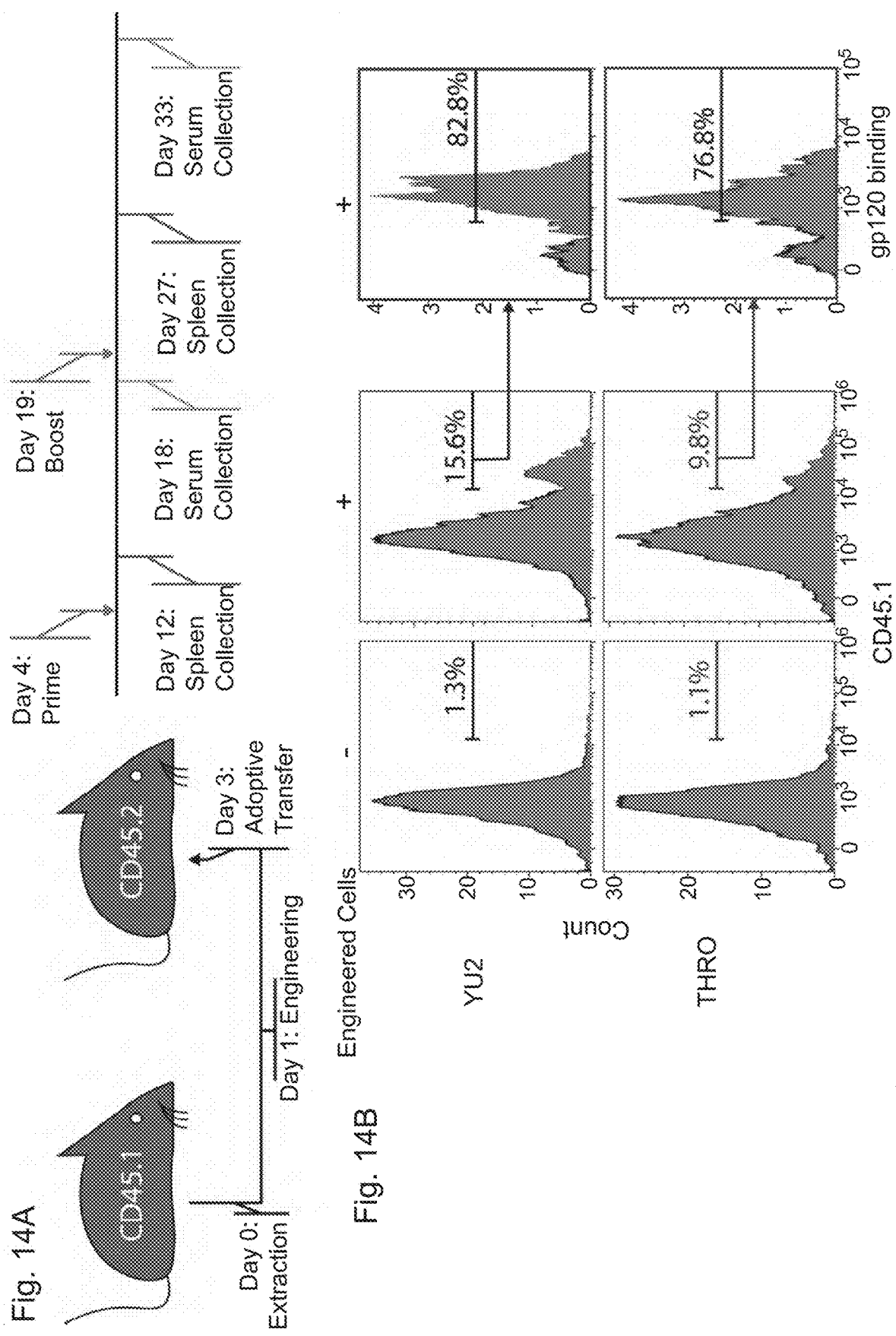

FIG. 14A: Experimental scheme of the in vivo assays. Splenic B cells from C57BL/6 CD45.1 mice were engineered and infused to otherwise syngeneic CD45.2 recipient mice. Different mice groups were immunized on the following day with gp120 antigens from either the THRO4156.18 (THRO) or the YU2.DG (YU2) HIV strains. When boosted by an additional injection, the mice received the same antigen as in prime injection. Different mice groups were sacrificed 8 days following injections for spleen collection or bled 14 days after injection for serum collection.

FIG. 14B: Representative analysis by flow cytometry of engineered cells accumulation in the GCs of mice immunized with either the YU2.DG or the THRO4156.18 gp120 antigens, 8 days following a prime antigen injection. Gating on live, singlets, B220+, GL-7+.

FIG. 14C: Quantification of 14B. Each dot represents an independent assay. Error bars represent SD.

FIG. 14D: Representative analysis by flow cytometry of CD45.1 expression among gp120 binding GC cells. Pre-gating on singlets, live, B2220+, GL-7+

FIG. 14E: Quantification of 14D. Each dot represents an independent assay. Error bars represent SD.

Figures 15A, 15B:
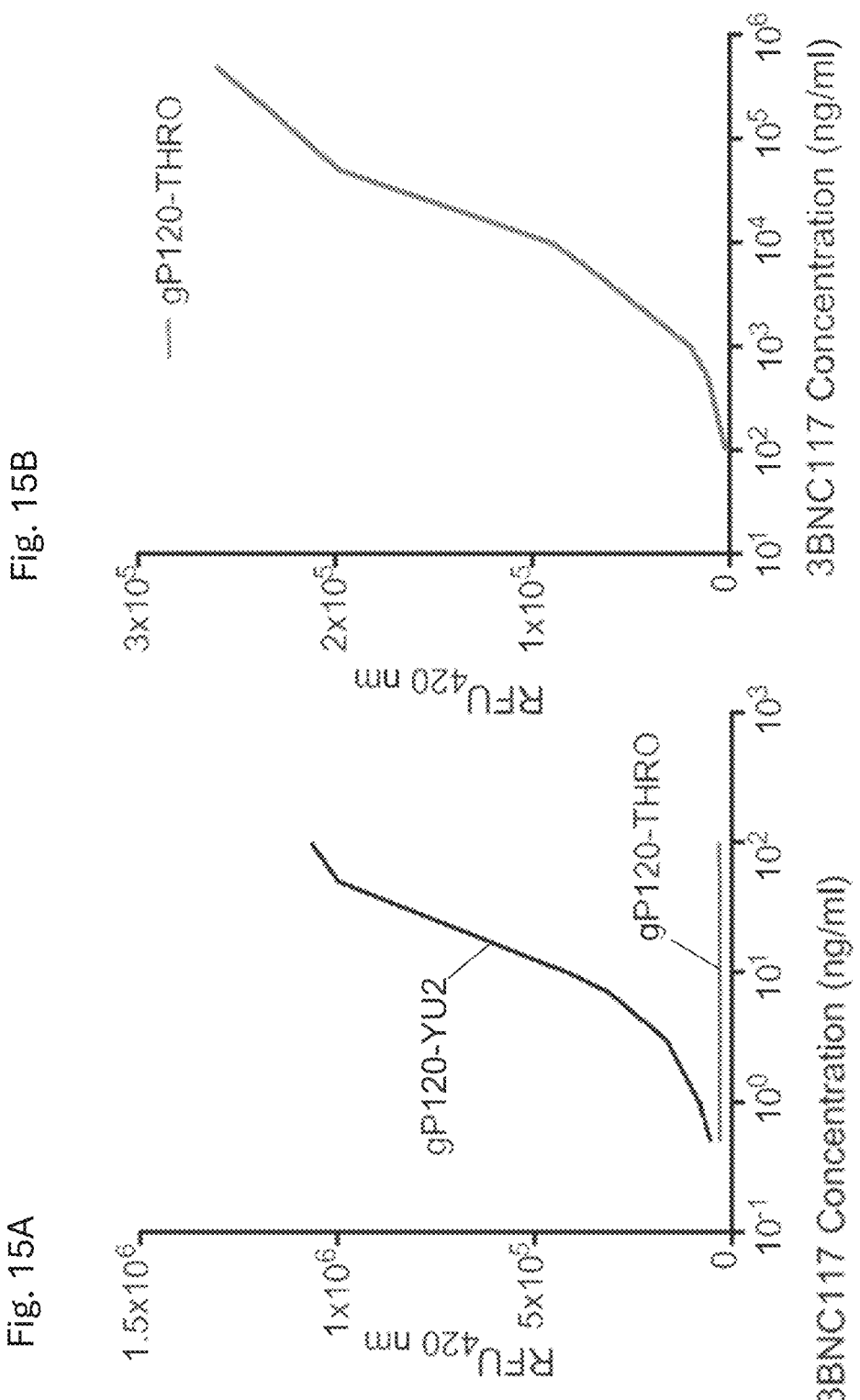

FIG. 15A-15B: Analysis by ELISA

FIG. 15A: Elisa analysis for the binding of 3BNC117 to the YU2.DG antigen.

FIG. 15B: Elisa analysis for the binding of 3BNC117 to the THRO4156.18 gp120 antigen.

Figure 16:
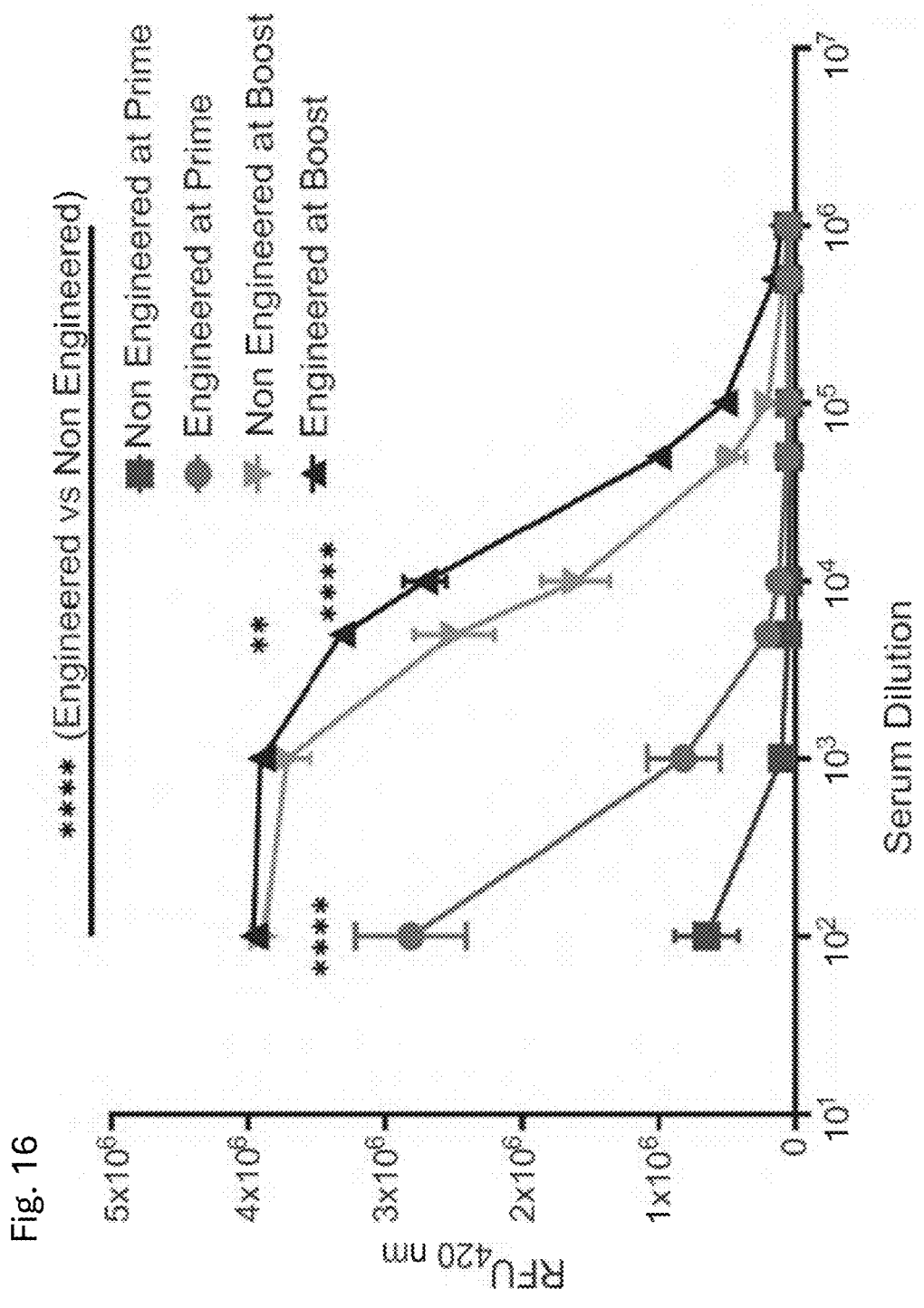

FIG. 16: gp120-YU2 specific ELISA of sera from mice immunized with gp120-YU2.DG.

Asterisks above points in the graph indicate comparison between the two points below them. Asterisks above the whole graph indicate group comparison between the sera coming from mice receiving engineered cells (circle and triangle) to the sera coming from mice receiving non-engineered cells (square and inverted triangle). N=3, **=pv<0.0001, =pv<0.01; three-way ANOVA and Tukey's multiple comparison test.

FIG. 17A-17F: Adoptively transferred engineered B cells can lead to memory retention upon immunization FIG. 17A: ELISA of sera collected 14 days following either prime or boost immunization. Quantified using an anti-idiotypic antibody to 3BNC117. ****=pv<0.0001, *=pv<0.05; two-way ANOVA FIG. 17B: Analysis by flow cytometry of CD45.1 expression and gp120 binding in the GCs of mice following prime or boost immunizations, gating on live, singlets, B220+, GL-7+, **=pv<0.0001, *=pv<0.001; two-way ANOVA.

FIG. 17C-17D: Analysis by flow cytometry, as in B, for immunizations with either the THRO4156.18 (THRO, C) or the YU2.DG (YU2, D) gp120 antigens, with the addition of the mice cohorts: "late primed" (in dark gray), "no boost" (in light gray), prime+boost (gray) and "no antigen" (in black). AT=Adoptive Transfer. N≥3.

Figures 17E, 17F:
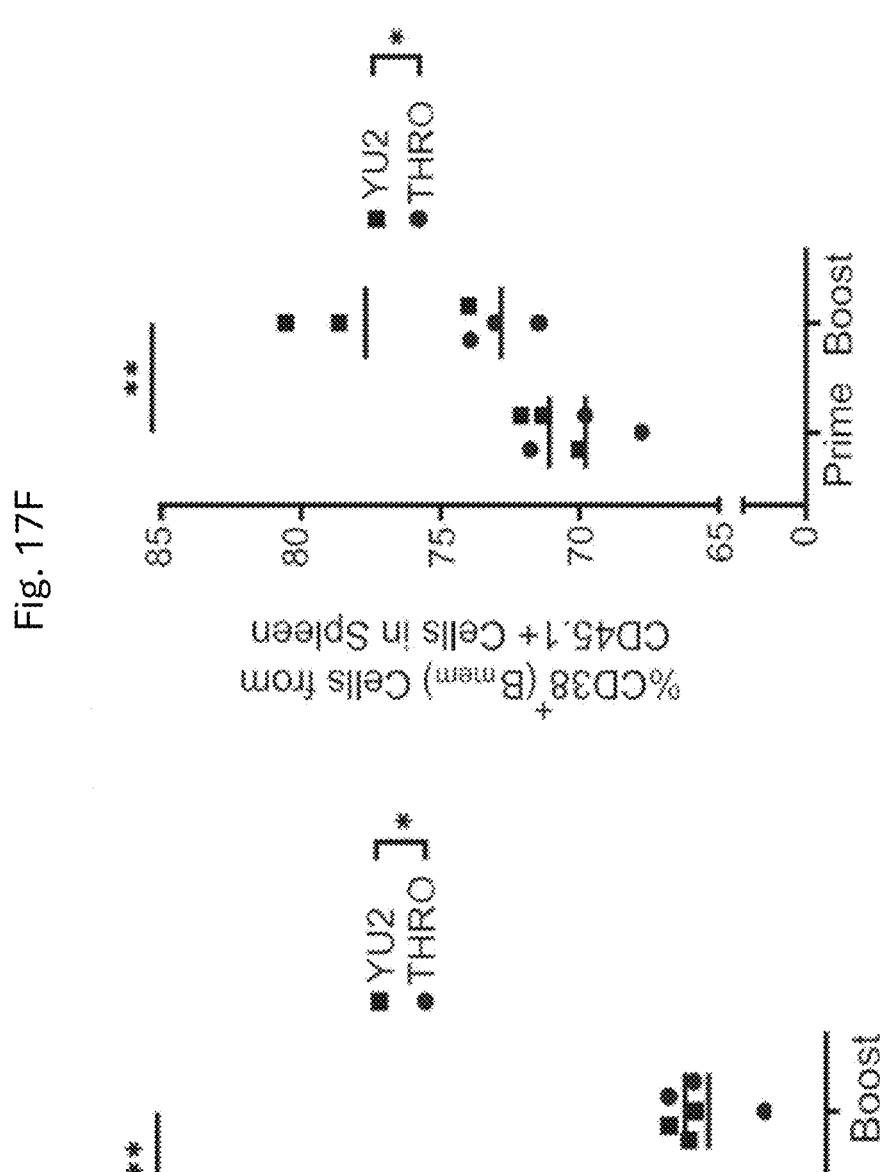

FIG. 17E-17F: Analysis by flow cytometry of CD138 or CD38 expression (FIG. 17E, 17F, respectively) among donor derived cells in the spleens of recipient mice after prime or boost immunizations by the gp120 antigens from either the THRO4156.18 (THRO, Red) or the YU2.DG (YU2, Blue) HIV strains, gated on live, singlets, CD45.1+. *=pv<0.001, =pv<0.01, *=pv<0.05; two-way ANOVA.

Figure 18:
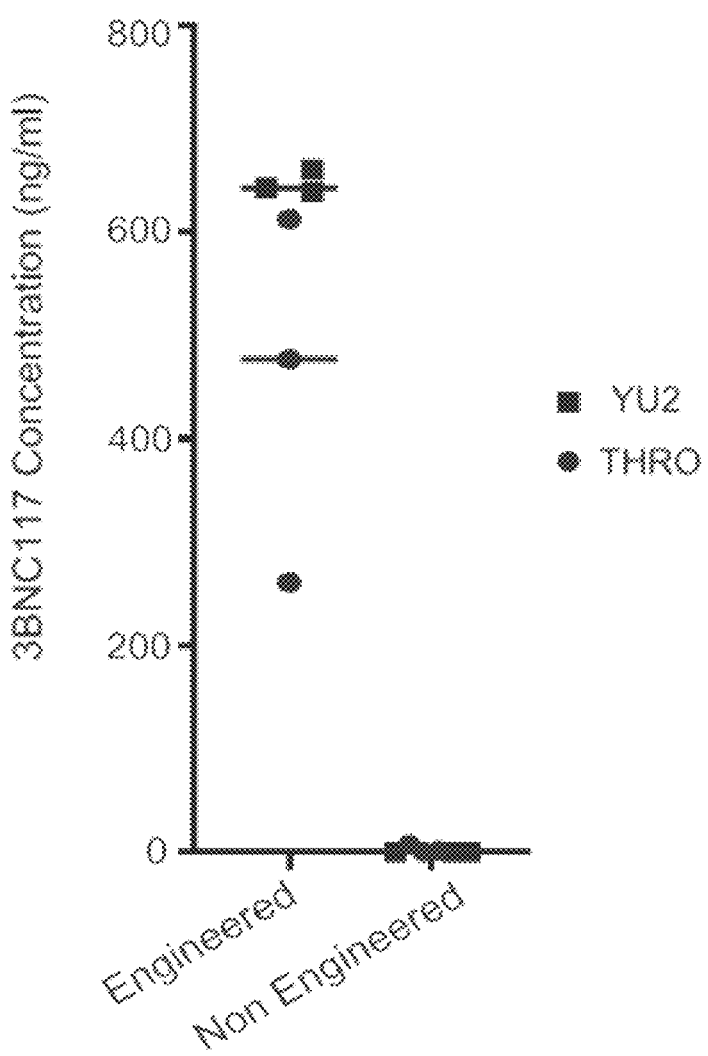

FIG. 18: ELISA of serafrom mice receiving engineered or non-engineered cells.

The sera were collected 14 days after boost immunizations. Immunizations with either the YU2 or the THRO antigens. Quantification using an anti-idiotypic antibody to 3BNC117.

Figures 19A, 19B:
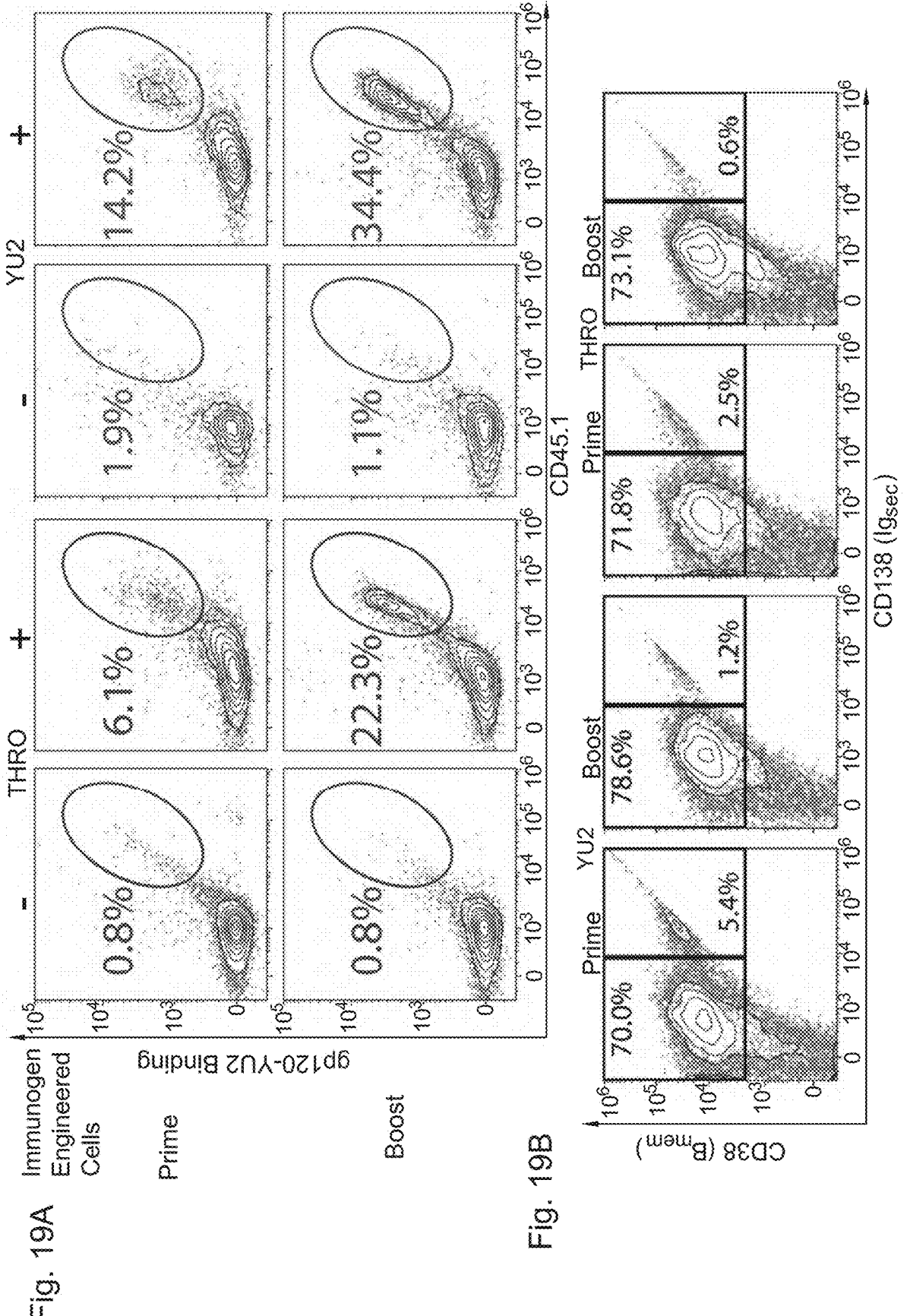

FIG. 19A-19B: Flow cytometry.

FIG. 19A: Representative flow cytometry for FIG. 17B. Gating on singlets, alive, B220+, GL-7+

FIG. 19B: Representative flow cytometry for FIG. 17E. Gated on live, singlets, CD45.1+.

FIG. 20A-20E: Adoptively transferred engineered B cells can undergo CSR and SHM upon immunization.

FIG. 20A: Isotype specific anti-idiotypic ELISA measuring 3BNC117 isotypes in mice sera collected after boost immunizations. *=pv<0.05, =pv<0.01, *=pv<0.001; two-way ANOVA, Dunnett's multiple comparisons for group comparisons, unpaired t-test for single dilution comparison.

FIG. 20B: Analysis by flow cytometry of IgA and CD45.1 expression among GC cells after prime and boost immunizations, gating on live, lymphocytes, GL-7+, B220+. **=pv<0.01; two-way ANOVA FIG. 20C: Representative flow cytometry of IgA expression before (out of CD19+, live, singlets) or after transfer and prime immunization (out of live, singlets, GL-7+, B220+)

Figure 20D:
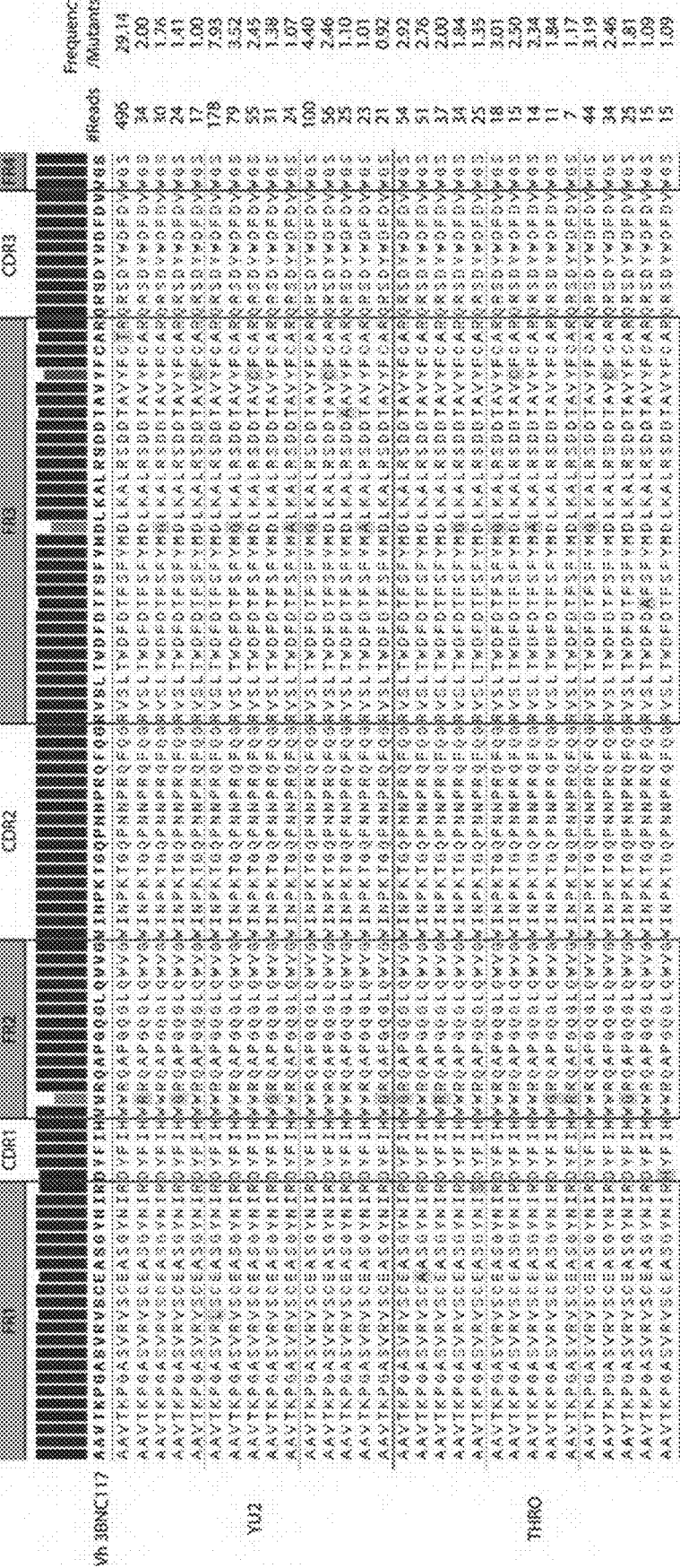

FIG. 20D: Multiple alignment of the original 3BNC117 amino acid sequence (as denoted by SEQ ID NO. 154) to that of the most dominant mutant variants found in the spleens of mice receiving prime immunization with either the THRO4156.18 or YU2.DG gp120 antigens. Sequences of the different mutated variants from mice immunized with the YU2.DG antigen are denoted by SEQ ID NO. 155-169 (from top) and sequences of the different mutated variants from mice immunized with the THRO4156.18 G antigen are denoted by SEQ ID NO. 170-184. Number of reads found for each variant and frequency amongst mutant sequences is presented on the right. The dark longitudinal bars represent conservation level. Annotation of functional antibody segments is presented on the top.

FIG. 20E: Quantitation of D. Substitution frequency is calculated as the number of substitutions divided by the length of the functional segment. Error bars represent SEM.

Figure 21:
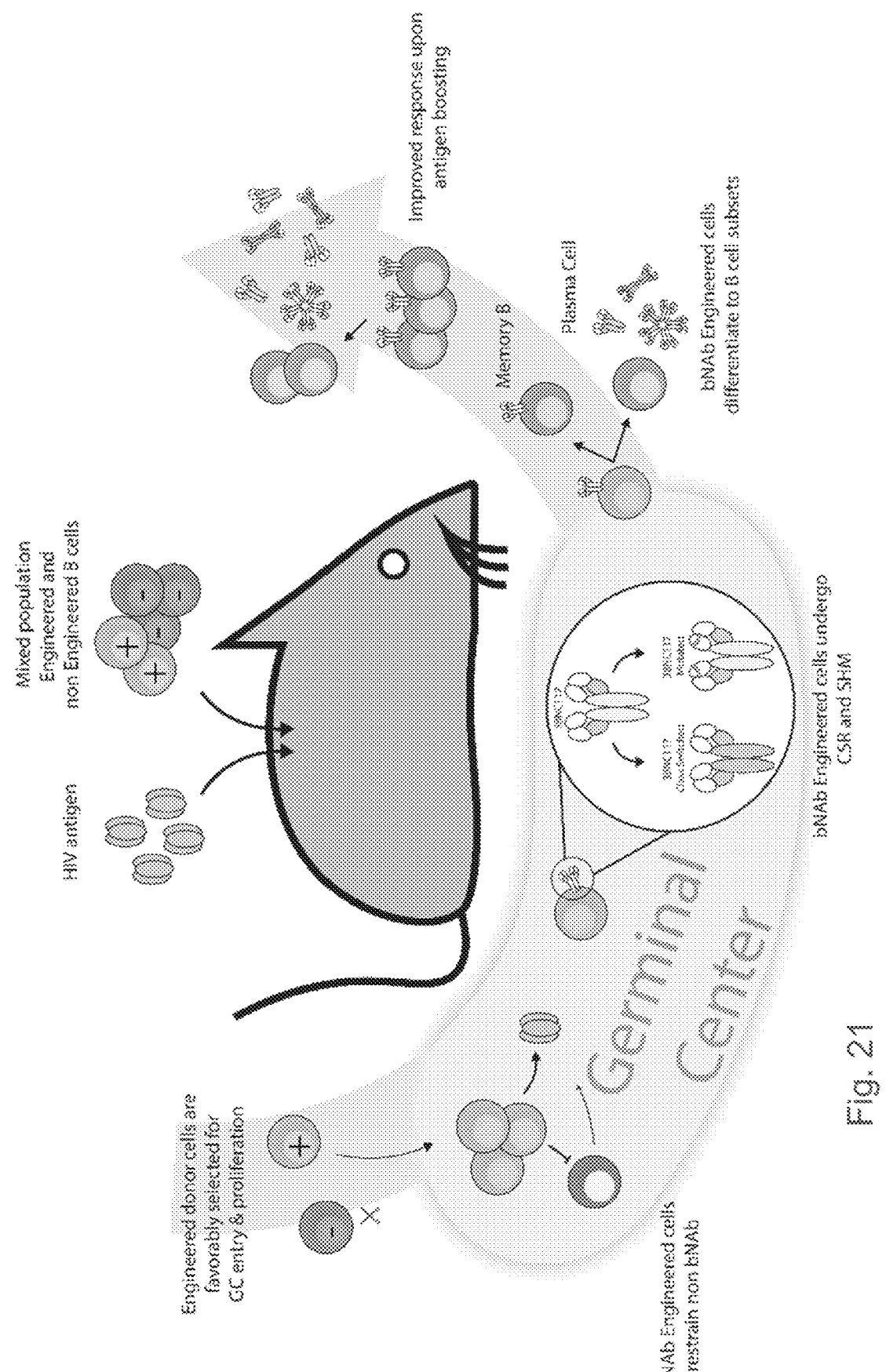

FIG. 21: Adoptive transfer of engineered B cells allows for antigen induced activation and memory retention in mice.

Scheme of the evolution of engineered B cells following engraftment.

Figure 22A:
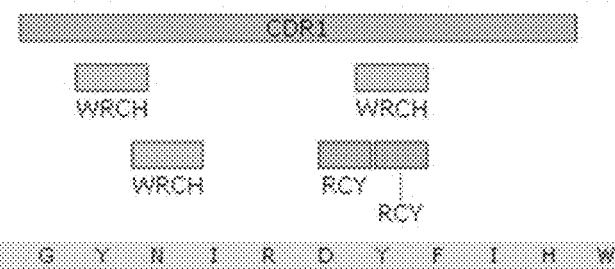
Figure 22B:
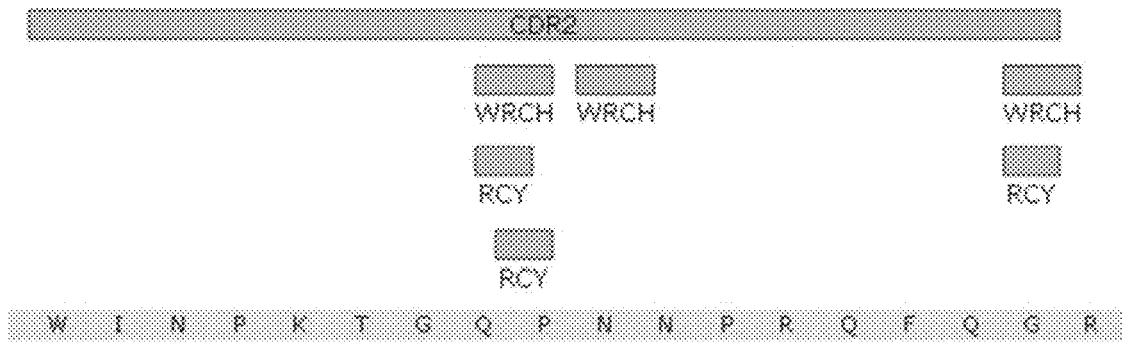
Figure 22C:
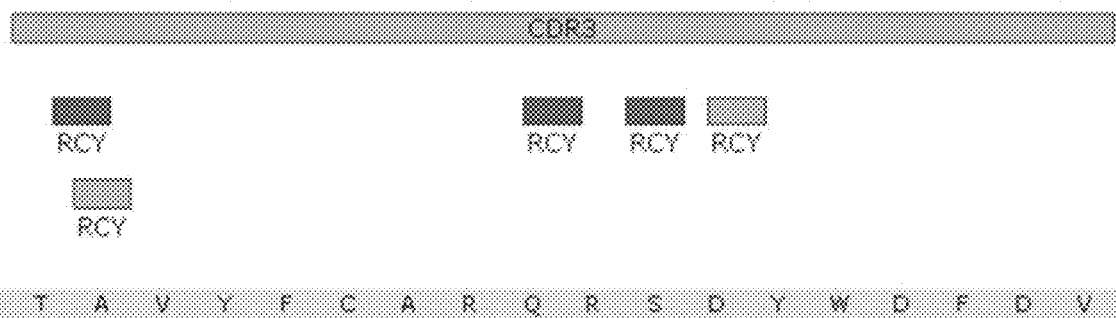

FIG. 22A-22C: Schematic representation of the hotspots found in the CDRs of the heavy chain variable region in the ADN170 derivative (original version).

FIG. 22A: Schematic representation of the hotspots found in CDR1. Features in grey are WRCH/DGYW or RCY/RGY spots which were not modified. The top and the bottom DNA sequences are as denoted by SEQ ID NO: 39 and SEQ ID NO: 40 respectively. The amino acid sequence is as denoted by SEQ ID NO: 43.

FIG. 22B: Schematic representation of the hotspots found in CDR2. Features in grey are WRCH/DGYW or RCY/RGY spots which were not modified. The top and the bottom DNA sequences are as denoted by SEQ ID NO: 44 and SEQ ID NO: 45 respectively. The amino acid sequence is as denoted by SEQ ID NO: 48.

FIG. 22C: Schematic representation of the hotspots found in CDR3. Features in light grey are WRCH/DGYW or RCY/RGY spots which were not modified. Features in dark gray are hotspots which were removed in the next versions. The top and the bottom DNA sequences are as denoted by SEQ ID NO: 49 and SEQ ID NO: 50 respectively. The amino acid sequence is as denoted by SEQ ID NO: 53.

Figure 23A:
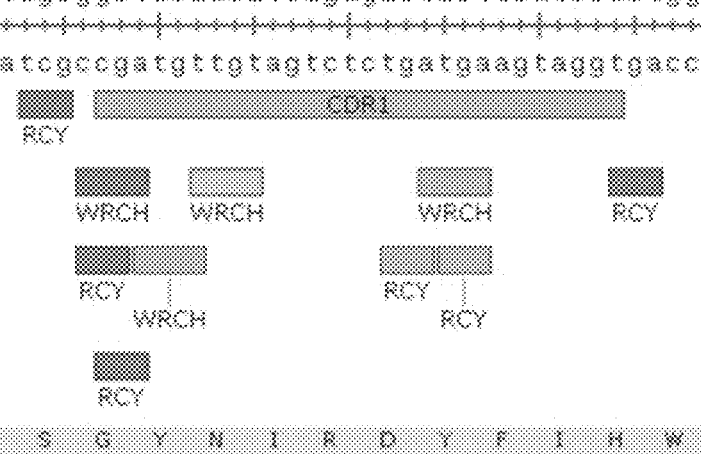
Figure 23B:
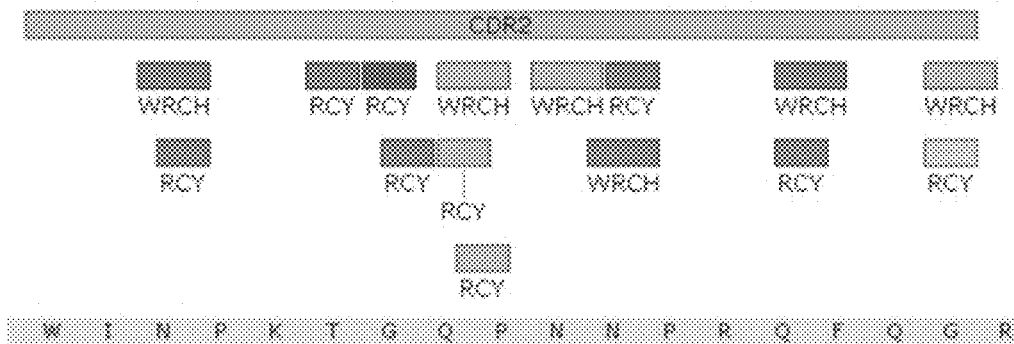
Figure 23C:
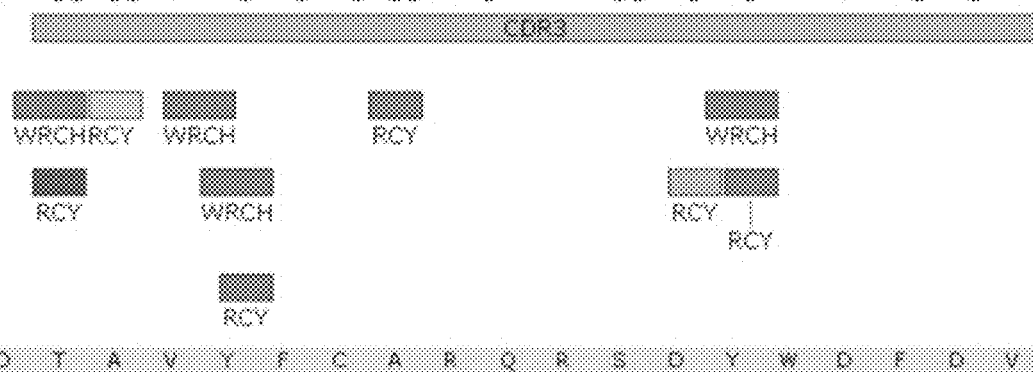

FIG. 23A-23C: Schematic representation of the hotspots found in the CDRs of the heavy chain variable region in the ADN170 derivative following GeneART optimization.

FIG. 23A: Schematic representation of the hotspots found in CDR1. Features in light grey are WRCH/DGYW or RCY/RGY spots which were not modified. Features in gray are new spots added by GeneART optimization. The top and the bottom DNA sequences are as denoted by SEQ ID NO: 55 and SEQ ID NO: 56 respectively. The amino acid sequence is as denoted by SEQ ID NO: 58.

FIG. 23B: Schematic representation of the hotspots found in CDR2. Features in light grey are WRCH/DGYW or RCY/RGY spots which were not modified. Features in gray are new spots added by GeneART optimization. Features in dark gray are hotspots which were removed in the next versions. The top and the bottom DNA sequences are as denoted by SEQ ID NO: 59 and SEQ ID NO: 60 respectively. The amino acid sequence is as denoted by SEQ ID NO: 48.

FIG. 23C: Schematic representation of the hotspots found in CDR3. Features in light grey are WRCH/DGYW or RCY/RGY spots which were not modified. Features in green are new spots added by GeneART optimization. Features in dark gray are hotspots which were removed in the next versions. The top and the bottom DNA sequences are as denoted by SEQ ID NO: 62 and SEQ ID NO: 63 respectively. The amino acid sequence is as denoted by SEQ ID NO: 53.

Figure 24A:
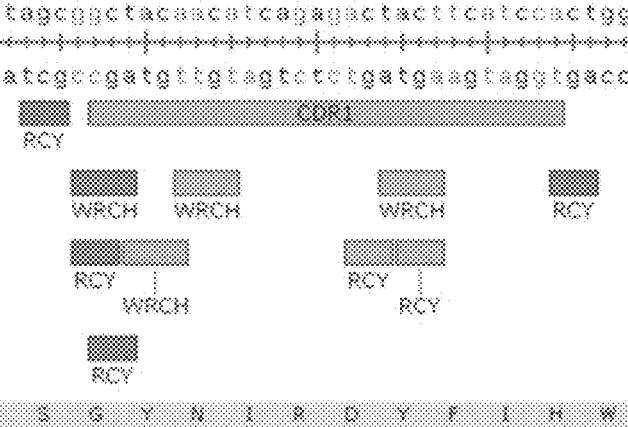
Figure 24B:
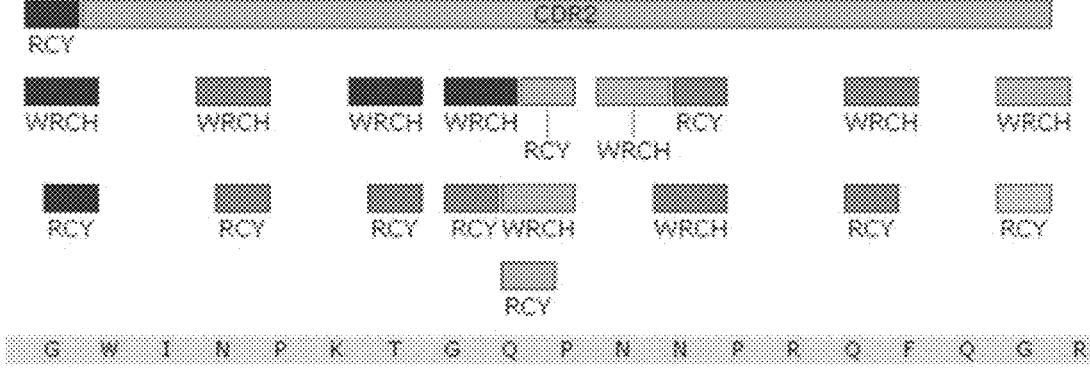
Figure 24C:
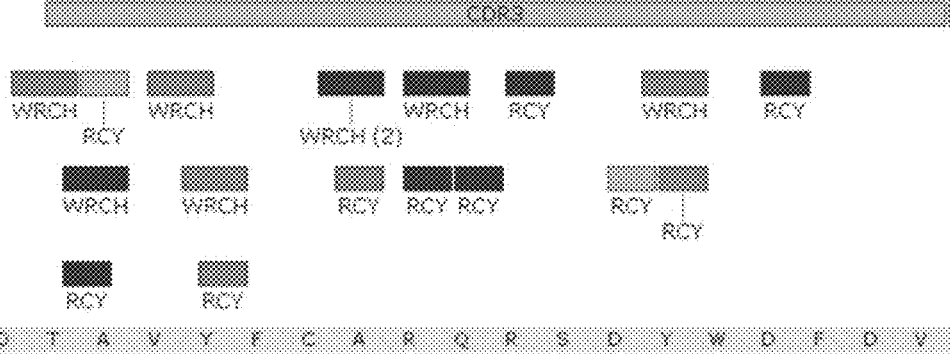

FIG. 24A-24C: Schematic representation of the hotspots found in the CDRs of the heavy chain variable region in the ADN170 derivative following ADN's SHM optimization.

FIG. 24A: Schematic representation of the hotspots found in CDR1. Features in light grey are WRCH/DGYW or RCY/RGY spots which were not modified. Features in gray are new spots added by GeneART optimization. The top and the bottom DNA sequences are as denoted by SEQ ID NO: 66 and SEQ ID NO: 67 respectively. The amino acid sequence is as denoted by SEQ ID NO: 58.

FIG. 24B: Schematic representation of the hotspots found in CDR2. Features in light grey are WRCH/DGYW or RCY/RGY spots which were not modified. Features in gray are new spots added by GeneART optimization. Features in darker gray are new spots added by ADN's SHM optimization. The top and the bottom DNA sequences are as denoted by SEQ ID NO: 69 and SEQ ID NO: 70 respectively. The amino acid sequence is as denoted by SEQ ID NO: 72.

FIG. 24C: Schematic representation of the hotspots found in CDR3. Features in light grey are WRCH/DGYW or RCY/RGY spots which were not modified. Features in gray are new spots added by GeneART optimization. Features in dark gray are new spots added by ADN's SHM optimization. The top and the bottom DNA sequences are as denoted by SEQ ID NO: 73 and SEQ ID NO: 74 respectively. The amino acid sequence is as denoted by SEQ ID NO: 53.

FIG. 25A-25C: Schematic representation of the hotspots found in the CDRs of the light chain variable region in the ADN170 derivative.

FIG. 25A: Schematic representation of the hotspots found in CDR1. Features in light grey are WRCH/DGYW or RCY/RGY spots which were not modified. Features in dark gray are hotspots which were removed in the next versions. The top and the bottom DNA sequences are as denoted by SEQ ID NO: 77 and SEQ ID NO: 78 respectively. The amino acid sequence is as denoted by SEQ ID NO: 81.

FIG. 25B: Schematic representation of the hotspots found in CDR2. Features in dark gray are hotspots which were removed in the next versions. The top and the bottom DNA sequences are as denoted by SEQ ID NO: 82 and SEQ ID NO: 83 respectively. The amino acid sequence is as denoted by SEQ ID NO: 86.

FIG. 25C: Schematic representation of the hotspots found in CDR3. Features in light grey are WRCH/DGYW or RCY/RGY spots which were not modified. Features in dark gray are hotspots which were removed in the next versions. The top and the bottom DNA sequences are as denoted by SEQ ID NO: 87 and SEQ ID NO: 88 respectively. The amino acid sequence is as denoted by SEQ ID NO: 91.

FIG. 26A-26C: Schematic representation of the hotspots found in the CDRs of the light chain variable region in the ADN170 derivative following GeneART optimization.

FIG. 26A: Schematic representation of the hotspots found in CDR1. Features in light grey are WRCH/DGYW or RCY/RGY spots which were not modified. Features in gray are new spots added by GeneART optimization. The top and the bottom DNA sequences are as denoted by SEQ ID NO: 93 and SEQ ID NO: 94 respectively. The amino acid sequence is as denoted by SEQ ID NO: 96.

FIG. 26B: Schematic representation of the hotspots found in CDR2. Features in gray are new spots added by GeneART optimization. The top and the bottom DNA sequences are as denoted by SEQ ID NO: 97 and SEQ ID NO: 98 respectively. The amino acid sequence is as denoted by SEQ ID NO: 100.

FIG. 26C: Schematic representation of the hotspots found in CDR3. Features in light grey are WRCH/DGYW or RCY/RGY spots which were not modified. Features in gray are new spots added by GeneART optimization. The top and the bottom DNA sequences are as denoted by SEQ ID NO: 101 and SEQ ID NO: 102 respectively. The amino acid sequence is as denoted by SEQ ID NO: 91.

Figure 27A:
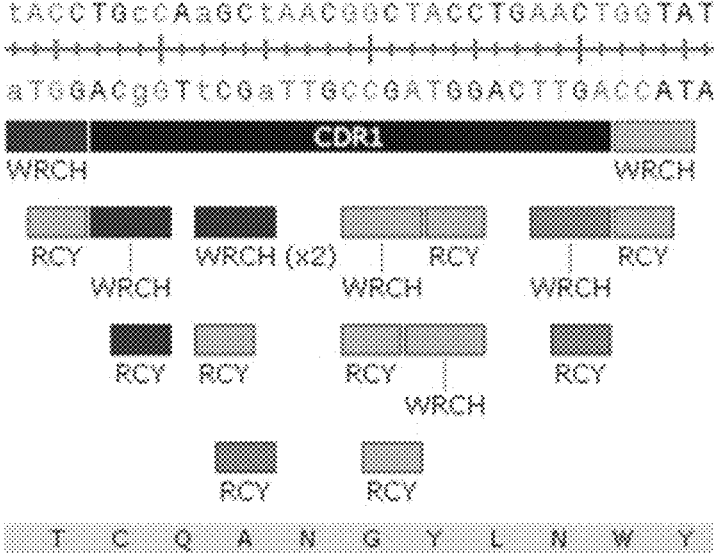
Figure 27B:
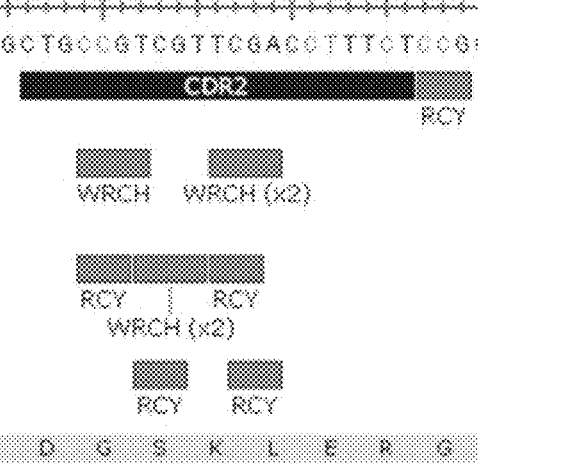
Figure 27C:
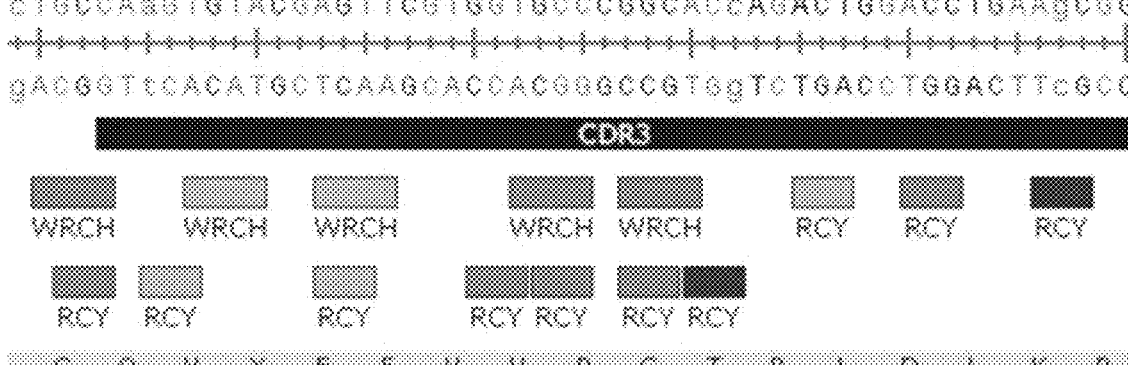

FIG. 27A-27C: Schematic representation of the hotspots found in the CDRs of the light chain variable region in the ADN170 derivative following ADN's SHM optimization.

FIG. 27A: Schematic representation of the hotspots found in CDR1. Features in light grey are WRCH/DGYW or RCY/RGY spots which were not modified. Features in green are new spots added by GeneART optimization. Features in dark gray are new spots added by ADN's SHM optimization. The top and the bottom DNA sequences are as denoted by SEQ ID NO: 104 and SEQ ID NO: 105 respectively. The amino acid sequence is as denoted by SEQ ID NO: 107.

FIG. 27B: Schematic representation of the hotspots found in CDR2. Features in light grey are WRCH/DGYW or RCY/RGY spots which were not modified. Features in gray are new spots added by GeneART optimization. The top and the bottom DNA sequences are as denoted by SEQ ID NO: 108 and SEQ ID NO: 109 respectively. The amino acid sequence is as denoted by SEQ ID NO: 100.

FIG. 27C: Schematic representation of the hotspots found in CDR3. Features in light grey are WRCH/DGYW or RCY/RGY spots which were not modified. Features in gray are new spots added by GeneART optimization. Features in dark gray are new spots added by ADN's SHM optimization. The top and the bottom DNA sequences are as denoted by SEQ ID NO: 111 and SEQ ID NO: 112 respectively. The amino acid sequence is as denoted by SEQ ID NO: 91.

FIG. 28A-28E: Synonymous re-coding of 3BNC117.

Figures 28A, 28B, 28E:
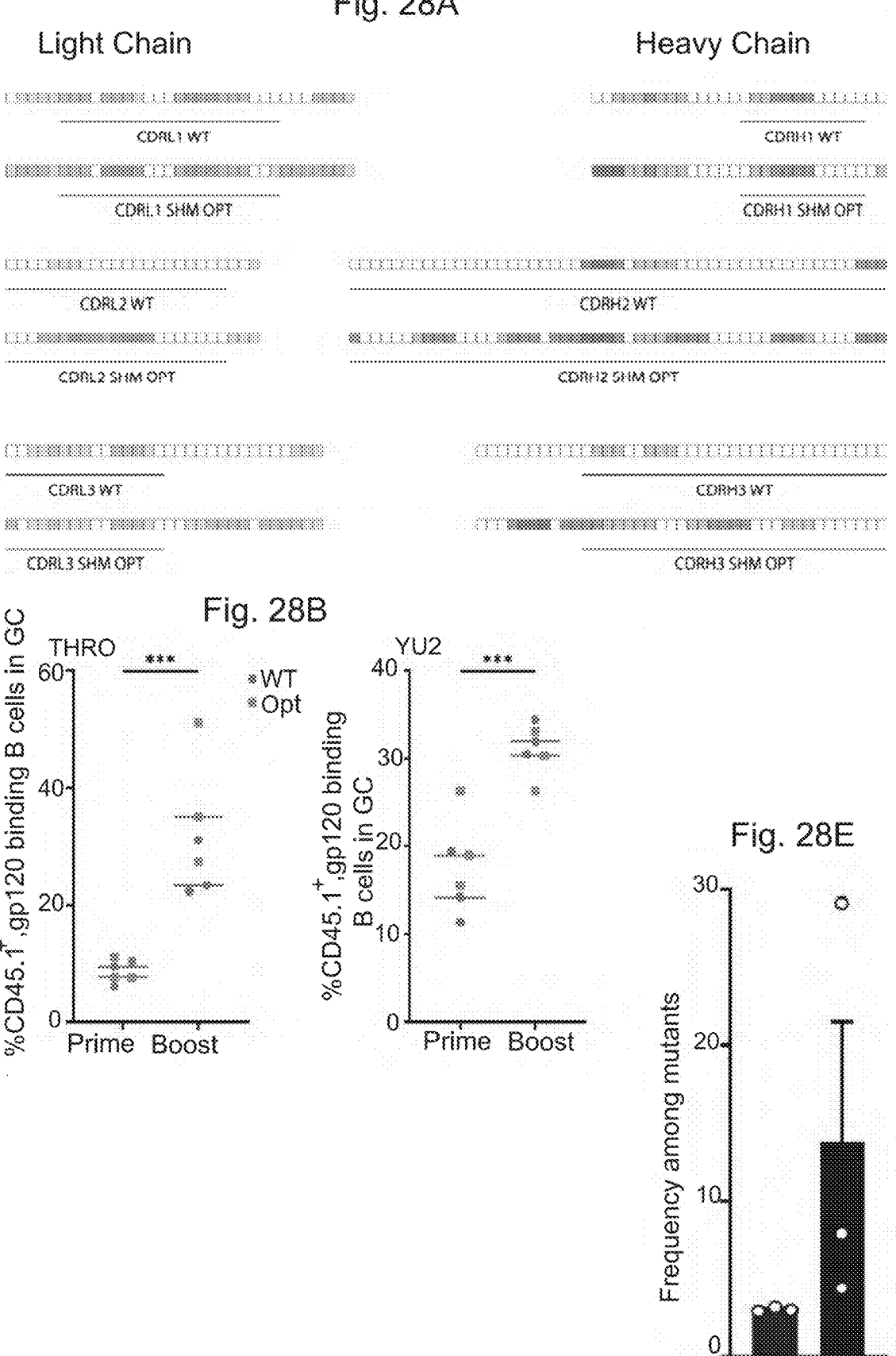

FIG. 28A: Synonymous re-coding of 3BNC117 to include more AID hotspots for enhanced SHM potential. The scheme depicts the loci surrounding CDR loops for the Kappa Light Chain (left) and Heavy Chain (right) of 3BNC117. Each box represents a base pair. Bars below indicate the CDR loops. Colors, either the left gray boxes for the light chain or the right gray boxes for the heavy chain, represent hotspots (either RCY or WRCH). For each base-pair, the stronger the color is (saturation), the more potentially-overlapping hotspots are encoded.

FIG. 28B: Analysis by flow cytometry of CD45.1 expression and gp120 binding in the GCs of mice following prime or boost immunizations of mice receiving B cells engineered with either 3BNC117-wt or 3BNC117-opt, gating on live, singlets, B220+, GL-7+.

Figure 28C:
Figure 28D:
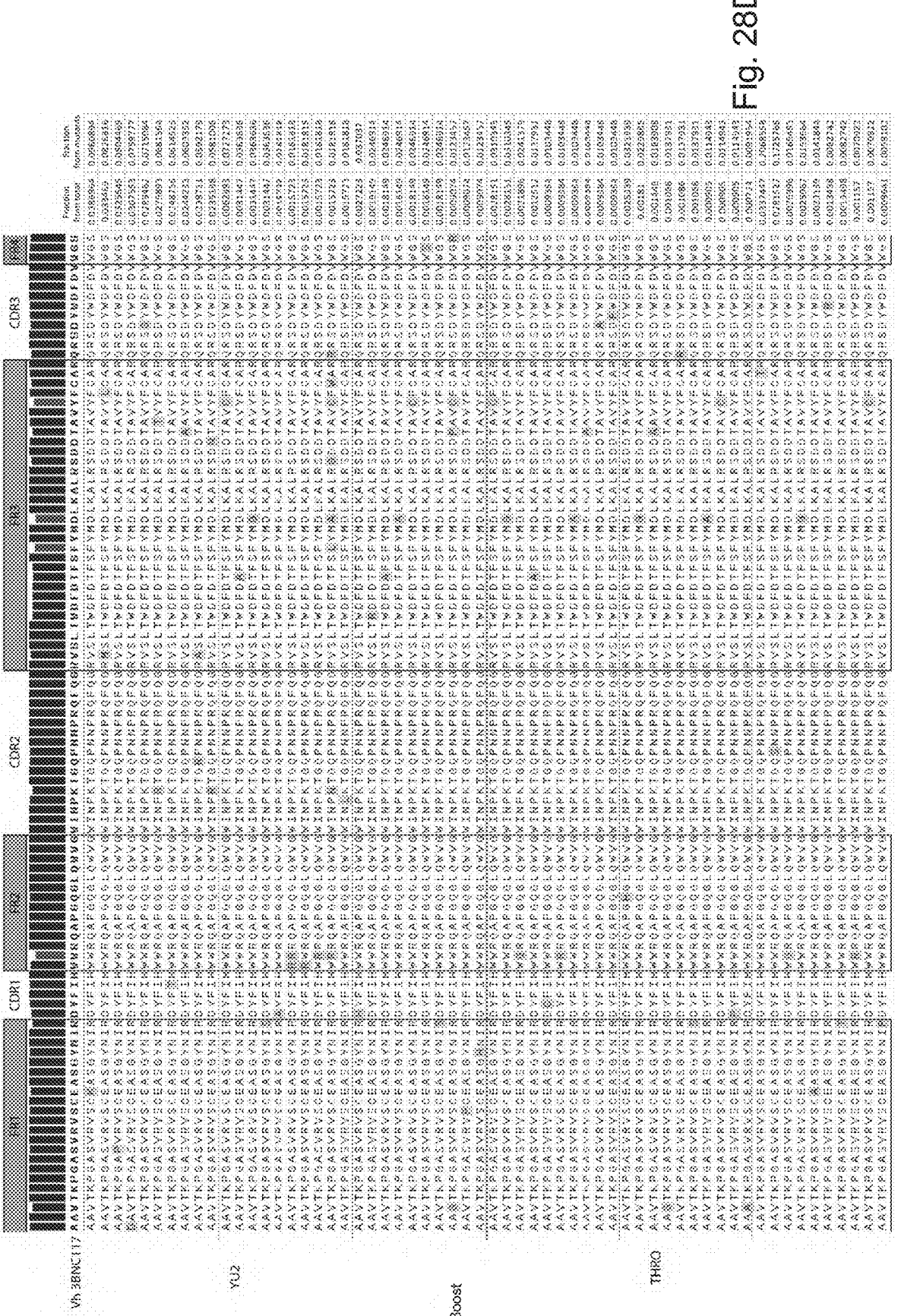

FIG. 28C: Multiple alignment of the original 3BNC117 amino acid sequence (as denoted by SEQ ID NO. 154), to that of the most dominant mutant variants found in the spleens of mice receiving prime immunization with either the THRO4156.18 or YU2.DG gp120 antigens. Sequences of the different mutated variants from mice immunized with the YU2.DG antigen are denoted by SEQ ID NOs. 155-159, 185-189, 160-164, 190-194, 165-169 and 195-199 (from top), and sequences of the different mutated variants from mice immunized with the THRO4156.18 G antigen are denoted by SEQ ID NO. 170-174, 200-204, 175-179, 205-209, 180-184 and 210-214. Fraction from total reads, or to mutant reads indicated on the left. The dark longitudinal bars represent conservation level. Annotation of functional antibody segments is presented on the top FIG. 28D: Multiple alignment of the original 3BNC117 amino acid sequence (as denoted by SEQ ID NO. 154), to that of the most dominant mutant variants found in the spleens of mice receiving boost immunization with either the THRO4156.18 or YU2.DG gp120 antigens. Sequences of the different mutated variants from mice immunized with the YU2.DG antigen are denoted by SEQ ID NOs. 215-244 (from top), and sequences of the different mutated variants from mice immunized with the THRO4156.18 G antigen are denoted by SEQ ID NO. 245-274. Fraction from total reads, or to mutant reads indicated on the left. The dark longitudinal bars represent conservation level. Annotation of functional antibody segments is presented on the top.

FIG. 28E: Frequency comparison between the most abundant mutants coming from mice immunized with either the YU2.DG or THRO4156.18 gp120 antigens.

FIG. 29A-29I: Flow cytometry analysis of efficiency of editing of two constructs ADN171 (non-hotspot optimized) and ADN171XS (hotspot optimized).

FIG. 29A: Graph showing comparison of percentage of gp120-YU2 binding cells in splenocytes transduced with the ADN171 construct versus the ADN171XS construct.

FIG. 29B: Flow cytometry of unstained control splenocytes transduced with the ADN171.

FIG. 29C: Flow cytometry of stained splenocytes transduced with the ADN171 construct but with no gRNA.

FIG. 29D: Flow cytometry of stained splenocytes transduced with the ADN171 construct with gRNA-Plate A.

FIG. 29E: Flow cytometry of stained splenocytes transduced with the ADN171 construct with gRNA-Plate B.

FIG. 29F: Flow cytometry of unstained control splenocytes transduced with the ADN171XS.

FIG. 29G: Flow cytometry of stained splenocytes transduced with the ADN171XS construct but with no gRNA.

FIG. 29H: Flow cytometry of stained splenocytes transduced with the ADN171XS construct with gRNA-Plate A.

FIG. 29I: Flow cytometry of stained splenocytes transduced with the ADN171XS construct with gRNA-Plate B.

Figure 30:
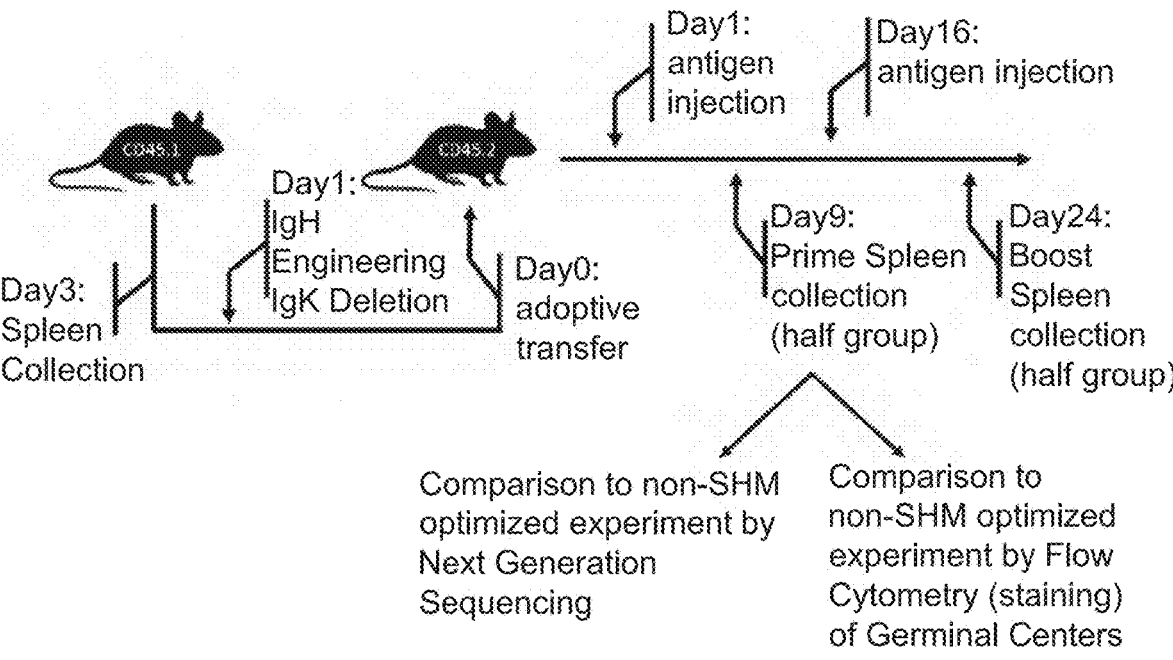

FIG. 30: Adoptive transfer of SHM optimized sequences. Figure illustrates the experimental scheme of adoptive transfer of SHM optimized sequences.

Figure 31:
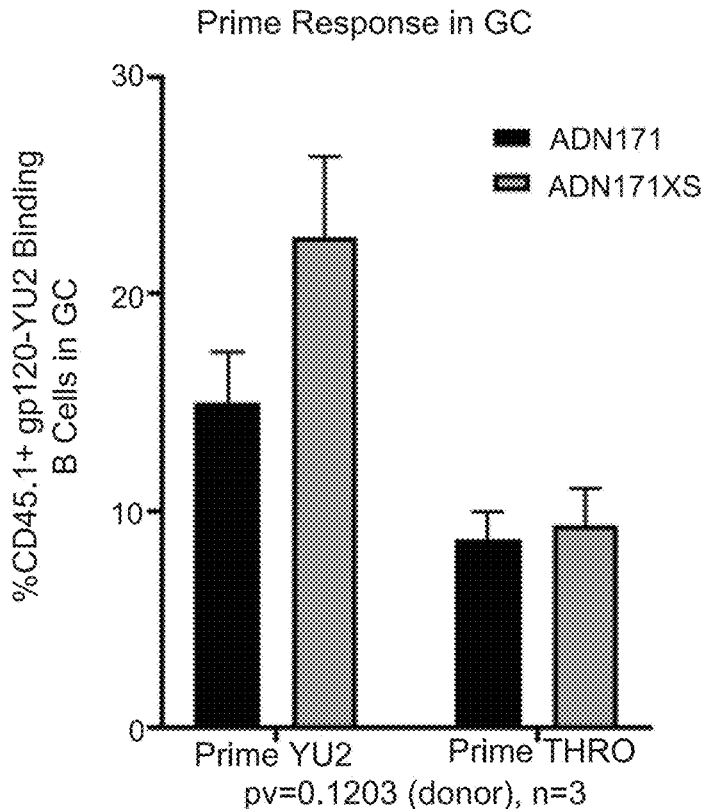

FIG. 31: Prime response in germinal centers following prime immunization.

Graph showing prime response in germinal centers following prime immunization as monitored by double positives CD45.1, gp120-YU2 binding B cells following injection with splenocytes transduced either with SHM optimized construct (ADN171XS) or non SHM optimized construct (ADN171).

FIG. 32A-32B: NGS sequencing of SHM optimized mouse.

Figure shows Next-Generation Sequencing (NGS) results of immunoglobulin sequences obtained from a mouse receiving ADN171XS edited cells, immunized with gp120-YU2.

FIG. 32A. shows the amino acid sequence of the resulting CDR2, as denoted by SQ ID NO. 115. Relative heights of the amino acid residues represent the frequency of the amino acids.

FIG. 32B. shows the amino acid sequence of the resulting full variable heavy chain (VH), relative height represents information content, as denoted by SQ ID NO. 116.

FIG. 33: High prevalence for mutations in the heavy chain CDR2 loop.

The figure demonstrates high prevalence for mutations in the heavy chain CDR2 loop and amino acid involved in gp120 interaction as monitored by NGS sequencing in a single mouse receiving SHMopt donor and prime immunization with YU2. Sequence logo of the CDR loops of 3BNC117 is shown. Black dots above show the amino acids involved in gp120 binding by the VRC01 class antibodies. Gray dots above show >10% frequency of mutations in the experiment. Almost no mutations occurred in the CDR1 or CDR3 loops. CDR1, CDR2, and CDR3, comprise the amino acid sequence as denoted by SEQ ID NO. 283, 284 and 285, respectively.

Figure 34:
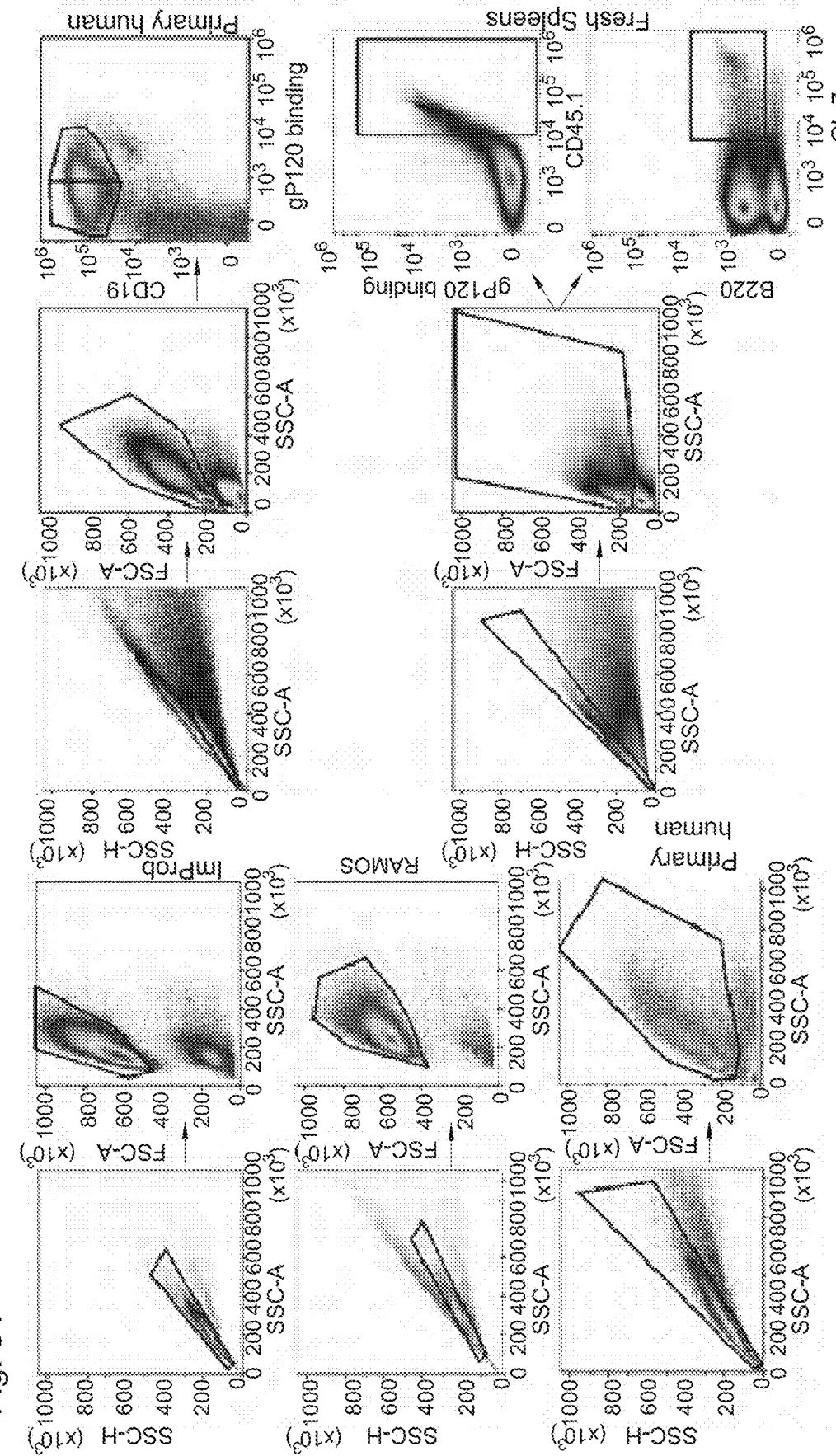

FIG. 34: Gating strategy.

Gating strategy for flow cytometry experiments presented in Examples 5, 6, 9 and 11.

FIG. 35A-35D. Successful use of the endogenous VH promoter by cassette that includes SA.

FIG. 35A. is a schematic representation of the ADN174 construct. The Splice Acceptor (SA) is followed by a 2A peptide. Downstream of the 3BNC117 expression cassette, a Splice Donor is encoded.

FIG. 35B. Demonstration by RT-PCR of both transcription and correct splicing between the endogenous J segment and ADN174. This is following integration of ADN174 into the mH69 site in a proB cell line. Only when the specific gRNA mH69 was given together with the Cas9 protein and the donor cassette ADN174 that the correct amplicon size will be found, marked as an arrow.

FIG. 35C. Same as (FIG. 35B) but for splicing between the ADN174 donor cassette and the endogenous IgHM constant.

FIG. 35D. Schematic representation of the primers used in (FIG. 35B) and (FIG. 35C).

Figure 36A:
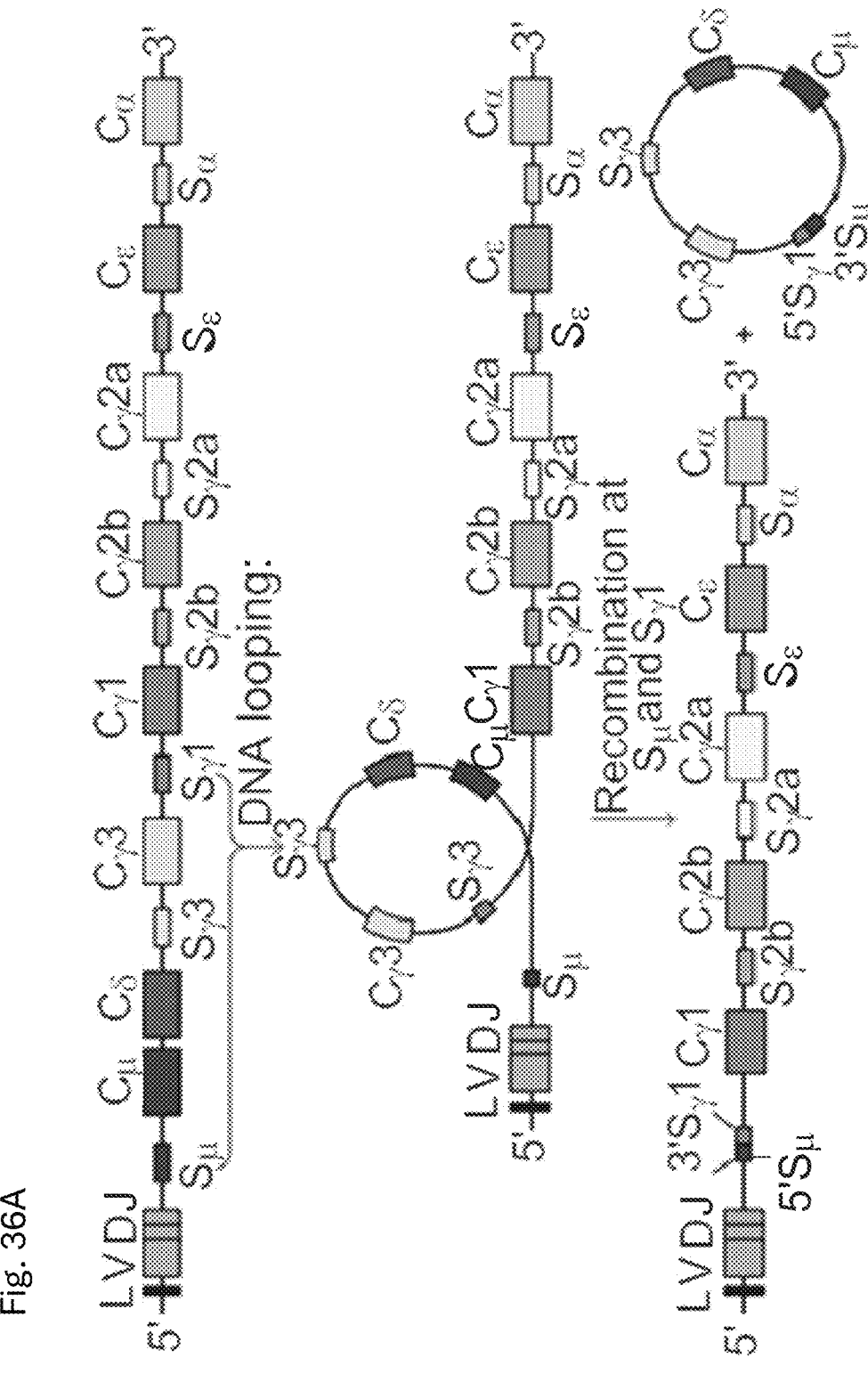
Figure 36B:
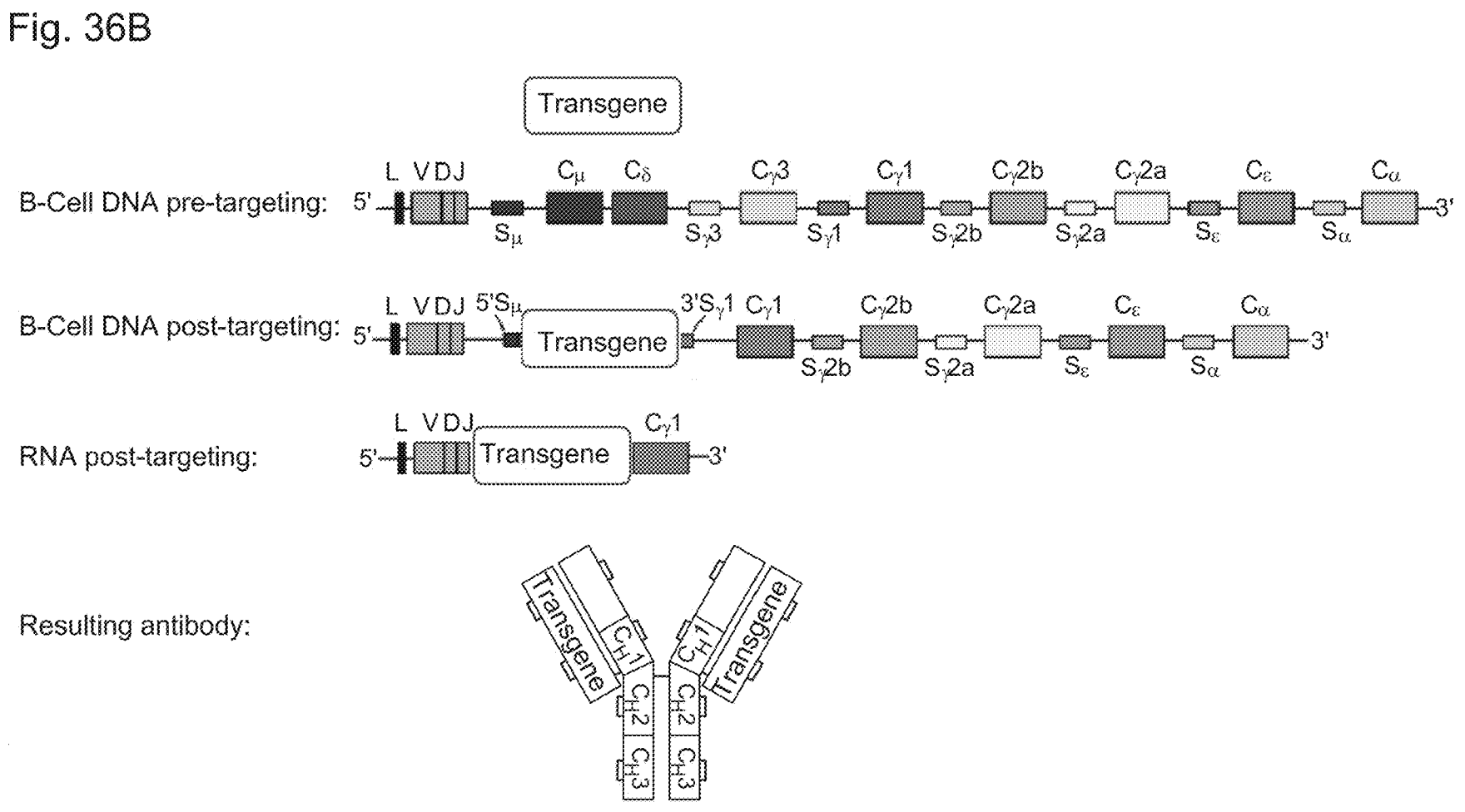

FIG. 36A-36B: A scheme for CSR targeting to the IgH locus.

FIG. 36A: A scheme describing CSR recombination process in the genome of activated mouse B-cells (Adapted from Kuby Immunology, 4th edition).

FIG. 36B: A scheme describing a transgene (white rectangle) entry to a Double strand breaks DSB that is generated in the process of CSR in the IgH locus.

FIG. 37A-37D: CSR targeting of a GFP construct to the IgH locus of murine activated B-cells. Activated murine B-cells were transduced with rAAV containing the SFFV-GFP-SD construct.

FIG. 37A: CSR is induced in murine B-cells with, or without, IL4. The upper panel shows typical morphologies of resting and activated B-cells as seen under the microscope. The lower panel shows cognate IgM and IgG1 expression.

FIG. 37B: Amaxa electroporation of activated and non-activated murine B-cells with a pMaxGFP, 24 h post-LPS activation. Matching flow cytometry analysis of GFP expression is shown, live cells were gated according to fsc/ssc.

Figures 37C, 37D:
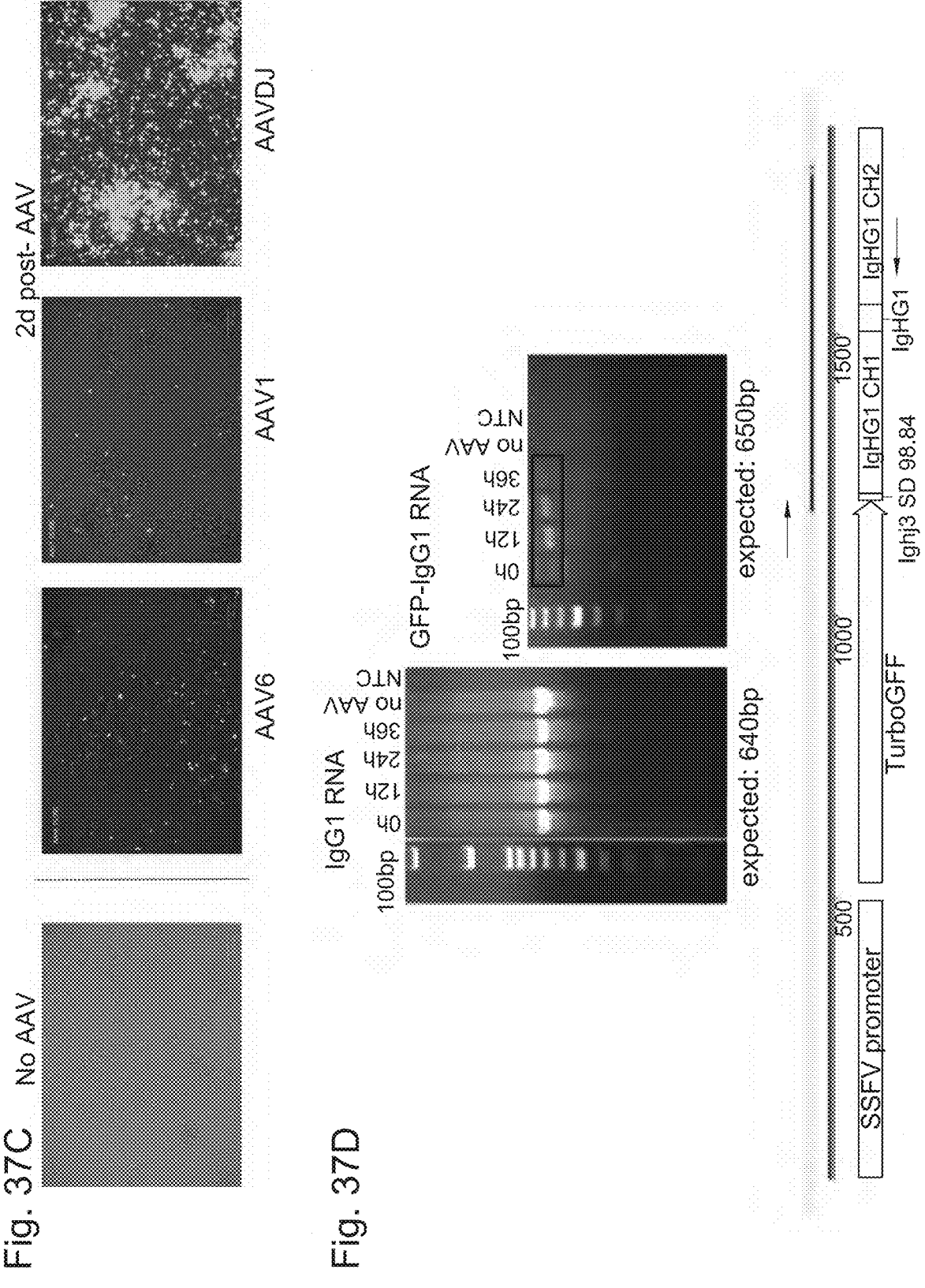

FIG. 37C: Immunofluorescent pictures following transduction of activated murine B-cells with AAV serotypes 6,1 and DJ, 20 h post-LPS activation. The MOI was 10,000 vg/cell.

FIG. 37D: Agarose gel electrophoresis of an RT-PCR product of splicing between an SFFV-GFP-sd construct and the IgG1 locus, following AAV transduction of murine B-cells.

To the right: IgG1 RNA as a positive control; to the left: GFP—IgG1 junctions. The red open rectangle marks the expected bands. The bottom scheme shows the expected RT-PCR product. The gray arrows indicate the forward and reverse primers used for the RT-PCR reaction. The alignment of the RT-PCR product sequence with the expected sequence is shown above the scheme, as full red arrows indicate a complete alignment.

FIG. 38A-38F: CSR targeting of a Palivizumab construct (ADN191), or a construct encoding the 3BNC17 antibody to the IgH locus of murine activated B-cells.

Figures 38A, 38B:
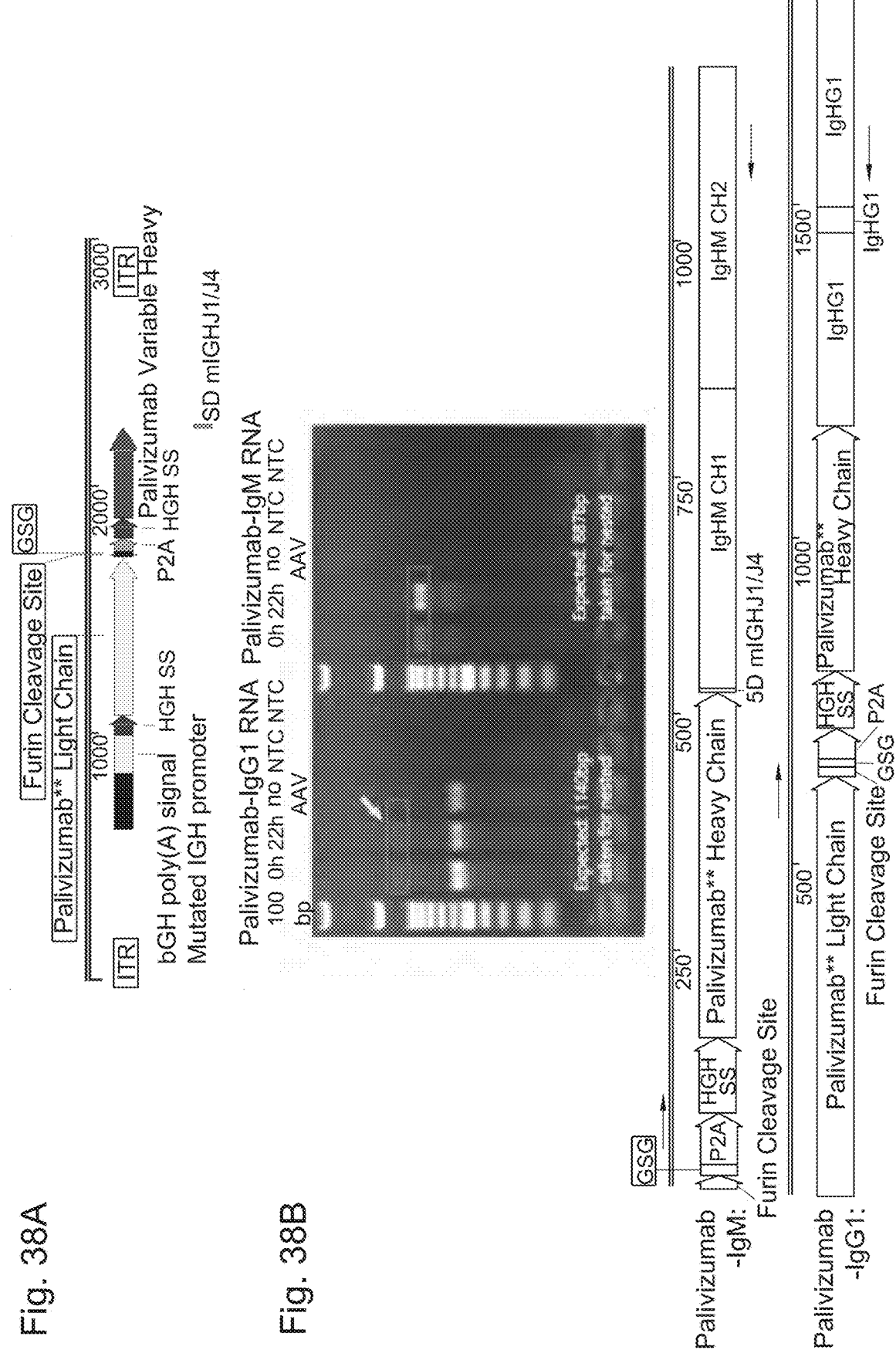

FIG. 38A: A scheme of the targeting ssAAV ADN191 construct, composing a 5' polyA signal (dark gray rectangle) followed by a mutated V region minimal promoter (bright gray rectangle); the complete Palivizumab light chain (light gray arrow); a P2A cassette (middle blue arrow); the variable heavy segment of the Palivizumab heavy chain (gray arrow) and the J1/J4 splice donor (grey rectangle). The ssAAV ITRs are shown as dark blue rectangles.

FIG. 38B: Agarose gel electrophoresis of RT-PCR products of splicing between the ADN191 construct and the IgH locus, following AAV transduction of murine B-cells. Red open rectangles mark the expected bands. The bottom schemes represent the expected.

FIG. 38C-38F. B-cells engineered without nucleases secrete high amounts of transgenic antibodies upon adoptive transfer in immunocompetent mice FIG. 38C. A timeline for murine B-cell culture and engineering pre-transfer.

Figures 38C, 38D, 38E:
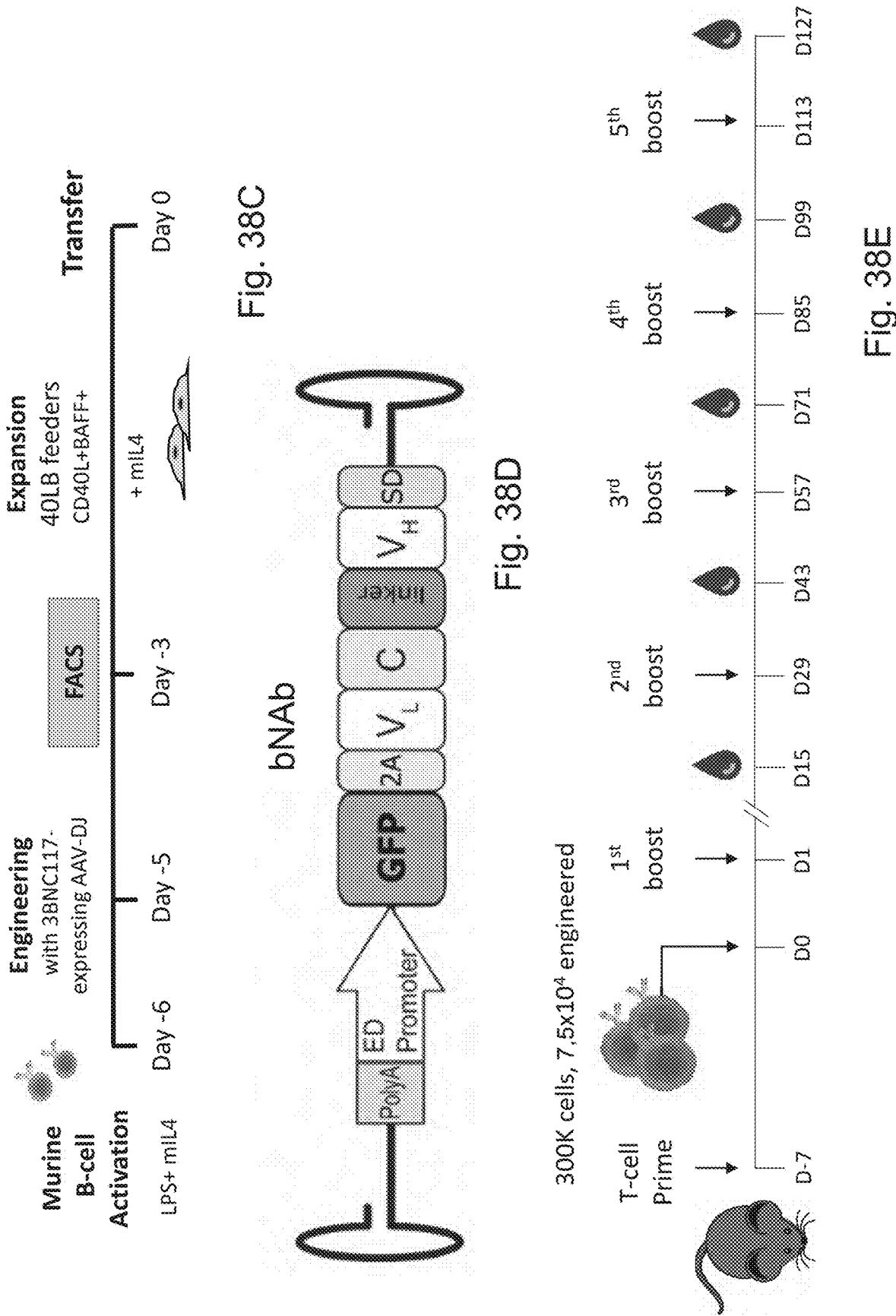

FIG. 38D. The AAV construct used for targeting.

FIG. 38E. A timeline for the adoptive transfer of cells engineered as in (FIG. 38C).

Figures 38F, 39A:
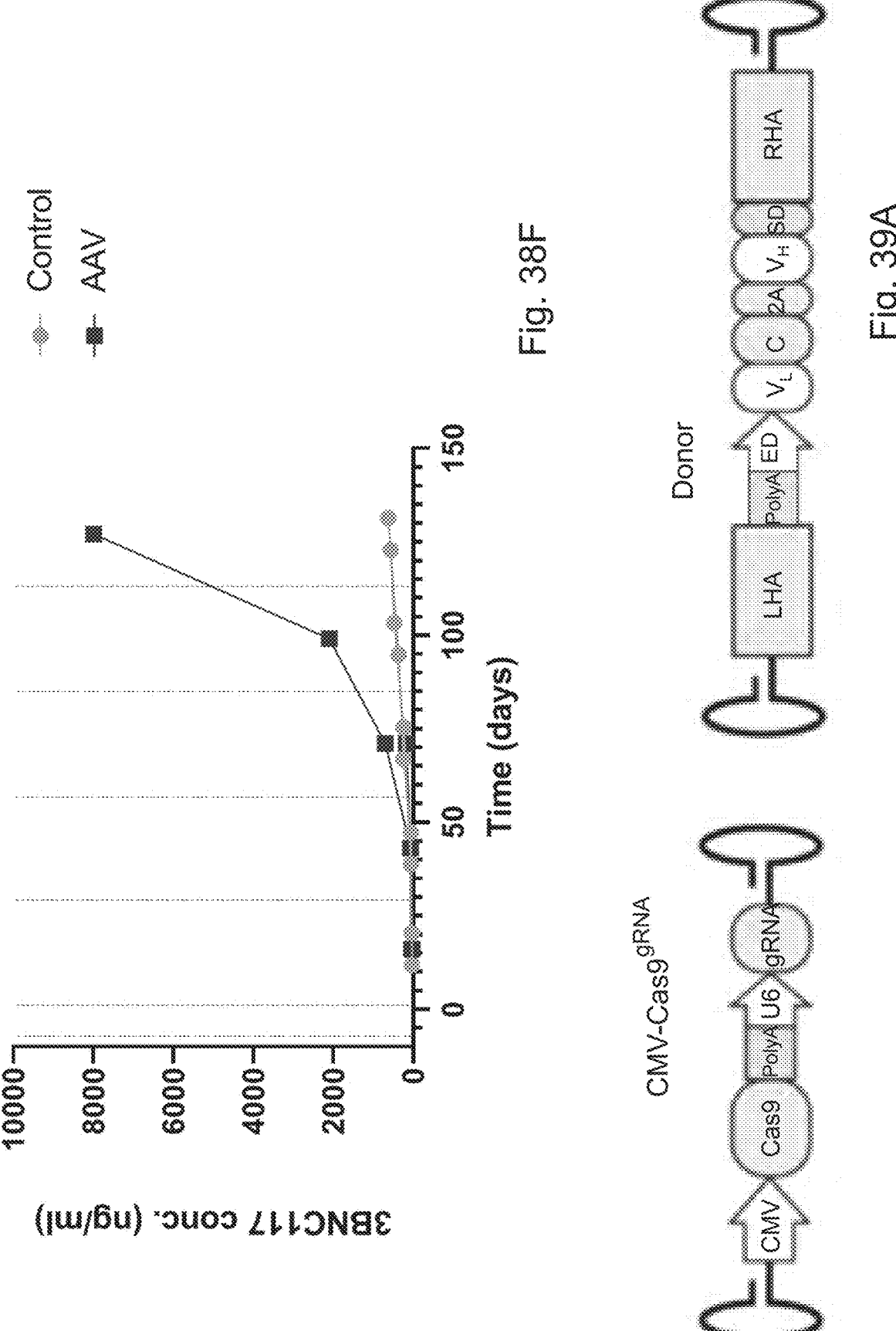

FIG. 38F. ELISA analysis on mice sera that were taken at the timepoints indicated in (38E), comparing the 3BNC117-IgG secretion levels of treated mice vs. control mice that received non-engineered cells. Dashed vertical lines indicate immunizations. The graph representing the $2^{nd}$ mouse in the treated group is discontinued since the mouse died during the bleeding procedure.

FIG. 39A-39E: In vivo engineering of B cells to express an anti-HIV bNAb

FIG. 39A. Vector design. The expression of saCas9 and the sgRNA is driven by the CMV and U6 promoters, respectively 15. The Donor vector encodes the light chain (VL-C), and the variable heavy chain (VH) of the 3BNC117 antibody under the regulation of an enhancer dependent (ED) promoter. A splice donor (SD) sequence downstream to the VH segment facilitates splicing with the endogenous constant segment upon integration into the IgH locus (FIG. 40), while an upstream polyadenylation (polyA) signal prevents undesired splicing between the endogenous VH and constant segments7. The donor cassette is targeted by homology directed repair (HDR) to the IgH locus, using the flanking homology arms (LHA and RHA)

FIG. 39B. Experimental scheme. Immunizations are indicated in black, above the timeline. Blood collections are indicated in red, below the timeline. A single injection of AAVs occurs at day 6, with 5E11 vg per mouse for each vector.

FIG. 39C. 3BNC117 IgG titers as quantified by ELISA using an anti-idiotypic antibody to 3BNC117. The black arrows indicate immunizations and the blue arrow indicates the AAV injection. Mean and SEM are indicated. *=pv<0.05, two-way ANOVA of CMV-Cas9gRNA+Donor as compared to the Donor group. n=3.

FIG. 39D. Area under the curve (AUC) of C. *=pv<0.05, **=pv<0.01 unpaired t-test. n=3.

FIG. 39E. Transduction neutralization of TZM.bl cells by the YU2.DG (left) and JRFL (right) HIV pseudoviruses in the presence of IgGs purified form day 136 sera. Neutralization is calculated as percent reduction from maximal luminescence per sample. The PBS control received immunizations as in C, while the naïve control represents serum IgG from an untreated mouse. *=pv<0.05, **=pv<0.01 Two-way ANOVA with Šidák's multiple comparison for time points comparison to PBS. AUC bar graphs are available in FIG. 44.

FIG. 40A-40E: Targeting an antibody to the IgH locus of B cells allows for antigen induced activation, SHM, CSR and affinity maturation FIG. 40A. Engineering scheme depicting the integration site of the 3BNC117 cassette into the J-C intron of the IgH locus. 3BNC117 is targeted using CRISPR/Cas9 downstream of the last J segment (J4) and upstream of the intronic enhancer (iEμ), class switch recombination locus (CSR) and the IgH Cμ exons.

Figures 40A, 40B:
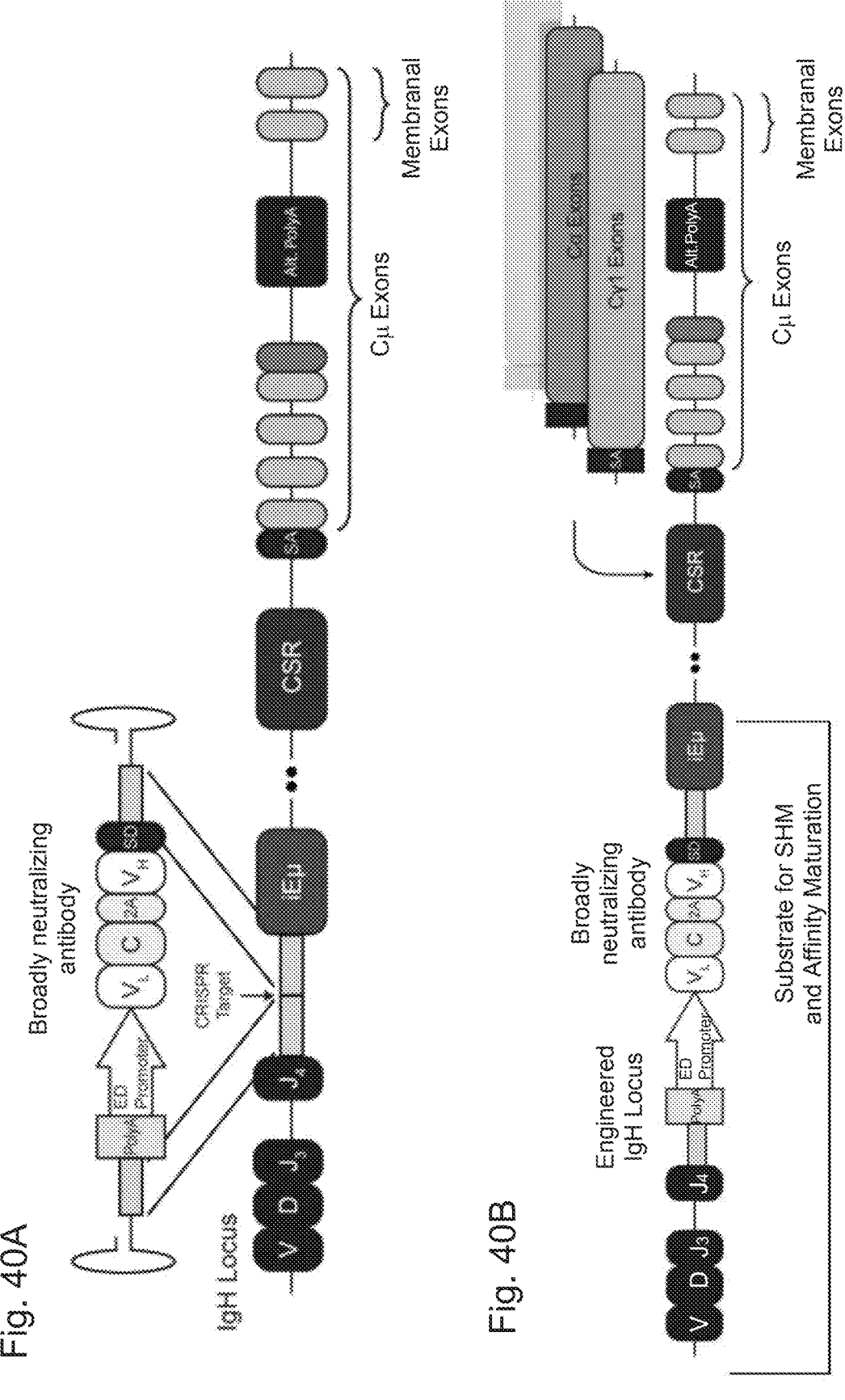

FIG. 40B. The integrated antibody may undergo somatic hyper mutation (SHM) and CSR. Indicated below is the area targeted by AID for SHM. The arrow indicates a CSR event where the IgHCμ exons will be replaced by exons coding for another constant domain. For the IgHCμ exons we indicate the alternative polyA, active when the antibody is secreted, and the membranal exons, expressed when the polyA is not active.

FIG. 40C. The bNAb mRNA is terminated by alternative poly adenylation sites allowing for membranal (BCR) or soluble expression, before and after differentiation into a plasma cell, respectively. mRNA (above) and protein (below) scheme of a BCR or soluble antibody.

FIG. 40D. The donor AAV does not code for the constant domain, rather it uses a splice donor (SD) to splice with the endogenous constant. Therefore, when an engineered cell undergoes CSR the integrated antibody may be expressed as a different isotype. mRNA (above) and protein (below) scheme of the antibody with different classes.

FIG. 40E. The bNAb is targeted to an AID active locus. Therefore, SHM in the antibody coding genes may allow for clonal expansion due to affinity maturation. mRNA (above) and protein (below) scheme of the antibody undergoing SHM.

Figure 41A:
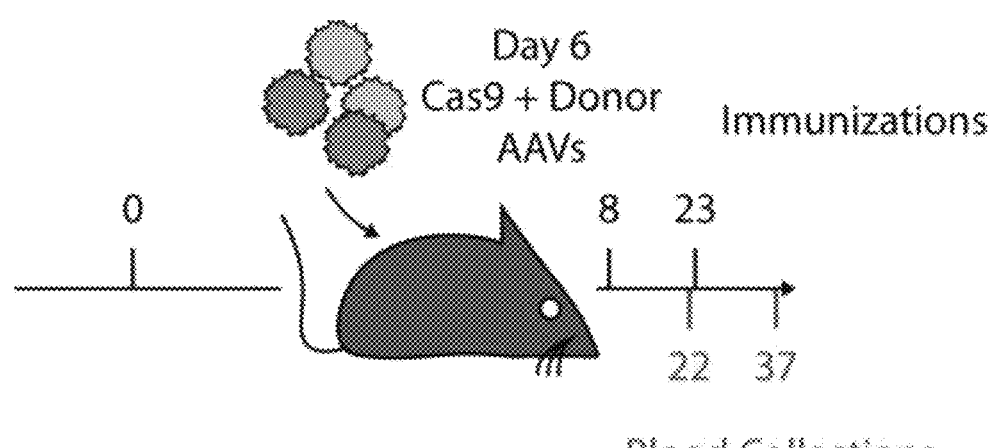
Figure 41B:
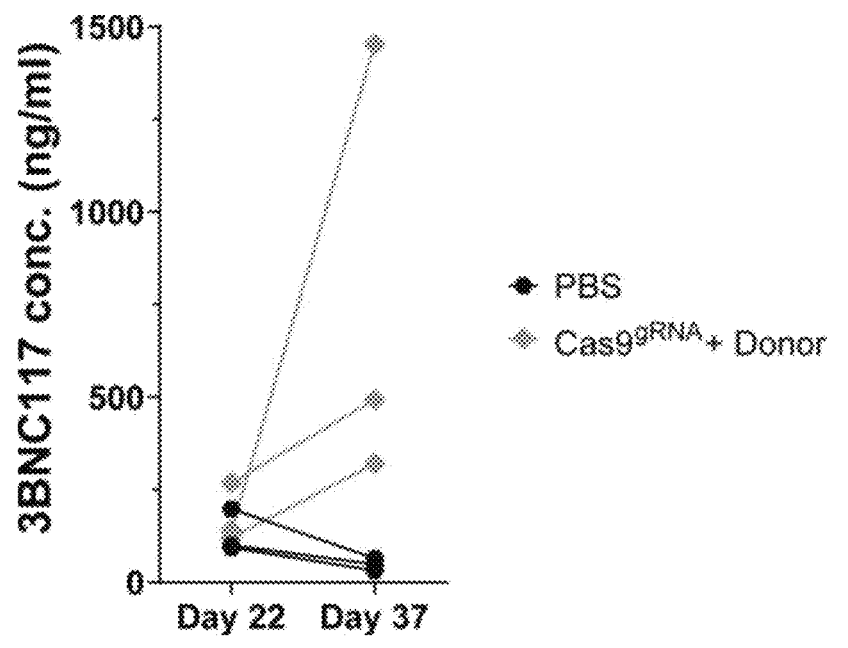

FIG. 41A-41B: In vivo engineered B cells are activated by the BG505 MD39 HIV antigen FIG. 41A. Experimental scheme. Immunizations are indicated in black, above the timeline. Blood collections are indicated in red, below the timeline. A single injection of AAVs occurs at day 6.

FIG. 41B. 3BNC117 IgG titers as quantified by ELISA, using an anti-idiotypic antibody as compared to a PBS injected group, similarly immunized with gp120. *=pv<0.05 matched, two-way ANOVA with Šidák's multiple comparison. In this figure the PBS group is the same as described in FIG. 59C.

Figures 42A, 42B:
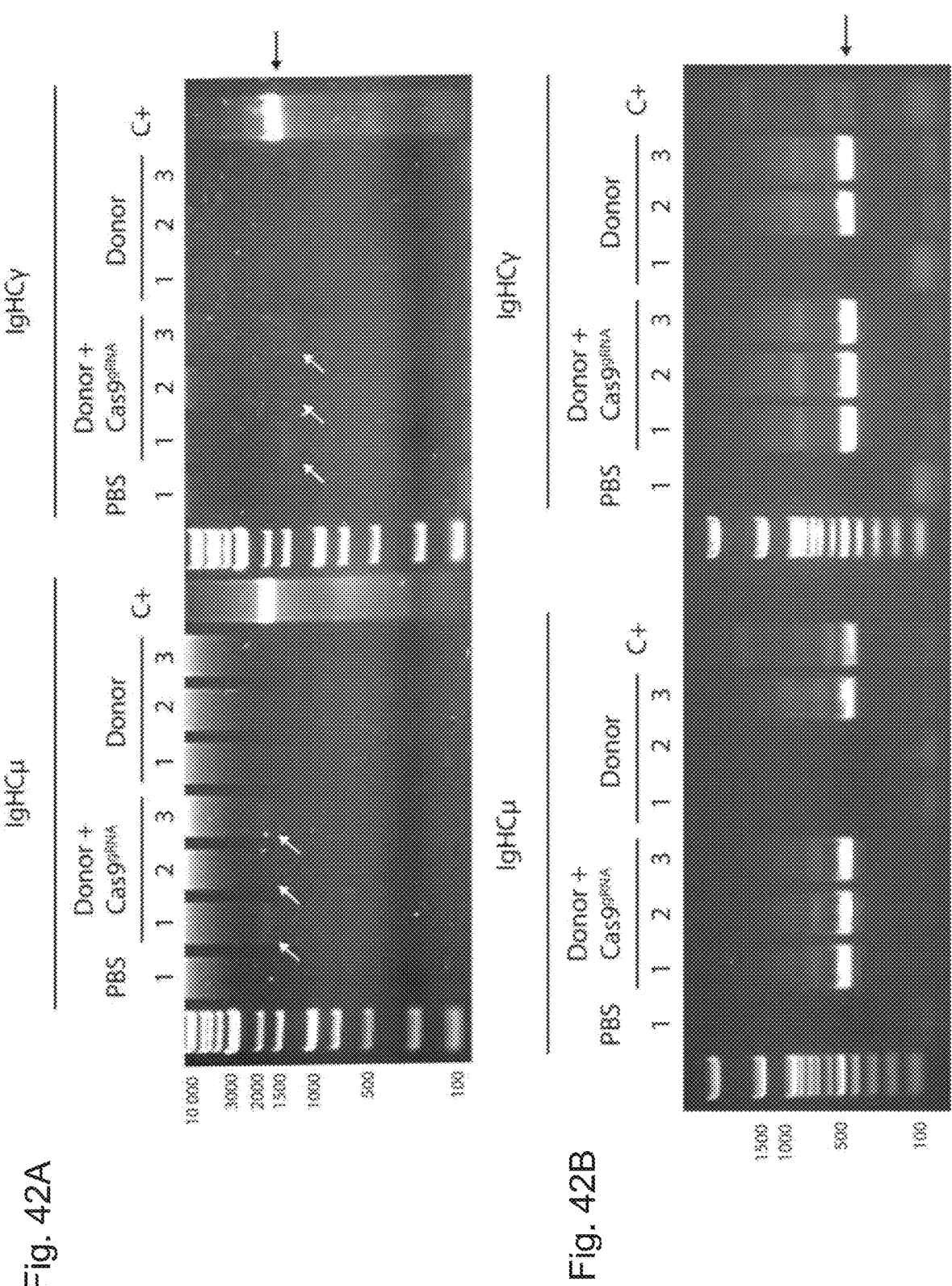

FIG. 42A-42C: Validation of on-target integration

FIG. 42A. RT-PCR on RNA from sorted, 3BNC117+, CD19+, CD4− blood lymphocytes from day 37. A reverse primer was used in a membranal exon of either IgHCμ or IgHCγ (all subtypes) and a forward primer on the VH of the coded 3BNC117. Numbers indicate different mice, injected with either (a) PBS, (b) the donor vector and the CMV-Cas9gRNA vector, or (c) the donor vector only, as indicated above the gels. Control sample comes from in-vitro engineered primary mouse splenic lymphocytes. Ladder sizes are indicated on the left. Arrow indicates the expected amplicon size.

FIG. 42B. Total DNA from the previous reaction was purified and a semi-nested PCR with the same forward primer and a reverse primer on the CH1 of the constant domains. Ladder sizes are indicated on the left. Arrow indicates the expected amplicon size.

FIG. 42C. Sanger sequencing alignment and chromatogram of the purified amplicon from the previous step. Reference sequences are indicated above. For the IgHCγ, each subtype reference is indicated.), as denoted by SEQ ID NO. 286 (Reference), SEQ ID NO. 286 (Donor+Cas9gRNA1 IgM), SEQ ID NO. 287 (Reference IgHCγ1), SEQ ID NO. 288 (Reference IgHCγ2b), SEQ ID NO. 289 (Reference IgHCγ3), SEQ ID NO. 290 (Reference IgHCγ2c/a), SEQ ID NO. 291 (Donor 3), and SEQ ID NO. 292 (Donor+Cas9gRNA1 IgG).

FIG. 43A-43D: Multiple isotypes of the 3BNC117 antibody are expressed by engineered B cells FIGS. 43A-43D. ELISA for each isotype, with the AUC comparison on the right.

Figure 43D:
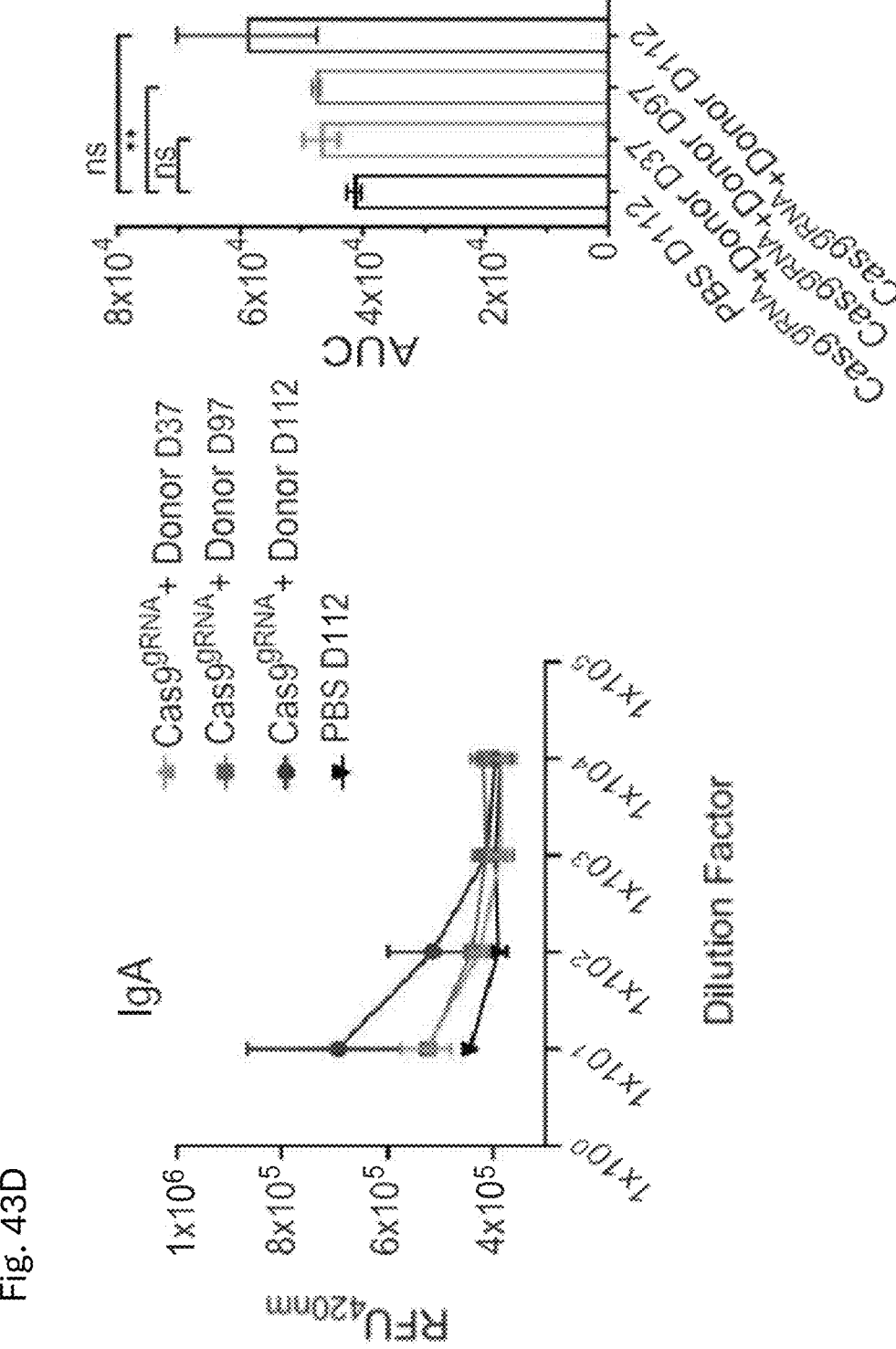

FIG. 43A. IgM; FIG. 43B. IgG1; FIG. 43C. IgG2c; FIG. 43D. IgA;

All samples come from the CMV-Cas9gRNA+Donor injected mice, at different time points as indicated in each legend. Mean and SD are indicated. For AUC, *=pv<0.05, =pv<0.01, *=pv<0.001, unpaired t-test. n=3.

Figure 44B:
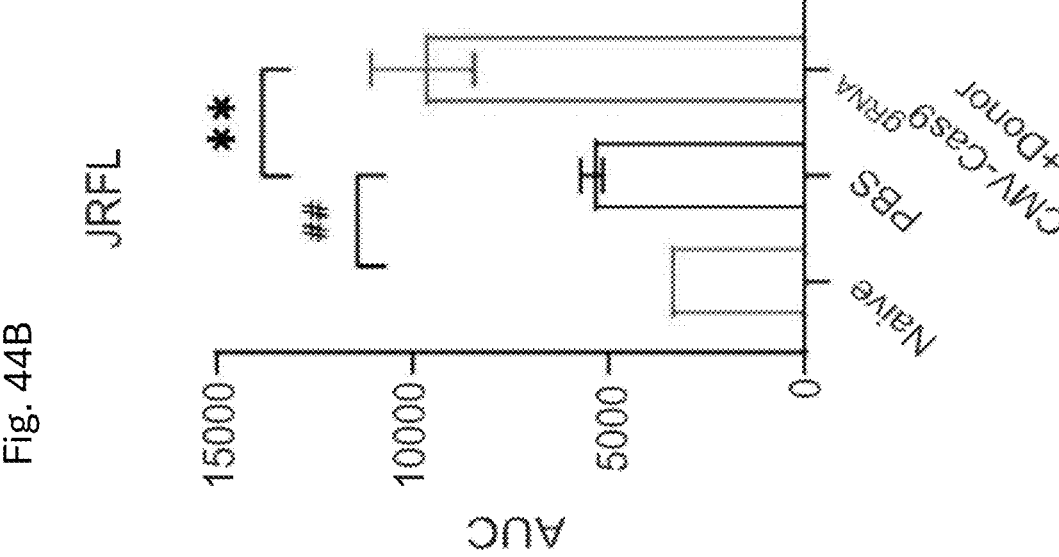
Figure 44A:
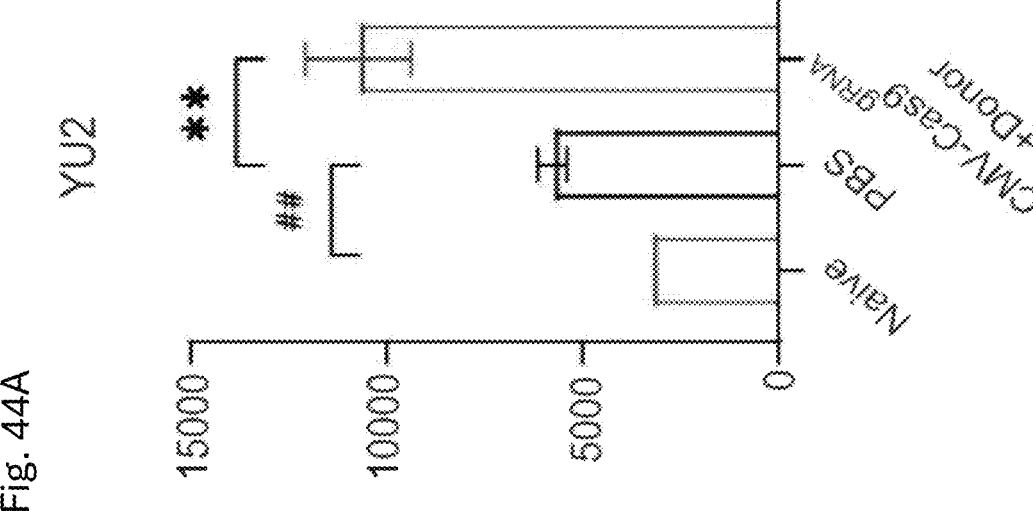

FIG. 44A-44B: Area under the Curve (AUC) of FIG. 39E for

FIG. 44A. YU2.DG

FIG. 44B. JRFL

**=pv<0.01with unpaired t-test for CMV-Cas9gRNA+Donor to PBS comparison and ##=pv<0.01 with one-sample t-test for Naïve to PBS comparison. n=3 for CMV-Cas9gRNA+Donor and PBS. Naïve sample from a single, non-immunized, non-AAV-injected mouse.

FIG. 45A-45F: In-vivo engineered B-cells are found in lymphatic tissues 130 days following AAV injection.

FIG. 45A. Flow cytometry plots demonstrating 3BNC117 expression among blood B cells (CD19+, CD4−).

FIG. 45B. Quantification of blood 3BNC117-expressing cells over time. The black arrows indicate immunizations and the blue arrow indicates AAV injection. ****=pv<0.0001 Two-way ANOVA with Šidák's multiple comparison for time points comparison to PBS. n=3.

FIG. 45C. Area under the Curve (AUC) analysis of the data presented in B n=3.

FIG. 45D. Flow cytometry plots demonstrating 3BNC117 expression of cells with a germinal center phenotype (GL7+, CD95/Fas+) in the spleen. Pre-gated on live, singlets.

FIG. 45E. quantification of D. Mean is indicated by the bars, ns=non-significant, **=pv<0.01 One way ANOVA with Tukey's multiple comparison.

FIG. 45F. Pie charts of 3BNC117 VH variants amplified from spleen and liver DNA at day 136. Red shading indicates expanded variants that are shared between the liver and the spleen. Blue shading indicates the R30K variant. Numbers in the middle of the pies indicate the total frequency of mutant reads in these samples.

Figures 46A, 46B, 46C:
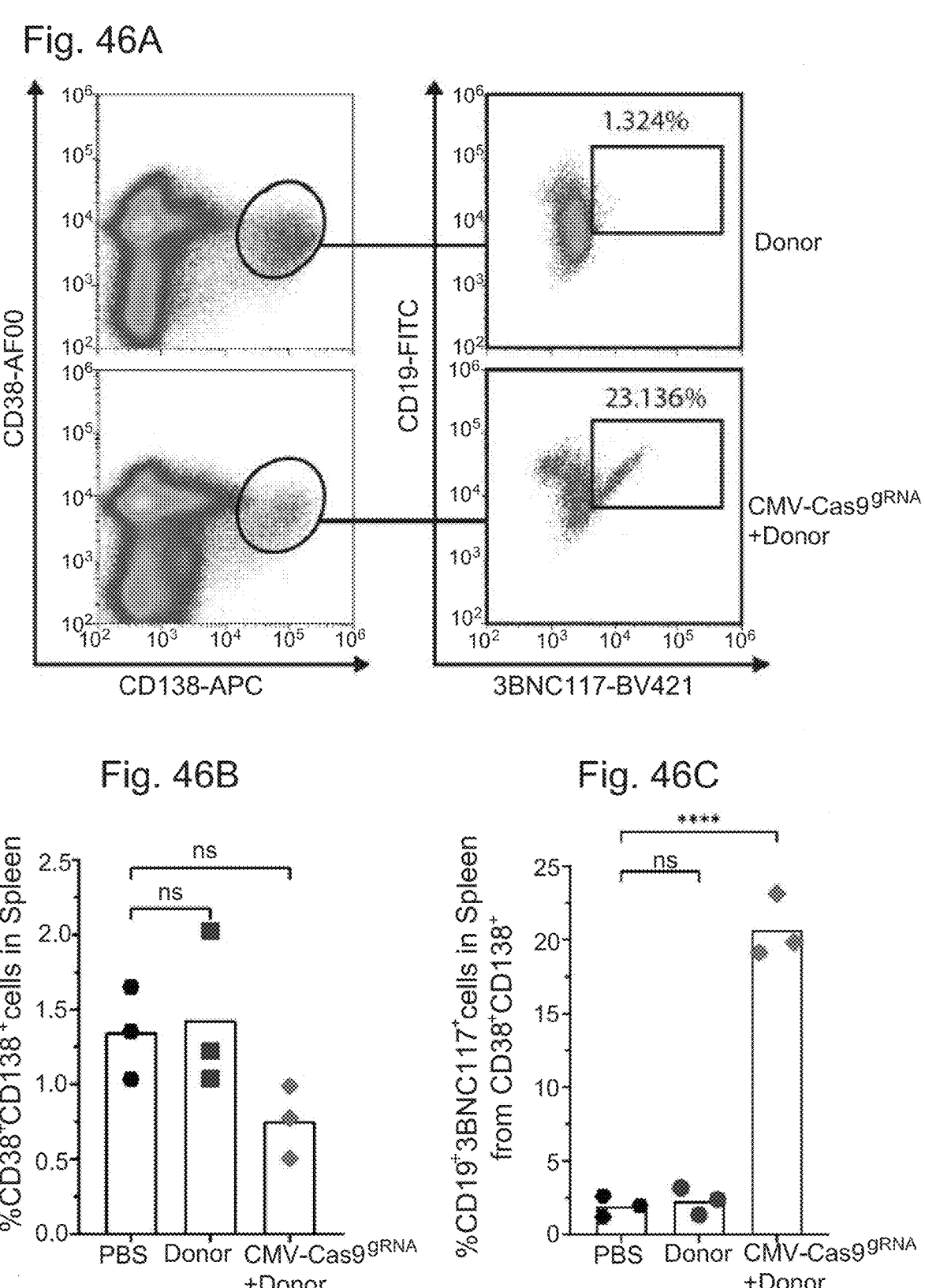

FIG. 46A-46C: 3BNC117 expression among plasmablasts

FIG. 46A. Flow cytometry plots demonstrating 3BNC117 expression among plasmablasts (CD38+, CD138+, CD19+) in the spleen at day 136.

FIG. 46B. Quantification of A for total plasmablasts (CD38+ CD138+).

FIG. 46C. Quantification of A. for engineered plasmablasts (CD38+ CD138+ 3BNC117). Mean is indicated by the bars. ns=non-significant, ****=pv<0.0001, One-way ANOVA with Tukey's multiple comparison. Pre-gating for A. is live, singlets.

Figure 47:
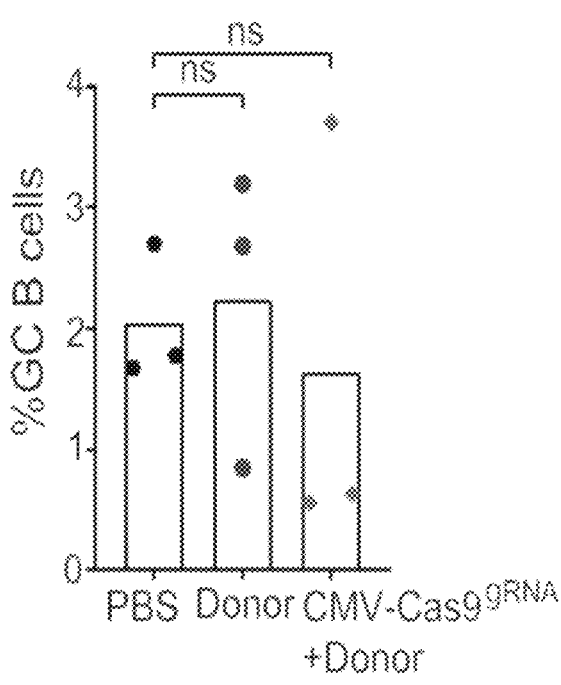

FIG. 47: Flow cytometry of total GL7+ Fas+ GC B cells

Quantification by flow cytometry of total GL7+ Fas+ GC B cells in spleens at day 136. Mean is indicated by the bars. ns=non-significant, One-way ANOVA with Tukey's multiple comparison.

Figure 48A:
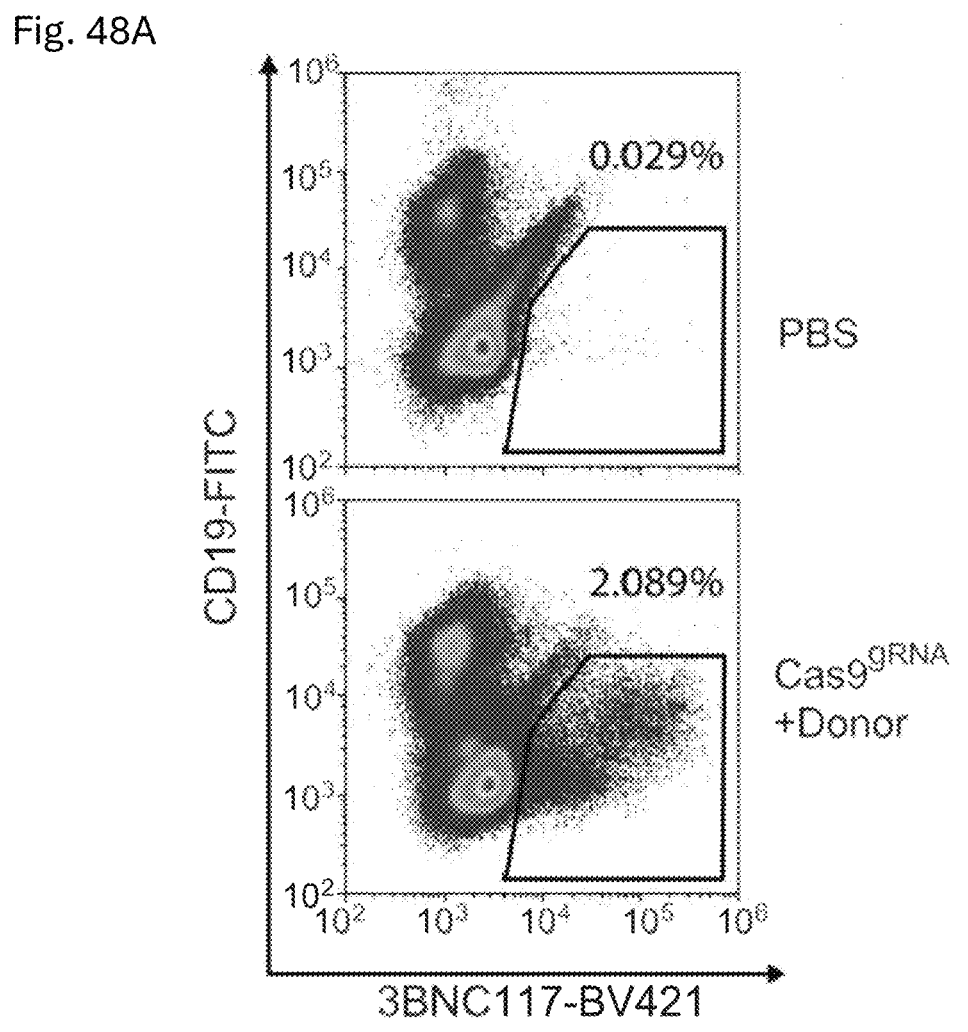
Figures 48B, 48C:
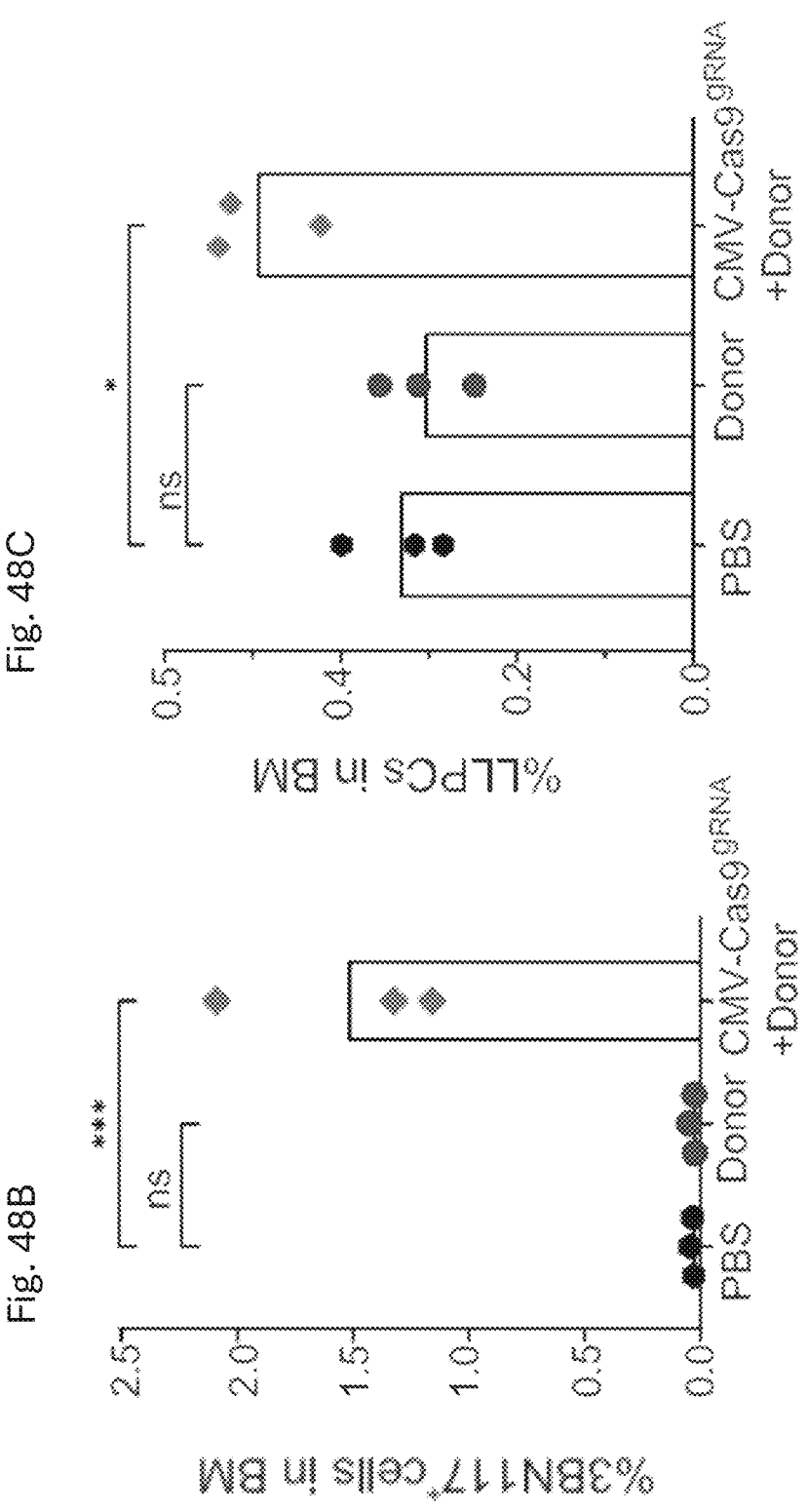

FIG. 48A-48B: 3BNC117-expressing B cells in the bone marrow

FIG. 48A. Flow cytometry plots demonstrating the presence of 3BNC117-expressing B cells in the bone marrow.

FIG. 48B. Quantification of A.

FIG. 48C. Quantification of total long-lived plasma cells (LLPCs) (CD19low CD138+). Mean is indicated by the bars. ns=non-significant, *=pv<0.05, ***=pv<0.001 One-way ANOVA with Tukey's multiple comparison.

Figure 49:
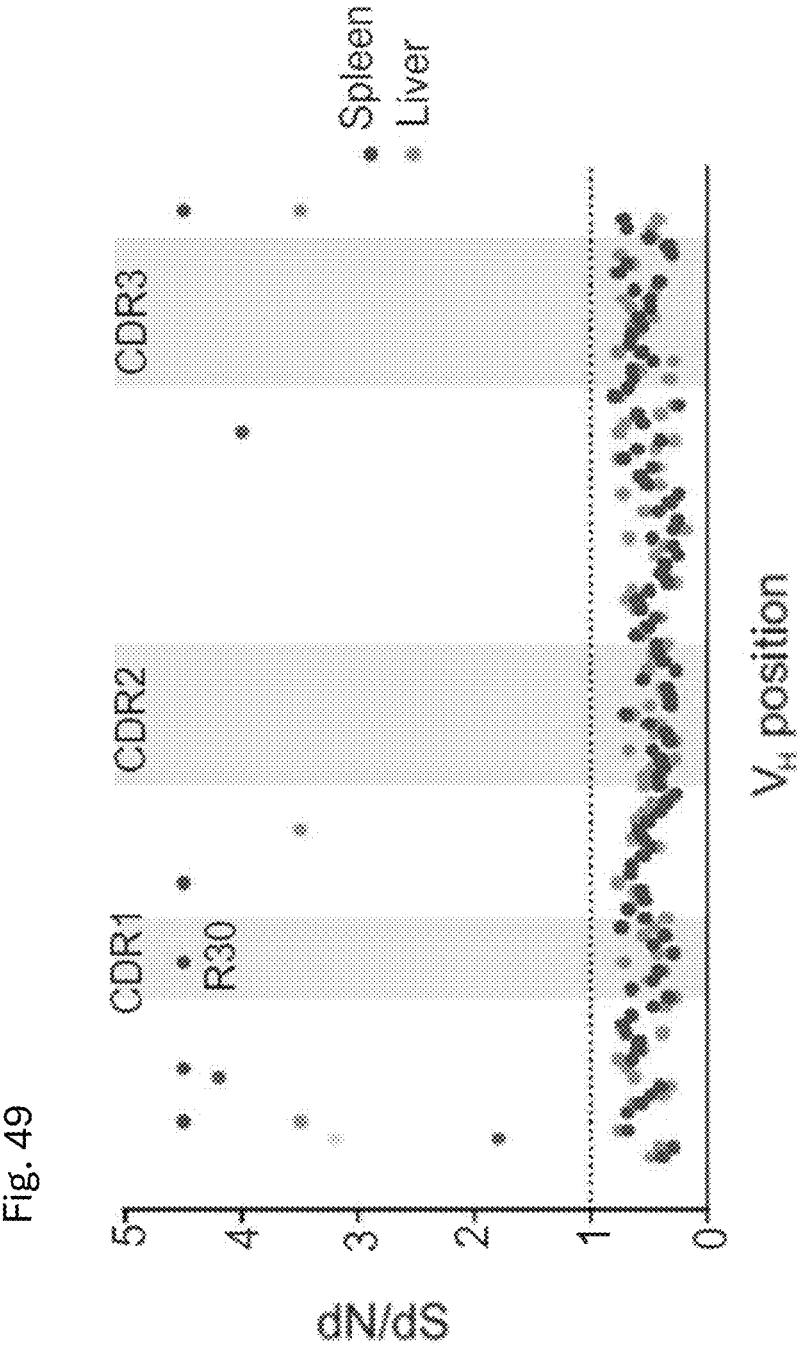

FIG. 49: dN/dS analysis of the VH segment dN/dS values for the positions along the VH segment based on Illumina sequencing of DNA amplified from the spleen (blue) or liver (orange) of a single mouse. Light shading indicates lower boundary value <1. Grey shading indicates CDR loops. The R30 position is indicated.

FIG. 50A-50E: AAV biodistribution and saCas9 off-target cleavage analysis reveal a high safety profile FIG. 50A. Donor AAV copy number quantification by qPCR in indicated tissues at day 136 in mice injected with two AAVs as in FIG. 39A.

Figures 50A, 50B, 50C:
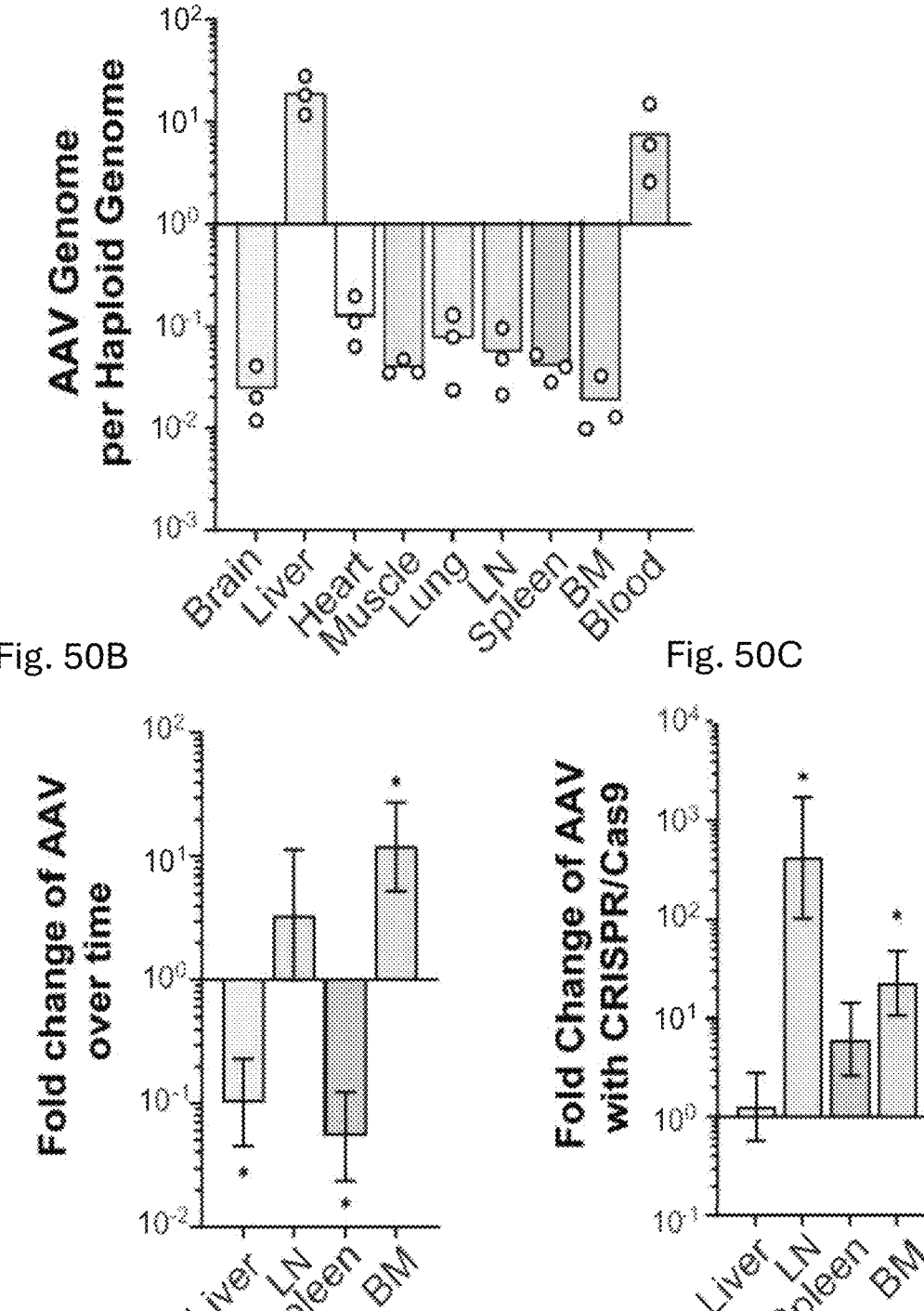

FIG. 50B. Relative copy number of donor AAV between day 37 and day 136 in selected tissues.

FIG. 50C. Relative copy number of donor AAV between mice injected with two AAVs as in FIG. 39A and mice injected with donor AAV only, at day 136. For 50B. and 50C. Mean, upper and lower boundaries are indicated. *=pv<0.05 for comparison between the two time points or mice groups, respectively, unpaired t-test. n=3.Y axis in 50A-50C uses a log scale.

Figure 50D:
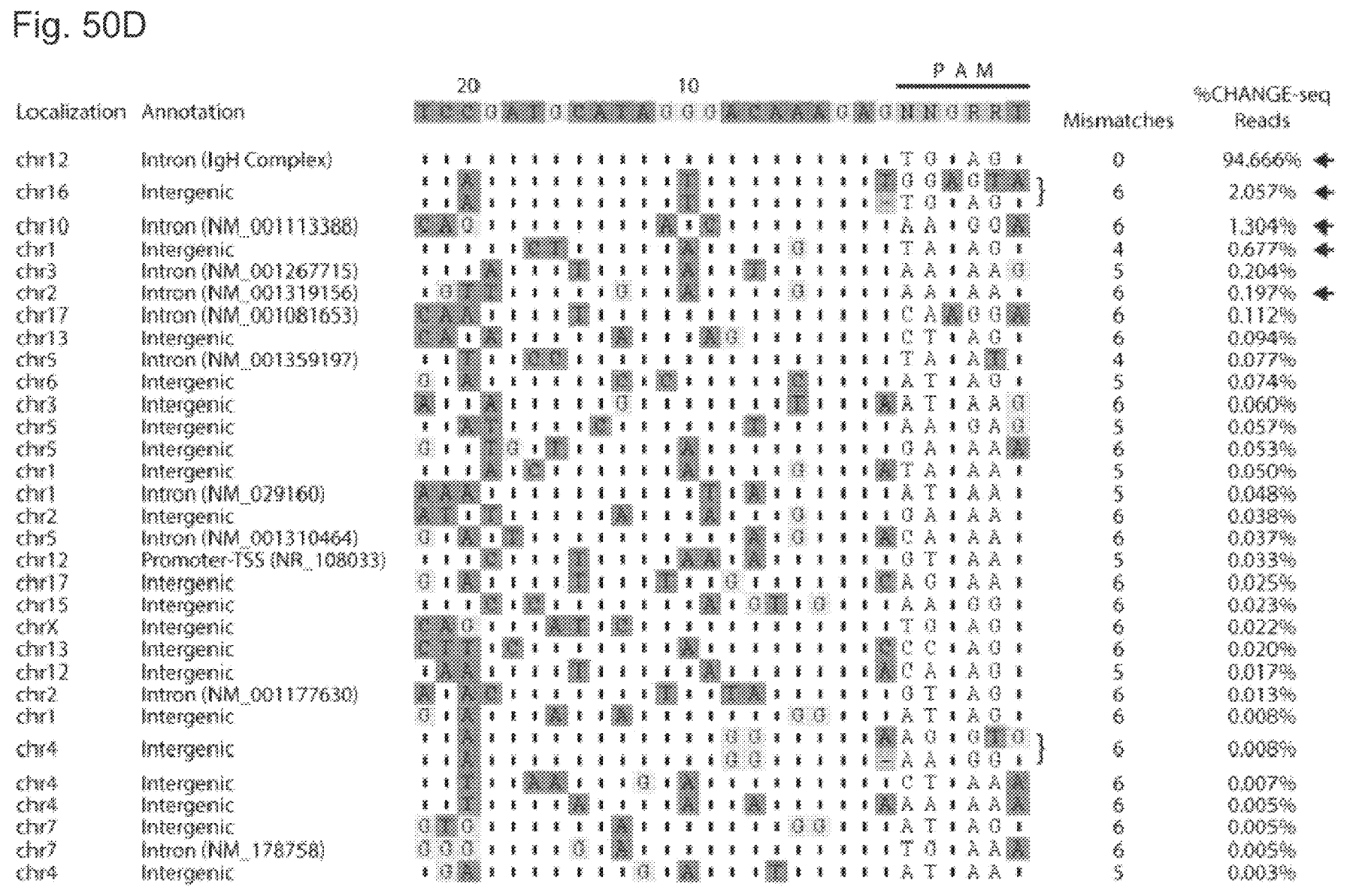

FIG. 50D. Unbiased CHANGE-seq analysis of potential saCas9 off-target cleavage with the sgRNA used in this study. Localization, annotation in the genome, number of mismatches and % read counts are indicated for each on- or off-target site. Sequence of the sgRNA with the PAM is indicated on the top. Black arrows indicate target sites used for in-vivo analysis. Mismatches between off-target sites and intended sgRNA target are color-coded.

Figure 50E:
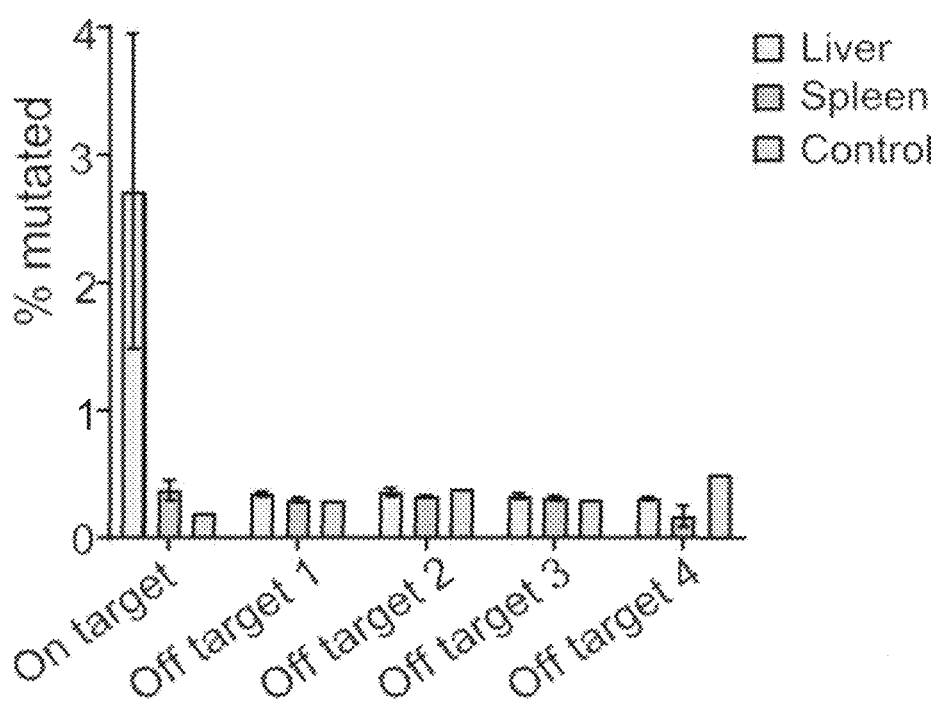

FIG. 50E. On- and off-target saCas9 cleavage of target sites indicated in D. by black arrows, in the spleen (mauve) and liver (beige) of mice injected with two AAVs as in FIG. 39A at day 136 as compared to uncut splenic lymphocytes DNA. Mean with SEM is indicated.

Figure 51A:
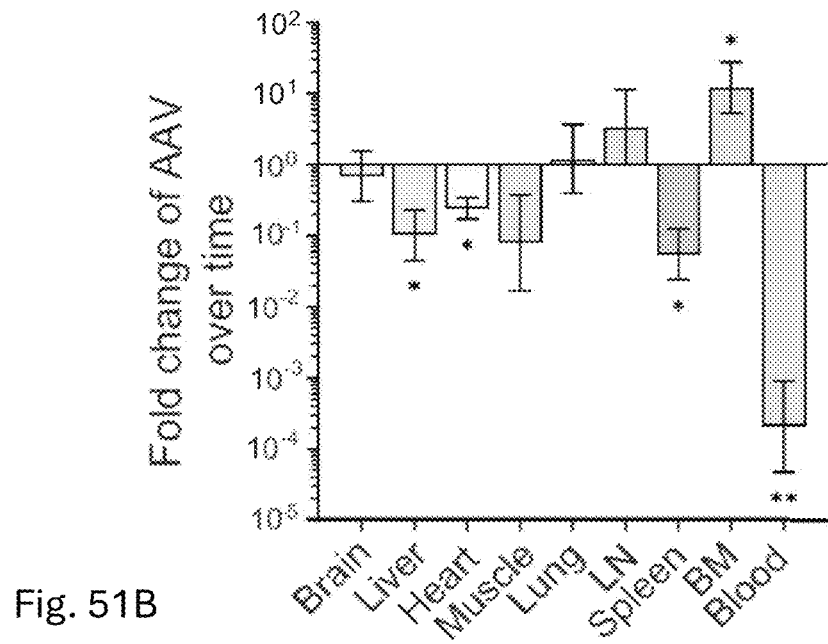
Figure 51B:
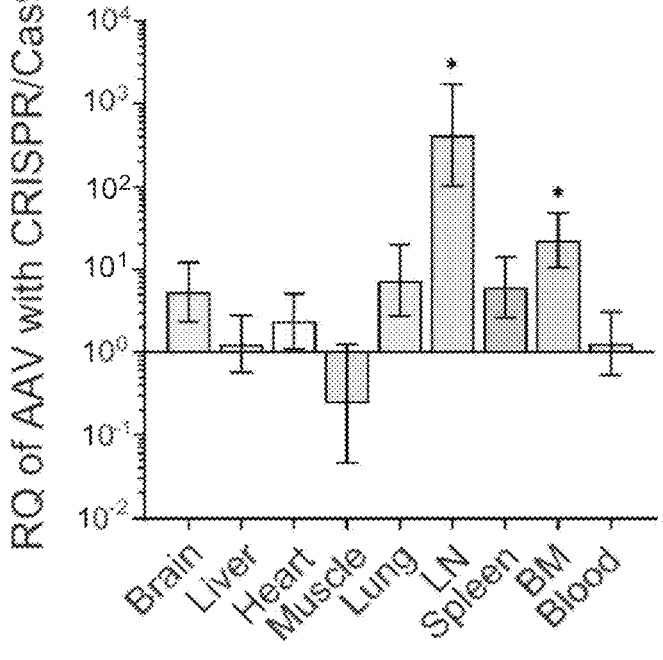

FIG. 51A-51B: Donor AAV copy number

FIG. 51A. Fold change of donor AAV copy number over time, as determined by qPCR. Mean with upper and lower boundaries are indicated. *=pv<0.05 and **=pv<0.01 for unpaired t-test comparing the two time points, day 37 and day 136.

FIG. 51B. Relative quantity of Donor AAV in the CMV-Cas9gRNA+donor group as compared to the donor only group, at day 136. Mean with upper and lower boundaries are indicated. n=3. For both 51A. and 51B. data presented includes samples presented in FIGS. 50B-50C and samples from additional tissues.

Figure 52:
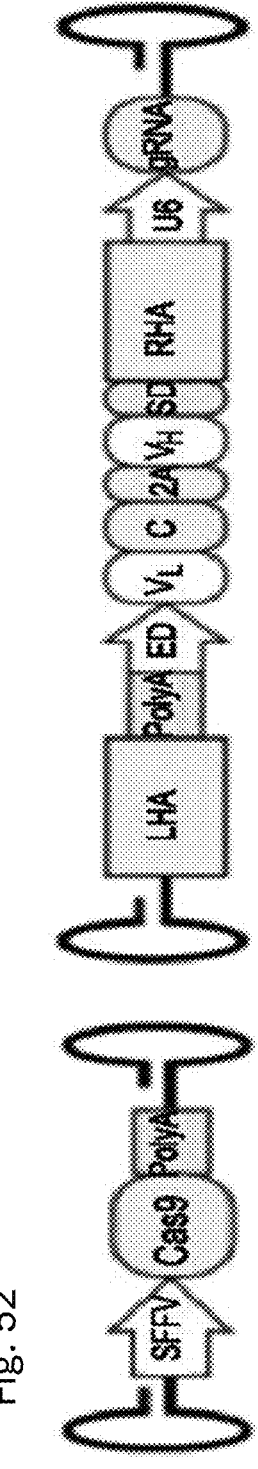

FIG. 52: Vector maps

Schematic illustration of the vector maps of the AAVs coding for the Donor$^{gRNA}$ and the SFFV-Cas9.

Figure 53:
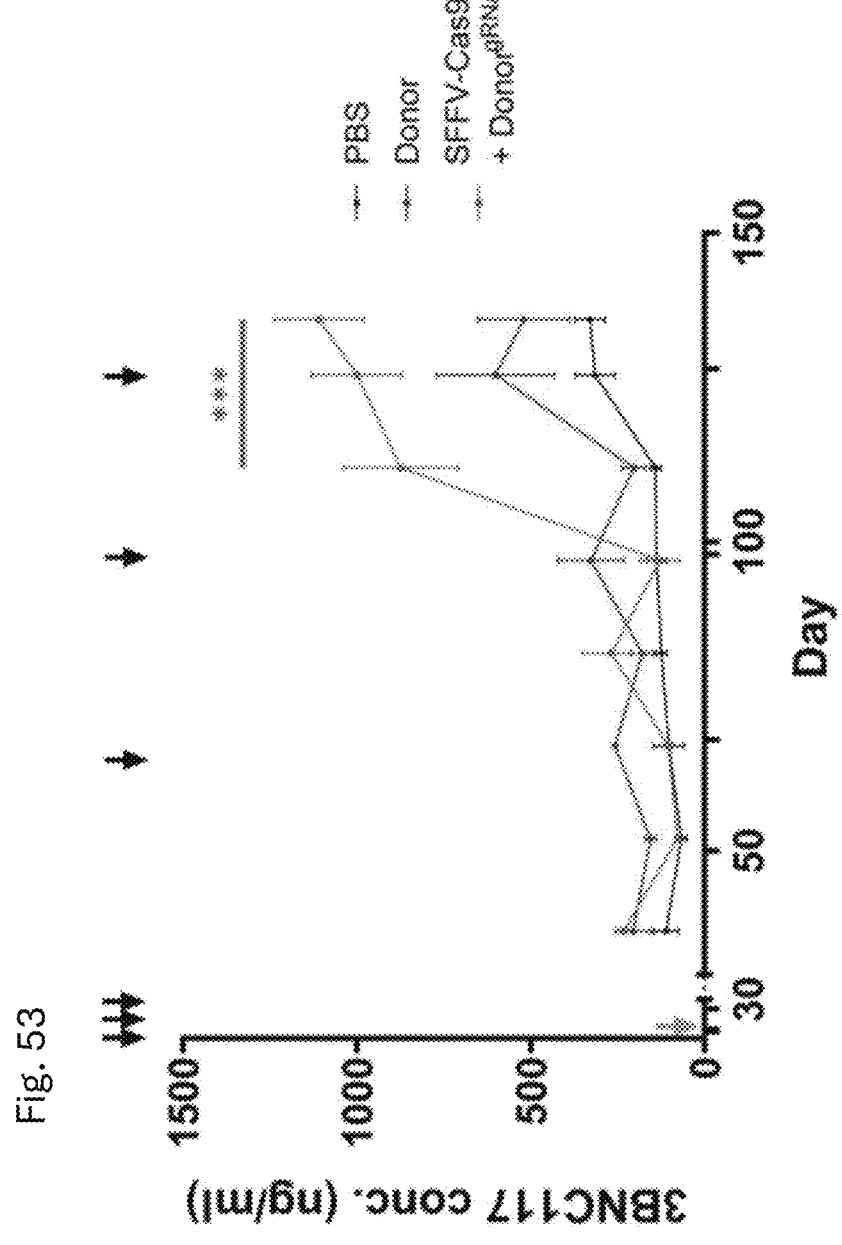

FIG. 53: 3BNC117 IgG titers

3BNC117 IgG titers as quantified by ELISA over time in the SFFV-Cas9+Donor$^{gRNA}$ group. The black arrows indicate immunizations and the blue arrow indicates AAV injection. Mean and SEM are indicated. *=pv<0.001 for two-way ANOVA comparing the SFFV-Cas9+Donor$^{gRNA}$ group to the Donor group. n=3. In this figure, the PBS and Donor control groups are the same as for FIG. 39C**.

Figure 54:
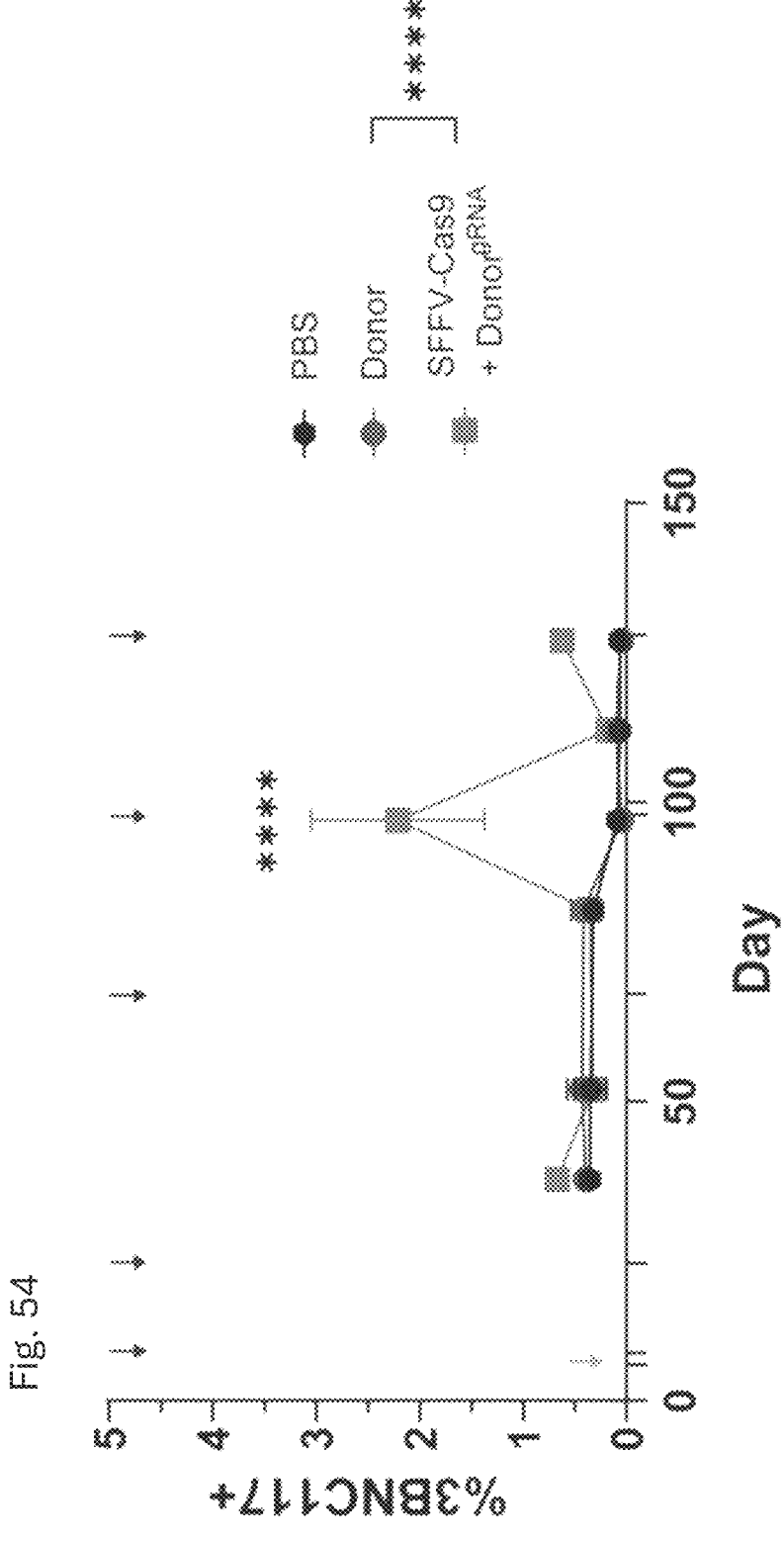

FIG. 54: 3BNC117+, CD19+, CD4− blood lymphocytes flow cytometry

3BNC117+, CD19+, CD4− blood lymphocytes as followed by flow cytometry over time in the SFFV-Cas9+Donor$^{gRNA}$ group. The black arrows indicate immunizations and the blue arrow indicates AAV injection. **=pv<0.0001 Two-way ANOVA with Šidák's multiple comparison for time points comparison to PBS. n=3. In this figure, the PBS and Donor control groups are the same as for FIG. 45B**.

Figure 55:
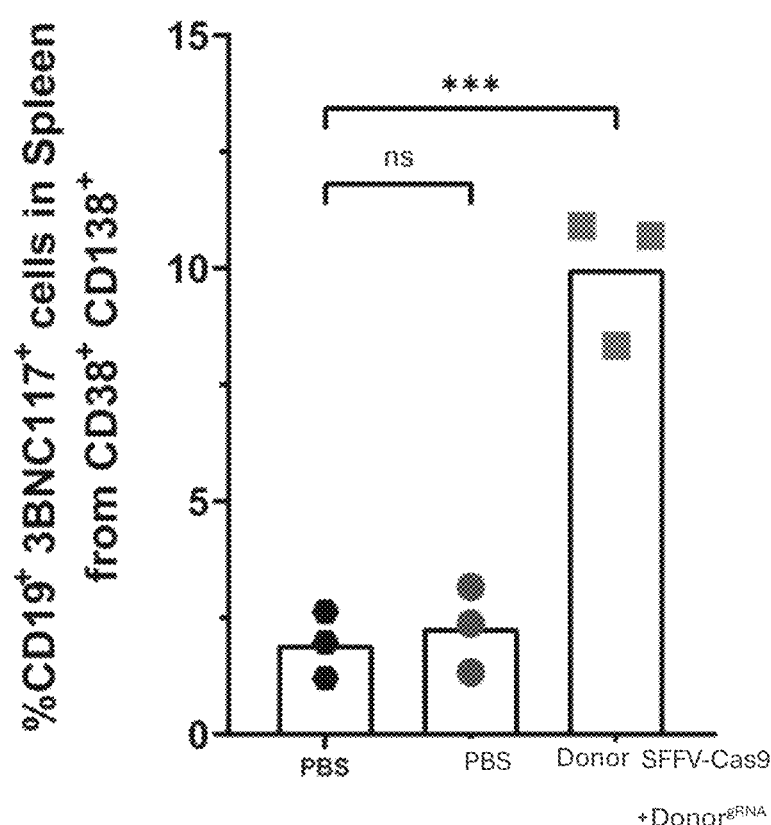

FIG. 55: 3BNC117+, CD19+, CD38+, CD138+ plasmablasts-flow cytometry Quantification by flow cytometry of 3BNC117+, CD19+, CD38+, CD138+ plasmablasts in the spleens of the SFFV-Cas9+donorgRNA group at day 136. Mean is indicated by the bars. *=pv<0.001, one-way ANOVA with Tukey's multiple comparison. In this figure, the PBS and Donor control groups are the same as for FIG. 46**.

Figure 56:
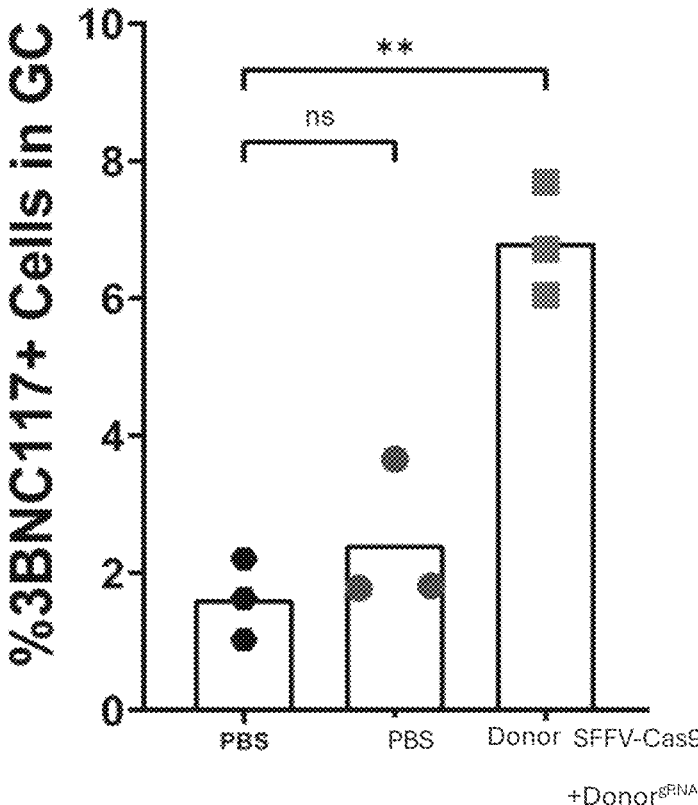

FIG. 56: GL7+, Fas/CD95+ GC B cells—flow cytometry

Quantification by flow cytometry of GL7+, Fas/CD95+ GC B cells in the spleens of the SFFV-Cas9+DonorgRNA group at day 136. Mean is indicated by the bars. =pv<0.01, one-way ANOVA with Tukey's multiple comparison. In this figure, the PBS and Donor control groups are the same as for FIG. 45E**.

Figure 57:
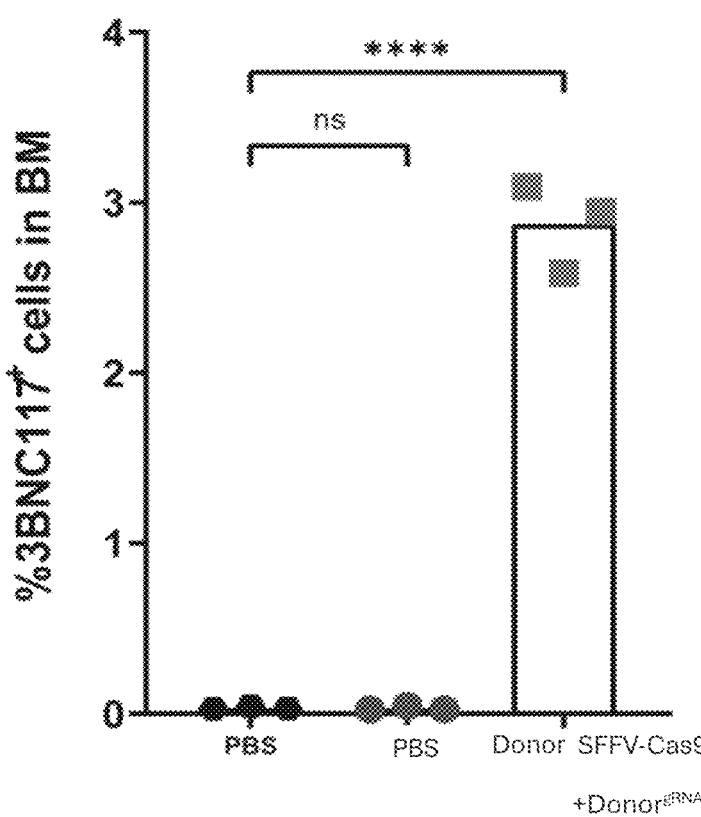

FIG. 57: 3BNC117+ cells in total bone marrow (BM)—flow cytometry Quantification by flow cytometry of 3BNC117+ cells in total bone marrow (BM) of the SFFV-Cas9+DonorgRNA group at day 136. Mean is indicated by the bars. **=pv<0.0001, one-way ANOVA with Tukey's multiple comparison. In this figure, the PBS and Donor control groups are the same as for FIG. 48B**.

Figure 58A:
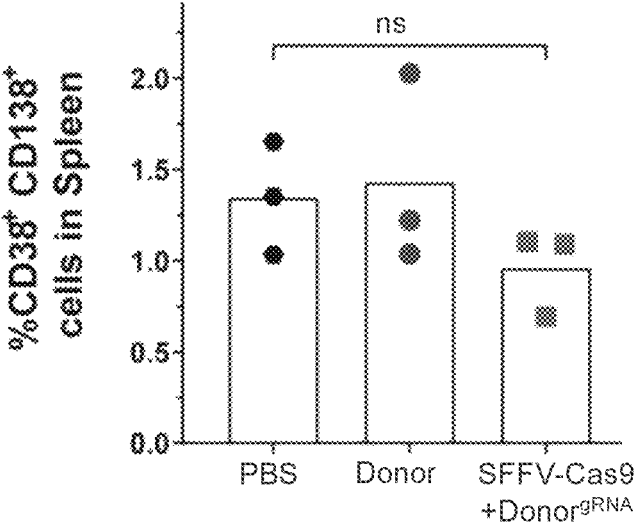
Figure 58B:
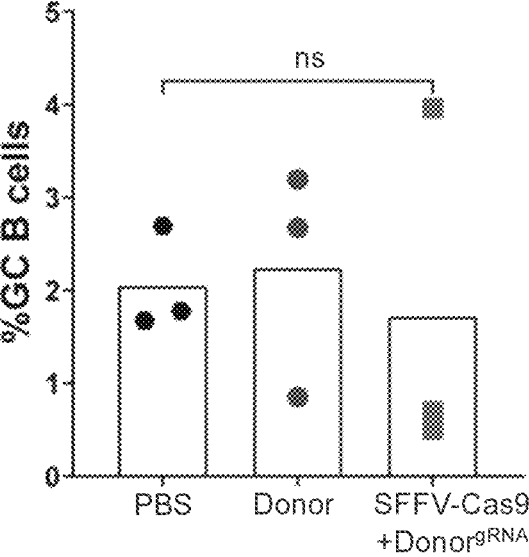
Figure 58C:
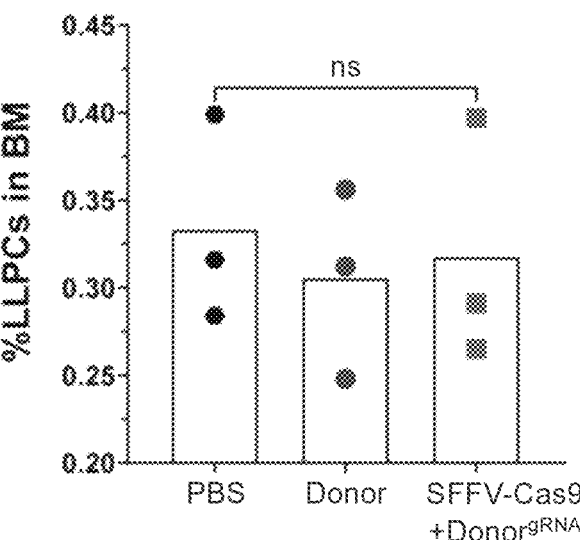

FIG. 58A-C: Assessing overall immune homeostasis

Quantification by flow cytometry of:

FIG. 58A total CD38+ CD138+ plasmablasts in spleen.

FIG. 58B total GL7+, Fas+ GC B cells in the spleen.

FIG. 58C total CD19low, CD138+ long-lived plasma cells (LLPCs) in bone marrow.

Samples collected at day 136. Mean is indicated by the bars. ns=non-significant, one-way ANOVA with Tukey's multiple comparison. In this figure, the PBS and Donor control groups are the same as for FIG. 46B, 47, 48C.

FIG. 59A-59E: Safety may be improved by coding saCas9 and the sgRNA on separate AAVs and by expressing saCas9 under the regulation of a B-cell specific promoter FIG. 59A. Map of the AAV vectors used. saCas9 is expressed under the CD19 promoter, while the sgRNA is coded on the donor vector, outside of the homology arms.

Figure 59A:
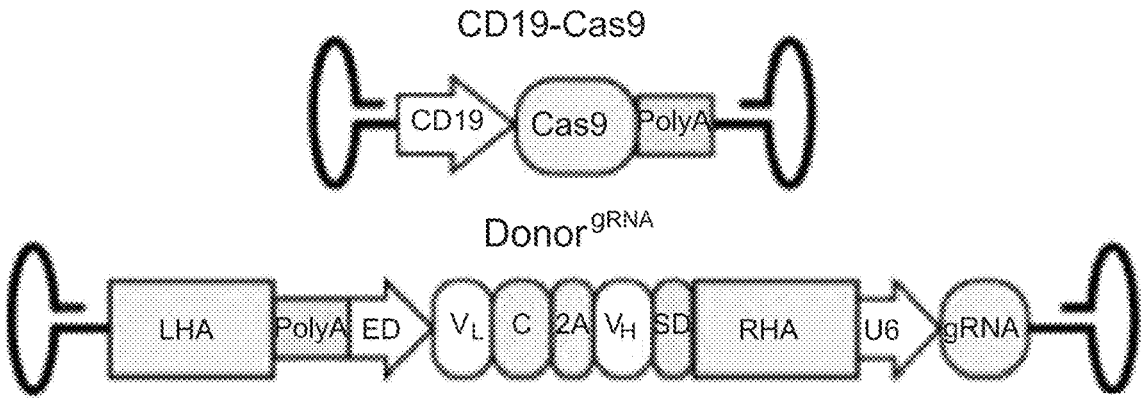
Figure 59B:
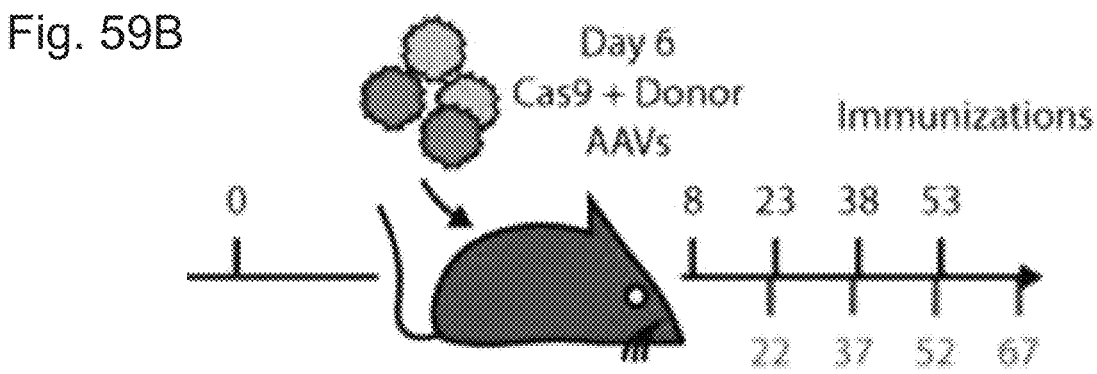

FIG. 59B. Experimental scheme. Mice were immunized according to the timeline in black (top), and bled as indicated in red (bottom).

Figure 59C:
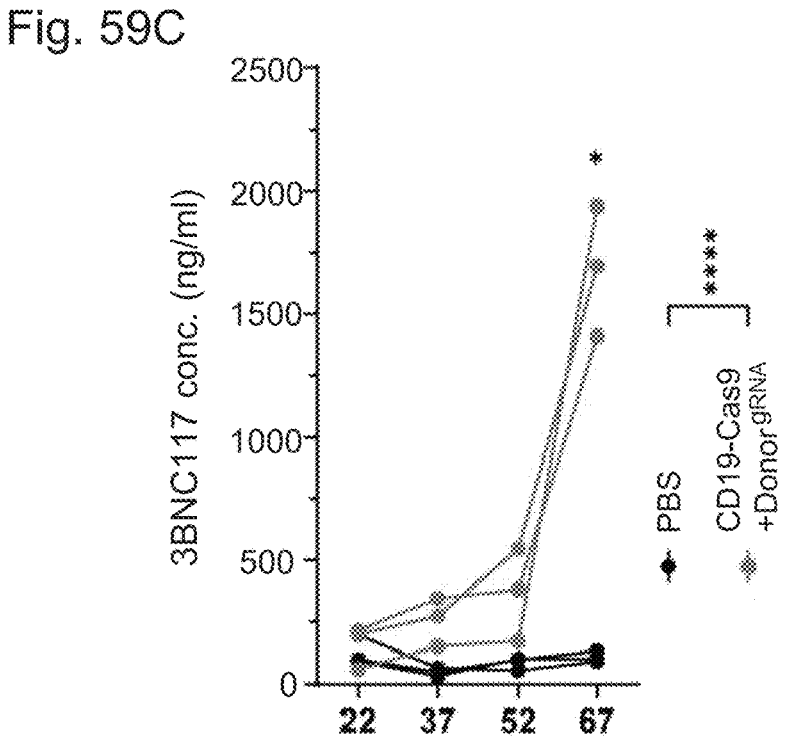

FIG. 59C. 3BNC117 IgG titers as quantified by ELISA with an anti-idiotypic antibody. Titers peak following the fourth immunization after AAV injection. Each line represents a mouse. *=pv<0.05 and ****=pv<0.0001 for Two-way ANOVA with Šidák's multiple comparison for time point comparison.

Figure 59D:
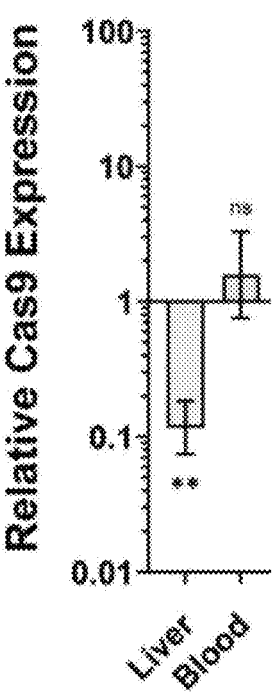

FIG. 59D. Relative saCas9 expression, depicted as the ratio between saCas9 expression from the CD19 promoter and saCas9 expression from the SFFV promoter. Error bars correspond to lower and upper boundaries derived from unpaired t test. For 59A. and 59B., ns=non-significant, **=pv<0.01. n=3.

Figure 59E:
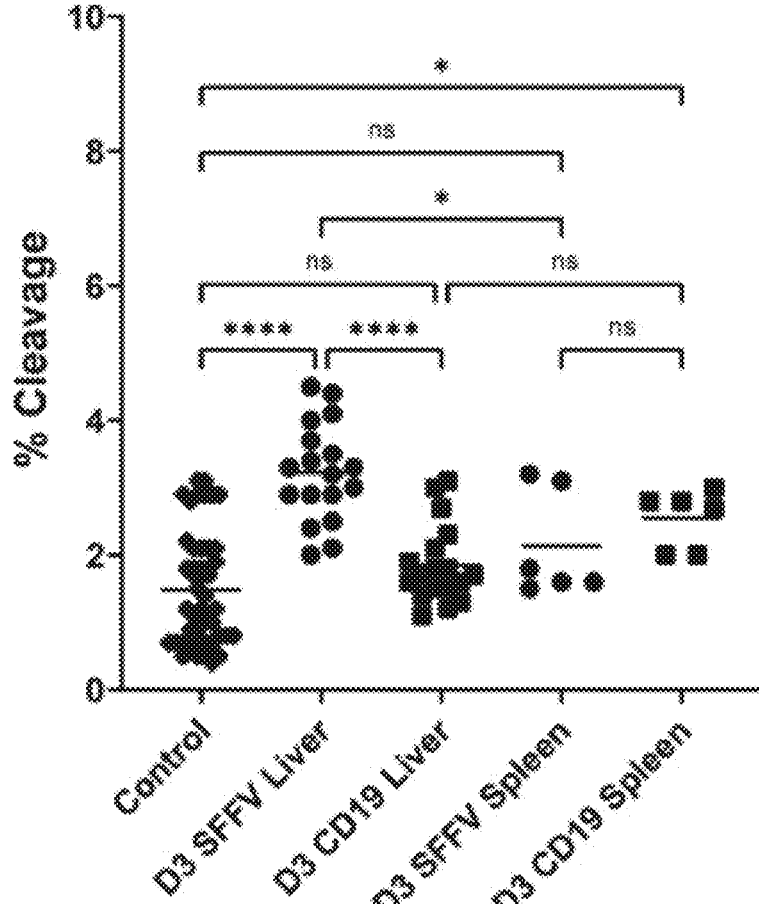

FIG. 59E. TIDE analysis of on-target cleavage in the indicated tissues using either SFFV or CD19 driven saCas9 expression. Control samples come from naive splenic lymphocytes. ns=non-significant, *=pv<0.05 and ****pv<0.0001 One-way ANOVA with Tukey's multiple comparison.

Figure 60:
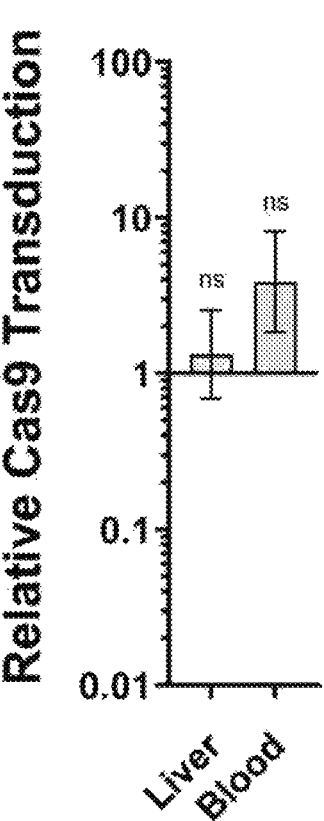

FIG. 60: saCas9 coding AAV copy number

Relative copy number of the saCas9 coding AAV, entailing either the CD19 or SFFV promoters, in liver and blood. Error bars correspond to lower and upper boundaries derived from unpaired t test for A. and B., ns=non-significant. n=3.

DETAILED DESCRIPTION OF THE INVENTION

Engineering B cell receptors to have desired specificities may have diverse clinical applications, addressing conditions including but not limited to cancer, autoimmune disease, pathogenic infections and drug abuse.

The present invention describes novel technologies allowing the engineering of B cells for the expression of a transgenic B cell receptor (BCR) and subsequent antigen-induced activation. Uniquely, the methods of the invention enable the well-controlled in vivo production and secretion of desired antibodies and thus represent a potent and sustained immunotherapy that is further augmented by affinity maturation, class switch recombination, and the retention of immunological memory.

More specifically, the inserted sequence of interest encoding the transgenic B cell receptor, comprising in some embodiments thereof, at least one segment coding for the variable part of a desired heavy chain (VH). The inserted sequence also encodes a splice donor site (SD). In some embodiments, the SD is located downstream to this VH, or any other sequence of interest. The DNA is inserted into the genome of B cells at a site that is upstream to part of the IgH locus coding for the constant segments. Thus, subsequent to on-target insertion and transcription, the transgenic VH would be fused by splicing to the endogenous constant segment. It would further allow the resulting BCR to be subjected to somatic hypermutation (SHM) and affinity maturation, as well as class switch recombination (CSR also called isotype switch) and memory retention. As being directed to a target location within the J-C intron that is not included in the endogenous variable region, the methods of the invention further allow the use of universal homology arms in the donor cassette. These universal homology arms may support specific integration of the nucleic acid sequence of interest provided by said cassette, to the target site within the J-C intron, in any B cell in a particular species. Still further, in some embodiments, the cassette of the invention may further comprise at least one SA. In yet some further embodiments, the SA may be located upstream to the VH, allowing the use of the endogenous VH promoter for transcription of the transgenic nucleic acid sequence of interest provided by the cassette of the invention.

Thus, in a first aspect, the present invention relates to a method of genetic engineering of a B cell receptor (BCR) in a mammalian cell of the B cell lineage. More specifically, the method of the invention may comprise the step of contacting the cell with at least one nucleic acid cassette comprising at least one nucleic acid sequence of interest or with any vector or vehicle comprising the cassette. In some specific embodiments, the nucleic acid sequence of interest comprised within the cassette used by the methods of the invention may comprise a nucleic acid sequence coding for at least one variable domain of at least one immunoglobulin heavy chain (VH), and at least one splice donor site (SD). In some embodiments, the VH is followed by the SD, specifically, the SD is located downstream to the VH. It should be noted that in some embodiments, the nucleic acid cassette used by the methods of the invention targets the insertion of the nucleic acid sequence of interest into a target genomic sequence within the Immunoglobulin heavy chain (IgH) locus. in yet some further embodiments, the target sequence or site, is comprised within the intron residing between the last J segment of the variable region of the IgH, and the constant region of the IgH (referred to herein as the J-C intron). In more specific embodiments, the target sequence may be located upstream of at least one splice acceptor site of the constant domain of the heavy chain of the BCR. The invention provides methods for targeted insertion of a nucleic acid sequence of interest into a target genomic sequence within the Immunoglobulin Heavy chain (IgH) locus. This target sequence is also referred to herein as a target site or target locus. As used herein, a "target sequence", "target site" or "target locus" is a region of DNA into which a nucleic acid sequence of interest is integrated, inserted and recombined within e.g. a region of DNA in a target cell. etc. In some specific embodiments the target locus is within the chromosomal DNA of the target cell. It should be noted that "target genomic locus" or "target sequence" is the site of modification of an endogenous chromosomal locus by the insertion into, integration into, or replacement of the endogenous sequence using the nucleic acid cassette of the invention.

It should be noted that the target site for the cassette of the invention is the IgH locus. More specifically, Immunoglobulin heavy locus, also known as IgH, is a region on human chromosome 14 (at 14q32.33, Gene ID: 3492), and mouse chromosome 12, that contains the genes encoding the heavy chains of antibodies. The locus includes V (variable), D (diversity), J (joining), and C (constant) segments, and IGHA, IGHG, IGHD, IGHE and IGHM constant regions. In humans for example, the VH region contains 123 $V_H$ segments, of which 79 are pseudogenes and 44 have an open reading frame. The $V_H$ genes are grouped into 7 $V_H$ families based on their high sequence homology and not by their location on chromosome 14q32. $V_H3$ is the largest family followed by $V_H4$ and $V_H1$. $V_H6$-1 is the most proximal to the $D_HJ_H$ loci. The $D_H$ region contains 27 $D_H$ segments, of which 25 have been shown to be involved in creation of human antibody. Seven $D_H$ families are classified based on sequence homology. $D_H7$-27 is closest to the $J_H$ locus. Six $J_H$ segments are functional. It should be understood that the cassette used by the invention targets the nucleic acid sequence of interest into the specific target site within the IgH locus. By "targeting the insertion of the nucleic acid sequence of interest into a target genomic sequence", as used herein is meant in some embodiments, directing, leading to and ensuring the specific insertion of the sequence of interest into the desired target site. More specifically, that the insertion of the sequence of interest predominantly (specifically, 50%, 55%, 60%, 65%, 70%, 75%, 80%, 85%, 90%, 95%, 99.9% or more, specifically, 100%) occurs in the desired target site, with minimal (45% or less) non-target insertion. In some specific embodiments, such targeted insertion is achieved by inclusion of target recognition elements (e.g., recognition sites) in the cassettes used by the invention and/or as additional elements provided with the cassette (e.g. gRNAs), as will be discussed herein after.

In some specific embodiments, the target genomic sequence within the IgH locus may be located downstream to the J region of the variable domain of the heavy chain. In yet some other optional embodiments, the target genomic sequence may be located upstream of the class switch recombination (CSR) region of said heavy chain. Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR region of the heavy chain of the BCR.

In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR region of the heavy chain.

It should be understood that in some embodiments, the insertion of the sequence of interest to the target site must retain, at least in part, the class switch recombination mediated by the CSR region, and optionally, at least part of the enhancer activity.

Figure 1A:
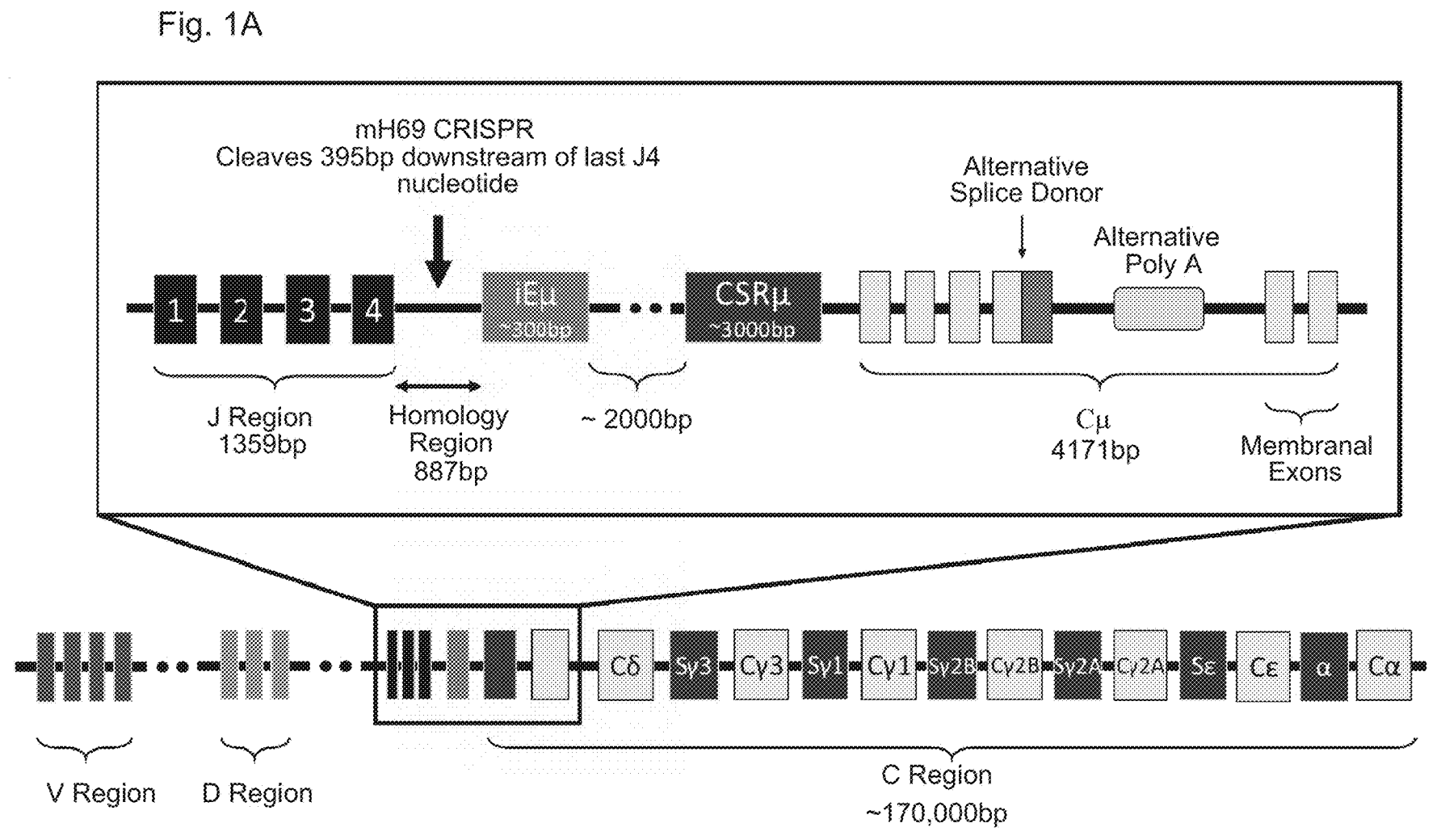

As shown in FIGS. 1A (mouse) and 1D (human), the region indicated therein as the "homology region", downstream to the variable J region and upstream to the enhancer region may be used as a target site for insertion of the nucleic acid sequence of interest by the methods and cassettes of the invention. As shown by FIG. 1A, the enhancer is located about 887 nucleotides downstream to the fourth segment of the variable J region, and the CSR is located about 3187 nucleotides downstream to the variable J region of the mouse heavy chain. Similarly, as shown in FIG. 1D, the enhancer is located about 827 nucleotides downstream to the sixth segment of the variable J region, and the CSR is located about 2809 nucleotides downstream to the variable J region of the human heavy chain. Thus, in some embodiments, the target genomic site may be located between the last J segment of the variable domain and the enhancer of the heavy chain.

In some specific embodiments, the integration site may be located between 1 to about 800 or more nucleotides downstream to the J region of the variable domain of the heavy chain, provided that the enhancer located about 827 nucleotides downstream to the sixth segment of the human J region, or 887 nucleotides downstream to the fourth segment of the human J region of the mouse variable domain of the heavy chain, retains at least partially, any enhancing function thereof.

In more specific embodiments, the target genomic sequence may be located between about 1 to about 800 or more nucleotides downstream to the J region of the variable domain of said heavy chain. Specifically, 1 to 887, 1 to 886, 1 to 885, 1 to 884, 1 to 883, 1 to 882, 1 to 881, 1 to 880, 1 to 879, 878, 877, 876, 875, 874, 873, 872, 871, 870, 869, 868, 867, 866, 865, 864, 863, 862, 861, 860, 859, 858, 857, 856, 854, 853, 852, 851, 850, 849, 848, 847, 846, 845, 844, 843, 842, 841, 840, 839, 838, 837, 836, 835, 834, 833, 832, 831, 830, 829, 828, 827, 826, 825, 824, 823, 822, 821, 820, 819, 818, 817, 816, 815, 814, 813, 812, 811, 810, 809, 808, 807, 806, 805, 804, 803, 802, 801, 800, or between about 1 to about 750, 700, 650, 600, 550, 500, 450, 400, 350, 300, 250, 200, 150, 100, 50, 40, 30, 20, 10, or less, nucleotides downstream to the variable J region.

In some embodiments, the target site for the nucleic acid sequence of interest in accordance with the invention may be located between 1 to 800 nucleotides or more, but up to 827 nucleotides downstream to the sixth segment of the human variable J region (J6). In yet some other embodiments, the target site for the nucleic acid sequence of interest in accordance with the invention may be located between 1 to 800 nucleotides or more, but up to 887 nucleotides downstream to the fourth segment of the variable J region of the mouse variable domain of the heavy chain (J4). It should be noted that in some further alternative embodiments, the target genomic sequence may be located between the enhancer and the CSR region. Thus, in some embodiments, the target site may be located between about 1100 to about 3200 nucleotides downstream to J region of the variable domain of the heavy chain. In more specific embodiments, such target site may be located between about 1400 to about 2800 or more nucleotides downstream to the sixth segment of the J region of the variable domain of the human heavy chain. In yet some further embodiments, such target site may be located between about 1187 to about 3187 nucleotides downstream to the fourth segment of the J region of the variable domain of the mouse heavy chain. Still further, in some embodiments, the target site may be located downstream to the sixth segment of the J region, provided that such site is not the J-gene break site.

The target locus for insertion within the IgH chain, in the J-C intron (the intron residing between the J region of the variable domain and the constant region), is indicated herein in relative terms, referred to the distance from the J region of the variable domain. The specific site is described as upstream or 5', or alternatively, downstream or 3' to a specific position. It should be noted that in some embodiments, each of the indicated genetic elements may be located either 5' or 3', or both, at the 5' and 3' (or in other words upstream and/or downstream), to the nucleic acid sequence of interest in the cassette provided by the invention and defined herein for all aspects of the invention.

It should be noted that in some embodiments, as being located within a non-variable region (e.g., the J-C intron), the target site allows specific targeting using universal homology arms, specifically, homology arms that are directed to sequences that are conserved in any B cell of a specific specie.

It should be noted that the terms used herein "5'" or "upstream" and "3'" or "downstream" both refer to a relative position in DNA or RNA. Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the DNA or RNA molecule and downstream is toward the 3' end. When considering double-stranded DNA, upstream is toward the 5' end of the protein coding strand for the gene in question and downstream is toward the 3' end. Due to the anti-parallel nature of DNA, this means the 3' end of the mRNA template strand is upstream of the gene and the 5' end is downstream. As used herein, the term "5'" refers to the part of the strand that is closer to the 5' end or 5' terminus, i.e. to the extremity of the DNA or RNA strand that has a phosphate group attached to the fifth carbon in the sugar-ring of the deoxyribose or ribose at its terminus. Furthermore, the term "3'" refers to the part of the strand that is closer to the 3' end or 3' terminus, i.e. to the extremity of the DNA or RNA strand that has a hydroxyl group linked to the 3rd carbon in the sugar-ring of the deoxyribose or ribose at its terminus.

As noted above, the target site may be in some embodiments upstream to the CSR region. More specifically, the CSR region is the genomic region within the IgH, necessary for Class switching that occurs by a deletional recombination between two different switch (S) regions, each of which is associated with a heavy chain constant (CH) region gene. Class switch recombination (CSR) is instigated by activation-induced cytidine deaminase (AID), which converts cytosines in S regions to uracils. The uracils are subsequently removed by two DNA repair pathways, resulting in mutations, single-strand DNA breaks, and the double-strand breaks required for CSR.

CSR is occurring between switch (S) regions, which are located upstream of all the $C_H$ genes except Cδ, and are one to 10 kb in length. Recombination occurs between DNA double-strand breaks (DSBs) introduced into the donor Sμ region and a downstream/acceptor S region located from ~65 to 160 kb downstream, although occasionally downstream S regions can subsequently recombine with a S region farther downstream. S regions are G-rich and also have a high density of WGCW (A/T-G-C-A/T) motifs, the preferred target for activation-induced cytidine deaminase (AID), the enzyme that initiates CSR by deaminating cytosines (dC) within S region DNA, converting dC to dU. Subsequently, enzymes of the base excision repair (BER) and mismatch repair (MMR) pathways convert the dU's to DNA double-strand breaks (DSBs), which are required for CSR. The DSBs are subsequently recombined by an end-joining type of DNA recombination, predominantly by non-homologous end-joining (NHEJ). The use of NHEJ rather than homologous recombination is consistent with the facts that S region DSBs are induced and recombined during G1 phase, and that different S regions do not share long stretches of identity, which are required for homologous recombination.

In some specific embodiments, the insertion of the nucleic acid sequence of interest retains, at least in part, the function of at least one of the CSR and the enhancer regions.

More specifically, in some embodiments, the insertion of the nucleic acid sequence of interest provided by the cassette of the invention into the specific target site within the IgH locus should retain, preserve, hold, maintain and keep at least in part, specifically, about 10% or more, specifically, 15%, 20%, 25%, 30%, 35%, 40%, 45%, 50%, 55%, 60%, 65%, 70%, 75%, 80%, 85%, 90%, 95%, 99.9% or more, specifically, 100%, of the function of the CSR region, specifically in the CSR process as defined above for the transgenically inserted sequence of interest. Similarly, in some embodiments, the insertion of the nucleic acid sequence of interest retains, at least 10% or more, specifically, 15%, 20%, 25%, 30%, 35%, 40%, 45%, 50%, 55%, 60%, 65%, 70%, 75%, 80%, 85%, 90%, 95%, 99.9% or more, specifically, 100%, of the enhancer activity in enhancing transcription of the inserted sequence.

As indicated above, the nucleic acid sequence of interest may comprise at least one splice donor site and is inserted upstream of at least one splice acceptor site of the constant region. As demonstrated by Example 12, by providing an SA site upstream to the transgenic VH of the cassette of the invention, the nucleic acid sequence of interest is effectively transcribed using the endogenous VH promoter.

Thus, in some embodiments, the cassette of the invention may further comprise at least one SA. In yet some further embodiments, the SA may be located upstream to the VH in the donor cassette, allowing the use of the endogenous VH promoter for transcription of the transgenic nucleic acid sequence of interest provided by the cassette of the invention.

More specifically, the introduced nucleic acid sequence of interest (e.g., nucleic acid sequence that encodes at least the VH fragment of an antibody of interest) is transcribed as a fusion to the endogenous VDJ transcript. This transgenic exogenous sequence can be separately translated using IRES or 2A peptide, or alternatively, released to function separately from the endogenous VDJ by incorporating a protease cleavage site (e.g., a furin site). Thus, in some specific and non-limiting configuration of the cassette of the invention, a splice acceptor (SA) or a minimal promoter (MP) may be included. The cassette encodes an antibody light chain (VLJLCL) and a variable region of a heavy chain (VHDHJH) separated by a 2A peptide (SA-VLJLC-2A-VHDHJH-SD). Upon integration, transcription and splicing, the transgene is first expressed as a BCR on naïve B cells. Following antigen-induced activation and affinity maturation the transgene is also expressed as antibodies of different classes being secreted from plasma cells. Similar example with a minimal promoter may be: MP-VLJLC-2A-VHDHJH-SD.

In this connection, splicing is the editing of the nascent precursor messenger RNA (pre-mRNA) transcript. After splicing, introns are removed, and exons are joined together. Introns often reside within the sequence of eukaryotic protein-coding genes. Within the intron, a donor site (5' end of the intron), a branch site (near the 3' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. Upstream (5'-ward) from the AG there is a region high in pyrimidines (C and U), or polypyrimidine tract. Further upstream from the polypyrimidine tract is the branch point, which includes an adenine nucleotide involved in lariat formation. A splice donor (SD) may be provided downstream of the receptor/Ab gene to facilitate utilization of the endogenous C segment(s) of the BCR upon integration, transcription and splicing.

In particular, the SD is required to allow class switching of targeted Abs. Thus, in some embodiments, the SD may be located 3' to the nucleic acid sequence of interest. In some embodiments, the SD may comprise the nucleic acid sequence as denoted by SEQ ID NO: 21 (e.g., SD as provided in ADN157CF2 and ADN191), SEQ ID NO: 22 (as provided in ADN171), SEQ ID NO: 23 (50 bp SD as provided in ADN157CF2), SEQ ID NO: 24 (50 bp SD as provided in ADN191), SEQ ID NO: 25 (50 bp SD as provided in ADN171), SEQ ID NO: 26 (152/153/155), SEQ ID NO: 27 (156), SEQ ID NO: 28 (159 (ADNSA)) or SEQ ID NO. 145, that is the SD as provided in the ADN171XS. As indicated above, the nucleic acid sequence of interest comprised within the nucleic acid cassette used by the methods of the invention may further comprise at least one nucleic acid sequence coding for at least one variable domain of an immunoglobulin light chain (VL). In yet some further embodiments, the nucleic acid sequence of interest may further comprise a nucleic acid sequence coding for the constant domain of the immunoglobulin light chain, thereby encoding the entire immunoglobulin light chain. More specifically, two loci are present for light chains, the immunoglobulin (Ig)κ light chain gene (IGK, at 2p11.2) and the Igλ light chain gene (IGL, 22q11.2) loci, and the variable region of the immunoglobulin light chain comprises the V and J segments. Thus, in some embodiments, the cassette of the invention may comprise at least one nucleic acid sequence encoding the VL and VJ segments of the light chain variable region (VL). In some further embodiments, the cassette of the invention may comprise at least one nucleic acid sequence that further encodes the constant region of the light chain (CL).

It should be noted that in some embodiments, the immunoglobulin light chain encoded by the nucleic acid sequence of interest provided by the methods of the invention may successfully pair with the heavy chain. In some embodiments, a successful pairing in accordance with the invention is meant pairing of the transgenic light chain encoded by the nucleic acid sequence of interest provided with the cassette of the invention, with the transgenic VH provided by the cassette.

In yet some further embodiments, the sequence of such VL and said IgH may be joined by at least one linker and may be coded as a single polypeptide. In some specific embodiments, the antibody encoded by the donor cassette of the invention may be transcribed and translated as a single chain antibody. In yet some further specific embodiments, such single-chain antibody may comprise the transgenic VL, CL (either kappa or lambda), VH and the endogenous CH. In yet some alternative embodiments, the sequence of the IgL and the VH may be encoded as separate polypeptides. In still some further embodiments, such separated polypeptides may be encoded on a polycistronic vector. Still further, in some embodiments, to ensure successful pairing of the transgenic immunoglobulin light chain (IgL) with the VH provided by the cassette of the invention, ablation of the endogenous Immunoglobulin light chin (either the kappa or the lambda) or reduction of the expression of the endogenous light and or heavy chains, may be performed. As shown by Example 6, by targeted destruction of the endogenous IgK encoding sequences in the cell (using site specific nuclease such as the CRISPR/Cas), one can ensure successful pairing of the heavy chain with the transgenic light chain provided by the cassette of the invention. Thus, in some optional embodiments, the method of the invention may further comprise the step of reducing, attenuating, decreasing or ablating the expression of the endogenous light chain, as discussed in the Examples. In yet some additional optional embodiments, the method of the invention may further comprise the step of reducing, attenuating, decreasing or ablating the expression of the endogenous heavy chain. In more specific embodiments, such reduction, attenuation, decrease or ablation of at least one of the endogenous IgL, IgK or the other IgH, may involve the use of nucleic acid based attenuators (e.g. shRNA), or nucleases (e.g., CRISPR/Cas systems).

Still further, in some embodiments, the nucleic acid sequence of interest provided by the cassette used by the methods of the invention may comprise a sequence encoding a signal peptide. In yet some further specific embodiments, such signal peptide may be any one of HGH leader sequence as demonstrated in Example 3 or alternatively, a human IgH variable leader sequence or a IgK variable leader as demonstrated by Example 4. In some further embodiments, the HGH leader sequence may comprise the nucleic acid sequence as denoted by SEQ ID NO: 37.

In some specific and non-limiting embodiments, the nucleic acid sequence of interest may comprise a nucleic acid sequence encoding at least one variable domain of the heavy chain of an antibody of interest or of any fragment/s or chimera/s thereof, specifically, any antigen-binding fragments thereof.

In yet some further embodiments, the nucleic acid sequence of interest may further comprise a sequence encoding a variable light chain of an antibody of interest. In some further embodiments, the nucleic acid sequence of interest may further comprise a sequence encoding the entire light chain of an antibody of interest.

In certain embodiments, such antibody of interest or any antigen-binding fragments thereof, encoded by the nucleic acid sequence of interest in accordance with the invention, may be any one of full length antibody, antibody fragment, a single-chain antibody, specifically, a single-chain antibody comprising the transgenic VL, CL (either kappa or lambda), VH and the endogenous CH.

In yet some further embodiments, the antibody encoded by the donor cassette of the invention may be a single-chain variable fragment (scFv), bi-specific antibody, tri-specific antibody, Bi-specific T-cell engagers (BiTE) and variable new antigen receptor antibody (V-NAR).

The invention provides methods for engineering B cells for antigen-induced secretion of antibodies of interest or of any antigen-binding fragments or domains thereof, as discussed herein above.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen or antigen-binding scaffolds. The antigen binding domains in accordance with the invention may recognize and bind a specific antigen or epitope. It should be therefore noted that the term "binding specificity", "specifically binds to an antigen", "specifically immuno-reactive with", "specifically directed against" or "specifically recognizes", when referring to an antigen or particular epitope, refers to a binding reaction which is determinative of the presence of the epitope in a heterogeneous population of proteins and other biologics. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. Still further, as indicated above, an "antigen-binding domain" can comprise or consist of an antibody or antigen-binding fragment of an antibody. The term "antibody" as used herein, means any antigen-binding molecule or molecular complex comprising at least one complementarity determining region (CDR) that specifically binds to or interacts with a particular antigen or any epitope thereof. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

A typical antibody is composed of two immunoglobulin (Ig) heavy chains and two Ig light chains. In humans, antibodies are encoded by three independent gene loci, namely the immunoglobulin heavy locus (IgH) on chromosome 14, containing the gene segments for the immunoglobulin heavy chain, the immunoglobulin kappa (κ) locus (IgK) on chromosome 2, containing the gene segments for part of the immunoglobulin light chain and the immunoglobulin lambda (λ) locus (IgL) on chromosome 22, containing the gene segments for the immunoglobulin light chain.

The antibody and BCR heavy chains comprises 51 Variable (V) gene segments, 27 Diversity (D) gene segments, 6 Joining (J) gene segments. The antibody and BCR light chains comprises 40 Vκ, 31 Vλ, 5 Jκ, 4 Jλ gene segments.

Still further, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)).

Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain.

The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

The antibody suitable for the invention may also be a bi-specific antibody (such as Bi-specific T-cell engagers-BiTEs) or a tri-specific antibody.

The antibody suitable for the invention may also be a variable new antigen receptor antibody (V-NAR). VNARs are a class of small, immunoglobulin-like molecules from the shark immune system. Humanized versions of VNARs could be used to bind protein epitopes that are difficult to access using traditional antibodies.

It should be understood that an antibody of interest or any antigen-binding fragments thereof, encoded by the nucleic acid sequence of interest in accordance with the invention may be directed to any antigen of interest, specifically cells any antigen specific for a pathologic disorder. In more specific embodiments, the antibody of interest may be directed against antigens specific for proliferative disorders, specifically, tumor associated antigens (TAAs), or antigens specific for any pathogen, specifically, viral, bacterial, fungal or parasitic pathogen. Specific pathogens applicable in the present invention are described in more detail herein after.

In some specific embodiments, the BCR or antibody of interest encoded by the nucleic acid sequence of interest of the cassette used by the methods of the invention, may be at least one antibody directed against at least one of a viral antigen and a tumor associates antigen (TAA).

Tumor or cancer associated antigen (TAA), as used herein may be an antigen that is specifically expressed, over expressed or differentially expressed in tumor cells. In yet some further embodiments, TAA can stimulate tumor-specific T-cell immune responses. Exemplary tumor antigens that may be applicable in the present invention, include, but are not limited to, RAGE-1, tyrosinase, MAGE-1, MAGE-2, NY-ESO-1, Melan-A/MART-1, glycoprotein (gp) 75, gp100, MUC1, beta-catenin, PRAME, MUM-1, WT-1, CEA, PR-1 CD45, glypican-3, IGF2B3, Kallikrein4, KIF20A, Lengsin, Meloe, MUC5AC, survivin, CLPP, Cyclin-A1, SSX2, XAGE1b/GAGED2a, MAGE-A3, MAGE-A6, LAGE-1, CAMEL, hTRT and Eph. and TRP-1. Still further, TAA may be recognized by CD8+ T cells as well as CD4+ T cells. Non limiting examples of TAA recognized by CD8+ T cells may be CSNK1A1, GAS7, HAUS3, PLEKHM2, PPP1R3B, MATN2, CDK2, SRPX (P55L), WDR46 (T227I), AHNAK (S4460F), COL18A1 (S126F), ERBB2 (H197Y), TEAD1 (L209F), NSDHL (A290V), GANAB (S184F), TRIP12 (F1544S), TKT (R438W), CDKN2A (E153K), TMEM48 (F169L), AKAP13 (Q285K), SEC24A (P469L), OR8B3 (T190I), EXOC8 (Q656P), MRPS5 (P59L), PABPC1 (R520Q), MLL2, ASTN1, CDK4, GNL3L, SMARCD3, MAGE-A6, MED13, PAS5A WDR46, HELZ2, AFMID, CENPL, PRDX3, FLNA, KIF16B, SON, MTFR2 (D626Y), CHTF18 (L769V), MYADM (R30W), NUP98 (A359D), KRAS (G12D), CASP8 (F67V), TUBGCP2 (P293L), RNF213 (N1702S), SKIV2L (R653H), H3F3B (A48T), AP15 (R243Q), RNF10 (E572K), PHLPPI (G566E) and ZFYVE27 (R6H). Non limiting examples of TAA recognized by CD4+ T cells may be ERBB2IP (E805G), CIRHIA (P333L), GART (V551A), ASAP1 (P941L), RND3 (P49S), LEMD2 (P495L), TNIK (S502F), RPS12 (V104I), ZC3H18 (G269R), GPD2 (E426K), PLEC (E1179K), XPO7 (P274S), AKAP2 (Q418K) and ITGB4 (S1002I). Non-limiting examples of MHC class II-restricted antigens may be Tyrosinase, gp100, MART-1, MAGE-A1, MAGE-A2, MAGE-A3, MAGE-A6, LAGE-1, CAMEL, NY-ESO-1, hTRT and Eph.

Cancer antigen and tumor antigen are used interchangeably herein. The antigens may be related to cancers that include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenstrom; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer;

Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sezary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenstrom macroglobulinemia and Wilms tumor (kidney cancer).

Still further, in some embodiments, a few examples of antibodies used in the treatment of cancer that may be applicable in the present invention include, but are not limited to monoclonal antibodies such as Bevacizumab (UNII: 2S9ZZM9Q9V), Cetuximab (UNII: PQX0D8J21J), Panitumumab (UNII: 6A901E312A), Rituximab (UNII: 4F4X42SYQ6), Alemtuzumab (UNII: 3A189DH42V), Ipilimumab (UNII: 6T8C155666, Yervoy), that is a check point inhibitor, specifically, a monoclonal antibody that works to activate the immune system by targeting CTLA-4, Trastuzumab (UNII: P188ANX8CK, formerly ticilimumab, CP-675,206) is a fully human monoclonal antibody against CTLA-4, ibritumomab tiuxetan (UNII: 4Q52C550XK), lambrolizumab (formerly MK-3475, Pembrolizumab, Keytruda® UNII: DPT0O3T46P), that is a check point inhibitor, specifically, a humanized antibody that targets programmed cell death (PD-1), Nivolumab (Opdivo® UNII: 31YO63LBSN) is an Fab fragment of an antibody that binds the extracellular domain of PD-1, Atezolizumab (trade name Tecentriq) is a fully humanized, engineered monoclonal antibody of IgG1 isotype against the protein programmed cell death-ligand 1 (PD-L1), Avelumab (trade name Bavencio) is a fully human monoclonal antibody that targets PD-L1, Durvalumab is a human immunoglobulin G1 kappa (IgG1κ) monoclonal antibody that blocks the interaction of PD-L1 with the PD-1 and CD80 (B7.1) molecules and Tremelimumab (formerly ticilimumab; UNII: QEN1X95CIX) that is a check point inhibitor and ado-trastuzumab emtansine (UNII: SE2KH7T06F). In some specific embodiments, the antibody of interest may be an antibody or BCR directed against a viral antigen. It should be appreciated that any of the viral pathogens discussed herein after, is applicable in this aspect, as well as in all aspects of the invention.

In some particular embodiments, BCRs and/or antibodies applicable in the methods, and encoded by the cassettes and compositions of the invention may be directed against any antigen derived from a pathogen, specifically, viral, bacterial, fungal, parasitic pathogen and the like. In some specific embodiments, the viral pathogen may be of any of the following orders, specifically, Herpesvirales (large eukaryotic dsDNA viruses), Ligamenvirales (linear, dsDNA (group I) archaean viruses), Mononegavirales (include nonsegmented (−) strand ssRNA (Group V) plant and animal viruses), Nidovirales (composed of (+) strand ssRNA (Group IV) viruses), Ortervirales (single-stranded RNA and DNA viruses that replicate through a DNA intermediate (Groups VI and VII)), Picornavirales (small (+) strand ssRNA viruses that infect a variety of plant, insect and animal hosts), Tymovirales (monopartite (+) ssRNA viruses), Bunyavirales contain tripartite (−) ssRNA viruses (Group V) and Caudovirales (tailed dsDNA (group I) bacteriophages).

In yet some further specific embodiments, the antibodies encoded by the cassettes of the invention may be specifically directed against DNA viruses, specifically, any virus of the following families: the Adenoviridae family, the Papovaviridae family, the Parvoviridae family, the Herpesviridae family, the Poxviridae family, the Hepadnaviridae family and the Anelloviridae family.

In yet some further specific embodiments, the antibodies encoded by the cassettes of the invention may be specifically directed against RNA viruses, specifically, any virus of the following families: the Reoviridae family, Picornaviridae family, Caliciviridae family, Togaviridae family, Arenaviridae family, Flaviviridae family, Orthomyxoviridae family, Paramyxoviridae family, Bunyaviridae family, Rhabdoviridae family, Filoviridae family, Coronaviridae family, Astroviridae family, Bornaviridae family, Arteriviridae family, Hepeviridae family and the Retroviridae family.

In more specific embodiments, the antibody of interest may be directed against any antigen derived from a viral pathogen of the order Mononegavirales. In yet some further embodiments, the antibody of interest may be directed against an antigen derived from a virus of the family Pneumoviridae. In more specific embodiments antibody or BCR of interest may be directed against any antigen derived from a viral pathogen of the genus *Orthopneumovirus*. In some specific embodiments, such viral antigen may be an antigen specific for respiratory syncytial virus (RSV), for example, any one of the Human respiratory syncytial virus (HRSV), A2 and B1, the bovine respiratory syncytial virus (BRSV) and the murine pneumonia virus (MPV). In more specific embodiments, the antibody of interest may be directed against the human RSV. In yet some further specific embodiments, the anti-RSV antibody may be the anti-RSV palivizumab antibody. More specifically, Palivizumab (brand name Synagis, manufactured by MedImmune) is a humanized monoclonal antibody (IgG) directed against an epitope in the A antigenic site of the F protein of RSV.

In some specific embodiments, the nucleic acid sequence of interest provided by the cassette in accordance with the invention may comprise the full light chain of the anti-RSV antibody palivizumab followed by a 2A peptide sequence and the coding sequence for the variable domain of the palivizumab heavy chain terminating with an SD. In addition, an HGH leader sequence preceded each chain, may be also included as demonstrated by Example 3. In some further embodiments, the HGH leader sequence may comprise the nucleic acid sequence as denoted by SEQ ID NO: 37.

In yet some further specific embodiments, the antibody of interest may be directed against any antigen derived from a viral pathogen of the family Retroviridae. In yet some further embodiments, the antibody of interest may be directed against an antigen derived from a virus of the subfamily Orthoretrovirinae. In more specific embodiments antibody of interest may be directed against any antigen derived from a viral pathogen of the genus *Lentivirus*, specifically, of the species human immunodeficiency virus (HIV). In yet some further embodiments, the antibody of interest in accordance with some embodiments of the invention may be an anti-HIV-1 antibody. In yet some further specific embodiments the antibody of interest may be the anti-HIV 3BNC117 antibody. More specifically, the 3BNC117, as used herein, is a neutralizing antibody (bNAb) directed against the CD4 binding site of HIV-1 Env.

In some specific embodiments, the cassette provided and used by the methods, compositions, systems and cells of the invention may comprise a sequence encoding the full light chain of the anti-HIV antibody 3BNC117 followed by a sequence coding for a 2A peptide and the coding sequence for the variable domain of the 3BNC117 heavy chain terminating with an SD. The cassette of the invention may further comprise human IgH variable leader sequences, as demonstrated by Examples 4 and 5.Thus, in some embodiments, the cassettes provided by the invention and used by the methods and compositions described herein, may comprise as an at least one nucleic acid sequence of interest, a nucleic acid sequence encoding the antibodies that comprise an amino acid sequence as denoted by SEQ ID NO. 29 (the VL and VH), that comprise the HV as denoted by SEQ ID NO. 30, and the VL as denoted by SEQ ID NO. 150 (variable regions of the heavy and light chains of Palivizumab, respectively), and SEQ ID NO. 31(the VL and VH), that comprise the HV as denoted by SEQ ID NO. 32, and the VL as denoted by SEQ ID NO. 151 (variable regions of the light and heavy chains of 3BNC117, respectively).

Specific embodiments that relate to particular viruses associated with specific disorders are specified herein below. It should be understood that any of the viral pathogens and any of the bacterial, fungal and parasite pathogen described herein after, are also applicable in connection with the antigens derived therefrom that are recognized by the antibodies encode by the cassettes of the invention.

Still further, in some embodiments, the cassette used by the methods of the invention may further comprise at least one genetic element. In some specific embodiments, such genetic element may be at least one of: an internal ribosome entry site (IRES), a 2A peptide coding sequence, a promoter or any functional fragments thereof, a polyadenylation site, a signal peptide a stop codon, and a transcription enhancer.

As indicated above, the cassette of the invention enables targeted insertion of a nucleic acid sequence of interest into a specific genomic sequence within the IgH locus. In more specific embodiments, the target sequence may be located upstream of at least one splice acceptor site of the constant domain of the heavy chain of the BCR. It should be therefore appreciated that in some embodiments, the cassette used by the methods of the invention may further comprise targeting elements facilitating the specific recognition and targeted insertion to the target site. Thus, according to some embodiments, the cassette of the invention may be flanked at the 5' and/or 3' thereof by at least one of (i) homology arms, for integration by homologous recombination; and (ii) recognition sites for a site-specific nuclease, a site-specific integrase or a site-specific recombinase.

The term "flanked" as used herein refers to a nucleic acid sequence positioned between two defined regions. For example, as indicated above, the nucleic acid sequence of interest is flanked by a first and optionally, a second nucleic acid sequence that may be at least one of (i) homology arms, for integration of the nucleic acid of interest into the desired target site, by homologous recombination; and (ii) recognition sites for a site-specific nuclease, a site-specific integrase or a site-specific recombinase. The particular recognition elements are provided by the invention (e.g., gRNAs) for the specific gene editing systems used herein, and also by the flanking sequences in the cassette of the invention that enable homologous recombination and insertion of the nucleic acid of interest to the desired target site. In some embodiments, the first nucleic acid sequence is positioned 5' (or upstream) to the nucleic acid sequence of interest and the optional second nucleic acid sequence is positioned 3' (or downstream) to the nucleic acid sequence of interest, and vis versa.

In some specific embodiments, the insertion of the nucleic acid sequence of interest of the cassette used by the method of the invention, into the target genomic locus may be mediated by any gene editing system, for example, by gene editing system based on at least one of a site-specific nuclease, a class switch recombination, a site specific integrase, a site-specific recombinase and a recombination activating gene (RAG) -catalyzed recombination.

More specifically, site specific nucleases are any nucleases that induce directly or indirectly a single strand break (SSB) or double strand break (DSB) in a target DNA sequence. Specific nucleases applicable in the present invention are discussed in detail herein after.

In some specific embodiments as also demonstrated by Examples 10 and 11, the nucleic acid of interest provided by the cassette of the invention may be integrated into the specific target site within the IgH locus, using CSR. As indicated herein before, Class-switch recombination (CSR) is a biological mechanism that changes a B cell's production of antibodies from one type to another, such as from the isotype IgM to the isotype IgG. During this process, the constant-region portion of the antibody heavy chain is changed, but the variable region of the heavy chain stays the same.

Naïve mature B cells produce both IgM and IgD, which are the first two heavy chain segments in the immunoglobulin locus. After activation, these B cells undergo antibody class switching to produce IgG, IgA or IgE antibodies. The order of the heavy chain exons are as follows: μ—IgM, δ-IgD, γ3—IgG3, γ1—IgG1, α1—IgA1, γ2—IgG2, γ4—IgG4, ε—IgE, α2—IgA2.

During CSR, double-stranded breaks are generated in DNA at conserved nucleotide motifs, called switch (S) regions, which are upstream from gene segments that encode the constant regions of antibody heavy chains; these occur adjacent to all heavy chain constant region genes with the exception of the δ-chain. DNA is nicked and broken at two selected S-regions by the activity of a series of enzymes, including Activation-Induced (Cytidine) Deaminase (AID), uracil DNA glycosylase and apyrimidic/apurinic (AP)-endonucleases. The intervening DNA between the S-regions is subsequently deleted from the chromosome, removing unwanted μ or δ heavy chain constant region exons and allowing substitution of a γ, α or ε constant region gene segment. The free ends of the DNA are rejoined by a process called non-homologous end joining (NHEJ) to link the variable domain exon to the desired downstream constant domain exon of the antibody heavy chain. In the absence of non-homologous end joining, free ends of DNA may be rejoined by an alternative pathway biased toward microhomology joins. With the exception of the μ and δ genes, only one antibody class is expressed by a B cell at any point in time.

In yet some further embodiments, the nucleic acid sequence of interest (e.g., the immunoglobulin light chain and heavy chain provided by the cassette of the invention) may be inserted into the target site within the IgH locus, using a site specific integrase and/or by a site specific recombinase that mediates a site specific recombination.

"Site-specific recombination" as used herein (also known as sequence-specific or conservative site-specific recombination), is a genetic recombination process in which DNA strand exchange takes place between segments possessing only a limited degree of sequence homology. As a non-limited example, site-specific-recombination occurs between specific sites on bacteriophage genome, such as λ or the coliphage HK022 and bacterial DNA molecules (e.g. *E. coli*). Site-specific-recombination is guided primarily by proteins that recognize particular DNA sequences, which include site-specific recombinases or integrases.

Most site-specific recombinases are grouped into one of the two families, namely the tyrosine recombinase family and the serine recombinase family, based on the active amino acid and recombination mechanism. The names stem from the conserved nucleophilic amino acid residue that they use to attack the DNA and which becomes covalently linked to it during strand exchange. Among the known members of the tyrosine recombinases, are lambda (λ) integrase (Gene ID: 6065335), Cre (from the P1 phage, Gene ID: 2777477), including its derivative and FLP (from yeast *S. cerevisiae*, having the accession number BBa_K313002). The serine recombinases include enzymes such as gamma-delta resolvase (from the Tn1000 transposon), the Tn3 resolvase (from the Tn3 transposon) and the φC31 integrase (from the φC31 phage, Gene ID: 2715866) or similar ones. The HK022 integrase is a 357 amino acid protein (accession number P16407) as denoted by SEQ ID NO. 13. The gene encoding the Integrase (Int) recombinase of coliphage HK022, also termed "HK022p28 lambda family integrase, gp29" or "Enterobacteria phage HK022" consists of the nucleic acid sequence as denoted by Gene ID 1262484.

The Integrase (Int) recombinase of coliphage HK022 naturally mediates integration and excision of the bacteriophage into and out of the chromosome of its *Escherichia coli* host, using a mechanism that is similar to that used by coliphage k integrase. In both phages, site-specific recombination reactions occur between two defined pairs of DNA attachment (att) sites. In nature, integration results from recombination between the phage attP site and the bacterial host attB, and excision occurs between the recombinant attR and attL sites that flank the integrated prophage. In addition to Int, these reactions require DNA-bending accessory proteins.

In yet some further embodiments, the specific insertion of the nucleic acid sequence of interest provided by the cassette of the invention into the target site within the IgH locus may be mediated by an endogenous or exogenously added RAG. Thus, in some embodiments, the insertion of the nucleic acid sequence of interest of the invention into the target genomic locus may be mediated by RAG-catalyzed recombination. This specific insertion is based on RAG complex expressed in the target cells, that catalyze the specific recombination. By "recombination" it is meant a process of exchange of genetic information between two polynucleotides. RAG catalyzed recombination as used herein, refers to recombination process performed by the RAG complex, for example, during V(D)J recombination. More specifically, the V(D)J recombination process cleaves and splices variable (V), diversity (D), and joining (J) non-contiguous immunoglobulin (Ig) segments in the genome. Ig heavy chains and T cell receptor (TCR) β chains are formed by sequential steps of D-J and V-DJ recombination, while Ig light chains and TCR α chains are generated by direct VJ recombination. The critical cleavage step in V(D)J recombination is executed by the lymphocyte-specific enzyme containing the multi-domain proteins recombination-activating gene 1 and 2 (RAG1 and RAG2). These two recombination-activating gene products, whose cellular expression is restricted to lymphocytes during their developmental stages, are essential to the generation of mature B and T lymphocytes. RAG recognizes specific recombination signal sequences (RSSs) flanking the 3' end of the V, D, and J segments. RSSs are in some embodiments, genetic elements composed of a conserved heptamer (consensus: 5'CACAGTG-3'), a poorly conserved spacer of either 12±1 or 23±1 bp, and a conserved nonamer (consensus: 5'-ACAAAAACC-3') as revealed by sequence alignments of RSSs. These RSSs are designated as 12-RSS or 23-RSS after the length of the spacer. Recombination can only occur between one gene coding segment flanked by a 12-RSS and another segment flanked by a 23-RSS, establishing the 12/23 rule.

As referred to herein as RAG catalyzed recombination is meant that the RAG complex catalyzes two consecutive reactions, nicking (strand cleavage) and hairpin formation (strand transfer), without dissociation. First, it binds either a 12-RSS substrate or a 23-RSS substrate and introduces a nick precisely at the junction between the coding segment and the RSS. Interactions with both the conserved heptamer and nonamer are required for optimal RAG activity because considerable sequence variation in endogenous RSSs substantially affects RAG binding affinity and recombination frequency. When a 12-RSS and a 23-RSS are bound to the same RAG, a synaptic, paired complex (PC) is formed. Next, upon PC formation, the free 3'-hydroxyl released from the nicking step attacks the opposing strand to create a hairpin coding segment and a blunt signal end, generating the cleaved signal complex (CSC). Dissociation of gene segment hairpins results in a signal end complex (SEC). Proteins in the classical non-homologous end joining (NHEJ) DNA repair pathway are recruited to the RAG complex to process and join the coding segments. High-mobility group (HMG) proteins such as HMGB1 have been shown to stimulate RAG's activity in DNA binding, nicking, and hairpin formation, presumably by inducing RSS bending.

In some specific embodiments, the targeted insertion of the nucleic acid sequence of interest may be mediated by a site-specific nuclease. In more specific embodiments, the site-specific nuclease may be at least one programmable engineered nuclease (PEN).

The term "programmable engineered nucleases (PEN)" as used herein also known as "molecular DNA scissors", refers to enzymes either synthetic or natural, used to replace, eliminate or modify sequences in a highly targeted way. PEN target and cut specific genomic sequences (recognition sequences) such as DNA sequences. The at least one PEN may be derived from natural occurring nucleases or may be an artificial enzyme, all involved in DNA repair of double strand DNA lesions and enabling direct genome editing. In some alternative or additional embodiments the gene editing compound according with the present disclosure encompasses also any nucleic acid molecule comprising at least one nucleic acid sequence encoding the PEN or any kit, composition or vehicle comprising the at least one PEN, or any nucleic acid sequence encoding PEN.

In yet some further specific embodiments, such nucleases may include RNA guided nucleases such as CRISPR-Cas (e.g., Cas9/Cpf1/CTc(1/2/3), SpCas9, SaCas9, engineered Cas9, and any mutants or fusion proteins thereof, for example, dCas9-Fok1, and the like). In yet some alternative embodiments, other nucleases such as ZFN, TALEN, Homing endonuclease, Meganuclease, Mega-TALEN may be used by the methods of the invention for targeted insertion of the nucleic acid sequence of interest.

More specifically, in some embodiments, the at least one PEN may be at least one of a mega nuclease, a zinc finger nuclease (ZFN), a transcription activator-like effector-based nuclease (TALEN), or a clustered regularly interspaced short palindromic repeats (CRISPR/Cas) system.

In some embodiments, the at least one PEN may be a mega nuclease. Mega nucleases are endodeoxyribonucleases characterized by a large recognition site (double-stranded DNA sequences of 12 to 40 base pairs); such that this site generally occurs only once in any given genome. Meganucleases are specific naturally occurring restriction enzymes and include among others, the LAGLIDADG family of homing endonucleases, mostly found in the mitochondria and chloroplasts of eukaryotic unicellular organisms.

In some embodiments, the at least one PEN may be a megaTAL. MegaTALs are fusion proteins that combine homing endonucleases, such as LAGLIDADG family, with the modular DNA binding domains of TALENs.

In some alternative embodiments, the at least one PEN may be a zinc finger nuclease (ZFN). ZFNs are artificial restriction enzymes generated by fusing a zinc finger DNA-binding domain to a DNA-cleavage domain. Zinc finger domains can be engineered to target specific desired DNA sequences, enabling ZFN to target unique sequences within complex genomes.

In yet some other embodiments, the at least one PEN may be a transcription activator-like effector-based nuclease (TALEN). TALEN are restriction enzymes that can be engineered to cut specific sequences of DNA. TALEN are made by fusing a TAL effector DNA-binding domain to a DNA cleavage domain (a nuclease which cuts DNA strands).

In some specific embodiments, the targeted insertion of the nucleic acid sequence of interest may be mediated by a PEN that may comprise at least one clustered regulatory interspaced short palindromic repeat (CRISPR)/CRISPR associated (cas) protein system. The Clustered Regularly Interspaced Short Palindromic Repeats (CRISPR) system is a bacterial immune system that has been modified for genome engineering.

CRISPR-Cas systems fall into two classes. Class 1 systems use a complex of multiple Cas proteins to degrade foreign nucleic acids. Class 2 systems use a single large Cas protein for the same purpose. More specifically, Class 1 may be divided into types I, III, and IV and class 2 may be divided into types II, V, and VI.

Thus, in some embodiments, the Cas protein may be a member of at least one of CRISPR-associated system of Class 1 and Class 2. In some embodiments, the cas protein may be a member of at least one of CRISPR-associated system of any one of type II, type I, type III, type IV, type V and type VI. As used herein, CRISPR arrays also known as SPIDRs (Spacer Interspersed Direct Repeats) constitute a family of DNA loci that are usually specific to a particular bacterial species. The CRISPR array is a distinct class of interspersed short sequence repeats (SSRs) that were first recognized in *E. coli*. In subsequent years, similar CRISPR arrays were found in *Mycobacterium tuberculosis, Haloferax mediterranei, Methanocaldococcus jannaschii, Thermotoga maritima* and other bacteria and archaea. It should be understood that the invention contemplates the use of any of the known CRISPR systems, particularly any of the CRISPR systems disclosed herein. The CRISPR-Cas system has evolved in prokaryotes to protect against phage attack and undesired plasmid replication by targeting foreign DNA or RNA. The CRISPR-Cas system, targets DNA molecules based on short homologous DNA sequences, called spacers that exist between repeats. These spacers guide CRISPR-associated (Cas) proteins to matching (and/ or complementary) sequences within the foreign DNA, called proto-spacers, which are subsequently cleaved. The spacers can be rationally designed to target any DNA sequence, for example, the target sequence within the IgH locus. Moreover, this recognition element may be designed separately to recognize and target any desired target.

In some specific embodiment, the RNA guided DNA binding protein nuclease of the system of the invention may be a CRISPR Class 2 system. In yet some further particular embodiments, such class 2 system may be a CRISPR type II system.

The type II CRISPR-Cas systems include the 'HNH'-type system (*Streptococcus*-like; also known as the Nmeni sub-type, for *Neisseria meningitidis* serogroup A str. Z2491, or CASS4), in which Cas9, a single, very large protein, seems to be sufficient for generating crRNA and cleaving the target DNA, in addition to the ubiquitous Cas1 and Cas2. Cas9 contains at least two nuclease domains, a RuvC-like nuclease domain near the amino terminus and the HNH (or McrA-like) nuclease domain in the middle of the protein, but the function of these domains remains to be elucidated. However, as the HNH nuclease domain is abundant in restriction enzymes and possesses endonuclease activity responsible for target cleavage.

Still further, it should be noted that type II system comprise at least one of cas9, cas1, cas2 csn2, and cas4 proteins. It should be appreciated that any type II CRISPR-Cas systems may be applicable in the present invention, specifically, any one of type II-A or B. Thus, in yet some further and alternative embodiments, at least one cas gene used in the methods, compositions, cells, uses and cassettes of the invention may be at least one cas protein of type II CRISPR system (either typeII-A, typeII-B or typeII-C). In more particular embodiments, at least one cas protein of type II CRISPR system used by the methods and systems of the invention may be the cas9 protein. It should be appreciated that such system may further comprise at least one of cas1, cas2, csn2 and cas4 genes. Thus, in some specific embodiments, the Cas protein in use by the methods of the invention may be Cas9 or any fragments, mutants, fusion proteins, variants or derivatives thereof.

Double-stranded DNA (dsDNA) cleavage by Cas9 is a hallmark of "type II CRISPR-Cas" immune systems. The CRISPR-associated protein Cas9 is an RNA-guided DNA endonuclease that uses RNA:DNA complementarity to a target site (proto-spacer). After recognition between Cas9 and the target sequence double stranded DNA (dsDNA) cleavage occur, creating the double strand brakes (DSBs).

CRISPR type II system as used herein requires the inclusion of two essential components: a "guide" RNA (gRNA) and a non-specific CRISPR-associated endonu-clease (Cas9). Guide RNA (gRNA), as used herein refers to a synthetic fusion of the endogenous tracrRNA with a targeting sequence (also named crRNA), providing both scaffolding/binding ability for Cas9 nuclease and targeting specificity. Also referred to as "single guide RNA" or "sgRNA".

In CRISPR systems based on PAM sequence recognition like CRISPR Type II, the PAM is absolutely necessary for target binding and the exact sequence is dependent upon the species of Cas9 (5′ NGG 3′ for *Streptococcus pyogenes*

Cas9). In certain embodiments, Cas9 from *S. pyogenes* may be used in the methods, cells compositions, cassettes and systems of the invention. Nevertheless, it should be appre-ciated that any known Cas9 may be applicable. Non-limiting examples for Cas9 useful in the present disclosure include but are not limited to *Streptococcus pyogenes* (SP), also indicated herein as SpCas9, *Staphylococcus aureus* (SA), also indicated herein as SaCas9, *Neisseria meningitidis* (NM), also indicated herein as NmCas9, *Streptococcus thermophilus* (ST), also indicated herein as StCas9 and *Treponema denticola* (TD), also indicated herein as TdCas9. In some specific embodiments, the Cas9 of *Streptococcus pyogenes* M1 GAS. Still further, it should be appreciated that type V CRISPR/Cas, including Cas12a, Cpf1 (type VI), C2C1 (type V-B), Cas13 (type VI), specifically, C2C2 and CasRx are also applicable in the present invention. Still further, in some embodiments, CasX, is also applicable in the methods of the invention.

As indicated above, the gene editing system of the inven-tion may be provided as nucleic acid molecules, specifically in a delivery vector or vehicle. However, it should be appreciated that any of the gene editing systems used, may be also administered as a protein complex, or alternatively, as a ribonucleoprotein complex.

More specifically, when gene editing system is used by the invention such system may be delivered either as nucleic acid sequences encoding the components of this system, e.g., constructs comprising nucleic acid sequences that encode the CRISPR/Cas protein, for example, Cas9 and the specific gRNAs. Non-limiting examples for using Cas9 in the methods of the invention are provided by Examples 1-9. However, it should be appreciated that the invention further encompasses in some embodiments thereof the option of using Cas9/gRNA Ribonucleoprotein complexes (Cas9 RNPs), that comprise purified Cas9 and purified gRNAs delivered as functional complexes. In some particular embodiments, purified gRNAs can be generated by PCR amplification of annealed gRNA oligos or in vitro transcrip-tion of a linearized gRNA containing plasmid. Cas9 (or any variant of Cas9 as discussed herein) can be purified from bacteria through the use of bacterial Cas9 expression plas-mids. In yet some further embodiments, the Cas9 RNP delivery to target cells may be carried out in some specific and non-limiting embodiments, via lipid-mediated transfec-tion or electroporation. Thus, in some specific embodiments, the method of the invention may further comprise the step of contacting the cell with at least one of:

(a) at least one CRISPR/cas protein, or any nucleic acid molecule encoding said Cas protein; and (b) at least one nucleic acid sequence comprising at least one guide RNA (gRNA) that targets the insertion of the nucleic acid sequence of interest into a target genomic sequence within the IgH locus, or any nucleic acid sequence encoding said gRNA; or any kit, composition or vehicle comprising at least one of (a) and (b).

It should be noted that the Cas protein and the specific gRNA may be provided either as a protein and gRNA, or alternatively, as nucleic acid sequences encoding these two elements, either in two separate nucleic acid molecules (e.g., two separate constructs), or in one nucleic acid molecule (e.g., a construct encoding both).

Thus, in some embodiments, when the CRISPR/Cas sys-tem is used as a gene editing tool, the method of the invention may comprise the step of contacting the cell with the cassette of the invention or with any vector or vehicle thereof and in addition, contacting, either concomitantly or simultaneously, the cell with the components of the CRISPR/Cas system as specified above. In yet some alternative embodiments, the cassette of the invention and nucleic acid sequences encoding components of the CRISPR system as discussed above, or of any other gene editing system, may be provided in a single construct.

In some specific embodiments, the Cas protein used by the method of the invention may be a member of a CRISPR-associated system type II of Class 2.

In more specific embodiments, the Cas protein may be Cas9 or any fragments, mutants, fusion proteins, variants or derivatives thereof. In yet some further specific embodiments, the Cas protein may be any one of the *Staphylococcus aureus* (saCas9) and *Streptococcus pyogenes* Cas9 (sp-Cas9).

A non-limiting example for targeted insertion of the nucleic acid sequence of interest into one optional target site located between about 1 to 800 nucleotides downstream of the fourth segment of the J region of the mouse heavy chain is provided by the invention using the CRISPR/Cas system.

In more specific embodiments, such target site is located between about 350 to 450 nucleotides downstream to the J region. As demonstrated by the Examples 1 to 5, this target site designated herein as mH69, allows successful and functional integration of the nucleic acid sequence of interest (e.g., integration that allows CSR). In yet some further particular and non-limiting embodiments, the target sequence within the IgH for the mH69 gRNA, may be also referred to herein as the protospacer, may be comprised within the nucleic acid sequence as denoted by SEQ ID NO. 15, that further includes the Protospacer adjacent motif (PAM) recognized by the Cas9 protein used (specifically, saCas9 and spCas9). Thus, in some embodiments where the CRISPR system is used for insertion, a gRNA that targets the Cas9 to the mH69 site may be used by the methods of the invention. In more specific embodiments, such gRNA may comprise the nucleic acid sequence as denoted by any one of SEQ ID NO: 16, when provided in a plasmid and SEQ ID NO: 17, when provided as an sgRNA. Still further additional gRNAs applicable in the present invention include the gRNA of SEQ ID NO. 119 and the gRNA of SEQ ID NO. 117 (human and mouse IgH, respectively), and the gRNA of SEQ ID NO. 118 and SEQ ID NO. 120 (human IgL, respectively).

In some specific embodiments, when the CRISPR system is used by the method of the invention as a gene editing system, the cassette used by the methods of the invention may further comprise homology arms facilitating the integration of the nucleic acid sequence of interest into the target site. In some particular and non-limiting embodiments, where the mH69 site is used, such homology arms may comprise the nucleic acid sequence as denoted by SEQ ID NO. 34 and 35.

As shown in Example 13, targeted insertion of the nucleic acid sequence of interest into the IgH locus, may be facilitated using the class switch recombination process. Thus, in yet some further embodiments, the targeted insertion of the nucleic acid sequence of interest may be mediated by the class switch recombination. In more specific embodiments, the class witch recombination may be catalyzed by activation induced cytidine deaminase (AID), as specifically discussed above.

In yet some further embodiments, such method may further involve the step of activating the cell of the B lineage. In some specific and non-limiting embodiments, the activation step may involve depletion of IL-4. In some embodiments, the IL-4 concentration may be between 5 and 20 ng/ml.

In some further embodiment the IL-4 concentration may be 10 ng/ml. In yet some further embodiments, such activation may involve addition of an effective amount of Lipopolysaccharides (LPS). In some embodiments, the LPS concentration may be between 5 and 20 µg/ml. In some further embodiment the LPS concentration may be 10 µg/ml.

It must be understood that in some embodiments, where the insertion of the nucleic acid sequence provided by the cassette of the invention into the target site within the IgH locus is mediated by any other nuclease, recombinase or integrase, specific reagents and components enabling the integration should be provided by the methods of the invention. Similarly to the methods involving the use of the CRISPR system, where the method of the invention further comprises the steps of providing the CRSPR/Cas protein or any nucleic acid sequence encoding such protein as well as the gRNAs or any nucleic acid sequence encoding the gRNAs. More specifically, the methods of the invention may further comprise additional step of providing any reagent or proteins required for facilitating integration by the integrase or recombinase used, or any nucleic acid sequence encoding such proteins or elements.

Still further, in some embodiments, the cassette used by the method of the invention may be comprised within a nucleic acid vector. In more specific embodiments, such vector may be any one of a viral vector, a non-viral vector and a naked DNA vector.

In more specific embodiments, the cassette used by the invention may be comprised within a viral vector. Non-limiting examples for such viral vectors include any one of recombinant adeno associated vectors (rAAV), adenoviral vector (Ad), single stranded AAV (ssAAV), self-complementary rAAV (scAAV), Simian vacuolating virus 40 (SV40) vector, Adeno virus vector, helper-dependent Adeno viral vector, retroviral vector and lentiviral vector.

In yet some further embodiments, the cassette used by the methods of the invention may be comprised within a non-viral vector, such vector may be any one of plasmid, minicircle and linear DNA.

In some further embodiments, the cassette used by the methods of the invention may be comprised within a naked DNA vector, in some embodiments, such vector may be any one of plasmid, minicircle and linear DNA. In yet some further embodiments, the DNA to be inserted may alternatively be constructed as part of a non-viral vector, such as a polyplex, a liposome, a lipopolyplex, a dendrisome, a nano-carrier, an exosome, and more. Delivery of the DNA to be inserted or of the vector coding for the DNA to be inserted can take place in vivo or ex vivo using autologous or allogeneic cells. In some specific embodiments, the DNA to be inserted may be provided as naked circular or linear DNA through electroporation, nucleofection, sonoporation, lipofection, glycofection, SQZ, and more. It should be noted that any vector disclosed herein after in connection with other aspects of the invention may be also encompassed by the vectors applicable in the present aspect. In some alternative embodiments of the methods of the invention, the nucleic acid sequence coding for at least one variable domain of at least one of an immunoglobulin heavy chain and an immunoglobulin light chain, further comprises at least one exogenous hotspot motif/s for somatic hypermutation/s. In some embodiments, the somatic hyper mutation/s retain or minimally change the protein translated from the nucleic acid sequence. It should be noted that in some embodiment the exogenous or ectopic hotspots comprised within the immunoglobulin heavy and/or light chain sequence/s are non-naturally occurring hotspots resulting from substitution of at least one nucleic acid in the original sequence.

In some embodiments, the hotspot motif is at least one of WRCH, DGYW, RCY, RGY and any C nucleotide, said W is any one of A or T, R is A or G, H is A or C or T, D is A or G or T and Y is C or T, and wherein said hot spot motif is incorporated in at least one of the coding strand and the template strand.

As noted by the following claims, the methods of the invention involve the step of contacting the target cells with the cassette of the invention, or any vector, composition or vehicle comprising the cassette. The term "contacting" means to bring, put, incubate or mix together. More specifically, in the context of the present invention, the term "contacting" includes all measures or steps, which allow the positioning of the nucleic acid cassettes of the present invention such that they are in direct or indirect contact with the target cell/s.

To induced DNA integration either in vitro or in vivo, the nucleic acid cassette of the invention may be provided to and/or contacted with the target cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The nucleic acid cassette may be provided to the target cells one or more times, e.g. one time, twice, three times, or more than three times, and the cells allowed to incubate with the nucleic acid cassette for some amount of time following each contacting event e.g. 16-24 hours or more.

It should be noted that in certain embodiments, the methods of the invention may further comprise the step of selecting the engineered B cells that express the engineered BCR of the invention, specifically when performed in vitro or ex vivo. In yet some further embodiments, the selection step may involve the selection of cells that express the engineered BCR using affinity methods for detecting tags or sequences specific for the transgenic BCR.

In yet another aspect, the invention relates to a method of genetic engineering of a BCR of a cell of the B cell lineage in a mammalian subject in need thereof. In more specific embodiments, the method of the invention may comprise the step of administering to the subject an effective amount of at least one nucleic acid cassette comprising at least one nucleic acid sequence of interest or of any vector or vehicle comprising the cassette. In some specific embodiments, the nucleic acid sequence of interest comprised within the cassette used by the methods of the invention may comprise a nucleic acid sequence coding for at least one variable domain of an immunoglobulin heavy chain and a splice donor site. In more specific embodiments, the nucleic acid cassette may target the insertion of the nucleic acid sequence of interest into a target genomic sequence within the IgH locus, upstream of at least one splice acceptor site of the constant domain of the heavy chain. in yet some further embodiments, the target site may be located within the J-C intron of the IgH gene. In some specific embodiments, the target genomic sequence within the IgH locus may be located downstream to the J region of the variable domain of the heavy chain. In yet some other optional embodiments, the target genomic sequence may be located upstream of the CSR region of said heavy chain. Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR region of the heavy chain of the BCR.

In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain. It should be understood that in some embodiments, the insertion of the sequence of interest into the target site must retain, at least in part, the class switch recombination mediated by the CSR region, and optionally, at least part of the enhancer activity.

It should be understood that the target sequence as defined herein before in connection with other aspects of the invention is also applicable for the present aspect.

In some embodiments, the nucleic acid sequence of interest comprised within the cassette used by the methods of the invention may comprise at least one splice acceptor site (SA). In yet some further embodiments, the SA may be located upstream to the VH.

As indicated above, the nucleic acid sequence of interest comprised within the nucleic acid cassette used by the methods of the invention may further comprise at least one nucleic acid sequence coding for at least one variable domain of at least one VL. In yet some further embodiments, the nucleic acid sequence of interest may further comprise a nucleic acid sequence coding for the constant domain of the immunoglobulin light chain (CL). Thus, the nucleic acid of interest encodes the entire light chain. It should be noted that in some embodiments, the immunoglobulin light chain encoded by the nucleic acid sequence of interest provided by the methods of the invention may be able to successfully pair with the heavy chain. As indicated above, in some embodiments, the method may further comprise the step of ablating the endogenous IgK or Igλ genes to ensure pairing with the light chain of the transgene (e.g., the heavy chain that includes the inserted VH and the inserted light chain). In yet some further embodiments, the sequence of such VL and said IgH may be joined by at least one linker and are coded as a single polypeptide.

Still further, in some specific embodiments, the exogenous at least one VL (optionally with at least one LC) and the at least one VH provided by the donor cassette of the invention, with the endogenous CH, may be transcribed and translated as a single chain antibody or as a single chain polypeptide. More specifically, a single-chain antibody comprising the transgenic VL, CL (either kappa or lambda), VH (VJD) and the endogenous CH.

In yet some alternative embodiments, the sequence of the IgL and the VH may be encoded as separate polypeptides. In still some further embodiments, such separated polypeptides may be encoded on a polycistronic vector.

In yet some further embodiments, the nucleic acid sequence of interest provided by the cassette used by the methods of the invention may comprise a sequence encoding a signal peptide or any possible leader. In yet some further specific embodiments, such signal peptide may be any one of HGH leader sequence as demonstrated in Example 3 or alternatively, a human IgH variable leader sequence or IgK variable leader sequence as demonstrated by Example 4. In some further embodiments, the HGH leader sequence may comprise the nucleic acid sequence as denoted by SEQ ID NO: 37.

In some specific and non-limiting embodiments, the nucleic acid of interest may comprise a nucleic acid sequence encoding at least one variable domain of the heavy chain of an antibody of interest or of any fragment/s or chimera/s thereof, specifically, any antigen-binding fragments thereof.

In yet some further embodiments, the nucleic acid sequence of interest may further comprise a sequence encoding a variable light chain of an antibody of interest. In some further embodiments, the nucleic acid sequence of interest may further comprise a sequence encoding the light chain of an antibody of interest.

In yet some further embodiments, such antibody of interest or any antigen-binding fragments thereof, encoded by the nucleic acid sequence of interest in accordance with the invention, may be any one of full length antibody, antibody fragment, a single-chain antibody, single-chain variable fragment (scFv), bi-specific antibody, tri-specific antibody, Bi-specific T-cell engagers (BiTE) and variable new antigen receptor antibody (V-NAR).

It should be understood that an antibody of interest or any antigen-binding fragments thereof, encoded by the nucleic acid sequence of interest in accordance with the invention may be directed to any antigen of interest, specifically any antigen specific for a pathologic disorder. In more specific embodiments, the antibody of interest may be directed against antigens specific for proliferative disorders, specifically, TAAs, or antigens specific for any pathogen, specifically, viral, bacterial, fungal and parasitic pathogen.

In some specific embodiments, the antibody of interest encoded by the nucleic acid sequence of interest of the cassette used by the methods of the invention, may be at least one antibody directed against at least one of a viral antigen and a TAA.

In some specific embodiments, the antibody of interest may be an antibody directed against a viral antigen. As indicated above, any of the viral pathogens discussed herein after, is applicable in this aspect. In more specific embodiments, the antibody of interest may be directed against any antigen derived from a viral pathogen of the order Mononegavirales. In yet some further embodiments, the antibody of interest may be directed against an antigen derived from a virus of the family Pneumoviridae. In more specific embodiments antibody of interest may be directed against any antigen derived from a viral pathogen of the genus Orthopneumovirus. In some specific embodiments, such viral antigen may be an antigen specific for RSV. In yet some further specific embodiments, the anti-RSV antibody may be the anti-RSV palivizumab antibody.

In some specific embodiments, the nucleic acid sequence of interest in accordance with the invention may comprise the full light chain of the anti-RSV antibody palivizumab followed by a 2A peptide sequence and the coding sequence for the variable domain of the palivizumab heavy chain terminating with an SD. In addition, an HGH leader sequence preceded each chain, may be also included as demonstrated by Example 3. In some further embodiments, the HGH leader sequence may comprise the nucleic acid sequence as denoted by SEQ ID NO: 37.

In yet some further specific embodiments, the antibody of interest may be directed against any antigen derived from a viral pathogen of the family Retroviridae. In yet some further embodiments, the antibody of interest may be directed against an antigen derived from a virus of the subfamily Orthoretrovirinae. In more specific embodiments antibody of interest may be directed against any antigen derived from a viral pathogen of the genus Lentivirus, specifically, of the species HIV. In further embodiments, the antibody of interest in accordance with some embodiments of the invention may be an anti-HIV antibody. In yet some further specific embodiments the antibody of interest may be the anti-HIV 3BNC117 antibody.

In some specific embodiments, the cassette used by the methods of the invention may comprise a sequence encoding the full light chain of the anti-HIV antibody 3BNC117 followed by a sequence coding for a 2A peptide and the coding sequence for the variable domain of the 3BNC117 heavy chain terminating with an SD. The cassette of the invention may further comprise human IgH variable leader sequences, as demonstrated by Example 4.

Still further, in some embodiments, the cassette used by the methods of the invention may further comprise at least one genetic element. In some specific embodiments, such genetic element may be at least one of: IRES, a 2A peptide coding sequence, a promoter or any functional fragments thereof, a polyadenylation site, a signal peptide a stop codon, and a transcription enhancer.

In some specific embodiments, the antibody encoded by the donor cassette of the invention may be transcribed and translated as a single chain antibody. In yet some further specific embodiments, such single-chain antibody may comprise the transgenic VL, CL (either kappa or lambda), VH and the endogenous CH.

As indicated above, the cassette of the invention used by the methods of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette used by the methods of the invention may further comprise targeting elements facilitating the specific recognition and targeted insertion to the target site. Thus, according to some embodiments, the cassette of the invention may be flanked at the 5' and/or 3' thereof by at least one of (i) homology arms, for integration by homologous recombination; and (ii) recognition sites for a site-specific nuclease, a site-specific integrase or a site-specific recombinase. All target sites and sequences are as described herein before in connection with other aspects of the invention.

In some specific embodiments, the insertion of the nucleic acid sequence of interest of the cassette used by the method of the invention, into the target genomic locus may be mediated by any gene editing system, for example, at least one of a site-specific nuclease, a class switch recombination, a site specific integrase, a site-specific recombinase and a RAG-catalyzed recombination, as disclosed herein before.

In some specific embodiments, the targeted insertion of the nucleic acid sequence of interest may be mediated by a site-specific nuclease. In more specific embodiments, the site-specific nuclease may be at least one PEN. In some specific embodiments, the targeted insertion of the nucleic acid sequence of interest may be mediated by the CRISPR system. Thus, in some specific embodiments, the method of the invention may further comprise the step of contacting the cell, and/or administering the subject, with at least one of: (a) at least one CRISPR/cas protein, or any nucleic acid molecule encoding said Cas protein; and (b) at least one nucleic acid sequence comprising at least one guide RNA (gRNA) that targets the insertion of the nucleic acid sequence of interest into a target genomic sequence within the IgH locus, or any nucleic acid sequence encoding said gRNA; or any kit, composition or vehicle comprising at least one of (a) and (b).

As indicated above, the Cas protein and the specific gRNA may be provided either as a protein and gRNA, or alternatively, as nucleic acid sequences encoding these two elements, either in two separate nucleic acid molecules, or in one nucleic acid molecule.

Thus, in some embodiments, when the CRISPR/Cas system is used as a gene editing tool, the method of the invention comprises the step of contacting the cell with the cassette of the invention or with any vector or vehicle thereof and in addition, contacting, either concomitantly or simultaneously, the cell, or administering the subject, with the components of the CRISPR/Cas system as specified above.

In some specific embodiments, the Cas protein used by the method of the invention may be a member of a CRISPR-associated system type II of Class 2. In more specific embodiments, the Cas protein may be Cas9 or any fragments, mutants, variants or derivatives thereof.

As being directed to a target location within the J-C intron that is not included in the endogenous variable region of the IgH locus, the methods of the invention further allow the use of universal homology arms in the donor cassette used by the methods of the invention. These universal homology arms may support specific integration of the nucleic acid sequence of interest provided by said cassette, to the target site within the J-C intron, in any B cell in a particular species.

In yet some further embodiments, the targeted insertion of the nucleic acid sequence of interest may be mediated by the class switch recombination. In more specific embodiments, the class witch recombination may be catalyzed by AID. In yet some further embodiments, such method may further involve the step of activating the cell of the B lineage, specifically, a B cell. In some specific and non-limiting embodiments, the activation step may involve depletion of IL-4. In yet some further embodiments, such activation may involve addition of an effective amount of LPS.

Still further, in some embodiments, the cassette used by the method of the invention may be comprised within a nucleic acid vector. In more specific embodiments, such vector may be any one of a viral vector, a non-viral vector and a naked DNA vector.

It should be understood that all vectors described by the invention in connection with other aspects, are also applicable in the present aspect. It should be noted that in certain embodiments, the methods of the invention may further comprise the step of selecting the engineered B cells that express the engineered BCR of the invention, specifically when performed in vitro or ex vivo.

The method of the invention provides genetic engineering of a BCR in a cell of the B lineage in a mammalian subject. In some embodiments, such subject is suffering from a pathologic disorder.

More specifically, such disorder may be at least one of a proliferative disorder, an inflammatory disorder, an infectious disease caused by a pathogen and an autoimmune-disease. It should be noted that the disorders specified in connection with other aspects of the invention, are also applicable for this aspect. In some alternative and specific embodiments, the nucleic acid sequence of the methods of the invention coding for at least one variable domain of at least one of an immunoglobulin heavy chain and an immunoglobulin light chain, further comprises at least one exogenous, ectopic or non-naturally occurring hotspot motif/s for somatic hypermutation/s. Such somatic hyper mutation/s retain or minimally change the protein translated from said nucleic acid sequence.

In more specific embodiments, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand.

Still further, in some embodiments, the methods of the invention may further comprise the step of activating said cell in the subject by at least one of Toll-like receptor (TLR)-mediated activation and cluster of differentiation 40 (CD40)-ligation. More specifically, Toll-like receptors (TLRs) are a class of proteins that play a key role in the innate immune system. They are single, membrane-spanning, non-catalytic receptors usually expressed on sentinel cells such as macrophages and dendritic cells, that recognize structurally conserved molecules derived from pathogens. The TLRs include TLR1, TLR2, TLR3, TLR4, TLR5, TLR6, TLR7, TLR8, TLR9, TLR10, TLR11, TLR12, and TLR13 (the last three are not found in humans). The ability of immune system to recognize molecules that are broadly shared by pathogens is thus in part, due to the presence of the toll-like receptors (TLRs) that are expressed on the membranes of leukocytes including dendritic cells, macrophages, natural killer cells, cells of the adaptive immunity (T and B lymphocytes) and non-immune cells (epithelial and endothelial cells, and fibroblasts). The binding of ligands to the TLR marks the key molecular events that ultimately lead to innate immune responses and the development of antigen-specific acquired immunity. Upon activation, TLRs recruit adapter proteins within the cytosol of the immune cell in order to propagate the antigen-induced signal transduction pathway. These recruited proteins are then responsible for the subsequent activation of other downstream proteins, including protein kinases (IKKi, IRAK1, IRAK4, and TBK1) that further amplify the signal and ultimately lead to the upregulation or suppression of genes that orchestrate inflammatory responses and other transcriptional events. Some of these events lead to cytokine production, proliferation, and survival, while others lead to greater adaptive immunity.

In some specific embodiments, the step of activation of the TLR in human cells is performed by using an anti-RP105 (TLR4 homologue) antibody. Thus, in some embodiments, the subject is further administered either concomitantly or simultaneously with TLR activating agent. Mouse B cells may be activated by the TLR4 agonist LPS. In some embodiments, the methods of genetic engineering of a BCR of a cell of the B cell lineage in a mammalian subject in need thereof, wherein contacting the cell with the cassette is performed in a subject. Thus, the method comprises the step of administering to the subject the cassette of the invention or any vector, system or compositions thereof. In some embodiments, the methods result in secretion of the antibodies in the subject. In yet some further aspect thereof, the invention provides a method of engineering a mammalian cell of the B lineage for antigen-induced secretion of an antibody of interest, or of any fragment thereof, specifically, an antigen-binding fragment thereof. More specifically, the method of the invention may comprise the step of contacting the cell with at least one nucleic acid cassette comprising at least one nucleic acid sequence of interest or with any vector or vehicle comprising said cassette. In some specific embodiments, the nucleic acid sequence of interest comprised within the cassette used by the method of the invention may comprise a nucleic acid sequence coding for at least one variable domain of the immunoglobulin heavy chain of the antibody of interest and at least one splice donor site. More specifically, the variable domain of the heavy chain is followed by the splice donor site.

It should be noted that in some embodiments, the nucleic acid cassette used by the methods of the invention targets the insertion of the nucleic acid sequence of interest into a target genomic sequence within the IgH locus. In more specific embodiments, the target sequence is located upstream of at least one splice acceptor site of the constant domain of said heavy chain of said BCR. In some embodiments, the cassette of the invention may further comprise at least one SA. In yet some further embodiments, the SA may be located upstream to the VH in the donor cassette, allowing the use of the endogenous VH promoter for transcription of the transgenic nucleic acid sequence of interest provided by the cassette of the invention.

It should be noted that the methods of the invention provide an engineered mammalian cell of the B lineage, specifically, a B cell that is capable of antigen-induced and well controlled secretion of an antibody of interest. The cell engendered by the method of the invention further retains the affinity maturation, class switch recombination, and the retention of immunological memory, and therefore may be applicable in immunotherapy.

In some specific embodiments, the target genomic sequence within the IgH locus may be located downstream to the J region of the variable domain of the heavy chain. In yet some other optional embodiments, the target genomic sequence may be located upstream of the CSR of said heavy chain.

Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR region of the heavy chain of the BCR.

In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain. It should be understood that in some embodiments, the insertion of the sequence of interest to the target site must retain, at least in part, the class switch recombination mediated by the CSR region, as discussed above in connection with other aspects of the invention and optionally, at least part of the enhancer activity. It should be appreciated that the target site specified herein before in connection with other aspects of the invention, is also applicable for the present aspect.

As indicated above, the nucleic acid sequence of interest comprised within the nucleic acid cassette used by the methods of the invention may further comprise at least one nucleic acid sequence coding for at least one variable domain of at least one VL. In yet some further embodiments, the nucleic acid sequence of interest may further comprise a nucleic acid sequence coding for the constant domain of the immunoglobulin light chain, thereby encoding the entire light chain, specifically, the variable and the constant domains.

It should be noted that in some embodiments, the immunoglobulin light chain encoded by the nucleic acid sequence of interest provided by the methods of the invention may be able to successfully pair with the heavy chain. In yet some further embodiments, the sequence of such VL and said IgH may be joined by at least one linker and are coded as a single polypeptide. Still further, in some embodiments, to ensure parring of both transgenic immunoglobulin chains and avoiding paring with the endogenous heavy or light chains, the method of the invention may further comprise the step of ablating the endogenous light (either κ or λ) chains as discussed above. Still further, in some optional embodiments, the invention may further comprise the step of ablating the endogenous heavy (either μ, δ, α, ε, or γ) chains.

In yet some alternative embodiments, the sequence of the IgL and the VH may be encoded as separate polypeptides. In still some further embodiments, such separated polypeptides may be encoded on a polycistronic vector. In some specific embodiments, the exogenous at least one VL (optionally with at least one LC) and the at least one VH provided by the donor cassette of the invention, with the endogenous CH, may be transcribed and translated as a single chain antibody.

In yet some further embodiments, the nucleic acid sequence of interest provided by the cassette used by the methods of the invention may comprise a sequence encoding a signal peptide. In yet some further specific embodiments, such signal peptide may be any one of HGH leader sequence as demonstrated in Example 3 or alternatively, a human IgH variable leader sequence or IgK leader sequence as demonstrated by Example 4. In some further embodiments, the HGH leader sequence may comprise the nucleic acid sequence as denoted by SEQ ID NO: 37.

In some specific and non-limiting embodiments, the nucleic acid of interest may comprise a nucleic acid sequence encoding at least one variable domain of the heavy chain of an antibody of interest or of any fragment/s or chimera/s thereof, specifically, any antigen-binding fragments thereof.

In yet some further embodiments, the nucleic acid sequence of interest may further comprise a sequence encoding a variable light chain of an antibody of interest. In some further embodiments, the nucleic acid sequence of interest may further comprise a sequence encoding the light chain of an antibody of interest. In yet some further embodiments, such antibody of interest or any antigen-binding fragments thereof, encoded by the nucleic acid sequence of interest in accordance with the invention, may be any one of full length antibody, antibody fragment, single chain antibody, scFv, bi-specific antibody, tri-specific antibody, BiTE and V-NAR.

It should be understood that an antibody of interest or any antigen-binding fragments thereof, encoded by the nucleic acid sequence of interest in accordance with the invention may be directed to any antigen of interest, specifically any antigen specific for a pathologic disorder. In more specific embodiments, the antibody of interest may be directed against antigens specific for proliferative disorders, specifically, TAAs, or antigens specific for any pathogen, specifically, viral, bacterial, fungal or parasitic pathogen. In some specific embodiments, the antibody of interest encoded by the nucleic acid sequence of interest of the cassette used by the methods of the invention, may be at least one antibody directed against at least one of a viral antigen and a TAA.

In some specific embodiments, the antibody of interest may be an antibody directed against a viral antigen as described herein before. In further specific embodiments, such viral antigen may be an antigen specific for RSV. In yet some further specific embodiments, the anti-RSV antibody may be the anti-RSV palivizumab antibody. In some specific embodiments, the nucleic acid sequence of interest in accordance with the invention may comprise the full light chain of the anti-RSV antibody palivizumab followed by a 2A peptide sequence and the coding sequence for the variable domain of the palivizumab heavy chain terminating with an SD. In addition, an HGH leader sequence preceded each chain, may be also included as demonstrated by Example 3. In some further embodiments, the HGH leader sequence may comprise the nucleic acid sequence as denoted by SEQ ID NO: 37.

In yet some further specific embodiments, the antibody of interest may be directed against any antigen derived from HIV. In yet some further embodiments, the antibody of interest in accordance with some embodiments of the invention may be an anti-HIV antibody. In yet some further specific embodiments the antibody of interest may be the anti-HIV 3BNC117 antibody. In some specific embodiments, the cassette used by the methods of the invention may comprise a sequence encoding the full light chain of the anti-HIV antibody 3BNC117 followed by a sequence coding for a 2A peptide and the coding sequence for the variable domain of the 3BNC117 heavy chain terminating with an SD. The cassette of the invention may further comprise human IgH or IgK variable leader sequences, as demonstrated by Examples 4, 5 and 12. Still further, in some embodiments, the cassette used by the methods of the invention may further comprise at least one genetic element. In some specific embodiments, such genetic element may be at least one of: at least one SA, an IRES, a 2A peptide coding sequence, a promoter or any functional fragments thereof, a polyadenylation site, a signal peptide a stop codon, and a transcription enhancer.

As indicated above, the cassette of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette used by the methods of the invention may further comprise targeting elements facilitating the specific recognition and targeted insertion to the target site. Thus, according to some embodiments, the cassette of the invention may be flanked at the 5' and/or 3' thereof by at least one of (i) homology arms, for integration by homologous recombination; and (ii) recognition sites for a site-specific nuclease, a site-specific integrase or a site-specific recombinase.

In some specific embodiments, the insertion of the nucleic acid sequence of interest of the cassette used by the method of the invention, into the target genomic locus may be mediated by any gene editing system, for example, at least one of a site-specific nuclease, a class switch recombination, a site specific integrase, a site-specific recombinase and a RAG-catalyzed recombination.

In some specific embodiments, the targeted insertion of the nucleic acid sequence of interest may be mediated by a site-specific nuclease. In more specific embodiments, the site-specific nuclease may be at least one PEN. In some specific embodiments, the targeted insertion of the nucleic acid sequence of interest may be mediated by the CRISPR system. Thus, in some specific embodiments, the method of the invention may further comprise the step of contacting the cell with at least one of (a) at least one CRISPR/cas protein, or any nucleic acid molecule encoding said Cas protein; and (b) at least one nucleic acid sequence comprising at least one gRNA that targets the insertion of the nucleic acid sequence of interest into a target genomic sequence within the IgH locus, or any nucleic acid sequence encoding said gRNA; or any kit, composition or vehicle comprising at least one of (a) and (b). The Cas protein and the specific gRNA may be provided either as a protein and gRNA, or alternatively, as nucleic acid sequences encoding these two elements, either in two separate nucleic acid molecules, or in one nucleic acid molecule. Thus, in some embodiments, when the CRISPR/Cas system is used as a gene editing tool, the method of the invention comprises the step of contacting the cell with the cassette of the invention or with any vector or vehicle thereof and in addition, contacting, either concomitantly or simultaneously, the cell with the components of the CRISPR/Cas system as specified above. In some specific embodiments, the Cas protein used by the method of the invention may be a member of a CRISPR-associated system type II of Class 2. In more specific embodiments, the Cas protein may be Cas9 or any fragments, mutants, variants or derivatives thereof. In yet some specific embodiments, saCas9 or spCas9 may be used.

It should be appreciated that in some embodiments, since the target location of the cassette of the invention resides within the J-C intron that is not included in the endogenous variable region of the IgH locus, the methods of the invention further allow the use of universal homology arms in the donor cassette. These universal homology arms may support specific integration of the nucleic acid sequence of interest provided by said cassette, to the target site within the J-C intron, in any B cell in a particular species. A non-limiting example for targeted insertion of the nucleic acid sequence of interest is located between about 350 to 450 nucleotides downstream to the J region and is designated herein as mH69. In some specific embodiments, the target site comprises the nucleic acid sequence as denoted by SEQ ID NO. 33. In yet some further embodiments, the target sequence comprises the protospacer sequence as well as the PAM sequence, as denoted by SEQ ID NO. 15.

Thus, in some embodiments where the CRISPR system is used for insertion, a gRNA that targets the Cas9 to the mH69 site may be used by the methods of the invention. In yet some further specific embodiments such gRNA may comprise the nucleic acid sequence as denoted by any one of SEQ ID NO. 16 and 17. In some specific embodiments, the cassette used by the methods of the invention may further comprise homology arms facilitating the integration of the nucleic acid sequence of interest into the target site, such homology arms may comprise the nucleic acid sequence as denoted by SEQ ID NO. 34 and 35.

As shown in Example 13, targeted insertion of the nucleic acid sequence of interest into the IgH locus, may be facilitated using the class switch recombination process. Thus, in yet some further embodiments, the targeted insertion of the nucleic acid sequence of interest may be mediated by the class switch recombination. In more specific embodiments, the class witch recombination may be catalyzed by AID. In yet some further embodiments, such method may further involve the step of activating the cell of the B lineage. In some specific and non-limiting embodiments, the activation step may involve depletion of IL-4. In yet some further embodiments, such activation may involve addition of an effective amount of LPS. In yet some further embodiments, the methods of the invention may further comprise the step of activating said cell by at least one of TLR-mediated activation and CD40-ligation. In yet some further embodiments, the method of the invention may further comprise the step of selecting the engineered B cells that express the engineered BCR of the invention, specifically when performed in vitro or ex vivo. In yet some further embodiments, where the targeted insertion of the nucleic acid sequence of interest by the methods is performed in vivo, all contact steps with the target cell (of the B linage) may be performed in vivo, by administering the cassette or any vector, composition or system thereof, to the subject in need.

Still further, in some embodiments, the cassette used by the method of the invention may be comprised within a nucleic acid vector. In more specific embodiments, such vector may be any one of a viral vector, a non-viral vector and a naked DNA vector.

In some specific alternative embodiments of the methods of the invention, the nucleic acid sequence coding for at least one variable domain of at least one of an immunoglobulin heavy chain and an immunoglobulin light chain, further comprises at least one exogenous, ectopic or non-naturally occurring hotspot motif/s for somatic hypermutation/s, said somatic hyper mutation/s retain or minimally change the protein translated from said nucleic acid sequence.

In more specific embodiments, the hotspot motif is at least one of WRCH, DGYW, RCY, RGY and any C nucleotide, said W is any one of A or T, R is A or G, H is A or C or T, D is A or G or T and Y is C or T. More specifically, the hot spot motif is incorporated in at least one of the coding strand and the template strand. It should be appreciated that all vectors described by the invention are applicable in the present aspect. It should be noted that when performed in vivo in a subject, contacting the cell with the cassette is performed in some embodiments by administering to the subject an effective amount of at least one nucleic acid cassette comprising at least one nucleic acid sequence of interest or of any vector or vehicle comprising the cassette or any system thereof, as disclosed by the invention.

In yet another aspect, the invention relates to an engineered mammalian cell of the B lineage expressing a genetically engineered BCR. It should be noted that in some embodiments, the cell provided by the invention is transduced or transfected with at least one nucleic acid cassette comprising at least one nucleic acid sequence of interest or of any vector or vehicle comprising the cassette. In some specific embodiments, the nucleic acid sequence of interest comprised within the cassette used for the engineered cell of the invention may comprise a nucleic acid sequence coding for at least one variable domain of at least one immunoglobulin heavy chain and at least one splice donor site. In some embodiments, the variable domain is followed by the SD site. It should be noted that in some embodiments the nucleic acid cassette used for the engineered cells of the invention may target the insertion of the nucleic acid sequence of interest into a target genomic sequence within the IgH locus. In more specific embodiments, the target sequence may be located upstream of at least one splice acceptor site of the constant domain of said heavy chain of said BCR. In yet some further embodiments, the target site may be within the J-C intron of the IgH. Still further, in some embodiments, the cassette of the invention may further comprise at least one SA. In yet some further embodiments, the SA may be located upstream to the VH, allowing the use of the endogenous VH promoter for transcription of the transgenic nucleic acid sequence of interest provided by the cassette of the invention.

In some specific embodiments, the cell of the invention is a B cell. More specifically, the mammalian cells of the B cell lineage provided by the invention may be any lymphocytes of the B lineage. The engineered B cells disclosed herein are also provided by the invention. "Lymphocytes" are mononuclear nonphagocytic leukocytes found in the blood, lymph, and lymphoid tissues. They are divided on the basis of ontogeny and function into two classes, B and T lymphocytes, responsible for humoral and cellular immunity, respectively. Most are small lymphocytes 7-10 μm in diameter with a round or slightly indented heterochromatic nucleus that almost fills the entire cell and a thin rim of basophilic cytoplasm that contains few granules. When "activated" by contact with antigen, small lymphocytes begin macromolecular synthesis, the cytoplasm enlarges until the cells are 10-30 μm in diameter, and the nucleus becomes less completely heterochromatic; they are then referred to as large lymphocytes or lymphoblasts. These cells then proliferate and differentiate into B and T memory cells and into the various effector cell types: B cells into plasma cells and T cells into helper, cytotoxic, and suppressor cells.

Still further, in some embodiments, the cells provided by the invention are applicable in the methods and compositions of the invention may be a B cell progenitor. B cells develop from hematopoietic stem cells (HSCs) that originate from bone marrow. Their development into B cells occurs in several stages, each marked by various gene expression patterns and immunoglobulin H chain and L chain gene loci arrangements, the latter due to B cells undergoing V(D)J recombination as they develop.

To ensure proper development, B cells undergo two types of selection while developing in the bone marrow. Positive selection occurs through antigen-independent signaling involving both the pre-BCR and the BCR. If these receptors do not bind to their ligand, B cells do not receive the proper signals and cease to develop. Negative selection occurs through the binding of self-antigen with the BCR; if the BCR can bind strongly to self-antigen, then the B cell undergoes one of four fates: clonal deletion, receptor editing, anergy, or ignorance (B cell ignores signal and continues development). This negative selection process leads to a state of central tolerance, in which the mature B cells does not bind with self-antigens present in the bone marrow.

The development process in the bone marrow occurs in germinal Centers. B cell lymphopoiesis in the bone marrow is as follows: Pro-B cells, Pre-B-I cells, Pre-B-II large cells, Pre-B-II small cells and Immature B cells. To complete development, Immature B cells migrate from the bone marrow to the spleen as well as pass through two transitional stages: T1 and T2. Throughout their migration to the spleen and after spleen entry, they are considered T1 B cells. Within the spleen, T1 B cells transition to T2 B cells. T2 B cells differentiate into either follicular (FO) B cells or marginal zone (MZ) B cells depending on signals received through the BCR and other receptors. Once differentiated, they are now considered mature B cells, or naive B cells. While immature and during the T1 phase, B cells express BCR of class IgH, but BCR expression changes to the classes IgM and IgD after transition into the T2 phase and while mature up to activation. In yet some further embodiments, the cells provide by the invention, targeted by the cassette administered to the subject by the method of the invention may be splenocytes of any subsect, or any lymphocytes obtained or present in lymph nodes and bone marrow.

In some embodiments, the engineered B cells of the invention may be primary B cells.

Primary B cells are cells that were obtained for culture directly from a subject. In contrast, secondary cell culture are obtained from an already established primary culture.

Still further, in some embodiments, the engineered B cells of the invention may be B cells of a B cell line, specifically immortalized B cells. Immortalized B cells are a population of cells from a multicellular organism which would normally not proliferate indefinitely but, due to mutation, have evaded normal cellular senescence and instead can keep undergoing division. These B cells can therefore be grown for prolonged periods in vitro. An example of immortalized B cells are Epstein-Barr virus (EBV)-immortalized B cells.

It should be understood that the B cells as defined herein are applicable for any of the methods, compositions, systems, or any aspect of the invention. It should be appreciated that the engineered B cell provided by the invention enables the genetically engineered BCR to be subjected to somatic hypermutation (SHM) and affinity maturation, as well as class switch recombination (CSR also called isotype switch) and memory retention. Moreover, the engineered B cells of the invention retain the ability of homing to germinal centers in a mammalian subject.

More specifically, Homing is the phenomenon whereby cells migrate to the organ of their origin.

By homing, transplanted hematopoietic cells are able to travel to and engraft or establish residence in the bone marrow. Various chemokines and receptors are involved in the homing of hematopoietic stem cells. Lymphocyte homing refers to adhesion of the circulating lymphocytes in blood to specialized endothelial cells within lymphoid organs. These diverse tissue-specific adhesion molecules on lymphocytes (homing receptors) and on endothelial cells (vascular addressins) contribute to the development of specialized immune responses. Naive lymphocytes are able to circulate into secondary lymphoid tissues, Peyer's patches, lymph nodes, and the spleen. Because they have not yet been exposed to antigen, these lymphocytes are undifferentiated and express few homing receptors. High endothelial venules (HEVs) are cells found in secondary lymphoid organs that express large quantities of cell adhesion molecules, enabling undifferentiated lymphocytes to bind. After entering lymph nodes and Peyer's patches via HEVs, naive T and B cells are exposed to antigen circulating in lymph and differentiate to contribute to the adaptive immune response. HEVs develop from cytokine production after exposure to antigen and express adhesion molecules from the selectin family, mucin-like family, and the Ig superfamily. Mature lymphocytes are constantly recirculating in the blood and can traffic to secondary lymphoid tissue as well as target tissue including mucosal tissues of the lamina propria, inflammation, and other extralymphoid immune effector sites. Lymphocyte homing receptor expression is altered by antigen exposure. This function enables the adaptive immune system to specialize an immune response in different parts of the body.

Upon exposure to antigens, lymphocytes lack homing ability during a period of sessile differentiation and cell division, and antigen specific lymphocytes are stored in the spleen for 1-3 days. Subsequently, antigen-stimulated B and T cells express homing receptors particularly for the HEV in initial site of immunization tissue. Furthermore, lymphocytes can alter cell adhesion molecule "activatability" to increase binding ability. Organ-specific lymphocyte homing is important for antigen-specificity and in avoiding autoimmune cross-reactions.

The germinal center (GC) is a specialized microenvironment formed within the B cell follicles of secondary lymphoid tissues upon infection or immunization. The GC is divided into two distinct compartments. The dark zone (DZ) that contains a network of CXCL12-producing reticular cells (CRCs) and is the site of GC B cell proliferation and somatic hypermutation (SHM). Centroblasts then follow a CXCL13 gradient to enter the light zone (LZ) as centrocytes through their expression of CXCR5. In the LZ, centrocytes capture antigen presented on follicular dendritic cells (FDCs) which they internalize, process and subsequently present to T follicular helper (Tfh) cells in order to undergo selection. This process is regulated by T follicular regulatory (Tfr) cells which are also present in the LZ. Upon receiving survival signals from Tfh cells, centrocytes re-enter the DZ for further rounds of proliferation and SHM after which they exit the GC as memory B cells or high-affinity antibody-secreting plasma cells.

Affinity maturation is the process by which Follicular B helper T cells (Tfh) activated B cells produce antibodies with increased affinity for antigen during the course of an immune response. With repeated exposures to the same antigen, a host will produce antibodies of successively greater affinities. A secondary response can elicit antibodies with several fold greater affinity than in a primary response. Affinity maturation primarily occurs on surface immunoglobulin of germinal center B cells and as a direct result of somatic hypermutation (SHM) and selection by Tfh cells.

The process involves two interrelated processes, occurring in the germinal centers of the secondary lymphoid organs:

Somatic hypermutation: Mutations in the variable, antigen-binding coding sequences of the immunoglobulin genes.

Clonal selection: B cells that have undergone SHM must compete for limiting growth resources, including the availability of antigen and paracrine signals from Tfh cells. The follicular dendritic cells (FDCs) of the germinal centers present antigen to the B cells, and the B cell progeny with the highest affinities for antigen, having gained a competitive advantage, are favored for positive selection leading to their survival. Positive selection is based on steady cross-talk between Tfh cells and their cognate antigen presenting GC B cell. Because a limited number of Tfh cells reside the germinal center, only highly competitive B cells stably conjugate with Tfh cells and thus receive T cell-dependent survival signals. B cell progeny that have undergone SHM, but bind antigen with lower affinity will be out-competed, and be deleted. Over several rounds of selection, the resultant secreted antibodies produced will have effectively increased affinities for antigen.

Immunological memory is the ability of the immune system to quickly and specifically recognize an antigen that the body has previously encountered and initiate a corresponding immune response. Generally these are secondary, tertiary and other subsequent immune responses to the same antigen. Immunological memory is responsible for the adaptive component of the immune system i.e. the memory T and B cells. Immunological memory is the basis of vaccination.

Memory B cells are plasma cells that are able to produce antibodies for a long time. Unlike the naive B cells involved in the primary immune response the memory B cell response is slightly different. The memory B cell has already undergone clonal expansion and differentiation and affinity maturation, so it is able to divide multiple times faster and produce antibodies with much higher affinity (especially IgG). Memory B cell activity in secondary lymphatic organs is highest during the first 2 weeks after infection. Subsequently, after 2 to 4 weeks its response declines. After the germinal center reaction the memory plasma cells are located in the bone marrow which is the main site of antibody production within the immunological memory.

In some specific embodiments, the target genomic sequence within the IgH locus may be located downstream to the J region of the variable domain of the heavy chain. In yet some other optional embodiments, the target genomic sequence may be located upstream of the CSR of said heavy chain.

Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR of the heavy chain of the BCR.

In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain.

In some embodiments, the insertion of the sequence of interest to the target site must retain, at least in part, the class switch recombination mediated by the CSR region, and optionally, at least part of the enhancer activity, as indicated herein before.

It should be understood that the description of the target site as disclosed in connection with other aspects of the invention is also applicable for the present aspect. As indicated above, the nucleic acid sequence of interest comprised within the nucleic acid cassette of the cell of the invention may further comprise at least one nucleic acid sequence coding for at least one variable domain of at least one VL. In yet some further embodiments, the nucleic acid sequence of interest may further comprise a nucleic acid sequence coding for the constant domain of the immunoglobulin light chain, so the nucleic acid sequence of interest may encode the entire immunoglobulin light chain. In some specific embodiments, the antibody encoded by the donor cassette of the invention may be transcribed and translated as a single chain antibody. In yet some further specific embodiments, such single-chain antibody may comprise the transgenic VL, CL (either kappa or lambda), VH and the endogenous CH. In yet some further embodiments, the nucleic acid sequence of interest provided by the cassette used to engineer the B cells of the invention may comprise a sequence encoding a signal peptide. In yet some further specific embodiments, such signal peptide may be any one of HGH leader sequence as demonstrated in Example 3 or alternatively, a human IgH variable leader sequence or IgK variable leader sequence as demonstrated by Example 4. In some further embodiments, the HGH leader sequence may comprise the nucleic acid sequence as denoted by SEQ ID NO: 37. It should be understood that any other suitable leader sequences are also applicable in the present invention. In some specific and non-limiting embodiments, the nucleic acid of interest may comprise a nucleic acid sequence encoding at least one variable domain of the heavy chain of at least one antibody of interest or of any fragment/s or chimera/s thereof, specifically, any antigen-binding fragments thereof.

In yet some further embodiments, such antibody of interest or any antigen-binding fragments thereof, encoded by the nucleic acid sequence of interest in accordance with the cell of the invention, may be any one of full length antibody, antibody fragment, single chain antibody, scFv, bi-specific antibody, tri-specific antibody, BiTE and V-NAR. It should be understood that an antibody of interest or any antigen-binding fragments thereof, encoded by the nucleic acid sequence of interest in accordance with the cell of the invention, may be directed to any antigen of interest, specifically any antigen specific for a pathologic disorder. In more specific embodiments, the antibody of interest may be directed against antigens specific for proliferative disorders, specifically, TAAs, antigens specific for any pathogen, specifically, viral, bacterial, fungal or parasitic pathogen, or antigens associated with a metabolic disorder or a cardio vascular disease (CVD).

In some specific embodiments, the antibody of interest expressed by the cell of the invention may be an antibody directed against a viral antigen. It should be noted that any of the viruses disclosed by the invention are applicable for this aspect as well. In some specific embodiments, such viral antigen may be an antigen specific for RSV. In yet some further specific embodiments, the anti-RSV antibody may be the anti-RSV palivizumab antibody.

In yet some further embodiments, the antibody of interest in accordance with some embodiments of the invention may be an HIV antibody. In yet some further specific embodiments the antibody of interest produced by the cell of the invention may be the anti-HIV 3BNC117 antibody.

In some specific embodiments, the cassette used by the cell of the invention may comprise a sequence encoding the full light chain of the anti-HIV antibody 3BNC117 followed by a sequence coding for a 2A peptide and the coding sequence for the variable domain of the 3BNC117 heavy chain terminating with an SD. The cassette of the cell of the invention may further comprise human IgH variable leader sequences, as demonstrated by Examples 4, 5 and 12.

Still further, in some embodiments, the cassette used to engineer the cell of the invention may further comprise at least one genetic element. In some specific embodiments, such genetic element may be at least one of: at least one SA, an IRES, a 2A peptide coding sequence, a promoter or any functional fragments thereof, a polyadenylation site, a signal peptide a stop codon, and a transcription enhancer. As indicated above, the cassette of the cell of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette used to engineer the cell of the invention may further comprise targeting elements facilitating the specific recognition and targeted insertion to the target site. Thus, according to some embodiments, the cassette of the invention may be flanked on at the 5' and/or 3' thereof by at least one of (i) homology arms, for integration by homologous recombination; and (ii) recognition sites for a site-specific nuclease, a site-specific integrase or a site-specific recombinase.

In some specific embodiments, the insertion of the nucleic acid sequence of interest of the cassette used by the cell of the invention, into the target genomic locus may be mediated by any gene editing system, for example, at least one of a site-specific nuclease, a class switch recombination, a site specific integrase, a site-specific recombinase and a RAG-catalyzed recombination.

In some specific embodiments, the targeted insertion of the nucleic acid sequence of interest to the cell of the invention may be mediated by the CRISPR system. In some specific embodiments, the Cas protein used by for engineering the cell of the invention may be a member of a CRISPR-associated system type II of Class 2. In more specific embodiments, the Cas protein may be Cas9 or any fragments, mutants, fusion proteins thereof, variants or derivatives thereof.

In yet some further embodiments, the targeted insertion of the nucleic acid sequence of interest to the specific target site in the cell of the invention may be mediated by the class switch recombination. In more specific embodiments, the class witch recombination may be catalyzed by AID. According to some further embodiments, the cell of the invention may be further activated by depleting IL-4, as discussed above.

Still further, in some embodiments, the cassette used by the cell of the invention may be comprised within a nucleic acid vector. In more specific embodiments, such vector may be any one of a viral vector, a non-viral vector and a naked DNA vector. It should be understood that the description of any vectors as disclosed in connection with other aspects of the invention is also applicable for the present aspect.

Still further, it should be understood that the invention further encompasses any population of any of the B cells provided by the invention, specifically, the engineered B cells provided herein, or any preparation thereof, as well as any use of the population of such cells. It should be noted that in some embodiments, any B cell may be used by the invention, with the proviso that said B cell is not a germline B cell. Still further, it should be appreciated that in some embodiments the population of any of the B cells provided by the invention may comprise at least 5% or more engineered B cells of the invention, specifically, at least 10%, 15%, 20%, 25%, 30%, 35%, 40%, 45%, 50%, 55%, 60%, 65%, 70%, 75%, 80%, 85%, 90%, 95%, 99.9% or more, specifically, 100% of the cells of the population of cells provided by the invention may be the engineered B cells of the invention.

In yet a further aspect, the invention provides a genetically engineered BCR comprising an amino acid sequence of interest. It should be noted that the amino acid sequence of interest of the BCR of the invention may comprise at least one variable domain of at least one immunoglobulin heavy chain. In more specific embodiments, the BCR may be engineered by targeted insertion of at least one ectopic nucleic acid sequence of interest comprising a nucleic acid sequence encoding the at least one variable domain of an immunoglobulin heavy chain and a splice donor site, into a target genomic sequence within the IgH locus, upstream of at least one splice acceptor site of the constant domain of an immunoglobulin heavy chain in a mammalian cell of the B lineage. In some embodiments, the target gene sequence may be comprised within the J-C intron of the IgH gene.

Still further, in some embodiments, the cassette used for the BCR of the invention may further comprise at least one SA. In yet some further embodiments, the SA may be located upstream to the VH, allowing the use of the endogenous VH promoter for transcription of the transgenic nucleic acid sequence of interest provided by the cassette of the invention.

In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain. In some embodiments, the insertion of the sequence of interest to the target site must retain, at least in part, the class switch recombination mediated by the CSR region, and optionally, at least part of the enhancer activity, as defined herein above in connection with other aspects of the invention. It should be understood that the exact location of the target insertion site is as defined by the invention in connection with other aspects. As indicated above, the BCR of the invention may further comprise at least one variable domain of at least one VL. In yet some further embodiments, the BCR of the invention may further comprise the constant domain of the immunoglobulin light chain, so the entire light chain is comprised within the BCR. In some specific embodiments, the BCR of the invention may be transcribed and translated as a single chain antibody. In some specific and non-limiting embodiments, the BCR of the invention may comprise a nucleic acid sequence encoding at least one variable domain of the heavy chain of an antibody of interest or of any fragment/s or chimera/s thereof, specifically, any antigen-binding fragments thereof. In yet some further embodiments, the BCR may further comprise variable light chain of an antibody of interest.

In yet some further embodiments, such antibody of interest or any antigen-binding fragments thereof, expressed by the engineered BCR of the invention, may be any one of full length antibody, antibody fragment, single chain antibody, scFv, bi-specific antibody, tri-specific antibody, BiTE and V-NAR. It should be understood that an antibody of interest or any antigen-binding fragments thereof, expressed by the engineered BCR of the invention, may be directed to any antigen of interest, specifically any antigen specific for a pathologic disorder. In more specific embodiments, the antibody of interest may be directed against antigens specific for proliferative disorders, specifically, TAAs, antigens specific for disorders caused by any pathogen, specifically, viral, bacterial, fungal or parasitic pathogen/s, or disorders associated with metabolic disorders or CVDs (e.g., PCSK9).

In some specific embodiments, the antibody of interest expressed by the engineered BCR of the invention, may be at least one antibody directed against at least one of a viral antigen and a TAA, as specified herein before.

In some specific embodiments, the antibody of interest expressed by the BCR of the invention may be an antibody directed against a viral antigen. It should be appreciated that any of the viral pathogens discussed herein after, is applicable in this aspect. In more specific embodiments, the antibody of interest may be directed against any antigen derived from RSV. In yet some further specific embodiments, the anti-RSV antibody may be the anti-RSV palivizumab antibody. In some specific embodiments, the variable domains of the light and heavy chains of the palivizumab antibody may comprise the amino acid sequence as denoted by SEQ ID NO. 29 (the VL and VH), that comprise the HV as denoted by SEQ ID NO. 30, and the VL as denoted by SEQ ID NO. 150.

In yet some further embodiments, the antibody of interest expressed by the engineered BCR of the invention in accordance with some embodiments of the invention may be an antibody directed against any antigen derived from HIV. In yet some further embodiments, the antibody of interest expressed by the engineered BCR of the invention in accordance with some embodiments of the invention may be an HIV antibody. In yet some further specific embodiments the antibody of interest may be the anti-HIV 3BNC117 antibody.

In some specific embodiments, the variable domains of the light and heavy chains of the 3BNC117 antibody may comprise the amino acid sequence as denoted by SEQ ID NO. 31(the VL and VH), that comprise the HV as denoted by SEQ ID NO. 32, and the VL as denoted by SEQ ID NO. 151.

Still further, in some embodiments, the cassette encoding the engineered BCR of the invention may further comprise at least one genetic element. In some specific embodiments, such genetic element may be at least one of: at least one SA, an IRES, a 2A peptide coding sequence, a promoter or any functional fragments thereof, a polyadenylation site, a signal peptide a stop codon, and a transcription enhancer.

As indicated above, the cassette encoding the engineered BCR of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette encoding the engineered BCR of the invention may further comprise targeting elements facilitating the specific recognition and targeted insertion to the target site. Thus, according to some embodiments, the cassette encoding the engineered BCR of the invention may be flanked at the 5' and/or 3' thereof by at least one of (i) homology arms, for integration by homologous recombination; and (ii) recognition sites for a site-specific nuclease, a site-specific integrase or a site-specific recombinase, as discussed for other aspects of the invention.

It should be appreciated that as described herein before, the homology arms used by the invention may be universal homology arms. In some specific embodiments, the insertion of the nucleic acid sequence of interest of the cassette encoding the engineered BCR of the invention, into the target genomic locus may be mediated by any gene editing system, for example, at least one of a site-specific nuclease, a class switch recombination, a site specific integrase, a site-specific recombinase and a RAG-catalyzed recombination. In some specific embodiments, the targeted insertion of the nucleic acid sequence of interest may be mediated by a site-specific nuclease. In some specific embodiments, the targeted insertion of the nucleic acid sequence of interest encoding the engineered BCR of the invention may be mediated by the CRISPR system. In yet some further embodiments, the targeted insertion of the nucleic acid sequence of interest encoding the engineered BCR of the invention to the specific target site in the accordance with the invention may be mediated by the class switch recombination. In more specific embodiments, the class witch recombination may be catalyzed by AID. Still further, in some embodiments, the cassette encoding the engineered BCR of the invention may be comprised within a nucleic acid vector. In more specific embodiments, such vector may be any one of a viral vector, a non-viral vector and a naked DNA vector. It should be understood that the description of vectors as disclosed in connection with other aspects of the invention is also applicable for the present aspect. In some particular and alternative embodiments, the nucleic acid sequence coding for at least one variable domain of at least one of an immunoglobulin heavy chain and an immunoglobulin light chain, of the genetically engineered B cell receptor of the invention, further comprise at least one exogenous hotspot motif/s for somatic hypermutation/s. In some embodiments, the somatic hyper mutation/s retain or minimally change the protein translated from said nucleic acid sequence. In yet some further embodiments, the hotspot motif is at least one of WRCH, DGYW, RCY, RGY and any C nucleotide, said W is any one of A or T, R is A or G, H is A or C or T, D is A or G or T and Y is C or T. More specifically, the hot spot motif is incorporated in at least one of the coding strand and the template strand.

As indicated above, the invention provides genetically engineered B cell receptors and methods for preparations thereof. The B-cell receptor or BCR is a transmembrane receptor protein located on the outer surface of B cells. The B-cell receptor is composed of two elements, specifically, (i) a membrane-bound immunoglobulin molecule of one isotype (IgD, IgM, IgA, IgG, or IgE) with the exception of the presence of an integral membrane domain, these are identical to their secreted forms; and (ii) a signal transduction moiety composed of a heterodimer called Ig-α/Ig-β (CD79), bound together by disulfide bridges. Each member of the dimer spans the plasma membrane and has a cytoplasmic tail bearing an immuno-receptor tyrosine-based activation motif (ITAM). In some embodiments, the polypeptide provided by the invention may be any of the genetically engineered BCRs of the invention, or any derivatives, variants or fragments thereof, as well as any antibody derived therefrom. It should be thus understood that the invention therefore encompasses any BCR disclosed by the invention, as well as any antibody derived therefrom. Moreover, the invention encompasses any BCR prepared by any of the methods of the invention as well as any antibody derived from such BCRs, and any BCR or derived antibody encoded by any of the nucleic acid cassettes of the invention as disclosed herein. Non-limiting embodiments for such BCRs may include the BCRs that comprise the amino acid sequences encoded by the nucleic acid sequence as denote by SEQ ID NO. 29, 30 (palivizumab), SEQ ID NO. 31, 32 (3BNC117), as well as any BCR comprising any optimized variable region sequences as shown in Examples 12 and 13, and provided for 3BNC117 by the amino acid sequences as denoted by SEQ ID NO. 42 (CDR1 of the heavy chain HCDR-1), SEQ ID NO. 47 and 115 (HCDR-2), SEQ ID NO. 52 (HCDR-3), SEQ ID NO. 116(VH-variable heavy chain), SEQ ID NO. 80 (CDR-1 of the light chain LCDR-1), SEQ ID NO. 85 (LCDR-2), and SEQ ID NO. 90 (LCDR-3).

Still further, the invention further encompasses any BCR or antibody that comprise an amino acid sequence encoded by a nucleic acid sequence that comprise at least one of the nucleic acid sequences as denoted by SEQ ID NO. 41, 57 or 68 (CDRs-1 of the heavy chain HCDR-1), SEQ ID NO. 46, 61 or 71 and 115 (HCDRs-2), SEQ ID NO. 51, 64, 65 (HCDRs-3), SEQ ID NO. 38, 54 or 65 (VH-variable heavy chain), SEQ ID NO. 79, 95 or 106 (CDRs-1 of the light chain LCDR-1), SEQ ID NO. 84, 99 or 110 (LCDRs-2), and SEQ ID NO. 89, 103 or 113 (LCDR-3), and SEQ ID NO. 76, 92 or 114 that encode the variable region of the light chain of this antibody (3BNC117). In yet some further embodiments, it should be understood that the invention further encompasses the antibody variants encoded by any of the optimized sequences as denoted by any one of SEQ ID NO. 155 to 274. It should be understood that the invention encompasses BCRs and antibodies comprising the amino acid sequences as specified above or any derivatives or homologs thereof.

The term "polypeptide" as used herein refers to amino acid residues, connected by peptide bonds. A polypeptide sequence is generally reported from the N-terminal end containing free amino group to the C-terminal end containing free carboxyl group and may include any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man. More specifically, "Amino acid sequence" or "peptide sequence" is the order in which amino acid residues connected by peptide bonds, lie in the chain in peptides and proteins. The sequence is generally reported from the N-terminal end containing free amino group to the C-terminal end containing amide. Amino acid sequence is often called peptide, protein sequence if it represents the primary structure of a protein, however one must discern between the terms "Amino acid sequence" or "peptide sequence" and "protein", since a protein is defined as an amino acid sequence folded into a specific three-dimensional configuration and that had typically undergone post-translational modifications, such as phosphorylation, acetylation, glycosylation, manosylation, amidation, carboxylation, sulfhydryl bond formation, cleavage and the like.

It should be appreciated that the invention encompasses the use of any variant or derivative of the polypeptides of the invention, specifically any polypeptide comprising at least one of the amino acid sequences as denoted by any one of SEQ ID NO. 42, SEQ ID NO. 47, SEQ ID NO. 115, SEQ ID NO. 52, SEQ ID NO. 116, SEQ ID NO. 80, SEQ ID NO. 85 and SEQ ID NO. 90, and any polypeptides that are substantially identical or homologue to the polypeptides encoded by the nucleic acid sequence of the invention, as indicated herein above. The term "derivative" is used to define amino acid sequences (polypeptide), with any insertions, deletions, substitutions and modifications to the amino acid sequences (polypeptide) that do not alter the activity of the original polypeptides. By the term "derivative" it is also referred to homologues, variants and analogues thereof. Proteins orthologs or homologues having a sequence homology or identity to the proteins of interest in accordance with the invention, specifically, receptors, chimeras and antibodies described herein, may share at least 50%, at least 60% and specifically 65%, 70%, 75%, 80%, 85%, 90%, 91%, 92%, 93%, 94%, 95%, 96%, 97%, 98%, 99%, or higher, specifically as compared to the entire sequence of the proteins of interest in accordance with the invention, specifically, any one of SEQ ID NO. 29, 30 (palivizumab), SEQ ID NO. 31, 32 (3BNC117), SEQ ID NO. 42, SEQ ID NO. 47, SEQ ID NO. 115, SEQ ID NO. 52, SEQ ID NO. 116, SEQ ID NO. 80, SEQ ID NO. 85 and SEQ ID NO. 90.

In some embodiments, derivatives refer to polypeptides, which differ from the polypeptides specifically defined in the present invention by insertions, deletions or substitutions of amino acid residues. It should be appreciated that by the terms "insertion/s", "deletion/s" or "substitution/s", as used herein it is meant any addition, deletion or replacement, respectively, of amino acid residues to the polypeptides disclosed by the invention as indicated above, of between 1 to 50 amino acid residues, between 20 to 1 amino acid residues, and specifically, between 1 to 10 amino acid residues. More particularly, insertion/s, deletion/s or substitution/s may be of any one of 1, 2, 3, 4, 5, 6, 7, 8, 9, or 10 amino acids. It should be noted that the insertion/s, deletion/s or substitution/s encompassed by the invention may occur in any position of the modified peptide, as well as in any of the N' or C' termini thereof. With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention. For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:

1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

More specifically, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar "hydrophobic" amino acids are selected from the group consisting of Valine (V), Isoleucine (I), Leucine (L), Methionine (M), Phenylalanine (F), Tryptophan (W), Cysteine (C), Alanine (A), Tyrosine (Y), Histidine (H), Threonine (T), Serine (S), Proline (P), Glycine (G), Arginine (R) and Lysine (K); "polar" amino acids are selected from the group consisting of Arginine (R), Lysine (K), Aspartic acid (D), Glutamic acid (E), Asparagine (N), Glutamine (Q); "positively charged" amino acids are selected form the group consisting of Arginine (R), Lysine (K) and Histidine (H) and wherein "acidic" amino acids are selected from the group consisting of Aspartic acid (D), Asparagine (N), Glutamic acid (E) and Glutamine (Q).

Variants of the polypeptides of the invention may have at least 80% sequence similarity or identity, often at least 85% sequence similarity or identity, 90% sequence similarity or identity, or at least 95%, 96%, 97%, 98%, or 99% sequence similarity or identity at the amino acid level, with the protein of interest, such as the various polypeptides of the invention. It should be understood that the percentage of similarity or identity refer to the similarity or identity to the entire sequences as denoted by any one of SEQ ID NO. 42, SEQ ID NO. 47, Seq Id No. 115, SEQ ID NO. 52, SEQ ID NO. 116, SEQ ID NO. 80, SEQ ID NO. 85 and SEQ ID NO. 90.

Another aspect of the invention relates to a nucleic acid cassette comprising at least one nucleic acid sequence of interest. It should be noted that the sequence of interest may comprise a nucleic acid sequence coding for at least one variable domain of an immunoglobulin heavy chain and a splice donor site. In some specific embodiments the sequence coding for the VH is followed by the SD site. In some embodiments, the nucleic acid cassettes of the invention may target the insertion of the nucleic acid sequence of interest into a target genomic sequence within the IgH locus, upstream of at least one splice acceptor site of a constant domain of an immunoglobulin heavy chain in a mammalian cell of the B cell lineage. In some embodiments, the cassettes of the invention may direct the insertion or integration of the nucleic acid sequence of interest into a specific target site within the J-C intron of the IgH, that resides between the last J segment of the variable domain of the heavy chain (VH), and the constant region of the heavy chain (CH). In some embodiments, the cassette of the invention may further comprise at least one SA. In yet some further embodiments, the SA may be located upstream to the VH in the donor cassette, allowing the use of the endogenous VH promoter for transcription of the transgenic nucleic acid sequence of interest provided by the cassette of the invention.

More specifically, the introduced nucleic acid sequence of interest (e.g., nucleic acid sequence that encodes at least the VH fragment of an antibody of interest) is transcribed as a fusion to the endogenous VDJ transcript. This transgenic exogenous sequence can be separately translated using IRES or 2A peptide, or alternatively, released to function separately from the endogenous VDJ by incorporating a protease cleavage site (e.g., a furin site). Thus, in some specific and non-limiting configuration of the cassette of the invention, a splice acceptor (SA) or a minimal promoter (MP) may be included. The cassette encodes an antibody light chain (VLJLCL) and a variable region of a heavy chain (VHDHJH) separated by a 2A peptide (SA-VLJLC-2A-VHDHJH-SD). Upon integration, transcription and splicing, the transgene is first expressed as a BCR on naïve B cells. Following antigen-induced activation and affinity maturation the transgene is also expressed as antibodies of different classes being secreted from plasma cells. Similar example with a minimal promoter may be: MP-VLJLC-2A-VHDHJH-SD. The invention involve the provision of a nucleic acid cassette, that is used in the methods, cells, compositions and uses described in all aspects of the invention. The term "nucleic acid cassette" refers to a polynucleotide sequence comprising at least one regulatory sequence operably linked to a sequence encoding a nucleic acid sequence of interest.

All elements comprised within the cassette of the invention are operably linked together. The term "operably linked", as used in reference to a regulatory sequence and a structural nucleotide sequence, means that the nucleic acid sequences are linked in a manner that enables regulated expression of the linked structural nucleotide sequence.

In some embodiments, the nucleic acid cassettes contain at least one nucleic acid sequence/s of interest, e.g., an antibody of interest, or any fragments thereof. In other embodiments, the nucleic acid cassette may contain one or more genetic elements e.g. expression control sequences and at least one nucleic acid sequence/s of interest. In some embodiments, the nucleic acid cassettes of the invention may be comprised within a vector. Still further, vectors may comprise one, two, three, four, five or more nucleic acid cassettes. The nucleic acid cassette may be positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. The cassette may have its 3' and 5' ends adapted for ready insertion into a vector, e.g., it may possess restriction endonuclease sites at each end. In some specific embodiments, the target genomic sequence within the IgH locus may be located downstream to the J region of the variable domain of the heavy chain. In yet some other optional embodiments, the target genomic sequence targeted by the cassette of the invention, may be located upstream of the CSR of said heavy chain. Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR of the heavy chain of the BCR. In yet some further embodiments, the target genomic sequence targeted by the cassette of the invention, may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain. It should be understood that in some embodiments, the insertion of the sequence of interest to the target site must retain, at least in part, the class switch recombination mediated by the CSR region, and optionally, at least part of the enhancer activity, specifically, as indicated in connection with other aspects of the invention.

It should be appreciated that all specific locations of the specific target site specified in connection with other aspects of the invention are also applicable in the present aspect. As indicated above, the nucleic acid sequence of interest comprised within the nucleic acid cassette of the invention may further comprise at least one nucleic acid sequence coding for at least one variable domain of at least one VL. In yet some further embodiments, the nucleic acid sequence of interest of the cassette of the invention may further comprise a nucleic acid sequence coding for the constant domain of the immunoglobulin light chain, thereby the nucleic acid sequence of interest encodes the entire light chain. In yet some further embodiments, the sequence of such VL and said IgH may be joined by at least one linker and are coded as a single polypeptide. In some specific embodiments, the antibody encoded by the donor cassette of the invention may be transcribed and translated as a single chain antibody. In yet some further specific embodiments, such single-chain antibody may comprise the transgenic VL, CL (either kappa or lambda), VH and the endogenous CH.

In yet some alternative embodiments, the sequence of the IgL and the VH may be encoded as separate polypeptides. In still some further embodiments, such separated polypeptides may be encoded on a polycistronic vector. Still further, it should be appreciated that the cassettes of the invention may comprise at least one nucleic acid sequence of interest, more specifically, between about one or more, to about 100 or more, specifically, at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more nucleic acid sequences of interest that may be either different or identical sequences.

In yet some further embodiments, the nucleic acid sequence of interest provided by the cassette of the invention may comprise a sequence encoding a signal peptide. In yet some further specific embodiments, such signal peptide may be any one of HGH leader sequence as demonstrated in Example 3 or alternatively, a human IgH variable leader sequence or IgK variable leader sequence as demonstrated by Examples 4, 5 and 12. In some further embodiments, the HGH leader sequence may comprise the nucleic acid sequence as denoted by SEQ ID NO: 37.

In some specific and non-limiting embodiments, the nucleic acid of interest of the cassette of the invention may comprise a nucleic acid sequence encoding at least one variable domain of the heavy chain of an antibody of interest or of any fragment/s or chimera/s thereof, specifically, any antigen-binding fragments thereof. In yet some further embodiments, the nucleic acid sequence of interest of the cassette of the invention may further comprise a sequence encoding a variable light chain of an antibody of interest. In some further embodiments, the nucleic acid sequence of interest may further comprise a sequence encoding the light chain of an antibody of interest.

In yet some further embodiments, such antibody of interest or any antigen-binding fragments thereof, encoded by the nucleic acid sequence of interest of the cassette of the invention, may be any one of full length antibody, antibody fragment, single chain antibody, scFv, bi-specific antibody, tri-specific antibody, BiTE and V-NAR. It should be understood that an antibody of interest or any antigen-binding fragments thereof, encoded by the nucleic acid sequence of interest of the cassette of the invention may be directed to any antigen of interest, specifically any antigen specific for a pathologic disorder. In more specific embodiments, the antibody of interest may be directed against antigens specific for proliferative disorders, specifically, TAAs, or antigens specific for any condition caused or associated with at least one pathogenic agent, specifically, any pathogen, specifically, viral, bacterial, fungal or parasitic pathogen.

In some specific embodiments, the antibody of interest may be an antibody directed against a viral antigen. It should be appreciated that any of the viral pathogens discussed herein after, is applicable in this aspect. In more specific embodiments, the antibody of interest may be directed against any antigen derived from a viral pathogen, for example, any of the viral pathogens disclosed by the invention in connection with other aspects of the invention. In some embodiments, an antigen derived from RSV. In yet some further specific embodiments, the anti-RSV antibody may be the anti-RSV palivizumab antibody.

In some specific embodiments, the nucleic acid sequence of interest in accordance with the cassette of the invention may comprise the full light chain of the anti-RSV antibody palivizumab followed by a 2A peptide sequence and the coding sequence for the variable domain of the palivizumab heavy chain terminating with an SD. In addition, an HGH leader sequence preceded each chain, may be also included as demonstrated by Example 3. In some further embodiments, the HGH leader sequence may comprise the nucleic acid sequence as denoted by SEQ ID NO: 37. In some embodiments, the cassette may comprise the nucleic acid sequence as denoted by SEQ ID NO. 29 (the VL and VH), that comprise the HV as denoted by SEQ ID NO. 30, and the VL as denoted by SEQ ID NO. 150, encoding the light and the heavy chains of palivizumab, respectively.

In yet some further embodiments, the antibody of interest in accordance with some embodiments of the invention may be an antibody directed against any antigen derived from HIV. In yet some further embodiments, the antibody of interest expressed by the engineered BCR of the invention in accordance with some embodiments of the invention may be an HIV antibody. In yet some further specific embodiments the antibody of interest may be the anti-HIV 3BNC117 antibody. In some specific embodiments, the cassette of the invention may comprise a sequence encoding the full light chain of the anti-HIV antibody 3BNC117 followed by a sequence coding for a 2A peptide and the coding sequence for the variable domain of the 3BNC117 heavy chain terminating with an SD. The cassette of the invention may further comprise human IgH or IgK variable leader sequences, as demonstrated by Examples 4, 5 and 12.

In some embodiments, the cassette may comprise the nucleic acid sequence as denoted by SEQ ID NO. 31(the VL and VH), that comprise the HV as denoted by SEQ ID NO. 32, and the VL as denoted by SEQ ID NO. 151, encoding the light and the heavy chains of 3BNC117, respectively.

In some specific embodiments, the cassette of the invention may comprise the nucleic acid sequences as denoted by any one of SEQ ID NO. 41, 57 or 68 (CDRs-1 of the heavy chain HCDR-1), SEQ ID NO. 46, 61 or 71 and 115 (HCDRs-2), SEQ ID NO. 51, 64, 65 (HCDRs-3), SEQ ID NO. 38, 54 or 65 (VH-variable heavy chain), SEQ ID NO. 79, 95 or 106 (CDRs-1 of the light chain LCDR-1), SEQ ID NO. 84, 99 or 110 (LCDRs-2), and SEQ ID NO. 89, 103 or 113 (LCDR-3), and SEQ ID NO. 76, 92 or 114 that encode the variable region of the light chain of this antibody (3BNC117).

Still further, the invention further encompasses cassettes comprising the constructs designated ADN171, ADN171XS, ADN221, ADN191 and adn174, that comprise the nucleic acid sequence as denoted by any one of SEQ ID NO. 146, 147, 148, 149 and 275, respectively. In some embodiments, the cassette of the invention may further comprise at least one genetic element. In some specific embodiments, such genetic element may be at least one of: at least one SA, an IRES, a 2A peptide coding sequence, a promoter or any functional fragments thereof, a polyadenylation site, a signal peptide a stop codon, and a transcription enhancer.

By internal ribosome entry sequences (IRES) sequence is meant, a nucleotide sequence that allows for translation initiation in an end-independent manner, as part of the protein synthesis. IRES are able to recruit the eukaryotic ribosome to the mRNA and to provide two separate places where a ribosome may initiate translation on a single mRNA. IRES elements enable to create multigene, or polycistronic, messages since they are able to bypass the ribosome scanning model of 5' methylated Cap dependent translation and begin translation at internal sites. Multiple open reading frames can be transcribed together, each separated by an IRES, creating polycistronic messages. By virtue of the IRES element, each open reading frame is accessible to ribosomes for efficient translation.

By an "2A peptide sequence", it is meant a nucleotide sequence that allows for the initiation of protein translation in the middle of a messenger RNA (mRNA) sequence. More specifically, a 2A peptide sequence or a CHYSEL site causes a eukaryotic ribosome to release the growing polypeptide chain, but continue translating, thereby giving rise to two separate polypeptides from a single translating ribosome. An expression cassette using a 2A peptide may be therefore used for two or more nucleic acid sequences of interest. In some embodiments, this sequence may be used to separate the coding region of two or more polypeptides encoded by two or more nucleic acid sequences of interest. As a non-limiting example, the sequence encoding the 2A peptide may be between a first coding region and a second coding region. In other embodiments, the 2A peptide may be used in the polynucleotides of the present invention to produce two, three, four, five, six, seven, eight, nine, ten or more proteins, or any other product of the nucleic acid sequence of interest provided by the invention. In certain embodiments, non-limiting example for 2A-peptide that may be used by the invention may be the Picornaviruse 2A peptide (P2A). In some specific embodiments, the 2A peptide sequence may comprise the nucleic acid sequence as denoted by SEQ ID NO: 18. In some embodiments, a Furin cleavage site coding sequence followed by a glycine serine glycine linker (GSG) coding sequence may be placed before the 2A peptide. In some specific embodiments, the Furin-GSG sequence may comprise the nucleic acid sequence as denoted by SEQ ID NO: 19. As used herein, a "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

In some embodiments, promoters applicable in the present invention may be either inducible or constitutive. In yet some further embodiments, a functional fragment of a promoter applicable in the methods and cassettes of the invention may be a minimal promoter. The term "minimal promoter" includes partial promoter sequences that define the start site of transcription for the linked sequence to be transcribed which by itself is not capable of initiating transcription. Thus, the activity of such a minimal promoter is dependent upon the binding of a transcriptional activator to an operatively linked regulatory sequence, e.g., enhancer. In certain embodiments a minimal promoter may be included in the cassettes of the invention. In some specific embodiment, the minimal promoter may be a variant of IgH mutated minimal promoter. In yet some alternative embodiments, a minimal promoter applicable in the present invention may be an IgK Minimal Promoter. In more specific embodiments such minimal promoter may comprise the nucleic acid sequence as denoted by SEQ ID NO: 20.

A "constitutive promoter" refers to a promoter that allows for continual transcription of the coding sequence or gene under its control. In yet some further embodiments, a promoter suitable in the cassette of the invention may be an inducible promoter. An "inducible promoter" refers to a regulatory region that is operably linked to one or more genes, wherein expression of the gene(s) is increased in the presence of an inducer of said regulatory region. An "inducible promoter" refers to a promoter that initiates increased levels of transcription of the coding sequence or gene under its control in response to a stimulus or an exogenous environmental condition. It should be noted that in some embodiments, the promoter used in some of the cassettes disclosed by the invention is an enhancer dependent (ED) promoter, that initiates transcription only when located in the vicinity of at least one enhancer (in a sufficient distance). It should be appreciated that the promoters suitable for the present invention may be either endogenous or heterologous. The phrase "endogenous promoter" includes a promoter that is naturally associated, e.g., in a wild-type organism, with an endogenous gene. Thus, in some specific embodiments, the cassette of the invention may comprise or operably liked to an endogenous promoter, for example, the endogenous promoter of the Ig heavy chain or the Ig light chain. It should be appreciated that such endogenous promoter may be either ectopically added or may be used in its original endogenous location.

In yet some further embodiments, the cassette of the invention may comprise heterologous promoter. The term "heterologous" includes a promoter from a different source or gene. It should be understood that in some embodiments, a promoter comprised within the nucleic acid cassette of the invention may be located 5' to the nucleic acid sequence of interest. In some embodiments, relevant promoters that may be used by the methods and cassettes of the invention may include but are not limited to CMV promoter, SFFV promoter, EF1alpha promoter, AAT promoter, BgH promoter and any appropriate promoter.

In some embodiments, the HGH and the IGH promoters may be used for the cassettes of the invention. In some specific embodiments, the IGH promoter is used. It should be noted that any known IGH promoted may be used or any variants and mutants thereof. In some non-limiting embodiments, a mutated IGH promoter is used. In more particular embodiments, such mutated promoter comprises the nucleic acid sequence as denoted by SEQ ID NO. 152.

In yet some further embodiments, the cassettes provided by the invention and by the methods and compositions of the invention may further comprise at least one degron sequence. Degrons are readily understood by the skilled artisan as amino acid sequences that control the stability of the protein of which they are part. In some embodiments, a suitable degron comprised within the nucleic acid cassette of the invention may be constitutive. In yet some further embodiments, the degron may exerts its influence on protein in an inducible manner. In some embodiments, the degron sequence may be located 5' to the nucleic acid sequence of interest. In yet some further embodiments, the nucleic acid cassette provided by the invention and by the methods and compositions of the invention may comprise at least one signal peptide leader. "Signal peptide leader", as used herein, shall mean a peptide chain (of about 3-60 amino acids long) that directs the post-translational transport of a protein to the endoplasmic reticulum and may be cleaved off. In some embodiments, the signal peptide may be located 5' to the nucleic acid sequence of interest. In some further embodiments, the nucleic acid cassette provided by the invention and by the methods and compositions of the invention may comprise at least one mRNA stabilizing sequence. As used herein, a mRNA stabilizing sequence refers to a nucleic acid sequence that enables to extend the life-time of a mRNA strand. Non limiting examples of mRNA stabilizing elements may include Polyadenylation, 3' untranslated regions (3'-UT) such as histone mRNA 3'-terminal stem-loop, AU-rich elements (AUREs), Iron-responsive element and Long-range stem loop of insulin-like growth factor II (IGF II), mRNA cap. In some embodiments, the mRNA stabilizing sequence may be located 3' to the nucleic acid sequence of interest. In yet some further embodiments, the cassette provided by the invention and by the methods and compositions of the invention may comprise at least one stop codon. A stop codon (or termination codon) is a nucleotide triplet within messenger RNA that signals a termination of translation into proteins. Stop codons signal the termination of this process by binding release factors, which cause the ribosomal subunits to disassociate, releasing the amino acid chain. There are three different stop codons in RNA; UAG ("amber"), UAA ("ochre"), UGA ("opal"), in DNA; TAG ("amber"), TAA ("ochre"), TGA ("opal" or "umber"). It should be noted that in some embodiments, the stop codon may be located 3' to the nucleic acid sequence of interest. In yet some further embodiments, the cassette provided by the invention and by the methods and compositions of the invention may comprise at least one 3-frame stop codon sequence. More specifically, the cassette may comprise protein translation stop codons in each frame of translation, so that translation from the transcripts of any nucleic acid sequence of interest is halted at the point of insertion. Each translation stop sequence (known henceforth as a "3 frame stop codon sequence") carries stop codons in all 3 frames of translation. In some embodiments, the 3 frame stop codon sequence may be located 5' to the nucleic acid sequence of interest.

Still further, in certain embodiments, the cassette provided by the invention and by the methods and compositions of the invention may comprise a nucleic acid sequence encoding at least one protein stabilizing sequence. A protein stabilizing sequence relates to an amino acid sequence useful for stabilization of otherwise unstable proteins, particularly proteolytically sensitive proteins. The stabilization sequence may include a limited number of amino acids ranging from about ten to about 50 residues. The amino acids is such that the secondary and tertiary structure assumes the form of an outwardly directed, properly aligned hydrophobic face and a positively charged polar face. In some embodiments, the protein stabilizing sequence may be located 5' to the nucleic acid sequence of interest. Still further, in some embodiments, the cassette provided by the invention and by the methods and compositions of the invention may comprise at least one polyadenylation sequence.

Polyadenylation is the addition of a poly(A) tail to a messenger RNA consisting of multiple adenosine monophosphates. In eukaryotes, polyadenylation is part of the process that produces mature messenger RNA (mRNA) for translation. The process of polyadenylation begins as the transcription of a gene terminates. The 3'-most segment of the newly made pre-mRNA is first cleaved off by a set of proteins; these proteins then synthesize the poly(A) tail at the RNA's 3' end.

The polyadenylation signal varies between groups of eukaryotes. Most human polyadenylation sites contain the AAUAAA sequence. In some embodiments, the polyadenylation sequence may be located 3' to the nucleic acid sequence of interest. According to some embodiments of the invention that nucleic acid sequence of interest may be inserted upstream of the endogenous enhancer of the IgH. Still further, in some alternative embodiments, the cassette provided by the invention and by the methods and compositions of the invention may comprise at least one enhancer. A transcription enhancer is a short (50-1500 bp) region of DNA that can be bound by proteins (activators) to increase the likelihood that transcription of a particular gene will occur. These proteins are usually referred to as transcription factors. Enhancers are generally cis-acting, but can also be trans-acting (acting away from the gene) and can be located up to 1 Million bp (1,000,000 bp) away from the gene and can be upstream or downstream from the start site, and either in the forward or backward direction. There are hundreds of thousands of enhancers in the human genome. The invention thus encompasses in some embodiments thereof the use of any suitable enhancer. In some embodiments, the enhancer sequence may be located 3' to the nucleic acid sequence of interest.

The cassette of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette used by the methods of the invention may further comprise targeting elements facilitating the specific recognition and targeted insertion to the target site. Thus, according to some embodiments, the cassette of the invention may be flanked at the 5' and/or 3' thereof by at least one of (i) homology arms, for integration by homologous recombination; and (ii) recognition sites for a site-specific nuclease, a site-specific integrase or a site-specific recombinase. It should be appreciated that as described herein before, the homology arms used by the invention may be universal homology arms.

All elements required for successful targeting and recombination of the nucleic acid sequence of interest included by the cassettes of the invention, are as defined in connection with other aspects of the invention.

In some specific embodiments, the insertion of the nucleic acid sequence of interest of the cassette of the invention, into the target genomic locus may be mediated by any gene editing system, for example, at least one of a site-specific nuclease, a class switch recombination, a site specific integrase, a site-specific recombinase and a RAG-catalyzed recombination.

In some specific embodiments, the targeted insertion of the nucleic acid sequence of interest provided by the cassette of the invention may be mediated by a site-specific nuclease. In more specific embodiments, the site-specific nuclease may be at least one programmable engineered nuclease (PEN). It should be noted that any of the PENs described herein before are also applicable in the present aspect. In some specific embodiments, the targeted insertion of the nucleic acid sequence of interest by the cassette of the invention may be mediated by the CRISPR system. Thus, in some specific embodiments, in addition to the cassette of the invention, the invention further provides at least one of (a) at least one CRISPR/cas protein, or any nucleic acid molecule encoding said Cas protein; and (b) at least one nucleic acid sequence comprising at least one gRNA that targets the insertion of the nucleic acid sequence of interest into a target genomic sequence within the IgH locus, or any nucleic acid sequence encoding said gRNA; or any kit, composition or vehicle comprising at least one of (a) and (b).

A non-limiting example for targeted insertion of the nucleic acid sequence of interest into one optional target site located between about 1 to 800 nucleotides downstream of the fourth segment of the J region of the mouse heavy chain is provided by the invention using the CRISPR/Cas system.

In more specific embodiments, such target site is located between about 350 to 450 nucleotides downstream to the J region, and is designated herein as mH69. In some embodiments, the target site within the IgH, may comprise the nucleic acid sequence as denoted by SEQ ID NO. 33, or SEQ ID NO. 15. Thus, in some embodiments where the CRISPR system is used for insertion, the cassette of the invention may further comprise homology arms that facilitate recognition of the specific Mh69 target site. In some specific and non-limiting embodiments, such homology arms may comprise the nucleic acid sequence as denoted by SEQ ID NO. 34 and 35. In yet some further embodiments, the cassette of the invention may be provided with at least one gRNA that targets the Cas9 to the mH69 site. In more specific embodiments, such gRNA may comprise the nucleic acid sequence as denoted by any one of SEQ ID NO: 16 and 17.

In yet some further alternative embodiments, the targeted insertion of the nucleic acid sequence of interest comprised within the cassette of the invention may be mediated by the class switch recombination. In more specific embodiments, the class witch recombination may be catalyzed by AID. Still further, similarly to the CRISPR/Cas system, when other gene editing systems are used, for example, any integrase or recombinase, as well as the endogenous AID or RAG, the cassette of the invention may further comprise sequences that encode such gene editing proteins (e.g. recombinases), and/or any further element required for performing the insertion of the sequence of interest into the specific target site within the IgH.

In yet some further embodiments, the AID, and/or RAG may be provided endogenously by the target cell (a lymphocyte of the B cell lineage). in such case, the cassette of the invention may further include elements that facilitate the recognition of RAG or AID (demonstrated by Examples 12-13).

The invention provides nucleic acid cassette, and methods, cells, uses and compositions using the cassette. The term "nucleic acid", "nucleic acid sequence", or "polynucleotide" and "nucleic acid molecule" refers to polymers of nucleotides, and includes but is not limited to deoxyribonucleic acid (DNA), ribonucleic acid (RNA), DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included. The terms should also be understood to include, as equivalents, analogs of either RNA or DNA made from nucleotide analogs, and, as applicable to the embodiment being described, single-stranded (such as sense or antisense) and double-stranded polynucleotides. Preparation of nucleic acids is well known in the art. Still further, it should be understood that the invention encompasses as additional aspects thereof any vector or vehicle that comprise any of the cassettes described by the invention.

Still further, in some embodiments, the cassette used by the invention may be comprised within a nucleic acid vector. In more specific embodiments, such vector may be any one of a viral vector, a non-viral vector and a naked DNA vector.

Vectors, as used herein, are nucleic acid molecules of particular sequence can be incorporated into a vehicle that is then introduced into a host cell, thereby producing a transformed host cell. A vector may include nucleic acid sequences that permit it to replicate in a host cell, such as an origin of replication. A vector may also include one or more selectable marker genes and other genetic elements known in the art, including promoter elements that direct nucleic acid expression. Many vectors, e.g. plasmids, cosmids, minicircles, phage, viruses, etc., useful for transferring nucleic acids into target cells may be applicable in the present invention. The vectors comprising the nucleic acid (s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as AAV, MMLV, HIV-1, ALV, etc. Vectors may be provided directly to the subject cells. In other words, the cells are contacted with vectors comprising the cassettes of the invention that comprise the nucleic acid sequence of interest such that the vectors are taken up by the cells. Methods for contacting cells with nucleic acid vectors that are plasmids, such as electroporation, calcium chloride transfection, and lipofection, are well known in the art. DNA can be introduced as naked nucleic acid, as nucleic acid complexed with an agent such as a liposome or poloxamer, or can be delivered by viruses (e.g., adenovirus, AAV). More specifically, in some embodiments, the vector may be a viral vector. In yet some particular embodiments, such viral vector may be any one of recombinant adeno associated vectors (rAAV), single stranded AAV (ssAAV), self-complementary rAAV (scAAV), Simian vacuolating virus 40 (SV40) vector, Adenovirus vector, helper-dependent Adenoviral vector, retroviral vector and lentiviral vector. As indicated above, in some embodiments, viral vectors may be applicable in the present invention. The term "viral vector" refers to a replication competent or replication-deficient viral particle which are capable of transferring nucleic acid molecules into a host. The term "virus" refers to any of the obligate intracellular parasites having no protein-synthesizing or energy-generating mechanism. The viral genome may be RNA or DNA contained with a coated structure of protein of a lipid membrane. Examples of viruses useful in the practice of the present invention include baculoviridiae, parvoviridiae, picornoviridiae, herepesviridiae, poxviridiae, adenoviridiae, picotmaviridiae. The term recombinant virus includes chimeric (or even multimeric) viruses, i.e. vectors constructed using complementary coding sequences from more than one viral subtype.

In some embodiments, the cassette of the invention may be comprised within an Adeno-associated virus (AAV). The term "adenovirus" is synonymous with the term "adenoviral vector". AAV is a single-stranded DNA virus with a small (~20 nm) protein capsule that belongs to the family of parvoviridae, and specifically refers to viruses of the genus adenoviridiae. The term adenoviridiae refers collectively to animal adenoviruses of the genus mastadenovirus including but not limited to human, bovine, ovine, equine, canine, porcine, murine and simian adenovirus subgenera. In particular, human adenoviruses includes the A-F subgenera as well as the individual serotypes thereof the individual serotypes and A-F subgenera including but not limited to human adenovirus types 1, 2, 3, 4, 4a, 5, 6, 7, 8, 9, 10, 11 (AdllA and Ad IIP), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Due to its inability to replicate in the absence of helpervirus coinfections (typically Adenovirus or Herpesvirus infections) AAV is often referred to as dependovirus. AAV infections produce only mild immune responses and are considered to be nonpathogenic, a fact that is also reflected by lowered biosafety level requirements for the work with recombinant AAVs (rAAV) compared to other popular viral vector systems. Due to its low immunogenicity and the absence of cytotoxic responses AAV-based expression systems offer the possibility to express genes of interest for months in quiescent cells. Production systems for rAAV vectors typically consist of a DNA-based vector containing a transgene expression cassette, which is flanked by inverted terminal repeats. Construct sizes are limited to approximately 4.7-5.0 kb, which corresponds to the length of the wild-type AAV genome. rAAVs are produced in cell lines. The expression vector is co-transfected with a helper plasmid that mediates expression of the AAV rep genes which are important for virus replication and cap genes that encode the proteins forming the capsid.

Recombinant adeno-associated viral vectors can transduce dividing and non-dividing cells, and different rAAV serotypes may transduce diverse cell types. These single-stranded DNA viral vectors have high transduction rates and have a unique property of stimulating endogenous Homologous Recombination without causing double strand DNA breaks in the host genome.

It should be appreciated that many intermediate steps of the wild-type infection cycle of AAV depend on specific interactions of the capsid proteins with the infected cell. These interactions are crucial determinants of efficient transduction and expression of genes of interest when rAAV is used as gene delivery tool. Indeed, significant differences in transduction efficacy of various serotypes for particular tissues and cell types have been described. Thus, in some embodiments AAV serotype 6 may be suitable for the methods of the invention. In yet some further embodiments, AAV serotype 8 may be suitable for the methods of the invention. In some embodiments, the AAV serotype 6 may be encoded by the nucleic acid sequence as denoted by GenBank accession number AF028704.1.

In some specific embodiments, the AAV serotype 6 may be encoded by the nucleic acids sequence as denoted by SEQ ID NO: 143. In some embodiments, the AAV serotype 8 may be encoded by the nucleic acid sequence as denoted by GenBank accession number NC_006261.1. In some specific embodiments, the AAV serotype 8 may be encoded by the nucleic acids sequence as denoted by SEQ ID NO: 144.

It is believed that a rate-limiting step for the AAV-mediated expression of transgenes is the formation of double-stranded DNA. Recent reports demonstrated the usage of rAAV constructs with a self-complementing structure (scAAV) in which the two halves of the single-stranded AAV genome can form an intra-molecular double-strand. This approach reduces the effective genome size usable for gene delivery to about 2.3 kB, but leads to significantly shortened onsets of expression in comparison with conventional single-stranded AAV expression constructs (ssAAV). Thus, in some embodiments, ssAAV may be applicable as a viral vector by the methods of the invention.

In yet some further embodiments, HDAd vectors may be suitable for the methods of the invention.

The Helper-Dependent Adenoviral (HDAd) vectors HDAds have innovative features including the complete absence of viral coding sequences and the ability to mediate high level transgene expression with negligible chronic toxicity. HDAds are constructed by removing all viral sequences from the adenoviral vector genome except the packaging sequence and inverted terminal repeats, thereby eliminating the issue of residual viral gene expression associated with early generation adenoviral vectors. HDAds can mediate high efficiency transduction, do not integrate in the host genome, and have a large cloning capacity of up to 37 kb, which allows for the delivery of multiple transgenes or entire genomic loci, or large cis-acting elements to enhance or regulate tissue-specific transgene expression. One of the most attractive features of HDAd vectors is the long term expression of the transgene. Still further, in some embodiments, SV40 may be used as a suitable vector by the methods of the invention. SV40 vectors (SV40) are vectors originating from modifications brought to Simian virus-40 an icosahedral papovavirus. Recombinant SV40 vectors are good candidates for gene transfer, as they display some unique features: SV40 is a well-known virus, non-replicative vectors are easy-to-make, and can be produced in titers of 10(12) IU/ml. They also efficiently transduce both resting and dividing cells, deliver persistent transgene expression to a wide range of cell types, and are non-immunogenic. Present disadvantages of rSV40 vectors for gene therapy are a small cloning capacity and the possible risks related to random integration of the viral genome into the host genome. In certain embodiments, an appropriate vector that may be used by the invention may be a retroviral vector. A retroviral vector consists of proviral sequences that can accommodate the gene of interest, to allow incorporation of both into the target cells. The vector may also contain viral and cellular gene promoters, to enhance expression of the gene of interest in the target cells. Retroviral vectors stably integrate into the dividing target cell genome so that the introduced gene is passed on and expressed in all daughter cells. They contain a reverse transcriptase that allows integration into the host genome. In yet some alternative embodiments, lentiviral vectors may be used in the present invention. Lentiviral vectors are derived from lentiviruses which are a subclass of Retroviruses. Commonly used retroviral vectors are "defective", i.e. unable to produce viral proteins required for productive infection. Rather, replication of the vector requires growth in a packaging cell line. To generate viral particles comprising the cassette with the nucleic acids sequence of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the cassette of the invention that contains the nucleic acids sequence of interest into packaging cell lines and of collecting the viral particles that are generated by the packaging lines are well known in the art. Nonviral vectors, in accordance with the invention, refer to all the physical and chemical systems except viral systems and generally include either chemical methods, such as cationic liposomes and polymers, or physical methods, such as gene gun, electroporation, particle bombardment, ultrasound utilization, and magnetofection. Efficiency of this system is less than viral systems in gene transduction, but their cost-effectiveness, availability, and more importantly reduced induction of immune system and no limitation in size of transgenic DNA compared with viral system have made them attractive also for gene delivery.

For example, physical methods applied for in vitro and in vivo gene delivery are based on making transient penetration in cell membrane by mechanical, electrical, ultrasonic, hydrodynamic, or laser-based energy so that DNA entrance into the targeted cells is facilitated.

In more specific embodiments, the vector may be a naked DNA vector. More specifically, such vector may be for example, a plasmid, minicircle or linear DNA. Naked DNA alone may facilitate transfer of a gene (2-19 kb) into skin, thymus, cardiac muscle, and especially skeletal muscle and liver cells when directly injected. It enables also long-term expression. Although naked DNA injection is a safe and simple method, its efficiency for gene delivery is quite low.

Minicircles are modified plasmid in which a bacterial origin of replication (ori) was removed, and therefore they cannot replicate in bacteria. Linear DNA or Doggybone™ are double-stranded, linear DNA construct that solely encodes an antigen expression cassette, comprising antigen, promoter, polyA tail and telomeric ends. It should be appreciated that all DNA vectors disclosed herein, may be also applicable for all cassettes used in the methods, cassettes and compositions of the invention, as described herein. Still further, it must be appreciated that the invention further provides any vectors or vehicles that comprise any of the nucleic acid cassettes disclosed by the invention, as well as any host cell expressing the nucleic acid cassettes disclosed by the invention.

It should be further appreciated that the invention provides any BCR or antibody encoded by any of the cassettes of the invention.

Still further, the invention also provides any system comprising (a) at least one cassette as defined by the invention; and (b) at least one reagent required for gene editing and insertion of the sequence of interest (the engineered BCR) encoded by the cassette of the invention into the target locus. For example, any integrase, recombinase, site specific nuclease as discussed herein or any additional factor or any nucleic acid sequence encoding the same. A non-limiting example for such system may comprise (a) any of the cassettes of the invention; and (b) at least one CRSPR/Cas protein and at least one gRNA or any nucleic acid sequence encoding at least one of said Cas and gRNA.

Another aspect of the invention relates to a host cell transduced or transfected with at least one nucleic acid cassette comprising at least one nucleic acid sequence of interest. More specifically, the sequence of interest may comprise a nucleic acid sequence coding for at least one variable domain of an immunoglobulin heavy chain and a splice donor site. In some embodiments, the VH is followed by the SD site. It should be noted that in some embodiments the nucleic acid cassette used for the host cell of the invention targets the insertion of the nucleic acid sequence of interest into a target genomic sequence within the IgH locus. In more specific embodiments, the target sequence is located upstream of at least one splice acceptor site of the constant domain of said heavy chain of the BCR in the cell of the invention or with any vector comprising said cassette. In some embodiments, the nucleic acid sequence of interest comprised within the cassette of the host cell of the invention may comprise at least one SA. In yet some further embodiments, the SA may be located upstream to the VH. In some embodiments, the host cell of the invention is transduced or transfected with any of the nucleic acid cassettes or systems or with any system or composition comprising said cassette, as also provided and defined by the invention. In some specific embodiments, the cassette of the invention introduces the nucleic acid of interest in a target locus of a mammalian cell that is considered herein as a host cell. The term "host cell" includes a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell". As used herein, a cell has been "transformed" or "transfected" by exogenous or heterologous DNA, e.g. the cassette of the invention, when such DNA has been introduced inside the cell. The transforming DNA may be integrated (covalently linked) into the genome of the cell.

With respect to the present invention, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. It should be appreciated that in some embodiments, the host cells of the invention may be any engineered B cells of the invention or any cell population comprising, at least in part, the B cells of the invention. Still further, the invention further encompasses any population of cells comprising at least 5%, 10%, 15%, 20%, 25%, 30%, 35%, 40%, 45%, 50%, 55%, 60%, 65%, 70%, 75%, 80%, 85%, 90%, 95%, 99.9% or more, specifically, 100%) specifically, 10%, 15%, 20%, 25%, 30%, 35%, 40%, 45%, 50%, 55%, 60%, 65%, 70%, 75%, 80%, 85%, 90%, 95%, 99.9% or more, specifically, 100% of the host cells of the invention.

In yet another aspect, the invention provides a pharmaceutical composition comprising at least one nucleic acid cassette, any BCR encoded by said cassette, or any vector or cell comprising said cassette. Still further, the composition of the invention may comprise any system comprising the cassette of the invention or any BCR or engineered B cell provided by the invention. In some embodiments, the nucleic acid cassette of the composition of the invention may comprise at least one nucleic acid sequence of interest. In some specific embodiments, the nucleic acid sequence of interest comprised within the cassette used for the composition of the invention may comprise a nucleic acid sequence coding for at least one variable domain of at least one immunoglobulin heavy chain and a splice donor site. It should be noted that in some embodiments the nucleic acid cassette used for the composition of the invention targets the insertion of the nucleic acid sequence of interest into a target genomic sequence within the IgH locus. In more specific embodiments, the target sequence is located upstream of at least one splice acceptor site of the constant domain of said heavy chain of said BCR. It should be noted that optionally, the composition of the invention may further comprise at least one of pharmaceutically acceptable carrier/s, diluent/s, excipient/s and additive/s.

In some specific embodiments, the composition of the invention may comprise a therapeutically effective amount of any of the nucleic acid cassettes disclosed by the invention, or with any vector comprising said cassette. In yet some further embodiments, the composition of the invention may comprise any of the engineered B cells provided by the invention as described herein.

Still further, the composition of the invention may comprise as an active ingredient any engineered BCR as described herein as well as any antibodies derived therefrom.

As indicated above, in some optional embodiments, the compositions of the invention may further comprise at least one of pharmaceutically acceptable carrier/s, diluent/s, excipient/s and additive/s.

The compositions of the invention may comprise an effective amount of the cassette of the invention or of any vector thereof or of any cell comprising the same, or any BCR as described by the invention, or any antibody derived therefrom. The term "effective amount" relates to the amount of an active agent present in a composition, specifically, the cassette of the invention as described herein that is needed to provide a desired level of active agent in the bloodstream or at the site of action in an individual (e.g., the thymus or bone marrow) to be treated to give an anticipated physiological response when such composition is administered. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein. An "effective amount" of a the cassette of the invention can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

The pharmaceutical compositions of the invention can be administered and dosed by the methods of the invention, in accordance with good medical practice, systemically, for example by parenteral, e.g. intrathymic, into the bone marrow and intravenous. It should be noted however that the invention may further encompass additional administration modes. In other examples, the pharmaceutical composition can be introduced to a site by any suitable route including intraperitoneal, subcutaneous, transcutaneous, topical, intramuscular, intraarticular, subconjunctival, or mucosal, e.g. oral, intranasal, or intraocular administration.

Local administration to the area in need of treatment may be achieved by, for example, by local infusion during surgery, topical application, direct injection into the specific organ (bone marrow, spleen, lymph nodes), etc. More specifically, the compositions used in any of the methods of the invention, described herein before, may be adapted for administration by parenteral, intraperitoneal, transdermal, oral (including buccal or sublingual), rectal, topical (including buccal or sublingual), vaginal, intranasal and any other appropriate routes. Such formulations may be prepared by any method known in the art of pharmacy, for example by bringing into association the active ingredient with the carrier(s) or excipient(s).

More specifically, pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general formulations are prepared by uniformly and intimately bringing into association the active ingredients, specifically, the cassette, BCR, cells and systems of the invention with liquid carriers or finely divided solid carriers or both, and then, if necessary, shaping the product. The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations. It should be understood that in addition to the ingredients particularly mentioned above, the formulations may also include other agents conventional in the art having regard to the type of formulation in question. Still further, pharmaceutical preparations are compositions that include one or more targeting cassette present in a pharmaceutically acceptable vehicle.

"Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle", when referred to the compositions in the present aspect, refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of the BCR engineered targeting cassette, the BCR, cells and systems of the invention, can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

Still further, the composition/s of the invention and any components thereof may be applied as a single daily dose or multiple daily doses, preferably, every 1 to 7 days. It is specifically contemplated that such application may be carried out once, twice, thrice, four times, five times or six times daily, or may be performed once daily, once every 2 days, once every 3 days, once every 4 days, once every 5 days, once every 6 days, once every week, two weeks, three weeks, four weeks or even a month. The application of the combination/s, composition/s and kit/s of the invention or of any component thereof may last up to a day, two days, three days, four days, five days, six days, a week, two weeks, three weeks, four weeks, a month, two months three months or even more. Specifically, application may last from one day to one month. Most specifically, application may last from one day to 7 days.

In yet another aspect, the invention provides a method for treating, preventing, ameliorating, inhibiting or delaying the onset of a pathologic disorder in a mammalian subject. More specifically, the therapeutic method of the invention may comprise the step of administering to the treated subject an effective amount of at least one of (a) nucleic acid cassette; (b) a vector comprising said nucleic acid cassette; and (c) a cell transduced or transfected with the nucleic acid cassette or with any vector comprising said cassette. The subject may be according to some embodiments, administered with any composition comprising (a), (b), (c) or any combinations thereof. In yet some further embodiments, the subject may be administered with any of the engineered BCRs provided by the invention. In more specific embodiments, the cassette used by the method of the invention may comprise at least one nucleic acid sequence of interest comprising a nucleic acid sequence coding for at least one variable domain of an immunoglobulin heavy chain and at least one splice donor site. In some specific embodiments, the VH sequence is followed by the SD site. More specifically, the nucleic acid cassette used by the methods of the invention may target the insertion of the nucleic acid sequence of interest into a target genomic sequence within the IgH locus, upstream of at least one splice acceptor site of a constant domain of an immunoglobulin heavy chain in a mammalian cell of the B cell lineage. In some specific embodiments, the target genomic sequence within the IgH locus may be located downstream to the J region of the variable domain of the heavy chain. In yet some other optional embodiments, the target genomic sequence may be located upstream of the CSR of said heavy chain. Thus, in some embodiments, the target genomic sequence within the IgH locus may be located downstream to the J region and upstream of at least one splice acceptor site of the constant domain of the heavy chain of the BCR. In yet some further specific embodiments, the target genomic sequence within the IgH locus may be located downstream to the J region of the variable domain of the heavy chain and upstream of the CSR of the heavy chain of the BCR in at least one B cell of the treated subject. In yet some further embodiments, the target genomic sequence may be located downstream to the last segment of the J region of the variable domain and upstream to the enhancer region of the heavy chain. In yet some alternative embodiments, the target site for inserting the nucleic acid sequence of interest may be located between the enhancer and the CSR regions, specifically, downstream to the enhancer region and upstream to the CSR of the heavy chain. In some embodiments, the nucleic acid sequence of interest comprised within the cassette used by the methods of the invention may comprise at least one SA. In yet some further embodiments, the SA may be located upstream to the VH.

It should be understood that in some embodiments, the insertion of the sequence of interest to the target site must retain, at least in part, the class switch recombination mediated by the CSR region, and optionally, at least part of the enhancer activity. It should be appreciated that all specific locations of the specific target site specified in connection with other aspects of the invention are also applicable in the present aspect.

As indicated above, the nucleic acid sequence of interest comprised within the nucleic acid cassette used by the methods of the invention may further comprise at least one nucleic acid sequence coding for at least one VL. In yet some further embodiments, the nucleic acid sequence of interest provided by the methods of the invention may further comprise a nucleic acid sequence coding for the constant domain of the immunoglobulin light chain, thereby the entire light chain is encoded by the nucleic acid sequence of interest.

It should be noted that in some embodiments, the immunoglobulin light chain encoded by the nucleic acid sequence of interest provided by the methods of the invention may successfully pair with the heavy chain.

In yet some further embodiments, to ensure correct pairing of both transgenic VL and VH, an additional step of reducing, attenuating, decreasing or ablating the expression of the endogenous light chain (either kappa or lambda) may be further performed, as discussed in connection with other aspects of the invention. In yet some additional optional embodiments, the method of the invention may further comprise the step of reducing, attenuating, decreasing or ablating the expression of the endogenous heavy chain. In more specific embodiments, such reduction, attenuation, decrease or ablation of at least one of the endogenous IgL, IgK or the other IgH, may involve the use of nucleic acid based attenuators (e.g. shRNA), or nucleases (e.g., CRISPR/Cas systems). In yet some further embodiments, the nucleic acid sequence of interest provided by the cassette used by the methods of the invention may comprise a sequence encoding a signal peptide. In yet some further specific embodiments, such signal peptide may be any one of HGH leader sequence as demonstrated in Example 3 or alternatively, a human IgH or IgK variable leader sequence as demonstrated by Example 4. In some further embodiments, the HGH leader sequence may comprise the nucleic acid sequence as denoted by SEQ ID NO: 37. In some specific and non-limiting embodiments, the nucleic acid of interest may comprise a nucleic acid sequence encoding at least one variable domain of the heavy chain of an antibody of interest or of any fragment/s or chimera/s thereof, specifically, any antigen-binding fragments thereof. In yet some further embodiments, the nucleic acid sequence of interest may further comprise a sequence encoding a variable light chain of an antibody of interest. In some further embodiments, the nucleic acid sequence of interest may further comprise a sequence encoding the light chain of an antibody of interest. In some specific embodiments, the exogenous at least one VL (optionally with at least one LC) and the at least one VH provided by the donor cassette of the invention, with the endogenous CH, may be transcribed and translated as a single chain antibody. In yet some further embodiments, such antibody of interest or any antigen-binding fragments thereof, encoded by the nucleic acid sequence of interest in accordance with the method of the invention, may be any one of full length antibody, antibody fragment, single chain antibody, scFv, bi-specific antibody, tri-specific antibody, BiTE and V-NAR.

It should be understood that an antibody of interest or any antigen-binding fragments thereof, encoded by the nucleic acid sequence of interest, or by the cassette used by the methods in accordance with the invention may be directed to any antigen of interest, specifically any antigen specific for a pathologic disorder, specifically, the same pathologic disorder of the treated subject.

In more specific embodiments, the antibody of interest may be directed against antigens specific for proliferative disorders, specifically, TAAs, or antigens specific for any pathogen, specifically, viral, fungal, parasitic or bacterial pathogen, or directed against any antigen connected to CVCs, or any antigen associated with any metabolic disorder. In some specific embodiments, the antibody of interest encoded by the nucleic acid sequence of interest of the cassette used by the methods of the invention, may be at least one antibody directed against at least one of a viral antigen and a TAA.

In such case, the methods of the invention may be applicable for treating infectious diseases caused by a pathogen, for example, a viral pathogen. Alternatively, the methods of the invention may be applicable for treating proliferative disorders, such as cancer, as specified herein after.

In some specific embodiments, the antibody of interest may be an antibody directed against a viral antigen. It should be appreciated that any of the viral pathogens discussed herein after, is applicable in the present aspect. In more specific embodiments, the antibody of interest may be directed against any antigen derived from any viral pathogen as indicated herein before. In some specific embodiments, such viral antigen may be an antigen specific for RSV. In yet some further specific embodiments, the anti-RSV antibody may be the anti-RSV palivizumab antibody.

In yet some further embodiments, the antibody of interest in accordance with some embodiments of the invention may be an antibody directed against any antigen derived from HIV. In yet some further embodiments, the antibody of interest expressed by the engineered BCR of the invention in accordance with some embodiments of the invention may be an HIV antibody. In yet some further specific embodiments the antibody of interest may be the anti-HIV 3BNC117 antibody.

Still further, in some embodiments, the cassette used by the methods of the invention may further comprise at least one genetic element. In some specific embodiments, such genetic element may be at least one of at least one SA, an IRES, a 2A peptide coding sequence, a promoter or any functional fragments thereof, a polyadenylation site, a signal peptide a stop codon, and a transcription enhancer. As indicated above, the cassette of the invention enables targeted insertion of a nucleic acid sequence of interest into a specific genomic sequence within the IgH locus. In more specific embodiments, the target sequence is located upstream of at least one splice acceptor site of the constant domain of the heavy chain of the BCR. It should be therefore appreciated that in some embodiments, the cassette used by the methods of the invention may further comprise targeting elements facilitating the specific recognition and targeted insertion to the target site. Thus, according to some embodiments, the cassette used by the therapeutic methods of the invention may be flanked on at the 5' and/or 3' thereof by at least one of (i) homology arms, for integration by homologous recombination; and (ii) recognition sites for a site-specific nuclease, a site-specific integrase or a site-specific recombinase. It should be appreciated that as described herein before, the homology arms used by the invention may be universal homology arms.

In some specific embodiments, the insertion of the nucleic acid sequence of interest of the cassette used by the methods of the invention, into the target genomic locus may be mediated by any gene editing system, for example, at least one of a site-specific nuclease, a class switch recombination, a site specific integrase, a site-specific recombinase and a RAG-catalyzed recombination.

In some specific embodiments, the targeted insertion of the nucleic acid sequence of interest may be mediated by the CRISPR system. Thus, in some specific embodiments, the method of the invention may further comprise the step of administering to the treated subject, or alternatively, ex vivo contacting a cell that will be administered to the subject with at least one of (a) at least one CRISPR/cas protein, or any nucleic acid molecule encoding said Cas protein; and (b) at least one nucleic acid sequence comprising at least one gRNA that targets the insertion of the nucleic acid sequence of interest into a target genomic sequence within the IgH locus, or any nucleic acid sequence encoding said gRNA; or any kit, composition or vehicle comprising at least one of (a) and (b). Thus, in some embodiments, when the CRISPR/Cas system is used as a gene editing tool, and engineering of a B cell is performed in vivo in the treated subject, the method of the invention comprises the step of administering the subject with the cassette of the invention or with any vector or vehicle thereof and in addition, administering, either concomitantly or simultaneously, the subject with the components of the CRISPR/Cas system as specified above.

It should be noted that any of the cassettes of vectors thereof disclosed by the invention or any cells provided by the invention may be applicable in the therapeutic method discussed herein. As shown in Example 13, targeted insertion of the nucleic acid sequence of interest into the IgH locus, may be facilitated using the class switch recombination process. Thus, in yet some further embodiments, the targeted insertion of the nucleic acid sequence of interest may be mediated by the class switch recombination. In more specific embodiments, the class witch recombination may be catalyzed by AID. According to these embodiments, for activating class switch, the method of the invention may further comprise the step of activating B cells by reducing IL-4 levels, for example, by applying an effective amount of LPS. Still further, in some specific embodiments, the nucleic acid sequence coding for at least one variable domain of at least one of an immunoglobulin heavy chain and an immunoglobulin light chain, used by the methods of the invention may further comprise at least one exogenous hotspot motif/s for somatic hypermutation/s. More specifically, the somatic hyper mutation/s retain or minimally change the protein translated from said nucleic acid sequence.

In more specific embodiments, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand. In some specific embodiments, where manipulation of the BCR is performed in vivo, the treated subject may be administered with a nucleic acid vector comprising the cassette of the invention. Such vector may be any one of a viral vector, a non-viral vector and a naked DNA vector. In more specific embodiments, the cassette used by the invention may be comprised within a viral vector. Non-limiting examples for such viral vectors include any one of rAAV, ssAAV, scAAV, SV40 vector, Adeno virus vector, helper-dependent Adeno viral vector, retroviral vector and lentiviral vector. In yet some further embodiments, the cassette used by the methods of the invention may be comprised within a non-viral vector, such vector may be any one of plasmid, minicircle and linear DNA. In some further embodiments, the cassette used by the methods of the invention may be comprised within a naked DNA vector, in some embodiments, such vector may be any one of plasmid, minicircle and linear DNA.

As indicated above, the therapeutic method of the invention may involves an in vivo engineering of the BCR in a cell of the B cell lineage of the treated subject. In such cases, the nucleic acid cassette of the invention or any vector comprising the cassette may be administered to the treated subject by at least one of systemic injection, bone marrow injection, splenic injection and lymph node injection.

In yet some alternative embodiments, engineering the BCR may be performed ex vivo, and the treated subject is administered with an engineered cell of the B lineage, specifically, an engineered B cell. More specifically, in some embodiments, the treated subject may be administered with at least one cell transduced or transfected with the nucleic acid cassette of the invention or any vector or vehicle comprising the cassette. Thus, the method of the invention also encompasses the option that the targeted insertion of the nucleic acid sequence of interest to cells of the subject may be performed ex vivo, to cells of the subjects (cells of autologous source) or alternatively, to cells of allogeneic source or of a syngeneic source. These cells may be than administered to the subject by adoptive transfer. The term "adoptive transfer" as herein defined applies to all the therapies that consist of the transfer of components of the immune system, specifically cells that are already capable of mounting a specific immune response. In such option, the targeted insertion of the nucleic acid sequence of interest is performed in cells of an autologous or allogeneic source, that are then administered to the subject, specifically, by adoptive transfer.

In some embodiments, the cells transduced or transfected with the nucleic acid cassette provided by the invention may be cells of an autologous source. The term "autologous" when relating to the source of cells, refers to cells derived or transferred from the same subject that is to be treated by the method of the invention. The term "allogenic" when relating to the source of cells, refers to cells derived or transferred from a different subject, referred to herein as a donor, of the same species.

It should be noted that both, the bone marrow injection as well as systemic injection (e.g., intravenous IV), may be specifically suitable for targeting B cells by the nucleic acid cassette of the invention. It is to be understood that other localized injection are also suitable, for example intra-lymph node injection or intra-spleen injection, and may be used to deliver a vector to the lymph node and the spleen, respectively. More specifically, in some embodiments, the subcutaneous route (SC) may be generally considered to be most appropriate for targeting to the lymph nodes.

Conventional SC formulations are such as Aqueous solutions, Oily solutions, Suspensions and Simple emulsions. Specific technologies associated with SC delivery are via Modified release SC formulations such as Biodegradable in situ implants, Biodegradable microspheres, Osmotically controlled implants, Liposomes, Lipid nanoparticles. Relevant commercially available products may include but are not limited to Alzamer® Depot™, DUROS®, Stealthl (ALZA Corporation), Atrigel® (Atrix Laboratories), SABER® (Durect Corp),ProLease (Alkermes Inc), Depo-Foam® (SkyePharma Inc),SupraVail™ (Phares Drug Delivery AG).

Still further, the method of the invention may further comprise in some specific and optional embodiments, the step of activating the TLR in the subject. More specifically, especially a subject administered by the cassette of the invention or any system or composition comprising the same, where the manipulation of the B cells occurs in vivo.

In some embodiments, the method of the invention is directed at treating a pathologic disorder. In more specific embodiments, such disorder may be at least one of a proliferative disorder, an inflammatory disorder, an infectious disease caused by a pathogen, an autoimmune-disease as well as CVDs and metabolic conditions. Thus, in some specific embodiments, the subject treated by the method of the invention may be a subject suffering of an immune-related disorder. An "Immune-related disorder" or "Immune-mediated disorder", as used herein encompasses any condition that is associated with the immune system of a subject, more specifically through inhibition of the immune system, or that can be treated, prevented or ameliorated by reducing degradation of a certain component of the immune response in a subject, such as the adaptive or innate immune response.

An immune-related disorder may include infectious condition (e.g., by a pathogen, specifically, viral, bacterial or fungal infections), inflammatory disease, autoimmune disorders, metabolic disorders and a proliferative disorders, specifically, cancer. In some specific embodiments wherein the immune-related disorder or condition may be a primary or a secondary immunodeficiency.

In some specific embodiments, the methods of the invention may be used for treating proliferative disorders. As used herein to describe the present invention, "proliferative disorder", "cancer", "tumor" and "malignancy" all relate equivalently to a hyperplasia of a tissue or organ. If the tissue is apart of the lymphatic or immune systems, malignant cells may include non-solid tumors of circulating cells.

Malignancies of other tissues or organs may produce solid tumors. In general, the methods of the present invention may be applicable for treatment of a patient suffering from any one of non-solid and solid tumors. Malignancy, as contemplated in the present invention may be any one of carcinomas, melanomas, lymphomas, leukemias, myeloma and sarcomas. Carcinoma as used herein, refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges. Melanoma as used herein, is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes. Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. The epithelium lines the surface of structures throughout the body, and is the origin of cancers in the breast, colon, and pancreas.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Further malignancies that may find utility in the present invention can comprise but are not limited to hematological malignancies (including lymphoma, leukemia and myeloproliferative disorders, as described above), hypoplastic and aplastic anemia (both virally induced and idiopathic), myelodysplastic syndromes, all types of paraneoplastic syndromes (both immune mediated and idiopathic) and solid tumors (including GI tract, colon, lung, liver, breast, prostate, pancreas and Kaposi's sarcoma. The invention may be applicable as well for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma. It should be appreciated that for treating cancer, the cassette of the invention or any compositions or methods thereof may facilitate targeted insertion or antibody or receptor as described herein before, that are specifically directed at TAAs. It should be understood that the invention thus encompasses the treatment of any of the malignancies described in this context, specifically any malignancies described in connection with associated TAAs as described herein before in connection with other aspects of the invention. In yet some further embodiments, and of particular relevance are patients' populations diagnosed with one of autoimmune disorders, also referred to as disorders of immune tolerance, when the immune system fails to properly distinguish between self and non-self-antigens.

Thus, according to some embodiments, the method of the invention may be used for the treatment of a patient suffering from any autoimmune disorder. In some specific embodiments, the methods of the invention may be used for treating an autoimmune disease such as for example, but not limited to, inflammatory bowel disease (IBD), ulcerative colitis, Crohn's disease, fatty liver disease, Lymphocytic colitis, Ischaemic colitis, Diversion colitis, Behçet's syndrome, Indeterminate colitis, rheumatoid arthritis, systemic lupus erythematosus (SLE), Graft versus Host Disease (GvHD), Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM) and NIDDM, multiple sclerosis (MS), myasthenia gravis, plexus disorders e.g. acute brachial neuritis, polyglandular deficiency syndrome, primary biliary cirrhosis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, arthritis, alopecia areata, polymyalgia rheumatica, Wegener's granulomatosis, Reiter's syndrome, ankylosing spondylitis, pemphigus, bullous pemphigoid, dermatitis herpetiformis, psoriatic arthritis, reactive arthritis, and ankylosing spondylitis, inflammatory arthritis, including juvenile idiopathic arthritis, gout and pseudo gout, as well as arthritis associated with colitis or psoriasis, Pernicious anemia, some types of myopathy and Lyme disease (Late).

In yet some other embodiments, the methods of the invention may be also applicable for treating a subject suffering from an infectious disease. More specifically, such infectious disease may be any pathological disorder caused by a pathogen. As used herein, the term "pathogen" refers to an infectious agent that causes a disease in a subject host. Pathogenic agents include prokaryotic microorganisms, lower eukaryotic microorganisms, complex eukaryotic organisms, viruses, fungi, mycoplasma, prions, parasites, for example, a parasitic protozoan, yeasts or a nematode.

In yet some further embodiments, the methods of the invention may be applicable in boosting the immune response against a pathogen that may be in further specific embodiment, a viral pathogen or a virus. The term "virus" as used herein, refers to obligate intracellular parasites of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. It should be noted that the term "viruses" is used in its broadest sense to include viruses of the families adenoviruses, papovaviruses, herpesviruses: simplex, varicella-zoster, Epstein-Barr (EBV), Cytomegalo virus (CMV), pox viruses: smallpox, vaccinia, hepatitis B (HBV), rhinoviruses, hepatitis A (HBA), poliovirus, respiratory syncytial virus (RSV), Middle East Respiratory Syndrome (MERS), Severe acute respiratory syndrome (SARS), rubella virus, hepatitis C (HBC), arboviruses, rabies virus, influenza viruses A and B, measles virus, mumps virus, human deficiency virus (HIV), HTLV I and II, Dengue virus and Zika virus.

In some further embodiments, the methods of the invention may be applicable for immune-related disorder or condition that may be a pathologic condition caused by at least one pathogen. It should be appreciated that an infectious disease as used herein also encompasses any infectious disease caused by a pathogenic agent, specifically, a pathogen. Pathogenic agents include prokaryotic microorganisms, lower eukaryotic microorganisms, complex eukaryotic organisms, viruses, fungi, prions, parasites, yeasts, toxins and venoms. In yet some other specific embodiments, the methods and composition of the invention may be applicable for treating an infectious disease caused by bacterial pathogens. More specifically, a prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes.* A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum,* are also encompassed by the invention. A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balan-*

*tidium coli, Toxoplasma gondii, Cryptosporidium* or *Leishmania*. More specifically, in certain embodiments the methods and compositions of the invention may be suitable for treating disorders caused by fungal pathogens. The term "fungi" (or a "fungus"), as used herein, refers to a division of eukaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei. It should be noted that "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

As noted above, the present invention also provides for the methods and compositions for the treatment of a pathological disorder caused by "parasitic protozoan", which refers to organisms formerly classified in the Kingdom "protozoa". They include organisms classified in Amoebozoa, Excavata and Chromalveolata. Examples include *Entamoeba histolytica, Plasmodium* (some of which cause malaria), and *Giardia lamblia*. The term parasite includes, but not limited to, infections caused by somatic tapeworms, blood flukes, tissue roundworms, ameba, and *Plasmodium, Trypanosoma, Leishmania,* and *Toxoplasma* species. As used herein, the term "nematode" refers to roundworms. Roundworms have tubular digestive systems with openings at both ends. Some examples of nematodes include, but are not limited to, basal order Monhysterida, the classes Dorylaimea, Enoplea and Secernentea and the "Chromadorea" assemblage.

In yet some further specific embodiments, the present invention provides compositions and methods for use in the treatment, prevention, amelioration or delay the onset of a pathological disorder, wherein said pathological disorder is a result of a prion. As used herein, the term "prion" refers to an infectious agent composed of protein in a misfolded form. Prions are responsible for the transmissible spongiform encephalopathies in a variety of mammals, including bovine spongiform encephalopathy (BSE, also known as "mad cow disease") in cattle and Creutzfeldt-Jakob disease (CJD) in humans. All known prion diseases affect the structure of the brain or other neural tissue and all are currently untreatable and universally fatal. It should be appreciated that an infectious disease as used herein also encompasses any pathologic condition caused by toxins and venoms.

Thus, the methods of the invention may offer a promising therapeutic modality for a variety of innate and acquired immunodeficiencies caused by immunosuppressive treatments (chemo- and radiotherapy), pathogenic infections, cancer and HSCT. More specifically, Immunodeficiency (or immune deficiency) is a state in which the immune system's ability to fight infectious disease and cancer is compromised or entirely absent. Most cases of immunodeficiency are acquired ("secondary") due to extrinsic factors that affect the patient's immune system. Examples of these extrinsic factors include viral infection, specifically, HIV, extremes of age, and environmental factors, such as nutrition. In the clinical setting, the immunosuppression by some drugs, such as steroids, can be either an adverse effect or the intended purpose of the treatment. Examples of such use are in organ transplant surgery as an anti-rejection measure and in patients suffering from an overactive immune system, as in autoimmune diseases. Immunodeficiency also decreases cancer immuno-surveillance, in which the immune system scans the cells and kills neoplastic ones. Still further, Primary immunodeficiencies (PID), also termed innate immunodeficiencies, are disorders in which part of the organism immune system is missing or does not function normally. To be considered a primary immunodeficiency, the cause of the immune deficiency must not be caused by other disease, drug treatment, or environmental exposure to toxins). Most primary immune-deficiencies are genetic disorders; the majority is diagnosed in children under the age of one, although milder forms may not be recognized until adulthood. While there are over 100 recognized PIDs, most are very rare. There are several types of immunodeficiency that include, Humoral immune deficiency (including B cell deficiency or dysfunction), which generally includes symptoms of hypogammaglobulinemia (decrease of one or more types of antibodies) with presentations including repeated mild respiratory infections, and/or agammaglobulinemia (lack of all or most antibody production) and results in frequent severe infections (mostly fatal); T cell deficiency, often causes secondary disorders such as acquired immune deficiency syndrome (AIDS); Granulocyte deficiency, including decreased numbers of granulocytes (called as granulocytopenia or, if absent, agranulocytosis) such as of neutrophil granulocytes (termed neutropenia); granulocyte deficiencies also include decreased function of individual granulocytes, such as in chronic granulomatous disease; Asplenia, where there is no function of the spleen; and Complement deficiency in which the function of the complement system is deficient. Secondary immunodeficiencies occur when the immune system is compromised due to environmental factors.

Such factors include but are not limited to radiotherapy as well as chemotherapy. While often used as fundamental anti-cancer treatments, these modalities are known to suppress immune function, leaving patients with an increased risk of infection; indeed, infections were found to be a leading cause of patient death during cancer treatment. Neutropenia was specifically associated with vulnerability to life-threatening infections following chemotherapy and radiotherapy. In more specific embodiments, such secondary immunodeficiency may be caused by at least one of chemotherapy, radiotherapy, biological therapy, bone marrow transplantation, gene therapy, adoptive cell transfer or any combinations thereof.

As described herein above, the invention provides in some aspects thereof therapeutic and prophylactic methods. It is to be understood that the terms "treat", "treating", "treatment" or forms thereof, as used herein, mean preventing, ameliorating or delaying the onset of one or more clinical indications of disease activity in a subject having a pathologic disorder. Treatment refers to therapeutic treatment. Those in need of treatment are subjects suffering from a pathologic disorder. Specifically, providing a "preventive treatment" (to prevent) or a "prophylactic treatment" is acting in a protective manner, to defend against or prevent something, especially a condition or disease.

The term "treatment or prevention" as used herein, refers to the complete range of therapeutically positive effects of administrating to a subject including inhibition, reduction of, alleviation of, and relief from, an immune-related condition and illness, immune-related symptoms or undesired side effects or immune-related disorders. More specifically, treatment or prevention of relapse or recurrence of the disease, includes the prevention or postponement of development of the disease, prevention or postponement of development of symptoms and/or a reduction in the severity of such symptoms that will or are expected to develop. These further include ameliorating existing symptoms, preventing-additional symptoms and ameliorating or preventing the underlying metabolic causes of symptoms. It should be appreciated that the terms "inhibition", "moderation", "reduction", "decrease" or "attenuation" as referred to herein, relate to the retardation, restraining or reduction of a process by any one of about T % to 99.9%, specifically, about T % to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9%, 100% or more.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively. The term "amelioration" as referred to herein, relates to a decrease in the symptoms, and improvement in a subject's condition brought about by the compositions and methods according to the invention, wherein said improvement may be manifested in the forms of inhibition of pathologic processes associated with the immune-related disorders described herein, a significant reduction in their magnitude, or an improvement in a diseased subject physiological state.

The term "inhibit" and all variations of this term is intended to encompass the restriction or prohibition of the progress and exacerbation of pathologic symptoms or a pathologic process progress, said pathologic process symptoms or process are associated with. The term "eliminate" relates to the substantial eradication or removal of the pathologic symptoms and possibly pathologic etiology, optionally, according to the methods of the invention described herein. The terms "delay", "delaying the onset", "retard" and all variations thereof are intended to encompass the slowing of the progress and/or exacerbation of a disorder associated with the immune-related disorders and their symptoms slowing their progress, further exacerbation or development, so as to appear later than in the absence of the treatment according to the invention. As indicated above, the methods and compositions provided by the present invention may be used for the treatment of a "pathological disorder", specifically, immune-related disorders as specified by the invention, which refers to a condition, in which there is a disturbance of normal functioning, any abnormal condition of the body or mind that causes discomfort, dysfunction, or distress to the person affected or those in contact with that person. It should be noted that the terms "disease", "disorder", "condition" and "illness", are equally used herein. It should be appreciated that any of the methods and compositions described by the invention may be applicable for treating and/or ameliorating any of the disorders disclosed herein or any condition associated therewith. It is understood that the interchangeably used terms "associated", "linked" and "related", when referring to pathologies herein, mean diseases, disorders, conditions, or any pathologies which at least one of share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms. The present invention relates to the treatment of subjects or patients, in need thereof. By "patient" or "subject in need" it is meant any organism who may be affected by the above-mentioned conditions, and to whom the therapeutic and prophylactic methods herein described are desired, including any vertebrate, specifically mammals such as humans, domestic and non-domestic mammals such as canine and feline subjects, bovine, simian, equine and rodents, specifically, murine subjects. More specifically, the methods of the invention are intended for mammals. By "mammalian subject" is meant any mammal for which the proposed therapy is desired, including human, livestock, equine, canine, and feline subjects, most specifically humans. It should be appreciated that the invention may be applicable for any vertebrates, for example, avian subjects, and fish.

As described above, the nucleic acid cassette of the invention may be administered by the methods of the invention either ex vivo, by introduction thereof into cells that are being transplanted or transferred to the treated subject, or alternatively in vivo, where the cassette or any vector, systems or composition thereof are directly administered to the subject. It should be therefore understood that the number of administrations of treatment to a subject may vary. Introducing the genetically modified cells that comprise the cassette of the invention, into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated. In other aspects of the invention as discussed above, the nucleic acid cassette for insertion of a nucleic acid sequence of interest is employed to modify cellular DNA in vivo. In these in vivo embodiments, the nucleic acid cassette of the invention may be administered directly to the individual. The nucleic acid cassette may be administered by any of a number of well-known methods in the art for the administration of nucleic acids to a subject. The nucleic acid cassette can be incorporated into a variety of formulations. More particularly, nucleic acid cassette of the present invention can be formulated into pharmaceutical compositions by combination with appropriate pharmaceutically acceptable carriers or diluents. Appropriate pharmaceutical composition applicable for this aspect are as described in more detail in connection with other aspects of the invention. It should be noted that the invention further encompasses the option of combining the ex vivo or in vivo therapy disclosed by the invention, with any further conventional therapeutic approaches used in the art. For example, for cancer patients, the method of the invention may be further combined with any other therapy, for example at least one of, irradiation, chemotherapy, hormonal therapy or immunotherapy using a biological agent.

Still further aspect of the invention relates to an effective amount of at least one nucleic acid cassette or any vehicle or cell comprising such cassette or any composition thereof for use in a method for treating, preventing, ameliorating, inhibiting or delaying the onset of a pathologic disorder in a mammalian subject. In more specific embodiments, the cassette used herein may comprise at least one nucleic acid sequence of interest comprising a nucleic acid sequence coding for at least one variable domain of an immunoglobulin heavy chain and a splice donor site. In more specific embodiments, the nucleic acid cassette may target the insertion of the nucleic acid sequence of interest into a target genomic sequence within the IgH locus, upstream of at least one splice acceptor site of a constant domain of an immu-noglobulin heavy chain in a mammalian cell of the B cell lineage. In some embodiments, the nucleic acid sequence of interest comprised within the cassette used by the methods of the invention may comprise at least one SA. In yet some further embodiments, the SA may be located upstream to the VH.

It should be appreciated that all embodiments that define the cassette used by the therapeutic methods of the invention, as well as any embodiment discussed in connection with the therapeutic methods of the invention are also applicable in the present aspect as well.

As shown by Examples 10 and 11, the inventors clearly demonstrated improved therapeutic results when optimized sequences were used for the cassettes encoding the engi-neered BCRs of the invention. Thus, another aspect of the invention relates to a method of genetic engineering of a BCR in a primary mammalian cell of the B cell lineage. More specifically, the method comprises the step of con-tacting the cell with at least one nucleic acid cassette comprising at least one nucleic acid sequence of interest or with any vector or vehicle comprising the cassette. It should be noted that in some embodiments, the nucleic acid sequence of interest comprises a nucleic acid sequence coding for at least one variable domain of an immunoglobu-lin gene. In more specific embodiments, the nucleic acid sequence further comprises at least one exogenous hotspot motif/s for somatic hypermutation/s. It should be understood that the somatic hyper mutation/s retain or minimally change the protein translated from said nucleic acid sequence.

In some embodiments, the hotspot motif is at least one of WRCH, DGYW, RCY, RGY and any C nucleotide. More specifically, the W is any one of adenosine (A) or thymidine (T), R is A or guanosine (G), H is A or cytidine (C) or T, D is A or G or T and Y is C or T. In more specific embodiments, the hot spot motif is incorporated in at least one of the coding strand and the template strand. Somatic hypermutation (SHM) occurs in response to antigen-dependent B cell activation in specialized lymphoid structures termed germi-nal centers (GCs). SHM introduces mainly point mutations into V exons. GC B cells with SHMs that result in increased BCR antigen-binding affinity are positively selected, leading to affinity maturation, and those that decrease BCR affinity or cause loss of BCR expression are negatively selected. Both V exon SHM and Class Switch Recombination are initiated by Activation-Induced Cytidine Deaminase (AID). AID acts as a mutagen by deamination of cytosine and converting it to uracil (C→U) in single-strand DNA, leading upon DNA replication to transition mutation replacing C by T and converting the C:G nucleotide pair into T:A pair ('phase 1A' mutations).

Deamination of C also triggers multiple pathways of base excision and mismatch repair that lead to the generation of somatic point mutations not only in the initial C/G target nucleotides but also in neighboring regions, including A/T nucleotides. Within the rearranged IgV-genes, predominant AID-targeting sites are targeted to the underlined C/G in certain hotspot motifs such as the WRCH/DGYW (with the palindromic AGCT motif representing a canonical example) and RCY/RGY as well as the WA/TW motifs. More spe-cifically, W is any one of adenosine (A) or thymidine (T), R is A or guanosine (G), H is A or cytidine (C) or T, D is A or G or T and Y is C or T. In yet some further embodiments, hotspot motifs applicable in the invention may further include WRCY (that in some embodiments with AGCT being favored and AGCC or TGCG being disfavored), and TAA motifs, as well as the CRCY, ATCT, the WRCR, and the WRCW motifs.

In some specific embodiments, the nucleic acid sequence of interest used by the methods of the invention may comprise a nucleic acid sequence coding for at least one variable domain of an immunoglobulin heavy chain and at least one splice donor site. In some embodiments, such nucleic acid cassette targets the insertion of the nucleic acid sequence of interest into a target genomic sequence within at least one immunoglobulin locus downstream to the J region of the variable domain and optionally, upstream of the CSR region of the heavy chain. In some embodiments, the nucleic acid sequence of interest comprised within the cassette used by the methods of the invention may comprise at least one SA. In yet some further embodiments, the SA may be located upstream to the VH. In more specific embodiments, the target genomic sequence may be located: either (i), downstream to the last segment of the J region of the variable domain and upstream to the enhancer region of said heavy chain; or (ii) downstream to the enhancer region and upstream to the CSR of said heavy chain. In yet some alternative embodiments, the mammalian cell of the method of the invention express the recombination activating gene (RAG) complex. According to such embodiments, the at least one nucleic acid cassette comprise the nucleic acid sequence/s of interest and at least one recognition signal sequence (RSS). It should be noted that the nucleic acid cassette targets the insertion of the nucleic acid sequence of interest into a target genomic sequence within at least one immunoglobulin locus. In more specific embodiments, the insertion of said nucleic acid sequence of interest into the target genomic locus is mediated by RAG-catalyzed recom-bination between at least one genomic RSS flanking the target genomic locus and at least one RSS comprised within said nucleic acid cassette. In some embodiments, the nucleic acid cassette is flanked on one or both the 5' and 3' ends thereof by RSS. In yet some further embodiments, the RSS are at least one of 12 RSS, 23 RSS and 22 RSS. In yet another aspect, the invention provides a method of genetic engineering of a BCR of a cell of the B cell lineage in a mammalian subject in need thereof. In more specific embodiments, the method comprising the step of adminis-tering to the subject an effective amount of at least one nucleic acid cassette comprising at least one nucleic acid sequence of interest or of any vector or vehicle comprising said cassette. More specifically, the nucleic acid sequence of interest comprises a nucleic acid sequence coding for at least one variable domain of an immunoglobulin gene. In yet some further embodiments, the nucleic acid sequence fur-ther comprises at least one exogenous hotspot motif/s for somatic hypermutation/s, said somatic hyper mutation/s retain or minimally change the protein translated from said nucleic acid sequence.

In some embodiment, the hotspot motif is at least one of WRCH, DGYW, RCY, RGY and any C nucleotide, said W is any one of A or T, R is A or G, H is A or C or T, D is A or G or T and Y is C or T. It should be noted that the hot spot motif may be incorporated in at least one of the coding strand and the template strand. In yet some further specific embodiments, the nucleic acid sequence of interest of the methods of the invention may comprise a nucleic acid sequence coding for at least one variable domain of an immunoglobulin heavy chain and at least one splice donor site. In such embodiments, the nucleic acid cassette targets the insertion of the nucleic acid sequence of interest into a target genomic sequence within at least one immunoglobulin locus downstream to the J region of the variable domain. Optionally, upstream of the CSR region of the heavy chain.

In some embodiments, the target genomic sequence may be located: (i) downstream to the last segment of the J region of the variable domain and upstream to the enhancer region of said heavy chain; or (ii) downstream to the enhancer region and upstream to the CSR of said heavy chain. In some embodiments, the nucleic acid sequence of interest comprised within the cassette used by the methods of the invention may comprise at least one SA. In yet some further embodiments, the SA may be located upstream to the VH. In yet some alternative embodiments, the mammalian cell express the RAG complex. Thus, in some optional embodiments the target genomic sequence may be located within or upstream to the J region. In more specific embodiments, the target genomic sequence may be located within the variable domain of the immunoglobulin locus (specifically, the IgH locus), specifically, within any of the V, D or J regions. According to such embodiments, the at least one nucleic acid cassette comprise the nucleic acid sequence/s of interest and at least one RSS. More specifically, the nucleic acid cassette targets the insertion of the nucleic acid sequence of interest into a target genomic sequence within at least one immunoglobulin locus. In more specific embodiments, the insertion of the nucleic acid sequence of interest into the target genomic locus is mediated by RAG-catalyzed recombination between at least one genomic RSS flanking the target genomic locus and at least one RSS comprised within said nucleic acid cassette.

A further aspect of the invention relates to a method of engineering a mammalian cell of the B lineage for antigen-induced secretion of an antibody of interest, or of any antigen-binding fragment thereof. More specifically, the method of the invention may comprise the step of contacting the cell with at least one nucleic acid cassette comprising at least one nucleic acid sequence of interest or with a vector comprising said cassette. More specifically, the nucleic acid sequence of interest comprises a nucleic acid sequence coding for at least one variable domain of an immunoglobulin gene. In yet some further embodiments, the nucleic acid sequence further comprises at least one exogenous hotspot motif/s for somatic hypermutation/s. It should be noted that the somatic hyper mutation/s retain or minimally change the protein translated from said nucleic acid sequence.

In some embodiments, the hotspot motif may be at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand.

In some specific embodiments, the nucleic acid sequence of interest comprises a nucleic acid sequence coding for at least one variable domain of an immunoglobulin heavy chain and at least one splice donor site. In such embodiments, the nucleic acid cassette targets the insertion of the nucleic acid sequence of interest into a target genomic sequence within at least one immunoglobulin locus downstream to the J region of the variable domain and optionally, upstream of the CSR region of the heavy chain. In some embodiments, the nucleic acid sequence of interest comprised within the cassette used by the methods of the invention may comprise at least one SA. In yet some further embodiments, the SA may be located upstream to the VH.

In yet some further specific embodiments, the target genomic sequence may be located: (i) downstream to the last segment of the J region of the variable domain and upstream to the enhancer region of said heavy chain; or (ii) downstream to the enhancer region and upstream to the CSR of said heavy chain. In some alternative embodiments of the methods of the invention, the mammalian cell express the RAG complex and may therefore use the V(D)J recombination for incorporation of the nucleic acid of interest into the target genomic locus. In such embodiments, the at least one nucleic acid cassette comprise the nucleic acid sequence/s of interest and at least one RSS. In some embodiments, the nucleic acid cassette targets the insertion of the nucleic acid sequence of interest into a target genomic sequence within at least one immunoglobulin locus. More specifically, the insertion of said nucleic acid sequence of interest into the target genomic locus is mediated by RAG-catalyzed recombination between at least one genomic RSS flanking the target genomic locus and at least one RSS comprised within said nucleic acid cassette Thus, in some optional embodiments the target genomic sequence may be located within or upstream to the J region. In more specific embodiments, the target genomic sequence may be located within the variable domain of the immunoglobulin locus (specifically, the IgH locus), specifically, within any of the V, D or J regions It should be understood that in certain embodiments, the engineered BCR produced by the methods of the invention may be produced as a single chain antibody, as described herein above (e.g., comprising exogenous VL, CL, VH and endogenous VC).

Still further, the invention relates in another aspect thereof to an engineered mammalian cell of the B lineage expressing a genetically engineered BCR. The cell of the invention is transduced or transfected with at least one nucleic acid cassette comprising at least one nucleic acid sequence of interest or of any vector or vehicle comprising the cassette. In some embodiments, the nucleic acid sequence of interest comprises a nucleic acid sequence coding for at least one variable domain of an immunoglobulin gene. In more specific embodiments, the nucleic acid sequence further comprises at least one exogenous hotspot motif/s for somatic hypermutation/s. It should be noted that the somatic hyper mutation/s retain or minimally change the protein translated from said nucleic acid sequence.

In some embodiments, the hotspot motif is at least one of WRCH, DGYW, RCY, RGY and any C nucleotide, said W is any one of A or T, R is A or G, H is A or C or T, D is A or G or T and Y is C or T. In some embodiments, the hot spot motif is incorporated in at least one of the coding strand and the template strand. In some embodiments, the nucleic acid sequence of interest of the engineered mammalian cell of the invention, comprises a nucleic acid sequence coding for at least one variable domain of an immunoglobulin heavy chain and at least one splice donor site. In some embodiments, the nucleic acid cassette targets the insertion of the nucleic acid sequence of interest into a target genomic sequence within at least one immunoglobulin locus downstream to the J region of the variable domain and optionally, upstream of the CSR region of the heavy chain. In some embodiments, the nucleic acid sequence of interest comprised within the cassette used for the engineered cell of the invention may comprise at least one SA. In yet some further embodiments, the SA may be located upstream to the VH.

In yet some further embodiments of the engineered mammalian cell of the invention, the target genomic sequence is located: (i) downstream to the last segment of the J region of the variable domain and upstream to the enhancer region of said heavy chain; or (ii) downstream to the enhancer region and upstream to the CSR of said heavy chain. In yet some alternative embodiments of the engineered mammalian cell of the invention, such mammalian cell express the RAG complex. In such embodiments, the targeted insertion of the nucleic acid sequence of interest may be incorporated into the target locus, via V(D)J recombination. In such case, the least one nucleic acid cassette may comprise the nucleic acid sequence/s of interest and at least one RSS. In more specific embodiments, the nucleic acid cassette targets the insertion of the nucleic acid sequence of interest into a target genomic sequence within at least one immunoglobulin locus. Moreover, in some embodiments, the insertion of the nucleic acid sequence of interest into the target genomic locus is mediated by RAG-catalyzed recombination between at least one genomic RSS flanking the target genomic locus and at least one RSS comprised within the nucleic acid cassette. Thus, in some optional embodiments the target genomic sequence may be located within or upstream to the J region. In more specific embodiments, the target genomic sequence may be located within the variable domain of the immunoglobulin locus (specifically, the IgH locus), specifically, within any of the V, D or J regions.

It should be understood that the engineered mammalian cell of the invention may express in some embodiments the engineered BCR as a single chain antibody as discussed above.

In yet some further aspect, the invention provides a genetically engineered BCR comprising an amino acid sequence of interest. More specifically, the nucleic acid sequence of interest encoding the amino acid sequence of the genetically engineered BCR of the invention, may comprises a nucleic acid sequence coding for at least one variable domain of an immunoglobulin gene. In some embodiments, the nucleic acid sequence further comprises at least one exogenous hotspot motif/s for somatic hypermutation/s. More specifically, the somatic hyper mutation/s retain or minimally change the protein translated from said nucleic acid sequence. In yet some further embodiments, the BCR of the invention is engineered by targeted insertion of said nucleic acid sequence of interest into a target genomic sequence within at least one immunoglobulin locus, in a mammalian cell of the B lineage. In more specific embodiments, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand. In some embodiments, the engineered BCR of the invention is expressed as a single chain antibody as discussed above. Another aspect of the invention relates to a nucleic acid cassette comprising at least one nucleic acid sequence of interest. More specifically, the nucleic acid sequence of interest comprises a nucleic acid sequence coding for at least one variable domain of an immunoglobulin gene. In some embodiments, such nucleic acid sequence further comprises at least one exogenous hotspot motif/s for somatic hypermutation/s.

In some embodiments, the exogenous or ectopic hotspots comprised within the immunoglobulin heavy and/or light chain sequence/s are non-naturally occurring hotspots resulting from substitution of at least one nucleic acid in the original sequence. The hotspots are therefore incorporated in the sequences. It should be understood that the somatic hyper mutation/s retain or minimally change the protein translated from said nucleic acid sequence. In yet some further embodiments, the nucleic acid cassette targets the insertion of the nucleic acid sequence of interest into a target genomic sequence within at least one immunoglobulin locus, in a mammalian cell of the B cell lineage.

In some embodiments of the nucleic acid cassette of the invention, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand. In some embodiments, the cassette of the invention may further comprise at least one SA. In yet some further embodiments, the SA may be located upstream to the VH in the donor cassette, allowing the use of the endogenous VH promoter for transcription of the transgenic nucleic acid sequence of interest provided by the cassette of the invention. More specifically, the introduced nucleic acid sequence of interest (e.g., nucleic acid sequence that encodes at least the VH fragment of an antibody of interest) is transcribed as a fusion to the endogenous VDJ transcript. This transgenic exogenous sequence can be separately translated using IRES or 2A peptide, or alternatively, released to function separately from the endogenous VDJ by incorporating a protease cleavage site (e.g., a furin site). Thus, in some specific and non-limiting configuration of the cassette of the invention, a splice acceptor (SA) or a minimal promoter (MP) may be included. The cassette encodes an antibody light chain (VLJLCL) and a variable region of a heavy chain (VHDHJH) separated by a 2A peptide (SA-VLJLC-2A-VHDHJH-SD). In some particular embodiments, the cassettes provided by the present aspect further encompasses any cassette comprising the nucleic acid sequence encoding the optimized antibodies, specifically, the nucleic acid sequences as denoted by any one of SEQ ID NO. 155 to 274. In yet some further embodiments, it must be understood that in some embodiments any of the cassettes disclosed herein may be incorporated in any of the vectors described by the invention, specifically, viral vectors, more specifically, AAV.

Still further, in another aspect, the invention provides a host cell transduced or transfected with at least one nucleic acid cassette or any vector or vehicle thereof. It should be noted that the host cell of the invention may be transduced or transfected with any of the nucleic acid cassettes described by the invention.

In yet some further aspect, the invention provides a pharmaceutical composition comprising at least one nucleic acid cassette, or any vector or cell comprising the cassette. More specifically, the cassette of the composition of the invention may comprise at least one nucleic acid sequence of interest comprising a nucleic acid sequence coding for at least one variable domain of an immunoglobulin gene. More specifically, the nucleic acid sequence further comprises at least one exogenous hotspot motif/s for somatic hypermutation/s. It should be noted that the somatic hyper mutation/s retain or minimally change the protein translated from the nucleic acid sequence. In yet some further embodiments, the nucleic acid cassette targets the insertion of the nucleic acid sequence of interest into a target genomic sequence within the at least one immunoglobulin locus in a mammalian cell of the B cell lineage. In yet some optional embodiments of the compositions of the invention, the composition further comprise at least one of pharmaceutically acceptable carrier/s, diluent/s, excipient/s and additive/s. In yet some further embodiments of the compositions of the invention, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand.

Another aspect of the invention relates to a method for treating, preventing, ameliorating, inhibiting or delaying the onset of a pathologic disorder in a mammalian subject. In some embodiments, the method comprising the step of administering to the subject an effective amount of at least one of: (a) nucleic acid cassette; (b) a vector comprising said nucleic acid cassette; and (c) a cell transduced or transfected with the nucleic acid cassette. In some embodiments, the cassette comprises at least one nucleic acid sequence of interest comprising a nucleic acid sequence coding for at least one variable domain of an immunoglobulin gene. In more specific embodiments, the nucleic acid sequence further comprises at least one exogenous hotspot motif/s for somatic hypermutation/s. In some embodiments, the somatic hyper mutation/s retain or minimally change the protein translated from the nucleic acid sequence. In some further embodiments, the nucleic acid cassette targets the insertion of said nucleic acid sequence of interest into a target genomic sequence within at least one immunoglobulin locus in a mammalian cell of the B cell lineage.

In some embodiments, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand. In some specific embodiments, the nucleic acid sequence of interest comprises a nucleic acid sequence coding for at least one variable domain of an immunoglobulin heavy chain and at least one splice donor site. According to such embodiments of the methods of the invention, the nucleic acid cassette targets the insertion of the nucleic acid sequence of interest into a target genomic sequence within at least one immunoglobulin locus downstream to the J region of the variable domain and optionally, upstream of the CSR region of the heavy chain. In some embodiments, the nucleic acid sequence of interest comprised within the cassette used by the invention may comprise at least one SA. In yet some further embodiments, the SA may be located upstream to the VH. In yet some further specific embodiments, the target genomic sequence is located: (i) downstream to the last segment of the J region of the variable domain and upstream to the enhancer region of said heavy chain; or (ii) downstream to the enhancer region and upstream to the CSR of said heavy chain. In some alternative embodiments of the methods of the invention, the mammalian cell express the RAG complex. In such embodiments, integration using the V(D)J recombination may be applied. In such embodiments, the at least one nucleic acid cassette used by the methods of the invention may comprise said nucleic acid sequence/s of interest and at least one RSS. In yet some further specific embodiments, the nucleic acid cassette targets the insertion of the nucleic acid sequence of interest into a target genomic sequence within at least one immunoglobulin locus. Thus, in some optional embodiments the target genomic sequence may be located within or upstream to the J region. In more specific embodiments, the target genomic sequence may be located within the variable domain of the immunoglobulin locus (specifically, the IgH locus), specifically, within any of the V, D or J regions. In yet some further embodiments, the insertion of said nucleic acid sequence of interest into the target genomic locus is mediated by RAG-catalyzed recombination between at least one genomic RSS flanking the target genomic locus and at least one RSS comprised within said nucleic acid cassette. Still further, the invention provides an effective amount of at least one nucleic acid cassette or any vehicle or cell comprising said cassette or any composition thereof for use in a method for treating, preventing, ameliorating, inhibiting or delaying the onset of a pathologic disorder in a mammalian subject. In more specific embodiments, the cassette comprises at least one nucleic acid sequence of interest comprising a nucleic acid sequence coding for at least one variable domain of an immunoglobulin gene. Still further, the nucleic acid sequence further comprises at least one exogenous hotspot motif/s for somatic hypermutation/s, thereby synonymously recoding the sequence. In some embodiments, the somatic hyper mutation/s retain or minimally change the protein translated from said nucleic acid sequence.

In some specific embodiments, the hotspot motif is at least one of WRCH, DGYW, RCY, RGY and any C nucleotide, said W is any one of A or T, R is A or G, H is A or C or T, D is A or G or T and Y is C or T. In yet some further embodiments, the hot spot motif is incorporated in at least one of the coding strand and the template strand. It must be understood that any of the antibodies produced by the methods, cassettes and cells of the invention as described herein, may be in some embodiments produced as a single chain antibody as discussed herein before.

The methods, cassettes, compositions and systems described herein in connection with all aspects of the invention, target and modify specific genomic loci that encode the immunoglobulin heavy chains. In some embodiments, the target genomic loci, specifically, the J-C intron is referred to herein as "recipient" nucleic acids. The nucleic acid sequence of interest that is provided by the cassettes of the invention and is specifically incorporated into the target site within the recipient nucleic acid sequence, specifically, the J-C intron of the IgH loci of the target B cell, is referred to herein in some embodiments, as the "donor" nucleic acid sequence.

The terms heterologous, exogenous or transgenic are sometime used interchangeably herein to describe the nucleic acid sequences of interest provided by the donor cassettes of the invention. In some embodiments these heterologous, exogenous or transgenic nucleic acid sequences refer to any nucleic acid sequence that is not native to the specific cell or location (the recipient), not naturally occurring, and exogenously or artificially inserted into the target site within the J-C-intron of the IgH of the B cells of the invention. In some specific embodiments, such sequences may be obtained either from the same or alternatively from different species or subjects.

In some cases, the nucleic acid sequence of interest comprised within the donor cassette of the invention described in connection with different aspects of the invention, may encode at least one VH of at least one antibody of interest. In yet some other embodiments, at least one VL and optionally at least one CL may be also included in the donor cassette used and provided by the invention. In some embodiments, the length of such nucleic acid sequence of interest provided by the cassette of the invention may range between about 100,000 nucleotides or more, to about 10 nucleotides or less. More specifically, the length of the nucleic acid sequence of interest may be about 100,000 nucleotides in length, or less than 75,000 nucleotides in length or less than 50,000 nucleotides in length, or less than 40,000 nucleotides in length, or less than 30,000 nucleotides in length, or less than 20,000 nucleotides in length, or less than 15,000 nucleotides in length, or less than 10,000 nucleotides in length, or less than 5000 nucleotides in length, or less than 1000 nucleotides in length, or less than 900 nucleotides in length, or less than 800 nucleotides in length, or less than 700 nucleotides in length, or less than 600 nucleotides in length, or less than 500 nucleotides in length, or less than 450 nucleotides in length, or less than 400 nucleotides in length, or less than 300 nucleotides in length, or less than 200 nucleotides in length, or less than 100 nucleotides in length, or less than 50 nucleotides in length, or less than 40 nucleotides in length, or less than 30 nucleotides in length, or less than 20 nucleotides in length, or less than 10 nucleotides in length.

All scientific and technical terms used herein have meanings commonly used in the art unless otherwise specified. The definitions provided herein are to facilitate understanding of certain terms used frequently herein and are not meant to limit the scope of the present disclosure. The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. Thus, as used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, and/or parts, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format.

It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. It is appreciated that certain features of the invention, which are, for clarity, described in the context of separate embodiments, may also be provided in combination in a single embodiment.

Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof. It must be noted that, as used in this specification and the appended claims, the singular forms "a", "an" and "the" include plural referents unless the content clearly dictates otherwise.

EXAMPLES

Materials and Reagents

TABLE 1

| list of antibodies | | |
| --- | --- | --- |
| Antibody | Provider | Cat# |
| His-probe (H-15) rabbit polyclonal IgG | SantaCruz Biotechnology | sc-803 |
| Goat Anti-Rabbit IgG H&L (FITC) | Abcam | ab6717 |
| APC anti-mouse IgM | BioLegend | 406509 |
| BV421 Anti mouse IgG1 | BD Horizon | 562580 |
| human anti-palivizumab HRP conjugated | BioRad | HCA262P |
| Goat anti-Horseradish peroxidase Cy3 conjugated | Jackson ImmunoResearch | 323-165-021 |
| Anti Ig K Light Chain VioBlue, mouse | Miltenyi Biotec | 130-105-860 |

TABLE 2

| list of primers | | |
| --- | --- | --- |
| Primer Name | Sequence | SEQ ID NO: |
| Furine Cleavage F1 | cgcgcgaaacgcGGAAG | 1 |
| P2A F1 | GAGACGTGGAGGAGAACCCTG | 2 |
| mini P for 170 F | ATGTCCATTCTAGATCTTAAGTTTGTGAGGTGTGTCGAC | 3 |

TABLE 2-continued list of primers

| Primer Name | Sequence | SEQ ID NO: |
|---|---|---|
| GFP for 151 F | ATCTAGACCTAGGATGCCCGCCATGAAGATCG | 4 |
| mIgHJ degenerate F | GGRACCWCTSTCACMGTCTCCTCAG | 5 |
| m3'IgHJ4-F1 | GGATATTTGTCCCTGAGGGAGCC | 6 |
| m3'IgHJ4-R1 | GCTCCACCAGACCTCTCTAGACAG | 7 |
| mIgHM CH2 R1 | CGTGGTGGGACGAACACATTTAC | 8 |
| mIgHG M R1 | CCACCACAGAGGAGAAGATCCAC | 9 |
| mIgHA CH2 R1 | CATGTGAGGCTGGCATCTGAAC | 10 |
| mIgHG1 CH1 R | CCAGGTCACTGTCACTGGCTC | 11 |
| mIgHJ4 F1 | GGTCAAGGAACCTCAGTCACCG | 12 |
| mIgHM M1 R1 | GCAGTGGTCCACAGGTTCTCAAAG | 13 |
| copGFPm R1 | GTGTTGGTGTAGCCGCCGTTG | 14 |

Experimental Procedures crRNA and sgRNA design. gRNA sequences were as follow (PAM sequences highlighted in bold): mouse IgH: CGATGCATAGGGACAAAGAGTGG as denoted by SEQ ID NO: 117, mouse IgK: TGGTGCAGCATCAGCCCCT-GAGG as denoted by SEQ ID NO: 118, human IgH: GGAAAGAGAACTGTCGGAGTGGG as denoted by SEQ ID NO: 119 and human IgK: TGGTGCAGC-CACAGTTCCTGAGG as denoted by SEQ ID NO: 120. Murine and human IgK gRNAs were chosen for their capacity to cleave in the splice acceptor site of the respective IgK. Murine and human IgH gRNAs sequence were chosen for their immediate proximity to saCas9 gRNA sequence. Benchling online gRNA analysis tool was used to assess for potential target sites.

Plasmid cloning. For the murine donor plasmid, two intronic sequences directly adjacent to the murine target gRNA (homology arms) were PCR amplified using primers: Forward: ATTAAT-TAAGCGGCCGCGTAAGAATGGCCTCTCCAGGTCTT as denoted by SEQ ID NO: 121; Reverse: CTC-CACTCCTCGAGTTTGTCCCTATGCATCG (reverse) as denoted by SEQ ID NO: 122; Forward GGACAAACTCGAGGAGTGGAGTGGGGC) as denoted by SEQ ID NO: 123; Reverse: ACGCGTGTACACTAGTC-CAACTCAACATTGCTCAATTCATTTAAAA ATAT-TTGA AACT as denoted by SEQ ID NO: 124; from the ImProB cell line. The fragments encompass the intron 3'J4-5'iEμ, 426 bp and 521 bp respectively. Fragments were inserted by In-Fusion assembly into pAB270 (Barzel, A. et al. Nature 517, 360-364 (2015)), cut with NheI and SpeL. Finally, the nucleic acid sequences as denoted by SEQ ID NO: 125 for the 3BNC117-wt donor or SEQ ID NO: 153 for the 3BNC117-opt donor were inserted in the XhoI restriction site by Gibson Assembly (NEB). For the human donor plasmid, the intronic sequences were amplified using prim-ers:Forward primer: CGCGATGCATTAAT-TAAGCGGCCGCGTAAGAATGGCCACTCTA GGGCC as denoted by SEQ ID NO: 126; Reverse primer: CCCACTCCCTCGAGGACAGTTCTCTTTCC as denoted by SEQ ID NO: 127; Forward primer: AACTGTCCTCGAGGGAGTGGGTGAATCC as denoted by SEQ ID NO: 128; Reverse primer: GATAT-CACGCGTGTACACTAGTACAGCACTGTGCTAGTAT-TTCTTAGCT as denoted by SEQ ID NO: 129; and Gibson Assembled into pAB270 NheI-SpeI restricted. The nucleic acid sequence as denoted by SEQ ID NO: 130 was inte-grated at the XhoI restriction site.

For the CMV-Cas9gRNA vector, pX60115 (Addgene) was cleaved with BsaI and pre-annealed, phosphorylated (PNK, NEB), sgRNA coding oligo-deoxynucleotides were ligated using T4 DNA Ligase (NEB). For the CD19-Cas9 vector, pAB27026 was cleaved using NotI and SpeL (NEB) and an saCas9 coding fragment, amplified from pX601, as well as the murine CD19 promoter, amplified from wild type C57BL/6OlaHsd genomic DNA, were assembled using Hi-Fi DNA Assembly Mix (NEB). For the SFFV-Cas9 vector, pAB270 was cleaved with NotI and SpeI (NEB). The fragment coding the SFFV promoter was amplified from GW175 (Kay Lab, Stanford) and the saCas9 was amplified from pX601. The fragments were assembled using Hi-Fi DNA Assembly Mix (NEB). For the DonorgRNA vector, the U6-gRNA fragment was amplified from ligated pX601 with the murine IgH sgRNA used in this study, and the fragment was assembled using Hi-Fi DNA Assembly Mix (NEB) into the donor vector pADN171XS7, following cleavage with SpeI (NEB). All fragments for cloning were amplified using PrimeStar MAX (Takara).

rAAV production and purification. rAAV-DJ donors (Grimm, D. et al. J. Virol. 82, 5887-5911 (2008)) were produced in 293t cell lines by transient transfection. In short, 10-14 15 cm dishes were transfected when cells were 80% confluent pAd5 (helper plasmid), rAAVDJ or rAAV6 genome plasmid and Donor plasmid at a 3:1:1 ratio in Polyethylenimine (PEI)(Merck). In total each plate was teransfected with 41,250 ng of DNA. Purification was performed with the AAVpro Extraction Kit (Takara) accord-ing to manufacturer protocol and titer quantification by qPCR with SYBRGreen (ThermoFisher).

Electroporation grade plasmid purifications. Each plas-mid taken for electroporation was cultured for 32 h in 500 mL SB supplemented with Ampicillin. Plasmid extraction was performed with two E.N.Z.A Plasmid DNA Maxi kit columns (Omega bio-tek) according to manufacturer protocols. Elutes were supplemented with 1/100 volume 3M NaOAc and 3 times volume absolute EtOH, froze for 1 h at −80° C. and precipitated for 2 h in 4° C. at 5000 rpm. Precipitate was washed twice in 70% EtOH at 15 krpm in 4° C., dried completely and resuspended in T1E0.1 Buffer. Only concentrations above 5000 ng/ml were used for transfections.

Generation of DNA sequence for Palivizumab genetic delivery. Palivizumab (MEDI-493) VH and VL were reverse translated from the published sequence (Johnson, S. & Oliver, C. J. Infect. Dis. 1215-1224 (1997)). SD site was added based on the endogenous mIgHJ1/4 SD sequence. Kappa constant was taken from ProB genomic DNA. In this construct, the HGH signal sequence was used and added a Furin-GSG-2A sequence as described previously (Fang, J. et al. Nat. Biotechnol. 23, 584-590 (2005)). The sequence for the minimal promoter was taken from a previously described sequence (Lieber, A., et al. FEBS Lett. 282, 225-227 (1991)). Multiple in-silico files were also generated to control the translation frame, after genomic DNA insertion and splicing.

Generation of DNA sequence for 3BNC117 genetic delivery. VRC01-class, gp120 CD4bs binding antibody 3BNC117 VH and VL were taken as from the published sequence (Accession numbers HE584538.1 & HE584537.1). Next, SHM hotspots (Laskov, R., et al. Mol. Immunol. 48, 733-745 (2011)) were added where possible, in the CDR loops. The same Furin-GSG-2A sequence as for the MEDI-493 was taken. The endogenous, natural leader peptides from the V sequences that generated the 3BNC117 VH and VL, (IgKV1D-33 & IgHV1-2) were added in their spliced from. From these sequences, splice donor and splice acceptor sites were removed that gave a score >0.6 using a splice prediction tool, by silent mutations. Finally, translation frame was controlled by generation of in-silico files mimicking genomic DNA insertion and mRNA splicing.

Cell lines and cultures. Immortalized Pro-B cells (Lenden H. et al. J. Immunol. Methods 451, 71-77 (2017)), A-20 (Kim, K. J. Immunology 59, 15-21 (1986)), IgM+ and IgA+ i.29 (Sitia, R., i.29. J. Immunol. 127, 1388-1394 (1981)) were cultured in 75 cm² flasks at 37° C., with 5% $CO_2$, in 1640 RPMI (Biological Industries) supplemented with 10% Heat Inactivated Fetal Bovine Serum (HI FBS)(Merck), 50 μM β-Mercaptoethanol and Penicillin Streptomycin (P/S) (ThermoFisher). 293t cells were cultured in Dulbecco's Modified Eagle Medium (DMEM) (Biological Industries) supplemented with 10% FBS (Merck) and P/S. Trypsinization of this cell line was performed when confluency reached ~80%, and pre-washed with Phosphate Buffered Saline (PBS) (Biological Industries). For cell lines, ImProB, A-20 and i.29 IgA, electroporations were performed with 18.3 pmol Cas9 and 22 pmol gRNA, at 1.0E5 cells/μl in OptiMEM for 10 μl tips in a Neon electroporation system (Invitrogen). For the human cell line, parameters were: 1350 v 30 ms 1pulse and for the murine cell lines: 1600 v 20 ms, 1pulse. All cell lines were grown in 1640 RPMI supplemented with 10% HI FBS, 50 μM β-Mercaptoethanol and P/S. Transductions were performed with a 50,000 MOI of rAAV-DJ for murine cell lines, and a 130,000 MOI of rAAV-DJ for human cell line. Efficiency of editing was determined 3 days following electroporation. For plasmid electroporations we used 3 μg plasmid DNA/1E06 cells/10 μl Neon tip.

Primary cells in-vitro culture and activation. Whole spleens were extracted from 6-8 weeks old mice and tissue was mechanistically crushed in PBS to be filtered in 70 μm Cell Stainer (Corning). Following Red Blood Cell lysis (Biolegend) cells were plated at 3.0E6 cells/ml in 1640 RPMI supplemented with 10% HI FBS, 50 μM β-Mercaptoethanol, P/S, 10 μg/ml LPS (SantaCruz Biotechnology) and 10 ng/ml IL4 (Peprotech). Cells were cultured 16-24 h and washed twice in PBS before transfections and plated in the same activation medium without P/S after electroporation. Cells were cultured 16-24 h and washed in PBS before transfections and plated in the same activation medium without P/S for 8-16 h following electroporations. Parameters were 1750 v 20 ms 1pulse at 4.0E5 cells/μl in buffer R for 10μl tips. For RNP, Cas9 (IDT) and gRNA (IDT) complexes assembly were generated 20 min prior of transfection with 18.3 pmol Cas9 66 pmol gRNA per 1E06 cells. Transductions were performed no later than 5 min following electroporation with 10,000 MOI AAV-6 and cells were analyzed 2 days following electroporation for flow cytometry and assessment of gRNA activity.

Primary human cultures. For human cells, whole blood was obtained from the blood bank (Magen David Adom, Sheiba Medical Center) in accordance with Tel Aviv University Review Board and PBMCs were extracted using Lymphocyte Separation Medium (mpbio). Remnants of red blood cells were lysed as described above. B cells were enriched using the negative selection Easysep human B cell isolation kit (Stemcell) and plated in 1640 RPMI supplemented with 10% HI FBS, 50 μM β-Mercaptoethanol, P/S, 2 μg/ml RP105 (LEAF, anti-human CD180, Biolegend) and 10 ng/ml IL7. A short sentence about being used for subsequent analysis (the subsequent analysis will be detailed in a different section). For human primary cells parameters were 1750 v 20 ms 1pulse and in a Neon electroporation system (Invitrogen) at 4.0E5 cells/μl in buffer R for 10 μl tips. For RNP, Cas9 (IDT) and gRNA (IDT) complexes assembly were generated 20 min prior of transfection with 18.3 pmol Cas9 66 pmol gRNA per 1E06 cells. Transductions were performed no later than 5 min following electroporation with 10,000 MOI AAV-6. Efficiency of editing was determined 2 days following electroporation.

Mouse studies. 6-10 weeks old C57BL/6OlaHsd (Envigo) mice were housed and kept at ambient temperature of 19-23° C., humidity of 45-65% and with a 12 h light/12 h dark cycle. Immunizations with gp120-YU2 or MD39-ferritin were performed as previously described, using 20 μg/mouse of antigen in Alum (Invitrogen)7,8. For AAV injections, mice were anesthetized with 0.1 mg/g and 0.001 mg/g Ketamine and Xylazine, respectively, and were injected by 5E11 vg/vector/100 μl/mouse in PBS. Blood samples from mice were collected in heparin. Cells and serum were separated by centrifugation. Serum was collected from the supernatant. For spleens, whole spleens were extracted from mice and mechanically crushed in PBS to be filtered in a 70 μm cell strainer (Corning). For bone marrow, cells were flushed from the posterior femur and tibia. For blood, spleen and bone marrow, cells were processed with red blood cell lysis buffer (Biolegend) and plated in 1640 RPMI (Biological Industries) supplemented with 10% HI FBS (Biological Industries) until processing. Muscle tissue was processed from femoral muscles. Right or left lung were processed for pulmonic tissue. Right or left hemispheres were processed for brain tissue. Lobes were processed for liver tissue and whole heart was used for cardiac tissue. For lymph nodes, inguinal and cervical lymph nodes were pooled for processing.

Antibodies and Env proteins expression and purification. For Env proteins, plasmid encoding His-tagged gp140YU2 was transfected into Expi293F cells at a density of 2.0E6 cells/ml in Expi293 Expression Medium (ThermoFisher) using ExpiFectamine (ThermoFisher) according to manufacturer protocols. Supernatants were collected 7 days later and bound with Ni-NTA Agarose (Qiagen) in 20 mM Sodium Phosphate, 0.5M NaCl, 10 mM Imidazol (ID). Beads were washed twice with the same buffer before mounting on gravity-flow Polypropylene columns (Biorad). Chromatography elution was performed in three fractions: 50, 100 and 200 mM ID. Elutes were buffer exchanged to PBS using Amicon Ultra-15 Centrifugal Filter Units (Merck). For 3BNC117, 7.5 μg of plasmid encoding the light chain pADN210 and 22.5 μg of plasmid encoding heavy chain pADN211 were co-trasfected into 1 30 mL flask of Expi293F cells at a density of 2.0E6 cells/ml in Expi293 Expression Medium (ThermoFisher) using ExpiFectamine (ThermoFisher) according to manufacturer protocols. Purification of the supernatant, 7 days post transfection, was performed using MabSelect (GE Healthcare) following manufacturer recommendations.

Electroporations and Transductions. Neon Electroporation (Invitrogen) was performed in 10 μL tips (Invitrogen). For all electroporations, 1.0E6 cells were pre-washed twice with PBS and resuspended in electroporation medium. Cells were electroporated with 3p g of electroporation grade DNA with the following settings: ProB cells at 1600 v, 20 ms, 1pulse. i.29 at 1400 ms, 20 ms, 1pulse. A-20 at 1300 v, 20 ms, 1pulse. Splenocytes at 1350 v, 30 ms, 1pulse. For DNA only electroporations, Neon Buffer R was replaced with Opti-MEM (Life Technologies) and Neon Buffer E1 with Opti-MEM 10% Glycerol. Cells post electroporations were plated in antibiotic free medium, which was added 16 h after. For RNP, Cas9 and gRNA (ThermoFisher) complexes assembly and electroporations were proceeded according to manufacturer protocols. Transductions were performed 10 min after electroporations at 2.0E6 cell/ml with a MOI of 50,000.

Reverse transcriptions and Polymerase Chain Reactions. Reverse transcriptions were executed on total RNA extracted using QuickRNA microPrep kit (Zymo Research) from 1-2E06 cells 3 days following transfection with CRISPR-RNPs and AAV transduction, cells transfected without the gRNA otherwise similarly treated were used as control. 500-1500 ng of extracted RNA were used for RT reaction using either M-MLV (Promega) or RevertAid (ThermoFisher) reverse transcriptase with oligo dT according to respective manufacturer instructions. Subsquent to RT reactions, PCR reactions were done using Maxima HotStart GreenMix at 30 to 35cycles using the appropriate primers. The following primers were used for the experiments of Examples 5, 6 and 8: CGCGCGAAACGCGGAAG (forward) as denoted by SEQ ID NO:131 and for mouse IgG2a: CCACCACAGAGGAGAAGATCCAC (reverse) as denoted by SEQ ID NO:132, for mouse IgM: CGTGGTGGGACGAACACATTTAC (reverse) as denoted by SEQ ID NO:133; for mouse IgA: CATGTGAGGCTGG-CATCTGAAC (reverse) as denoted by SEQ ID NO:134.

For assessment of gRNA activity, genomic DNA was extracted using Quick DNA miniprep kit (Zymo Research) and 300-500 ng genomic DNA was amplified by PCR using PrimeSTAR MAX (Takara) for 30-35cyles using the following primers: mouse IgH: GGATATTTGTCCCTGAGG-GAGCC (forward) as denoted by SEQ ID NO: 135; GCCATCTTGACTCCAACTCAACATTG (reverse) as denoted by SEQ ID NO: 136; mouse IgK: AGTC-CAACTGTTCAGGACGCC (forward) as denoted by SEQ ID NO: 137; GTGTGGCTAAAAATTGTCCCATGTGG (reverse) as denoted by SEQ ID NO: 138; human IgH:

GCTGAGGAATGTGTCTCAGGAGC (forward) as denoted by SEQ ID NO: 139; CCTCAATTCCAGACA-CATATCACTCATGG (reverse) as denoted by SEQ ID NO: 140; human IgK: GCTGGAACAGTCAGAAGGTGGAG (forward) as denoted by SEQ ID NO: 141; GCTGTCCTTGCTGTCCTGCT (reverse) as denoted by SEQ ID NO: 142. Amplicon DNA was denatured and reannealed in a thermocycler prior to cleaving by T7 Endonuclease 1 (New England Biolabs) in a 30 min reaction. Proteinase K was supplemented to the reaction and incubated for an additional 15 min at 37° C. Cleavage was analyzed by agarose gel electrophoresis and quantified using Biovision (Vilber Lourmat) using a rolling ball for background substration. Efficiency was calculated as % gene modification=$100 \times (1-(1-\text{fraction cleaved})^{1/2})$. Agarose (Hy-labs) was supplemented to 40 mM Tris, 20 mM Acetate, 1 mM EDTA for a final concentration of 1-2%. Gels were run at 160 v for 20-30 mins. DNA ladders used were either 100 bp DNA Ladder H3 RTU or 1 kb DNA Ladder RTU (GeneDireX).

Flow Cytometry. For samples from recipient (CD45.2) mice, cells were stained immediately following extraction. Samples were washed and resuspended in Staining Buffer (Biolegend). Antibodies were added and binding occurred for 20 min in the dark at room temperature. Samples were then washed and resuspended in Staining Buffer before reading in Attune NxT (Life technologies). For indirect Flow cytometry samples were incubated for 5 min with primary gp120-YU2.DG at 1ug in 100 μl, washed and conjugated antibodies were added in 100 μl for 15 min followed by additional washing and acquisition. For pERK, cells were incubated for 3 min at 37° C. in 100 μl PBS before supplementing 5 μg gp120-YU2.DG, incubated for one more minute, immediately put on ice for diluted by a factor of 10 with ice-cold 1:1 MetOH:Acetone and incubated for 20 min at −20 C. Cells were then washed and stained as described above. For viability staining, Propidium Iodide (eBioscience) was added immediately before acquisition. Antibodies, used in various combinations were FITC labeled mouse CD45.1 (Invitrogen), BV421 labeled anti-mouse IgG1 (BD Bioscience), BV786 labeled anti-mouse IgA (BD Bioscience), BV421 or FITC labeled anti mouse CD19 (Biolegend), Alexa Fluor 700 labeled anti CD45RA/B220 (Biolegend), APC labeled anti-mouse CD138 (Biolegend), Pacific blue or PerCPCy5.5 labeled anti-mouse GL7 antigen (Biolegend), PE labeled anti-mouse CD80 (Biolegend), PE labeled anti Mo/Hu pERK1/2 (eBioscience), Alexa Fluor 700 labeled anti mouse CD38 (eBioscience), Alexa fluor 488 or Alexa fluor 594 or FITC or Alexa fluor 648 labeled anti his tag (MBL or Biolegend), Vioblue anti-mouse IgK (MACS), BV421 anti-human IgK (Biolegend). For assessment of IgK ablation, the following equation was used:

$$100 - \left(\left(\left(100 - IgK_{nogRNA}^{-}\right) \times 100\right)/\left(100 - IgK_{+gRNA}^{-}\right)\right).$$

ERK phosphorylation was assessed as previously described (Abbott, R. K. et al. Immunity 48, (2017)). In short, cells were washed and resuspended in PBS at 2E06 cells/ml. Cells were incubated for 3 min at 37° C. before supplementing by 5 μg of the YU2.DG gp120 antigen, incubated for one more minute and immediately put on ice and diluted by a factor of 2 with MetOH and incubated for 15 min at −20° C. before staining. Pre-gating for all experiments as in FIG. 34.

Data was compiled and analyzed using Kaluza Analysis 2.1 (Beckman Coulter).

Flow Cytometry for in vivo experiments: Harvested cells from spleen, bone marrow or blood were resuspended in cell staining buffer (Biolegend) and incubated with 2 g/100 1 of human anti-3BNC117 for 10 mins, washed and resuspended again in cell staining buffer containing primary antibodies. Secondary staining was performed in the dark, for 15 mins, with anti-human IgG1 AF647 (Abcam) or anti-human IgK BV421 (Biolegend). A list of antibodies and respective dilutions used in these experiments can be found in Supplementary Table 1. Then, cells were washed and data acquisition was performed on a CytoFLEX (Beckman Coulter) or FACS Aria III (BD Biosciences) for experiments involving cell sorting. Data were compiled and analyzed using Kaluza Analysis 2.1 (Beckman Coulter).

Western Blot. For in-vitro cultured primary lymphocytes secretion. Supernatants were collected and loaded with with Tris Glycine Sample Buffer (Life technologies) and optionally with NuPAGE reducing agent (Invitrogen) on Tris-Glycine gels (Invitrogen). Transfer occurred in 25 mM Tris 190 mM Glycine 20% MethOH to Trans-Blot Turbo (Bio-rad) Nitrocellulose membranes. Washing was done in TBST and Blocking with 3% BSA in TBST. HRP conjugated antibodies were allowed to bind overnight in Blocking buffer at 4° C. and membranes were washed multiple times before detection. Detection was done with EZ-ECL (Biological Industries) according to manufacturer protocol with an Amersham Imager 600 (GE Healthcare).

Enzyme Linked Immunosorbent assay. High binding micro-plates (greiner bio-one) were coated with 5 µg/ml of anti-idiotipe for 3BNC117 or 2 µg/ml gp120 in PBS overnight at 4° C. Plates were washed with PBST and blocked for two hours with 5% BSA in PBST, washed again and detection antibodies, anti-mouse IgA(abcam) or anti-mouse IgG or anti-mouse IgG1 or anti-mouse IgM (Jackson ImmunoResearch) were provided for an additional incubation of two hours at 2 µg/ml in PBST. Before detection with QuantaBlu (ThermoFisher) according to manufacturer protocols, plates were washed for an additional round. Detection was done in a Synergy M1 Plate reader (Biotek). The concentration of antigen specific antibodies was determined by reference to the dilution factor of the standard curve. The gp120 Env protein from THRO4156 clone 18 SVPB15 (GenBank accession number AY835448) was cloned in pcDNA3.1. gp120-YU2.DG was previously described (Yang, X. et al. Virol. 78, 12975-12986 (2004)) (for expression under the human CD5 leader sequence, and with a His-tag (6×) on the C terminus. Plasmids encoding gp120 were transfected into Expi293F cells at a density of 2E6 cells/ml in Expi293 Expression Medium (ThermoFisher) using ExpiFectamine (ThermoFisher) according to manufacturer protocols. Supernatants were collected 7 days later and bound with Ni-NTA Agarose (Qiagen) in 20 mM Sodium Phosphate, 0.5M NaCl, 10 mM Imidazole (ID). Beads were washed twice with the same buffer before mounting on gravity-flow Polypropylene columns (Biorad). Chromatography elution was performed in three fractions: 50, 100 and 200 mM ID. Elutes were buffer exchanged to PBS using Amicon Ultra-15 Centrifugal Filter Units (Merck) following filtration in 0.22 µm filter unit (Millex). For 3BNC117 and anti-idiotypic antibodies, 7.5 µg of a plasmid encoding the light chain and 22.5 µg of plasmid encoding heavy chain were co-transfected into Expi293F cells at a density of 2.0E6 cells/ml in Expi293 Expression Medium (ThermoFisher) using ExpiFectamine (ThermoFisher) according to manufacturer protocols. Purification of the supernatant, 7 days post transfection, was performed using MabSelect (GE Healthcare) following manufacturer recommendations.

Cleavage efficiency assays. Efficiency of Cas9 induced DSB was performed as previously described (Sentmanat, M. Sci. Rep. 8, 1-8 (2018)). In short, 300 ng of extracted genomic DNA was taken for PCR. From this reaction isovolumetric quantities were taken for analytic Agarose gel electrophoresis, for Sanger sequencing and for T7E1 assay. For T7E1, isovolumetric quantities of the reactions were put in NEB Buffer 2 (New England BioLabs) and DNA was denatured and reannealed in a thermocycler. T7 Endonuclease 1 (New England Biolabs) was added to the reaction and incubated at 37° C. for 20 min. Proteinase K was supplemented to the reaction and incubated for an additional 15 min at 37° C., cleavage was analyzed by Agarose gel electrophoresis and quantification was performed on unsaturated pictures, with area equivalent band definition using Bio-Vision (Villber). For TIDE, Sanger sequencing chromatography was analyzed with the online software (Desktop Genetics) using standard settings.

Agarose gel electrophoresis. Agarose (Hy-labs) was supplemented to 40 mM Tris, 20 mM Acetate, 1 mM EDTA for a final concentration of 1-2% depending on the gel. Gels were run at 160 v for 20-30 min. DNA ladders (markers) used were either 100 bp DNA Ladder H3 RTU (GeneDireX) or 1 Kb DNA Ladder RTU (GeneDireX). When needed, DNA was premixed with Gel Loading dye purple 6× (New England BioLabs).

Sequencing. All sequencings were performed by the ZABAM unit of Tel Aviv University.

Adoptive transfers, immunizations and serum collection. Engineered splenic cells were transferred to 6-9 weeks old female CD45.2 otherwise syngeneic C57BL/6 mice (Envigo) retro-orbitally at 1,500,000 to 2,200,000 cells/100 µl/mice in Mg+2 Ca+2 supplemented PBS with 5% Horse Serum. Mice were anesthetized with 0.1 mg/g Ketamine 0.01 mg/g Xylazine prior to transfer. Number of cells to be transferred was set to be 112,500 gp120 binding cells and ratio of cells was determined by flow cytometry prior to infusion. Cells were diluted in gRNA-transfected cells if needed and counted in a TC-20 automatic cell counter (Biorad). For immunizations, gp120 in PBS (200 µg/ml for 100 µl/20 µg/mice) was mixed at a 1:1 ratio with Alhydrogel 2% (Invitrogen) and injected intraperitoneally. Blood samples were collected by terminal bleeding in heparin. Sera from the different mice were distilled by repeated light centrifugation and collection of the supernatant until no erythrocytes were found. All mouse experiments were done with approval of TAU ethical committees.

In-vitro Activation assay. Pro B engineered cells were washed and resuspended in Cell Staining Buffer (BioLegend) at 2E06 cell/ml. Cells were incubated for 3 min at 37° C. before supplementing 5 µg gp120, incubated for one more minute and immediately put on ice and diluted by a factor of 2 with Fixing Buffer (1:1 MetOH:Acetone), incubated for 3 min on ice and provided with 0.5 volume of Permeabilization Buffer (0.1% NP40 in PBS). Cells were then stained at R.T. for 20 min, washed and resuspended before Flow Cytometry.

SHM optimization of mouse splenocytes. Whole spleens were extracted from 5-8 weeks old CD45.1 C57BL/6 mice and tissue was mechanistically crushed in PBS to be filtered in 70 µm Cell Stainer (Corning). Following Red Blood Cell lysis (Biolegend) cells were plated at 3.0E6 cells/ml in 1640 RPMI supplemented with 10% HI FBS, 50 µM β-Mercaptoethanol, P/S, 10 µg/ml LPS (SantaCruz Biotechnology)

and 10 ng/ml IL4 (Peprotech). Cells were cultured 16-24 h and washed twice in PBS before transfections and plated in the same activation medium without P/S after electroporations). Neon Electroporation (Invitrogen) was performed in 10 μL tips (Invitrogen). For all electroporations, 4E6 cells were pre-washed with PBS and resuspended in electroporation buffer R. Splenocytes were electroporated at 1350 v, 30 ms, 1pulse. Cells post electroporations were plated in antibiotic free medium, which was added 16 h after. For RNP, Cas9 and gRNA (ThermoFisher, IDT) complexes assembly and electroporations were proceeded using 36 pmol Cas9 pre-incubated with 88 pmol gRNA for each complex/2E6 cells. Transductions were performed not later than 5 min after electroporations at 4E6 cell/ml with a MOI of 50,000 of AAVDJ ADN171 (non-hotspot optimized) or AAVDJ ADN171XS (hotspot optimized). Efficiency of editing was performed two days after editing of the cells by Flow Cytometry. All experiments were brought to 7.5% gp120-YU2 binding cells from total pool. Engineered splenic cells were transferred to CD45.2 immunocompetent syngeneic mice (C57BL/6) retro-orbitally at 1,500,000 cells/100 μl/mice in physiological saline, for ~1E5 edited cells. The next day, gp120, either YU2 or THRO, in PBS (200 μg/ml for 100 μl/20 μg/mice) was mixed at a 1:1 ratio with Alhydrogel 2% (Invitrogen) and injected intraperitoneally. Spleens were collected 8 days post immunization for Flow Cytometry or FACS. For NGS, 25E3 splenic lymphocytes cells were sorted for CD45.1+ and RNA extracted using Quick RNA MicroPrep (Zymo Research). First round of PCR using gene specific primers for ADN171/XS and reverse pan-IgG primers using the Nextera index kit. PCR1/2 products are purified using AmpPure XP beads as instructed by the manufacturer, with quality control steps including Qubit and Tapestation. To increase the diversity of the segment of interest, both variable length amplicons (N nucleotide addition to the primers, up to 7 Ns) and high concentrations of PhiX (25%) were used. The samples are loaded with a 600 v3 kit for MiSeq sequencing.

Illumina sequencing and analysis. cDNA was generated from Quick RNA Microprep (Zymo) extracted RNA of total splenic lymphocyte populations with RevertAid using Oligo-dT primers. For Initial PCR amplification, VH fragments were amplified with the proofreading PrimeStarMAX polymerase (Takara) for 40 cycles. Libraries were purified using AMPureXP beads at a 0.7:1 ratio. Combined libraries were loaded at 5 pM with 25% PhiX control (Illumina). Sequencing was performed in a high-throughput MiSeq machine using the v2 Nano reagent kit 2×250 (Illumina) at the Genomic Reserach Unit (GRU) at the Faculty of Life Sciences, Tel Aviv University. Raw fastq files were submitted to Fast Length Adjustment of Short Reads (FLASH, Magoč, T. & Salzberg, S. L. FLASH: Bioinformatics 27, 2957-2963 (2011)) and resultant paired-end fasta files were submitted to the international ImMunoGeneTics database (IMGT) High V-Quest for V gene sequence alignment and germ-line gene assignment (Brochet, X., et al. Nucleic Acids Res. 36, 503-508 (2008)). IMGT aligned sequences were then processed by a series of quality control filters to remove truncated sequences, contained stop codons or ambiguous sequencing reads.

CHANGE-Seq

Genomic DNA from spleens of wild type C57BL/6OlaHsd using Gentra PureGene Tissue Kit (Qiagen) and quantified using Qubit (Invitrogen) according to manufacturer instructions. CHANGE-seq was performed as previously described20. Briefly, purified genomic DNA was tagmented with a custom Tn5-transposome to an average length of 400 bp, followed by gap repair with Kapa HiFi HotStart Uracil+ DNA Polymerase (KAPA Biosystems) and Taq DNA ligase (NEB). Gap-repaired tagmented DNA was treated with USER enzyme (NEB) and T4 polynucleotide kinase (NEB). Intramolecular circularization of the DNA was performed with T4 DNA ligase (NEB) and residual linear DNA was degraded by a cocktail of exonucleases containing Plasmid-Safe ATP-dependent DNase (Lucigen), Lambda exonuclease (NEB) and Exonuclease I (NEB). In vitro cleavage reactions were performed with 125 ng of exonuclease-treated circularized DNA, 90 nM of EnGen® Sau Cas9 protein (NEB), NEB buffer 3.1 (NEB) and 270 nM of sgRNA (Synthego), in a 50 μl volume. Cleaved products were A-tailed, ligated with a hairpin adaptor (NEB), treated with USER enzyme (NEB) and amplified by PCR with barcoded universal primers NEBNext Multiplex Oligos for Illumina (NEB), using Kapa HiFi Polymerase (KAPA Biosystems). Libraries were quantified by qPCR (KAPA Biosystems) and sequenced with 151 bp paired-end reads on an Illumina MiniSeq instrument. CHANGE-seq data analyses were performed using open-source CHANGE-seq analysis software (github.com/tsailabSJ/changeseq).

Neutralization Assay:

Under sterile BSL2/3 conditions, the PSG3 plasmid was co-transfected into HEK293T cells along with JRFL or YU2 HIV envelope plasmids using Lipofectamine 2000 transfection reagent (ThermoFisher Scientific) to produce single-round of infection competent pseudo-viruses representing multiple clades of HIV. 293T cells were plated in advance overnight with DMEM medium+10% FBS+1% Pen/Strep+1% L-glutamine. Transfection was done with Opti-MEM transfection medium (Gibco) using Lipofectamine 2000. Fresh medium was added 12 h after transfection. Supernatants containing the viruses were harvested 72 h later. In sterile 96-well plates, 25 μl of virus was immediately mixed with 25 μl of serially diluted (2×) protein A/G purified IgG (ThermoFisher) from mouse sera (starting at 500 μg/ml) and incubated for one hour at 37° C. to allow for antibody neutralization of the pseudoviruses. 10,000 TZM-bl cells/well (in 50 μl of media containing 20 μg/ml Dextran) were directly added to the antibody virus mixture. Plates were incubated at 37° C. for 48 h. Following the infection, TZM-bl cells were lysed using 1× luciferase lysis buffer (25 mM Gly-Gly pH 7.8, 15 mM MgSO4, 4 mM EGTA, 1% Triton X-100). Neutralizing ability disproportionate with luciferase intensity was then read on a Biotek Synergy 2 (Biotek) with luciferase substrate according to the manufacturer's instructions (Promega).

Statistical Analysis. Statistical Analysis was performed using GraphPad Prism 8 to calculate p-values with two-way ANOVA or unpaired two tailed Student's t-tests. For ANOVA, Tukey's multiple comparisons were performed were indicated. Outliers were identified using the ROUT method at Q=1%. Variances were analyzed using the F-test, Welch's correction was applied if significant.

Example 1

Establishing the Feasibility of Using a Target Site within a Murine IgH Locus

Figures 1B, 1C:
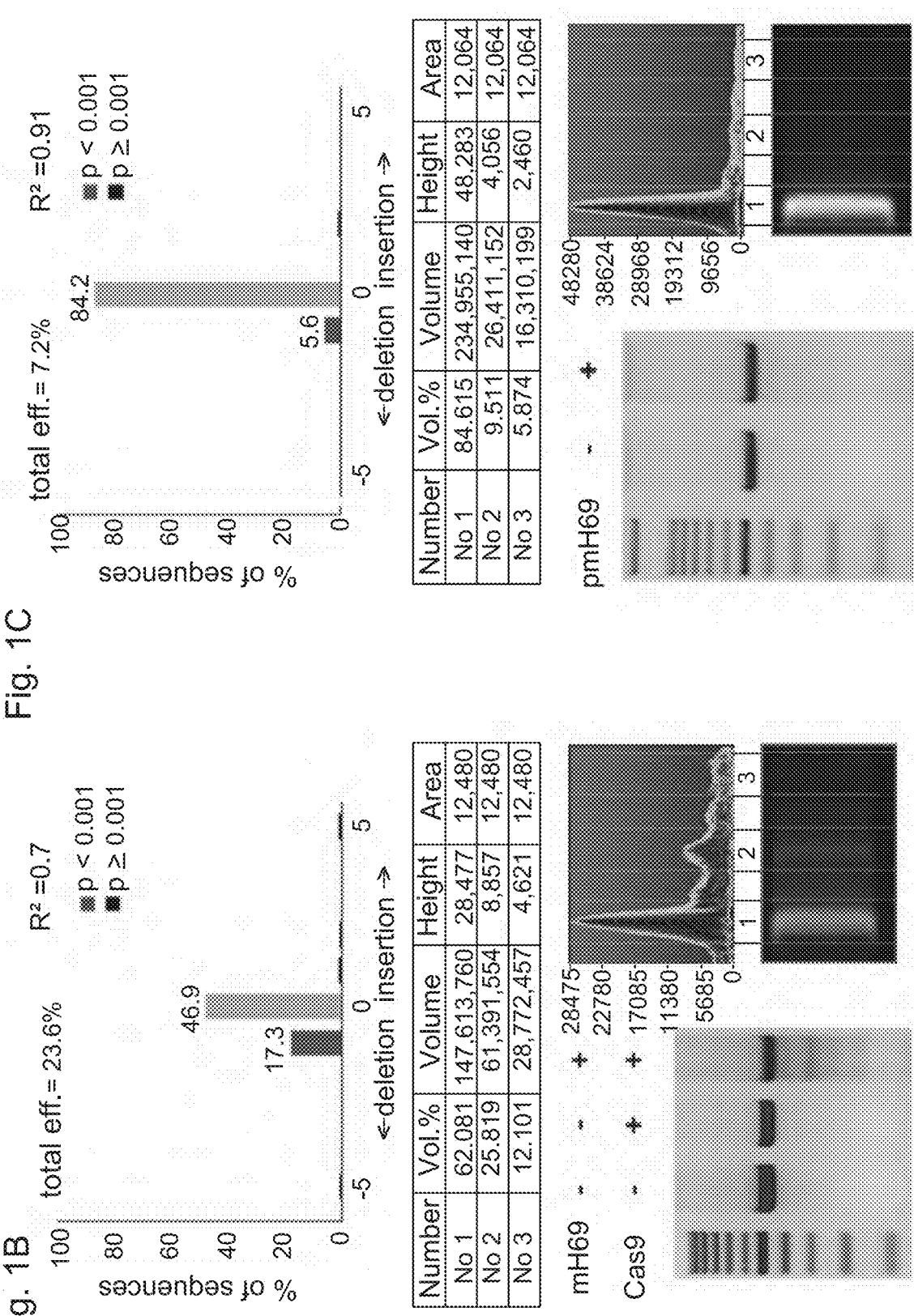
Figure 1D:
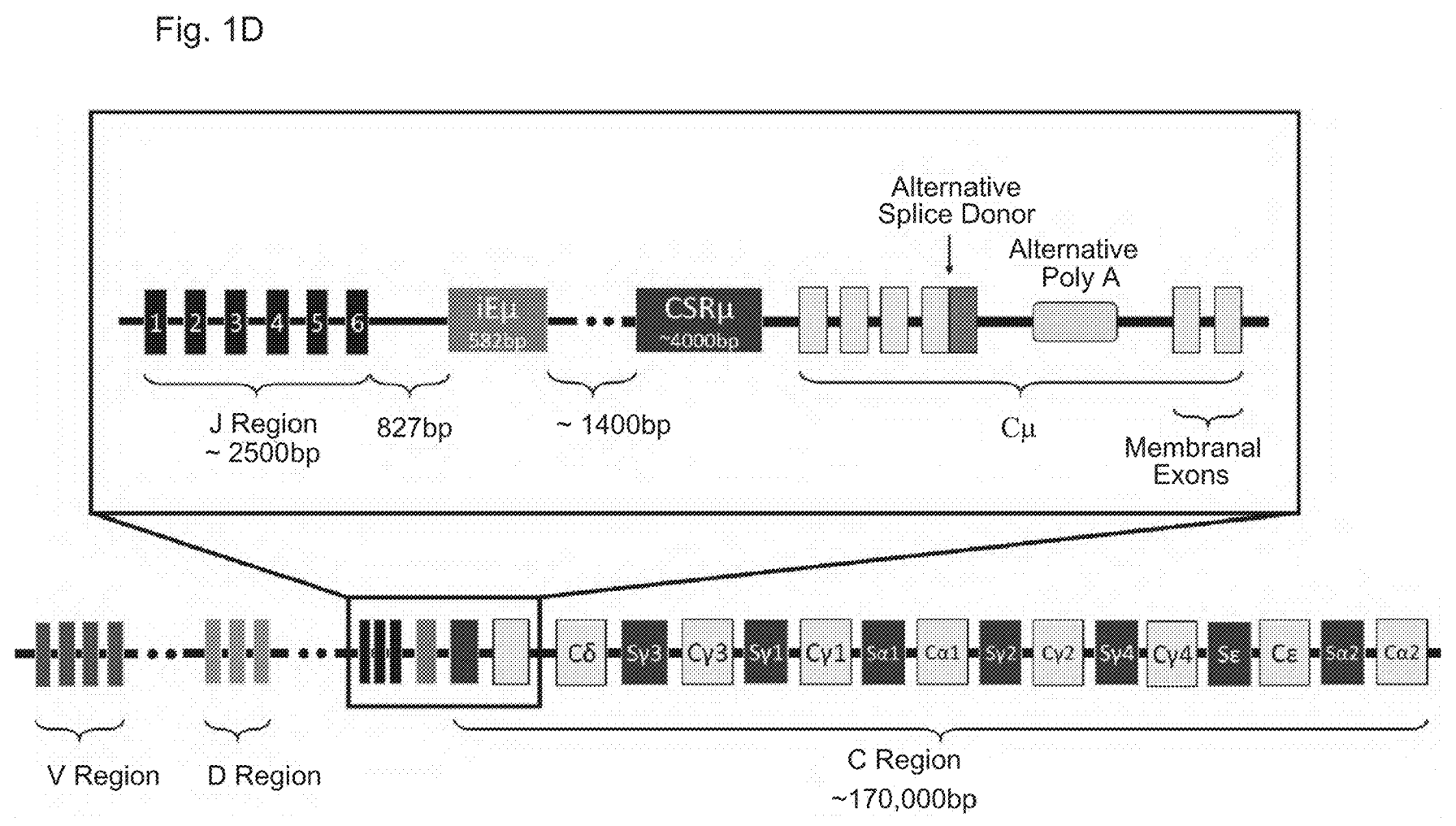

For engineering B cells for the expression of a desired transgenic B cell receptor (BCR) and subsequent antigen-induced activation for secretion of desired antibodies, the transgene must be inserted in a particular position that retain the natural well-controlled process involving affinity maturation, class switch recombination, and the retention of immunological memory. The inventors therefore elected as a target genomic locus for insertion of the desired sequence a site within the IgH locus, upstream of at least one splice acceptor site of a constant segment. The inventors first examined the recognition of such site by an RNA guided nuclease. Thus, cleavage by CRISPR/Cas9 at the mH69 site, situated downstream to the J region of the murine immunoglobulin heavy chain, was tested. The mH69 site is contained in the nucleic acid sequence as denoted by: SEQ ID NO: 33 found in the mouse IgH. The homology arms chosen for the Homology Directed Repair did not include the last J segment or the intronic Enhancer (iEμ) (as schematically represented in FIG. 1A). The nucleic acid sequence of the Left Homology Arm that was used in all the donors is as denoted by SEQ ID NO: 34. The nucleic acid sequence of the Right Homology Arm that was used in all the donors is as denoted by SEQ ID NO: 35. The gRNA used herein is denoted by SEQ ID NO: 16 and 17. As can be seen in FIG. 1D, the locus of the human IgH locus is very similar to the IgH locus of the mouse. TIDE or T7E1 analysis were performed and revealed efficient cleavage by CRISPR/Cas9 in a pro-B cell line, using mH69 guide RNA delivered either by ribonucleoprotein (RNP) transfection (FIG. 1B) or by transfection of a plasmid expressing both Cas9 and mH69 (FIG. 1C).

Example 2

Integration of GFP Constructs into the Cleavage Site within the IgH Locus Using CRISPR Technology Next, a GFP construct, designated ADN151, was constructed and used to evaluate the feasibility of effective integration into the target site, specifically, the mH69 CRISPR/Cas9 cleavage site (schematically represented in FIG. 2A). Left and Right Homology Arms (LHA, RHA respectively) flanked the genetic insert composed of a mutated IgH promoter that drives GFP expression upon genomic insertion into the mH69 site at the IgH. PCR analysis was performed and demonstrated integration of the ADN151construct into the mH69 site of a pro B cell line (see FIG. 2B). GFP expression in in-vitro cultured primary lymphocytes was shown by Flow Cytometry analysis (FIG. 2C). Expression levels of GFP were captured at 4, 7, 10 and 14 days after transfection of the donor plasmid with a plasmid expressing Cas9 and the specific gRNA mH69 or a nonspecific gRNA mK64. While transfection of a non-integrating plasmid with a strong promoter driving GFP expression shows a rapid drop in expression levels, only the specific gRNA mH69, allowed the signal from ADN151 to remain strong and stable. In addition, integration of the ADN151 construct into the mH69 site, allowing GFP expression was successfully performed in in-vitro activated primary splenic lymphocytes (see FIG. 2D). Lymphocyte gating following Cas9 transfection was analyzed with or without the mH69 guide RNA. GFP marking was observed only upon co-transfection of the mH69 guide RNA. Another GFP construct, the ADN157CF2 construct as schematically represented in FIG. 3A was tested for integration into the mH69 site. The ADN157CF2 construct was similar to the ADN151 construct described in FIG. 2A except that the promoter was preceded by a polyA to terminate upstream transcription and that the GFP gene did not terminate with a stop codon and a polyA site. Instead, in the ADN157CF2 construct, the GFP gene was followed by a sequence coding for a 2A peptide and a splice donor. The splice donor allows splicing with endogenous constant upon integration at the mH69 site while the 2A peptide allows translation separation between the GFP and the constant without risking nonsensemediated decay. RT-PCR analysis was performed and demonstrated both transcription and correct splicing following integration of the ADN157CF2 construct into the mH69 site in a pro B cell line (see FIG. 3B). The desired mRNA was detected only when the mH69 was inserted as a guide with the Cas9 protein (FIG. 3B, second lane from left) or as a plasmid (FIG. 3B, fourth lane from left). Sequence alignments of the positive bands obtained by RT-PCR was performed and show that splicing occurred between the inserted sequence and different exons of the endogenous Cμ (see FIG. 3C). It should be noted that the sequence of the positive band is as denoted by SEQ ID NO. 36. GFP expression was then assayed by Flow Cytometry at 3,6 and 10 days after transfection of the donor plasmid with or without RNP in a pro B cell line (see FIG. 3D). Only RNP transfection allowed the signal from ADN157CF2 to remain strong and stable.

Example 3

Integration of the Palivizumab Construct Using CRISPR Technology

The inventors next examined functional integration of a desired antibody transgene into the mH69 site. Therefore, a construct comprising nucleic acid sequences encoding a desired antibody was constructed similarly to the ADN157CF2 construct, and designated ADN191. As schematically represented in FIG. 4A, the GFP gene was replaced by a bicistronic cassette. This cassette encoded the full light chain of the anti-RSV antibody palivizumab followed by a 2A peptide sequence and the coding sequence for the variable domain of the palivizumab heavy chain terminating with an SD. In addition, an HGH leader sequence preceded each chain to allow Endoplasmic Reticulum localization for secretion. Transcription and splicing, after integration into the mH69 cleavage site, allowed the translation of a full palivizumab BCR. PCR analysis was performed and demonstrated the integration of ADN191 into the mH69 site in a pro B cell line (see FIG. 4B, Left panel). In addition, RT-PCR analysis shows transcription and splicing with the endogenous Cp in a pro B cell line and with the endogenous Ca in the B cell line i29, following integration of ADN191 into the mH69 site (see FIG. 4B, 4C, 4D). Flow cytometry assays were performed and show palivizumab expression as a BCR on the membrane of a pro B cell line following CRISPR/Cas9 induced integration into the mH69 site (see FIG. 4E). Expression on the membrane of the cells was detected only when the mH69 guide was delivered, either coded on a co-transfected plasmid or as RNP, together with the Cas9 protein.

Example 4

Integration of the 3BNC117 Construct Using CRISPR Technology

The functional integration of an additional desired antibody was next examined. another construct was produced, named ADN171. As schematically represented in the ADN171 construct scheme of FIG. 5A, the bicistronic Palivizumab cassette was replaced by a bicistronic 3BNC117 cassette encoding the full light chain of the anti-HIV antibody 3BNC117 followed by a sequence coding for a 2A peptide and the coding sequence for the variable domain of the 3BNC117 heavy chain terminating with an SD. The HGH leader sequences were replaced by human IgK and IgH, respectively, variable leader sequences. Transcription and splicing, after integration into the mH69 cleavage site, allowed the translation of a full 3BN117 BCR. RT-PCR analysis was performed and demonstrated both transcription and splicing with the endogenous Cµ in a Pro B cell line (FIG. 5B), i.29 B cell line (p53–/–, IgM+ variant) (FIG. 5C)and activated primary mouse Splenocytes (see FIG. 5D). Likewise RT-PCR analysis shows transcription and splicing with the endogenous Cγ2A in the A-20 B cell line, the Cα in i.29 B cell line (IgA+ variant) and with the Cγ1 in activated primary mouse Splenocytes (see FIG. 5E, 5F, 5G, respectively). Flow cytometry demonstrated 3BNC117 expression as a membranal BCR and binding to the HIV antigen gp140 (see FIG. 6A-6B). 3BNC117 expression was detected as an IgM BCR in a pro B cell line, see FIG. 6C. Detection of 3BNC117 expression as an IgM BCR was also observed (FIG. 6D(i), top right) or an IgG BCR (FIG. 6D(ii), bottom right) in activated primary splenocytes. As shown by the figure, only when the gRNA mH69 was present, expression on the membrane of double positive cells was detected. Analysis by flow cytometry of 3BNC117 expressing activated primary splenocytes shows that most of these cells expressed the 3BNC117 as an IgM BCR (FIG. 6E). Since the ADN171 was secreted in the supernatant of in-vitro cultured primary cells, sandwich ELISA of supernatants collected 3 days after Electroporation and Transduction of activated splenocytes was performed and shows showing specific binding to HIV antigen gp140 with the isotype IgG (FIG. 6F) or to HIV antigen gp120 with the isotypes IgG and IgM (see FIG. 6G).

Example 5

Integration of the 3BNC117 Using the Bi-Cistronic bNAb Cassette

Still further, an additional example of HIV broadly neutralizing antibodies (bNAb) was performed. First, CRISPR/Cas9 and recombinant adeno associated viral vectors (rAAV) were used to target the integration of the 3BNC117 HIV-bNAb (Scheid, J. F. et al. Science (80). 333, 1633-1637 (2011)) under an Ig promoter variant into the J-C intron of the IgH locus (FIG. 7A). 3BNC117 is a potent CD4-mimic HIV-bNAb chosen because, in combination with the 10-1074 bNAb, it was recently shown to induce viral suppression in viremic individuals (Bar-On, Y. et al. Nat. Med. (2018)) and in individuals undergoing treatment interruption (Mendoza, P. et al. Nature 561, 479-484 (2018)). The bi-cistronic bNAb cassette encodes the full light chain and the variable segment of the heavy chain (VH) of 3BNC117 separated by a furin cleavage site and a 2A-peptide for ribosomal skipping. The VH is followed by a splice donor sequence to allow fusion to constant segments and initial expression of the bNAb as a membranal B cell receptor (BCR). This design may allow disruption of the endogenous IgH chain while facilitating antigen-induced activation of engineered B cells upon immunization, leading to differentiation into memory and plasma cells, as well as to CSR, SHM and affinity maturation (FIG. 7A). CRISPR/Cas9 gRNAs were designed to promote cleavage of either the murine or the human IgH J-C intron. The specific target positions were chosen to allow donor-vector design with sufficiently long homology arms that contain neither the potentially oncogenic intronic-enhancer nor sequences corresponding to genomic segments that may be deleted during VDJ recombination. CRISPR/Cas9 cleavage produced up to 33% and 21% InDels, by the TIDE assay, at the IgH locus of an immortalized pro B cell line (ImProB, Lenden Hasse, H. et al. J. Immunol. Methods 451, 71-77 (2017)) and the Ramos human B cell line, respectively (FIG. 8A). Different gRNAs were used to disrupt the respective endogenous kappa light chains (IgK) in order to avoid chain mispairing. The IgK gRNAs target the splice acceptor junctions of the IgK constant segments, in order to avoid targeting the IgK chain of the transgenic bNAb. Following CRISPR/Cas9 cleavage, IgK expression was ablated in up to 19% and 16% in the murine and human cell lines, respectively (FIG. 8B). Next, the CRISPR/Cas9 ribonucleoprotein (RNP) electroporation was combined with rAAV transduction. First an rAAV encoding a GFP-cassette was used to validate that the activity of the Ig promoter variant is dependent upon on-target integration next to the Intronic enhancer. Indeed, high and stable GFP expression was demonstrated in the ImProB cell line, but only when the appropriate gRNA was co-delivered (FIG. 9). When using the bNAb cassette (FIG. 7A), the combined CRISPR/Cas9 electroporation and rAAV transduction resulted in 3BNC117 BCR expression in 9% and 8% of cells in the murine and human lines, respectively (FIG. 10A). mRNA analysis confirmed splicing of the integrated 3BNC117 with the expected constant segment in each cell line (FIG. 10B).

Example 6

Toll-Like Receptor (TLR) Mediated Ex Vivo Activation

Efficient engineering of primary B cells may require activation through either the CD40 pathway [3, 5] or the TLR pathway [4]. CD40 ligation can produce germinal center (GC)-like B cells ex vivo and antibody secreting plasma cells upon adoptive transfer. However, B cells activated ex vivo through CD40 ligation are not activated further in vivo upon immunization. In particular, these cells do not home to GCs, do not establish immunological memory and do not undergo SHM and affinity maturation [5]. In contrast, TLR-pathway mediated activation of donor B cells, coming from a transgenic mouse, was recently shown to allow homing to recipient's GCs upon immunization [4]. Murine splenic B cells were therefore activated using the TLR4 agonist lipopolysaccharide (LPS) and activated human blood B cells using an antibody against the TLR4 homolog RP105 (FIG. 11A). CRISPR/Cas9 RNP electroporation led to 24% and 29% InDel formation at the mouse and human IgH loci, respectively (FIG. 11B), and led to IgK ablation in 26% and 45% of cells, in the respective species (FIG. 11C). Following a subsequent rAAV transduction, up to 18% and 11% of cells expressed the 3BNC117 BCR amongst the activated murine and human cells, respectively (FIG. 7B-7D). The distribution of phenotypes as well as isotypes was similar among 3BNC117 expressing and non-expressing cells (FIG. 11D-11E). 3BNC117 secretion was minor but detectable (FIG. 11F). Importantly, high viability was retained following activation, electroporation and transduction of both mouse and human cells (FIG. 11G). Finally, engineered B cells of both species could be further activated ex vivo by incubation with the HIV gp120 antigen, leading to ERK phosphorylation (FIG. 7E)

Example 7

Adoptive Transfer

The inventors next evaluated the feasibility of an ex vivo treatment, by examining the ability of adoptively transferred engineered B cells to secret desired antibodies. The adoptive transfer of activated primary splenocytes that were engineered with the ADN171 construct described in Example 4 to express the 3BNC117 was examined in mice, as illustrated in FIG. 12A. ELISA assay was performed and shows detection of anti-gp140 antibodies secreted with isotypes IgM or IgG, captured with gp140, from Serum of immunized mice at day 7 (see FIG. 12B-12C). In addition, RT-PCR analysis demonstrates that extracted splenocytes from adoptively transferred and immunized mice show presence of ADN171 only in pre-activated cells (see FIG. 12D). Other conditions for adoptive transfer of activated primary splenocytes engineered with the ADN171 construct to express the 3BNC117 was also examined in mice, as illustrated in FIG. 12E. ELISA assay on the sera collected from mice at day 11 shows that mice immunized with gp120 barely generated a response to the antigen, in contrast to the adoptively transferred mice with 3BNC117 engineered B cells (see FIG. 12F).

Example 8

In-Vitro B Cell Activation as Per Phosphorylated ERK.

The inventors next evaluated the BCR dependent activation of engineered B cells expressing an engineered 3BNC117 BCR. Following in-vitro activation of engineered Pro B cells using gp120, cells were monitored for phosphorylation of ERK (pERK), a known downstream effector in the BCR dependent activation (Abbott, R. K. et al. Immunity 48, (2017)). As shown in FIG. 13, only cells engineered for expression of 3BNC117 on their membrane showed an increase of phosphorylated ERK (pERK). This result demonstrates proper functional activation of the engineered B cells.

Example 9

In Vivo Functionality Assessment

Still further, in order to assess functionality in vivo, activated splenic B cells of CD45.1 C57BL/6 mice were first engineered to express 3BNC117, using the cassette of Examples 5 and 6, and the cells were then adoptively transferred into an otherwise syngeneic CD45.2 mice. Each recipient mouse received 1.5-2.2M donor cells, such that the number of 3BNC117 expressing cells transferred was set at 112,500. Different groups of mice subsequently received only prime or both prime and boost immunizations and were bled to assess serum antibody concentration or sacrificed to analyze the splenic B cell population (FIG. 14A). Different groups were immunized with the gp120 antigen of the YU2.DG HIV strain, efficiently neutralized by 3BNC117, or by the gp120 antigen of the THRO4156.18 HIV strain, which is poorly neutralized by 3BNC117 (Boumazos, S. et al. Cell 158, 1243-1253 (2014)). 3BNC117 has a much higher affinity to the YU2.DG antigen (FIG. 15A, 15B), but the antigens are otherwise comparable, both coming from clade B HIV-1 strains. While less than 10% of the transferred cells were gp120 binders, following immunization with either antigen, the vast majority of CD45.1 expressing cells in the GCs bound gp120 (FIG. 14B-14C), a strong indication for antigen-induced homing to GCs. Furthermore, while gp120 is immunogenic to mice, irrespective of B cell engineering (FIG. 16), 8 days following prime immunization with either antigen, relevant splenic GCs were monopolized by donor cells, with more than 90% of gp120 binding cells expressing CD45.1 (FIG. 14D-14E). Therefore, in patients, activation of engineered B cells encoding high-affinity antibodies may come at the expense of the lower affinity endogenous response (Cirelli, K. M. et al. Cell 177, 1-19 (2019); Woodruff, M. C., Kim, E. H., Luo, W. & Pulendran, B. Cell Rep. 25, 321-327.e3 (2018)).

Prime Immunizations with YU2.DG gp120 allowed higher serum concentrations of the 3BNC117 Ab compared to the concentrations following prime immunizations with THRO4156.18 (FIG. 17A). However, importantly, a log increase in serum Ab concentrations was measured following boost immunization, reaching nearly 1 g/ml using either of the antigens (FIG. 17A, FIG. 18). Such high 3BNC117 serum concentrations were previously demonstrated to allow broad HIV neutralization (Shingai, M. et al. J. Exp. Med. 211, 2061-2074 (2014)). The rate of engineered cells in the GCs has also significantly increased following boost immunization with either of the antigens (FIG. 17B, FIG. 19A). Compared to mice receiving both prime and boost immunizations, rates of engineered cells in the GCs were lower in mice analyzed at a late time point after receiving only an early prime immunization and in mice receiving only a late prime immunization (FIG. 17C-17D). Therefore, importantly, the boost effect can be strictly attributed to the retention of immunological memory. Indeed, immunophenotyping of the donor cells in the spleen revealed that the engineered cells were differentiating into both CD138$^+$ Ig secreting cells and CD38$^+$ memory B cells (B$_{mem}$) (FIG. 17E, FIG. 19B). Interestingly, immunization with the YU2.DG gp120 antigen induced higher rates of differentiation into memory B cell compared to immunization with the THRO4156.18 antigen. In addition, the rate of splenic memory B cells was increased while the rate of plasma cells was decreased following boost immunization with either of the antigens, in concordance with natural murine boost responses (Dogan, I. et al. Nat. Immunol. 10, 1292-1299 (2009)). CSR may be necessary to ensure both humoral and mucosal protection from HIV surge. Indeed, both IgG$_1$ and IgA isotypes of 3BNC117 antibodies were found in the sera of treated mice in addition to the IgM isotype (FIG. 20A). Similarly, engineered cells expressing the IgA isotype were found in the GCs of treated mice (FIG. 20B). CSR was more efficient when the YU2.DG gp120 antigen rather than the THRO4156.18 antigen was used for immunization, in agreement with the higher rates of splenic memory B cells in mice immunized by the YU2.DG antigen. However, the rate of IgA expressing cells in the GC was decreased upon boost immunization. Notably, rates of IgA expression among donor cells in the GCs, after immunizations with YU2.DG, were higher than the pre-implantation rates, implying antigen-induced in vivo CSR (FIG. 20C). A schematic representation summarizing the evolution of engineered B cells following engraftment is provided in FIG. 21.

Example 10

Incorporation of SHM Hotspots into the 3BNC117 Construct

Without being bound by the theory, the inventors hypothesized that antibody sequences in engineered B cells may also undergo SHM. However, this may be hindered by prior saturation of sequence hotspots for activation-induced-cytidine-deaminase (AID, catalyzing SHM) in the natively coded 3BNC117 [11-12]. To optimize affinity maturation of engineered B cells expressing the variable region of the anti-HIV 3BNC117 antibody, the CDR loops were filled in both variable sequences of SHM hotspots (defined as WRCH/DGYW and RCY/RGY) on both strands. An amount of 83 new hotspots comprising 39 new WRCH/DGYW sequences and 44 new RCY/RGY were generated as detailed in Table 3. The following methodology was employed: GeneART (ThermoFisher) codon optimization of the base sequence for the whole Vl/Vh segments was performed (ADN170 derivatives; sequences slightly changed from the 3BNC117 published sequence). Then additional RCY and WRCH sequences were manually added as follows: sequence almost matching the hotspots in the CDR loops were found by removing a single nucleotide from the full hotspot sequence using SnapGene software (GSL Biotech). Then the relevant spot was mutated when possible (silent mutations), and codons with a higher score for the *Mus musculus* genome were chosen. In some embodiments, the following steps were used: In a first step (1), searching for the sequence WNCH. The second step (2), involves looking for the relevant codon the N nucleotide stands for. The third step (3), involves changing the N nucleotide for a R nucleotide if mutation is silent. Lastly, the final step involves analysis of the whole variable sequences for splice donors/acceptors using the Splice Site Prediction tool by Neural Network (Berkeley). Three consecutives versions were thus generated, the original version, the GeneART version and the ADN's SHM optimized version. The ADN's SHM optimized version was then ordered for cloning. Only CDR loops and surroundings were changed between the GeneART and the ADN's SHM version. FIGS. 22-27 demonstrate the optimization steps performed in the 3BNC117 heavy and light chain CDRs coding sequences. More specifically, in FIGS. 22-27, features in light grey are WRCH/DGYW or RCY/RGY spots unchanged from previous version (present in ADN170 derivatives), features in gray are new spots for the GeneART version, dark gray spots were removed on the next version and darker gray spots were newly added in the ADN's SHM version. Nucleotides in red are unchangeable nucleotides (not all unchangeable nucleotides are annotated), in blue are nucleotides that were changed by ADN, and in green are remodified for manual SD/SA removal.

TABLE 3

Number of hotspots present in the initial version versus optimized AND's SHM version of the variable region of the heavy chain and the light chain in the 3BNC117 construct. WRCH/DGYW and RCY/RGY and C/G sequences were counted into the whole Variable sequence.

| Sequence | Hotspot | $V_H$ | $V_L$ |
|---|---|---|---|
| Initial | WRCH/DGYW | 16 | 19 |
| | RCY/RGY | 45 | 28 |
| | C/G | 204 | 144 |
| ADN's SHM opt | WRCH/DGYW | 38 | 36 |
| | RCY/RGY | 65 | 52 |
| | C/G | 220 | 170 |

The nucleic acid sequences of the variable regions of the heavy and light chains were then modified and are as detailed in Table 4.

TABLE 4

Sequence identity numbers of the nucleic acid sequences of the variable regions of the heavy and light chains of the 3BNC117 construct during optimization.

| | Variable heavy chain | CDR1 of Vh | CDR2 of Vh | CDR3 of Vh | Variable light chain | CDR1 of Vl | CDR2 of Vl | CDR3 of Vl |
|---|---|---|---|---|---|---|---|---|
| ADN170 | SEQ ID NO: 38 | SEQ ID NO: 41 | SEQ ID NO: 46 | SEQ ID NO: 47 | SEQ ID NO: 76 | SEQ ID NO: 79 | SEQ ID NO: 84 | SEQ ID NO: 89 |
| GeneART optimization | SEQ ID NO: 54 | SEQ ID NO: 57 | SEQ ID NO: 61 | SEQ ID NO: 64 | SEQ ID NO: 92 | SEQ ID NO: 95 | SEQ ID NO: 99 | SEQ ID NO: 103 |
| ADN's SHM optimization | SEQ ID NO: 65 | SEQ ID NO: 68 | SEQ ID NO: 71 | SEQ ID NO: 75 | SEQ ID NO: 114 | SEQ ID NO: 106 | SEQ ID NO: 110 | SEQ ID NO: 113 |

The amino acid sequences of the CDRs of both the heavy chain and the light chain were conserved during the optimization process and are as detailed in Table 5.

TABLE 5

Sequence identity numbers of the amino acid sequences of the CDRs of the variable regions of the heavy and light chains of the 3BNC117 construct.

| | CDR1 | CDR2 | CDR3 |
|---|---|---|---|
| Variable Heavy chain | SEQ ID NO: 42 | SEQ ID NO: 47 | SEQ ID NO: 52 |
| Variable Light chain | SEQ ID NO: 80 | SEQ ID NO: 85 | SEQ ID NO: 90 |

A schematic representation of the loci surrounding CDR loops for the Kappa Light Chain and Heavy Chain of 31BNC117 encoded donors either W. T. or recoded for SHM hotspots is provided in FIG. 28A.

Example 11

Adoptive Transfer of the SHM Hotspot Optimized 3BNC117 Construct

First engineered splenocytes transduced either with SHM optimized construct (named ADN171XS, and also referred to herein as 3BNC117-opt) or non SHM optimized construct (named ADN171) were produced in vitro. The percentage of gp120-YU2 binding cells was then analyzed by Flow cytometry (see FIG. 29A-29I). As seen in FIG. 29A, the percentage of gp120-YU2 binding cells in cells transduced with ADN171XS (3BNC117-opt) was equivalent to those transduced with ADN171 (3BNC117-wt), supporting that the amino acid sequence and thus the structure of the antibody was not altered by SHM optimization. Adoptive transfer of activated primary splenocytes that were engineered with the SHM optimized 3BNC117 construct (named ADN171XS) was then performed in mice, as illustrated in the scheme of FIG. 30. Flow cytometry and Next generation sequencing allow to analyze and compare the antibodies resulting from non-SHM optimized versus SHM-optimized sequences and assess affinity maturation. Cells standardized to be gp120-YU2 binders at 7.5% following either ADN171 or ADN171XS were injected into CD45.2 recipient mice. The following day, mice were immunized with either gp120-THRO or gp120-YU2 in alum. Spleens were collected at the prime response (see FIG. 30) and stained for CD45.1, gp120-YU2 binding, GL-7 and B220. FIG. 31 depicts double positive rates of CD45.1 gp120-YU2 binding from Germinal Center B cells (pre-gated on B220, GL-7, singlets, Alive lymphocytes). When comparing the effect of each construct over the other, prime YU2 seemed to imply a better response with ADN171XS (the percentage of CD45.1 and gp120-YU2 binding B cells in the germinal center was higher in mice which were injected with splenocytes transduced with SHM optimized construct (ADN171XS)). However, as shown in FIG. 28B, this response is not conserved in Boost YU2. Interestingly, Boost THRO seems to also imply a better response with ADN171 than ADN171XS, however, in a non-significant manner. The slight differences between FIGS. 31 and 28B may be due to updated gating strategy. Accumulation in mouse GCs following immunizations was similar whether the adoptively transferred B cells were engineered by a 3BNC117-wt or a 3BNC117-opt encoding rAAV vector (FIG. 28B). These results establish the feasibility of using the hotspot optimization for improving specific antigen recognition by antibodies produced by the genetically engineered B cells of the invention. FIG. 32 shows Next-Generation Sequencing (NGS) sequencing results of a mouse receiving the ADN171XS edited cells, immunized with gp120-YU2. More specifically, to verify the in vivo SHM optimization, RT-PCR analysis was performed on total spleen obtained from the recipient mice. The variable segments were amplified and sequenced using MiSeq (illumina). FIG. 32A shows the amino acid sequence of the SHM optimized CDR2 region of the variable heavy chain, as denoted by SEQ ID NO. 115. The relative height of the specific residues reflects the relative frequency of the amino acids in each particular position as obtained from a pool of 233 sequences obtained. RNA was harvested from the spleens of mice receiving 3BNC117-opt engineered cells and amplified the bNAb $V_H$ sequence from the cDNA for analysis by Illumina sequencing. FIG. 32B shows the amino acid sequence of the SHM optimized full variable heavy chain, as denoted by SEQ ID NO. 116. As shown by the figure, mutations occurred preferably in the CDR2 loop (residues 49-66), residues 77-79 were deleted and few mutations also led to variations in the CDR3 loop (residues 94-111), mainly at positions 94-99. Alternative residues present in each specific position are indicated in the figure and in the sequence listing.

FIG. 33, is an additional schematic representation of the high prevalence for mutations in the heavy chain CDR1, CDR2 and CDR3 loops and amino acid involved in gp120 interaction as monitored by NGS sequencing in a single mouse receiving SHM optimized donor and prime immunization with YU2. Thus, the improvement in antigen recognition is a clear result of the SHM optimization by the method of the invention. Still further, by analyzing the most abundant mutant clones from each mouse, a strongly biased distribution was found of mutations along the antibody sequence. In particular, even after normalizing to sequence length, amino acid substitutions could rarely be found in the clusters of differentiation (CDRs) while frameworks 2 and 3 were rich in substitutions (FIG. 20D-20E, FIG. 28C, 28D). The biased distribution indicates that the substitutions stem from true SHM and further implies that missense mutations at the CDRs, which often hinder antigen binding, preclude B cell retention in the GCs. However, some rare CDR mutations may facilitate affinity maturation. Indeed, the only variants reaching more than 10% frequency among the mutants in any of the mice were the substitutions P58S in CDR2 and A101T, which is in a border position, sometimes attributed to CDR3 (Lefranc, M. P. et al. Dev. Comp. Immunol. 27, 55-77 (2003)). In addition, the substitutions D86G, W37G/R, D86G/A and Y98C were found to be prevalent and common to different mice indicating biased SHM or convergence by selection. Interestingly, in mice immunized by the YU2.DG gp120 antigen, we found a trend for higher clonality of mutated alleles than in mice immunized by the THRO4156.18 antigen (FIG. 28E) While not being statistically significant, the trend is in line with the higher accumulation of engineered B cells (FIG. 17B) and the higher CSR rates (FIG. 20A-20C) in the GCs of mice immunized by the YU2.DG gp120 antigen.

Example 12

Successful Use of the Endogenous VH Promoter by Cassette that Includes SA

Safety may be increased by using promoter-less expression of the 3BNC117 anti-HIV bNAb cassette (also designated herein as ADN221), such expression may more strictly prevent expression from episomal leftovers or off target integrations. To demonstrate the feasibility of this strategy, the inventors next replaced the polyA and minimal promoter fragments of the bNAb cassette with a splice acceptor (SA), as illustrated in FIG. 35A, thereby creating the donor cassette ADN174 (as denoted by SEQ ID NO. 174). Following electroporation of the donor cassette ADN174 to proB cell line, RNA was extracted and cDNA generated using OdT primers. Next, the cDNA was amplified by PCR using primers P2A 174 R: CATGTCCAT-AGGTCCAGGGTTCTCCTC, as denoted by SEQ ID NO. 276 and a multiplex of primers sitting on the J segments, specifically, the mIgHJ1 F1 primer: GCACAGGGAC-CACGGTCAC, as denoted by SEQ ID NO. 277 and mIgHJ2 F1: GCCAAGGCACCACTCTCACAG, as denoted by SEQ ID NO. 278, and mIgHJ3 F1: GACTCTGGTCACTGTCTCTGCAG, as denoted by SEQ ID NO. 279 and mIgHJ4 F1: GGTCAAGGAACCTCAGT-CACCG, as denoted by SEQ ID NO. 280, for integration with the endogenous J segment of the IgH locus, and with P2A F1: GAGACGTGGAGGAGAACCCTG, as denoted by SEQ ID NO. 281 and mIgHM CH2 R1: CGTGGTGGGACGAACACATTTAC, as denoted by SEQ ID NO. 282, for integration with the IgHM constant exons. Successful integration, expression and splicing of the donor cassette (ADN174) with the endogenous J segment of the IgH locus of proB cell line was demonstrated by the RTPCR shown in FIGS. 35B and 35D, and between the donor cassette with the endogenous IgHM constant exons as shown by FIGS. 35C and 35D.

These results clearly establish the feasibility of targeting the J-C intron with a safe and effective cassette that uses the endogenous VH promoter.

Example 13

Integration of a GFP Construct Using Class Switch Recombination (CSR)

Next, the CSR technology was used in order to integrate a transgene into the IgH locus. The CSR process, as it occurs in nature is schematically represented in FIG. 36A. Once a B cell is activated and enters into the CSR process, Double strand breaks are formed in the particular region of interest and a ectopically added transgene may be introduced into the IgH locus (see FIG. 36B). CSR was then induced in murine B-cells (splenocytes) with IL4 in order to produce activated B-cells (comparison between activated and non-activated B-cells is provided in FIG. 37A). Activated B cells as well as non-activated B cells were then transduced with rAAV containing a GFP construct comprising SFFV promotor-GFP gene-SD. GFP fluorescent cells were obtained only with activated B cells (FIG. 37B). Different AAV serotypes were then tested on activated murine B-cells: AAV serotypes 6,1 and DJ, post-LPS activation (MOI: 10,000 vg/cell). The AAV-DJ provides the highest number of GFP positive cells (see FIG. 37C). The integration of the GFP construct was also validated by RT-PCR analysis (see FIG. 37D).

Example 14

Integration of the Palivizumab or the 3BNC117 Antibody Construct Using Class Switch Recombination (CSR)

Next, the Palivizumab construct (ADN191) was targeted to the IgH locus of murine activated B-cells via ssAAV, using the CSR process. The construct is schematically represented in FIG. 38A and comprises a 5' polyA signal followed by a mutated V region minimal promoter, the complete Palivizumab light chain, a P2A cassette, the variable heavy segment of the Palivizumab heavy chain and the J1/J4 splice donor. RT-PCR analysis revealed correct splicing between the ADN191 construct and the IgH locus, following AAV transduction of murine B-cells (see FIG. 38B).

B-Cells Engineered Using CSR Secrete High Amounts of Transgenic Antibodies Upon Adoptive Transfer in Immunocompetent Mice Encouraged by the successful integration of the GFP and the Palivizumab constructs into the IgH locus, the inventors next used the CSR technology in order to integrate the 3BNC117 anti-HIV bNAb cassette into the IgH locus. CSR was then induced in murine B-cells (splenocytes) with LPS+mIL4 to activate B-cells, followed by transduction of the activated B cells with 3BNC117-expressing AAV-DJ. FIG. 38C shows the experiment time-line where 6 days prior to adoptive transfer, murine B cells were activated, following transduction of the AAV construct shown in FIG. 38D. A timeline for the adoptive transfer of cells engineered is shown in FIG. 38E. FIG. 38F discloses the ELISA analysis on mice sera that were taken at the timepoints indicated in the time-line (FIG. 38E), comparing the 3BNC117-IgG secretion levels of treated mice vs. control mice that received non-engineered cells. These results therefore demonstrate the feasibility of successfully integrating a functional antibody encoding cassette into the IgH locus using CSR.

Example 15

In Vivo Engineering of B Cells to Express an Anti-HIV bNAb

Following the accomplishment of ex-vivo engineering, activation and adoptive transfer of B cells, that resulted in successful in-vivo differentiation into memory and plasma cells, as well as to CSR, SHM and affinity maturation, as determined by the preceding Examples, the inventors next demonstrated the feasibility of promoting in vivo engineering of B cells. A pair of AAV-DJ vectors [Grimm, D. et al. *J. Virol.* 82, 5887-5911 (2008)]. was used, one coding for saCas9 [Ran, F. A. et al. *Nature* 520, 186-191 (2015)] and the other coding for the 3BNC117 anti-HIV bNAb [Scheid, J. F. et al. *Science* 333, 1633-1637 (2011)](FIG. 39A). In the first set of experiments, the saCas9 is expressed from the ubiquitously active CMV promoter, and the sgRNA, targeting saCas9 to the IgH locus, is coded on the same AAV. The bNAb, in turn, is coded as a bi-cistronic cassette under the control of an IgH-enhancer-dependent promoter and flanked by homology arms to the desired saCas9 cut-site within the J-C intron of the IgH locus (FIG. 40). The bNAb cassette includes the full light chain and the variable segment of the heavy chain ($V_H$) being separated by a sequence coding for a Furin cleavage site and for a 2A-peptide. A splice donor sequence follows the $V_H$ gene segment in order to allow its fusion to constant IgH exons, upon integration into the locus and subsequent transcription and splicing. This design facilitates disruption of the endogenous IgH locus and initial bNAb expression as a membranal B cell receptor (BCR). Importantly, this allows for subsequent activation of the engineered B cells upon antigen-binding, which leads to differentiation into memory and plasma cells.

B cell activation is required for efficient AAV transduction. Subsequent activation signals for the engineered B cells may benefit from prior priming of T helper cells and from presentation of appropriate immune complexes by follicular dendritic cells. AAV injections to mice were thus preceded by pre-immunizations, modeling a pre-existing infection. In particular, C57BL/6 mice were immunized with 20 µg of the gp120 HIV antigen, which is the target of 3BNC117. On day 6 post-immunization, each mouse was injected with 5E11 vg of a bNAb coding (donor) vector, 5E11 vg of the saCas9 coding vectors, or both (FIG. 39B). The mice then received additional immunizations at days 8, 23, 68, 98 and 128. Following the boosting regimen, mice receiving both a donor vector and an saCas9 vector had up to 5 µg/ml of the 3BNC117 bNAb in their blood (FIG. 39C-39D). While this experiment used the monomeric gp120 antigen of the clade B HIV strain YU2.DG, high titers could also be obtained in an independent experiment using the clade A, BG505-based native trimer nanoparticle immunogen (MD39-ferritin) [Steichen, J. M. et al. *Immunity* 45, 483-496 (2016)], attesting for the breadth of the 3BNC117 expressing cells in vivo (FIG. 41). Mice injected with both a donor vector and an saCas9 vector had much higher 3BNC117 titers than mice receiving donor vector only. Nevertheless, 3BNC117 titers in mice receiving only the donor vector exceeded the background levels measured in mice injected with PBS (FIG. 39D). Indeed, integration of the antibody gene into the IgH locus was evident by nested RT-PCR followed by Sanger sequencing on splenic B cell RNA from mice receiving dual vector injection as well as from two of the mice injected with the donor vector only (FIG. 42). Notably, engineered cells have secreted antibodies of multiple isotypes (FIG. 43). Finally, IgG purified from treated mice can neutralize autologous YU2.DG and heterologous JRFL HIV pseudoviruses (FIG. 39E, FIG. 44). This demonstrates a potent and functional bNAb response from in-vivo engineered B cells upon vaccination.

Example 16

Rate of In Vivo B Cell Engineering at the Cellular Level

Next, the inventors used flow cytometry to estimate the engineering rates at the cellular level.

The frequency of 3BNC117-expressing cells reached 1-3% of total blood B cells following the later immunizations in all mice injected with both a bNAb vector and an saCas9 vector, but not in mice injected with PBS or with the bNAb vector alone (FIG. 45A-45C). Upon sacrificing the mice at day 136, 8 days after the last immunization, up to 23% of the plasmablasts in the spleen expressed 3BNC117 (FIG. 46). In addition, the rate of 3BNC117-expressing splenic cells was between 5% to 10% among germinal center (GC) B cells (FIG. 45D-45E, FIG. 47), while between 1% to 2% of bone marrow lymphocytes were 3BNC117-expressing B cells (FIG. 48). No significant expression of 3BNC117 was detected in mice receiving donor vector alone in any of the tissues.

Example 17

Somatic HyperMutation (SHM) and Clonal Selection of In Vivo Engineered B Cells

In order to study somatic hypermutation and clonal selection, the inventors extracted DNA from the liver and the spleen of one of the treated mice at day 136 and performed Illumina sequencing of amplified 3BNC117 VH segments. Much of the mutation repertoire was shared between the liver and the spleen and may thus reflect heterogeneity in AAV production that is subjected to little or no selection. In particular, all the 3BNC117 VH variants found to be over-represented in the liver are also over-represented in the spleen. Importantly however, the inverse is not true. The CDR1 substitution R30K is the most prevalent substitution in the spleen. It accounts for more than 20% of all mutants in the spleen but is found at very low abundance in the liver (FIG. 45F). Indeed, bNAbs of the VRC01 family were shown to have side chain interactions with the HIV gp120 antigen at position 3016 One may speculate that the conservative R30K substitution in 3BNC117 relieves some steric clash upon binding to monomeric gp120. Including R30K, a total of five different positions along the VH segment showed signs of positive selection in the spleen by dn/ds analysis (FIG. 49), although analysis may be less informative regarding the two positions at the distal extremes, which are assigned high dn/ds values also in the liver. The inventors therefore concluded that the in vivo engineering and immunization scheme has led to clonal expansion that is limited in span but pronounced in its magnitude.

Example 18

AAV Biodistribution and saCas9 Off-Target Cleavage Analysis Reveal a High Safety Profile Next, the inventors assessed the possible off-target effects of the demonstrated in vivo engineering approach. First, the inventors quantified the copy number of the bNAb cassette from various tissues. Then bNAb cassette was found at a high copy number in the liver at day 37 (FIG. 50A) and the levels were reduced by only 10-fold at day 136 (FIG. 50B), reflecting high retention of AAV episomes in the liver. High copy number was also found in the blood at day 37, but levels dropped sharply by day 136, perhaps due to multiple cell divisions (FIG. 51A). Interestingly, the AAV copy number in the bone marrow was significantly increased from day 37 to day 136, and a non-significant similar trend was also detected in the lymph nodes, indicating the possible accumulation of 3BNC117-expressing cells in these tissues (FIG. 50B). The copy number in the liver was similar whether or not the saCas9 coding AAV was co-injected to the mice. In contrast, donor AAV copy number in the lymph nodes and in the bone-marrow was found to be logs higher with saCas9 AAV co-injection, signifying the selection of 3BNC117-expressing B cells (FIG. 50C, FIG. 51B). To define the genome-wide off-target activity of SaCas9, circularization for high-throughput analysis of nuclease genome-wide effects was performed by sequencing (CHANGE-seq) [Lazzarotto, C. R. et al. Nat. Biotechnol. (2020)] on genomic DNA from C57BL/6 mice. Thirty-one on- and off-target sites were identified, characterizing the sgRNA target site as highly specific (CHANGE-seq specificity ratio=0.95) (FIG. 50D). Targeted sequencing was then performed on four off-target sites and the on-target site using genomic DNA from liver and spleen of treated mice and from a negative control mouse. Relative to control DNA from the spleen of an untreated mouse, a trend for a higher mutation rate, indicating error prone repair of CRISPR/Cas9 induced double-stranded DNA breaks, was evident at the IgH on-target site but not in any of the tested off-target sites (FIG. 50E).

Example 19

Safety Improvement of the In Vivo System

The coding of the sgRNA together with the saCas9 on the same AAV is predicted to allow DNA cleavage in many cells that are not co-transduced with the donor AAV. The resulting, non-productive, cleavage may be avoided if the sgRNA cassette is instead separated from saCas9 gene and coded on the donor AAV (FIG. 52). Repeating the above mouse experiments (FIG. 39B) with this new pair of AAVs allowed high 3BNC117 titers following repeated immunizations (FIG. 53), and the frequency of 3BNC117-expressing cells reached 0.5%-3% of total blood B cells (FIG. 54). Upon sacrificing the mice at day 136, up to 10% of splenic plasmablasts expressed 3BNC117 (FIG. 55). In addition, up to 7% of splenic B cells with a germinal center phenotype expressed 3BNC117 (FIG. 56), while 3% of the bone marrow lymphocytes were 3BNC117-expressing B cells (FIG. 57). These results are of the same range as those obtained when the sgRNA was coded together with the saCas9, although direct side by side comparison is hindered by the use of different ubiquitously active promoters. Importantly, the overall numbers of splenic plasmablasts, germinal center B cells and bone marrow plasma cells were similar to those in the control groups (FIG. 58), mitigating concerns of B cell neoplasm. In order to further increase the safety of our approach, the saCas9 was next coded under the control of the CD19, B cell specific, promoter [Moreau, T., et al., Mol. Ther. 10, 45-56 (2004)](FIG. 59A). In particular, C57BL/6 mice were immunized with 20 µg of HIV gp120, and 6 days later each mouse was co-injected with one vector coding for the bNAb and for the sgRNA and with a second vector coding for saCas9, regulated by the CD19 promoter (FIG. 59A, 59B). The mice then received additional immunizations at days 8, 23, 38, and 53. Following the boosting regimen, treated mice had up to 2 µg/ml of the 3BNC117 bNAb in their blood (FIG. 59C), attesting that replacing the promoter did not preclude the therapeutic effect. Different groups of mice were sacrificed for on-target cleavage analysis 3 days after having been co-injected with the donor+sgRNA vector and with a second vector coding for saCas9 under the control of either the ubiquitously active SFFV promoter or the B cell specific CD19 promoter. Similar transduction rates were obtained for vectors coding the saCas9 under the regulation of the CD19 or SSFV promoters (FIG. 60). However, the CD19 promoter significantly reduced saCas9 expression in the liver, but not in peripheral blood mononuclear cell (PBMCs, FIG. 59D). Importantly, the rates of on-target cleavage in the liver, as measured by TIDE analysis, were significantly above background only when using the SFFV promoter, rather than the CD19 promoter, to drive saCas9 expression (FIG. 59E). Therefore, separating the coding of saCas9 and the sgRNA between the two AAVs and expressing saCas9 under a B cell specific promoter reduce undesired cleavage to below the limit of detection while allowing high 3BNC117 titers following immunizations.

Eliciting a specific, neutralizing antibody response to hypervariable viruses is a long-standing challenge in medicine. B cell engineering provides an opportunity to express desired therapeutic antibodies for adaptive immunity. Here, the inventors uniquely demonstrate that B cells can be safely and robustly engineered in vivo. A single, systemic dose of dual AAV-DJ coding for CRISPR/Cas9 and donor cassette in mice allowed for site-specific integration, with limited off-target Cas9 expression and DNA double-strand breaks. Upon immunizations, the engineered B cells undergo antigen-induced activation leading to memory retention, clonal selection and differentiation into plasma cells that secrete the bNAb at neutralizing levels. Future modifications may include coding the bNAb as a single chain to reduce mis-pairing of the bNAb heavy chain with the endogenous light chain. Such single chain coding can further allow the expression of bi-specific bNAbs, which may be required to provide long-term protection from HIV resurgence1. Safety may be further improved by using more specific nucleases and by having the bNAb gene preceded by a splice acceptor rather than by a promoter, to reduce expression from off-target integration. Both safety and efficacy may benefit from embedding B cell specific targeting moieties in the AAV vector or in a non-viral alternative. The therapeutic impact of the approach presented by the present disclosure may best be evaluated in nonhuman primates with HIV-like infections. Finally, in vivo B cell engineering may have diverse future applications as it may be used to address other persistent infections as well as to treat autoimmune disease, genetic disorders, and cancer.

The invention claimed is:

1. A method of genetically engineering a primary mammalian cell of the B lineage for expression of an engineered B cell receptor (BCR) and for antigen-induced secretion of an antibody of interest or antigen binding fragment thereof or chimera thereof from said cell and or progeny cell thereof, said method comprising a step of contacting a primary mammalian cell of the B lineage with at least one nucleic acid cassette comprising at least one nucleic acid sequence of interest, or with any vector or vehicle comprising said cassette, wherein said nucleic acid sequence of interest comprises at least one nucleic acid sequence coding 5' to 3' for (i) at least one variable domain of an immunoglobulin heavy chain or any binding fragment or chimera thereof, and (ii) at least one variable domain of an immunoglobulin light chain or any binding fragment or chimera thereof, and at least one splice donor site (SD), wherein said cassette is flanked on the 5' and 3' ends thereof by universal homology arms for integrating by homologous recombination, wherein said universal homology arms target the insertion of said nucleic acid cassette comprising said nucleic acid sequence of interest into a target genomic sequence within the immunoglobulin heavy chain (IgH) locus, downstream to the last segment of the J region of said IgH locus and upstream of an enhancer region of said IgH locus of said heavy chain of said BCR, and wherein said method genetically engineers the primary cell of the B cell lineage to express an engineered BCR and to secrete the antibody of interest or antigen-binding fragment thereof or chimera thereof by antigen-induced activation from said cell and or progeny thereof.

2. The method according to claim 1, wherein said target genomic sequence within the IgH locus is located at least 100 nucleotides downstream to the J region of the variable domain.

3. The method according to claim 1, wherein said cassette further comprises at least one exogenous hotspot motif for somatic hypermutations, said somatic hypermutations retaining or minimally changing the protein translated from said nucleic acid sequence.

4. The method according to claim 1, wherein said cassette is flanked on at least one of the 5' and 3' ends thereof by at least recognition sites for a site-specific nuclease, wherein the insertion of said nucleic acid sequence of interest into the target genomic locus is mediated by said site-specific nuclease, and optionally, said nuclease is at least one programmable engineered nuclease (PEN), wherein said PEN comprises at least one clustered regulatory interspaced short palindromic repeat (CRISPR)/CRISPR associated (cas) protein system, and wherein said method further comprises the step of contacting said cell with at least one of:

(a) one or more of CRISPR/cas protein, or any nucleic acid molecule encoding said Cas protein; and (b) one or more of nucleic acid sequence comprising at least one guide RNA (gRNA) that targets the insertion of said nucleic acid sequence of interest into a target genomic sequence within the IgH locus, or any nucleic acid sequence encoding said gRNA; or any kit, composition or vehicle comprising at least one of (a) and (b).

5. The method according to claim 1, wherein said contacting the cell with said at least one nucleic acid cassette is performed in a mammalian subject, the method comprising a step of administering to said subject an effective amount of the at least one nucleic acid cassette comprising said at least one nucleic acid sequence of interest or of any vector or vehicle comprising said cassette.

6. The method according to claim 5, wherein said mammalian subject is suffering from a pathologic disorder.

7. The method according to claim 1, wherein said antibody of interest or antigen binding fragment or chimera thereof comprises at least one antibody of interest or antigen binding fragment or chimera thereof that is directed against an antigen associated with a pathologic disorder, said antigen comprising a viral antigen, a bacterial antigen, a fungal antigen, a parasite antigen, or a tumor associated antigen (TAA).

8. A genetically engineered mammalian cell of the B lineage engineered to express an engineered B cell receptor (BCR) and to secrete an antibody of interest or an antigen-binding fragment thereof upon antigen induction, or a population of said engineered cells, or any composition thereof, said cell comprising at least one exogenous nucleic acid sequence of interest coding for at least one variable domain of an immunoglobulin light chain and at least one variable domain of an immunoglobulin heavy chain of said antibody of interest or an antigen-binding fragment thereof upstream of an at least one splice donor site (SD), integrated within the IgH locus downstream to the last segment of the J region of the variable domain and upstream of an enhancer region of said IgH locus of said heavy chain, optionally, wherein said nucleic acid sequence coding for the at least one variable domain of at least one of an immunoglobulin light chain and an immunoglobulin heavy chain, further comprises at least one exogenous hotspot motif for somatic hypermutation, wherein said somatic hypermutation retains or minimally changes the protein translated from said nucleic acid sequence.

* * * * *